(12) United States Patent
Krasnoperov et al.

(10) Patent No.: US 9,533,026 B2
(45) Date of Patent: *Jan. 3, 2017

(54) POLYPEPTIDE COMPOUNDS FOR INHIBITING ANGIOGENESIS AND TUMOR GROWTH

(71) Applicant: VasGene Therapeutics, Inc., Agoura Hills, CA (US)

(72) Inventors: Valery Krasnoperov, South Pasadena, CA (US); Nathalie Kertesz, Agoura Hills, CA (US); Ramachandra Reddy, Conshohocken, PA (US); Parkash Gill, Agoura Hills, CA (US); Sergey Zozulya, San Diego, CA (US)

(73) Assignee: VASGENE THERAPEUTICS, INC, Los Angeles, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/887,819

(22) Filed: May 6, 2013

(65) Prior Publication Data

US 2014/0107030 A1    Apr. 17, 2014

Related U.S. Application Data

(63) Continuation of application No. 13/420,776, filed on Mar. 15, 2012, now abandoned, which is a continuation of application No. 12/584,993, filed on Sep. 14, 2009, now abandoned, which is a continuation of application No. 11/234,482, filed on Sep. 23, 2005, now abandoned.

(60) Provisional application No. 60/612,488, filed on Sep. 23, 2004.

(51) Int. Cl.
| | |
|---|---|
| A61K 38/00 | (2006.01) |
| A61K 39/00 | (2006.01) |
| A61K 38/38 | (2006.01) |
| A61K 47/48 | (2006.01) |
| C07K 14/715 | (2006.01) |

(52) U.S. Cl.
CPC ....... *A61K 38/385* (2013.01); *A61K 47/48215* (2013.01); *C07K 14/715* (2013.01); *A61K 38/00* (2013.01)

(58) Field of Classification Search
None
See application file for complete search history.

(56) References Cited

U.S. PATENT DOCUMENTS

| | | | |
|---|---|---|---|
| 5,264,209 A | 11/1993 | Mikayama et al. | |
| 5,512,591 A | 4/1996 | Halperin et al. | |
| 5,624,899 A | 4/1997 | Bennett | |
| 5,635,177 A | 6/1997 | Bennett et al. | |
| 5,693,762 A | 12/1997 | Queen et al. | |
| 5,770,599 A | 6/1998 | Gibson et al. | |
| 5,795,734 A | 8/1998 | Flanagan et al. | |
| 5,824,303 A | 10/1998 | Bartley et al. | |
| 5,864,020 A | 1/1999 | Bennett | |
| 6,015,711 A | 1/2000 | Olson et al. | |
| 6,303,769 B1 | 10/2001 | Cerretti | |
| 6,413,730 B1 | 7/2002 | Holland | |
| 6,423,685 B1 | 7/2002 | Drummond et al. | |
| 6,440,954 B1 | 8/2002 | Haber et al. | |
| 6,479,459 B1 | 11/2002 | Cerretti | |
| 6,492,140 B2 | 12/2002 | Cerretti | |
| 6,514,497 B1 | 2/2003 | Briskin et al. | |
| 6,579,683 B2 | 6/2003 | Wang et al. | |
| 6,673,343 B2 | 1/2004 | Bennett et al. | |
| 6,864,227 B1 | 3/2005 | Wang et al. | |
| 6,887,674 B1 | 5/2005 | Wang et al. | |
| 6,916,625 B2 | 7/2005 | Wang et al. | |
| 6,926,898 B2 | 8/2005 | Rosen et al. | |
| 7,163,808 B2 | 1/2007 | Anderson et al. | |
| 7,576,052 B2 | 8/2009 | Kahn et al. | |
| 7,585,967 B2 | 9/2009 | Reddy et al. | |
| 7,700,297 B2 | 4/2010 | Wang et al. | |
| 7,741,272 B2 | 6/2010 | Wang et al. | |
| 7,862,816 B2 | 1/2011 | Krasnoperov et al. | |
| 2002/0103358 A1 | 8/2002 | Cerretti et al. | |
| 2002/0142444 A1 | 10/2002 | Caras | |
| 2003/0157712 A1 | 8/2003 | Daniel et al. | |
| 2004/0110150 A1 | 6/2004 | Koller et al. | |
| 2004/0136983 A1 | 7/2004 | Ague! | |
| 2004/0171123 A1* | 9/2004 | Rosen et al. | 435/69.7 |
| 2004/0234520 A1 | 11/2004 | Ague! et al. | |

(Continued)

FOREIGN PATENT DOCUMENTS

| | | |
|---|---|---|
| EP | 0 442 724 | 8/1991 |
| EP | 0 633 315 | 1/1995 |

(Continued)

OTHER PUBLICATIONS

Kashiwa-Kawai et al. A variant transcript encoding a soluble truncated form of the human Eph receptor family tyrosine kinase, EphB4v is generated by alternative splicing. Meiji Seika Kenkyu Nenpo (1998), 37, 15-26.*

Adams, R.H., et al., "Eph Receptors and Ephrin Ligands: Essential Mediators of Vascular Development," *Trends. Cardiovasc. Med.*, 10:183-188 (2000).

Adams, R.H., et al., "Roles of ephrinB ligands and EphB receptors in cardiovascular development: demarcation of arterial/venous domains, vascular morphogenesis, and sprouting angiogenesis," Genes Dev. 13:295-306 (1999).

(Continued)

*Primary Examiner* — Maher Haddad
(74) *Attorney, Agent, or Firm* — Craig A Crandall

(57) ABSTRACT

In certain embodiments, this present invention provides polypeptide compositions, including compositions containing a modified polypeptide, and methods for inhibiting Ephrin B2 or EphB4 activity. In other embodiments, the present invention provides methods and compositions for treating cancer or for treating angiogenesis-associated diseases.

7 Claims, 113 Drawing Sheets

(56) References Cited

U.S. PATENT DOCUMENTS

| | | |
|---|---|---|
| 2004/0247592 A1 | 12/2004 | Roitman et al. |
| 2005/0049176 A1 | 3/2005 | Kiener et al. |
| 2006/0204512 A1 | 9/2006 | Krasnoperov et al. |
| 2006/0241027 A1 | 10/2006 | Hauser et al. |
| 2006/0286102 A1* | 12/2006 | Jin ................ C07K 14/705 424/143.1 |
| 2007/0207952 A1 | 9/2007 | Silva et al. |

FOREIGN PATENT DOCUMENTS

| | | |
|---|---|---|
| EP | 0 999 278 | 5/2000 |
| WO | WO 93/00425 | 1/1993 |
| WO | WO 93/15201 | 8/1993 |
| WO | WO 94/10202 | 5/1994 |
| WO | WO 94/11020 | 5/1994 |
| WO | WO 95/27061 | 10/1995 |
| WO | WO 96/01839 | 1/1996 |
| WO | WO 96/02645 | 2/1996 |
| WO | WO 96/03043 | 2/1996 |
| WO | WO 96/09384 | 3/1996 |
| WO | WO 96/13518 | 5/1996 |
| WO | WO 96/23000 | 8/1996 |
| WO | WO 96/26958 | 9/1996 |
| WO | WO 96/36713 | 11/1996 |
| WO | WO 97/09427 | 3/1997 |
| WO | WO 97/23629 | 7/1997 |
| WO | WO 97/43960 | 11/1997 |
| WO | WO 97/44453 | 11/1997 |
| WO | WO 98/01548 | 1/1998 |
| WO | WO 98/43960 | 10/1998 |
| WO | WO 98/45331 | 10/1998 |
| WO | WO 98/45708 | 10/1998 |
| WO | WO 99/08696 | 2/1999 |
| WO | WO 99/17796 | 4/1999 |
| WO | WO 99/45026 | 9/1999 |
| WO | WO 99/52541 | 10/1999 |
| WO | WO 00/24413 | 5/2000 |
| WO | WO 00/30673 | 6/2000 |
| WO | WO 01/49743 | 7/2001 |
| WO | WO 01/81377 | 11/2001 |
| WO | WO 02/11785 | 2/2002 |
| WO | WO 02/26827 | 4/2002 |
| WO | WO 02/058538 | 8/2002 |
| WO | WO 02/061055 | 8/2002 |
| WO | WO 02/079382 | 10/2002 |
| WO | WO 02/102854 | 12/2002 |
| WO | WO 02/102972 | 12/2002 |
| WO | WO 02/102973 | 12/2002 |
| WO | WO 03/000113 | 1/2003 |
| WO | WO 03/004057 | 1/2003 |
| WO | WO 03/094859 | 11/2003 |
| WO | WO 2004/014292 | 2/2004 |
| WO | WO 2004/020468 | 3/2004 |
| WO | WO 2004/024773 | 3/2004 |
| WO | WO 2004/080425 | 9/2004 |
| WO | WO 2004/091375 | 10/2004 |
| WO | WO 2005/048917 | 6/2005 |
| WO | WO 2005/051307 | 6/2005 |
| WO | WO 2005/090406 | 9/2005 |

OTHER PUBLICATIONS

Andres, A. C. et al., "Expression of two novel eph-related receptor protein tyrosine kinases in mammarv aland development and carcinoaenesis," Oncoaene, 9:1461-1467 (1994).
Asahara, T. et al., "Isolation of Putative Progenitor Endothelial Cells for Angiogenesis," Science, 275:964-967 (1997).
Batlle, E., et al., "EphB receptor activity suppresses colorectal cancer progression," Nature, 435(23):1126-1130 (2005).
Benjamin I et al., Immunity, A Short Course, 2nd Ed., Wiley-Liss pub. p. 40 (1992).
Bennett et al., "Extracellular Domain-IgG Fusion Proteins for Three Human Natriuretic Peptide Receptors," The Journal of Biological Chemistry, vol. 266(34), pp. 23060-23067 (1991).

Bennett, B. D. et al., "Molecular cloning of a ligand for the EPH-related receptor protein-tyrosine kinase Htk," Proc. Natl. Acad. Sci. USA, 92:1866-1870 (1995).
Bennett, B.D., et al., "Cloning and Characterization of HTK, a Novel Transmembrane Tyrosine Kinase of the EPH Subfamily," The Journal of Biological Chemistry, 269(19): 14211-14218 (1994).
Berclaz, G., et al., "Activation of the receptor protein tyrosine kinase EphB4 in endometrial hyperplasia and endometrial carcinoma," Ann Oneal., 14:220-226 (2003).
Berclaz, G., et al., "Expression of the receptor protein tyrosine kinase myk-1/htk in normal and malignant mammary epithelium," Biochem Biophys Res Commun., 24;226:869-875 (1996).
Berclaz, G., et al., "Loss of EphB4 receptor tyrosine kinase protein expression during carcinoqenesis of the human breast," Oncoloqy Reports, 9(5):985-989, (2002).
Bergemann, A. D. et al., "ELF-2, a New Member of the Eph Ligand Family Is Segmentally Expressed in Mouse Embryos in the Region of the Hindbrain and Newly Forming Semites," Molecular and Cellular Bioloqv, 15(9):4921-4929 (1995).
Bos et al., "PD153035, a Tyrosine Kinase Inhibitor, Prevents Epidermal Growth Factor Receptor Activation and Inhibitors Growth of Cancer Cells in a Receptor Number-dependent Manner," Clinical Cancer Research, 3:2099-2106 (1997).
Bowie et al., "Deciphering the message in protein sequences: tolerance to amino acid substitutions," Science, vol. 247(4948), pp. 1306-1310 (1990).
Boyd, W.A., et al., "Isolation and Characterization of a Novel Receptor-type Protein Tyrosine Kinase (hek) from a Human Pre-B Cell Line," The Journal of Biological Chemistry, 267(5):3262-3267 (1992).
Brambilla, R., et al., "Membrane-bound LERK2 ligand can signal through three different Eph-related receptor tyrosine kinases," EMBO J., 14:3116-3126 (1995).
Brehmer et al., "Cellular Targets of Gefitinib," Cancer Research, 65(2):379-382 (2005).
Breier et al., Angiogenesis in Embryos and Ischemic Diseases, Thrombosis and Haemostasis 78(1):678-683 (1997).
Bruckner et al., "Tyrosine Phosphorylaton of Transmembrane Ligands for Eph Receptors," Science, 275:1640-1643 (1997).
Bruhl, T., et al., "Homeobox A9 Transcriptionally Regulates the EphB4 Receptor to Modulate Endothelial Cell Migration and Tube Formation," Circ. Res., 743-751 (2004) [Epub ahead of print] DOI 10.1161/01res0000120861.27064.09.
Burgess et al., "Possible dissociation of the heparin-binding and mitogenic activities of heparin-binding (acid fibroblast) growth factor-1 from its receptor-binding activities by site-directed mutagenesis of a single lysine residue," Journal of Cell Biology, vol. 111, pp. 2129-2138 (1990).
Caplen, N.J., "RNAI as a Gene Therapy Approach," Expert Opin. on Biol. Therapy, 3(4):575-586, (2003).
Carbone, M., et al., "The pathogenesis of mesothelioma," Semin. Oneal., 29(1):2-17 (2002).
Chang, M.W., et al., "Adenovirus-Mediated Over-Expression of the Cyclin/Cyclin-Dependent Kinase Inhibitor, p21 Inhibits Vascular Smooth Muscle Cell Proliferation and Neointima Formation in the Rat Carotid Artery Model of Balloon Angioplasty," J. C/in. Invest., 96:2260-2268 (1995).
Cheng, N., et al., "The ephrins and Eph receptors in angiogenesis," Cytokine & Growth Factor Reviews, 13:75-85 (2002).
Chrencik et al., "Structural and biophysical characterization of the EphB4/EphrinB2 protein-protein interaction and receptor specificity," J. Biol. Chem. 281:38:28185-92 (2006).
Chrencik et al., Three-dimensional Structure of the EphB2 Receptor in Complex with an Antagonistic Peptide Reveals a Novel Mode of Inhibition, J. Biol. Chem. 282: 36505-36513 Sep. 26, 2007 Epub.
Coffman, K.T., et al., "Differential EphA2 Epitope Display on Normal versus Malignant Cells," Cancer Research, 63:7907-7912 (2003).
Cowan, C.A., et al., "Ephrins in reverse, park and drive," Trends in Cell Biology, 12(7):339-346 (2002).

(56) References Cited

OTHER PUBLICATIONS

Cromer et al., "Identification of genes associated with tumorigenesis and metastatic potential of hypopharyngeal cancer by microarray analysis," Oncogene, Basingstoke, Hants, GB, 23(14):2484-2498, (2004).
Davis, S., et al., "Ligands for EPH-related receptor tyrosine kinases that require membrane attachment or clusterina for activitv," Science, 266(5186):816-819 (1994).
Dermer, G., "Another Anniversary for the War on Cancer," Bio/Technolog, 12:320 (1994).
Dodelet, V.C. et al., "Eph Receptors and Ephrin Ligands: Embryogenesis to Tumorigenesis," Oncogene, 19(49): 5614-19 (2000).
Durbin, L., et al., "Eph signaling is required for segmentation and differentiation of the somites," Genes & Development, 12:3096-3109 (1998).
Easty et al., "Abnormal Protein Tyrosine Kinase Gene Expression During Melanoma Progression and Metastasis," Int. J. Cancer, 60:129-136 (1995).
Easty et al., "Cytokine 861 as a growth factor for metastatic melanomas and increasing expression of its receptor ECK during melanoma progression," Proceedings of the American Association for Cancer Research, 35(356) (1994) abstract only.
Easty, et al., "Expression of Eck and Lerk-1 During Melanoma Progression," P137 St. George's Hospital Medical School, London, JK and Western Infirmary, Glasgow, UK, Br. J. Cancer 78(1):137 (1998).
Fabes et al., "Accumulation of the Inhibitory Receptor EphA4 May Prevent Regeneration of Corticospinal Tract Axons Following Lesion," Eur. J. Neurosci., 23(7):1721-1730 (2006) (Abstract).
Feldman, L.J., et al., "Perspectives of Arterial Gene Therapy for the Prevention of Restenosis," Cardiovasc. Res., 32:194-207 (1996).
Folkman et al., "Angiogenic Factors," Science, 235:442-447 (1987).
Folkman, "Angiogenesis in cancer, vascular, rheumatoid and other disease," Nature Medicine, 1:27-31, (1995).
Folkman, J. et al., "Blood Vessel Formation: What Is Its Molecular Basis?" Cell, 87:1153-1155 (1996).
Folkman, J., "Angiogenic Therapy of the Human Heart," Circulation, 97(7): 628-29 (1998).
Folkman, J., "Antiangiogenic Gene Therapy," Proc. Natl. Acad. Sci. USA., 95:9064-66 (1998).
Folkman, J., "Fighting Cancer by Attacking Its Blood Supply," Sci. Am., 275(3): 150-54 (1996).
Fox et al., Invasiveness of breast carcinoma cells and transcript profile: Eph receptors and ephrin ligands as molecular markers of potential diagnostic and prognostic application, Biochim. Biophys. Res. Comm. 318(4):882-892 (2004).
Freshney, R. Ian, Culture of Animal Cells: A Manual of Basic Technigue, pp. 3-4 (1983).
Fuller, T., et al., "Forward EphB4 signaling in endothelial cells controls cellular repulsion and segregation from ephrinB2 positive cells," J. Cell Sci., 116:2461-2470 (2003).
Gale et al., "Eph receptors and ligands comprise two major specificity subclasses and are reciprocally compartmentalized during embryogenesis," Neuron 17:9-19 (1996).
Gale, N.W. et al., "Growth Factors Acting Via Endothelial Cell-Specific Receptor Tyrosine Kinases: VEGFs, Angiopoietins, and Ephrins in Vascular Development," Genes Dev., 13:1055-66 (1999).
Gale, N.W., et al., "Ephrin-82 Selectively Marks Arterial Vessels and Neovascularization Sites in the Adult, with Expression in Both Endothelial and Smooth-Muscle Cells," Dev. Biol., 230: 151-160 (2001).
GenBank Accession No. P52803. (1996).
Genetech's Response to Final Office Action on U.S. Appl. No. 09/442,898, filed Mar. 29, 2002.
Gerety, S.S., et al., "Symmetrical mutant phenotypes of the receptor EphB4 and its specific transmembrane ligand ephrin-82 in cardiovascular development," Mol. Cell, 4:403-414 (1999).

Gill, P.S., et al., "Epidemic (AIDS-related) Kaposi's sarcoma: Epidemiology pathogenesis and treatment," AIDS Updates, (7) 1-11 (1994).
Glassberg et al., "Cultured endothelial cells derived from the human iliac arteries," In Vitro, 18:859-866 (1982).
Goetz et al., "Long-term serial cultivation of arterial and capillary endothelium from adult bovine brain," In Vitro Cellular and Developmental Bioloqv, 21 :172-180 (1985).
Gura, T., "Systems for Identifying New Drugs Are Often Faulty," Science, 278:1041-1042 (1997).
Guzman, R.J., et al., "In Vivo Suppression of Injury-Induced Vascular Smooth Muscle Cell Accumulation Using Adenovirus-Mediated Transfer of the Herpes Simplex Virus Thymidine Kinase Gene," Proc. Natl. Acad. Sci. USA, 91:10732-10736 (1994).
Hafner et al., "Differential Gene Expression of Eph Receptors and Ephrins in Benign Human Tissues and Cancers," Clinical Chemistry, 50(3):490-499 (2004).
Hafner, et al., "Loss of Eph 86 expression in metastatic melanoma," International Journal of Oncoloqv, 23:1553-1559 (2003).
Hamada, K., Distinct roles of ephrin-82 forward and EphB4 reverse signaling in endothelial cells, Arterioscler. Thromb. Vase. Biol., 23:190-197 (2003).
Hausner, C., "Organogenesis Vascular Graft Becomes Physiologically-Responsive Living Tissue After Implantation fonlinel," Nature Biotechnol., (1999).
He et al., "The Effect of Soluble EphrinB4 Receptor on Laser-Induced Choroidal Neovascularization," IOVS, 45:U804 (2004).
Henkemeyer, M., et al., "Nuk Controls Pathfinding of Commissural Axons in the Mammalian Central Nervous System," Cell, 86:35-46 (1996).
Himanen et al., Crystal structure of the ligand-binding domain of the receptor tyrosine kinase EphB2, Nature 396:486-491 (1998).
Himanen, J.P., et al., "Eph receptors and ephrins," Intl. J. Biochem. & Cell Bio., 35:130-134 (2003).
Himanen, J.P., et al., "Eph signaling: a structural view," Trends in Neurosciences, 26(1):46-51 (2003).
Hirai, H., "A novel putative tyrosine kinase receptor encoded by the eph gene," Science, 238:1717-1720 (1987).
Holder and Klein, Eph Receptors and ephrins: effectors of morphogenesis, Development 126(10):2033-2041 (1999).
Inada et al., Selective expression of the receptor tyrosine kinase, HTK, on human erythroid proaenitor cells, Blood 89(8):2757-2765 (1997).
Indolfi, C., et al., "Inhibition of Cellular ras Prevents Smooth Muscle Cell Proliferation After Vascular Injury In Vivo," Nature Med., 1(6):541-545 (1995).
Kashiwa-Kawai, A variant transcript encoding a soluble truncated form of the human Eph receptor family tyrosine kinase, EphB4v is generated by alternative splicing, Scientific Reports of Meiji Seika Kaisha, 1998, vol. 37 abstract.
Kenyon, B.M., et al., "A Model of Angiogenesis in the Mouse Cornea," Invest Ophthalmol. Vis. Sci., 37:1625-1632 (1996).
Keogh, M-C, et al., "Design of a Muscle Cell-Specific Expression Vector Utilising Human Vascular Smooth Muscle ?—Actin Regulatory elements," Gene Therapy, 6:616-628 (1999).
Kertesz et al., "The soluble extracellular domain of EphB4 (sEphB4) antagonized EphB4-EphrinB2 interaction, modulates angiogenesis, and inhibits tumor growth," Blood 107(6):2330-2338 (2006).
Kiessig et al., "Application of a green fluorescent fusion protein to study protein-protein interactions by electrophoretic methods," Electrophoresis, vol. 22, pp. 1428-1435 (2001).
Kitamura et al., "Chemical Engineering of the Monoclonal Antibody A7 by Polyethylene Glycol for Targeting Cancer Chemotherapy", Cancer Research, vol. 51, pp. 4310-4315 (1991).
Kiyokawa, E., et al., "Overexpression of ERK, an EPH family receptor protein tyrosine kinase, in various human tumors," Cancer Res., 54:3645-3650 (1994).
Kullander, K., et al., "Mechanisms and functions of eph and ephrin signalling," Nature Reviews, Molecular Cell Bioloav, 3:475-486 (2002).

(56) References Cited

OTHER PUBLICATIONS

Lackmann, et al., "Distinct Subdomains of the EphA3 Receptor Mediate Ligand Binding and Receptor Dimerization," *The Journal of Bioloqical Chemistrv*, 273 (32):20228-20237 (1998).
Leger et al., "Identification of CJC-1131-Albumin Bioconjugate as a Stable and Bioactive GLP-1/7-36 Analoa," Bioraanic & Med. Chem. Ltrs 14:4395-4398 (2004).
Li, J., et al., "Expression of the SM22x Promoter in Transgenic Mice Provides Evidence for Distinct Transcriptional Regulatory Programs in Vascular and Visceral Smooth Muscle Cells," *J. Cell Biol.*, 132:849-59 (1996).
Lin, P., et al., "Antiangiogenic Gene Therapy Targeting the Endothelium-Specific Receptor Tyrosine Kinase Tie2," *Proc. Natl. Acad. Sci., USA*, 95:8829-8834 (1998).
Magal et al., Rapid Communication: 861, a Ligand for the Eck Receptor Protein-Tyrosine Kinase, Exhibits Neuroptrophic Activity in Cultures of Rat Spinal Cord Neurons, J. Neuroscience Res. 43:735-744 (1996).
Magal, et al., "861, a Ligand for the Eck Receptor Protein-Tyrosine Kinase, Exhibits Neurotrophic Activity in Cultures of Rat Spinal Cord Neurons," *Journal of Neuroscience Research*, 43:735-744 (1996).
Martiny-Baron et al., Inhibition of Tumor Growth and Angiogenesis by Soluble EphB4, Neoolasia 6(3):248-257 (2004).
Maru, et al., "Evolution, Expression, and Chromosomal Location of a Novel Receptor Tyrosine Kinase Gene, eph," *Molecular and Cellular Biology*, 8(9):3770-3776 (1998).
Maru, et al., "Overexpression confers an oncogenic potential upon the eph gene," *Oncogene*, 5:445-447 (1990).
Mellitzer, G., et al., "Control of cell behavior by signalling through Eph receptors and ephrins," Neurobiology, 10:400-408 (2000).
Mellitzer, G., et al., "Eph Receptors and Ephrins Restrict Cell Intermingling and Communication," *Nature*, 400:77-82 (1999).
Miki et al., "Association of Ash/Grb-2 with Dynamin through the Src Homology 3 Domain", The Journal of Bioloqical Chemistrv, vol. 269(8), DD. 5489-5492 (1994).
Munarini, N., "Altered mammary epithelial development, pattern formation and involution in transgenic mice expressing the EphB4 receptor tyrosine kinase," J. Cell. Sci., 115(Pt 1):25-37 (2002).
Nakanuma, Y. et al., "Succinylated Wheat Germ Agglutinin Lectin Binding in Intrahepatic Vessels: A New Histochemical Tool," *Arch. Pathol. Lab. Med.*, 117:809-811 (1993).
Niklason, L.E., et al., "Functional Arteries Grown In Vitro," *Science*, 284:489-493 (1999).
Niklason, L.E., et al., "Morphologic and Mechanical Characteristics of Engineered Bovine Arteries," *J. Vase. Sura.*, 33:628-638 (2001).
Nikolova, et al., "Cell-type specific and estrogen dependent expression of the receptor tyrosine kinase EphB4 and its ligand ephrin-82 during mammary gland morphogenesis," *Journal of Cell Science*, 111:2741-2751 (1998).
Nomura, A.M., et al., "Prostate cancer: a current perspective," Epidemiol Rev., 13:200-227 (1991).
Noren et al., The EphB4 receptor suppresses breast cancer cell tumorigenicity through an Abl-Crk pathway, Nature Cell Bio. 8:815-825 (2006).
Noren et al., "Interplay Between EphB4 on Tumor Cells and Vascular Ephrin-82 Regulates Tumor Growth," *Proceedings* of the National *Academy* of Sciences of USA, National Academy of Science, 101(15):5583-5588 (2004).
Ogle et al., "The Role of Vascular Smooth Muscle Cell Integrins in the Compaction and Mechanical Strengthening of a Tissue-Engineered Blood Vessel," *Tissue Engineering*, 5(4):387-402 (1999).
Orioli, D., et al., "Sek4 and Nuk Receptors Cooperate in Guidance of Commissural Axons and in Palate Formation," *Embo J.*, 15(22):6035-6049. (1996).
Pandey et al., "Role of 861, the ligand for the eek receptor tyrosine kinase, in TNF-a-induced anaioaenisis" *Science*, 268:567-569 (1996).

Parangi et al., "Antiangiogenic therapy of transgenic mice impairs de nova tumor growth," *Proc. Natl. Acad. Sci. USA*, 93:2002-2007 (1996).
Pasquale, E.B., "The Eph family of receptors," Curr. Opin. Cell Biol., 9:608-615 (1997).
Peng et al., "Regulation of Ca2+-activated K+ channels in pulmonary vascular smooth muscle cells: role of nitric oxide," *J. Applied Physiol.*, 81 :1264-1272 (1996).
Perrin et al., "Expression, Purification, and Characterization of a Soluble Form of the First Extracellular Domain of the Human Type 1 Corticotropin Releasing Factor Receptor*," The Journal of Biological Chemistry, vol. 276(34), pp. 31528-31534 (2001).
Presta et al., "Humanization of an Anti-Vascular Endothelial Growth Factor Monoclonal Antibody for the Therapy of Solid Tumors and Other Disorders," *Cancer Research*, 57:4593-4599 (1997).
R&D systems. Recombinant Mouse EphB4/Fc chimera. Nov. 14, 2000. p. 1.
Ramchandran et al., Mettaloprotease-mediated cleavage secretion of pulmonary ACE by vascular endothelial and kidnev epithelial cells,: *Am. J. Phvsioloav*, 271 :H744-751 (1996).
Risau, W., "Mechanisms of angiogenesis," *Nature*, 386:671-674 (1997).
Sakano, S., et al., "Characterization of a ligand for receptor protein-tyrosine kinase HTK expressed in immature hematopoietic cells," Oncoaene., 13:813-822 (1996).
Santa Cruz Biotech Inc. datasheet for EphB4(H-200).
Santa Cruz Biotechnology, Inc., "EphB4 (N-19): sc-7285", retrieved from the Internet: URL:http://www.genetimes.com .en/support/pd f-ds/7200-7299/sc-7285.pdf (1999).
Santa Cruz, "EphB4 (N-19): sc-7285," Product Catalog of Santa Cruz Biotechnology, Apr. 1999 (undated).
Schmucker, D., et al., "Signaling Downstream of Eph Receptors and Ephrin Ligands," Cell, 105:701-704 (2001).
Seffernick et al., "Melamine Deaminase and Atrazine Chlorohydrolase: 98 Percent Identical but Functionally Different", Journal of Bacteriology, vol. 183(8), pp. 2405-2410 (2001).
Shepard, et al., "Monoclonal Antibody Therapy of Human Cancer: Taking the HER2 Protooncogene to the Clinic," *Journal of Clinical Immunology*, 11(3):117-127 (1991).
Shin, D., et al., "Expression of ephrinB2 identifies a stable genetic difference between arterial and venous vascular smooth muscle as well as endothelial cells, and marks subsets of microvessels at sites of adult neovascularization," Dev. Biol. 230:139-150 (2001).
Simonet, S., et al., "Venous and Arterial Endothelial Cells Respond Differently to Thrombin and its Endogenous Receptor Agonist," *European Journal of Pharmacology*, 216:135-137 (1992).
Simons, M., et al., "Antisense c-myb Oligonucleotides Inhibit Intimal Arterial Smooth Muscle Cell Accumulation In Vivo," *Nature*, 359(6390):67-70 (1992).
Sinha, et al., "Expression of EphB4 in head and neck squamous cell carcinoma" Ear, Nose and Throat Journal, 82(11), pp. 866, 869-870 & 887 (2003).
Sinha, U.K., et al., "Expression of EphB4 in head and neck squamous cell carcinoma," ENT J 82:721-723 (2003).
Sola et al., "Transgenic Mice Secreting Coronavirus Neutralizing Antibodies into the Milk", Journal of Virology, vol. 72(5), pp. 3762-3772 (1998).
Staton et al., Current Methods for Assaying Angiogenesis in vitro and in vivo, Int. J. Exp. Path. 85:233-248 (2004).
Stein, E. et al., "Eph receptors discriminate specific ligand oligomers to determine alternative signaling complexes, attachment, and assembly responses," *Genes & Development*, 12:667-678 (1998).
Stein, E. et al., "Nck Recruitment to Eph Receptor, EphB1/ELK, Couples Ligand Activation to c-Jun Kinase," *The Journal of Bioloqical Chemistrv*, 273(3):1303-1308 (1998).
Steinle, J.J., et al., "Eph 84 receptor signaling mediates endothelial cell migration and proliferation via the phosphatidylinositol 3-kinase pathway," J. Biol. Chem., 277(46):43830-5 (Nov. 15, 2002) (Epub Sep. 13, 2002).
Stephenson, S.A., "Receptor protein tyrosine kinase EphB4 is up-regulated in colon cancer," BMC Mol. Biol., 2:15 (2001).

(56) References Cited

OTHER PUBLICATIONS

Sturz, et al.,"EphB4 signaling is capable of mediating ephrinB2-induced inhibition of cell migration," *Biochemical and Biophysical Research Communications*, 313:80-88 (2004).
Sunassee, et al., "Tumour angiogenesis: Hitting cancer where it hurts," *Current Biology*, 7(5):R282-R285 (1997).
Takai, N., et al., "Expression of receptor tyrosine kinase EphB4 and its ligand ephrin-82 is associated with malignant potential in endometrial cancer," Oneal Rep., 8:567-573 (2001).
Tallquist, M.D., et al., "Growth Factor Signaling Pathways in Vascular Development," *Oncogene*, 18(55):7917-7932 (1999).
Tang, X.X., et al., "Coexpression of transcripts encoding EphB receptor protein tyrosine kinases and their ephrin-B ligands in human small cell lung carcinoma," Clin. Cancer Res., 5:455-460 (1999).
The Eph Nomenclature Committee, "Unified Nomenclature for Eph Family Receptors and Their Liaands, the Eohrins," *Cell*, 90:403-404 (1997).
Thurston et al., "Permeability-related changes revealed at endothelial cell borders in inflamed venules by lectin binding," *American Journal of Physiology*, 271 :H2547-H2562 (1996).
Tsui, L.V., et al., "p27-p16 Fusion Gene Inhibits Angioplasty-Induced Neointimal Hyperplasia and Coronary Artery Occlusion," *Circ. Res.*, 89:323-328 (2001).
Twardowski et al., "Clinical trials of antiangiogenic agents," *Current Opinion in Oncology*, 9:584-589 (1997).
Van De Wiei et al., "Factors that define the susceptibility of endothelial cells to tumor necrosis factor and lipid A," *Immunopharmacology*, 23:49-56 (1992).
Vasgene Therapeutics, Inc., "Statement of Grounds of Opposition," In the Matter of European Patent No. 1135153 (EP-B-1135153), (2006).
Vector Laboratories, "Wheat Germ Agglutinin (WGA)," [online; downloaded Jun. 12, 2006].
Von Der Leyen, H.E., et al., "Gene Therapy Inhibiting Neointimal Vascular Lesion: In Vivo Transfer of Endothelial Cell Nitric Oxide Synthase Gene," *Proc. Natl. Acad. Sci.*, 92:1137-1141 (1995).
Wang et al., "Molecular Distinction and Angiogenic Interactions Between Embryonic Arteries and Veins Revealed By EphrinB2 and Its Receptor EphB4," *Circulation: Melvin L. Marcus Younq Investiqator Award*, Abstract 341 (1998).

Wang, H. U. et al., "Eph Family Transmembrane Ligands Can Mediate Repulsive Guidance of Trunk Neural Crest Migration and Motor Axon Outgrowth," *Neuron*, 18:383-396 (1997).
Wang, H., "Transmembrane Ephrin Ligands in Neural and Vascular Development," DAI, 59(11): 5721 (1999).
Wang, H.U., et al., "Molecular distinction and angiogenic interaction between embryonic arteries and veins revealed by ephrin-82 and its receptor Eph-84," Cell 93:741-753 (1998).
Wang, Eph tumour suppression: the dark side of Gleevec, Nat. Cell Biol. 8(8):785-786 (2006).
Waugh, J.M., et al., "Thrombomodulin Overexpression to Limit Neointima Formation," *Circulation*, 102:332-337 (2000).
Win Law, "Angiogenesis in the Pathobiology and Treatment of Vascular and Malignant Diseases," *Ann. Thorac. Surg.*, 64:1204-1211 (1997).
Xia et al., "Up-Regulation of EphB4 in Mesothelioma and Its Biological Significance", Clinical Cancer Research, vol. 11(12), pp. 4305-4315 (2005).
Xu et al., Eph-related receptors and their ligands: mediators of contact dependent cell interactions, J. Mol. Med. 75:576-586 (1997).
Xu, et al., "Function of the Eph-related kinase rtk1 in patterning of the zebrafish forebrain," *Nature*, 381:19-322 (1996).
Yamamoto et al., "Differences in Cellular Responses to Mitogens in Arterial Smooth Muscle Cells Derived From Patients With Moyamoya Disease," *Stroke*, 29:1188-1193 (1998).
Yancopoulos, G. D. et al., "Vasculogenesis, Angiogenesis, and Growth Factors: Ephrins Enter the Frav at the Border," Cell, 93:661-664 (1998).
Yang et al., "Gene Targets of Antisense Therapies in Breast Cancer," Expert Opin. on Therapeutic Taraets, 6(3):375-385, (2002).
Yuan, et al., "Syndecan-1 up-regulated by ephrinB2/EphB4 plays dual roles in inflammatory anaioaenesis," *Blood*, 104(4):1025-1033 (2004).
Zetter, "Angiogenesis and Tumor Metastasis," *Annu. Rev. Med*, 49:407-424, (1998).
Zhang, X-Q, et al., "Stromal Cells Expressing ephrin-B2 Promote the Growth and Sprouting of Ephrin-B2+ Endothelial Cells," *Blood*, 98: 1028-37 (2001).
Zhou, "The Eph Family Receptor and Ligands," *Pharmacol. Ther.* ,77( 3) 151-181(1998).

* cited by examiner

Amino acid sequence of the B4ECv3 protein

MELRVLLCWASLAAALEETLLNTKLETADLKWVTFPQVDGQWEELSG
LDEEQHSVRTYEVCEVQRAPGQAHWLRTGWVPRRGAVHVYATLRFTM
LECLSLPRAGRSCKETFTVFYYESDADTATALTPAWMENPYIKVDTV
AAEHLTRKRPGAEATGKVNVKTLRLGPLSKAGFYLAFQDQGACMALL
SLHLFYKKCAQLTVNLTRFPETVPRELVVPVAGSCVVDAVPAPGPSP
SLYCREDGQWAEQPVTGCSCAPGFEAAEGNTKCRACAQGTFKPLSGE
GSCQPCPANSHSNTIGSAVCQCRVGYFRARTDPRGAPCTTPPSAPRS
VVSRLNGSSLHLEWSAPLESGGREDLTYALRCRECRPGGSCAPCGGD
LTFDPGPRDLVEPWVVVRGLRPDFTYTFEVTALNGVSSLATGPVPFE
PVNVTTDREVPPAVSDIRVTRSSPSSLSLAWAVPRAPSGAWLDYEVK
YHEKGAEGPSSVRFLKTSENRAELRGLKRGASYLVQVRARSEAGYGP
FGQEHHSQTQLDESEGWREQGSKRAILQIEGKPIPNPLLGLDSTRTG
HHHHHH

Fig. 1

Amino acid sequence of the B4ECv3NT protein

MELRVLLCWASLAAALEETLLNTKLETADLKWVTFPQVDGQWEELSGL
DEEQHSVRTYEVCEVQRAPGQAHWLRTGWVPRRGAVHVYATLRFTMLE
CLSLPRAGRSCKETFTVFYYESDADTATALTPAWMENPYIKVDTVAAE
HLTRKRFGAEATGKVNVKTLRLGPLSKAGFYLAFQDQGACMALLSLHL
FYKKCAQLTVNLTRFPETVPRELVVPVAGSCVVDAVPAPGPSPSLYCR
EDGQWAEQPVTGCSCAPGFEAAEGNTKCRACAQGTFKPLSGEGSCQPC
PANSHSNTIGSAVCQCRVGYFRARTDPRGAPCTTPPSAPRSVVSRLNG
SSLHLEWSAPLESGGREDLTYALRCRECRPGGSCAPCGGDLTFDPGPR
DLVEFWVVRGLRPDFTYTFEVTALNGVSSLATGPVPFEPVNVTTDRE
VPPAVSDIRVTRSSPSSLSLAWAVPRAPSGAWLDYEVKYHEKGAEGPS
SVRFLKTSENRAELRGLKRGASYLVQVRARSEAGYGPFGQEHHSQTQL
DESEGWREQGSKRAILQISSTVAAARV

Fig. 2

Amino acid sequence of the B2EC protein

MAVERDSVWKYCWGVLMVLCRTAISKSIVLEPIYWNSSNSKFLPGQGL
VLYPQIGDKLDTICPKVDSKTVGQYEYYKVYMVDKDQADRCTIKKENT
PLLNCAKPDQDIKFTIKPQEFSPNLWGLEFQKNKDYYIISTSNGSLEG
LDNQEGGVCQTRAMKILMKVGQDASSAGSTRNKDPTRRPELEAGTNGR
SSTTSPFVKPNPGSSTDGNSAGHSGNNILGSEVGSHHHHHH

Fig. 3

Amino acid sequence of the B4ECv3-FC protein

MELRVLLCWASLAAALEETLLNTKLETADLKWVTFPQVDGQWEEL
SGLDEEQHSVRTYEVCEVQRAPGQAHWLRTGWVPRRGAVHVYATL
RFTMLECLSLPRAGRSCKETFTVFYYESDADTATALTPAWMENPY
IKVDTVAAEHLTRKPGAEATGKVNVKTLRLGPLSKAGFYLAFQD
QGACMALLSLHLPYKKCAQLTVNLTRFPETVPRELVVPVAGSCVV
DAVPAPGPSPSLYCREDGQWAEQPVTGCSAPGFEAAEGNTKCRA
CAQGTFKPLSGEGSCQPCPANSHSNTIGSAVCQCRVGYFRARTDP
RGAPCTTPPSAPRSVVSRLNGSSLHLEWSAPLESGGREDLTYALR
CRECRPGGSCAPCGGDLTFDPGPRDLVEPWVVVRGLRPDFTYTFE
VTALNGVSSLATGPVPFEPVNVTTDREVPPAVSDIRVTRSSPSSL
SLAWAVPRAPSGAWLDYEVKYHEKGAEGPSSVRPLKTSENRAELR
GLKRGASYLVQVRARSEAGYGPFGQEHHSQTQLDESEGWREQDPE
PKSCDKTHTCPPCPAPELLGGPSVFLFPPKPKDTLMISRTPEVTC
VVVDVSHEDPEVKFNWYVDGVEVHNAKTKPREEQYNSTYRVVSVL
TVLHQDWLNGKEYKCKVSNKALPAPIEKTISKAKGQPREPQVYTL
PPSRDELTKNQVSLTCLVKGFYPSDIAVEWESNGQPENNYKTTPP
VLDSDGSFFLYSKLTVDKSRWQQGNVFSCSVMHEALHNHYTQKSL
SLSPGK

Fig. 4

Amino acid sequence of the B2EC-FC protein

MAVRRDSVWKYCWGVLMVLCRTAISKSIVLEPIYWNSSNSKPLPGQ
GLVLYPQIGDKLDIICPKVDSKTVGQYEYYKVYMVDKDQADRCTTK
KENTPLLNCAKPDQDIKFTIKFQEFSPNLWGLEFQKNKDYYIISTS
NGSLEGLDNQEGGVCQTRAMKILMKVGQDASSAGSTRNKDPTRRPE
LEAGTNGRSSTTSPFVKPNPGSSTDGNSAGHSGNNILGSEVDPEPK
SCDKTHTCPPCPAPELLGGPSVFLFPPKPKDTLMISRTPEVTCVVV
DVSHEDPEVKFNWYVDGVEVHNAKTKPREEQYNSTYRVVSVLTVLH
QDWLNGKEYKCKVSNKALPAPIEKTISKAKGQPREPQVYTLPPSRD
ELTKNQVSLTCLVKGFYPSDIAVEWESNGQPENNYKTTPPVLDSDG
SFFLYSKLTVDKSRWQQGNVFSCSVMHEALHNHYTQKSLSLSPGK

Fig. 5

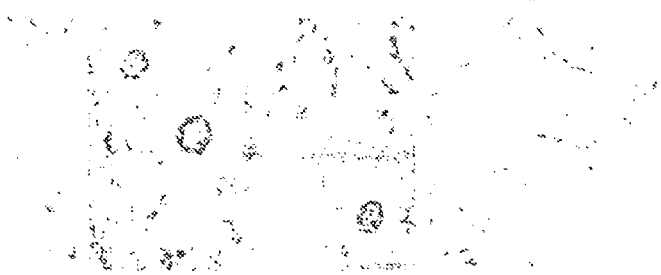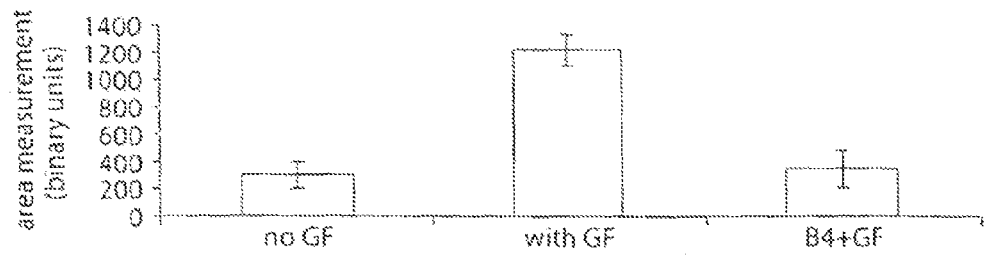
Fig. 21

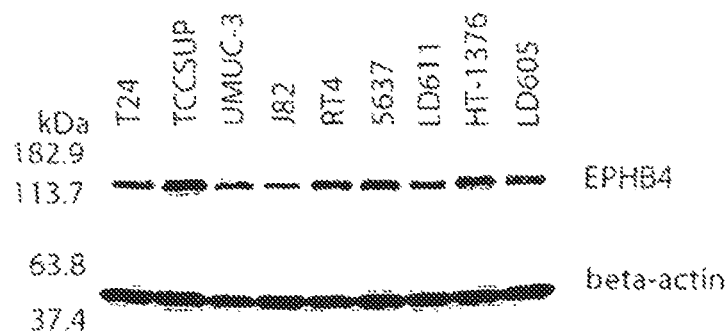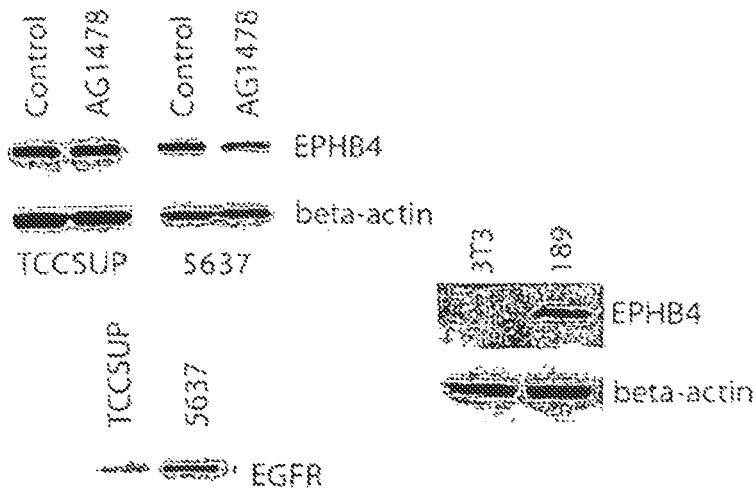
Fig. 51

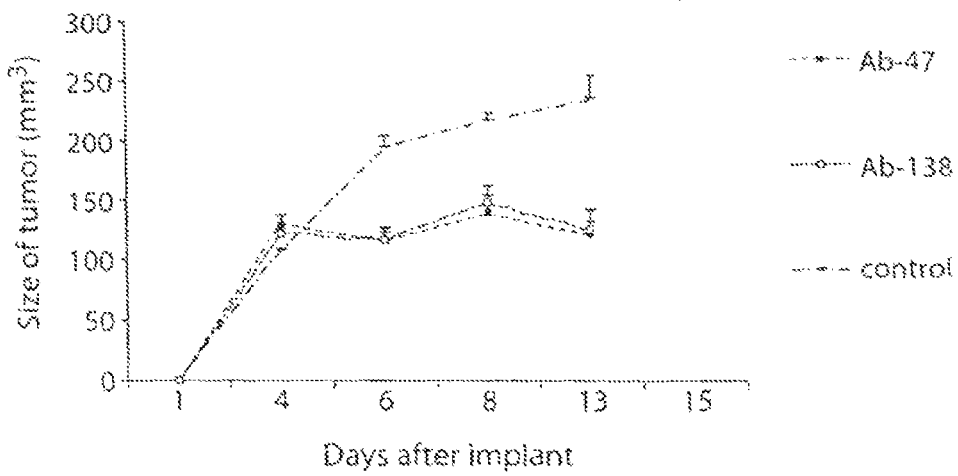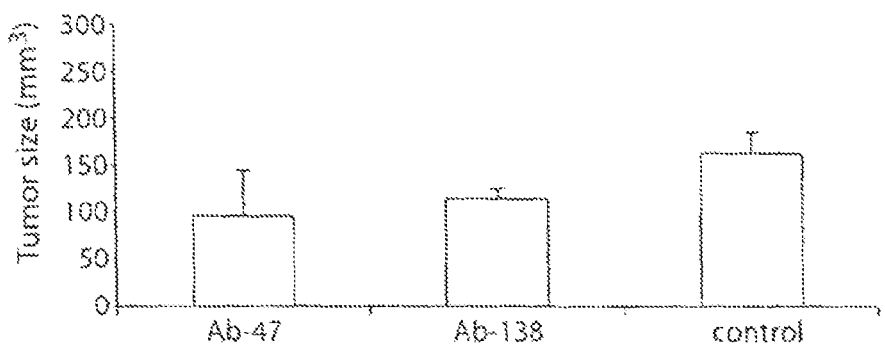
Fig. 60

EphB4 gene

```
   1 ggggtttcat catgttggcc aggctggtct tgaactcctg acctcaaatg atccgcctgc
  61 ctctgcctcc aaaatgctg ggactacagg cgtgagccac cgcgcccgcc acacccacct
 121 tttctttacc gttgtttcct cgatttttct ctactccta gcgcagctta gtgcgcgcct
 181 cctctgcaca ttttcaggg cttgttgcg cgcacagtag gtccccaaca ctgaatgttt
 241 atggggtgac tgtgtgaacg ttcgctgcaa ggctatccaa actgggattg ctccttgagg
 301 ccccctgggc ggccgtcaat tctccaaagc ttctactccc ttttccttcc tttcccccaa
 361 aaacgcagtc cctgcgccca ctagagggtg gtgggcgcat ccaagagcgg catctagagt
 421 ccgcagcaag gtcagagcgg gctttgtgtg cgcggtgaac atttacgtgc acgcctgggc
 481 ggccctccgt gttgctgctg gtgtgtgtt tctctgctc cctggtgcca gcgggttcag
 541 ggctgtccc ggggtccct gggccccagc ccgacatgc tcggtcctgg acagcgcgca
 601 ccgccacggc gcacatctgg gcggtcccgg ggttcctcac ccgccgccc tccccttct
 661 ccaaactttc tctcaacttc ccgacctgct ccactcggtg ccctatccg cttccctcat
 721 gaattattca gtagcgtgag ctccaatcag cgcgccgggg gctcactcgc ggagccccg
 781 cgttgggaga gctgccccg ccccccgcga gcccctccct ccgggcccg gcgccgccg
 841 gcccagttcc agcgcagctc agccctgcc cggccggcc cgcccggctc cgcgccgcag
 901 tctccctccc tcccgctccg tccccgctcg ggctccacc atccccgccc gcgaggagag
 961 cactcggccc ggggcgcga gcagagccac tccagggagg ggggagacc gcgagcggcc
1021 ggctcagccc ccgccaccc ggggcgggacc ccgaggcccc ggagggaccc caactccagc
1081 cacgtcttgc tgcgcgcccg cccggcgcgg ccactgccag cacgtccgg gaccgcgcc
1141 cgcgcgcgcg gcacagacgc ggggccacac tggcgccga gcccggtgc ccgcacgct
1201 cgcatgggcc cgcgctgagg gccccgacga ggagtcccgc gcggagtatc ggcgtccacc
1261 cgcccaggga gagtcagacc tgggggggcg agggccccc aaactcagtt cggatcctac
1321 ccgagtgagg cggcgccatg gagctccggg tgctgctctg ctgggttcg ttggccgcag
1381 ctttggaagg tgagttcct tgcggggggg ggcgcacccc gtcactcctg ggacctccc
1441 cccaacatct gggcctcgga gtggagggc cggctctga ctacccctac ccgggcactg
1501 cagtcccaaa cacttcggac cgatagtgct ggaacgggag ggggcggga agaggcgcc
1561 cgacgggtag tggagttttc ttttgtttgg gaaagagatg gagtctggct acgaccgggg
1621 acattccct gcccgggctc ccgaacttc cactgctgat tacatacgcc cctggctgcc
1681 tttcctttcc tcctacccc actattcaaa actatctgca aagtttctgt cccagtccca
1741 cctcccgacg tacatgaggg aaggtttctg gagaagcaac agcagacaag gcacaactttt
1801 tgtgctagg ccctaaaacg accccagcg ccaattcctt agcgatcaca ccttgatcct
1861 ccagttccac actcctgcaa caggatggcc tcctttgcat tcacacagca aaccccaaa
1921 ccgtctccc gccactgct cctgccctg tatagggtg gctccttggt ttctacagge
1981 tgcacccat cccttttaaat gcggtctaga cccggccc aggtgagtcc cgggcttccc
2041 ttgagaccta ggagcgggta gaaactgacc tacacagcc ccaggtagaa actgacctac
2101 acagccccca catcgccta actaaccag tctatctccc acctcctggt ctctccaagc
2161 atttctttgg ccatggatcg ctgtcctcc tggtccccta aagggggagc caagagccct
2221 agaaactctc ctgtgtccct aatgtccttt cagtgagctg ccaacacccc cctttctctg
2281 tctggtatga aagtggttat ggggcggtag gctatgaggg actccaaag ggaaggattc
2341 agcggcgtta gaaaaccct ctccccctgg ctgggcagga ctgccctggg ctggggatca
2401 aaggctaggt gtggggttgg gagtgagggg aggcttgccc agctcagaga acggagaagg
2461 gggaacaaaa accatgaacg aggggaagag gaaggccaaa gggtggaaa accacgagg
2521 acgaggtgtg gtgagaagga agacgcaaa gaggaaatgg tgattgtgac acctattacc
2581 tgagtgttc caagcaccag gcctgtgctg agcgccttac aaatattaat ttcacccatc
```

Fig.61A

```
2641 cagcaacgct aagggtggtg ctattattgc cccatttttt cagatgagga ggctggggct
2701 tagttaaggt taagtagttt atccaaggcc ctgtgccgcg aggaacagtg agaagtggag
2761 gccgaaagcg aaggagagat agtgactgtc agaaagagaa acggaggtgg acagagagtg
2821 gaggagagat aggtgagaga catgcgaact gacagatcaa agcgtggctg cagtgagct
2881 gggacgcaga aagggagcct gcgcttgctc tgggctgcgg acagccgag gcagagacag
2941 tgtgtaaatt ggagacagga aaacactatc ccggctggaa caatggaggg tggagacggc
3001 agcctctatc caccccttc ccagaacccg ggcatcctgt cccagtgag cagggctgtc
3061 tcttgccacc catggggacc ttgcgcctct cacctcaggc tggctggctt cccatctgac
3121 ccctagctgg aggacatcat ttggtcccca ggaagaggct gcctcaccca ccctatttct
3181 ctctctcct gcagctccca tggggtggga gccaggtgtt ctggctccca tctccaccct
3241 tccagcgcc caatgccccc cacattgccg gccccgagg ggattcctgt acccctcctc
3301 ctccactctc cactgccagg ggctgtgcag tttttcctaa tcccccct tcctccagtg
3361 cctgtccct cccgatga tccgagccaa gccaggtgtg ttcacccctc ccattcatac
3421 cgcccccag aatctcctcc cctctgcctt cccataacca aatccagatg tgaggcctcg
3481 gcgggagcct gggaaccta gcatcccgac ctccagtgct tcctgatcag ggcactcgtg
3541 gggagggagg tactgggatg ggggccaggg ctatgcccca ggcacggagc gctcccttca
3601 aggagggaag gacggggtgt ttggtctgaa agcagagagg ggtcttggac agggaatgaa
3661 attgtgggt agagaggctg attctgggac ttagggagg aaacgtggag gctgagacaa
3721 gaggttcccc tcccacacca gcagcctctg ctcgtggggg tcaggaccag ggcgcagctc
3781 tcattttaac cctttctgag ctgccgcccc ttctcccgt acattttgat ctccctccct
3841 cctccaggga ggcctagatc tggggtatcc aagggagcc ccatgcctac cagatgttgg
3901 gggtggggtt ggcacttcagc agaagaggcc agaaatcagg cgggtgcaga gggcagggct
3961 tgctccccctc ttggcccccc aactcctcta gctcagagct aagaggatcc acctgcctcg
4021 gttccaggg atctggtctc cctgacctcc ctcccccacc ccaggcactg actctgtctc
4081 tctgtctgtc tcagagacc tgctgaacac aaaattggaa actgctgatc tgaagtgggt
4141 gacattccct caggtggacg ggcaggtgag agctgcaccc aggagctgga gctctggagg
4201 gaaactgagg gaggagaggg cgcctgtgcc gctgctttc tgtgtgccac tcctctcccc
4261 tgtccccca gatgacagca gcccagcag tgtcgtctga gccttctca gaggcgcct
4321 cctcgcagta ccagcagccc cctttctca gtccctctca cttatagga ttcacccat
4381 gcagccctct ccctggcggc tcccagccc ccttgctgac ctccttctct gcacagtggg
4441 aggaactgag cggctggat gaggaacagc acagcgtgcg cacctacgaa gtgtgtgacg
4501 tgcagcgtgc cccgggccag gccactggc ttcgcacagg ttgggtccca cggcggggcg
4561 ccgtccacgt gtacgccacg ctgcgcttca ccatgctcga gtgcctgtcc ctgcctcggg
4621 ctgggcgctc ctgcaaggag accttcaccg tcttctacta tgagagcgat cgggacacgg
4681 ccaggccct cacgcagcc tggatggaga acctacat caaggtacct gggtgcccc
4741 agggctcagc cacagccaag gtgggattcc agccagcagg ccgtggcct ggagggcagc
4801 cgatgtagtt gcgaggcctc tggcccgcgc gctggggct ggaagcagga ggcttaggtc
4861 tggggaggga agggggtgat cttctgggcg gaggagcaga atatacgggg gctgctggc
4921 ccggccccca gggagcccca aggtcaggc ttctcctcca gtcacctcaa ccacctacc
4981 ccactgtgct ccagcacac tgagtttctc ccattcctg actgcacctg gctggtttcc
5041 agctcaagac ttgcagcgg tgatgtctcc acctggggc ctctctgcct ctcacacccc
5101 tacttgtctt cggagttcca gctcccgaga tcttgcctgt gccaccttgg ctgactctct
5161 cctccctaca atcctgcata ccctctgtcca cctgcctgtc tcggcactca ttttactta
5221 tttatttttc ttttatatct atatttttaa agcggggtct tctacgttac ccaggctggt
```

Fig.61B 5281 ctctaactcc tgggctcaag agatttctcc cacctcggcc tcctaaagtg ctgggattat
5341 aggcatgagg cactacgccc ggcctcatgg tactttataa cttccccagg attcattcat
5401 cgctgtctcc ttgactctga ggtcaaggcc tggcatggcg tcagtgtcag taaatgtttg
5461 tagaacgagt gaataaaaag ggggagaggt gcaggccaga ggccgggcat atcgcaggag
5521 ctttcaaagg ctgaatggac agtgtggggg cctgcagaaa gtgtgccctg ggaaggtgg
5581 agggaagatt ctggaacggg aaccaaggag gtcgggagg gtgagctggg aagaacacaa
5641 cagtccgctg gtcctcagg gagtggggac agcagcggtg tgcctcccc ccgccggcag
5701 gtggacacgg tggccgcgga gcatctcacc cggaagcgcc ctggggccga ggccacgggg
5761 aaggtgaatg tcaagacgct gcgtctggga ccgctaagca aggctggctt ctacctggcc
5821 ttccaggacc agggtgcctg catggccctg ctatcctgc acctcttcta caaaagtgc
5881 gccagctga ctgtgaacct gactcgattc cggagactg tgcctcggga gctggttgtg
5941 cccgtggccg gtagctgcgt ggtggatgcc gtcccgccc ctggcccag cccagcctc
6001 tactgccgtg aggatggcca gtgggccgaa aagccggtca cgggctgcag ctgtgctccg
6061 gggttcgagg cagctgaggg gaacaccaag tgcgaggtg agagctggag cttccctgc
6121 gactgctgct catccggggg agagtcctga actccactca ggaccaactt cttaagtttc
6181 catttgtat agttagatgt tgaaatggag gcttgctctg tcacccaggc tggagtgcag
6241 tggcacaatc tctgctcaac tgcaaccttt gctcccggg tcctgttca agcagttctc
6301 ctgcctcagc ctgtgagta gctgggacta caggcacacg ccaccacgcc cggctaattt
6361 ttgtatttta gtagagacgg ggtttcgcca tgttggccag gctggtctcg aactcctgac
6421 ctgaagtgat tgcccgcct cggcctccca aagtgctggg attacaggcg tgcgtcacca
6481 caccagctg gaaaaaaaaa agactttatt ttcacctgaa attcattaat ttccacttga
6541 aattccacct gcagttgtag caggacctga cacttgggcc ccatggaaat cacaggtatt
6601 gctgacaca gtggttcatg cccatagtgc cagcactttg agatgccaag gtgggaggat
6661 cacttgagcc caggagttcg agatcagcct gggtgacaga gcaagacccc gtctctaaaa
6721 aaaatttttt ttttttttc aagacagagt cttgctctgt cgcccaggct ggagtgcagt
6781 ggtgcgatct cggctcactg caagctccgc ctcccaagtt aacaccattc tcctgcctca
6841 gcctcccgag tagctgggac tacaggcccc gccaccacgc ccggctaatt tcttgtattt
6901 ttagtagaga tggagtttca ccgtgttagc caggatggtc tgatctcct gacctcatga
6961 tctgcccgcc ttggcctccc aaagtgctgg gattacaggt gtgagccacc acaccggat
7021 tacaaaaact tttagataa ttatctgggc gactgcctg accaacatgg agaaacctg
7081 tctctactaa aatacaaaa ttagccggac atggtgcgc atgcctgtaa tcccagctac
7141 tgggaggct gaggcaggag aatcatttga acccaggaag cagaggttgc ggtaagccga
7201 gatcatgcca ctgactccg gtctggagt gcactccaac aagaaggagt ttgctcttt
7261 ttgccaggc tggagtgcag tggtgggatc tcagctcacc gcaacctca ctccgggt
7321 tcaggcgatt ctcctgcctc agcctcccaa ggagtagctg ggattatagg tatgcatgt
7381 cacaccggc tactttgta ttttagtag aggcaggttt caccatgtt ggccaggctg
7441 gtcttgaact caagtgatct gccctctttg gcctccttct caggaaaaaa aaaaatcac
7501 aggtatttac aggccattcc aagtgccaaa agattgtttt tgctcatggt gacttcagta
7561 tcacagatgt taggagactt gctgctatat gttaagaaag aagcacaaat gttgctgtag
7621 cccaaactt tttcctcatg tttcattgca tttcagctta attggtttcc ctggtattcc
7681 tatgtatttt gtggagtgct tttaaatca taagttggag tagaggtctt tctgtgggct
7741 tcaccagact gccgagatca gggtcgaaac aggtgaggac ccttctctg gagagagtct
7801 cctttctcct ctaagaggaa aggttttgag atcttttgtc cattttccca cattagcact
7861 tcatcagcct taaaagaagc tggaattttt ttttttttt tggagatgg gatctcgata

Fig.61C

```
7921  tgttgccag gctggtcttg aacccctggg ctcaagcgat cctccagcct cagcctccca
7981  aagtgctggg attcgaggca tgagccaccg agccaccgt gcagatggat gttttttgtgc
8041  atgcttttga tgaatgcttt ctctctctca gcctgtgccc agggcacctt caagccctg
8101  tcaggagaag ggtcctgcca gccatgccca gcaatagcc actctaacac cattggatca
8161  gcgtctgcc agtgccgcgt cgggtacttc cgggcacgca cagaccccg gggtgcaccc
8221  tgcaccagta agtgacaagc accaggtgc agttcactgg ggaggggtca cagacctctg
8281  aggtggaccc tcacatggcc ccatcctcc ctgggcttct tccctttgtc cctggcatgc
8341  ttgtccctag cccggaggaa catgtggagc ccactgtctc caaggcaaga gtccagcatg
8401  gctgctggtg cctccattgc cctctcccca ccacgcaga gcaggtcggc ctctgcctga
8461  ctccctggtc tcctgcagcc cctccttcgg ctccgcggag cgtggtttcc cgcctgaacg
8521  gatcctcct gcacctggaa tggagtgccc ccctggagtc tggtggccga gaggacctca
8581  cctacgccct ccgctgccgg gagtgccgac ccggaggctc ctgtgcgccc tgcgggggag
8641  acctgactttt tgaccccggc cccgggacc tggtggagcc ctgggtggtg ttcgagggc
8701  tacgtcctga cttcacctat acctttgagg tcactgcatt gaacggggta tcctccttag
8761  ccacggggcc cgtcccattt gagcctgtca atgtcaccac tgaccgagag ggtgagactt
8821  ggggctggg gcggctggtg gtctggcggg agagatgtca ctgagggcct gaaggggaga
8881  ggcaggggct gtgaagttgg gtaccccgga agtgtgaggg gctaaggctt tggggcaag
8941  aggcagaaag agggcaatgg ctgggcgcag tggctcacgc ctgtaatccc agcactttca
9001  gaggctgaga caggcggatc acttgagccc tgagttcaa gaccagcctg ggtaacatag
9061  gaagatctct ctacaaaaaa taaaaatatt agccaggcga ggtggtgcat gcctgtggtc
9121  ccagctactc aagaggctga ggcaggagga ttgcttgagc ccaggagtcg gaggctgcag
9181  tgagctatga tcgcaccgct gcatgccagc ctgggtgaca gagcagtgtg agatcctctc
9241  tcaaaataaa tgaataagaa agagagggtg aggagctcgt aagctgggc tggagagtta
9301  agtacaggaa ggccccagt gggactgggg ccagagagaa tcagaaggaa ttctcgaaac
9361  agccagggg aaattgagac aagtgtagcc agcagaggaa gtgttggaaa agataaggga
9421  catggccagg ctgatcacaa ggtcaggagt tcaagactag cctggccaac gtggtgaaac
9481  cccatgtcta ctaaaaataa aaaattagc caggcatggt ggtgggcacc tgtaatccac
9541  ttgggaagca accagaagaa ttgcttgaac ccaggaggcg gaggttgcag taagctgaga
9601  ctgcgccact gcactccagc ctgggtgata gagcacgact ccgtctcgaa aaaaaaatt
9661  ttttttaagt taagggacag agctaccatg cacaagggtt ccctgtgtct ctgcctctca
9721  cagtacctcc tgcagtgtct gacatccggg tgacgcggtc ctcacccagc agcttgagcc
9781  tggcctgggc tgttccccgg gcacccagtg gggctgtgct ggactacgag gtcaaatacc
9841  atgagaaggt aaggccatcc ccagccctg ggtgggtgg gcaatgggtt gtgctctct
9901  ggctgggaca cctgggttgc aggcacctgg caggcattg aattccagct ctgccatgga
9961  ttccctgggc agccttgggt aagcccttg gcctgctga gctcagact cttcatctat
10021 aaaatagtta ctgtaatagt taccagcagc tggacacagt ggctgaggtt gggtgaggtg
10081 gctcacgcct gtaataccaa gcactttggg aggctgaggc gggcagaatg cttgagccta
10141 ggagtttgag accagcctgg gcaacatggt gaaacttcat ctctataaaa aacttaaaat
10201 gggccgggcg cggtagctta cgcctgtaat cccagcactt tgggaggccg aggtgggcgg
10261 atcacaaggt caggagtatc gagaccatcc tggctaacac ggtgaaaccc catctctact
10321 aaaatacaa aaaattagcc aggcgcggtg gcaggcgcct gtagtcccag ctactcggga
10381 ggctgaggca ggagaatggc gtgaaccagg aggcggagc ttgcagtgag ccgagatagc
10441 gccactgcag tccggcctgg gcgaaagaac aagactctgt ctcaaaaaaa aaaaaaaaa
10501 aaaaaaacg caaaaaatac ttaaaatgaa aaaattaga ctgggcacag tggctcatgc
```

Fig.61D

```
10561 ctgtaatccc ggcactttgg gaggccgagg tgggtagaac acctggggtg aagagttcga
10621 gaccagcctg gccaacaagg tgaaatcccc gtctctacta caaatagcaa aatcagctga
10681 gtgtgttggc gggcccctgt aatcccagct actcaggagg ctgagacagg agaatcactg
10741 gaaccaagt gattctcgac ttgaggtcga ggctgcagtg agtcgtgttt gcaccattgc
10801 attccagcct gagaaagtga gaccttgtct caaaaaaaag gaatgatatt atgaatacag
10861 cacatggctt gcatgcgtaa gttctcccaa aggcctcacc agttgcaagg caggctagtg
10921 atgggagtgg agggcgaggg aaggaggcag gaagagcaac aggaacttgg gtcccgggt
10981 gacggccacc ccactacctc tcccggacag ggcgccgagg gtccagcag cgtgcggttc
11041 ctgaagacgt cagaaaaccg ggcagagctg cggggctga agcggggagc cagctacctg
11101 gtgcaggtac gggcgcgctc tgaggccggc tacgggccct tcggccagga acatcacagc
11161 cagacccaac tggatggtga gcctgggaa gggggtgagg tggggggttg gaagacccc
11221 caaagttcct gggaagaccc caggtctcca aagtccatc atctttttt ttttttttt
11281 ttttgagat ggagtcttgc tctgtccctc aggctggagt gcagtggcac catctccgct
11341 cactgcaacc tccgcctccc ggattcaagc cattcctg cctcagcctc ccgagtagct
11401 gggattacag gcgcctgcca ccgcgctgg ccgattttt gtatttttag tagagacggg
11461 gcttcaccgc gttggccagg ctggtctcga actcctgacc ttgtgattcg cccgcctcgg
11521 cctcccgaag tgctgggatt acaggcatga gccactgcac ccggtcaaag tcctatcttc
11581 atgtccttct tcctgtggat cacatggcat gccctagaga ggagagaacg taagatgtcg
11641 aaaccaaaac caacagctga gttttgtgaa gtctggcctg cttcactctg taccccagg
11701 ctggagcgca gttgctcgat caaagctcac tgcacagcca ggcacagtgg ctcacctgt
11761 aaccccagca ctttgggagg ctgaagcagg aggatcactt gaggtcagga gttcgagacc
11821 agtctgacca gcatggtgaa accgcgtctc tactaaaaat atagaagtta gctgagcgtg
11881 gtggtgcaca cctgtaatcc cagctactcg ggaggctgag gcaggagaat cgcttgaacc
11941 tgggaggtgg aggttgcagt gagctgagat tgtgccagtg cactccagcc tggcaacag
12001 agcaagactc tgtctcaaaa aaaaaaagc tcacgcagg cttgacttt agcaacaacc
12061 tgacccctga gctcccatt ccccatccaa caaatggga atatcatgaa gcttcctgca
12121 gggctttgag gattggaggt aacaggttat ttttaatatg ctaggccagt ggcttctttt
12181 tttcttcac atttttttt ttgagacgga gtctcactct gttgcccagg ctggagtgcg
12241 gtggcgcgat ctcagctcac cgcaagctcc acctcctggt ctcgatctgc tgacctcctg
12301 atccacccgc ctcggcttcc cgaaatgctg ggactgctgg cgtgagccac cacgccggc
12361 ctaacttttt cttttttta agagacacgg tctttttat cacccaggct ggagtgcggt
12421 ggcaccatca tagctcattg cagcctacaa ctcccgagct caaccaatcc ttccaccttta
12481 gctccaag tagctgggca tatagcatg tgctaccgtg ctcaactaaa tttttttta
12541 tgttttgttg agacagtttc cctatgttgc ccaggctggt ctcaaattcc tgacctcgag
12601 caatcctccc gcatcggcct cccaaagtgc tgggattaca ggcatgagcc gccacaccca
12661 gcattggacc agtggctttc taaaccttgt aattttctgt aatagcttta ctgaaataca
12721 gttccctgc catacaattt gcctgttcaa agtgtacaat cgatgacttt tgatacattc
12781 acagaattgt gcagtcacca ccacaagtaa ttttgggaca tttcagcac cctcaaaaga
12841 gaccctatag ccttagcca tcacccccca ccagatctt tctgttgcct tagtccctgg
12901 caagcactaa cccacttct gtcttgaaat cttccagtgt ggtattttgt gactgttcac
12961 cgagcagaat gttttcaagg tttatgtatg ttgtagtata tatccgtggg ttttttggt
13021 tgtggcttgt ttttgtttg tttggaaac agggtatcgc tctgtcaccc aggctggagt
13081 gcagtggttc aattacagct cactgcagcc tcaacctccc aggctcaagt gatcctcca
13141 cctcagcctc ccaagcagct gggactgtag gcatgagcca ccatgcccag ctaattttt
```

Fig.61E

```
13201 ttggtatttt ttgtaaagac agggtttcac catgtttccc aggctggtct cgaactcctg
13261 agctcaggca atccaccoac ctcagcctcc caagtgctg tgattacagg catgagccac
13321 tggacctggc ctgttttttg ttttgtttt gaacacacga ttttgctttg tcacccaggc
13381 tggaatgtaa tggtctgatc atagtgcatt gcagcctcaa actcctgggc tcaagcgatc
13441 ctcctacctc agcctcctga gtatctggga ccacacgtgc tcaccaccat gcttggctaa
13501 ttattattat ttttgatag agacggggtc ttgctatgtt tccaggctg gtcttgaaca
13561 cctggcctca cacaatcctc ccacctcagt atctcagagt gtgggatta caggcatgag
13621 ccactgctcc tggccaatat ttcatttctt tttatggaga cgtaataatc agttgtatgg
13681 aaatagctga ttttgttttt tattgtatct tttggtgaac atttcaattg tatcgacttt
13741 ttggataaaa acctgaaaat gtttcacctt tagaacgttt cattgaatgg agatttttt
13801 gtggactctg gtatttatac tagaaccaaa tcaaaccac tctggcggct gggcatgcct
13861 aggctggttt gagactagcc tgtccaacct ggtgaaagcc catctctact aaaaatacac
13921 aaattagccg agcatggtgg tacacacctg taatcccagc tactcaggag gctgaggcag
13981 gagaatcgca gaacccggga ggcggagatt gcagtgagct gagattgcg cactgcactc
14041 cagcctgggc gacagagtga gactgcgtct caaaaaaaca aacaaaaat tactctggca
14101 gtaagaaaag atttcgaaac ttcctccctt gccctgaggt acttcagagg agcctgctgg
14161 cccctggggg agagtttgaa acccactgtt tgttccctga acttgcctgc ttgtgtcctc
14221 tccctccacc tgtccctgt actggggacc tgttctcagg agatcacagt tcattgctca
14281 aagccgggc tggggcctcc tacaggacca tcagttttctc ctgatcagca gcctttcctt
14341 ccgcagagag cgaggctgg cgggagcagc tggccctgat tgcgggcacg gcagtcgtgg
14401 gtgtggtcct ggtcctggtg gtcattgtgg tgcagttct ctgccatcagg taagggctct
14461 gacacccaga ggccctgga agccctcagt tgatggccac ctgcctgggt gctacaggac
14521 aagcctttct ggctgtcccc agcctctttt tacttgaaat cttctccaat cctgctcct
14581 tcctttggtg tgtgtgcctc ataaagatgt gtgactcagt ttaccttttg ttcctttccc
14641 atcggctaca ggaagcagag caatgggaga gaagcagaat attcggacaa acacggacag
14701 tatctcatcg gacatggtgg gttgccctaa tttgatggga atagggggctt ggggccgggt
14761 gtggtggctc ctatctataa tcccagcact ttgggaggca gaggtgggca gatcacttga
14821 ggtcaggagt tcgagaccag cctggccaac atgttgaaac tccatctcta taaaaatac
14881 atcagtcagc caggcatggt ggtgggcacc tgtaatccca gctactcagg aggctgaggc
14941 agaagaatca ttttaaccg ggaggcggag attgcagtga gccaagatcg cgccactgcg
15001 ctccaggcct gggtgacaga gcgagactcc atctcaggaa aaaaaaaaa aaaaaaaaa
15061 accacggaga cagggttttg gggctaaaag ctatgagccg agcctccgag tccagtggga
15121 gttaattccc agctgacggg gccctgcctg atttctcagg tactaaggtc tacatcgacc
15181 ccttcactta tgaagaccct aatgaggctg tgggaatt tgcaaaagag atcgatgtct
15241 cctacgtcaa gattgaagag gtgattggtg caggtgagag ccgaaggctg cccgggcacc
15301 tggaacgaa gcggggtgg gcaggccac actggagcgg gagagctgat gacctctgcg
15361 tccttgtttg aaggtgagtt tggcgaggtg tgccggggc ggctcaaggc ccagggaag
15421 aaggagagct gtgtggcaat caagaccctg aagggtggct acacggagcg gcagcgggt
15481 gagtttctga gcgaggctc catcatgggc cagttcgagc accccaatat catcgcctg
15541 gagggcgtgg tcaccaacag catgcccgtc atgattctca cagagttcat ggagaacgcc
15601 gcctggact ccttcctgcg ggtgagcacc ctcctgcct tctgcggcca ccggagttc
15661 ccacttacac ccagaggcca cttggttaa gaagccagga cagacagtgg gtccaggtc
15721 acctcctcca gcctttcct cttgggctaa gcctggtcc tctgcctttt ctttttta
15781 agacagagcc tcgtctgtc gcccaggctg gagtgcagtg gcgcgatctc ggctcattgc
```

Fig. 61F

```
15841 tgtctcaacc tccagggttc aagcgattct cctgcctcag tctcccaagt agctgggact
15901 ataggcatgc accaccatgc tgactaattt ttgtattttt agtagacaca gggtttcacc
15961 atgtaggcca ggctggtatc aaactcctga cctcaagtga tctccccacc tcagcctcc
16021 aaagtgctgg tattacaggt gtgaggcacc acgcctggcc agccctctgc ctttaatttt
16081 ccctctggga aaggctgggc tctgggacc ttcctttccc actgcccat acagctgaag
16141 gttgtcattc cttctttttt tttttaattt tgtttaatt gaattttttt ttttgagat
16201 ggagtttcac tcttgttgcc caggccggag tgcaatgca agatcttggc tcaccgcaac
16261 ctccgcctcc caggttcaag cgattctcct gcttagcct cccaagtagc tgggattata
16321 ggcatgtgcc accacgcttg actaatttg tattttagt agagacgggg gtttctctgt
16381 gttggtcagg ctggtctcga actcccgacc tcaggtgatc cgcctgcctc ggcctccaa
16441 agtgctggga ttacagacgt gagccaccgc gccggccaa ttttttttt tttttttaa
16501 gacagagtct cactctgtcc tctaggctgg agtgcagtgg tgcattcata gctcactgta
16561 gccttgacct cctgggctca agtgatcctc ccgcctcagc ctcctgagta gctggaacta
16621 cactcatgta ccaccatgct cagcaaattt ttaaaatttt ttgtagagac aggatctcga
16681 taggttgccc aggctggtct gaactcctgg cctcaagcga gctccctcc tcagcctcc
16741 acagcactgg gattgcaggc atgagccact gtgcctggcc tgtcattcct tctttgaca
16801 aatatttact gagtgctttc tacgcaccgg tcatcctccc agtcccagg ataaagcta
16861 tacacacggc aaactggatt tctcctcttg gggagcagag ggtctaatgg ggcaggggga
16921 ctgaaaatta gcaagtaaat agacaggctt tttaaaaaag taaacaaatc attcaaatg
16981 tgaaaaaaag caaacggggt ccttcatgca gatgtggcta gagaggaaag agaactgctt
17041 aatttatttg gtcactttac cagattttac tgactttttt ttttttta actttattaa
17101 gcttttcttt tttcttgaga tggagtttcc atctgtcacc caggctggag tgcagtggtg
17161 cgttcttggc tcaccgcaac gtccacctcc tgggttcaag tgattctcct gcctcagcct
17221 cctgagtagc tggaattgc atggcatgca ccaccatacc cagctgatgt ttgtatttt
17281 agtagagaca gggtttcatc atgttgccca ggctggtctt gaactcctgg gctcaagtga
17341 tccacccatc tcggccctc aaagtgctgg gattacaggc atgagccacc atgcctggcc
17401 taggcatctt ttaaaaaaa tcaaaacatt ttctatgta gcaaaataac attgcattga
17461 acagagttat agcgattccc tagcgtcatt gaatacccag ttgattttca cgtttctcta
17521 gttgtctaa agatgtcctt cactgctgct ttattccaac caggatccag ttcaagaccg
17581 ggctttgtac ctgttatta tatatatttt atttatttat tttagaaaca aggtcttgcc
17641 cttcgccca gtttagagtg cagtggtgca atcatagctc actgcagcct ccaaactcct
17701 tggctcaggt gatcctcctg cctcagccta ctggtagct ggaactacag gtgcacacca
17761 ccacacctgg ctaattttta aattttttac ggagatgggg gtctcgctat gttgcccagg
17821 ctggtctcaa actcctggac tcaagcgatc ctcctcctt aacctctcaa agtgctggga
17881 ttacaggcgt gagccaccac gcctgctgat tatatattt tcgagcctct ctaaatcttg
17941 agcagttcct catgatgaca ctgacacact gaagggttag gtcccttgtc cgctgaatg
18001 tcttgatttc tggatttatg aaattcttct tatgggatca tttagcttgt ctctctgtat
18061 ttcctgtaag agaagctcta tctgatgtgg ggttttttttg gtttgtttg ttgtttttt
18121 gagatggagt cctgctgtcg ccaggctgg agtgcagtgg cacaatctcg gctcactgca
18181 acctccgcct cctgggttca agagattctt ctgcctcagc ctcctgagta gctgggacta
18241 caggcgagtg ccaccatgcc cagctaattt ttgtatttt agtagagaca gggtttcacc
18301 atattggcca ggatggtctc gaacttctga cctgtgatc tgccaccac ctcagcctcc
18361 cacagtgctg ggattacagg catgagccac tatgcccggc taatttttgt attttagta
```

Fig. 61G

```
18421 gagacaggge ttegecatgt tggecaggct gatctgaaac ccctggecte aagccatcca
18481 ccctccttgg cctcccaaag tgctgggatt aaacgcgtga gccaccgtgc ctggtcgaag
18541 agacagaaag ggtcttaaag gttcagtgac acacacctgt aatcccagca ctttgggaag
18601 ctgaggctgg tggatcactc gaggccagga gttagagatc acctgggca acatggtgaa
18661 accccgtctc tacacaaaat acaaaaatgg gcagagcatg atggtgcata tctgtagtcc
18721 cagctactcg ggaggctgag gcgggaggat cacttaagcc tgggagatcg aggctgtagt
18781 gagccatcat tgcactactg cattccagcc tgggcgatcc catctcttaa aagagagag
18841 agatgggaag accagcacag gtgaaactgg tgaacagagg agatggta gatgctgcat
18901 tgggcagtgt gacgggaacc cgctggaggg ctttggcagg agagtagttt aagaggatcc
18961 cagctgggca cagtggctca cacttgtgat cccagcactt gggaggccg ggcaggtgg
19021 atcacttgag gtcaggagtt cgagaccagc ctggccaaca tggtgaaacc ctgtctgtac
19081 taaaaataca aaaccagcc aggcatggtg gtgcacccct gtaatcccag ctactcagga
19141 gactaagaca ggagaatcgc ttgaactcag gaggcagagg ttgcagtgag ccaagatcac
19201 gccacttac tccagcctgg gcagtagagc gagactccat ctcaaaaaaa taaataaata
19261 aaaagaccte tttgctgggt gctagggagc aagagcagga gctgggagag gcctgcagca
19321 gaagcctgtt gccagcatcc aggccgtggg gtgaagggaa gggtttggat tgggacatg
19381 tcttggaagc atcaccagca gaacttgctg atggattgga agtggctggt gagggagaa
19441 aggggtcaa aggaaactct gaggtctata ccctgaccat ctggcaagtg gtggtgttgc
19501 cacaaactga gcggggagta gggcaggtgc aggtctggag gatggattca aaattcagtt
19561 tttggagtct atgtccctgg ttctgtaggg ctgcagatgg tctgccaaat cttagcggaa
19621 cccagaatac gggatttgtt tactgtctgt gacttgttgg tttccctggt gagagcaaac
19681 tctttaaagg tcaaggttgg gcttcagacc ttggtttttg caccgatcat tggtcatact
19741 gcagttcctc actcttctct tgcaaatcca tacacagcta gtccaagaga gctgaacagc
19801 tttgtggttg gatcagcacc aatgtatctc cacctgtaga cgggttgctc aggtgactca
19861 tgcctgtaat cccagcacct tgggaggcca aggtgggaag attgcttgag gccaggagtt
19921 ggagacaagc ctgggaaaca cagtgagacc ccatatctac caaaaaaacc cctttgtttt
19981 aattagccag gtgcagtggt gtgcacctat agtcccagct actaaggagg ctgaggcaga
20041 aggatcattt gagcccagga gtttaaggct gcggtgaacc atgatcgtgc cactcactc
20101 caacctgggg gaaagaaaga gaccttgtct ctaaaaaaac taaaaacag aaaagcattt
20161 gttgagtatt tcctgggtat aaagcagtgt accaggttaa atggaaggaa agttgaaat
20221 aattttcaa ctcataatcc gattgggaga gactgaatgc ttaccattga gcaggaacc
20281 attgtaagca atgtgttgtg atactgtagc aagagctgag aaaacttggg aaaagagaaa
20341 ggaggaaggc tcacctgagg gagttggggg gcttgcccta caggtgagtt gtgaggtggg
20401 tctggaagtg acagatgcag tttaggaagt ggacgggagg ctgggtacgg tgactcaaca
20461 tctgtaatcc cagtgcttg ggagacccag gcggaaggat cgttcaggc caggagttaa
20521 agaccagcct gggcaacata gtgggaacct atctctacta aaaattaaaa aattatccag
20581 gcataatggc acatgcctat tgttccagct actcaggagg ctgcctgag cccaggaggt
20641 tgaggctgca gtgagctatg atggcaccac tgcactccag cctgggcgac agaacaagac
20701 cctgtctcta aaaaaaaag atgtggatgg gagggggaac ggtgggtggg ctgtcctcac
20761 caagccccca ccctatctgc tctccagcta acgacggac agttcacagt catccagctc
20821 gtgggcatgc tgcgggcat cgcctcggc atgggtacc ttccgagat gagctacgtc
20881 caccgagacc tggctgctcg caacatccta gtcaacagca acctcgtctg caaagtgtct
20941 gactttggcc tttcccgatt cctggaggag aactcttccg atcccactta cacgagctcc
21001 ctggtaatgc tgggggtaat actgggtgtg agcttcttag ggccaggtgg gcagggcagg
```

Fig. 61H

```
21061 ttggaaaggt gggaggctga gggtttggca gcctgctcc agggagagga tacaggagca
21121 ggctgtggt gggggacag tcagctccag gaagccgact tccagatgtc taggaaaata
21181 acagttggat aacctggca acatagcaag acccatctc tacaaaaaaa ttaaaagatt
21241 agccaggcgc agtggcatgc acctgtagtc ccagctactt ggaggttga ggcaggagga
21301 ttgttaagc ccaggagttg gaggctgcag tgagctatga atgtgccact gtactgcaga
21361 ctgggcgaca gagcaagacc ctgtctcaaa agaacagtgg ccaggtgtgg tggctcacgc
21421 ctgtaaatcc agcactttgg gaggctgagg caggaggatc gctgaggtc aggagttcga
21481 gaccagcctg gccaacatgg gaaaaccctg tctactaa aaatacaaaa ttagctgagg
21541 gtggtggtac acgcctgtaa tccagctac tcaggaggct gaggtaggag aaccagttga
21601 accgggagg cggagtttca gtgagccaag atcgcaccac tgcactccaa cctgggcaaa
21661 cagagttgga gagtaggagg cttgggcct gagctaggg gaaaaagcag aggcaggtgg
21721 gggactggg ggcagtgtgc tggtctggt gagtccctca gtgagtccc cagtcacct
21781 tttctccttt tctgcaggg aggaaagatt cccatcgat ggactgccc ggaggccatt
21841 gccttccgga agttcactc cgccagtgat gctggagtt acgggattgt gatgtgggag
21901 gtgatgtcat ttggggagag gccgtactgg gacatgagca atcaggacgt aagtgtcccg
21961 tggtcctacc aagcttcct cgagtgttct ctcacctggg atttggggt aagggtgggt
22021 tcccagagag tcatcactgc tggttcttg agaccatgga gatgacaaaa aggagaattg
22081 atctttgtat caaagagttg agatacaggg ccaggcctag tgctcaagc ctgtaatccc
22141 agcactttgg gaggccaagg tgggcagatc acctaaggtt aggagttcaa gaccagcctg
22201 gccaacatgg tgaaaccccg tctctaaaaa aatacaaaaa attagccag catgatggc
22261 gggtgcctgt aatcccagct actcaggagg ctgagacagg ataatcgctt gaacccagga
22321 acagaggttg cagtgagctg agatcacgcc attgctttcc agcctgggca actgagcgag
22381 actctgtctt aataaataaa taaaagagtt gggtacagca tatttgggtc gcagaaggat
22441 gcagagatgg agggcagggt tgagaggtaa catgtctgta tcatagccca agagctgctg
22501 gggccttcag ccacagagag cttcaactcc ggctaggagg attcctggat ctgttatttt
22561 ttggggggct gtggctccta tcctaccatc ttccaagtca ccatttctg ggcctgttag
22621 catctttgct tttctggac agcctcaccc agagcttctt ccctctttc caggtgatca
22681 atgccattga acaggactac cggtgcccca cgccccaga ctgtcccacc tcctccacc
22741 agctcatgct ggactgttgg cagaaagacc ggaatgcccg gcccgcttc acccaggtgg
22801 tcagcgcct ggacaagatg atccggaacc cgccagcct caaaatcgtg gccgggaga
22861 atggcgggtg aggactgcag agaatgggcc ctccttcccg ctctctgccc ccactccttg
22921 cccagaagtg tccgttcatt ggtgttgggt gggagggcct ctgtccgcct ctgcaaggct
22981 gggttccacc tcctccccg gacctgggcc tggtactcag cattcctccc catccttgcc
23041 cctaggcc tcacccctc tcctggacca gggcagcct cactactcag cttttggctc
23101 tgtgggcgag tgcttcggg ccatcaaaat gggaagatac gaagaaagtt tgcagcgc
23161 tggctttggc tccttcgagc tggtcagcca gatctgct gagtaagcag tgcaggagc
23221 tggagtgggg ctggagagc ggggcagctg gagtcaggcc cacgggtct ccaggggctt
23281 tgggtcag cttcgggtgc caatgctgtc ttcttgcact gcgtcatgc catgcctaga
23341 agggcccag aggagcagtc acagcccat ggagctgagg acccaaggac tatttggc
23401 cagcctgcc gcctcacctc ctcctgccat cacagccctg ggccatgcg cttccgcctc
23461 tcacttctag ctatctttgt gcatctatct gcattccagg ccggctctc acgtaacaa
23521 tgtgtcaact cgggttctct ttttccaacc ataaaggag aagattgggc taggttttgg
23581 agatcctctt cagcttttat gtgaaatggt tttatgattc cttgctccc aaaggctgcg
23641 tatcccact tggcctttgt ctgctactcc cccttctgc cttccgttc ctctcccaag
23701 atctcctctc accccaggtt gaataacaga aatagaagga ataaaatct gaaggccggg
23761 catggtggct catgcctgta atgccagcac tttgggaggc cgaggtgggc agatcacttg
```

Fig. 61I

```
23821 aggttaggag ttcgagacca ttgtggacaa cttggtgaaa ccttatgtct actaaaata
23881 caaaaattag ctgggcatgg tggtgcgtgc ctgtaatacc agctactgag gaggctgagg
23941 caggagaatc gcttgaaccc gggaggtgga ggttgcagtg agccgagatc gcaccactgc
24001 actccagcct ggatgacaga gtgaaattcc atctcaaaaa aaaaaaaaaa aaaaaaaag
24061 aaatgtaaag gccaggtggt ggctcacgcc tgtaatctca gcactttggg aggctcaggt
24121 ggaccgattg cttgagccca ggagtttgag agcagcctgg ccaaaatagc aaaacccat
24181 ctctacaaaa caaaaacaaa aaaattagct gggcatggtg gtgcgtgcct gtggtccag
24241 ctactcagga ggctagagcc agaggtctc aggccagtct gccctgcc cacggggct
24301 gggcacatcc ctccctaatt cttcccagcc tctctctgac ccaggggcc tcctctcct
24361 tttttccct tatctcagcc tccagccatc agcaacctcc tcttcctctc cacccagctc
24421 ttcctctccc acttcggcct tttctttctc acactccatt tccctctacg gcaatctgtg
24481 cagcctcttc cccagtctc atttgcgggg cttttctctc ttttcttcc ttccctggca
24541 cccaagccaa aggccctgcc tctggcatcc agccctaccc ccttctgcgg ttgcacagaa
24601 ggatggctgc ccagctctta aaaaactgc cgggaactg ttgacatctg ttctccctcc
24661 ccgctggct tttctgattg gcttacaatc ctgaggctag gaccgtctca ggagccaaga
24721 gaggagagcg gccacaggga acctagggtc tcaccaagct ctcctttcct tctgcaggga
24781 cctgctccga atcggagtca ctctggcggg acaccagaag aaaatcttgg ccagtgtcca
24841 gcacatgaag tccaggccca agccgggaac cccgggtggg acaggaggac cggcccagca
24901 gtactgacct gcaggaactc cccacccag ggacaccgcc tccccattt ccggggcaga
24961 gtggggactc acagaggccc ccagccctgt gcccgctgg attgcactt gagcccgtgg
25021 ggtgaggagt tggcaatttg gagagacagg atttgggggt tctgccataa taggagggga
25081 aaatcacccc ccagccacct cgggaactc cagaccaagg gtgaggcgc cttccctca
25141 ggactgggtg tgaccagagg aaaaggaagt gcccaacatc tccagcctc cccaggtgcc
25201 cccctcacct tgatgggtgc gttcccgcag accaagagag gtgtgactcc cttgcagct
25261 ccagagtggg ggggctgtcc caggggcaa gaagggtgt cagggccag tgacaaatc
25321 attggggttt gtagtcccaa cttgctgctg tcaccaccaa actcaatcat tttttttcct
25381 tgtaaatgcc cctccccag ctgtgccctt catattgaag gtttttgagt tttgttttg
25441 gtcttaattt ttctccccgt tccttttttg tttcttcgtc ttgtttttct accgtccttg
25501 tcataacttt gtgttggagg gaacctgttt cactatggcc tcctttgccc aagtcgaaac
25561 agggccccat catcatgtct gtttccagaa cagtgccttg gtcatcccac atccccggac
25621 cccgcctggg accccaagc tgtgtcctat gaagggtgt ggggtgaggt agtgaaagg
25681 gcggtagttg gtggtggaac ccagaaacgg acgccggtgc ttggaggggt tcttaaatta
25741 tatttaaaaa agtaactttt tgtataaata aaagaaaatg ggacgtgtcc cagctccagg
25801 ggtgatgggg gtgatggact agatttctaa ggagagtggg gctgggtagg gagggctttg
25861 tggctgaccg agaggtgtca gaggtctgga ggctgcaggg ctgtagggc tggaacttgg
25921 ttatcagccc caggtatgtt ttgaggtggt ggggtggggg ccgagcgaga tgaatcattc
25981 gcagctgctt ctaacgtctc
```

Fig. 61J

EphB4, mRNA

```
   1 ctcggccgg cggcgcgagc agagccactc cagggagggg gggagaccgc gagcggccgg
  61 ctcagccccc gccaccgggg gcgggacccc gaggccccgg agggacccca actccagcca
 121 cgtcttgctg cgcgccgcc cggcgcggcc actgccagca cgctccgggc ccgccgccg
 181 cgcgcgcggc acagacgcgg ggccacactt ggcgcgccg ccggtgccc cgcacgctcg
 241 catgggcccg cgctgagggc ccgacgagg agtcccgcgc ggagtatcgg cgtccaccg
 301 cccagggaga gtcagacctg gggggcgag ggccccccaa actcagttcg gatcctaccc
 361 gagtgaggcg gcgccatgga gctccgggtg ctgctctgct ggcttgtt ggccgcagct
 421 ttggaagaga ccctgctgaa cacaaaattg gaaactgctg atctgaagtg ggtgacattc
 481 cctcaggtgg acggcagtg ggaggaactg agcggcctgg atgaggaaca gcacagcgtg
 541 cgcacctacg aagtgtgtga cgtgcagcgt gccccgggcc aggccactg gcttcgcaca
 601 ggttgggtcc cacggcgggg cgccgtccac gtgtacgcca cgctgcgctt caccatgctc
 661 gagtgcctgt cctgcctcg ggctgggcg tctgcaagg agaccttcac cgtcttctac
 721 tatgagagcg atgcggacac ggccacggcc ctcacgcag ctggatgga gaaccctac
 781 atcaaggtgg acacggtggc cgcggagcat ctcacccga agcgccctgg ggccgaggcc
 841 acgggaagg tgaatgtcaa gacgctgcgt ctgggaccgc tcagcaaggc tggcttctac
 901 ctggccttcc aggaccaggg tgcctgcatg gcctgctat ccctgcacct cttctacaaa
 961 aagtgcgcc agctgactgt gaacctgact cgattcccgg agactgtgcc tcgggagctg
1021 gttgtgccg tggcggtag ctgcgtggtg gatgcgtcc cgccctgg cccagcccc
1081 agcctctact gccgtgagga tgccagtgg gccgaacagc cggtcacggg ctgcagctgt
1141 gctccggggt tcgaggcagc tgaggggaac accaagtgcc gagcctgtgc ccaggcacc
1201 ttcaagcccc tgtcaggaga agggtcctgc cagccatgcc cagccaatag ccactataac
1261 accattggat cagccgtctg ccagtgccgc gtgggtact tcgggcacg cacagacccc
1321 cggggtgcac cctgcaccac ccctcttcg gctccgcgga gcgtggtttc ccgcctgaac
1381 ggctcctccc tgcacctgga atggagtgcc ccctgagt ctggtggccg agaggacctc
1441 acctacgccc tccgctgccg ggagtgccga ccggaggct cctgcgcc ctgcgggga
1501 gacctgactt tgaccccgg ccccgggac ctggtgagc ctgggtggt ggttcgaggg
1561 ctacgtcctg acttcaccta taccttgag gtcactgcat tgaacgggt atcctctta
1621 gcacgggc ccgtcccatt tgagcctgtc aatgtcacca ctgaccgaga ggtacctcct
1681 gcagtgtctg acatccgggt gacgcggtcc tcaccagca gcttgagcct ggctggggct
1741 gttccccggg caccagtgg ggctgtgctg gactacgagg tcaaatacca tgagaaggc
1801 gccgagggtc ccagcagcgt gcggttcctg aagacgtcag aaaaccgggc agagctgcgg
1861 gggctgaagc ggggagccag ctactgggtg caggtacggg cgcgtctga ggcggctac
1921 ggcccttcg gccaggaaca tcacagcag accaactgg atgagagcga gggctggcgg
1981 gagcagctgg ccctgattgc gggcacggca gtcgtgggtg tggtcctggt cctggtggtc
2041 attgtggtcg cagttctctg cctcaggaag cagagcaatg ggagagaagc agaatattcg
2101 gacaaacacg gacagtatct catcggacat ggtactaagg tctacatcga ccccttcact
2161 tatgaagacc ctaatgaggc tgtgagggaa tttgcaaaag atcgatgt cctacgtc
2221 aagattgaag aggtgattgg tgcaggtgag tttggcgagg tgtgcggg gcggctcaag
2281 gccccaggga gaaggagag ctgtgtggca atcaagaccc tgaaggtgg ctacacggag
2341 cggcagcgc gtgagttct gagcgaggcc tccatcatgg gcagttcga gcacccaaat
2401 atcatccgcc tggagggcgt ggtcaccaac agcatgccg tcatgattct cacagagttc
2461 atggagaacg gcgccctgga catcttcctg aggctaaacg acggacagtt cacagtcatc
2521 cagctcgtgg gcatgctgcg gggcatcgcc tcgggcatgc ggtaccttgc cgagatgagc
2581 tacgtccacc gagacctggc tgctcgcaac atcctagtca acagcaacct cgtctgcaaa
```

Fig.62A

```
2641 gtgtctgact tggccttcc ccgattcctg gaggagaact cttccgatcc cacctacacg
2701 agctcctgg gaggaaagat tcccatccga tggactgccc cggaggccat tgccttccgg
2761 aagttcactt ccgccagtga tgcctggagt tacgggattg tgatgtggga ggtgatgtca
2821 tttggggaga ggccgtactg ggacatgagc aatcaggacg tgatcaatgc cattgaacag
2881 gactaccggc tgccccgcc ccagactgt cccacctcc tccaccagct catgctggac
2941 tgttggcaga aagaccggaa tgcccggccc cgcttcccca aggtggtcag cgccctggac
3001 aagatgatcc ggaacccgc cagcctcaaa atcgtggccc gggagaatgg cgggcctca
3061 caccctctcc tggaccagcg gcagcctcac tactcagctt ttggctctgt gggcgagtgg
3121 cttcgggcca tcaaatggg aagatacgaa gaaagtttcg cagccgctgg ctttggctcc
3181 ttcgagctgg tcagccagat ctctgctgag gacctgctcc gaatcggagt cactctggcg
3241 ggacaccaga agaaaatctt ggccagtgtc cagcacatga agtccaggc caagccggga
3301 accccgggtg ggacaggagg acggcccg cagtactgac ctgcaggaac tcccaccc
3361 agggacacg cctccccatt ttccgggca gagtgggac tcacagagc cccagccct
3421 gtgccccgct ggattgcact ttgagcccgt ggggtgagga gttggcaatt tggagagaca
3481 ggatttgggg gttctgccat aataggaggg gaaatcacc cccagccac ctcgggaac
3541 tccagaccaa gggtgagggc gcctttccct caggactggg tgtgaccaga ggaaaggaa
3601 gtgcccaaca tctcccagcc tccccaggtg ccccctcac cttgatgggt ggttcccgc
3661 agaccaaaga gagtgtgact cccttgccag ctccagagtg gggggctgt ccaggggc
3721 aagaagggt gtcagggccc agtgacaaaa tcattggggt ttgtagtccc aacttgctgc
3781 tgtcaccacc aaactcaatc atttttttcc cttgtaaatg ccctcccca agctgctgcc
3841 ttcatattga aggttttga gttttgtttt tggtcttaat ttttctccc gttcccttt
3901 tgtttcttcg ttttgttttt ctaccgtcct tgtcataact ttgtgttgga gggaacctgt
3961 ttcactatgg cctcctttgc ccaagttgaa acaggggccc atcatcatgt ctgtttccag
4021 aacagtgcct tggtaatccc acatcccgg acccgcctg ggaccccaa gctgtgtcct
4081 atgaaggggt gtgggtgag gtagtgaaaa gggcggtagt tggtggtgga acccagaaac
4141 ggacgcggt gcttggaggg gttcttaaat tatatttaaa aaagtaactt tttgtataaa
4201 taaaagaaaa tgggacgtgt cccagctcca ggggt
```

Fig. 62B

EphrinB2 Gene

```
   1 gcgcctggga gctgcctgcg ggcgcacgcc gtcttccccg ccagtctgcc ccggaggatt
  61 gggggtccca gcctgcgtcc cgtcagtccc ttcttggccc ggagtgcgcg gagctgggag
 121 tggcttcgcc atggctgtga aagggactc cgtgtggaag tactgctggg gtgttttgat
 181 ggttttatgc agaactgcga tttccaaatc gatagtttta gagcctatct attggaattc
 241 ctcgaactcc aagtaagtgg cgtccgcgat cccctatgt cccgccccg ggtccgccg
 301 cgccgtccgg gcgggaggag gggtcagtcc gcggggcctc ggagcctgtt tctggaacct
 361 cggttccccg tccccacc caaccccg cccatttca ctaggtggag actcctcgct
 421 cggctttcca acccgagccc cgctgaacg gacggtctct ccgcctttcc tccccgaac
 481 gctcccaggc gctaaaagct actatcggct cgggtgtcaa gtccgggaag gtgtccgatg
 541 gcgataccctg accctctcct gttttcgagg acgaaggaca tggccacaat ctaggctggc
 601 cggcacgcgg ggactggtgg gctctggaga gaggcggaga tgctgcattc gcggggagcg
 661 cgggcggcgt ggtccgggggc ccgcgggcgg gcgaccgggg tggcaggacg ctggcagcga
 721 agcgcgttct ggagagggga gcctggagtc gctacgctgc ccgcagagcc ctggagccgg
 781 ggcgccttgg caccgcgccg ccagcccgag ggtgcgcggg gagctcgcct gcttcgcagg
 841 agaactcggg cgtcgagccc tttcctccgc gccggggaga cgggccttag gcttctccct
 901 gagggccgc cgcacctcgg cctccgctt cgttcataag ccgtagccc cggagtatgc
 961 ggtctcgatg gccgacctga ttgtaatgca cttctataa aagcttaggg ccctgcccag
1021 tcgacactgc tcctgaagcc ttctccctcg ggaccctggt aggaatggga tccttaggat
1081 cagatttgct cttaccggac tctacagccg ggagcgagcc aggccttgtg gagagtaact
1141 ttcagtttgg gccaccagag tgcattcaga atttagaaaa tccatccat ccctaaatct
1201 gtgtggtcat aactcgtagt catctgggta ttcagtactg tgtatccct tatttcgaat
1261 cacagccaaa acatatttta cagaatcttg gaattgtagt ctcgggaaac ttggagaaga
1321 agtatgcaga cattagctgg tttctggaga aaacgtttga gatcagaagc aaaatcaatg
1381 gcctaattga agttgagcaa gttgggcctg gttttaggag aaaagaaatg ggggattgat
1441 ttagaaatca cgtcttaaag gagtgtgtcc attctcttaa aagtgtcaaa tttcaaattc
1501 actaacatgt taaccaagaa tcccttcatg aaaagggcga aaacgtcggt tacaaatcgg
1561 tttaaacaaa tgtttgtatg atgctagaag gcactttcaa caccgctcat acggagaagt
1621 tacttagctc tgcctccttc catgtagtct gctcttgcat ggattatatt tttaatgtaa
1681 attgttgtat ttgctgatga agtactggcg gcggcatctt tgcatcgatg ccggctcggg
1741 aggcgccagg tggtgccgga aggagccggg ctaggacctc gcgcagcagc gggtcccgga
1801 gtccgggaga ggcggcgggg cggcgaggc ggtcgcgggg agcccgcggc gccgctgccc
1861 gccggtgcc tccagaggtc actcttccat gcggaatcgc gcagcgccag gcctcgcccc
1921 tccccaggc cgctgctcc agccactctg cactttcact gaccggttct ctttgaggct
1981 gttttttttt ttcttatgag gatttaatat ttctgtttaa atctagttga aagcaattcc
2041 gttagcctct tcagcgttta gttcggtgtg tgtatcttta tctttgcgct atattaacta
2101 ttagtttgtg tgtatccggt aggagaatta gaaatacccta gttggagaa aagaaaagt
2161 agaacaatag ttatttcaac ctaaggttta gacgttaata acttcttttt gtaatgtgtc
2221 gagatggggg gtcctggggg gaggtgacag gtactcacca ctccccccc ccattctgat
2281 gatgaagatg agtctgtctt tccagctatg tccagacctg cgagggccct gcgtttctgg
2341 aagcctgccg tttgcgcggt tgaggttgct gctgctgtct tgtcctccac agcagcattt
2401 cttttaaaat tctcctgata acggcctgcc tggatgactg gataatgtgt gcctggaaaa
2461 ggtctccctt gcagctgaat gctagctcca gagatcagaa agatttcttc ctgtaggagc
2521 catagaaaag agtcctctct aagttttgga gaatgcatac aaccccctga tgacagggg
2581 tgctttcct tgggaagtt ttatatttat ttccagagga aagtttgaat cggtaaatat
```

Fig. 63A

```
2641 gatgtggcag gaaggtaatc aaatgcattg aagtttcaca tcagttccta tgaactgtgg
2701 aacaattcat ttgtaatgaa gccgccatca gtaattagat ttgtttcatt cagaggtcag
2761 cttttttagc aggtggtcga cacagggagc atgcagcagc tgtttggata caggtccag
2821 aaaaccctt gtaaattcag cgtctccgta actactttaa tcacattgtc ggctctccg
2881 tccctgactg tatgtaataa tggaaagatg tcctgcgtgc tgaaacagta gctgcctgt
2941 taggttattc acattgcttt gatacgttct ggtagagttg ggtccgttgt agccatttg
3001 gttgtttaaa gttttggttt ttttttttgtt ttttttttaa ttcagcagag aacagtaatg
3061 cctagcttcc gttttttaact taacacttca gtagaacatt ttcttccaag agggagattt
3121 tggcctaagt aaagtagtgg gctcttttt aaaaaaaaat taatttttact ttaatgtgag
3181 caaatctgta ttggtatggt gttctgcaat gcattacact gactttgaaa atttcgagta
3241 ctaatgcctt atgtctgggg ttaccattcc ctgtgcatca catactagtt agtaacata
3301 gcattttgct tttccatgt aattttttcc ctatataata ctggattcct gatactaatt
3361 gacttgatac aaaagaatgg ctggatgata tccagataac gtataataca tgggcttcac
3421 cacaatcagg ctctgaataa atacagacct gtcagagatt gataaaataa actacaatgg
3481 atagtgctgt ttaaacagtc cattcaataa catatataag ccagcctgcc ttccattgtg
3541 tctgaaattc ttattttgt aggtaaacaa atgcacattc agcactgatt gaatagccc
3601 ttgaactatg ctccacagtt tgcgtttggg ttaatcttgt cggttttaat atagagagaa
3661 aaaagctcaa agcaccaggg gtggaattgt tagtgctttc acatccacat tcctcacatt
3721 ttgtcaggat gataaactgt aggtaatgga ctgtcgttgt tctgcaggac aactgagcca
3781 ggcagagcac aaagactaag ctaaagcgat acctcacaac atgcttggta gccttctttt
3841 cagatgagaa tttatttgag aatcatgtgt ctagggactg cacatcttaa cctcaacagt
3901 tacagcttca agcccagaa acaggagctg gaggttaaga tgatttgcta agcacctggt
3961 tctaaatctt ttacaaagca taagctgttg acgctggttc tgccgacgca aagacatgca
4021 gatgactcca acatttccag aggcttctga cttaagctaa agtgtgtgga caggtgaatt
4081 cgccatgggc ctggagacca gattgctaaa aactatgtgt ttgaatggtt cctccagaca
4141 gagtcagctg aagaacaatt ggtggattta tattaaaacc tcttgtctgt aaacttactg
4201 aggtgcatcc ttcggttggt ggatcagtga gataattgcc ttcagatgga cattgcaact
4261 ggagcaacta aatccttgct gtcttttcctt ctctgaaat cttccaggta gctccgaga
4321 gcttcagtat gacaccaaac ttcgggcgac gttttagagt gcgttcacct aatgggaaac
4381 tattcgagat cccagcgtga ctgcagtaat ggtcataggg aatgggagtg gcagggaaa
4441 aggaaataca gattgtagac cctaataaaa aaattttag gaaagatatt tcttaaacgt
4501 tttatgagaa cttcattctt aaaatactta attgcaaatt agacaaatag aagtgctctt
4561 ctaaggaagg tgattaaact ggtcctccta tcagcctaat ctctgctgc ctttgctgct
4621 gacataaaga acctgttttt caggtcactt aatatacatc tacatagatt tgcttatgag
4681 ctcaccctt gtgtagcgga gtagagcctt aaagaggagt gctcaactgt ttaaaatatt
4741 ttgattaaaa tatgcagaac ccatagaact ataagcttct agtcaggaat tagctcttc
4801 agggaacagc tccccctc tttttaaggg gggaattaga aggaggctgg gggaggaata
4861 taagaacagc aaagaaggaa ggatagcaaa tgggacatgt tccgaacagc ttggaaaaac
4921 tcctgtggct tcattgtctc tataaagcca aagaatacaa agacataagc aattcagccc
4981 ttctcccatg atggaagatg taaaccgttg acatgcctcc cctgtttaac ttgtttaatt
5041 ctcattttaa attcagcacg atactagcg tgtgaactct gaagatttct ttagtaatcc
5101 attttgtagt tccgaatcaa aaacaaagtg aaagggtctg acacaatttg ctttatttt
5161 taggcaaatc aaccctggtc atagttaata agggattac aactcagact aggtctttac
5221 agatgtgatg taaatcaagg gcagagtata aagaaactga tccctttga ttgaagtata
```

Fig. 63B

```
5281 gtaaaaggc atagagaaac tagcagcagt aatctgattg tatggcaata aaaccaccat
5341 tttctgtctt tcagataaaa ataatgtggt aaatccatgc agttcataag atgtaaaggc
5401 agataaaggg tgaagccatg gcaacatata gattagcttg atgttagaaa tgacacgtct
5461 ctgaaaaggg cgcgggacga aggccttgc ctccaggctg ttgggcatta tgtgagaacc
5521 acacagactt ggaaactggg attaggaagt atgaaagctc tacttgtggt ctgggatggc
5581 tgaggcagta aagaaaagct gctcagtct tgctcattgg tggtggataa tatggcaaag
5641 gtagatttca ttgactgcct tttttataga ttgagattgg ggctgattaa aacttcagat
5701 cactgcagtt gttagggcct gggagatttt cctttttaac tcctggccta acagcagcag
5761 ccgttctgta ggattaactg cacttcgcgg tcgttgcctt aatctatttg ggcttcaggc
5821 agggacatgc tgggaaggaa cagagaccag aggggatagg tagggctggg gttatctgaa
5881 aagaaaacag agacctttg atttcagcca tctttcaga cccagctcc tctcccgctg
5941 catgggagaa gcaaaggtaa acaggacaca ttgtccctct ccctcagcca cagagctctt
6001 ctgtgagttt tgtctttccc accctggaaa aaagataaa atacaatttt taaaggggga
6061 gggaggaatt tagttttaat tcaaatgagt agtaatccaa tatgccaaaa gcagtgggct
6121 ctacctagat gtaattttac tcgtaaatgt gagtcttaaa ctttgagttg aatggggcag
6181 gctgttagag gtggtgtaaa ttacaggatt ataaaaatgt tagtgctgcc cagccttaaa
6241 gtcaaaaaca gaaaaatctc tgtgctgttg agtcttcccg ccctctctcc tgaacaacct
6301 tgtaagtaag ctagacttt gttttgcct tcatactttt ccattcagc cattaaacaa
6361 aataagccat tgaaaccacg attgggtcc atgcagagtg acatccgcaa tcgggtcaag
6421 ccagaaggaa atacttgctc gattgccccc tatttggcat tacaggaaag tctccacact
6481 ttggaagagt ctgaactctc aagacattga aaatgccaaa ggctgcaaac acctgtgtc
6541 ttcttgatg gagtgcatct tggtgtgttt tacaaagggg aattcagtgc tgttttttg
6601 ttgttgtgc tgtttttttt tttaaagag cagcataggg ccttctaga ctcttggatt
6661 ctgtgtctga caaaaatggt cattaaatga gcaatattat aatttagacc catttcactg
6721 attttgttcc aaattctcaa ctgacttgag catctgtttg gggctgtaga tacattgcc
6781 ttgttgactg ttttctcgt ttctatggga attactgtag ccattactat gtagctttca
6841 tagactcaaa acatttttaa agtattgcat ataggctggc catatccagt gctgttact
6901 ttaccttctt tttctaactt aatgcagcag tctgtattaa cagatccatt tcatttgtct
6961 agcttcatca gagagaggct accccctgat ttacaggctg ctcacatcca agcaccttgc
7021 attctacact tgacagtgat tgctaatggc ccattcaact aaagtatttg cttgttaaca
7081 gggaacagaa catgataaat gtccagcaag cttgctgcct ccttcagctt ttcaaacgca
7141 gactggtgca tatttatggc aggcaaatga caaagaaaa agctgaattg ccctggcctc
7201 cagcttcta tcagaaacag ggttaaagtg attaaagcaa tcattcaaga aagccctgcc
7261 gtttgtttac taaccttcat ccaacattta gctttgtagt ctacctgtga gaagatattt
7321 cagaagtatt agagataagg aaggaggatc tagcaaacca gtgaaaagag taggtgacca
7381 gttataaaat gctttccatg cacattgaat gcaggcgaa cctatttctg ttattccagc
7441 agacaatcag cagtggctct agattattaa catatttcc ttcatgtat aaattcaaat
7501 atgtaattct agtccaaagc attctgtggc tggtaagcac atacttgctg atttcaaata
7561 agaaaacata gcaaggaaa gctccattaa acaagttgtt ctgccctta gtaattctct
7621 aaacaagata ggaagaaaaa gtggacagta gtggagtatt aatagtgtgc tcttttcatt
7681 ctctaaagca cgagtaagta agcgttcaaa ctactctgtg gtgggcatac atttagagcg
7741 ctgtgaatga accactgctg ttctgccata cttaatttat ttatattat attttattt
7801 tattgttgtt tttatgtatt attataatta tttatttata ttactaattt attttctcaa
7861 tttaaatcct gttgcatcca attttaatta cagttttgt atctgccttc ccatacttgc
```

Fig. 63C

```
7921  tacccacgtc ccattgcca ctgcggcctt atccatgttt tctgtgtaca ccactctgt
7981  atcacccag aataattatg agtgctacc agactttga aaccactaga gtcaacatgt
8041  ttgtctttga ggaaagccaa tgatgcttta gcattttgg caggggtgga tgtgtgttta
8101  agtggggtgg gtgcagctcc ttattgtctg cctattctac tgttgttccc aatccacatt
8161  cctgcgggg cacctaacct gtgtgcatag caaagaattt ccgaccttca gagccagaag
8221  tgtttctcaa ttgatctctt ccagcctagg gttatagctg atgaattata atccttgctc
8281  tttccacacc tttacctggg cttaccatgg ccctaaaaca tttgcccaga atcagaattg
8341  tctcatgagt gagtggggca aggcaaatcc tgttccagac cagctgagaa tgtacctagc
8401  tgcagaagaa gttagaaagt gtcatctttt actatctac cagaactata ttgaggtac
8461  attttagatt taaaaaaaaa gcaagttctc gtaggccttg aatcccccc ttgctatggg
8521  aaaatggatc attattataa tggactgtcc agtaaagttc atgatttctc ctagacatgt
8581  tctctctctt tatgacctag atcaagagtg atctctttaa gtcttttctt cataatccca
8641  cagcactttg tacttagatg tacttagaaa gaaccatata cacggtacgt catgattgat
8701  atgcaagcct tcaccactct acctgtccta aaagtcaggg acacaccttc ttcatttcat
8761  cagtccctac ttctatccag cattggcatc cagtaagtat tagtggaatg gacagacaac
8821  ccgaatttgt gctgatgcca gtttaccctg ttttaactgt catcttctg ctactagaca
8881  tggatgagac ctgagacgat gggactgctc agaggtccct ggctcttgaa ctttagggca
8941  ccagaatccc ctgcagggct tgagaaaaca ggggtttctg ggcccaccc ccagagttcc
9001  tgattcctga ggtctgggt ggggcttgaa gatggacatg tttaacaagc tccaggtga
9061  cgctggcaac tgctgcctca gggccatgct gagaaccctc gcctacaca aacctttctg
9121  ggaaaacaac tcaacattaa agctgtttgg ggatctctga agaaatctgt agtccttgcc
9181  ttgttggggg agcatcaggg atctaaccat tgatggtgga gtatttgttg ttaattcagc
9241  aagcaactat taagtgttag gcctgttact cggctctaac aatacaaggc agagtgacct
9301  gtaccctcga gatttaaagt ctaagtcctg tagagagaag cccaggtggg agcaagcaca
9361  tttagagtta ggtgcttggt gcaaggtggg gacacagaag aagggaatgg catttgcctc
9421  tggaggggtc cggaaacagc ctagggagga ggagcttgag tcttgaaata ctgtgggcat
9481  ctctaagcaa agtcacagta gacagctgaa ataagaaaa tagtaagcaa gccaaagaaa
9541  cagtatttca gccaaggca gcgtgtgtct atcacgtcca cctgtgaaca cgtcccagga
9601  ttctctgcat ccggccattg ctaagacag atccctcaca ggaacagcta agcactgat
9661  ttcagctacc tgttcacgtg agaattatca gtacctactg cttttcaaaa tgagtatgat
9721  catggatagg tgaggcaatt cagtttgca gagacagtag ggcaagtgcc actgtagttt
9781  agttaagggc acatgcttta gagtttggct atgtgagtcc aatcccagtt tagccattta
9841  ttagctgggt agctttagga gcagtagcct tagtgtctct cagttgtccc atctctataa
9901  tagggacaat aacataatag tgctgaataa aagagtaaca aaatttggt caacatttaa
9961  tgtatttaaa gagctaagct ccgtgattgg cacaatgaac caatcaatca acaccagtt
10021 gttattaata aagtcagtt gaatatgtac tgtgtgcctg gccgtggttc aatttgcctt
10081 tgcatacaag gaaaaaatta aaatactctg ttaataaaga ctatagcata atactttcac
10141 cttaaacttc ttgatgttaa tttattttgt ttacctgcca aacttctact cattccttat
10201 gactttctgc tacatgaaac acctttgta attcttttgt cctattaaat taagttctct
10261 ctcctctgct ttcctgcttt tgtgcttttc taataacact tttaaccctg gactttctca
10321 ttcagctgtg caactgtgga ctgagaggag gctctttgaa ttcatttgt atattctagt
10381 agagagtact gtgagcagtt gggttgttga atgaatacat taattcaacc tggagggatg
10441 ggcagtattg cattttttac attgatatta catgatattt agaaaactgc ttaactggtg
10501 gacgtgttt tattaacagc attttgtgta tagcactcac tatgtgccag ctgctattct
```

Fig.63D

```
10561 aactgcctga caaatactcc tgaaaccttc atggtaacca tatgagggaa gcacttttaa
10621 tatatccata ataccaacgg ggagactgtg gccaaattgg ttaattaact tagccaaagt
10681 catattgaac taataagtgg atttaaaccc agctagtctg gggccagggt ccctctttta
10741 atcttctgcc tcctgcttat gctgttgcat ggagtagtct ttatcatata actaaattaa
10801 gcatgcattt gcttaaagca gtgcatacat gatggatcaa aaagtttgtg gtataattgg
10861 tttaattctg tcattatcca ttttgattta tagtcacttt cttatgatgg tcgtgtagtt
10921 ttaaatggaa cctttgaatc tttgatataa taaggttatg tcaaatcttg ggtataataa
10981 ggttataccc aatggaaaca gaataatgat cagcccattt aaagqatgac tggagagtta
11041 ttacaataca taatagtcat gcatatattg agtagtattc ctttggtaac attttccttt
11101 taaaaattgt aacatttgat tgttccttgt tgggagaaaa ggaggtcaga ttttgaggg
11161 gagatccatt tggtgagatg ctgagtgtgt gtcaagctaa ggagatagta tgacatcttt
11221 tttagagtct agtcacaatt aaatgccatt ttattttgga tttgggatc cgtgccagct
11281 tccagcttgt cagagctgag aagactcaaa tcaagtccag gcttatttct acagcaaact
11341 gggattctgg cttcttgccg gtggattcat tcagtacagc ccatctggct ttgatgttc
11401 tgcaagttg gagccatttg ttgaaggaag ccaggcggtg aatattggtg gtcctggggt
11461 tctcttgact ccaagtggtg cccttggtt tgcattttca ccatgcttag catctgctta
11521 cctggagacc atgcagccgc cggccagagg tctccaacaa ccaaatcttc atgccttta
11581 gaactcagag tccccagcac atcctccttc ctcctccttg tccaattact ttcatgcagt
11641 tctcagtagc tgcttgtttg aatcacttat agtatttaac ttctagggtg ttttttgggtt
11701 ttggtcaagg taattccagg ctgaatgtgg tgactaagca ggaaataaat gggtcgtcct
11761 caaagttaca gtggagcgct gtttctattt tcctaaggta cacagttgtg ggggcgatcc
11821 gtatggaagt caggaaccca gtcgattttt gcttccttt gatggtagca gtacagacct
11881 ggctgttttg tagcctgctt tgttttattt cctttcttc cctaacttca cgggctgtgg
11941 caaagccctg agacgtgcag gaaaatgtct cctgtcatac gccacagca gactagccc
12001 tgaccctcct ctgaagccca ggaaggaggt atctgtgaag cagcctgctt gtaaagcaat
12061 tgcacacagc cttgtaaact gtgttactgg gctgattata cttgattggc aaggtgaatc
12121 tcttatagca aaagagaact tggagagttt tatctcatct tatgccttat taatttgttc
12181 attcttaat tacacagcca ctattgagc accctattta tgcaaggtac ctggtcgggg
12241 gtcagggga gggtccatg gtaaacgaga cagactcaat cctggaggag caggaatggc
12301 agccctcgc tggctgttg gcccaccaa aagggaaagg tttcatttta ataatacatg
12361 ggtgaatcat ttttgtcaat aggcaaaatt ctttgtagtt aaaaaaaaat atgatggtag
12421 gaaggaaagg gatgggcaga gggttaaaac aaaagatatg ctctccctaa ctctagattg
12481 tagtattgtc atgcttgtca ctgtagctga attccatttc ttgagttttt tcaatgcca
12541 aggcattccc tgtatgactt agtgagcct tcatctccg cgattttttcc cattcaggta
12601 aatgagcaaa tggatttgaa cactcatatc taaaacaaga gagaaccagc tggaaatgcc
12661 ctttgaattt ctttctctat gtaaaccatt tttctttctg gtgcctcacc tataaataac
12721 aggagttcca ccttccttta tagactcttg ctgaaagcat ggtttggaac aagaccgtac
12781 aggtgcacac aaattacagt tgggaaagaa gctgcagtg catcttgtct ctgaaggtta
12841 tgaaatcctc ctttagtaa tggagctggc gtgatcaagc cagcaggatg aaattggca
12901 ttgtgagat caccccctt ctcacttgcc cactgtacat agcatccag ccttactctt
12961 caaatctcca cattttttct tatctagcta caaattcat aggctgattt tttggggtg
13021 cgtgtgtggt tttttttttg tttttttggt aaataaagac ctgcatttt attttgatat
13081 aggtggttga gtttgtctt taatttcatg acagagattt aactagtctc aactttgaa
13141 aagacaacaa tgatatttgg ggatcacaca cttaaagtta gatttctaga tgattaatac
```

Fig. 63E

```
13201 caaagtagat gattttttag cctcagccat ttataggtat gcccttctgt gaattttta
13261 tgacagtgaa aatcatggca cagataaaaa ttaaataaat acttctgtta ttttcctgaa
13321 gaaaaaaaaa aaaagcttaa actatgagaa tactgtcttt gagcacttta aaataaaatt
13381 gacttcagcc agcaggattt tgagcattac atcacaaata aaaacaaga ttaacatcaa
13441 aaggagtcag ttttcattca attgtgcagc actgtgggct gtgaaattta atattatttt
13501 gactcatatg ctaattgtag actgacagag gaaaatggat tgtgtttaaa taaaggata
13561 cacagcatca cacgcagctg tatcaaatac aagttgaggt ctttgggcca ggaactgggg
13621 gccctctagc tctgttattg cagattcaag tttgacaaat aaaactttcc tttagactgt
13681 agtttaatta ctttttttca aaggtatgcg tgatgaagag gcacaaatac acctcacctt
13741 gaagagttgc taaactggtt tgtgtgccga tcagttcacc gtgtgtttga atttctgtgc
13801 ttctcatctt tcctttctt gaaaagattt tgcttgtcat tggtgtgaat tgtaccccc
13861 acccccaccc atctagtctt tgctctcaga tttataacac tttaatggtt ccaaattgta
13921 tagcctgctc ttagacccct ttctttttcc ttgaataaat caggttcatg ttgcagacga
13981 tatttgtttt aggaaagtgt gaaagaaggg gcacctgtga aaacacgcaa ttgttccaac
14041 acacatatac atccaaatta aagcagaaaa tgtcaaagcc tccaatcact acctattc
14101 ttggagtttt aaagccgctg agaagatagt ggtgccctcg ctggaagttt taaggtaatt
14161 acttttact ctaagcagta gtatctggta acctaattcc gtataaacct gacaccctat
14221 cgctacaccc cagtatttct ctgatttcag aataagtctg cgtagaaact tgttctgatg
14281 ttaaagtgca aaaggggca gtaaagtgct atccacaaaa aaggaaaac attttccaag
14341 tattttcttat tactgcctgt gtcttttgta ggccctgcct ttattatttc atttttataac
14401 aaaactctta tgtttggggc attcagagaa taccttatta agctgttgca gcaatctagc
14461 attaaatgga agacatgcaa gactgaagat cctgcctgtt tatgaagtgt gccatcaaat
14521 tcacatgctc atgatgcaga gtccttcttt gggagtattc gtattccaa gtgcacagag
14581 cacttcggaa aggagccttg gtctttggtg ttaatgctct cctagctccg tatagatgtg
14641 gcaggccaa agtacatggt ggggtgaagg gtcaagggtt tgggcttatc cagagcagcg
14701 tgcatccttt gtcaggaggt gactggaaac accagccaat tacagcagaa ctgcagactg
14761 ctcatctgca ttcggaattg cagatgaacc agtttgtact cgacttctct tcttcactgt
14821 aggctttgac atttaattaa aaattaaagc cttttatgga aaagtacat gttttccaaa
14881 atgggtaaa ttcgaagtat acttgataca gaacactggc ttgggaataa acctgtgata
14941 ttacatgact tttggtttgc aactgctagg ctgagcctct ttgtaaagct gggatttaga
15001 atctttgaaa tgtttgtaca gttcaatgat taagcataaa ttgtatatat tccttttttt
15061 tcacttattt gagtaaacaa gttgttact acagcttctg tggactcaga gattatgta
15121 ttaaataggc cacaacttca actaggataa ttttatttat ctgcttgtta gggaattgca
15181 tcaaagtttt aagtctgtag gcattaaata ttttaaatgc ttattttaa agtcaattat
15241 gaaagatagc acaagtttt tctgaaacta cattaaaaaa ataatgtttt aatcttatca
15301 caaaagcatt gactatttat tgcaaagaaa acacagaaag caaaaatca ttctaagtcc
15361 accattcagt agcccaaagt ggtctcaggt aaaggcggtg tgtgtgacca tttgtttatg
15421 gttgtctccg tgcagtcagc aaaataaaca gaacaacatg ccatatatta ttgatgtgta
15481 tattttcaac tgaaattagc catctgctta caatgatcat atacactaat ggtataattt
15541 tgaaatgaaa agaaaaataa aataattctt tgtggagagt aatgcgaatt gacttatgaa
15601 tctcgcctg cttggcagtt tgctctagag gtagaagagc tttatgtgtg ggcctcctca
15661 cccccacac atttattctg ctcacactcg caccagcatc catgtcagga ctcaccttgt
15721 cctgttacat gagtaacatg gccctgattc tcaagtgcat gataactgcc ataattacac
15781 ataaatatta aatatttaaa tagatcttta cgtgtgtaat attaggtaga agtggctctg
```

Fig. 63F

```
15841 gatcgaatct gatgcttttt aaatagaagc tttcccacaa catttccaag cactgtcatc
15901 gtgtctgtct cgatttgggg tttacctggc ctagttatct gtctgggtgt agaaactggt
15961 agttcctgtt tgtatctttt ttgttctgat ctctttattc tgtgtcagct aaatattctt
16021 gcagtcagtt actaacatat taactcatcc ttgtttggaa actttggcat atccttccat
16081 ggtttccttc cgtggacctg tcgcgtctct caggagagcc accaggtata ttgtcacaca
16141 tttcgcatgt atttcagag actacagcag catcaagtgg cccccagcg atttgggttt
16201 tcttctcggt taatctacac tctttggcca accgtgagaa aacttgtaag aaggcatcag
16261 atgtttgtgc taaggtgcgt gtagtatggt cagaggaaga aagaagcagg gaaaatggag
16321 tggccgtggg tgggagggga agcagggagt gcaatttcgg gttcactaca cagctctcca
16381 taaacttctc cactgctggc ttcccacgga tcctcctatt acactgggca aagtgcagaa
16441 atagatcagg cgaccactgc ctccgtccat ttcccaggca ccctgtgaga ccgataatg
16501 caatacaggt cagcagaaaa gtcagactt gacatcccaa cgtgccatgg tctggtctgt
16561 gaatgaaaat cacatgaggt gacctctgaa ctctaagtgg ctggtttatg ttttcagtgt
16621 attaggcccg tgttttaaac aagcatgtgc tgtagtgta ggttaaaact ttctgttgtc
16681 ttcattaatt atgctgtgtt ctagtctatt aatattaaag aatattgtgt tgcataatga
16741 ctaatttttt tatttttggg agacggagtc ttgctctgtc accaggctg gagtgcagta
16801 gtgcgatctc ggctcactgc aacctccgcc tctcggattc aagcaattct ctgtctcagc
16861 ctcgagtaa ctaggactac aggcgcccgc caccatgccc agctaagtgt tgtattttta
16921 atagagacgg ggtttaccat ctttggccag gctggtcttg aactcctgac ctcgtgatcc
16981 acccgcctca gcctcccaaa gtgctgggat tataggcgtg agccaccacg cctggcaaca
17041 taaggactat ttttaaagt ttttacaatt atgactgtga agttgaaatg tctaaattat
17101 tagagatcca gttagatta ctaaatattt atgtctaatt gagatgatta gacttagcca
17161 aagtatccat gtagaagtat tagagtctag attggtgaaa aacttgaaaa agcttggctt
17221 aagttcaata ggtaatccaa gagtaaaaac agattccaat atcagatctt ttaccatag
17281 tcatgttaag ttggaagcc ctacttgagt gtttccagtt ttttccacat tatattgtgt
17341 ctatatttga ttcaaaggca gggcatctat tgtcttgctt aggactgatt cactgggaaa
17401 agccactgga gttgcctatt tccactcagt atgcctcact cttagagtag cttccatgg
17461 ttcccaggca ggccctccag tgagaatgca ccaagccaca cgccatggcc tgggaagcag
17521 tcctgaacct ggagattgtc ttgatggaaa ggaagaggca gccttccct cccaggaaga
17581 tagtagagag cctgctctga cttcgctcag ggatggaact ggtctggctc agttctctct
17641 cctgtgtggg acatgaatca ctcttggtgg tctttgcttt ttacttgggc ttaaaatcag
17701 cagactttat taaatgacac ctctctctaa ccactctctg tctgggcgaa gtttaacaag
17761 aacagcctcc cccatgtgg tatgggttgt aactgtggcg gttccctct gctgttttg
17821 gttacaagat gaacattatc tgaacacaca gaaagaaatc tgtatttggc atccataatg
17881 gaaagtcagt ttagtaattt aaacttagcc agttatcatc atcataattc ttttaacac
17941 tttcaaagtc agcataggag aagtgtattg ttaatatta caaatatttt agggcataga
18001 tagatgtgct gtgtagtttg atttgttaat gtgtctaagc aatcaaagca acagaattca
18051 aatataaacc ccatcacttc caaatagga actctgttta ctgacttgat tataacatat
18121 ggaactcaat tgttttccat taaaaaatga tactattagg aaactcaccc catttctttt
18181 tcatatatat tctgctattt gcataattgt ctggagtcca tatgtaatat taaatgtaaa
18241 acacaaatgc catgtagctg gtctgtttct tcctcaactt tggttcctg gcctctggg
18301 gaagggttgc acatctgagc cgtggtctca gatgactgcc tggaagaag cctcttcct
18361 tcaggcacca ctgatgtgtg cttggtgtgg agctagactt tccctggctc tccatgtgac
18421 gctcacatgt gcgtgtcttg atttcccttta acttcatggc ttatctatga acagcttgat
```

Fig. 63G

```
18481 ttggggaaa aaaatgtgtt tcccaatgct ggagttataa ttgaatgtgc tgcagtcaaa
18541 actgaaatgt gtgcagagaa aggggcttt tctgtcatg ctcattgggc accagtgtgt
18601 cttcacctgt tttgtgtgtt aggtccatgc gtcatgctga aatgaagaac atgggatgta
18661 tgggctttg gacagtgctg agccaaaagc aagtgctcaa aagcagctgt gtttgtatta
18721 ttagtggttc tggaggtggc tgattgcctt gcattttaag tagagaggga ttgtagaaga
18781 ctgccaatac ttagaacttt ttccagagag gaagggtcag aaactgcatc tgcagggctc
18841 cttgctctcc agaaatgcca gtgtgcctgg gagggcatct tcagaaatcc agtctctcct
18901 cctcagtgtg tcctgtaccg actagtggt tctgtcttca gaattcctat catgtctgtg
18961 atctgcaaat agtggtattt aattgactt caatttgtat aaatgttagc ttctatttgt
19021 tcattcctat tttttgttca attaatacat tatttattga gcatctactc tgtgtcagcc
19081 ccttgggtgt ttaatactga attagtcaca tgtgggactt gctgccctc agggagctag
19141 actataaatt cctaatgatc agtggtctcc atttttctgt cactcataat gtctggcaca
19201 acataggtta cttgagttgt tacactcaca gtactgttgt ttgctgccat ggtgctttag
19261 gaagtgtgag agttccgggg aggcagagtc aataatgcag actacacgta gtgaaaacat
19321 ggccaggaga gctgtagttc aggctctcag ctcaactgca ctctgtccac tgagaagcca
19381 taattttcttc acttaaagtg actgtgcgct atggctgttt atatatacgc ttaaaaagta
19441 aaagctgcta aaccactcaa ggattgggc cttttgtatt gatttaatta aaggaacaat
19501 cattgtttta atgagctcta gaaacaatta cttttgaaga gccgaggatc aaattcttgc
19561 ctcacgtttt gccacagtgt gttctgaaag gtgaattaat gcttttggaa tcatcaggaa
19621 tagtgagctt tgtcacgatt tacttttac aagcgtatct aatatgcata ttgaaatgtg
19681 agcctcccca ccacacttcc gctttgataa gcatccccg gattgccgtc actgaccatt
19741 atagattttt aacaagttg gacagtacac actgaatgaa aactttacat caaggaaggc
19801 ctggcgtgtt tgtaaaatga attaaaggc tcattaaatg atttatatga cttacgcctt
19861 ctgaaaatat ggcctcaaac acagagatcc ccaaagccac accgaccct gcgtccatg
19921 ttctcgacct caccgcatca gcaccagcaa gacctgtcgc tgagacggtg agtgatgaga
19981 gtcaagagga gtgacttgca tggcctggga ggaaacctcc tgtgaatctt tagtaaagca
20041 ggaaaaaaa aatcctcatg aaggaaacag gatcttggga gcatttgaa tgaagaagga
20101 gcttagtgag ccaaacttga gacatagggt gtaatgtggg agagttttaa gatttgcaga
20161 gatgtacagc ttgggagggg gtgtaatgca ttttcttaaa agagctgaat gaatggttga
20221 ggaaatgggt acatctggtt tggttaagga tcctaatctc tgaagcctgg gatgcccca
20281 gggcttgtaa tttaggaata cttccctaa tagtagctaa ccttatata gtgctgtctg
20341 tgcaggctac aaaaggagca gattaaggat agaaaaggtt tggagtgtat gagaaaccct
20401 aggcaggaat tgactcctgg tgtttgtaaa cctaaagat gtcctaaaaa ggtcaaggaa
20461 taagacagga gaaaaggaa atgtcaggaa gatgatcaat ttaatgttta tggaatttag
20521 tttgtactta ctgccggca tcttgcctga ggttttaaac ctcagcagca catcagaatt
20581 actgtgtgtg tgttggaggg gctggggag ataagaaat tagcctcatc ccaaacattc
20641 tgattcagtc tgttacttga gaaactgaat tgtgttttgt ccataaagaa gatgaaattg
20701 tctacagaga acacattgcc attcacaagg ttgaggggat accacagaga ggctccact
20761 gtgatttgca tttgtcaaaa gttctagaga attcttcaac agtacacaca tggttgtttt
20821 aaatatatca ttgttataaa aattcgtttt gagttctgtt tcacagaaag tttttttgaa
20881 tgaatgaatg tcatatatcc ttgctaaagg agctcagtta aaaaaaaggg gaccatcctt
20941 ctcttttggg ggttgtacag taacacattc ccaagaaaga ggtaacagcc acatacattt
21001 ttcttcccaa taaagagtgt gggttttaa tatgaatcca tagtatgatt tctgttatgt
21061 tttgtgctgc ttcataacca cactcatgca ctttcagaa aattaatacc attcattagc
```

Fig. 63H

```
21121 ataaatcata aactattccc ttggtatggg tttgaaattg gggtgccct atcatccttg
21181 cttratctct tagtgaatta tgaccctgta gtcatcatgg ctggtgggcg tctctggtta
21241 aagaaagggt tggattggaa ggattcagag gcgattcttt gttcttaggc tttaatattt
21301 taatgagcct gcaggcttgg ctgcttacga acgagctgag atttctaagt gtgttgttag
21361 tgttagcact tgtagaagga tgttcattag gaagttcttg tttcagtttt tcagagaaac
21421 tccccattaa gaaagatcat tcaggaacat ggctaccaag aaagaggaaa gggaggaggg
21481 aggcttcag ctataagcat taagggata ttgtatcagt agtcttagtt ctaaagatt
21541 gcttctgaga attaattgga gcaaatacat ctcaagggaa gaaaaaaaaa gatttatagg
21601 gcagggacag tagttgtcct tgcaagtaga ggacacttca ttttgcagct gaatcaatac
21661 cacaactaat tatttctggt tatcttttac gcatttgtaa gacattgctt ttgttcagtg
21721 taataaaaaa cccattgttt gatcagtgac tgactaatta tgataagtaa tttgaaacat
21781 tcttgatgaa actgtctgt taattaacat caacagcaca gggaaactaa caggacaaca
21841 aagtattagt ggatccactg ttccctccaa ttgacgagct ttctctgtgg catgcccaat
21901 aaactaaagc tgccaatggt taaaaataa caaacatgtg ggagatctga ctcaccacgg
21961 aggaagagtt atggtaaagt tacacaaagg agtactgaaa tattacaagc gaggggtgg
22021 taaagaaatg tcagcaggta gcctgatcct acagcttaga gtaaggaaag tggtttcttt
22081 ctgtcttttcc tttttcttt aaagcttaat tccaaaatac attcatccca tattgatctg
22141 aagtaagaga cttttgataa attaaagtgt gaatctgaaa atgtgtagtt tgggattatg
22201 ggcattgcct ggctatcttg taactgtcat taatactgtt aatttttatc aactcaatgg
22261 cttttttttc ttatgctttt agatttctac ctggacaagg actggtacta tacccacaga
22321 taggagacaa attggatatt atttgcccca agtggactc taaaactgtt ggcagtatg
22381 aatattataa agtttatatg gttgataaag accaagcaga cagatgcact attaagaagg
22441 aaaatacccc tctcctcaac tgtgccaaac cagaccaaga tatcaaattc accatcaagt
22501 tcaagaatt cagccctaac ctctgggtc tagaattca gaagaacaaa gattattaca
22561 ttatatgtaa gtataatttt attcatttat tttatagaaa ttaagataag ctatataggt
22621 ttgtatcaat tttttgtttc cttaaaatta ttgtgacaaa taattgatg aaaatctatg
22681 tggaaaaatt gtcccccccc ccttttttt tttcaaagaa aacttcattg aatttgggac
22741 cctgtgctac cagtattcat taagtataca tacccaaaga gaaaaaaaaa cactagaatt
22801 cttaatagta ttgaaataaa tgtattatat gaatatattc agcatctcta ctgacaaaac
22861 catttttaag gaccattggt ggattttgat aggtaaatct tgtgcattgc cttttctctt
22921 cacccatcca tccattcatt cactcattca tttcgtattt attctgtgcc agagactgtg
22981 cttaagggct agggattcag cagtgaaagg tggtaaaata gcatgttttc ctcaagaagt
23041 taacagtcta gagaagatgg agctcataaa ttcgaaagat ggggatgaca ggtcacatta
23101 aaaccagatt cagaagaaaa agacgaaact tggtttgctt agtacattac tctttttgc
23161 atacatatat ataatttgac acgctgtttc aagaagagat ggtacgtatc ccttgggtca
23221 tatctgaggc tgacttgtga ggatgtgaag tcagctgatg agcacatttg gagcccacgc
23281 ctactatgtt cagatatctc gtcagcgtca ttcccagggc ccaggtggt gttaaagtct
23341 aggtgactca gacagctgtt cgcgtcattc aagcaatgaa gtctttttc ttaatttctt
23401 tggtttaaaa ttatactcat aattaattgg gtgaatttt ccagtggctt ggttaccata
23461 gactttcagtt tattagggaa ctgctatctg ccactggttt attatttgcc ccaagtgga
23521 ctctaaaact ttaggtagga gactcttggt gatcaaactg aaactcttgc atctcaacct
23581 atgagccgca cttattgtt attttattt ttagagaca gggtctagct ttgttgcga
23641 ggctggcgtt cagtggcatg atcacagctc actgtagcct tgaactccag ggctcaagtg
23701 atcctcccac ctcagcctcc aagtagctcg gactacaggc atgtgccact gcacccagct
23761 caagagctac acttcaaagc acagaatgaa aacctatttt taaagccaac ttgatacata
```

Fig. 63I

```
23821 gagtagctta ccaagaatta gtaacaacaa cacaagaaa aaaagagag aatgtggtag
23881 agtatatact tagtaaggag taattattat aaaataaaag cattctgaaa tgaaacaggt
23941 agatggggtg gccaagtatg cagcatagta gggaaatctt tgaaaatgta aaatagttac
24001 caggtaaaat aaatggaaac tttaagcttt tggaagccta acaatgtatt tatattagta
24061 aagactttat ttttttattt tattttattt tattttgag acggagtctc tctctttcgt
24121 caggctggag tgcagtggcg tgatctcggc tcactgcaac ctccacctcc tgggttcaag
24181 tgattctcct gcctcagcct cccaagtagc tgggactaca ggtgtgcgct aattttgta
24241 ttttagtca agacggggtt tcaccatgtt ggccaggatc atctggatct cttgaccttg
24301 tgatccttcc gccttggcct cccaagtac tgggattcca ggcgtgagcc accgcgctg
24361 gcctagtaa agactttaa agtaagactt tttcagtgaa agctactgtt aggcatgaca
24421 tttacaggca actgaaactg atcagatgca tttattaaga aggttaatgc ccctaggtgg
24481 ggtgggagaa agaaggtcgt ggtacgggaa gagggacac actagagatg agatgcccta
24541 gggcagtgaa cgcatgtccc taatgcgtgg atgcagccca cgtccaccga taatgcgac
24601 acacccagag tctctcttct tactttagct tatgacttca cgaagaatgc tttgcaaatt
24661 ctaagttcgc actgggcgca agtggaattt tagtaaacat taagagttta accttagtg
24721 tgaaataata tgcaagatat gcaaataatt gttaccaac atctctttgc ttaatgtggt
24781 gagcatttaa taattgcttt ttattaatac atgagagatt tgtatttaga agcagtttaa
24841 tttataatta taatattaat ctacacaata acgacatcta ttatttctt tttttggaaa
24901 ctcttcatac cacactaaca ggttcattgc agttactgaa ctactctggc catcagagct
24961 ctccttagag ttacgattta ccatgcaaaa gcatatggta gctgggata aatgaatctt
25021 tcttaataca gaattgaggg tctcaagttt gaaactacga gaggctattt gaatgttgct
25081 ttgggggact gtcataaggg ctgggtggag gactcagggc taagaagttt gccaggaagt
25141 ccagttgaga ctttcagcag agttgaaaga cttccacgat ggcgtaggca gaggaaggcg
25201 tttcagatac ttgggaaaat atagaagcca atttctcacc caccctacag caaagctcat
25261 tgatctacaa gtttccctag aaaggaaatg ggaaatgcag agaacaaatg ttaaaatagt
25321 tttagaaatt aatattgact ttgtattgct tctgcataag ttccaagaca ccaaaacaat
25381 gaatggattt taaaagtca ctactttgca tatcagacaa atgcacacac acacacac
25441 acacacacac acacacacac acacacagtc aagctctgta ctggcttttt tgagaaggaa
25501 agtgtttgaa gttagtaatt tttatatcag tacatttata aatagtgcta ggtagcatga
25561 cggaaagtat taaaatttac atgtatattt ttaacacttc aaatcgttgg ttcactttga
25621 gacagtaaat aatattagca tttgagttca gcttaataa attctacatg ggtttaaccc
25681 caaatctgag tgtctagttg gtaagcgcct tcagaacgag cagtgttata ataaatatgt
25741 tattgtgtgc tggtttcttt ccatggagag gaaaagaga cctgatgctt tggaggagtg
25801 cttgactttt ccccagtgag gagtagtcca gagggactga cttgcattgg ggagtaccct
25861 acatgaacag catttcagaa gaattaaacc aggaacctag agtcctactt gctagtcctg
25921 cttcctaagc ttaatgagaa agtcaatttt attttctttga acttttaattt attttcctaa
25981 aaaacgcttt tagtattgtc attgttctgg ctaatgatgg cggtctcctc cagtttcaag
26041 ccaccttagg gctgggcata caaatgcaat ataggatcac ttgttagtgt ggtttcaaat
26101 ggacatgatc ctctgtaaat tcttaaaaaa cattaattt gatttgtggt gttacctgct
26161 ttaaacata gtcataacac ttgtgagttt cagacgtgaa tatgaatttt taatttgaac
26221 tgtactttta aacaactaa gtattaacta agtccctta ggagatatgt ggcaaactga
26281 tatgcatcct cattcattct tctcatagat ggttatttgt tttttaactt gtggcaaaat
26341 tatatatgaa tggtcaccga cttaaaatag tccacttaa attttttcaac tttctgatgg
```

Fig. 63J

```
26401 gttattgga gtattaaatg tatttcaat ttaatgatat tttcagctta ccttgtgctt
26461 atcaagtatc aagacatagc cccacctaag tcatggagca tctgtatatg ggttttatt
26521 cttgtttaga attgactttt tcaagtgacc tatttcagta attagccctg ggcctgattt
26581 gcataatgag atctcctaat cttcaagtaa tgcaagatg gagatattat ggccatgtgg
26641 tctgaagaga cctttcttt attatgttca gatctttaat tgccttaaaa atagagtagc
26701 taatttacct aacctctagt tattttatta ttgtctttaa agttttttt aatgttcatg
26761 aaataactgt tctgaaattg cctattttca aggaagctg tgtcttagac ttactaaatg
26821 ctccagttga tactgggaaa gccttcttgt gttcgtagcc ttatccgta gagtttctt
26881 tgcagcattt tctgtgcctg gtttagtttc tttcagagg cgacaccag agctgaatga
26941 gtcagcaggt tggtgtgtc gaccctttgc aacagctgtc cttacgaagg ttctgtgggc
27001 tggttattct accttcgcat aaaccttgc aaaataaccc acaaagaggt tttcgtcaca
27061 ctaccaaaat catgtgagtc agatggat gaaaaatgaa tgccattgtg ttcatacttt
27121 tccagtgaac agtagctaca gcagagctgt tagacaaaga aaaccgtatt aatgaagcgc
27181 ctcccaattt agcttcatat ggcttttgca ttatttgct gcaaaatccat agctaagaca
27241 catcttgtgg catagtccgt aagtcatctt tccgaaggac tgtttgatta aaggttgttc
27301 tgtgagatcc accctgtgtt gttcatggca tcctcttgga ggcctccctc actctccatg
27361 ccttggcaaa gtcttcctta aggaacactg aacaagtctg gagaagctgc catttcttag
27431 ggccctcatt ggttcagttg tctatagctt ttattttt attttttt taataaagag
27481 tatgtaaaat tggaaagctt cacaaacagc ttgctattt tttagacatg tactccactt
27541 ctaagcaaaa tcacaaaata aagtaaaatg cttccacaaa tataatgaaa caatattctt
27601 aaagaatcaa agcagaagaa cttcagagtc tgttgcttat gttaagcata tatttgtttc
27661 cttctctgct tttgattac ttattctgg ggtgtaggtt tgcaagtag tactgaaacg
27721 tactgaatgc actgttcttt agcaagatag ttacaggagc tttcaaatgt cctcttaaca
27781 tatagatttc ttttagaata tagaataatg tgtgggctgt ataagcgat tatgtgcttt
27841 atttgatgaa ttatttatgt acgataaatg tagcaaaagc cacatttcca tcattaaatg
27901 taatcccatt tggtgataca gcaacatcag cctgtcattt gggtcctctg attgagggggt
27961 gaggatttct gtttgatacc ttgtgcataa tggctgcgtt caagcattta aactcatttt
28021 tatttctaac ctacagctgt catctttgta ataggatatt catcagaatc ttgccagaga
28081 ctgtgcattt gggatcttgg gggatacagc accaccacca ccctcccct gtccaagaga
28141 aacagatcaa catcttaggt tgagagtctg ggtctggaa gacccgagtt cctgagtgcc
28201 ctttgacaag taacttaacc cctgtctgcc tcagtctctt catctgtaaa gtgggataa
28261 tgacagcacc tgcttcacag ggttgatggg aatccagatg tggtgggata tagaaaatgc
28321 ttattactc cacctttgac accaaataca taactaag agttaacttt ggagcagggg
28381 aggaagtgtg aggtccagg ctggaggcag acctgtgttc ggctgcaagc tggagaggat
28441 ggacccaaa agcttggctg atttgaagtc catccataaa atggaactcc agagagttta
28501 cacgtttcag taatgctgca taacttaatt ataagatctt ctctcttgt cttcttcag
28561 tgttataaaa gctcttttgt cctgagctt cctttaccaa gaaacatgaa tttatgtatc
28621 ttttgttca tggaattgcc caagctgtt agcagatcct tgtaagacc caaagagac
28681 agacagggga ggagtcttca gatacatata atcattttc ccaatttcca tgttaccagc
28741 cttgccagga ctttttctca gttcctgtt acacaatgaa aatagtgtct ctttattgat
28801 aattttagta gcatcctaat gtggtataaa tcgtcttcca gagaagaaaa tgtgtcaggg
28861 ttgcgttatc actgaggcta gctgggaaag tagatcagcc cattagtctg ataattcgaa
28921 gcgttgtttc tgttatttct gaacatcatg tgaactcctt ttctgggtgt attaaaggtt
28981 tttccagtgt gtgtcagtga gactcctgat tgaatttaat atgaataaag ataaattctt
29041 tacatttaag gattaaagtc tcagcttctg cttaacttga gattgcactg agaaactcct
```

Fig. 63K

```
29101 ggctctcggg tatagcggag tcacgacctg gggatgtctg tcccatatgg ctctgtgt
29161 aagaagaaaa agctgctgtg gacggagact ctgttcacat taaatgacat cacctaagcc
29221 atcatgacag caagaattat ttaggaattg ctcagaataa aactgccttc attatttcat
29281 aaaatgtatc ttggtatctt tagcacctta tttatggctt tttaaaggtt cactgggatt
29341 tataaataat tggacaatgc tagagaccta gtacaagaat gaaagaggac aggcttcttt
29401 cttaataacc tttaaacatt catcaggaag ataaaacttt aaagcaaaat aaaacacatg
29461 aaaatagcca agatgcacag accagacaag caaatactac tttaacttat ttgtatagtt
29521 cttaagagtc acatttgttc ctgaagtttc aaaatctcgg gctgagtgtt tgatcactta
29581 gggaagtgtt gtggccttca catactcttg tctcacttgt aagtctagaa acacaggtct
29641 tagagcaatt tttatcactg tgagaaagct gaaacttagt gtgagtagct tagtacaatt
29701 cagttggcca tcaaatgtca gaaacaaaac tcagtccagg gccgctggac ccttaggcg
29761 gcgttgttag tttaacacag tgcctcctgg gtccaaacat ctaagtgcac atgtagcaat
29821 agtaaagata gtatgtatgc atacataaca catatgtaga gacagcagag tatacgtaca
29881 cacatgttgc atacatagca acagcagaga agctcatgaa ctataaagga tggactgtat
29941 gcttgtatca gacatttgg tactgacgct ttgtcatata ttgtgtaaca tataaccagc
30001 ttgcaatcat ctgcccccaa agttgaacta agaaaatcct acagggtact aggaaaggaa
30061 ggccattggg aaaggtggt tatagtggca atttgttagc tcttatgaat ttttctttc
30121 tttttagaca tactcttaat tccattttt caataaatct atactatttt gtgttttat
30181 gttagcaagt actttaagcc cctcaataga aagttgctac atcatatagt gattaaaaat
30241 aaaaatctct caaacataca agtagaggtg gtatgagact tcaaattccc ttagccaagt
30301 acaagtgcag cagttttgtt ggctggctgg ctgcatagaa ggactgatgg attggcagac
30361 cctcaagctg gagtgtaatt gatctcatta cagaggagcc aggctgggtg acagttgtgc
30421 tttgcaagtg gttttttgca ttggtgaagt agccattttt gttgttcctg atgttaaaca
30481 ggggatgaag gtattctttt attggcacaa acgcgggaaa ttgctctgga ttcttagagg
30541 atagaacatg tccctggac ggaataaggt tcatgtgtag ggcaaattta datggggca
30601 ccttattggg gttactactg gtctctagat ggtcaaagca aacaacatgt ccatctaagc
30661 tgtgatgtcc atctaagctg tgtgtgtcca tgagagtgac gcatttctc ctctgcagtg
30721 ttgttatatt ctaaactgtc agcagacatt aattcggtcg ctggtgaagt cccaccgcct
30781 agagatgaac tctgcctccg atggatgttt tccacttcag tgccactgt ctgcaatta
30841 ctgggtcatt aatatcattg catgcaatta gtgacagtag aaagagctag agggttgtgg
30901 gatgtgcacc ctcccacca tgaactttt actctgaccc ttcccagct agaccttc
30961 gtatcttggc aaggatattt taatgattga gactgtcaga atcttcagag caggcactgg
31021 attatgtgct ggaaataatt cactcaaaca cctgcttctc catggttcag aatatttca
31081 ttagatatta tcactatccc ttccctggga agtttcattt ttaaaaatct gatgcttaag
31141 tacagctaat atagcaata gggaattatg ttttatcttt agaactctta cattattctt
31201 ttcttaaaa atgtgagctg agtcattgct attgcagtgg tcatctggcc gcctattttt
31261 aaaacacaat tcctctatct tagtagattt tggccatat taagcatatc aagaatgact
31321 ttttttttt caagacatgg ggtttattg gggcttata tacaaggaaa gagagagtcc
31381 agtggcagtg ggctggacaa gatatccaca tggcctgtg gcagtgagct gggcaggaaa
31441 actgcaactg cttgcaaaca gcatgtagtt catctatagc atttcactt aacaccacca
31501 agctaatgac ttccacctgg caaccttcat ttaatccaga acttaggacc tcgagtccct
31561 gtacggccca tgttccacag gatgggccga gggctcagct gttcctcata gacaaggaat
31621 gactctccac attggccact cccggattcc ctagctcagg acacatattc aggtgtgtct
31681 aaggctggct ctctatgtg aagttactta ttcttttacc attgactctc atgttccac
31741 tatattaagt ttttctgaat tactgtggca ataagaaacg gtcccttaaa ttatactaga
```

Fig. 63L

```
31801 agaaaagctt tttttttgtt ttgtttttta ttttgaaatt atgttaaatt tttttcctta
31861 actgagagat tccacctgca taaatcgtca taacttttaa cagtaagatc ttagacttag
31921 aaagtgatgt ttttcctcaa cagaatttat taaaaatcaa gacaccaagc tgttccaaac
31981 aatagtttga ggggaaataa aataaacaac tccataaata atcttatgtt gttaaacatg
32041 tctctagcaa aacaaacaaa caaaaagtc ggggttggg ggaggtgcag ttattgcca
32101 gtactgtctg gtctttctca gaaagcgtc agtgtacatc actgagcctg gacggtatgt
32161 tttcttgatc tataccccct atgtgtacat gtgcttgcac gcacacacat gtagacacgc
32221 acacatgtgc acctgccatc acttctgct cttccgtctt ttcactcttg agtgtctgta
32281 gccagtagct ttccaggtct gtatagtcaa agatacctat ggccctgaat gtcttcactg
32341 attgctattt gacattcata cggttttaa tggttaaaag gctttatgcg aaagctgtga
32401 tagaatttct cctgttctag atgtggtgtt tattgcttta tttgtgact tttctctcag
32461 tagattgacc ttctccctca gtgtccaagc ctgcatagc atgatggcac ctgtaaactc
32521 agttctgtat cctggtatcc ttttctcttcc caagtagaag caattaagta atatatgtca
32581 tcaaaaccttt taagtgcac atacaaacaa aatcaactta ccaaactgct tcaaagttgt
32641 tccatgttta acactcttct ttctgagctc tgggtagaat gtcctattat tgttcatcat
32701 gaatatttga aattaaagaa ataaaactgt accattttct ttaagagcat ccatttgtac
32761 ttgataacat cttcagtcat atttcaatgc tggcaaagag gaggggagtt ctaaactgtg
32821 actcaatttt agaatctact ttttccaaat tattctgttt agtgcagaaa actaattaat
32881 agtgttgcat agaaaagtca ctgaagctaa gccagttatt acttcttaat gcatgattta
32941 ctgctttaag ttttcaaaac acaaccatag caatgtggta ttaattcaag tgattcttcc
33001 tatcatattg aacgatattt tcacgggtga aaaactcaca catcctacat cactgatagt
33061 ttatacagtg ttttagctgt ggctccctgc atgcaaaata agagttaatc aaatgtcagt
33121 gagaaccatc tcatcaagta gagggcttgt tttgtttaaa ttaactttgc taagtataaa
33181 tttcttcttg aaaataaatt ctgggccggg cgcggtggct cacgcctgta atcctagcac
33241 tttgggaggc cgaggcgggc ggatcacgag gtcaggagat cgagaccaaa ctggctaaca
33301 ctgtgaaacc ccgtctctac taaaaataca aaaatgagc cgggtgtgt ggcgggctcc
33361 tgtagtccca gctactcggg aggctgaggc aggagaatgg cgtgaacctg ggaggcagag
33421 cttgtggtga gccaagatca caccactgca ctccagcctg ggtgacagag cgagactccg
33481 tctcaaaaaa aaaaaaagg aaaataaatt cttctgtatt tttctttctt caagtgaggc
33541 catttagggg aagtatacc ataaaacttg ctctaagata aggcaaattt ggtattatag
33601 gatgaagtgc tatgtgattt gaagtaatgc tgaatttttt aaatatatta actaaacaa
33661 gaataatgag gccctcggaa agtcatgatt atatttctca ttttctcat tttaaagcca
33721 cagtgaaaaa cacataaaag gaagaagtta gaaaaaaaaa tgaatgaaat tctttttttc
33781 cttttggcaa attaaataga tgtttctgtt tcagaagatt ttattaatta actttaaga
33841 aacagtcatt tattttggc attcagtgaa cactatcatt tccatgttta gaactttct
33901 tctaagttag catcttaaaa gataactgtg aaactcaagg cattcaacta cattaatttg
33961 agtttcagaa attgaattct tgtttctaga gtacatagtt tgaattgatg tcagggtgtt
34021 aaatagataa atcttagctt cctaggttgt atattcacac taattatttt tttatcagcc
34081 ttcttatttt tcaacttacc ttattctttt tgttttttg acactcagat ttgatagcc
34141 tgtggtagaa gaaaacagta atacagtttg gttgttgtt gtgtttgtgt ttattttaaa
34201 gtcacggctt tgctttccat gttgttactg gattatgctt ttttaattc ttcagtttgc
34261 caagataaca gtcttccgat cttcagaagt ctgtatcaag cttaaggaaa ctgatgtgta
34321 ggaagactgg cctaagaagt ccaaattagc aaggctagca tgtgaggaca tgctggaaaa
34381 gaatagttcc catagatatt gacagagaat gttcataaaa tgctacttgt tttgtggtta
34441 catgagagta acttgtgtcc agtgcagctg tatgtaaggg caacgttttt attctgacga
```

Fig. 63M

```
34501 ctctgtggtt ttcatgaccc tggatgctta tcatgtctct ctgttggact tcttcaacgg
34561 agttgataca aatacttgct tccaagtgtc catctgcct ctcctcatc ctggccccat
34621 acaaatacgc tacatttta aataatttga aatacctca atagtattta tatttcctgg
34681 tgcttcattc tttccataag aactgtgata ccattatcct gtaggatttt tttgtgcttc
34741 cccgtttcac atctctgtgc cagtgagacc catatatcgg tgcaaatcca gaagtttgat
34801 tgtccatctg attagcacac tgttagcaat gtggtggact aaacacagcc aagatgtggg
34861 gctggagctt agcctcctgg gagcagagcg gtgaacatca gatgaagaca tgtgaaaatg
34921 gagtactact tcctcttcct ggggatgggc taaaaagcac agccagaaat attcttgccc
34981 ttccagtctg ctttacagtt actcactggt tctcttttt ttcctactca gataaccagt
35041 atactcttcc cagtgactaa gaactgcaga taagtatagg tgcaaataga tgcaaaccg
35101 cagatggcag ctgtgtggtt tcagatgtgc tgcagaactt tagacgatg tgaacgaag
35161 gaactttttt gctgagcagt aatctctacc cactggaaat taggccctgg ggggaacaat
35221 gtagtgactt ctatatactt actacatgca gttagaccc tgaagcaaaa gcttttaaaa
35281 acaggctgta aaatgcccat gtatctttat taagcctatt ttccaactgg atagagaaat
35341 tttctggtaa ttttaaatt tgtaaagtct atttttttcc tgagccaagg gaaaaaaaat
35401 atctgggccc taaaagctta gttataacaa tgttatttt tctatctctg aatgattaaa
35461 tgtgatttca tttatgtagc aatactatga ttgtggctgc attagatcac gctgatagaa
35521 agatacaaag aaaaactaag tataatgaac taacaattta ttttcactct ttctctaagt
35581 taaaaattcc cagtacattc aaatgaacaa tgaaaataat tgcagaattg tctcctgaaa
35641 tggaaataga tttttttcc caagcattag caatttcttg ttattttca aaatcagcca
35701 ctaagccttt cagagcttct tggtgactat tgcaggagaa atcagaatat taatcttgtg
35761 gttttattc agagttcgct gccaggaagg aggtataatt gggataggag actttttttt
35821 tttagctgtg tcactgttca aggagggggg tttggaacct cagcataaga attacactct
35881 gtgatgagga tgtagcaggg gagaagaaag gtgattttca ctatgggaag ctatacttac
35941 atcaagtata aaatagactg aagtcattt gaattacgtt atacttgtaa agtttacctc
36001 ctggagtttc agttagtacc agtgtactaa ctggttaaaa acagttcatg gcaccttaga
36061 tcatttataa ctcatggcaa aaatctttcc tggtggaacg tgtaactgta ttttaaatgc
36121 ccctttataa gcaaccaagt atttgggatg ttatttgat attagtagtg aattttcag
36181 tatcttccag taccctttgc aagtcacagg ttgacttaaa aggaaagaa gcaaaatgct
36241 gaatatagca gaaaaactgt ctgcattcag actgttcagc ccacttttgc tccccacgtg
36301 gcaagcacac tcccccaaac aagcaatagc ctgtggcttc agaggaacct acaaaggcag
36361 catctgtaga ttttttcctte ttcaactcta agactgaat gtttccctct tccccacaca
36421 cttttttttt aaaccaagaa ataaaaagt tttcactctt aaggtgcaa agcagtttca
36481 ttcttatgca acacagcctt cctcctactg tcttatagtc tgtggatgtt aaattataga
36541 ttccaattga attttaatac tctagagatt ttacattgt ggttgtcaag acccgtttt
36601 ggtaaaccta gggagctccg cacaaaagca ttgatattca gaaaaggcac tgacctacaa
36661 attaaagaa aaaaaaatca aataatgtgc acctcttgtg cttccagttt gacaaagcag
36721 aagtcatcag cagtttctcc ctctgcagac gcagttctca attctattta caagtaactg
36781 ctctactgtg cctgttttc tcttgctgat actcatttaa ttgttttctt ttggatctg
36841 aatctttgac tgtctttcc ccctcaagat taaaataaat acatctgtat tcctccctt
36901 tctttctgtg cactgccctt cagatctcat ttgtcattt ttcagcttag tgttgaaact
36961 tttagcaaca aaagtcagt tacttacttt gagtaagtaa ctcaaagtaa gttaactttg
37021 agttgagtg cacttttgcg tgtaggttca tttatgtgct tgtgaattta aaacattgg
37081 gattccacct gaatgaagta aaccaaacat tttaaactat cagccagata gagacatcag
37141 cctttcactt ctttctatat gcagacatat cctaatttt tagaaaaatc aaataggaaa
```

Fig.63N

```
37201 attctcaaca attaattgaa gattatagct ctgctctgaa atggtccaga aataggatct
37261 gctcatagaa actcatagtt tgaagcctct gggaggaaag gatactttaa aatttagtca
37321 catatttgga ggaggaaaa gggaagagc agaatgaaga actgaaaaaa atcacacacc
37381 ggggcctgtc gtgaggtggg ggactggggg agggatagca ttaggagata tacctaatgt
37441 aaatgacgag ttaacaggcg cagcccacca acatggcaca cgtatacata tgtaacaaac
37501 ctgcacgttg tgcacatgta ccctagaact taaagtataa taaaaaaaaa ttttaatagc
37561 cccattaaat aattaaaaag attttttta gattcacaga agtgtacaaa attttaggt
37621 ttttttttt taagctgtc tgctgaatag ttcttaatg gtctacaatg tttgtatcta
37681 caaacagata ctgtctgctt cttactaccc ttcaagaca agtattatta tggcaattat
37741 tgcccagttt cccgggaaaa atttatccac agttacagaa gaatgagatg caattgtgag
37801 actgtaaagt ttaagcaagc actcagagaa gcacagtgat atgtatgcac agaagaggca
37861 gtctttgttt tgaggaaaac agtgaaagta aagttaattc aagaccacaa agacaagtaa
37921 ataagtgcct tattttgta gttaatataa tttcagtgga atgcatattt ctaccataaa
37981 tgcatataga acttgtttgc tgacctactg tttggaaaac aaacaatccc attagaagaa
38041 tgtctttggg atttattttt accagaaaat caatcctttt ttcagtccct tgcaaagtac
38101 agtgttacaa gccaagactt tgataatcag gtagaaaatg gatttaaatt gcagaaatgt
38161 atatgaaaca ctttgttcc ttgccccttg aactttaggg gaatgaaaat gtctagcact
38221 ctccaccttc ttttctctcc tggaacttga actgtaattc aaagcctgtt tctcattaaa
38281 gtacctggca gcctatctct ttacagcttg agttacaaag ctattcagag acctcgctgg
38341 tctaaagaga cagaacaagg atgtgtttaa atagagcata ggctgttgaa aaaaaaatg
38401 ctgaaaatgg taaaatgatt ctgtccttcc ttccactcct cactgctgag gtggagaggg
38461 aattcagttg gtgaacacca gcaagtggct ggtaaaagtc cccactttct ctccagggct
38521 gccacaggac ccagaatgag tggtgggcat gtgtgtgaac cctctattca gcagagttt
38581 tcccgcaaca ggtagtttgg ttgaagaggt tgactaaggt tgacattggc agtaataaca
38641 cgtatgttct tctgatttac aaaacgatgg aggaaaaggg ggagattttg aagacctgat
38701 ttctggtata cttcttaagc atgcataagg ctgaaaaaag aagacaaggg ttgtggagg
38761 ctcctggtct agtgtttaca gaacttggat gctgacaaa cagagcgtca agctaattgt
38821 tcttgaagca ggaaatctgc agtggaggaa gcaggtgtgg gggatgatt accacgtttg
38881 gaaatggctg cattaactat tttgctcttc tgagtttggc cccaaaagag tccatagact
38941 tttgaagga tgccatccct tttatttata gactaacatt aaatcagtca tttgtgaagg
39001 aaggagaaag tgcctaaata aatttggagt cagatagcat acgtgcggca gtgtttccga
39061 tatccattc tctttatttc ttttctttt tctttttggc tttcagcatc cccatacttt
39121 cagaaaactt gtgactaaga gtgaattctt attttcaaa ttgttttcag acatttcatg
39181 ttcatgtaaa cttggcttat tgattcctg attttctt attttttgt tttgtccatt
39241 ttattttaa tcagctacat caaatgggtc tttggagggc ctggataacc aggagggagg
39301 ggtgtgccag acaagagcca tgaagatcct catgaaagtt ggacaaggta agaccatct
39361 gctgctcat gacgccactg tgacctggtg tagccccag ctagtatggt gctaatgttg
39421 ccgatgccca ccttcattcg ctcttctttt tagtctttcaa agcaaacct tctgcactt
39481 gagccactga cagatttcct caagtcaatg tactaagctt ttattggaga tctaagagtt
39541 aagatcagca aggtagaatg tctattgcca tagatagata gatagataga tagataatag
39601 atagatagat agatagatag atatttcttt ttaaaagca aaacactttg gttcaaaatc
39661 aaatatccga gaatgaaaac taaagcttg tgcagttttg ctcattctg aatcttgact
39721 acagaagagt ttgttcatt gtgacttttc caatatagat aacctattgt gcagaaagaa
39781 ataattatc ttctaattaa aaattggtat agtagtcaat caacttgctc agttaaattg
39841 aaatgtcatc tgcaatgctt tgcctgccaa atgcaagaat ccctatagtt tccacagatg
```

Fig.63O

```
39901 gctcacgtt ctaaactct gaaataacta gtataaccat ttgttttaa aagaaaatt
39961 atattcttgt atttcacagt actttgcata aagactctta tgttcattgc tattcatgcc
40021 tgttgaaata tatatgcagc tcctaaagct agatattgtc agatgtctgt gccgtaatta
40081 atcattgtt tttcatatag atgcaagttc tgctggatca accaggaata aagatccaac
40141 aagacgtcca gaactagaag ctggtacaaa tggaagaagt tgacaacaa gtcccttgt
40201 aaaaccaaat ccaggtataa cagcatgatc tgtgtgtatg gaggtctgtg ggtaccacat
40261 tcttagtagt atcttaaaag gtagggcaga gtctaaagac ttctaaccag ttaggattag
40321 ctggaagtta cagtgatcag gaatctttgc tgtcagtgag tcattattaa ttcactcaa
40381 taagaacaaa ataactcatt ccaatgaaag tcatatattc aaaggagtag agttcatgag
40441 ctgtaagtgc cagttattag aactactctg tcaggccaaa ggtttcattg gctgacattt
40501 tatcaagctg gttgtcaact ccagcttaaa gctgatgtta atgtatatgt aattaatgtg
40561 ctaatcctc atctaattat atctaagcca cagagggttt aattgatcct cttctaaatt
40621 ttaaatggta acatttttaa atattgcata atagtatttt tcaggtggt tatcgttatt
40681 ttgtttcaca ttttccatgt aaaagaaaat attaaacagg tccctgacaa aagtgtagaa
40741 taccagataa aattgtccgt cgttgacctt cgtttcttta acagtcttgg aacaaatagt
40801 tctgtatttg ttaccatgct aatgaaggtt tatagagta gctgttgagc agacatcagc
40861 agttttgtat taggattgtt gtgtgcttgc tggtcgttg tgcaaattta tgtctgcag
40921 caatattcca tcccttcca agagtcaagg gggaagttg ttatttctaa ctttcaatga
40981 caagatgtgt caaattcttg tgacaaactg ataaatggat aatataatga tgccaggcag
41041 tttttagtg cttaacattt gggctggcag tctgttcggt gtgagagttt ctgctgcctt
41101 ccaaatatat ttaagtgta aatcaaataa tacagacgag ttacgagctg aacatttcc
41161 caggccccct cactcctcc gcgttcccga gctgttctgt tctgccagga ggcagggtc
41221 ttctttagaa ggcaggccct ttgaaggttt gcatgaaaat ccctttctca aaggaggcgg
41281 aagagcaata ccacataaac gctcacgct gacctggaga attggcaact tccctttttc
41341 ttccctgccg ctgcccagg ctggctgaca cgggttagaa gatgaagcaa gatcaagggc
41401 tggctgtcac cgaaagtctg tgctcttgct ggataatgat acaaggaaa cctgtggct
41461 tgggagggta gggaagtccc tcctagagat accctctcatt tccttttgcg ttgagctctt
41521 agacgaggta ttggcgaggc aaagtccagc ttctagttag taataagcct ggcttatttt
41581 tcacattttt aagggtcata aaagcagtcc gtctgaactg ggacagcagt aactatctct
41641 gaccttttct gtctccgcgt ctgcaggttc tagcacagac ggcaacagcg ccggacattc
41701 ggggaacaac atcctcggtt ccgaagtggc cttattgca gggattgctt caggatgcat
41761 catcttcatc gtcatcatca tcacgctggt ggtcctcttg ctgaagtacc ggaggagaca
41821 caggaagcac tgccgcagc acacgaccac gctgtcgctc agcacactgg ccacacccaa
41881 gcgcagcggc aacaacaacg gctcagagcc cagtgacatt atcatcccgc taaggactgc
41941 ggacagcgtc ttctgccctc actacgagaa ggtcagcggc gactacggc accggtgta
42001 catcgtccag gagatgcccc cgcagagccc ggcgaacatt tactacaagg tctgagaggg
42061 accctggtgg tactgtgct ttccagagg acacctaatg tccgatgcc tccttgagg
42121 gttgagagc ccgcgtgctg gagaattgac tgaagcacag cacggggga gagggacact
42181 cctcctcgga agagcccgtc gcgctggaca gttaactag tcttgtagca ttcggccttg
42241 gtgaacacac acgctccctg gaagctggaa gactgtgcag aagacgccca ttcggactgc
42301 tgtgccgcgt cccacgtatc ctcctcgaag ccatgtgctg cggtcactca ggcctctgca
42361 gaagccaagg gaagacagtg gtttgtggac gagagggctg tgagcatcct ggcaggtgcc
42421 ccaggatgcc acgcctggaa gggcaggctt ctgctggggg tgcattccc ccgcagtgca
42481 taccggactt gtcacacgga cctcggccta gttaaggtgt gcaaagatct ctagagttta
42541 gtccttactg tatcactcgt tctgttaccc agggctctgc agcactcac ctgagacctc
```

Fig. 63P

```
42601 cactccacat ctgcatcact catggaacac tcatgtctgg agtccctcc tccagccgct
42661 ggcaacaaca gcttcagtcc atgggtaatc cgttcataga aattgtgttt gctaacaagg
42721 tgcccttag ccagatgcta ggctgtctgc gaagaaggct aggagttcat agaagggagt
42781 gggctgggg aaagggctgg ctgcaattgc agctcactgc tgctgcctct gaaacagaaa
42841 gttggaaagg aaaaagaaa aaagcaatta ggtagcacag cactttggtt ttgctgagat
42901 cgaagaggcc agtaggagac acgacagcac acacagtgga ttccagtgca tgggaggca
42961 ctcgctgtta tcaaatagcg atgtgcagga agaaagccc ctcttcattc cggggaacaa
43021 agacgggtat tgttgggaaa ggaacaggct tggagggaag ggagaaagta ggccgctgat
43081 gatatattcg ggcaggactg ttgtggtact ggcaataaga tacacagctc cgagctgtag
43141 gagagtcggt ctgctttgga tgatttttta agcagactca gctgctatac ttatcacatt
43201 ttattaaaca cagggaaagc atttaggaga atagcagaga gccaaatctg acctaaaagt
43261 tgaaaagcca aaggtcaaac aggctgtaat tccatcatca tgttgttat taagaatcc
43321 ttatctataa aagtaggtc agatccccct cccccaggt tcttccttcc cctcccgatt
43381 gagccttacg cactttggt ttatgcggtg ctgtccgggt gccagggctg cagggtcggt
43441 actgatggag gctgcagcgc ccggtgctct gtgtcaaggt gaagcacata cggcagcct
43501 cttagagtcc ttaagacgga agtaaattat gatgtccagg gggagaagga agataggacg
43561 tatttataat aggtatatag aacacaaggg atataaaatg aaagattttt actaatatat
43621 attttaaggt tgcacacagt acacaccaga agatgtgaaa ttcatttgtg gcaattaagt
43681 ggtcccaatg ctcagcgctt aaaaaaacaa attggacagc tacttctggg aaaaacaaca
43741 tcattccaaa agaacaata atgagagcaa atgcaaaaat aaccaagtcc tccgaaggca
43801 tctcacggaa ccgtagacta ggaagtacga gcccacaga gcaggaagcc gatgtgactg
43861 catcatatat ttaacaatga caagatgttc cggcgtttat ttctgcgttg ggttttccct
43921 tgccttatgg gctgaagtgt tctctaga
```

Fig.63Q

EphrinB2, mRNA

```
   1 gcgggagct gggagtggct tcgccatggc tgtgagaagg gactccgtgt ggaagtactg
  61 ctggggtgtt ttgatggttt tatgcagaac tgcgatttcc aaatcgatag ttttagagcc
 121 tatctattgg aattcctcga actccaaatt tctacctgga caaggactgg tactatacCC
 181 acagatagga gacaaattgg atattatttg ccccaaagtg gactctaaaa ctgttggcca
 241 gtatgaatat tataaagttt atatggttga taagaccaa gcagacagat gcactattaa
 301 gaaggaaaat acccctctcc tcaactgtgc caaccagac caagatatca aattcaccat
 361 caagtttcaa gaattcagcc ctaacctctg gggtctagaa tttcagaaga caaagatta
 421 ttacattata tctacatcaa atgggtcttt ggagggcctg ataaccagg agggaggggt
 481 gtgccagaca agagccatga agatcctcat gaaagttgga caagatgcaa gttctgctgg
 541 atcaaccagg aataaagatc aacaagacg tccagaacta gaagctggta caaatggaag
 601 aagttcgaca acaagtccct ttgtaaaacc aaatccaggt tctagcacag acggcaacag
 661 cgccggacat tcggggaaca acatcctcgg ttccgaagtg gcttatttg cagggattgc
 721 ttcaggatgc atcatcttca tgtcatcat catcacgctg gtggtcctct tgctgaagta
 781 ccggaggaga cacaggaagc actgccgca gcacacgacc acgtgtcgc tcagcacact
 841 ggccacaccc aagcgcagcg gcaacaacaa cggctcagag ccagtgaca ttatcatccc
 901 gctaaggact gcggacagcg tcttctgccc tcactacgag aagtcagcg gggactacgg
 961 gcaccgtg tacatcgtcc aggagatgcc ccgcagagc cggcgaaca tttactacaa
1021 ggtctgagag ggacctggt ggtacctgtg ctttcccaga ggacacctaa tgtcccgatg
1081 cctccttga gggtttgaga gcccgcgtgc tggagaattg actgaagcac agcacgggg
1141 gagagggaca ctcctcctcg gaagagcccg tcgcgctgga cagcttacct agtcttgtag
1201 cattcggcct tgtgaacac acacgctcc tggaagctgg aagactgtgc agaagacgcc
1261 cattcggact gctgtgccgc gtccacgtc tcctcctcga agccatgtgc tcggtcact
1321 caggcctctg cagaagccaa gggaagacag tggtttgtgg acgagagggc tgtgagcatc
1381 ctggcaggtg cccaggatg ccacgcctgg aaggccggc ttctgctgg ggtgcattc
1441 ccccgcagtg catacggac ttgtcacacg gacctcggcc tagttaaggt gtgcaaagat
1501 ctctagagtt tagtccttac tgtctcactc gttctgttac ccagggctct gcagcacctc
1561 acctgagacc tccactccac atctgcatca ctcatggaac actcatgtct ggagtcccct
1621 cctccagccg ctggcaacaa cagcttcagt ccatgggtaa tccgttcata gaaattgtgt
1681 ttgctaacaa ggtgcccttt agccagatgc tagctgtct gcgaagaagg ctaggagttc
1741 atagaaggga gtggggctgg ggaagggct ggctgcaatt gcagctcact gctgctgcct
1801 ctgaaacaga aagttggaaa ggaaaaaga aaaagcaat taggtagcac agcactttgg
1861 ttttgctgag atcgaagagg ccagtaggag acacgacagc acacagtg gattccagtg
1921 catgggagg cactcgctgt tatcaaatag cgatgtgcag gaagaaaagc ccctcttcat
1981 tccggggaac aaagacgggt attgttggga aggaacagg cttggaggga agggagaaag
2041 taggccgctg atgatatatt cggcaggac tgttgtggta ctgcaataa gatacacagc
2101 tccgagctgt aggagagtcg gtctgtttg gatgattttt taagcagact cagctgctat
2161 acttatcaca ttttattaaa cacagggaaa gcatttagga aatagcaga gagccaaatc
2221 tgacctaaaa gttgaaaagc caaaggtcaa aacaggctgta attccatcat catcgttgtt
2281 attaaagaat cctatctat aaaaggtagg tcagatcccc ctccccccag gttcctcctt
2341 cccctccga ttgagcctta cgacactttg gttatgcgg tgctgtccgg gtgccaggc
2401 tgcagggtcg gtactgatgg aggctgcagc gcccggtgct ctgtcaag gtgaagcaca
2461 tacggcagac ctctagagt ccttaagacg gaagtaaatt atgatgtcca ggggagaag
2521 gaagatagga cgtatttata ataggtatat agaacacaag ggatataaaa tgaaagattt
2581 ttactaatat atatttaag gttgcacaca gtacacacca gaagatgtga aattcatttg
```

Fig.64A

```
2641 tggcaattaa gtggtcccaa tgctcagcgc ttaaaaaaac aaattggaca gctacttctg
2701 ggaaaaacaa catcattcca aaaagaacaa taatgagagc aaatgcaaaa ataaccaagt
2761 cctccgaagg catctcacgg aaccgtagac taggaagtac gagcccaca gagcaggaag
2821 ccgatgtgac tgcatcatat atttaacaat gacaagatgt tccggcgttt atttctgcgt
2881 tgggttttcc cttgcttat gggctgaagt gttctctaga atcagcagg tcacactggg
2941 ggcttcaggt gadgatttag ctgtggctcc ctcctcctgt cctacccgc accccctccc
3001 ttctgggaaa caagaagagt aaacaggaaa cctactttt atgtgctatg caaatagac
3061 atctttaaca tagtcctgtt actatggtaa cactttgctt tctgaattgg aagggaaaaa
3121 aaatgtagcg acagcatttt aaggttctca gacctccagt gagtacctgc aaaaatgagt
3181 tgtcacagaa attatgatcc tctatttcct gaacctggaa atgatgttgg tccaaagtgc
3241 gtgtgtgtat gtgtgagtgg gtgcgtggta tacatgtgta catatatgta taatatatat
3301 ctacaatata tattatatat atctatatca tatttctgtg gagggttgcc atggtaacca
3361 gccacagtac atatgtaatt ctttccatca cccaacctc tcctttctgt gcattcatgc
3421 aagagtttct tgtaagccat cagaagttac tttaggatg ggggagaggg gcgagaaggg
3481 gaaaaatggg aaatagtctg attttaatga aatcaaatgt atgtatcatc agttggctac
3541 gttttggttc tatgctaaac tgtgaaaaat cagatgaatt gataaaagag ttccctgcaa
3601 ccaattgaaa agtgttctgt gcgtctgttt tgtgtctggt gcagaatatg acaatctacc
3661 aactgtccct ttgtttgaag ttggtttagc tttgaaagt tactgtaaat gccttgcttg
3721 tatgatcgtc cctggtcacc cgactttgga atttgcacca tcatgtttca gtgaagatgc
3781 tgtaaatagg ttcagatttt actgtctatg gattggggt gttacagtag cctattcac
3841 ctttttaata aaaatacaca tgaaacaag aaagaaatgg cttttcttac ccagattgtg
3901 tacatagagc aatgttggtt ttttataaag tctaagcaag atgttttgta taaatctga
3961 attttgcaat gtatttagct acagcttgtt taacggcagt gtcattcccc tttgcactgt
4021 aatgaggaaa aaatggtata aaggttgcc aaattgctgc atatttgtgc cgtaattatg
4081 taccatgaat atttatttaa aatttcgttg tccaattgt aagtaacaca gtattatgcc
4141 tgagttataa atatttttt ctttcttgt tttatcttaa tagctgtca taggttttaa
4201 atctgcttta gttcacatt gcagttagcc ccagaaatg aaatccgtga agtcacattc
4261 cacatctgtt tcaaactgaa ttgttcttta aaaaataaa atattttttt cctatggaaa
4321 aaaaaaaaa aaaaa
```

Fig. 64B

EphB4 Precursor Protein

```
  1 melrvllcwa slaaalestl lntkletadl kwvtfpqvdg qweelsqlde eqhsvrtyev
 61 cdvqrapgqa hwlrtgwvpr rgavhvyatl rftmleclsl pragrscket ftvfyyesda
121 dtataltpaw menpyikvdt vaaehltrkr pgaeatgkvn vktlrlgpls kagfylafqd
181 qgacmallsl hlfykkcagl tvnltrfpet vprelvvpva gscvvdavps pgpspslyor
241 edgqwaeqpv tgcscapgfe aaegntkcra caqgtfkpls gegscqpcpa nshsntigsa
301 vcqcrvgyfr artdprgapc ttppsaprsv vsrlngsslh lewsaplesg gredltyalr
361 cracrpggsc apcggdltfd pgprdlvepw vvvrglrpdf tytfevtaln gvsslatgpv
421 pfepvnvttd revppavsdi rvtrsspssl slawavprap sgavldyevk yhekgaeqps
481 svrflktsen raelrglkrg asylvqvrar seagygpfgq ehhsqtqlde segwreqlal
541 iagtavgvv lvlvvivvav lclrkqsngr eaeysdkhgq ylighgtkvy idpftyedpn
601 eavrefakei dvsyvkieev igagefgevc rgrlkapgkk escvaiktlk ggyterqrre
661 flseasimgq fehpniirle gvvtnsmpvm iltefmenga ldsflrlndg qftviqlvgm
721 lrgiasgmry laemsyvhrd laarnilvns nlvckvsdfg lsrfleenss dptytsslgg
781 kipirvtape alafrkftsa sdawsygivm wevmsfgerp ywdmsnqdvi naieqdyrlp
841 pppdcptslh qlmldcwqkd rnarprfpqv vsaldkmirn paslkivare nggashplld
901 qrqphysafg svgewlraik mgryeesfaa agfgsfelvs qisaedllri gvtlaghqkk
961 ilasvqhmks qakpgtpggt ggpapqy
```

Fig. 65

EphrinB2

```
  1 mavrrdsvwk ycwgvlmvlc rtaisksivl epiywnssna kflpgqqlvl ypqigdkldi
 61 icpkvdsktv gqyeyykvym vdkdqadrct ikkentplla cakpdqdikf tikfqefspn
121 lwglefqknk dyyiistsng sleglndqeg gvcqtramki lmkvgqdass agstrnkdpt
181 rrpeleagtn grssttspfv kpnpgsstdg nsaghsgnni lgsevalfag iasgciifiv
241 iiitlvvlll kyrrhrkhs pqhttttsls tlatpkrsgn nngsepsdii iplrtadsvf
301 cphyekvsgd yghpvyivqe mppqspaniy ykv
```

Fig. 66

POLYPEPTIDE COMPOUNDS FOR INHIBITING ANGIOGENESIS AND TUMOR GROWTH

RELATED APPLICATIONS

This application is a continuation of U.S. application Ser. No. 13/420,776 filed Mar. 15, 2012, now abandoned, which is a continuation of U.S. application Ser. No. 12/584,993 filed Sep. 14, 2009, now abandoned, which is a continuation of U.S. application Ser. No. 11/234,482 filed Sep. 23, 2005, now abandoned, which claims the benefit of the filing date of U.S. Provisional Application No. 60/612,488 filed Sep. 23, 2004, the specifications of which are incorporated by reference herein in their entireties.

BACKGROUND OF THE INVENTION

Angiogenesis, the development of new blood vessels from the endothelium of a preexisting vasculature, is a critical process in the growth, progression, and metastasis of solid tumors within the host. During physiologically normal angiogenesis, the autocrine, paracrine, and amphicrine interactions of the vascular endothelium with its surrounding stromal components are tightly regulated both spatially and temporally. Additionally, the levels and activities of proangiogenic and angiostatic cytokines and growth factors are maintained in balance. In contrast, the pathological angiogenesis necessary for active tumor growth is sustained and persistent, representing a dysregulation of the normal angiogenic system. Solid and hematopoietic tumor types are particularly associated with a high level of abnormal angiogenesis.

It is generally thought that the development of tumor consists of sequential, and interrelated steps that lead to the generation of an autonomous clone with aggressive growth potential. These steps include sustained growth and unlimited self-renewal. Cell populations in a tumor are generally characterized by growth signal self-sufficiency, decreased sensitivity to growth suppressive signals, and resistance to apoptosis. Genetic or cytogenetic events that initiate aberrant growth sustain cells in a prolonged "ready" state by preventing apoptosis.

It is a goal of the present disclosure to provide agents and therapeutic treatments for inhibiting angiogenesis and tumor growth.

SUMMARY OF THE INVENTION

In certain aspects, the disclosure provides polypeptide agents that inhibit EphB4 or EphrinB2 mediated functions, including monomeric ligand binding portions of the EphB4 and EphrinB2 proteins. As demonstrated herein, EphB4 and EphrinB2 participate in various disease states, including cancers and diseases related to unwanted or excessive angiogenesis. Accordingly, certain polypeptide agents disclosed herein may be used to treat such diseases. In further aspects, the disclosure relates to the discovery that EphB4 and/or EphrinB2 are expressed, often at high levels, in a variety of tumors. Therefore, polypeptide agents that down-regulate EphB4 or EphrinB2 function may affect tumors by a direct effect on the tumor cells as well as an indirect effect on the angiogenic processes recruited by the tumor. In certain embodiments, the disclosure provides the identity of tumor types particularly suited to treatment with an agent that downregulates EphB4 or EphrinB2 function. In preferred embodiments, polypeptides disclosed herein are modified so as to have increased serum half-life in vivo.

In certain aspects, the disclosure provides soluble EphB4 polypeptides comprising an amino acid sequence of an extracellular domain of an EphB4 protein. The soluble EphB4 polypeptides bind specifically to an EphrinB2 polypeptide. The term "soluble" is used merely to indicate that these polypeptides do not contain a transmembrane domain or a portion of a transmembrane domain sufficient to compromise the solubility of the polypeptide in a physiological salt solution. Soluble polypeptides are preferably prepared as monomers that compete with EphB4 for binding to ligand such as EphrinB2 and inhibit the signaling that results from EphB4 activation. Optionally, a soluble polypeptide may be prepared in a multimeric form, by, for example, expressing as an Fc fusion protein or fusion with another multimerization domain. Such multimeric forms may have complex activities, having agonistic or antagonistic effects depending on the context. In certain embodiments the soluble EphB4 polypeptide comprises a globular domain of an EphB4 protein. A soluble EphB4 polypeptide may comprise a sequence at least 90% identical to residues 1-522 of the amino acid sequence defined by FIG. 65 (SEQ ID NO:10). A soluble EphB4 polypeptide may comprise a sequence at least 90% identical to residues 1-412 of the amino acid sequence defined by FIG. 65 (SEQ ID NO:10). A soluble EphB4 polypeptide may comprise a sequence at least 90% identical to residues 1-312 of the amino acid sequence defined by FIG. 65 (SEQ ID NO:10). A soluble EphB4 polypeptide may comprise a sequence encompassing the globular (G) domain (amino acids 29-197 of FIG. 65, SEQ ID NO:10), and optionally additional domains, such as the cysteine-rich domain (amino acids 239-321 of FIG. 65, SEQ ID NO:10), the first fibronectin type 3 domain (amino acids 324-429 of FIG. 65, SEQ ID NO:10) and the second fibronectin type 3 domain (amino acids 434-526 of FIG. 65, SEQ ID NO:10). Preferred polypeptides described herein and demonstrated as having ligand binding activity include polypeptides corresponding to 1-537, 1-427 and 1-326, respectively, of the amino acid sequence shown in FIG. 65 (SEQ ID NO:10). A soluble EphB4 polypeptide may comprise a sequence as set forth in FIG. 1 or 2 (SEQ ID Nos. 1 or 2). As is well known in the art, expression of such EphB4 polypeptides in a suitable cell, such as HEK293T cell line, will result in cleavage of a leader peptide. Although such cleavage is not always complete or perfectly consistent at a single site, it is known that EphB4 tends to be cleaved so as to remove the first 15 amino acids of the sequence shown in FIG. 65 (SEQ ID NO:10). Accordingly, as specific examples, the disclosure provides unprocessed soluble EphB4 polypeptides that bind to EphrinB2 and comprise an amino acid sequence selected from the following group (numbering is with respect to the sequence of FIG. 65, SEQ ID NO:10): 1-197, 29-197, 1-312, 29-132, 1-321, 29-321, 1-326, 29-326, 1-412, 29-412, 1-427, 29-427, 1-429, 29-429, 1-526, 29-526, 1-537 and 29-537. Additionally, heterologous leader peptides may be substituted for the endogenous leader sequences. Polypeptides may be used in a processed form, such forms having a predicted amino acid sequence selected from the following group (numbering is with respect to the sequence of FIG. 65, SEQ ID NO:10): 16-197, 16-312, 16-321, 16-326, 16-412, 16-427, 16-429, 16-526 and 16-537. Additionally, a soluble EphB4 polypeptide may be one that comprises an amino acid sequence at least 90%, and optionally 95% or 99% identical to any of the preceding amino acid sequences while retaining EphrinB2 binding activity. Preferably, any variations in the amino acid sequence from the sequence shown in FIG. 65 (SEQ ID NO:10) are conservative changes or deletions of no more than 1, 2, 3, 4 or 5 amino acids, particularly in a surface loop region. In certain embodiments, the soluble EphB4 polypeptide may inhibit the interaction between Ephrin B2 and EphB4. The soluble EphB4 polypeptide may inhibit clustering of or phosphorylation of Ephrin B2 or EphB4. Phosphorylation of EphrinB2 or EphB4 is generally considered to be one of the initial events in triggering intracellular signaling pathways regulated by these proteins. As noted above, the soluble EphB4 polypeptide may be prepared as a monomeric or multimeric fusion protein. The soluble polypeptide may include one or more modified amino acids. Such amino acids may contribute to desirable properties, such as increased resistance to protease digestion.

The present disclosure provides soluble EphB4 polypeptides having an additional component that confers increased serum half-life while still retaining EphrinB2 binding activity. In certain embodiments soluble EphB4 polypeptides are monomeric and are covalently linked to one or more polyoxyaklylene groups (e.g., polyethylene, polypropylene), and preferably polyethylene glycol (PEG) groups. Accordingly, one aspect of the invention provides modified EphB4 polypeptides, wherein the modification comprises a single polyethylene glycol group covalently bonded to the polypeptide. Other aspects provide modified EphB4 polypeptides covalently bonded to one, two, three, or more polyethylene glycol groups.

The one or more PEG may have a molecular weight ranging from about 1 kDa to about 100 kDa, and will preferably have a molecular weight ranging from about 10 to about 60 kDa or about 10 to about 40 kDa. The PEG group may be a linear PEG or a branched PEG. In a preferred embodiment, the soluble, monomeric EphB4 conjugate comprises an EphB4 polypeptide covalently linked to one PEG group of from about 10 to about 40 kDa (monoPEGylated EphB4), or from about 15 to 30 kDa, preferably via an s-amino group of EphB4 lysine or the N-terminal amino group. Most preferably, EphB4 is randomly PEGylated at one amino group out of the group consisting of the s-amino groups of EphB4 lysine and the N-terminal amino group.

In one embodiment, the pegylated polypeptides provided by the invention have a serum half-life in vivo at least 50%, 75%, 100%, 150% or 200% greater than that of an unmodified EphB4 polypeptide. In another embodiment, the pegylated EphB4 polypeptides provided by the invention inhibit EphrinB2 activity. In a specific embodiment, they inhibit EphrinB2 receptor clustering, EphrinB2 phosphorylation, and/or EphrinB2 kinase activity.

Surprisingly, it has been found that monoPEGylated EphB4 according to the invention has superior properties in regard to the therapeutic applicability of unmodified soluble EphB4 polypeptides and poly-PEGylated EphB4. Nonetheless, the disclosure also provides poly-PEGylated EphB4 having PEG at more than one position. Such polyPEGylated forms provide improved serum-half life relative to the unmodified form.

In certain embodiments, a soluble EphB4 polypeptide is stably associated with a second stabilizing polypeptide that confers improved half-life without substantially diminishing EphrinB2 binding. A stabilizing polypeptide will preferably be immunocompatible with human patients (or animal patients, where veterinary uses are contemplated) and have little or no significant biological activity.

In a preferred embodiment, the stabilizing polypeptide is a human serum albumin, or a portion thereof. A human serum albumin may be stably associated with the EphB4 polypeptide covalently or non-covalently. Covalent attachment may be achieved by expression of the EphB4 polypeptide as a co-translational fusion with human serum albumin. The albumin sequence may be fused at the N-terminus, the C-terminus or at a non-disruptive internal position in the soluble EphB4 polypeptide. Exposed loops of the EphB4 would be appropriate positions for insertion of an albumin sequence. Albumin may also be post-translationally attached to the EphB4 polypeptide by, for example, chemical cross-linking. An EphB4 polypeptide may also be stably associated with more than one albumin polypeptide. In some embodiments, the albumin is selected from the group consisting of a human serum albumin (HSA) and bovine serum albumin (BSA). In other embodiments, the albumin is a naturally occurring variant. In one preferred embodiment, the EphB4-HSA fusion inhibits the interaction between Ephrin B2 and EphB4, the clustering of Ephrin B2 or EphB4, the phosphorylation of Ephrin B2 or EphB4, or combinations thereof. In other embodiments, the EphB4-HSA fusion has enhanced in vivo stability relative to the unmodified wildtype polypeptide.

In certain aspects, the disclosure provides soluble EphrinB2 polypeptides comprising an amino acid sequence of an extracellular domain of an EphrinB2 protein. The soluble EphrinB2 polypeptides bind specifically to an EphB4 polypeptide. The term "soluble" is used merely to indicate that these polypeptides do not contain a transmembrane domain or a portion of a transmembrane domain sufficient to compromise the solubility of the polypeptide in a physiological salt solution. Soluble polypeptides are preferably prepared as monomers that compete with EphrinB2 for binding to ligand such as EphB4 and inhibit the signaling that results from EphrinB2 activation. Optionally, a soluble polypeptide may be prepared in a multimeric form, by, for example, expressing as an Fc fusion protein or fusion with another multimerization domain. Such multimeric forms may have complex activities, having agonistic or antagonistic effects depending on the context. A soluble EphrinB2 polypeptide may comprise residues 1-225 of the amino acid sequence defined by FIG. 66 (SEQ ID NO:11). A soluble EphrinB2 polypeptide may comprise a sequence defined by FIG. 3. As is well known in the art, expression of such EphrinB2 polypeptides in a suitable cell, such as HEK293T cell line, will result in cleavage of a leader peptide. Although such cleavage is not always complete or perfectly consistent at a single site, it is known that EphrinB2 tends to be cleaved so as to remove the first 26 amino acids of the sequence shown in FIG. 66 (SEQ ID NO:11). Accordingly, as specific examples, the disclosure provides unprocessed soluble EphrinB2 polypeptides that bind to EphB4 and comprise an amino acid sequence corresponding to amino acids 1-225 of FIG. 66 (SEQ ID NO:11). Such polypeptides may be used in a processed form, such forms having a predicted amino acid sequence selected from the following group (numbering is with respect to the sequence of FIG. 66, SEQ ID NO:11): 26-225. In certain embodiments, the soluble EphrinB2 polypeptide may inhibit the interaction between Ephrin B2 and EphB4. The soluble EphrinB2 polypeptide may inhibit clustering of or phosphorylation of EphrinB2 or EphB4. As noted above, the soluble EphrinB2 polypeptide may be prepared as a monomeric or multimeric fusion protein. The soluble polypeptide may include one or more modified amino acids. Such amino acids may contribute to desirable properties, such as increased resistance to protease digestion.

In certain aspects, the disclosure provides pharmaceutical formulations comprising a polypeptide reagent and a pharmaceutically acceptable carrier. The polypeptide reagent may be any disclosed herein, including, for example, soluble EphB4 or EphrinB2 polypeptides. Additional formulations include cosmetic compositions and diagnostic kits.

In certain aspects the disclosure provides methods of inhibiting signaling through Ephrin B2/EphB4 pathway in a cell. A method may comprise contacting the cell with an effective amount of a polypeptide agent, such as (a) a soluble polypeptide comprising an amino acid sequence of an extracellular domain of an EphB4 protein, wherein the EphB4 polypeptide is a monomer and binds specifically to an Ephrin B2 polypeptide; (b) a soluble polypeptide comprising an amino acid sequence of an extracellular domain of an Ephrin B2 protein, wherein the soluble Ephrin B2 polypeptide is a monomer and binds with high affinity to an EphB4 polypeptide.

In certain aspects the disclosure provides methods for reducing the growth rate of a tumor, comprising administering an amount of a polypeptide agent sufficient to reduce the growth rate of the tumor. The polypeptide agent may be selected from the group consisting of: (a) a soluble polypeptide comprising an amino acid sequence of an extracellular domain of an EphB4 protein, wherein the EphB4 polypeptide is a monomer and binds specifically to an Ephrin B2 polypeptide, and optionally comprises an additional modification to increase serum half-life, such as a PEGylation or serum albumin or both; (b) a soluble polypeptide comprising an amino acid sequence of an extracellular domain of an Ephrin B2 protein, wherein the soluble Ephrin B2 polypeptide is a monomer and binds with high affinity to an EphB4 polypeptide Optionally, the tumor comprises cells expressing a higher level of EphB4 and/or EphrinB2 than noncancerous cells of a comparable tissue.

In certain aspects, the disclosure provides methods for treating a patient suffering from a cancer. A method may comprise administering to the patient a polypeptide agent. The polypeptide agent may be selected from the group consisting of: (a) a soluble polypeptide comprising an amino acid sequence of an extracellular domain of an EphB4 protein, wherein the EphB4 polypeptide is a monomer and binds specifically to an Ephrin B2 polypeptide, and optionally comprises an additional modification to increase serum half-life, such as a PEGylation or serum albumin or both; (b) a soluble polypeptide comprising an amino acid sequence of an extracellular domain of an Ephrin B2 protein, wherein the soluble Ephrin B2 polypeptide is a monomer and binds with high affinity to an EphB4 polypeptide. Optionally, the cancer comprises cancer cells expressing EphrinB2 and/or EphB4 at a higher level than noncancerous cells of a comparable tissue. The cancer may be a metastatic cancer. The cancer may be selected from the group consisting of colon carcinoma, breast tumor, mesothelioma, prostate tumor, squamous cell carcinoma, Kaposi sarcoma, and leukemia. Optionally, the cancer is an angiogenesis-dependent cancer or an angiogenesis independent cancer. The polypeptide agent employed may inhibit clustering or phosphorylation of Ephrin B2 or EphB4. A polypeptide agent may be co-administered with one or more additional anti-cancer chemotherapeutic agents that inhibit cancer cells in an additive or synergistic manner with the polypeptide agent.

In certain aspects, the disclosure provides methods of inhibiting angiogenesis. A method may comprise contacting a cell with an amount of a polypeptide agent sufficient to inhibit angiogenesis. The polypeptide agent may be selected from the group consisting of: (a) a soluble polypeptide comprising an amino acid sequence of an extracellular domain of an EphB4 protein, wherein the EphB4 polypeptide is a monomer and binds specifically to an Ephrin B2 polypeptide, and optionally comprises an additional modification to increase serum half-life, such as a PEGylation or serum albumin or both; (b) a soluble polypeptide comprising an amino acid sequence of an extracellular domain of an Ephrin B2 protein, wherein the soluble Ephrin B2 polypeptide is a monomer and binds with high affinity to an EphB4 polypeptide.

In certain aspects, the disclosure provides methods for treating a patient suffering from an angiogenesis-associated disease, comprising administering to the patient a polypeptide agent. The polypeptide agent may be selected from the group consisting of: (a) a soluble polypeptide comprising an amino acid sequence of an extracellular domain of an EphB4 protein, wherein the EphB4 polypeptide is a monomer and binds specifically to an Ephrin B2 polypeptide, and optionally comprises an additional modification to increase serum half-life, such as a PEGylation or serum albumin or both; (b) a soluble polypeptide comprising an amino acid sequence of an extracellular domain of an Ephrin B2 protein, wherein the soluble Ephrin B2 polypeptide is a monomer and binds with high affinity to an EphB4 polypeptide. The soluble polypeptide may be formulated with a pharmaceutically acceptable carrier. An angiogenesis related disease or unwanted angiogenesis related process may be selected from the group consisting of angiogenesis-dependent cancer, benign tumors, inflammatory disorders, chronic articular rheumatism and psoriasis, ocular angiogenic diseases, Osler-Webber Syndrome, myocardial angiogenesis, plaque neovascularization, telangiectasia, hemophiliac joints, angiofibroma, telangiectasia psoriasis scleroderma, pyogenic granuloma, rubeosis, arthritis, diabetic neovascularization, vasculogenesis. A polypeptide agent may be co-administered with at least one additional anti-angiogenesis agent that inhibits angiogenesis in an additive or synergistic manner with the soluble polypeptide.

In certain aspects, the disclosure provides for the use of a polypeptide agent in the manufacture of medicament for the treatment of cancer or an angiogenesis related disorder. The polypeptide agent may be selected from the group consisting of: (a) a soluble polypeptide comprising an amino acid sequence of an extracellular domain of an EphB4 protein, wherein the EphB4 polypeptide is a monomer and binds specifically to an Ephrin B2 polypeptide, and optionally comprises an additional modification to increase serum half-life, such as a PEGylation or serum albumin or both; (b) a soluble polypeptide comprising an amino acid sequence of an extracellular domain of an Ephrin B2 protein, wherein the soluble Ephrin B2 polypeptide is a monomer and binds with high affinity to an EphB4 polypeptide.

In certain aspects, the disclosure provides methods for treating a patient suffering from a cancer, comprising: (a) identifying in the patient a tumor having a plurality of cancer cells that express EphB4 and/or EphrinB2; and (b) administering to the patient a polypeptide agent. The polypeptide agent may be selected from the group consisting of: (i) a soluble polypeptide comprising an amino acid sequence of an extracellular domain of an EphB4 protein, wherein the EphB4 polypeptide is a monomer and binds specifically to an Ephrin B2 polypeptide, and optionally comprises an additional modification to increase serum half-life, such as a PEGylation or serum albumin or both; (ii) a soluble polypeptide comprising an amino acid sequence of an extracellular domain of an Ephrin B2 protein, wherein the soluble Ephrin B2 polypeptide is a monomer and binds with high affinity to an EphB4 polypeptide.

In certain aspects, the disclosure provides methods for identifying a tumor that is suitable for treatment with an EphrinB2 or EphB4 antagonist. A method may comprise detecting in the tumor cell one or more of the following characteristics: (a) expression of EphB4 protein and/or mRNA; (b) expression of EphrinB2 protein and/or mRNA; (c) gene amplification (e.g., increased gene copy number) of the EphB4 gene; or (d) gene amplification of the EphrinB2 gene. A tumor cell having one or more of characteristics (a)-(d) may be suitable for treatment with an EphrinB2 or EphB4 antagonist, such as a polypeptide agent described herein.

Surprisingly, applicants have found that an EphB4 polypeptide lacking the globular domain can in fact inhibit tumor growth in a xenograft model, inhibit angiogenic tube formation of vascular endothelial cells and inhibit EphrinB2-activated autokinase activity of EphB4. While not wishing to be bound to any mechanism of action, it is expected that the polypeptide either prevents EphB4 aggregation or stimulates the elimination (e.g. by endocytosis) of EphB4 from the plasma membrane. Accordingly, the disclosure provides isolated soluble polypeptides comprising an amino acid sequence of a fibronectin type 3 domain of an EphB4 protein. Such polypeptides will preferably have a biological effect, such as inhibiting an activity (e.g. aggregation or kinase activity) of an EphB4 or EphrinB2 protein, and particularly the inhibition of tumor growth in a human or in a mouse xenograft model of cancer. Such polypeptides may also inhibit angiogenesis in vivo or in an cell-based assay system. Such polypeptides may not bind to EphrinB2 and may specifically exclude all of or the functional (e.g., EphrinB2 binding-) portions of the globular domain of an EphB4 protein. Such a polypeptide will preferably comprise amino acids corresponding to amino acids 324-429 and/or 434-526 of the sequence of FIG. 65 (SEQ ID NO:10), or sequences at least 90%, 95%, 98%, 99% identical thereto. An example of such a polypeptide is shown in SEQ ID NO: 15. Such a polypeptide may be modified in any of the ways described herein, and may be produced as a monomer or as a dimer or multimer comprising two or more such polypeptides, such as an Fc fusion construct. Dimers or multimers may be desirable to enhance the effectiveness of such polypeptides. All of the methods for producing and using such polypeptides are similar to those described herein with respect to other EphB4 polypeptides.

BRIEF DESCRIPTION OF THE DRAWINGS

FIG. 1 shows amino acid sequence of the B4ECv3 protein (predicted sequence of the precursor including uncleaved Eph B4 leader peptide is shown; SEQ ID NO:1).

FIG. 2 shows amino acid sequence of the B4ECv3NT protein (predicted sequence of the precursor including uncleaved Eph B4 leader peptide is shown; SEQ ID NO:2).

FIG. 3 shows amino acid sequence of the B2EC protein (predicted sequence of the precursor including uncleaved Ephrin B2 leader peptide is shown; SEQ ID NO:3).

FIG. 4 shows amino acid sequence of the B4ECv3-FC protein (predicted sequence of the precursor including uncleaved Eph B4 leader peptide is shown; SEQ ID NO:4).

FIG. 5 shows amino acid sequence of the B2EC-FC protein (predicted sequence of the precursor including uncleaved Ephrin B2 leader peptide is shown; SEQ ID NO:5).

FIG. 21 shows that B4v3 inhibits invasion and tubule formation by endothelial cells in the Matrigel assay. (A) to detect total invading cells, photographed at 20× magnification or with Masson's Trichrome Top left of A B displays section of a Matrigel plug with no GF, top right of A displays section with B4IgG containing GF and lower left section contains GF, and lower right shows GF in the presence of B4v3. Significant invasion of endothelial cells is only seen in GF containing Matrigel. Top right displays an area with a high number of invaded cells induced by B4IgG, which signifies the dimeric form of B4v3. The left upper parts of the pictures correspond to the cell layers formed around the Matrigel plug from which cells invade toward the center of the plug located in the direction of the right lower corner. Total cells in sections of the Matrigel plugs were quantitated with Scion Image software. Results obtained from two experiments with duplicate plugs are displayed as mean values±S.D.

FIG. 51 shows expression of EPHB4 in bladder cancer cell lines (A), and regulation of EPHB4 expression by EGFR signaling pathway (B).

FIG. 60 shows that systemic administration of EphB4 antibodies leads to tumor regression.

FIGS. 61A-J show a genomic nucleotide sequence of human EphB4 (SEQ ID NO:6).

FIGS. 62A-B show a cDNA nucleotide sequence of human EphB4 (SEQ ID NO:7).

FIGS. 63A-Q show a genomic nucleotide sequence of human Ephrin B2 (SEQ ID NO:8).

FIGS. 64A-B show a cDNA nucleotide sequence of human Ephrin B2 (SEQ ID NO:9).

FIG. 65 shows an amino acid sequence of human EphB4 (SEQ ID NO:10).

FIG. 66 shows an amino acid sequence of human Ephrin B2 (SEQ ID NO:11).

DETAILED DESCRIPTION OF THE INVENTION

I. Overview

Figure 6:
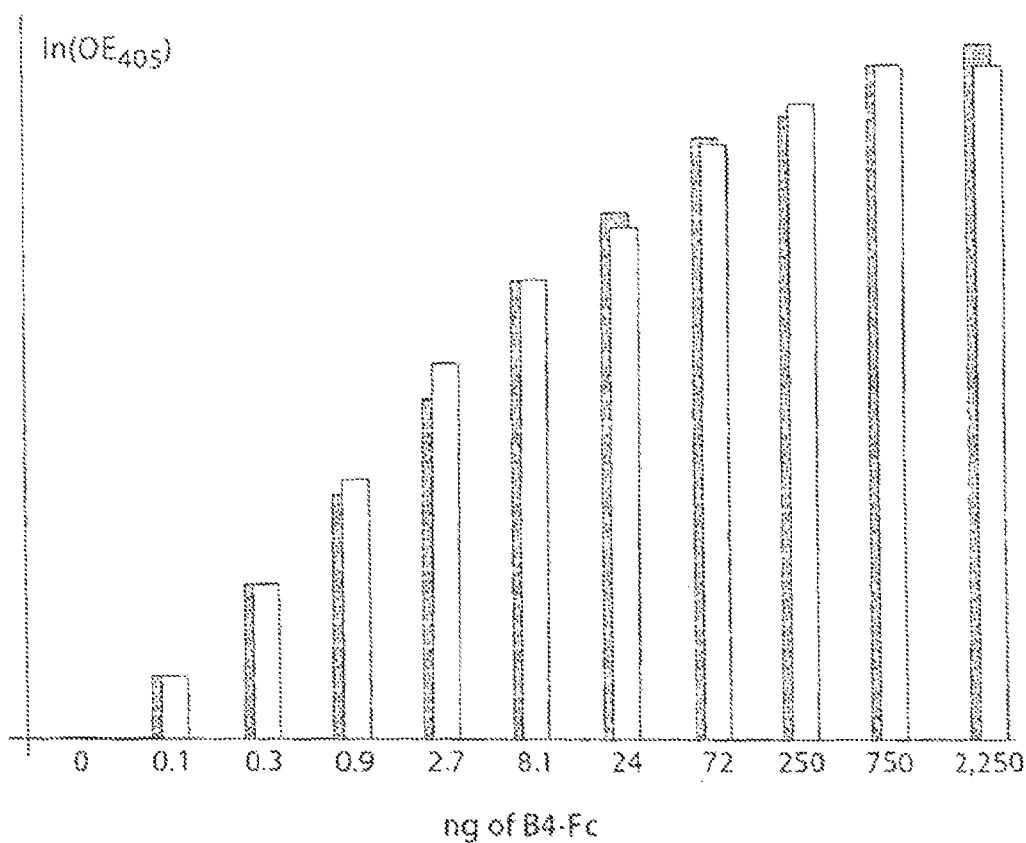
FIG. 6 shows B4EC-FC binding assay (Protein A-agarose based).

The current invention is based in part on the discovery that signaling through the ephrin/ephrin receptor (ephrin/eph) pathway contributes to tumorigenesis. Applicants detected expression of ephrin B2 and EphB4 in tumor tissues and developed anti-tumor therapeutic agents for blocking signaling through the ephrin/eph. In addition, the disclosure provides polypeptide therapeutic agents and methods for polypeptide-based inhibition of the function of EphB4 and/or Ephrin B2. Accordingly, in certain aspects, the disclosure provides numerous polypeptide compounds (agents) that may be used to treat cancer as well as angiogenesis related disorders and unwanted angiogenesis related processes. Applicants have generated modified forms of EphrinB2 and EphB4 polypeptides and have demonstrated that such modified forms have markedly improved pharmacokinetic properties. Accordingly, in certain aspects, the disclosure provides numerous polypeptide compounds (agents) that may be used to treat cancer as well as angiogenesis related disorders and unwanted angiogenesis related processes.

As used herein, the terms Ephrin and Eph are used to refer, respectively, to ligands and receptors. They can be from any of a variety of animals (e.g., mammals/non-mammals, vertebrates/non-vertebrates, including humans). The nomenclature in this area has changed rapidly and the terminology used herein is that proposed as a result of work by the Eph Nomenclature Committee, which can be accessed, along with previously-used names at web site http://www.eph-nomenclature.com.

The work described herein, particularly in the examples, refers to Ephrin B2 and EphB4. However, the present invention contemplates any ephrin ligand and/or Eph receptor within their respective family, which is expressed in a tumor. The ephrins (ligands) are of two structural types, which can be further subdivided on the basis of sequence relationships and, functionally, on the basis of the preferential binding they exhibit for two corresponding receptor subgroups. Structurally, there are two types of ephrins: those which are membrane-anchored by a glycerophosphatidylinositol (GPI) linkage and those anchored through a transmembrane domain. Conventionally, the ligands are divided into the Ephrin-A subclass, which are GPI-linked proteins which bind preferentially to EphA receptors, and the Ephrin-B subclass, which are transmembrane proteins which generally bind preferentially to EphB receptors.

The Eph family receptors are a family of receptor protein-tyrosine kinases which are related to Eph, a receptor named for its expression in an erythropoietin-producing human hepatocellular carcinoma cell line. They are divided into two subgroups on the basis of the relatedness of their extracellular domain sequences and their ability to bind preferentially to Ephrin-A proteins or Ephrin-B proteins. Receptors which interact preferentially with Ephrin-A proteins are EphA receptors and those which interact preferentially with Ephrin-B proteins are EphB receptors.

Figure 16:
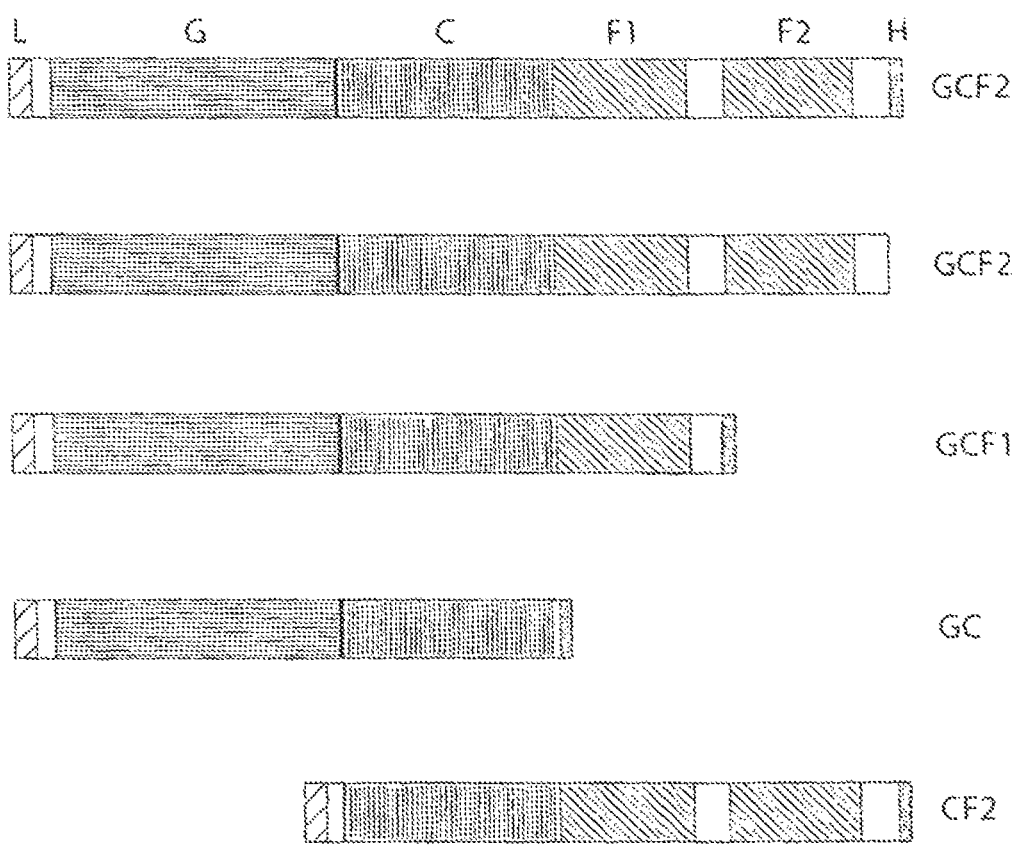
FIG. 16 shows the domain structure of the recombinant soluble EphB4EC proteins. Designation of the domains are as follows: L-leader peptide, G-globular (ligand-binding domain), C-Cys-rich domain, F1, F2-fibronectin type III repeats, H-6×His-tag.

Eph receptors have an extracellular domain composed of the ligand-binding globular domain, a cysteine rich region followed by a pair of fibronectin type III repeats (e.g., see FIG. 16). The cytoplasmic domain consists of a juxtamembrane region containing two conserved tyrosine residues; a protein tyrosine kinase domain; a sterile α-motif (SAM) and a PDZ-domain binding motif. EphB4 is specific for the membrane-bound ligand Ephrin B2 (Sakano, S. et al 1996;

Brambilla R. et al 1995). Ephrin B2 belongs to the class of Eph ligands that have a transmembrane domain and cytoplasmic region with five conserved tyrosine residues and PDZ domain. Eph receptors are activated by binding of clustered, membrane attached ephrins (Davis S et al, 1994), indicating that contact between cells expressing the receptors and cells expressing the ligands is required for Eph activation.

Upon ligand binding, an Eph receptor dimerizes and autophosphorylate the juxtamembrane tyrosine residues to acquire full activation (Kalo M S et al, 1999, Binns K S, 2000). In addition to forward signaling through the Eph receptor, reverse signaling can occur through the ephrin Bs. Eph engagement of ephrins results in rapid phosphorylation of the conserved intracellular tyrosines (Bruckner K, 1997) and somewhat slower recruitment of PDZ binding proteins (Palmer A 2002). Recently, several studies have shown that high expression of Eph/ephrins may be associated with increased potentials for tumor growth, tumorigenicity, and metastasis (Easty D J, 1999; Kiyokawa E, 1994; Tang X X, 1999; Vogt T, 1998; Liu W, 2002; Stephenson S A, 2001; Steube K G 1999; Berclaz G, 1996).

In certain embodiments, the present invention provides polypeptide therapeutic agents that inhibit activity of Ephrin B2, EphB4, or both. As used herein, the term "polypeptide therapeutic agent" or "polypeptide agent" is a generic term which includes any polypeptide that blocks signaling through the Ephrin B2/EphB4 pathway. A preferred polypeptide therapeutic agent of the invention is a soluble polypeptide of Ephrin B2 or EphB4. Another preferred polypeptide therapeutic agent of the invention is an antagonist antibody that binds to Ephrin B2 or EphB4. For example, such polypeptide therapeutic agent can inhibit function of Ephrin B2 or EphB4, inhibit the interaction between Ephrin B2 and EphB4, inhibit the phosphorylation of Ephrin B2 or EphB4, or inhibit any of the downstream signaling events upon binding of Ephrin B2 to EphB4. Such polypeptides may include EphB4 or EphrinB2 that are modified so as to improve serum half-life, such as by PEGylation or stable association with a serum albumin protein.

II. Soluble Polypeptides

Figure 14:
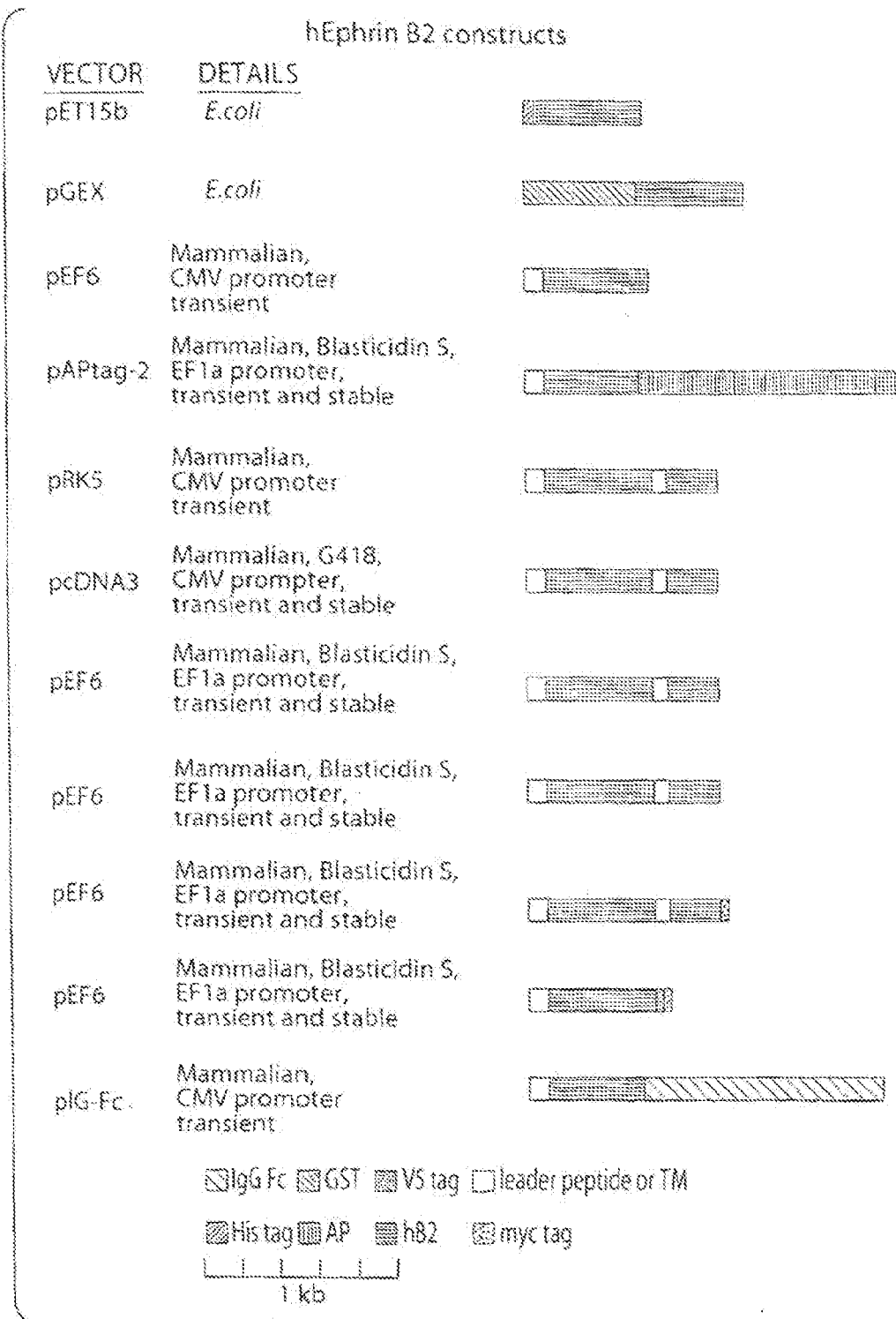
FIG. 14 is a schematic representation of human Ephrin B2 constructs.
Figure 15:
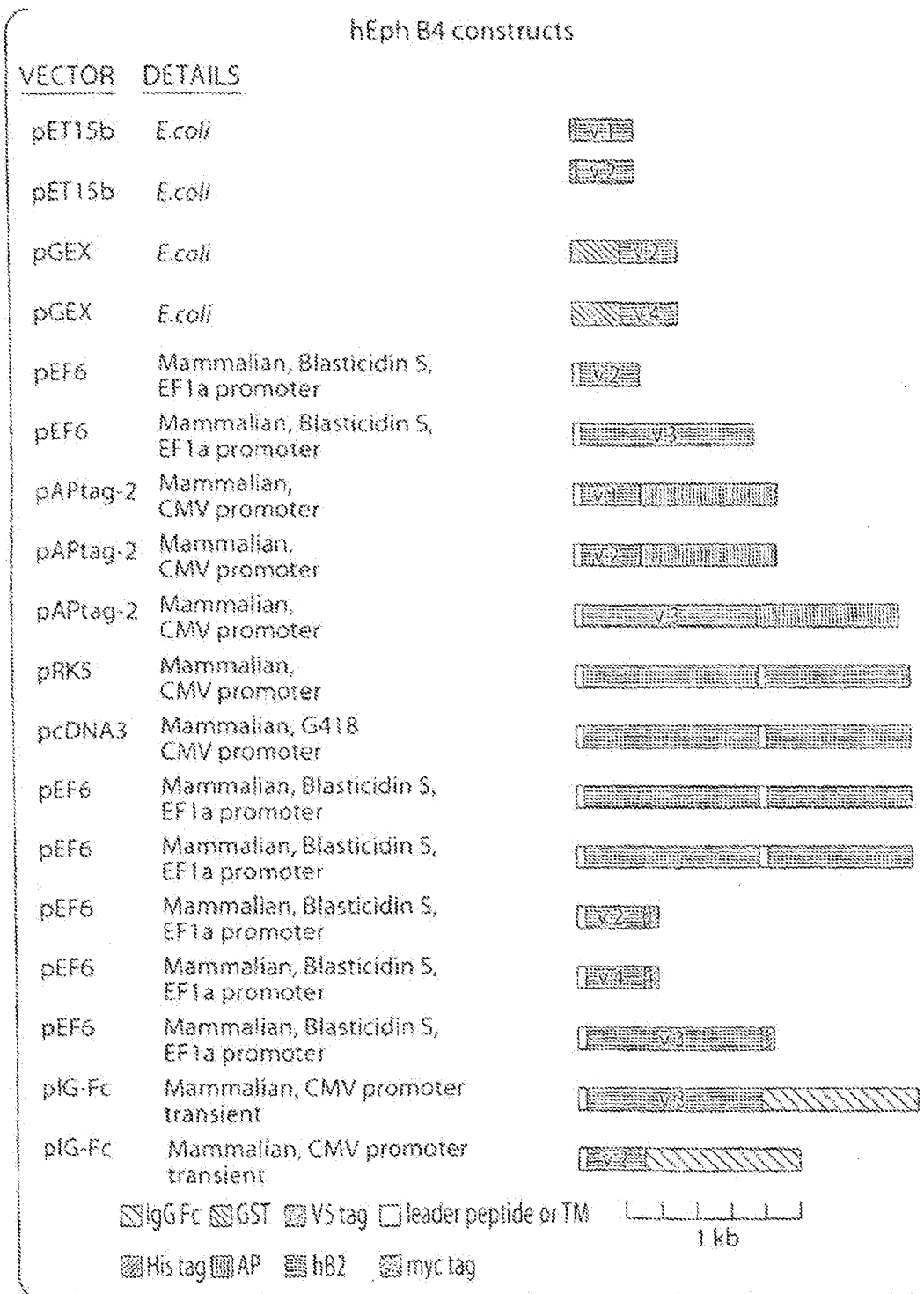
FIG. 15 is a schematic representation of human EphB4 constructs.

In certain aspects, the invention relates to a soluble polypeptide comprising an extracellular domain of an Ephrin B2 protein (referred to herein as an Ephrin B2 soluble polypeptide) or comprising an extracellular domain of an EphB4 protein (referred to herein as an EphB4 soluble polypeptide). Preferably, the subject soluble polypeptide is a monomer and is capable of binding with high affinity to Ephrin B2 or EphB4. In a specific embodiment, the EphB4 soluble polypeptide of the invention comprises a globular domain of an EphB4 protein. Specific examples EphB4 soluble polypeptides are provided in FIGS. 1, 2, and 15. Specific examples of Ephrin B2 soluble polypeptides are provided in FIGS. 3 and 14.

As used herein, the subject soluble polypeptides include fragments, functional variants, and modified forms of EphB4 soluble polypeptide or an Ephrin B2 soluble polypeptide. These fragments, functional variants, and modified forms of the subject soluble polypeptides antagonize function of EphB4, Ephrin B2 or both.

In certain embodiments, isolated fragments of the subject soluble polypeptides can be obtained by screening polypeptides recombinantly produced from the corresponding fragment of the nucleic acid encoding an EphB4 or Ephrin B2 soluble polypeptides. In addition, fragments can be chemically synthesized using techniques known in the art such as conventional Merrifield solid phase f-Moc or t-Boc chemistry. The fragments can be produced (recombinantly or by chemical synthesis) and tested to identify those peptidyl fragments that can function to inhibit function of EphB4 or Ephrin B2, for example, by testing the ability of the fragments to inhibit angiogenesis or tumor growth.

In certain embodiments, a functional variant of an EphB4 soluble polypeptide comprises an amino acid sequence that is at least 90%, 95%, 97%, 99% or 100% identical to residues 1-197, 29-197, 1-312, 29-132, 1-321, 29-321, 1-326, 29-326, 1-412, 29-412, 1-427, 29-427, 1-429, 29-429, 1-526, 29-526, 1-537 and 29-537 of the amino acid sequence defined by FIG. 65 (SEQ ID NO: 10). Such polypeptides may be used in a processed form, and accordingly, in certain embodiments, an EphB4 soluble polypeptide comprises an amino acid sequence that is at least 90%, 95%, 97%, 99% or 100% identical to residues 16-197, 16-312, 16-321, 16-326, 16-412, 16-427, 16-429, 16-526 and 16-537 of the amino acid sequence defined by FIG. 65 (SEQ ID NO:10).

In other embodiments, a functional variant of an Ephrin B2 soluble polypeptide comprises a sequence at least 90%, 95%, 97%, 99% or 100% identical to residues 1-225 of the amino acid sequence defined by FIG. 66 (SEQ ID NO: 11) or a processed form, such as one comprising a sequence at least 90%, 95%, 97%, 99% or 100% identical to residues 26-225 of the amino acid sequence defined by FIG. 66 (SEQ ID NO: 11).

In certain embodiments, the present invention contemplates making functional variants by modifying the structure of the subject soluble polypeptide for such purposes as enhancing therapeutic or prophylactic efficacy, or stability (e.g., ex vivo shelf life and resistance to proteolytic degradation in vivo). Such modified soluble polypeptide are considered functional equivalents of the naturally-occurring EphB4 or Ephrin B2 soluble polypeptide. Modified soluble polypeptides can be produced, for instance, by amino acid substitution, deletion, or addition. For instance, it is reasonable to expect, for example, that an isolated replacement of a leucine with an isoleucine or valine, an aspartate with a glutamate, a threonine with a serine, or a similar replacement of an amino acid with a structurally related amino acid (e.g., conservative mutations) will not have a major effect on the biological activity of the resulting molecule. Conservative replacements are those that take place within a family of amino acids that are related in their side chains.

This invention further contemplates a method of generating sets of combinatorial mutants of the EphB4 or Ephrin B2 soluble polypeptides, as well as truncation mutants, and is especially useful for identifying functional variant sequences. The purpose of screening such combinatorial libraries may be to generate, for example, soluble polypeptide variants which can act as antagonists of EphB4, EphB2, or both. Combinatorially-derived variants can be generated which have a selective potency relative to a naturally occurring soluble polypeptide. Such variant proteins, when expressed from recombinant DNA constructs, can be used in gene therapy protocols. Likewise, mutagenesis can give rise to variants which have intracellular half-lives dramatically different than the corresponding wild-type soluble polypeptide. For example, the altered protein can be rendered either more stable or less stable to proteolytic degradation or other cellular process which result in destruction of, or otherwise inactivation of the protein of interest (e.g., a soluble polypeptide). Such variants, and the genes which encode them, can be utilized to alter the subject soluble polypeptide levels by modulating their half-life. For instance, a short half-life can give rise to more transient biological effects and, when part of an inducible expression system, can allow tighter control of recombinant soluble polypeptide levels within the cell. As above, such proteins, and particularly their recombinant nucleic acid constructs, can be used in gene therapy protocols.

There are many ways by which the library of potential homologs can be generated from a degenerate oligonucleotide sequence. Chemical synthesis of a degenerate gene sequence can be carried out in an automatic DNA synthesizer, and the synthetic genes then be ligated into an appropriate gene for expression. The purpose of a degenerate set of genes is to provide, in one mixture, all of the sequences encoding the desired set of potential soluble polypeptide sequences. The synthesis of degenerate oligonucleotides is well known in the art (see for example, Narang, S A (1983) Tetrahedron 39:3; Itakura et al., (1981) Recombinant DNA, Proc. 3rd Cleveland Sympos. Macromolecules, ed. A G Walton, Amsterdam: Elsevier pp 273-289; Itakura et al., (1984) Annu. Rev. Biochem. 53:323; Itakura et al., (1984) Science 198:1056; Ike et al., (1983) Nucleic Acid Res. 11:477). Such techniques have been employed in the directed evolution of other proteins (see, for example, Scott et al., (1990) Science 249:386-390; Roberts et al., (1992) PNAS USA 89:2429-2433; Devlin et al., (1990) Science 249: 404-406; Cwirla et al., (1990) PNAS USA 87: 6378-6382; as well as U.S. Pat. Nos. 5,223,409, 5,198,346, and 5,096,815).

Alternatively, other forms of mutagenesis can be utilized to generate a combinatorial library. For example, soluble polypeptide variants (e.g., the antagonist forms) can be generated and isolated from a library by screening using, for example, alanine scanning mutagenesis and the like (Ruf et al., (1994) Biochemistry 33:1565-1572; Wang et al., (1994) J. Biol. Chem. 269:3095-3099; Balint et al., (1993) Gene 137:109-118; Grodberg et al., (1993) Eur. J. Biochem. 218:597-601; Nagashima et al., (1993) J. Biol. Chem. 268: 2888-2892; Lowman et al., (1991) Biochemistry 30:10832-10838; and Cunningham et al., (1989) Science 244:1081-1085), by linker scanning mutagenesis (Gustin et al., (1993) Virology 193:653-660; Brown et al., (1992) Mol. Cell. Biol. 12:2644-2652; McKnight et al., (1982) Science 232:316); by saturation mutagenesis (Meyers et al., (1986) Science 232:613); by PCR mutagenesis (Leung et al., (1989) Method Cell Mol Biol 1:11-19); or by random mutagenesis, including chemical mutagenesis, etc. (Miller et al., (1992) A Short Course in Bacterial Genetics, CSHL Press, Cold Spring Harbor, N.Y.; and Greener et al., (1994) Strategies in Mol Biol 7:32-34). Linker scanning mutagenesis, particularly in a combinatorial setting, is an attractive method for identifying truncated (bioactive) forms of the subject soluble polypeptide.

A wide range of techniques are known in the art for screening gene products of combinatorial libraries made by point mutations and truncations, and, for that matter, for screening cDNA libraries for gene products having a certain property. Such techniques will be generally adaptable for rapid screening of the gene libraries generated by the combinatorial mutagenesis of the subject soluble polypeptides. The most widely used techniques for screening large gene libraries typically comprises cloning the gene library into replicable expression vectors, transforming appropriate cells with the resulting library of vectors, and expressing the combinatorial genes under conditions in which detection of a desired activity facilitates relatively easy isolation of the vector encoding the gene whose product was detected. Each of the illustrative assays described below are amenable to high through-put analysis as necessary to screen large numbers of degenerate sequences created by combinatorial mutagenesis techniques.

In certain embodiments, the subject soluble polypeptides of the invention include a small molecule such as a peptide and a peptidomimetic. As used herein, the term "peptidomimetic" includes chemically modified peptides and peptide-like molecules that contain non-naturally occurring amino acids, peptoids, and the like. Peptidomimetics provide various advantages over a peptide, including enhanced stability when administered to a subject. Methods for identifying a peptidomimetic are well known in the art and include the screening of databases that contain libraries of potential peptidomimetics. For example, the Cambridge Structural Database contains a collection of greater than 300,000 compounds that have known crystal structures (Allen et al., Acta Crystallogr. Section B, 35:2331 (1979)). Where no crystal structure of a target molecule is available, a structure can be generated using, for example, the program CONCORD (Rusinko et al., J. Chem. Inf. Comput. Sci. 29:251 (1989)). Another database, the Available Chemicals Directory (Molecular Design Limited, Informations Systems; San Leandro Calif.), contains about 100,000 compounds that are commercially available and also can be searched to identify potential peptidomimetics of the EphB4 or Ephrin B2 soluble polypeptides.

In certain embodiments, the soluble polypeptides of the invention may further comprise post-translational modifications. Exemplary post-translational protein modification include phosphorylation, acetylation, methylation, ADP-ribosylation, ubiquitination, glycosylation, carbonylation, sumoylation, biotinylation or addition of a polypeptide side chain or of a hydrophobic group. As a result, the modified soluble polypeptides may contain non-amino acid elements, such as lipids, poly- or mono-saccharide, and phosphates. Effects of such non-amino acid elements on the functionality of a soluble polypeptide may be tested for its antagonizing role in EphB4 or Ephrin B2 function, e.g, it inhibitory effect on angiogenesis or on tumor growth.

In one specific embodiment of the present invention, modified forms of the subject soluble polypeptides comprise linking the subject soluble polypeptides to nonproteinaceous polymers. In one specific embodiment, the polymer is polyethylene glycol ("PEG"), polypropylene glycol, or polyoxyalkylenes, in the manner as set forth in U.S. Pat. No. 4,640,835; 4,496,689; 4,301,144; 4,670,417; 4,791,192 or 4,179,337. Examples of the modified polypeptide of the invention include PEGylated soluble Ephrin B2 and PEGylated soluble EphB4.

PEG is a well-known, water soluble polymer that is commercially available or can be prepared by ring-opening polymerization of ethylene glycol according to methods well known in the art (Sandler and Karo, Polymer Synthesis, Academic Press, New York, Vol. 3, pages 138-161). The term "PEG" is used broadly to encompass any polyethylene glycol molecule, without regard to size or to modification at an end of the PEG, and can be represented by the formula: $X-O(CH_2CH_2O)_{n-1}CH_2CH_2OH$ (1), where n is 20 to 2300 and X is H or a terminal modification, e.g., a $C_{1-4}$ alkyl. In one embodiment, the PEG of the invention terminates on one end with hydroxy or methoxy, i.e., X is H or $CH_3$ ("methoxy PEG"). A PEG can contain further chemical groups which are necessary for binding reactions; which results from the chemical synthesis of the molecule; or which is a spacer for optimal distance of parts of the molecule. In addition, such a PEG can consist of one or more PEG side-chains which are linked together. PEGs with more than one PEG chain are called multiarmed or branched PEGs. Branched PEGs can be prepared, for example, by the addition of polyethylene oxide to various polyols, including glycerol, pentaerythriol, and sorbitol. For example, a four-armed branched PEG can be prepared from pentaerythriol and ethylene oxide. Branched PEG are described in, for example, EP-A 0 473 084 and U.S. Pat. No. 5,932,462. One form of PEGs includes two PEG side-chains (PEG2) linked via the primary amino groups of a lysine (Monfardini, C., et al., Bioconjugate Chem. 6 (1995) 62-69).

PEG conjugation to peptides or proteins generally involves the activation of PEG and coupling of the activated PEG-intermediates directly to target proteins/peptides or to a linker, which is subsequently activated and coupled to target proteins/peptides (see Abuchowski, A. et al, *J. Biol. Chem.*, 252, 3571 (1977) and *J. Biol. Chem.*, 252, 3582 (1977), Zalipsky, et al., and Harris et. al., in: Poly(ethylene glycol) Chemistry: Biotechnical and Biomedical Applications; (J. M. Harris ed.) Plenum Press: New York, 1992; Chap. 21 and 22). It is noted that an EphB4 containing a PEG molecule is also known as a conjugated protein, whereas the protein lacking an attached PEG molecule can be referred to as unconjugated.

Any molecular mass for a PEG can be used as practically desired, e.g., from about 1,000 Daltons (Da) to 100,000 Da (n is 20 to 2300), for conjugating to Eph4 or EphrinB2 soluble peptides. The number of repeating units "n" in the PEG is approximated for the molecular mass described in Daltons. It is preferred that the combined molecular mass of PEG on an activated linker is suitable for pharmaceutical use. Thus, in one embodiment, the molecular mass of the PEG molecules does not exceed 100,000 Da. For example, if three PEG molecules are attached to a linker, where each PEG molecule has the same molecular mass of 12,000 Da (each n is about 270), then the total molecular mass of PEG on the linker is about 36,000 Da (total n is about 820). The molecular masses of the PEG attached to the linker can also be different, e.g., of three molecules on a linker two PEG molecules can be 5,000 Da each (each n is about 110) and one PEG molecule can be 12,000 Da (n is about 270).

In a specific embodiment of the invention, an EphB4 polypeptide is covalently linked to one poly(ethylene glycol) group of the formula: —CO—$(CH_2)_x$—$(OCH_2CH_2)_m$—OR, with the —CO (i.e. carbonyl) of the poly(ethylene glycol) group forming an amide bond with one of the amino groups of EphB4; R being lower alkyl; x being 2 or 3; m being from about 450 to about 950; and n and m being chosen so that the molecular weight of the conjugate minus the EphB4 protein is from about 10 to 40 kDa. In one embodiment, an EphB4 ε-amino group of a lysine is the available (free) amino group.

The above conjugates may be more specifically presented by formula (II): P—NHCO—$(CH_2)_x$—$(OCH_2CH_2)_m$—OR (II), wherein P is the group of an EphB4 protein as described herein, (i.e. without the amino group or amino groups which form an amide linkage with the carbonyl shown in formula (II); and wherein R is lower alkyl; x is 2 or 3; m is from about 450 to about 950 and is chosen so that the molecular weight of the conjugate minus the EphB4 protein is from about 10 to about 40 kDa. As used herein, the given ranges of "m" have an orientational meaning. The ranges of "m" are determined in any case, and exactly, by the molecular weight of the PEG group.

One skilled in the art can select a suitable molecular mass for PEG, e.g., based on how the pegylated EphB4 will be used therapeutically, the desired dosage, circulation time, resistance to proteolysis, immunogenicity, and other considerations. For a discussion of PEG and its use to enhance the properties of proteins, see N. V. Katre, Advanced Drug Delivery Reviews 10: 91-114 (1993).

In one embodiment of the invention, PEG molecules may be activated to react with amino groups on EphB4, such as with lysines (Bencham C. O. et al., Anal. Biochem., 131, 25 (1983); Veronese, F. M. et al., Appl. Biochem., 11, 141 (1985).; Zalipsky, S. et al., Polymeric Drugs and Drug Delivery Systems, adrs 9-110 ACS Symposium Series 469 (1999); Zalipsky, S. et al., Europ. Polym. J., 19, 1177-1183 (1983); Delgado, C. et al., Biotechnology and Applied Biochemistry, 12, 119-128 (1990)).

In one specific embodiment, carbonate esters of PEG are used to form the PEG-EphB4 conjugates. N,N'-disuccinimidylcarbonate (DSC) may be used in the reaction with PEG to form active mixed PEG-succinimidyl carbonate that may be subsequently reacted with a nucleophilic group of a linker or an amino group of EphB4 (see U.S. Pat. No. 5,281,698 and U.S. Pat. No. 5,932,462). In a similar type of reaction, 1,1'-(dibenzotriazolyl)carbonate and di-(2-pyridyl)carbonate may be reacted with PEG to form PEG-benzotriazolyl and PEG-pyridyl mixed carbonate (U.S. Pat. No. 5,382, 657), respectively.

In one embodiment, additional sites for PEGylation are introduced by site-directed mutagenesis by introducing one or more lysine residues. For instance, one or more arginine residues may be mutated to a lysine residue. In another embodiment, additional PEGylation sites are chemically introduced by modifying amino acids on EphB4. In one specific embodiment, carboxyl groups in EphB4 are conjugated with diaminobutane, resulting in carboxyl amidation (see Li et al., Anal Biochem. 2004; 330(2):264-71). This reaction may be catalyzed by 1-ethyl-3-(3-dimethylaminopropyl) carbodiimide, a water-soluble carbodiimide. The resulting amides can then conjugated to PEG.

PEGylation of EphB4 can be performed according to the methods of the state of the art, for example by reaction of EphB4 with electrophilically active PEGs (supplier: Shearwater Corp., USA, www.shearwatercorp.com). Preferred PEG reagents of the present invention are, e.g., N-hydroxysuccinimidyl propionates (PEG-SPA), butanoates (PEG-SBA), PEG-succinimidyl propionate or branched N-hydroxysuccinimides such as mPEG2-NHS (Monfardini, C., et al., Bioconjugate Chem. 6 (1995) 62-69). Such methods may used to PEGylated at an ε-amino group of an EphB4 lysine or the N-terminal amino group of EphB4.

In another embodiment, PEG molecules may be coupled to sulfhydryl groups on EphB4 (Sartore, L., et al., Appl. Biochem. Biotechnol., 27, 45 (1991); Morpurgo et al., Biocon. Chem., 7, 363-368 (1996); Goodson et al., Bio/Technology (1990) 8, 343; U.S. Pat. No. 5,766,897). U.S. Pat. Nos. 6,610,281 and 5,766,897 describes exemplary reactive PEG species that may be coupled to sulfhydryl groups.

In some embodiments where PEG molecules are conjugated to cysteine residues on EphB4, the cysteine residues are native to Eph4, whereas in other embodiments, one or more cysteine residues are engineered into EphB4. Mutations may be introduced into an EphB4 coding sequence to generate cysteine residues. This might be achieved, for example, by mutating one or more amino acid residues to cysteine. Preferred amino acids for mutating to a cysteine residue include serine, threonine, alanine and other hydrophilic residues. Preferably, the residue to be mutated to cysteine is a surface-exposed residue. Algorithms are well-known in the art for predicting surface accessibility of residues based on primary sequence or a protein. Alternatively, surface residues may be predicted by comparing the amino acid sequences of EphB4 an EphB2, given that the crystal structure of EphB2 has been solved (see Himanen et al., Nature. (2001) 20-27; 414(6866):933-8) and thus the surface-exposed residues identified. In one embodiment, cysteine residues are introduced into EphB4 at or near the N- and/or C-terminus, or within loop regions. Loop regions may be identified by comparing the EphB4 sequence to that of EphB2.

In some embodiments, the pegylated EphB4 comprises a PEG molecule covalently attached to the alpha amino group of the N-terminal amino acid. Site specific N-terminal reductive amination is described in Pepinsky et al., (2001) JPET, 297, 1059, and U.S. Pat. No. 5,824,784. The use of a PEG-aldehyde for the reductive amination of a protein utilizing other available nucleophilic amino groups is described in U.S. Pat. No. 4,002,531, in Wieder et al., (1979) J. Biol. Chem. 254, 12579, and in Chamow et al., (1994) Bioconjugate Chem. 5, 133.

In another embodiment, pegylated EphB4 comprises one or more PEG molecules covalently attached to a linker, which in turn is attached to the alpha amino group of the amino acid residue at the N-terminus of EphB4. Such an approach is disclosed in U.S. Patent Publication No. 2002/0044921 and in WO94/01451.

In one embodiment, EphB4 is pegylated at the C-terminus. In a specific embodiment, a protein is pegylated at the C-terminus by the introduction of C-terminal azido-methionine and the subsequent conjugation of a methyl-PEG-triarylphosphine compound via the Staudinger reaction. This C-terminal conjugation method is described in Cazalis et al., C-Terminal Site-Specific PEGylation of a Truncated Thrombomodulin Mutant with Retention of Full Bioactivity, *Bioconjug Chem*. 2004; 15(5):1005-1009.

Monopegylation of EphB4 can also be produced according to the general methods described in WO 94/01451. WO 94/01451 describes a method for preparing a recombinant polypeptide with a modified terminal amino acid alpha-carbon reactive group. The steps of the method involve forming the recombinant polypeptide and protecting it with one or more biologically added protecting groups at the N-terminal alpha-amine and C-terminal alpha-carboxyl. The polypeptide can then be reacted with chemical protecting agents to selectively protect reactive side chain groups and thereby prevent side chain groups from being modified. The polypeptide is then cleaved with a cleavage reagent specific for the biological protecting group to form an unprotected terminal amino acid alpha-carbon reactive group. The unprotected terminal amino acid alpha-carbon reactive group is modified with a chemical modifying agent. The side chain protected terminally modified single copy polypeptide is then deprotected at the side chain groups to form a terminally modified recombinant single copy polypeptide. The number and sequence of steps in the method can be varied to achieve selective modification at the N- and/or C-terminal amino acid of the polypeptide.

The ratio of EphB4 (or EphrinB2) to activated PEG in the conjugation reaction can be from about 1:0.5 to 1:50, between from about 1:1 to 1:30, or from about 1:5 to 1:15. Various aqueous buffers can be used in the present method to catalyze the covalent addition of PEG to EphB4. In one embodiment, the pH of a buffer used is from about 7.0 to 9.0. In another embodiment, the pH is in a slightly basic range, e.g., from about 7.5 to 8.5. Buffers having a pKa close to neutral pH range may be used, e.g., phosphate buffer.

In one embodiment, the temperature range for preparing a mono-PEG-EphB4 is from about 4° C. to 40° C., or from about 18° C. to 25° C. In another embodiment, the temperature is room temperature.

The pegylation reaction can proceed from 3 to 48 hours, or from 10 to 24 hours. The reaction can be monitored using SE-HPLC to distinguish EphB4, mono-PEG-EphB4 and poly-PEG-EphB4. It is noted that mono-PEG-EphB4 forms before di-PEG-EphB4. When the mono-PEG-EphB4 concentration reaches a plateau, the reaction can be terminated by adding a quenching agent to react with unreacted PEG. In some embodiments, the quenching agent is a free amino acid, such as glycine, cysteine or lysine.

Conventional separation and purification techniques known in the art can be used to purify pegylated EphB4 or EphrinB2 products, such as size exclusion (e.g. gel filtration) and ion exchange chromatography. Products may also be separated using SDS-PAGE. Products that may be separated include mono-, di-, tri-poly- and un-pegylated EphB4, as well as free PEG. The percentage of mono-PEG conjugates can be controlled by pooling broader fractions around the elution peak to increase the percentage of mono-PEG in the composition. About ninety percent mono-PEG conjugates represents a good balance of yield and activity. Compositions in which, for example, at least ninety-two percent or at least ninety-six percent of the conjugates are mono-PEG species may be desired. In an embodiment of this invention the percentage of mono-PEG conjugates is from ninety percent to ninety-six percent.

In one embodiment, pegylated EphB4 proteins of the invention contain one, two or more PEG moieties. In one embodiment, the PEG moiety(ies) are bound to an amino acid residue which is on the surface of the protein and/or away from the surface that contacts EphrinB2. In one embodiment, the combined or total molecular mass of PEG in PEG-EphB4 is from about 3,000 Da to 60,000 Da, optionally from about 10,000 Da to 36,000 Da. In a one embodiment, the PEG in pegylated EphB4 is a substantially linear, straight-chain PEG.

In one embodiment of the invention, the PEG in pegylated EphB4 or EphrinB2 is not hydrolyzed from the pegylated amino acid residue using a hydroxylamine assay, e.g., 450 mM hydroxylamine (pH 6.5) over 8 to 16 hours at room temperature, and is thus stable. In one embodiment, greater than 80% of the composition is stable mono-PEG-EphB4, more preferably at least 90%, and most preferably at least 95%.

In another embodiment, the pegylated EphB4 proteins of the invention will preferably retain at least 25%, 50%, 60%, 70% least 80%, 85%, 90%, 95% or 100% of the biological activity associated with the unmodified protein. In one embodiment, biological activity refers to its ability to bind to EphrinB2. In one specific embodiment, the pegylated EphB4 protein shows an increase in binding to EphrinB2 relative to unpegylated EphB4.

In a preferred embodiment, the PEG-EphB4 has a half-life ($t_{1/2}$) which is enhanced relative to the half-life of the unmodified protein. Preferably, the half-life of PEG-EphB4 is enhanced by at least 10%, 20%, 30%, 40%, 50%, 60%, 70%, 80%, 90%, 100%, 125%, 150%, 175%, 200%, 250%, 300%, 400% or 500%, or even by 1000% relative to the half-life of the unmodified EphB4 protein. In some embodiments, the protein half-life is determined in vitro, such as in a buffered saline solution or in serum. In other embodiments, the protein half-life is an in vivo half life, such as the half-life of the protein in the serum or other bodily fluid of an animal.

In certain aspects, functional variants or modified forms of the subject soluble polypeptides include fusion proteins having at least a portion of the soluble polypeptide and one or more fusion domains. Well known examples of such fusion domains include, but are not limited to, polyhistidine, Glu-Glu, glutathione S transferase (GST), thioredoxin, protein A, protein G, and an immunoglobulin heavy chain constant region (Fc), maltose binding protein (MBP), which are particularly useful for isolation of the fusion proteins by affinity chromatography. For the purpose of affinity purification, relevant matrices for affinity chromatography, such as glutathione-, amylase-, and nickel- or cobalt-conjugated resins are used. Another fusion domain well known in the art is green fluorescent protein (GFP). Fusion domains also include "epitope tags," which are usually short peptide sequences for which a specific antibody is available. Well known epitope tags for which specific monoclonal antibodies are readily available include FLAG, influenza virus haemagglutinin (HA), and c-myc tags. In some cases, the fusion domains have a protease cleavage site, such as for Factor Xa or Thrombin, which allows the relevant protease to partially digest the fusion proteins and thereby liberate the recombinant proteins therefrom. The liberated proteins can then be isolated from the fusion domain by subsequent chromatographic separation.

In certain embodiments, the soluble polypeptides of the present invention contain one or more modifications that are capable of stabilizing the soluble polypeptides. For example, such modifications enhance the in vitro half life of the soluble polypeptides, enhance circulatory half life of the soluble polypeptides or reducing proteolytic degradation of the soluble polypeptides.

In a further embodiment, a soluble polypeptide of the present invention is fused to a cytotoxic agent. In this method, the fusion acts to target the cytotoxic agent to a specific tissue or cell (e.g., a tumor tissue or cell), resulting in a reduction in the number of afflicted cells. Such an approach can thereby reduce symptoms associated with cancer and angiogenesis-associated disorders. Cytotoxic agents include, but are not limited to, diphtheria A chain, exotoxin A chain, ricin A chain, abrin A chain, curcin, crotin, phenomycin, enomycin and the like, as well as radiochemicals.

In certain embodiments, the soluble polypeptides of the present invention may be fused to other therapeutic proteins or to other proteins such as Fc or serum albumin for pharmacokinetic purposes. See for example U.S. Pat. Nos. 5,766,883 and 5,876,969, both of which are incorporated by reference. In some embodiments, soluble peptides of the present invention are fused to Fc variants. In a specific embodiment, the soluble polypeptide is fused to an Fc variant which does not homodimerize, such as one lacking the cysteine residues which form cysteine bonds with other Fc chains.

In some embodiments, the modified proteins of the invention comprise fusion proteins with an Fc region of an immunoglobulin. As is known, each immunoglobulin heavy chain constant region comprises four or five domains. The domains are named sequentially as follows: $CH_1$-hinge-CH2-CH3(-CH4). The DNA sequences of the heavy chain domains have cross-homology among the immunoglobulin classes, e.g., the CH2 domain of IgG is homologous to the CH2 domain of IgA and IgD, and to the CH3 domain of IgM and IgE. As used herein, the term, "immunoglobulin Fc region" is understood to mean the carboxyl-terminal portion of an immunoglobulin chain constant region, preferably an immunoglobulin heavy chain constant region, or a portion thereof. For example, an immunoglobulin Fc region may comprise 1) a CH1 domain, a CH2 domain, and a CH3 domain, 2) a CH1 domain and a CH2 domain, 3) a CH1 domain and a CH3 domain, 4) a CH2 domain and a CH3 domain, or 5) a combination of two or more domains and an immunoglobulin hinge region. In a preferred embodiment the immunoglobulin Fc region comprises at least an immunoglobulin hinge region a CH2 domain and a CH3 domain, and preferably lacks the CH1 domain.

In one embodiment, the class of immunoglobulin from which the heavy chain constant region is derived is IgG (Igγ) (γ subclasses 1, 2, 3, or 4). The nucleotide and amino acid sequences of human Fc .gamma.-1 are set forth in SEQ ID NOS: 5 and 6. The nucleotide and amino acid sequences of murine Fcγ-2a are set forth in SEQ ID NOS: 7 and 8. Other classes of immunoglobulin, IgA (Igα), IgD (Igδ), IgE (Igε) and IgM (Igμ), may be used. The choice of appropriate immunoglobulin heavy chain constant regions is discussed in detail in U.S. Pat. Nos. 5,541,087, and 5,726,044. The choice of particular immunoglobulin heavy chain constant region sequences from certain immunoglobulin classes and subclasses to achieve a particular result is considered to be within the level of skill in the art. The portion of the DNA construct encoding the immunoglobulin Fc region preferably comprises at least a portion of a hinge domain, and preferably at least a portion of a $CH_3$ domain of Fc γ or the homologous domains in any of IgA, IgD, IgE, or IgM.

Furthermore, it is contemplated that substitution or deletion of amino acids within the immunoglobulin heavy chain constant regions may be useful in the practice of the invention. One example would be to introduce amino acid substitutions in the upper CH2 region to create a Fc variant with reduced affinity for Fc receptors (Cole et al. (1997) J. IMMUNOL. 159:3613). One of ordinary skill in the art can prepare such constructs using well known molecular biology techniques.

In a specific embodiment of the present invention, the modified forms of the subject soluble polypeptides are fusion proteins having at least a portion of the soluble polypeptide (e.g., an ectodomain of Ephrin B2 or EphB4) and a stabilizing domain such as albumin. As used herein, "albumin" refers collectively to albumin protein or amino acid sequence, or an albumin fragment or variant, having one or more functional activities (e.g., biological activities) of albumin. In particular, "albumin" refers to human albumin or fragments thereof (see EP 201 239, EP 322 094 WO 97/24445, WO95/23857) especially the mature form of human albumin, or albumin from other vertebrates or fragments thereof, or analogs or variants of these molecules or fragments thereof.

The present invention describes that such fusion proteins are more stable relative to the corresponding wildtype soluble protein. For example, the subject soluble polypeptide (e.g., an ectodomain of Ephrin B2 or EphB4) can be fused with human serum albumin (HSA), bovine serum albumin (BSA), or any fragment of an albumin protein which has stabilization activity. Such stabilizing domains include human serum albumin (HSA) and bovine serum albumin (BSA).

In particular, the albumin fusion proteins of the invention may include naturally occurring polymorphic variants of human albumin and fragments of human albumin (See WO95/23857), for example those fragments disclosed in EP 322 094 (namely HA (Pn), where n is 369 to 419). The albumin may be derived from any vertebrate, especially any mammal, for example human, cow, sheep, or pig. Non-mammalian albumins include, but are not limited to, hen and salmon. The albumin portion of the albumin fusion protein may be from a different animal than the EphB4.

In some embodiments, the albumin protein portion of an albumin fusion protein corresponds to a fragment of serum albumin. Fragments of serum albumin polypeptides include polypeptides having one or more residues deleted from the amino terminus or from the C-terminus. Generally speaking, an HA fragment or variant will be at least 100 amino acids long, preferably at least 150 amino acids long. The HA variant may consist of or alternatively comprise at least one whole domain of HA. Domains, with reference to SEQ ID NO:18 in U.S. Patent Publication No. 2004/0171123, are as follows: domains 1 (amino acids 1-194), 2 (amino acids 195-387), 3 (amino acids 388-585), 1+2 (1-387), 2+3 (195-585) or 1+3 (amino acids 1-194+ amino acids 388-585). Each domain is itself made up of two homologous subdomains namely 1-105, 120-194, 195-291, 316-387, 388-491 and 512-585, with flexible inter-subdomain linker regions comprising residues Lys 106 to Glu119, Glu292 to Val315 and Glu492 to Ala511.

In one embodiment, the EphB4-HSA fusion has one EphB4 soluble polypeptide linked to one HSA molecule, but other conformations are within the invention. For example, EphB4-HSA fusion proteins can have any of the following formula: $R_1$-L-$R_2$; $R_2$-L-$R_1$; $R_1$-L-$R_2$-L-$R_1$; or $R_2$-L-R1-L-$R_2$; $R_1$-$R_2$; $R_2$-$R_1$; $R_1$-$R_2$-$R_1$; or $R_2$-$R_1$-$R_2$; wherein $R_1$ is a soluble EphB4 sequence, $R_2$ is HSA, and L is a peptide linker sequence.

In a specific embodiment, the EphB4 and HSA domains are linked to each other, preferably via a linker sequence, which separates the EphB4 and HSA domains by a distance sufficient to ensure that each domain properly folds into its secondary and tertiary structures. Preferred linker sequences (1) should adopt a flexible extended conformation, (2) should not exhibit a propensity for developing an ordered secondary structure which could interact with the functional EphB4 and HSA domains, and (3) should have minimal hydrophobic or charged character, which could promote interaction with the functional protein domains. Typical surface amino acids in flexible protein regions include Gly, Asn and Ser. Permutations of amino acid sequences containing Gly, Asn and Ser would be expected to satisfy the above criteria for a linker sequence. Other near neutral amino acids, such as Thr and Ala, can also be used in the linker sequence.

In a specific embodiment, a linker sequence length of about 20 amino acids can be used to provide a suitable separation of functional protein domains, although longer or shorter linker sequences may also be used. The length of the linker sequence separating EphB4 and HSA can be from 5 to 500 amino acids in length, or more preferably from 5 to 100 amino acids in length. Preferably, the linker sequence is from about 5-30 amino acids in length. In preferred embodiments, the linker sequence is from about 5 to about 20 amino acids, and is advantageously from about 10 to about 20 amino acids. Amino acid sequences useful as linkers of EphB4 and HSA include, but are not limited to, (SerGly$_4$)y wherein y is greater than or equal to 8, or Gly$_4$SerGly$_5$Ser. A preferred linker sequence has the formula (SerGly$_4$)$_4$. Another preferred linker has the sequence ((Ser-Ser-Ser-Ser-Gly)-3-Ser-Pro).

In one embodiment, the polypeptides of the present invention and HSA proteins are directly fused without a linker sequence. In preferred embodiments, the C-terminus of a soluble EphB4 polypeptide can be directly fused to the N-terminus of HSA or the C-terminus of HSA can be directly fused to the N-terminus of soluble EphB4.

In some embodiments, the immunogenicity of the fusion junction between HSA and EphB4 may be reduced the by identifying a candidate T-cell epitope within a junction region spanning a fusion protein and changing an amino acid within the junction region as described in U.S. Patent Publication No. 2003/0166877.

In certain embodiments, soluble polypeptides (unmodified or modified) of the invention can be produced by a variety of art-known techniques. For example, such soluble polypeptides can be synthesized using standard protein chemistry techniques such as those described in Bodansky, M. Principles of Peptide Synthesis, Springer Verlag, Berlin (1993) and Grant G. A. (ed.), Synthetic Peptides: A User's Guide, W. H. Freeman and Company, New York (1992). In addition, automated peptide synthesizers are commercially available (e.g., Advanced ChemTech Model 396; Milligen/Biosearch 9600). Alternatively, the soluble polypeptides, fragments or variants thereof may be recombinantly produced using various expression systems as is well known in the art (also see below).

III. Nucleic Acids Encoding Soluble Polypeptides

In certain aspects, the invention relates to isolated and/or recombinant nucleic acids encoding an EphB4 or Ephrin B2 soluble polypeptide. The subject nucleic acids may be single-stranded or double-stranded, DNA or RNA molecules. These nucleic acids are useful as therapeutic agents. For example, these nucleic acids are useful in making recombinant soluble polypeptides which are administered to a cell or an individual as therapeutics. Alternative, these nucleic acids can be directly administered to a cell or an individual as therapeutics such as in gene therapy.

In certain embodiments, the invention provides isolated or recombinant nucleic acid sequences that are at least 80%, 85%, 90%, 95%, 97%, 98%, 99% or 100% identical to a region of the nucleotide sequence depicted in SEQ ID Nos. 6-9. One of ordinary skill in the art will appreciate that nucleic acid sequences complementary to the subject nucleic acids, and variants of the subject nucleic acids are also within the scope of this invention. In further embodiments, the nucleic acid sequences of the invention can be isolated, recombinant, and/or fused with a heterologous nucleotide sequence, or in a DNA library.

In other embodiments, nucleic acids of the invention also include nucleotide sequences that hybridize under highly stringent conditions to the nucleotide sequence depicted in SEQ ID Nos. 6-9, or complement sequences thereof. As discussed above, one of ordinary skill in the art will understand readily that appropriate stringency conditions which promote DNA hybridization can be varied. One of ordinary skill in the art will understand readily that appropriate stringency conditions which promote DNA hybridization can be varied. For example, one could perform the hybridization at 6.0× sodium chloride/sodium citrate (SSC) at about 45° C., followed by a wash of 2.0×SSC at 50° C. For example, the salt concentration in the wash step can be selected from a low stringency of about 2.0×SSC at 50° C. to a high stringency of about 0.2×SSC at 50° C. In addition, the temperature in the wash step can be increased from low stringency conditions at room temperature, about 22° C., to high stringency conditions at about 65° C. Both temperature and salt may be varied, or temperature or salt concentration may be held constant while the other variable is changed. In one embodiment, the invention provides nucleic acids which hybridize under low stringency conditions of 6×SSC at room temperature followed by a wash at 2×SSC at room temperature.

Isolated nucleic acids which differ from the subject nucleic acids due to degeneracy in the genetic code are also within the scope of the invention. For example, a number of amino acids are designated by more than one triplet. Codons that specify the same amino acid, or synonyms (for example, CAU and CAC are synonyms for histidine) may result in "silent" mutations which do not affect the amino acid sequence of the protein. However, it is expected that DNA sequence polymorphisms that do lead to changes in the amino acid sequences of the subject proteins will exist among mammalian cells. One skilled in the art will appreciate that these variations in one or more nucleotides (up to about 3-5% of the nucleotides) of the nucleic acids encoding a particular protein may exist among individuals of a given species due to natural allelic variation. Any and all such nucleotide variations and resulting amino acid polymorphisms are within the scope of this invention.

In certain embodiments, the recombinant nucleic acids of the invention may be operably linked to one or more regulatory nucleotide sequences in an expression construct. Regulatory nucleotide sequences will generally be appropriate for a host cell used for expression. Numerous types of appropriate expression vectors and suitable regulatory sequences are known in the art for a variety of host cells. Typically, said one or more regulatory nucleotide sequences may include, but are not limited to, promoter sequences, leader or signal sequences, ribosomal binding sites, transcriptional start and termination sequences, translational start and termination sequences, and enhancer or activator sequences. Constitutive or inducible promoters as known in the art are contemplated by the invention. The promoters may be either naturally occurring promoters, or hybrid promoters that combine elements of more than one promoter. An expression construct may be present in a cell on an episome, such as a plasmid, or the expression construct may be inserted in a chromosome. In a preferred embodiment, the expression vector contains a selectable marker gene to allow the selection of transformed host cells. Selectable marker genes are well known in the art and will vary with the host cell used.

In certain aspect of the invention, the subject nucleic acid is provided in an expression vector comprising a nucleotide sequence encoding an EphB4 or Ephrin B2 soluble polypeptide and operably linked to at least one regulatory sequence. Regulatory sequences are art-recognized and are selected to direct expression of the soluble polypeptide. Accordingly, the term regulatory sequence includes promoters, enhancers, and other expression control elements. Exemplary regulatory sequences are described in Goeddel; *Gene Expression Technology: Methods in Enzymology*, Academic Press, San Diego, Calif. (1990). For instance, any of a wide variety of expression control sequences that control the expression of a DNA sequence when operatively linked to it may be used in these vectors to express DNA sequences encoding a soluble polypeptide. Such useful expression control sequences, include, for example, the early and late promoters of SV40, tet promoter, adenovirus or cytomegalovirus immediate early promoter, the lac system, the trp system, the TAC or TRC system, T7 promoter whose expression is directed by T7 RNA polymerase, the major operator and promoter regions of phage lambda, the control regions for fd coat protein, the promoter for 3-phosphoglycerate kinase or other glycolytic enzymes, the promoters of acid phosphatase, e.g., Pho5, the promoters of the yeast α-mating factors, the polyhedron promoter of the baculovirus system and other sequences known to control the expression of genes of prokaryotic or eukaryotic cells or their viruses, and various combinations thereof. It should be understood that the design of the expression vector may depend on such factors as the choice of the host cell to be transformed and/or the type of protein desired to be expressed. Moreover, the vector's copy number, the ability to control that copy number and the expression of any other protein encoded by the vector, such as antibiotic markers, should also be considered.

This invention also pertains to a host cell transfected with a recombinant gene including a coding sequence for one or more of the subject soluble polypeptide. The host cell may be any prokaryotic or eukaryotic cell. For example, a soluble polypeptide of the invention may be expressed in bacterial cells such as *E. coli*, insect cells (e.g., using a baculovirus expression system), yeast, or mammalian cells. Other suitable host cells are known to those skilled in the art.

Accordingly, the present invention further pertains to methods of producing the subject soluble polypeptides. For example, a host cell transfected with an expression vector encoding an EphB4 soluble polypeptide can be cultured under appropriate conditions to allow expression of the EphB4 soluble polypeptide to occur. The EphB4 soluble polypeptide may be secreted and isolated from a mixture of cells and medium containing the soluble polypeptides. Alternatively, the soluble polypeptides may be retained cytoplasmically or in a membrane fraction and the cells harvested, lysed and the protein isolated. A cell culture includes host cells, media and other byproducts. Suitable media for cell culture are well known in the art. The soluble polypeptides can be isolated from cell culture medium, host cells, or both using techniques known in the art for purifying proteins, including ion-exchange chromatography, gel filtration chromatography, ultrafiltration, electrophoresis, and immunoaffinity purification with antibodies specific for particular epitopes of the soluble polypeptides. In a preferred embodiment, the soluble polypeptide is a fusion protein containing a domain which facilitates its purification.

A recombinant nucleic acid of the invention can be produced by ligating the cloned gene, or a portion thereof, into a vector suitable for expression in either prokaryotic cells, eukaryotic cells (yeast, avian, insect or mammalian), or both. Expression vehicles for production of a recombinant soluble polypeptide include plasmids and other vectors. For instance, suitable vectors include plasmids of the types: pBR322-derived plasmids, pEMBL-derived plasmids, pEX-derived plasmids, pBTac-derived plasmids and pUC-derived plasmids for expression in prokaryotic cells, such as *E. coli*.

The preferred mammalian expression vectors contain both prokaryotic sequences to facilitate the propagation of the vector in bacteria, and one or more eukaryotic transcription units that are expressed in eukaryotic cells. The pcDNAI/amp, pcDNAI/neo, pRc/CMV, pSV2gpt, pSV2neo, pSV2-dhfr, pTk2, pRSVneo, pMSG, pSVT7, pko-neo and pHyg derived vectors are examples of mammalian expression vectors suitable for transfection of eukaryotic cells. Some of these vectors are modified with sequences from bacterial plasmids, such as pBR322, to facilitate replication and drug resistance selection in both prokaryotic and eukaryotic cells. Alternatively, derivatives of viruses such as the bovine papilloma virus (BPV-1), or Epstein-Barr virus (pHEBo, pREP-derived and p205) can be used for transient expression of proteins in eukaryotic cells. Examples of other viral (including retroviral) expression systems can be found below in the description of gene therapy delivery systems. The various methods employed in the preparation of the plasmids and transformation of host organisms are well known in the art. For other suitable expression systems for both prokaryotic and eukaryotic cells, as well as general recombinant procedures, see *Molecular Cloning A Laboratory Manual*, 2nd Ed., ed. by Sambrook, Fritsch and Maniatis (Cold Spring Harbor Laboratory Press, 1989) Chapters 16 and 17. In some instances, it may be desirable to express the recombinant SLC5A8 polypeptide by the use of a baculovirus expression system. Examples of such baculovirus expression systems include pVL-derived vectors (such as pVL1392, pVL1393 and pVL941), pAcUW-derived vectors (such as pAcUW1), and pBlueBac-derived vectors (such as the β-gal containing pBlueBac III).

Techniques for making fusion genes are well known. Essentially, the joining of various DNA fragments coding for different polypeptide sequences is performed in accordance with conventional techniques, employing blunt-ended or stagger-ended termini for ligation, restriction enzyme digestion to provide for appropriate termini, filling-in of cohesive ends as appropriate, alkaline phosphatase treatment to avoid undesirable joining, and enzymatic ligation. In another embodiment, the fusion gene can be synthesized by conventional techniques including automated DNA synthesizers. Alternatively, PCR amplification of gene fragments can be carried out using anchor primers which give rise to complementary overhangs between two consecutive gene fragments which can subsequently be annealed to generate a chimeric gene sequence (see, for example, *Current Protocols in Molecular Biology*, eds. Ausubel et al., John Wiley & Sons: 1992).

IV. Drug Screening Assays

There are numerous approaches to screening for polypeptide therapeutic agents as antagonists of EphB4, Ephrin B2 or both. For example, high-throughput screening of compounds or molecules can be carried out to identify agents or drugs which inhibit angiogenesis or inhibit tumor growth. Test agents can be any chemical (element, molecule, compound, drug), made synthetically, made by recombinant techniques or isolated from a natural source. For example, test agents can be peptides, polypeptides, peptoids, sugars, hormones, or nucleic acid molecules. In addition, test agents can be small molecules or molecules of greater complexity made by combinatorial chemistry, for example, and compiled into libraries. These libraries can comprise, for example, alcohols, alkyl halides, amines, amides, esters, aldehydes, ethers and other classes of organic compounds. Test agents can also be natural or genetically engineered products isolated from lysates or growth media of cells—bacterial, animal or plant—or can be the cell lysates or growth media themselves. Presentation of test compounds to the test system can be in either an isolated form or as mixtures of compounds, especially in initial screening steps.

For example, an assay can be carried out to screen for compounds that specifically inhibit binding of Ephrin B2 (ligand) to EphB4 (receptor), or vice-versa, e.g., by inhibition of binding of labeled ligand- or receptor-Fc fusion proteins to immortalized cells. Compounds identified through this screening can then be tested in animals to assess their anti-angiogenesis or anti-tumor activity in vivo.

In one embodiment of an assay to identify a substance that interferes with interaction of two cell surface molecules (e.g., Ephrin B2 and EphB4), samples of cells expressing one type of cell surface molecule (e.g., EphB4) are contacted with either labeled ligand (e.g., Ephrin B2, or a soluble portion thereof, or a fusion protein such as a fusion of the extracellular domain and the Fc domain of IgG) or labeled ligand plus a test compound (or group of test compounds). The amount of labeled ligand which has bound to the cells is determined. A lesser amount of label (where the label can be, for example, a radioactive isotope, a fluorescent or colorimetric label) in the sample contacted with the test compound(s) is an indication that the test compound(s) interferes with binding. The reciprocal assay using cells expressing a ligand (e.g., an Ephrin B2 ligand or a soluble form thereof) can be used to test for a substance that interferes with the binding of an Eph receptor or soluble portion thereof.

An assay to identify a substance which interferes with interaction between an Eph receptor and an ephrin can be performed with the component (e.g., cells, purified protein, including fusion proteins and portions having binding activity) which is not to be in competition with a test compound, linked to a solid support. The solid support can be any suitable solid phase or matrix, such as a bead, the wall of a plate or other suitable surface (e.g., a well of a microtiter plate), column pore glass (CPG) or a pin that can be submerged into a solution, such as in a well. Linkage of cells or purified protein to the solid support can be either direct or through one or more linker molecules.

In one embodiment, an isolated or purified protein (e.g., an Eph receptor or an ephrin) can be immobilized on a suitable affinity matrix by standard techniques, such as chemical cross-linking, or via an antibody raised against the isolated or purified protein, and bound to a solid support. The matrix can be packed in a column or other suitable container and is contacted with one or more compounds (e.g., a mixture) to be tested under conditions suitable for binding of the compound to the protein. For example, a solution containing compounds can be made to flow through the matrix. The matrix can be washed with a suitable wash buffer to remove unbound compounds and non-specifically bound compounds. Compounds which remain bound can be released by a suitable elution buffer. For example, a change in the ionic strength or pH of the elution buffer can lead to a release of compounds. Alternatively, the elution buffer can comprise a release component or components designed to disrupt binding of compounds (e.g., one or more ligands or receptors, as appropriate, or analogs thereof which can disrupt binding or competitively inhibit binding of test compound to the protein).

Fusion proteins comprising all, or a portion of, a protein (e.g., an Eph receptor or an ephrin) linked to a second moiety not occurring in that protein as found in nature can be prepared for use in another embodiment of the method. Suitable fusion proteins for this purpose include those in which the second moiety comprises an affinity ligand (e.g., an enzyme, antigen, epitope). The fusion proteins can be produced by inserting the protein (e.g., an Eph receptor or an ephrin) or a portion thereof into a suitable expression vector which encodes an affinity ligand. The expression vector can be introduced into a suitable host cell for expression. Host cells are disrupted and the cell material, containing fusion protein, can be bound to a suitable affinity matrix by contacting the cell material with an affinity matrix under conditions sufficient for binding of the affinity ligand portion of the fusion protein to the affinity matrix.

In one aspect of this embodiment, a fusion protein can be immobilized on a suitable affinity matrix under conditions sufficient to bind the affinity ligand portion of the fusion protein to the matrix, and is contacted with one or more compounds (e.g., a mixture) to be tested, under conditions suitable for binding of compounds to the receptor or ligand protein portion of the bound fusion protein. Next, the affinity matrix with bound fusion protein can be washed with a suitable wash buffer to remove unbound compounds and non-specifically bound compounds without significantly disrupting binding of specifically bound compounds. Compounds which remain bound can be released by contacting the affinity matrix having fusion protein bound thereto with a suitable elution buffer (a compound elution buffer). In this aspect, compound elution buffer can be formulated to permit retention of the fusion protein by the affinity matrix, but can be formulated to interfere with binding of the compound(s) tested to the receptor or ligand protein portion of the fusion protein. For example, a change in the ionic strength or pH of the elution buffer can lead to release of compounds, or the elution buffer can comprise a release component or components designed to disrupt binding of compounds to the receptor or ligand protein portion of the fusion protein (e.g., one or more ligands or receptors or analogs thereof which can disrupt binding of compounds to the receptor or ligand protein portion of the fusion protein). Immobilization can be performed prior to, simultaneous with, or after contacting the fusion protein with compound, as appropriate. Various permutations of the method are possible, depending upon factors such as the compounds tested, the affinity matrix selected, and elution buffer formulation. For example, after the wash step, fusion protein with compound bound thereto can be eluted from the affinity matrix with a suitable elution buffer (a matrix elution buffer). Where the fusion protein comprises a cleavable linker, such as a thrombin cleavage site, cleavage from the affinity ligand can release a portion of the fusion with compound bound thereto. Bound compound can then be released from the fusion protein or its cleavage product by an appropriate method, such as extraction.

V. Methods of Treatment

In certain embodiments, the present invention provides methods of inhibiting angiogenesis and methods of treating angiogenesis-associated diseases. In other embodiments, the present invention provides methods of inhibiting or reducing tumor growth and methods of treating an individual suffering from cancer. These methods involve administering to the individual a therapeutically effective amount of one or more polypeptide therapeutic agents as described above. These methods are particularly aimed at therapeutic and prophylactic treatments of animals, and more particularly, humans.

As described herein, angiogenesis-associated diseases include, but are not limited to, angiogenesis-dependent cancer, including, for example, solid tumors, blood born tumors such as leukemias, and tumor metastases; benign tumors, for example hemangiomas, acoustic neuromas, neurofibromas, trachomas, and pyogenic granulomas; inflammatory disorders such as immune and non-immune inflammation; chronic articular rheumatism and psoriasis; ocular angiogenic diseases, for example, diabetic retinopathy, retinopathy of prematurity, macular degeneration, corneal graft rejection, neovascular glaucoma, retrolental fibroplasia, rubeosis; Osler-Webber Syndrome; myocardial angiogenesis; plaque neovascularization; telangiectasia; hemophiliac joints; angiofibroma; telangiectasia psoriasis scleroderma, pyogenic granuloma, rubeosis, arthritis, diabetic neovascularization, vasculogenesis, hematopoiesis.

It is understood that methods and compositions of the invention are also useful for treating any angiogenesis-independent cancers (tumors). As used herein, the term "angiogenesis-independent cancer" refers to a cancer (tumor) where there is no or little neovascularization in the tumor tissue.

In particular, polypeptide therapeutic agents of the present invention are useful for treating or preventing a cancer (tumor), including, but not limited to, colon carcinoma, breast cancer, mesothelioma, prostate cancer, bladder cancer, squamous cell carcinoma of the head and neck (HNSCC), Kaposi sarcoma, and leukemia.

In certain embodiments of such methods, one or more polypeptide therapeutic agents can be administered, together (simultaneously) or at different times (sequentially). In addition, polypeptide therapeutic agents can be administered with another type of compounds for treating cancer or for inhibiting angiogenesis.

In certain embodiments, the subject methods of the invention can be used alone. Alternatively, the subject methods may be used in combination with other conventional anti-cancer therapeutic approaches directed to treatment or prevention of proliferative disorders (e.g., tumor). For example, such methods can be used in prophylactic cancer prevention, prevention of cancer recurrence and metastases after surgery, and as an adjuvant of other conventional cancer therapy. The present invention recognizes that the effectiveness of conventional cancer therapies (e.g., chemotherapy, radiation therapy, phototherapy, immunotherapy, and surgery) can be enhanced through the use of a subject polypeptide therapeutic agent.

A wide array of conventional compounds have been shown to have anti-neoplastic activities. These compounds have been used as pharmaceutical agents in chemotherapy to shrink solid tumors, prevent metastases and further growth, or decrease the number of malignant cells in leukemic or bone marrow malignancies. Although chemotherapy has been effective in treating various types of malignancies, many anti-neoplastic compounds induce undesirable side effects. It has been shown that when two or more different treatments are combined, the treatments may work synergistically and allow reduction of dosage of each of the treatments, thereby reducing the detrimental side effects exerted by each compound at higher dosages. In other instances, malignancies that are refractory to a treatment may respond to a combination therapy of two or more different treatments.

When a polypeptide therapeutic agent of the present invention is administered in combination with another conventional anti-neoplastic agent, either concomitantly or sequentially, such therapeutic agent is shown to enhance the therapeutic effect of the anti-neoplastic agent or overcome cellular resistance to such anti-neoplastic agent. This allows decrease of dosage of an anti-neoplastic agent, thereby reducing the undesirable side effects, or restores the effectiveness of an anti-neoplastic agent in resistant cells.

Pharmaceutical compounds that may be used for combinatory anti-tumor therapy include, merely to illustrate: aminoglutethimide, amsacrine, anastrozole, asparaginase, bcg, bicalutamide, bleomycin, buserelin, busulfan, campothecin, capecitabine, carboplatin, carmustine, chlorambucil, cisplatin, cladribine, clodronate, colchicine, cyclophosphamide, cyproterone, cytarabine, dacarbazine, dactinomycin, daunorubicin, dienestrol, diethylstilbestrol, docetaxel, doxorubicin, epirubicin, estradiol, estramustine, etoposide, exemestane, filgrastim, fludarabine, fludrocortisone, fluorouracil, fluoxymesterone, flutamide, gemcitabine, genistein, goserelin, hydroxyurea, idarubicin, ifosfamide, imatinib, interferon, irinotecan, ironotecan, letrozole, leucovorin, leuprolide, levamisole, lomustine, mechlorethamine, medroxyprogesterone, megestrol, melphalan, mercaptopurine, mesna, methotrexate, mitomycin, mitotane, mitoxantrone, nilutamide, nocodazole, octreotide, oxaliplatin, paclitaxel, pamidronate, pentostatin, plicamycin, porfimer, procarbazine, raltitrexed, rituximab, streptozocin, suramin, tamoxifen, temozolomide, teniposide, testosterone, thioguanine, thiotepa, titanocene dichloride, topotecan, trastuzumab, tretinoin, vinblastine, vincristine, vindesine, and vinorelbine.

These chemotherapeutic anti-tumor compounds may be categorized by their mechanism of action into, for example, following groups: anti-metabolites/anti-cancer agents, such as pyrimidine analogs (5-fluorouracil, floxuridine, capecitabine, gemcitabine and cytarabine) and purine analogs, folate antagonists and related inhibitors (mercaptopurine, thioguanine, pentostatin and 2-chlorodeoxyadenosine (cladribine)); antiproliferative/antimitotic agents including natural products such as vinca alkaloids (vinblastine, vincristine, and vinorelbine), microtubule disruptors such as taxane (paclitaxel, docetaxel), vincristin, vinblastin, nocodazole, epothilones and navelbine, epidipodophyllotoxins (etoposide, teniposide), DNA damaging agents (actinomycin, amsacrine, anthracyclines, bleomycin, busulfan, camptothecin, carboplatin, chlorambucil, cisplatin, cyclophosphamide, cytoxan, dactinomycin, daunorubicin, doxorubicin, epirubicin, hexamethylmelamineoxaliplatin, iphosphamide, melphalan, merchlorehtamine, mitomycin, mitoxantrone, nitrosourea, plicamycin, procarbazine, taxol, taxotere, teniposide, triethylenethiophosphoramide and etoposide (VP16)); antibiotics such as dactinomycin (actinomycin D), daunorubicin, doxorubicin (adriamycin), idarubicin, anthracyclines, mitoxantrone, bleomycins, plicamycin (mithramycin) and mitomycin; enzymes (L-asparaginase which systemically metabolizes L-asparagine and deprives cells which do not have the capacity to synthesize their own asparagine); antiplatelet agents; antiproliferative/antimitotic alkylating agents such as nitrogen mustards (mechlorethamine, cyclophosphamide and analogs, melphalan, chlorambucil), ethylenimines and methylmelamines (hexamethylmelamine and thiotepa), alkyl sulfonates-busulfan, nitrosoureas (carmustine (BCNU) and analogs, streptozocin), trazenes-dacarbazinine (DTIC); antiproliferative/antimitotic antimetabolites such as folic acid analogs (methotrexate); platinum coordination complexes (cisplatin, carboplatin), procarbazine, hydroxyurea, mitotane, aminoglutethimide; hormones, hormone analogs (estrogen, tamoxifen, goserelin, bicalutamide, nilutamide) and aromatase inhibitors (letrozole, anastrozole); anticoagulants (heparin, synthetic heparin salts and other inhibitors of thrombin); fibrinolytic agents (such as tissue plasminogen activator, streptokinase and urokinase), aspirin, dipyridamole, ticlopidine, clopidogrel, abciximab; antimigratory agents; antisecretory agents (breveldin); immunosuppressives (cyclosporine, tacrolimus (FK-506), sirolimus (rapamycin), azathioprine, mycophenolate mofetil); anti-angiogenic compounds (TNP-470, genistein) and growth factor inhibitors (vascular endothelial growth factor (VEGF) inhibitors, fibroblast growth factor (FGF) inhibitors); angiotensin receptor blocker; nitric oxide donors; anti-sense oligonucleotides; antibodies (trastuzumab); cell cycle inhibitors and differentiation inducers (tretinoin); mTOR inhibitors, topoisomerase inhibitors (doxorubicin (adriamycin), amsacrine, camptothecin, daunorubicin, dactinomycin, eniposide, epirubicin, etoposide, idarubicin and mitoxantrone, topotecan, irinotecan), corticosteroids (cortisone, dexamethasone, hydrocortisone, methylpednisolone, prednisone, and prenisolone); growth factor signal transduction kinase inhibitors; mitochondrial dysfunction inducers and caspase activators; and chromatin disruptors.

In certain embodiments, pharmaceutical compounds that may be used for combinatory anti-angiogenesis therapy include: (1) inhibitors of release of "angiogenic molecules," such as bFGF (basic fibroblast growth factor); (2) neutralizers of angiogenic molecules, such as an anti-βbFGF antibodies; and (3) inhibitors of endothelial cell response to angiogenic stimuli, including collagenase inhibitor, basement membrane turnover inhibitors, angiostatic steroids, fungal-derived angiogenesis inhibitors, platelet factor 4, thrombospondin, arthritis drugs such as D-penicillamine and gold thiomalate, vitamin $D_3$ analogs, alpha-interferon, and the like. For additional proposed inhibitors of angiogenesis, see Blood et al., Bioch. Biophys. Acta., 1032:89-118 (1990), Moses et al., Science, 248:1408-1410 (1990), Ingber et al., Lab. Invest., 59:44-51 (1988), and U.S. Pat. Nos. 5,092,885, 5,112,946, 5,192,744, 5,202,352, and 6,573,256. In addition, there are a wide variety of compounds that can be used to inhibit angiogenesis, for example, peptides or agents that block the VEGF-mediated angiogenesis pathway, endostatin protein or derivatives, lysine binding fragments of angiostatin, melanin or melanin-promoting compounds, plasminogen fragments (e.g., Kringles 1-3 of plasminogen), tropoin subunits, antagonists of vitronectin $\alpha_v\beta_3$, peptides derived from Saposin B, antibiotics or analogs (e.g., tetracycline, or neomycin), dienogest-containing compositions, compounds comprising a MetAP-2 inhibitory core coupled to a peptide, the compound EM-138, chalcone and its analogs, and naaladase inhibitors. See, for example, U.S. Pat. Nos. 6,395,718, 6,462,075, 6,465,431, 6,475,784, 6,482,802, 6,482,810, 6,500,431, 6,500,924, 6,518,298, 6,521,439, 6,525,019, 6,538,103, 6,544,758, 6,544,947, 6,548,477, 6,559,126, and 6,569,845.

Depending on the nature of the combinatory therapy, administration of the polypeptide therapeutic agents of the invention may be continued while the other therapy is being administered and/or thereafter. Administration of the polypeptide therapeutic agents may be made in a single dose, or in multiple doses. In some instances, administration of the polypeptide therapeutic agents is commenced at least several days prior to the conventional therapy, while in other instances, administration is begun either immediately before or at the time of the administration of the conventional therapy.

VI. Methods of Administration and Pharmaceutical Compositions

In certain embodiments, the subject polypeptide therapeutic agents (e.g., soluble polypeptides or antibodies) of the present invention are formulated with a pharmaceutically acceptable carrier. Such therapeutic agents can be administered alone or as a component of a pharmaceutical formulation (composition). The compounds may be formulated for administration in any convenient way for use in human or veterinary medicine. Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Formulations of the subject polypeptide therapeutic agents include those suitable for oral/nasal, topical, parenteral, rectal, and/or intravaginal administration. The formulations may conveniently be presented in unit dosage form and may be prepared by any methods well known in the art of pharmacy. The amount of active ingredient which can be combined with a carrier material to produce a single dosage form will vary depending upon the host being treated, the particular mode of administration. The amount of active ingredient which can be combined with a carrier material to produce a single dosage form will generally be that amount of the compound which produces a therapeutic effect.

In certain embodiments, methods of preparing these formulations or compositions include combining another type of anti-tumor or anti-angiogenesis therapeutic agent and a carrier and, optionally, one or more accessory ingredients. In general, the formulations can be prepared with a liquid carrier, or a finely divided solid carrier, or both, and then, if necessary, shaping the product.

Formulations for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a subject polypeptide therapeutic agent as an active ingredient.

In solid dosage forms for oral administration (capsules, tablets, pills, dragees, powders, granules, and the like), one or more polypeptide therapeutic agents of the present invention may be mixed with one or more pharmaceutically acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose, and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, cetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof; and (10) coloring agents. In the case of capsules, tablets and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols and the like.

Liquid dosage forms for oral administration include pharmaceutically acceptable emulsions, microemulsions, solutions, suspensions, syrups, and elixirs. In addition to the active ingredient, the liquid dosage forms may contain inert diluents commonly used in the art, such as water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor, and sesame oils), glycerol, tetrahydrofuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, coloring, perfuming, and preservative agents.

Suspensions, in addition to the active compounds, may contain suspending agents such as ethoxylated isostearyl alcohols, polyoxyethylene sorbitol, and sorbitan esters, microcrystalline cellulose, aluminum metahydroxide, bentonite, agar-agar and tragacanth, and mixtures thereof.

In particular, methods of the invention can be administered topically, either to skin or to mucosal membranes such as those on the cervix and vagina. This offers the greatest opportunity for direct delivery to tumor with the lowest chance of inducing side effects. The topical formulations may further include one or more of the wide variety of agents known to be effective as skin or stratum corneum penetration enhancers. Examples of these are 2-pyrrolidone, N-methyl-2-pyrrolidone, dimethylacetamide, dimethylformamide, propylene glycol, methyl or isopropyl alcohol, dimethyl sulfoxide, and azone. Additional agents may further be included to make the formulation cosmetically acceptable. Examples of these are fats, waxes, oils, dyes, fragrances, preservatives, stabilizers, and surface active agents. Keratolytic agents such as those known in the art may also be included. Examples are salicylic acid and sulfur.

Dosage forms for the topical or transdermal administration include powders, sprays, ointments, pastes, creams, lotions, gels, solutions, patches, and inhalants. The subject polypeptide therapeutic agents may be mixed under sterile conditions with a pharmaceutically acceptable carrier, and with any preservatives, buffers, or propellants which may be required. The ointments, pastes, creams and gels may contain, in addition to a subject polypeptide agent, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to a subject polypeptide therapeutic agent, excipients such as lactose, talc, silicic acid, aluminum hydroxide, calcium silicates, and polyamide powder, or mixtures of these substances. Sprays can additionally contain customary propellants, such as chlorofluorohydrocarbons and volatile unsubstituted hydrocarbons, such as butane and propane.

Pharmaceutical compositions suitable for parenteral administration may comprise one or more polypeptide therapeutic agents in combination with one or more pharmaceutically acceptable sterile isotonic aqueous or nonaqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents. Examples of suitable aqueous and nonaqueous carriers which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants, such as preservatives, wetting agents, emulsifying agents and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption, such as aluminum monostearate and gelatin.

Injectable depot forms are made by forming microencapsule matrices of one or more polypeptide therapeutic agents in biodegradable polymers such as polylactide-polyglycolide. Depending on the ratio of drug to polymer, and the nature of the particular polymer employed, the rate of drug release can be controlled. Examples of other biodegradable polymers include poly(orthoesters) and poly(anhydrides).

Depot injectable formulations are also prepared by entrapping the drug in liposomes or microemulsions which are compatible with body tissue.

Formulations for intravaginal or rectally administration may be presented as a suppository, which may be prepared by mixing one or more compounds of the invention with one or more suitable nonirritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the active compound.

In other embodiments, the polypeptide therapeutic agents of the instant invention can be expressed within cells from eukaryotic promoters. For example, a soluble polypeptide of EphB4 or Ephrin B2 can be expressed in eukaryotic cells from an appropriate vector. The vectors are preferably DNA plasmids or viral vectors. Viral vectors can be constructed based on, but not limited to, adeno-associated virus, retrovirus, adenovirus, or alphavirus. Preferably, the vectors stably introduced in and persist in target cells. Alternatively, viral vectors can be used that provide for transient expression. Such vectors can be repeatedly administered as necessary. Delivery of vectors encoding the subject polypeptide therapeutic agent can be systemic, such as by intravenous or intramuscular administration, by administration to target cells ex-planted from the patient followed by reintroduction into the patient, or by any other means that would allow for introduction into the desired target cell (for a review see Couture et al., 1996, TIG., 12, 510).

EXEMPLIFICATION

The invention now being generally described, it will be more readily understood by reference to the following examples, which are included merely for purposes of illustration of certain aspects and embodiments of the present invention, and are not intended to limit the invention.

Example 1

Soluble Derivatives of the Extracellular Domains of Human Ephrin B2 and EphB4 Proteins Soluble derivatives of the extracellular domains of human Ephrin B2 and EphB4 proteins represent either truncated full-length predicted extracellular domains of Ephrin B2 (B4ECv3, B2EC) or translational fusions of the domains with constant region of human immunoglobulins (IgG1 Fc fragment), such as B2EC-FC, B4ECv2-FC and B4ECv3-FC. Representative human Ephrin B2 constructs and human EphB4 constructs are shown FIGS. 14 and 15.

Figure 7:
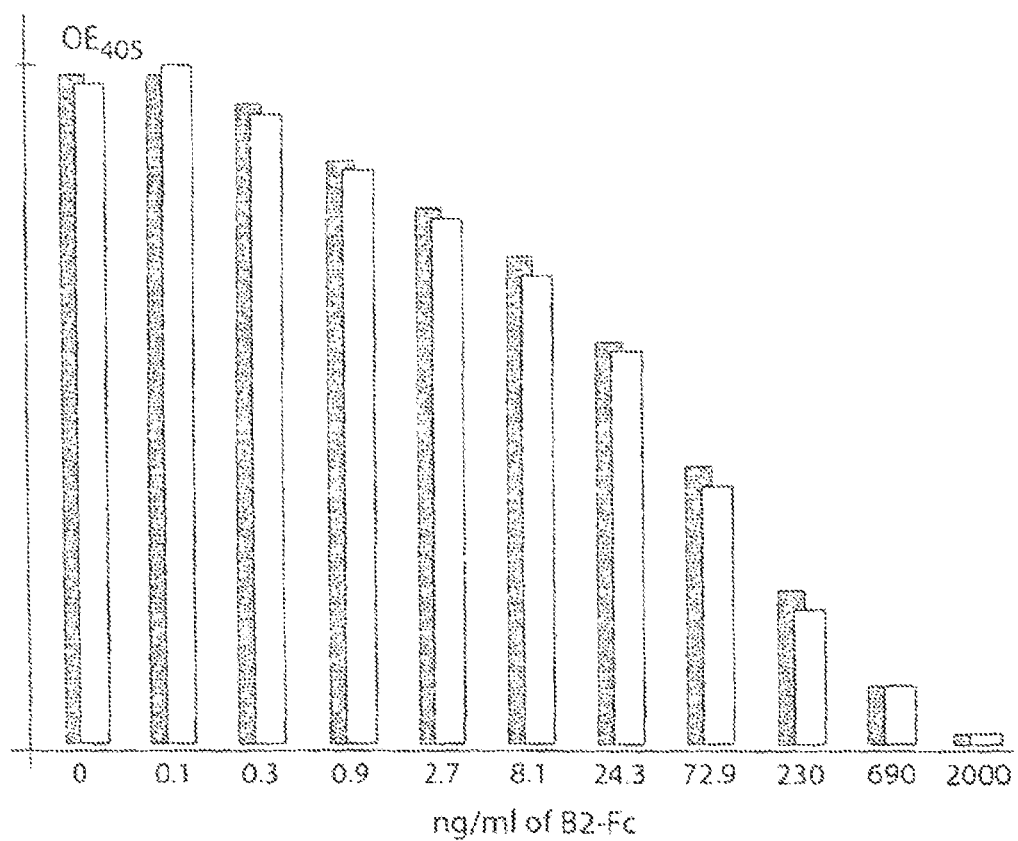
FIG. 7 shows B4EC-FC inhibition assay (Inhibition in solution).
Figure 8:
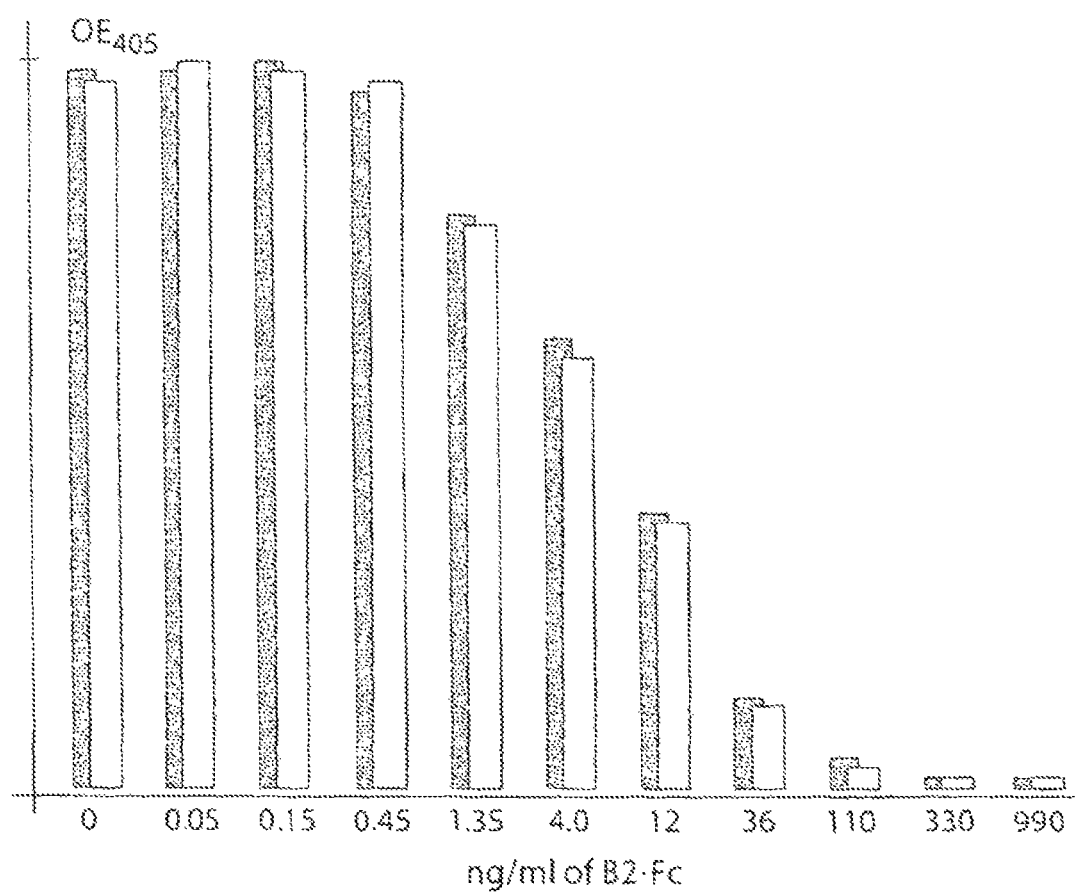
FIG. 8 shows B2EC-FC binding assay (Protein-A-agarose based assay).

The cDNA fragments encoding these recombinant proteins were subcloned into mammalian expression vectors, expressed in transiently or stably transfected mammalian cell lines and purified to homogeneity as described in detail in Materials and Methods section (see below). Predicted amino acid sequences of the proteins are shown in FIGS. 1-5. High purity of the isolated proteins and their recognition by the corresponding anti-Ephrin B2 and anti-EphB4 monoclonal or polyclonal antibodies were confirmed. The recombinant proteins exhibit the expected high-affinity binding, binding competition and specificity properties with their corresponding binding partners as corroborated by the biochemical assays (see e.g., FIGS. 6-8).

Figure 9:
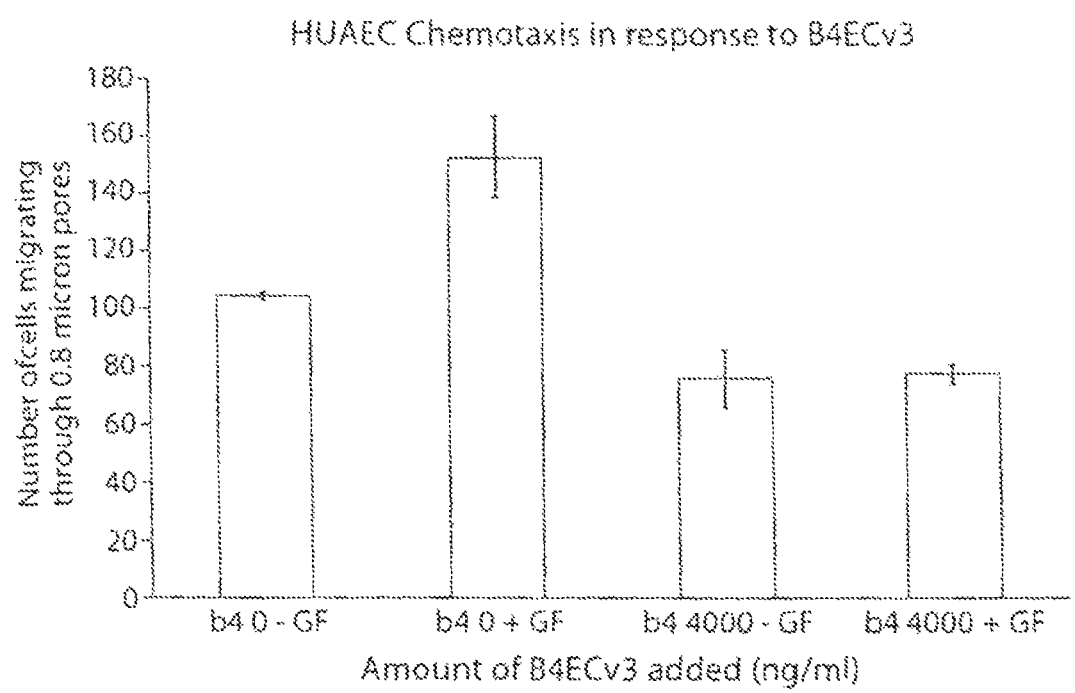
FIG. 9 shows chemotaxis of HUAEC in response to B4Ecv3.
Figure 10:
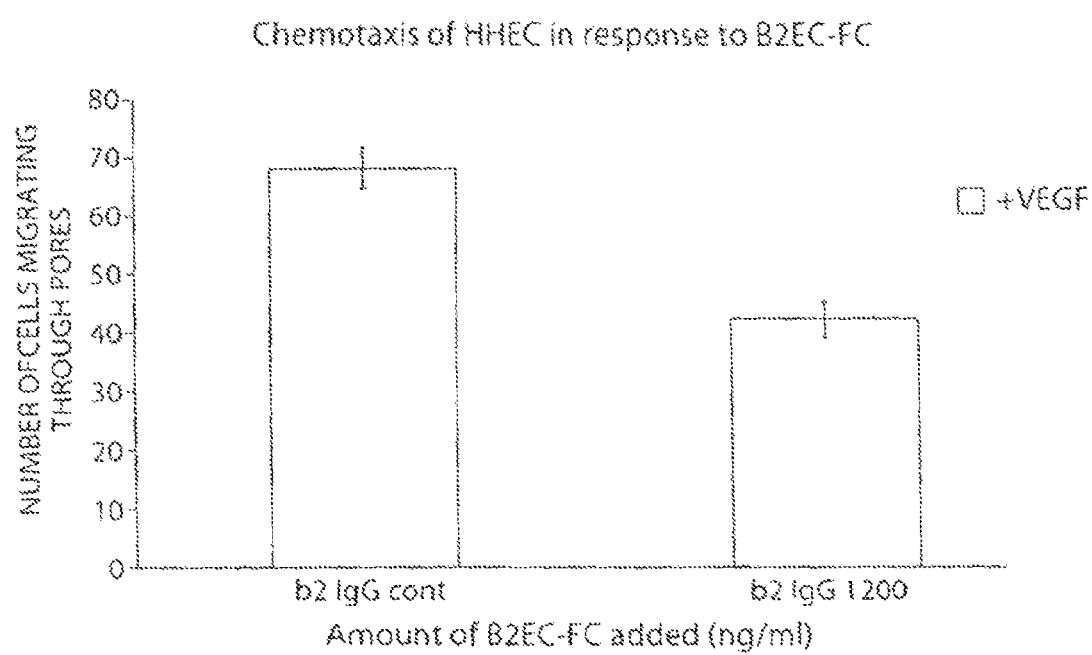
FIG. 10 shows chemotaxis of HHEC in response to B2EC-FC.
Figure 11:
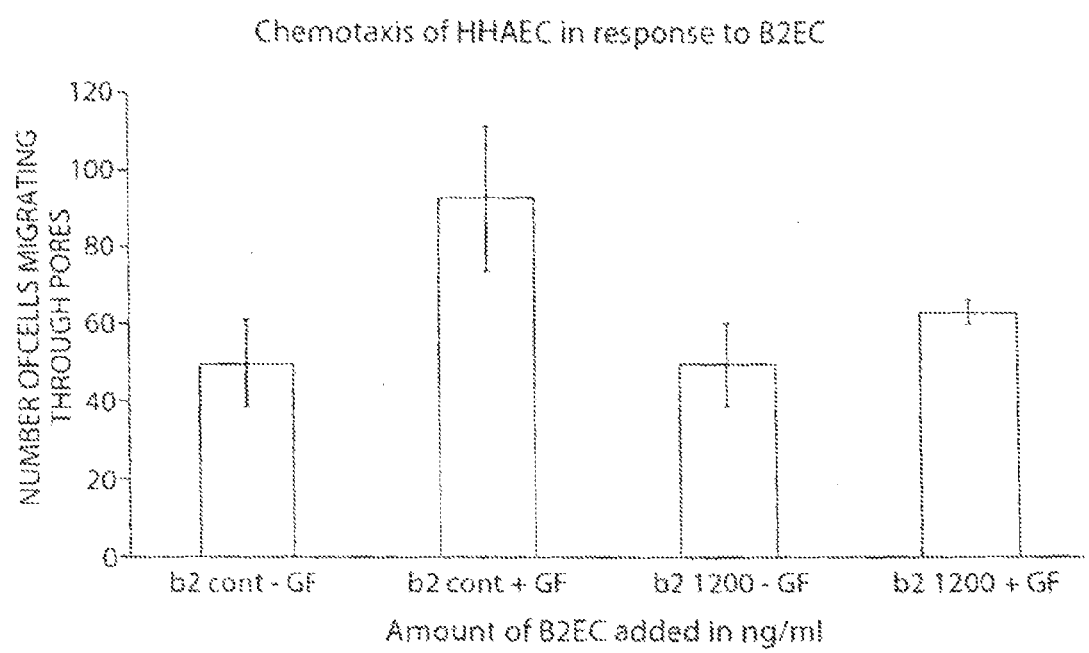
FIG. 11 shows chemotaxis of HHAEC in response to B2EC.
Figure 12:
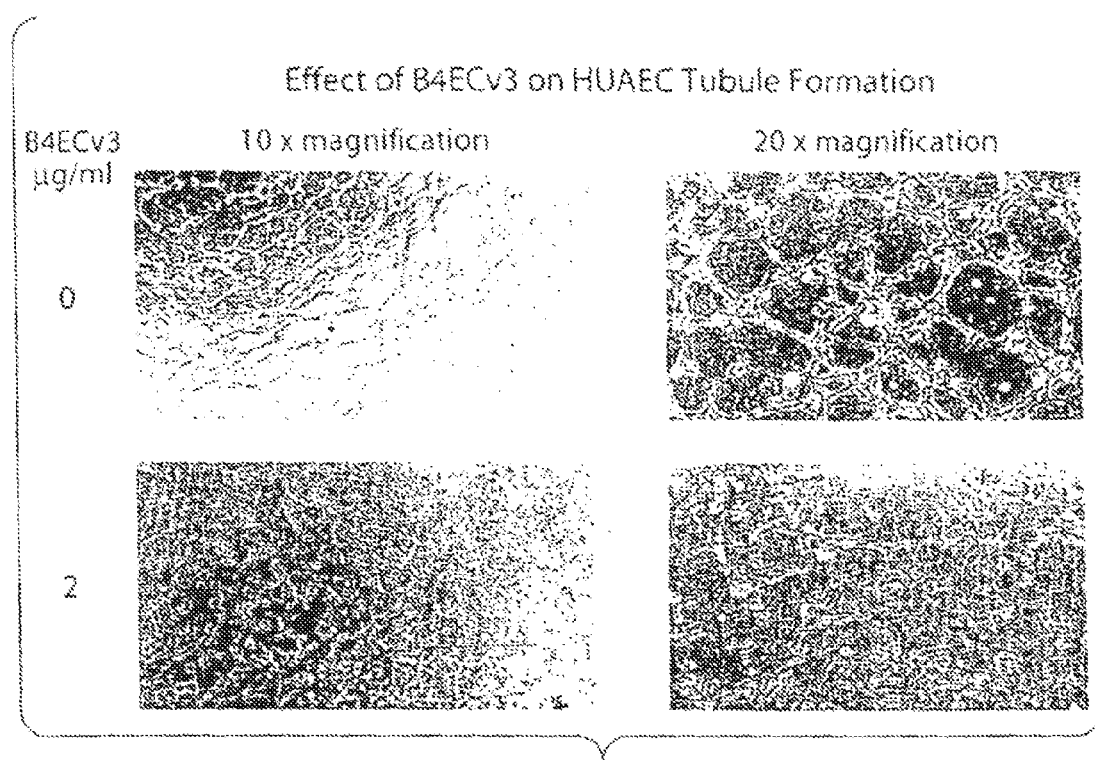
FIG. 12 shows effect of B4Ecv3 on HUAEC tubule formation.
Figure 13:
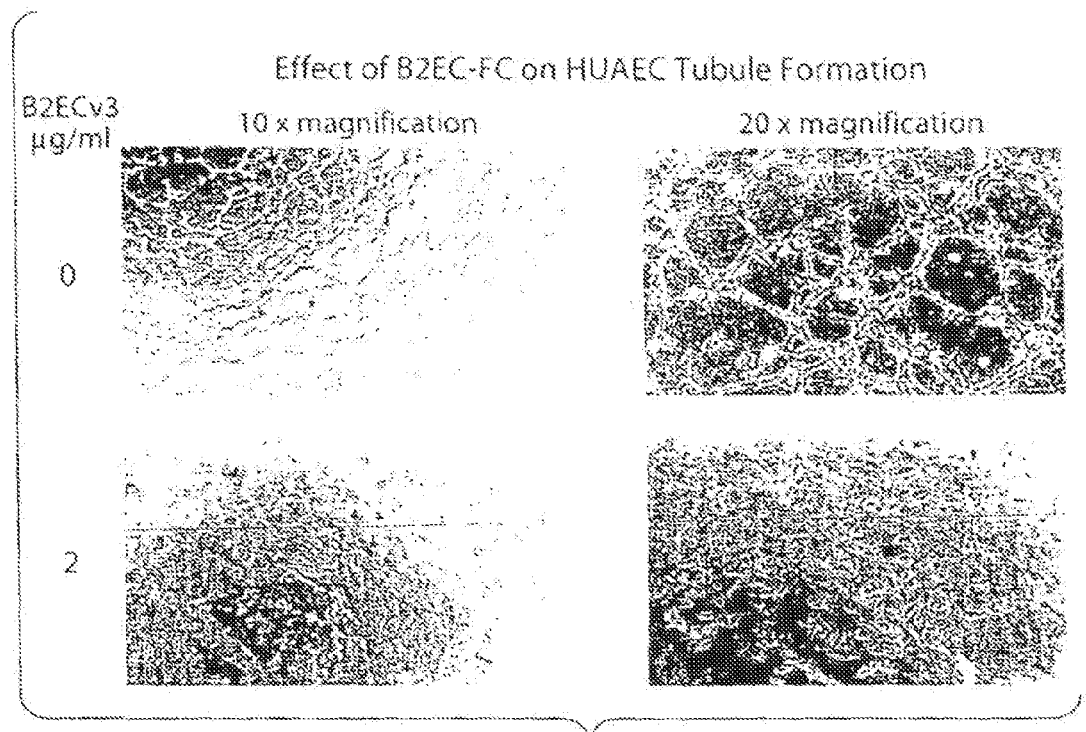
FIG. 13 shows effect of B2EC-FC on HUAEC tubule formation.

Such soluble derivative proteins human Ephrin B2 and EphB4 exhibit potent biological activity in several cell-based assays and in vivo assays which measure angiogenesis or anti-cancer activities, and are therefore perspective drug candidates for anti-angiogenic and anti-cancer therapy. B4ECv3 as well as B2EC and B2EC-FC proteins blocked chemotaxis of human endothelial cells (as tested with umbilical cord and hepatic AECs or VECs), with a decrease in degradation of the extracellular matrix, Matrigel, and a decrease in migration in response to growth factor stimuli (FIGS. 9-11). B4ECv3 and B2EC-FC proteins have potent anti-angiogenic effect as demonstrated by their inhibition of endothelial cell tube formation (FIGS. 12-13).

A detailed description of the materials and methods for this example may be found in U.S. Patent Publication No. 20050084873.

The sequence of the Globular domain+Cys-rich domain (B4EC-GC), precursor protein is (SEQ ID NO:12):

MELRVLLCWASLAAALEETLLNTKLETADLKWVTFPQVDGQWEELSG

LDEEQHSVRTYEVCEVQRAPGQAHWLRTGWVPRRGAVHVYATLRFTM

LECLSLPRAGRSCKETFTVFYYESDADTATALTPAWMENPYIKVDTV

AAEHLTRKRPGAEATGKVNVKTLRLGPLSKAGFYLAFQDQGACMALL

SLHLFYKKCAQLTVNLTRFPETVPRELVVPVAGSCVVDAVPAPGPSP

SLYCREDGQWAEQPVTGCSCAPGFEAAEGNTKCRACAQGTFKPLSGE

GSCQPCPANSHSNTIGSAVCQCRVGYFRARTDPRGAPCTTPPSAHHH

HHH

For many uses, including therapeutic use, the leader sequence (first 15 amino acids, so that the processed form begins Leu-Glu-Glu . . . ) and the c-terminal hexahistidine tag may be removed or omitted.

Sequence of the GCF precursor protein (SEQ ID NO:13):

MELRVLLCWASLAAALEETLLNTKLETADLKWVTFPQVDGQWEELSG

LDEEQHSVRTYEVCEVQRAPGQAHWLRTGWVPRRGAVHVYATLRFTM

LECLSLPRAGRSCKETFTVFYYESDADTATALTPAWMENPYIKVDTV

AAEHLTRKRPGAEATGKVNVKTLRLGPLSKAGFYLAFQDQGACMALL

SLHLFYKKCAQLTVNLTRFPETVPRELVVPVAGSCVVDAVPAPGPSP

SLYCREDGQWAEQPVTGCSCAPGFAEGNTKCRACAQGTFKPLSGEGS

CQPCPANSHSNTIGSAVCQCRVGYFRARTDPRGAPCTTPPSAPRSVV

SRLNGSSLHLEWSAPLESGGREDLTYALRCRECRPGGSCAPCGGDLT

FDPGPRDLVEPWVVVRGLRPDFTYTFEVTALNGVSSLATGPVPFEPV

NVHHHHHH

For many uses, including therapeutic use, the leader sequence (first 15 amino acids, so that the processed form begins Leu-Glu-Glu . . . ) and the c-terminal hexahistidine tag may be removed or omitted.

Amino acid sequence of encoded FL-hB4EC precursor (His-tagged) (SEQ ID NO:14):

MELRVLLCWASLAAALEETLLNTKLETADLKWVTFPQVDGQWEELSG

LDEEQHSVRTYEVCEVQRAPGQAHWLRTGWVPRRGAVHVYATLRFTM

LECLSLPRAGRSCKETFTVFYYESDADTATALTPAWMENPYIKVDTV

```
AAEHLTRKRPGAEATGKVNVKTLRLGPLSKAGFYLAFQDQGACMALL

SLHLFYKKCAQLTVNLTRFPETVPRELVVPVAGSCVVDAVPAPGPSP

SLYCREDGQWAEQPVTGCSCAPGFEAAEGNTKCRACAQGTFKPLSGE

GSCQPCPANSHSNTIGSAVCQCRVGYFRARTDPRGAPCTTPPSAPRS

VVSRLNGSSLHLEWSAPLESGGREDLTYALRCRECRPGGSCAPCGGD

LTFDPGPRDLVEPWVVVRGLRPDFTYTFEVTALNGVSSLATGPVPFE

PVNVTTDREVPPAVSDIRVTRSSPSSLSLAWAVPRAPSGAWLDYEVK

YHEKGAEGPSSVRFLKTSENRAELRGLKRGASYLVQVRARSEAGYGP

FGQEHHSQTQLDESEGWREQGSKRAILQIEGKPIPNPLLGLDSTRTG

HHHHHH
```

For many uses, including therapeutic use, the leader sequence (first 15 amino acids, so that the processed form begins Leu-Glu-Glu . . . ) and the c-terminal hexahistidine tag may be removed or omitted.

EphB4 CF$_2$ protein, precursor (SEQ ID NO:15):

```
MELRVLLCWASLAAALEETLLNTKLETQLTVNLTRFPETVPRELVVPV

AGSCVVDAVPAPGPSPSLYCREDGQWAEQPVTGCSCAPGFEAAEGNTK

CRACAQGTFKPLSGEGSCQPCPANSHSNTIGSAVCQCRVGYFRARTDP

RGAPCTTPPSAPRSVVSRLNGSSLHLEWSAPLESGGREDLTYALRCRE

CRPGGSCAPCGGDLTFDPGPRDLVEPWVVVRGLRPDFTYTFEVTALNG

VSSLATGPVPFEPVNVTTDREVPPAVSDIRVTRSSPSSLSLAWAVPRA

PSGAWLDYEVKYHEKGAEGPSSVRFLKTSENRAELRGLKRGASYLVQV

RARSEAGYGPFGQEHHSQTQLDESEGWREQGGRSSLEGPRFEGKPIPN

PLLGLDSTRTGHHHHHH
```

The precursor sequence of the preferred GCF2 protein (also referred to herein as GCF2F) is (SEQ ID NO:16):

```
MELRVLLCWASLAAALEETLLNTKLETADLKWVTFPQVDGQWEELSGL

DEEQHSVRTYEVCEVQRAPGQAHWLRTGWVPRRGAVHVYATLRFTMLE

CLSLPRAGRSCKETFTVFYYESDADTATALTPAWMENPYIKVDTVAAE

HLTRKRPGAEATGKVNVKTLRLGPLSKAGFYLAFQDQGACMALLSLHL

FYKKCAQLTVNLTRFPETVPRELVVPVAGSCVVDAVPAPGPSPSLYCR

EDGQWAEQPVTGCSCAPGFEAAEGNTKCRACAQGTFKPLSGEGSCQPC

PANSHSNTIGSAVCQCRVGYFRARTDPRGAPCTTPPSAPRSVVSRLNG

SSLHLEWSAPLESGGREDLTYALRCRECRPGGSCAPCGGDLTFDPGPR

DLVEPWVVVRGLRPDFTYTFEVTALNGVSSLATGPVPFEPVNVTTDRE

VPPAVSDIRVTRSSPSSLSLAWAVPRAPSGAWLDYEVKYHEKGAEGPS

SVRFLKTSENRAELRGLKRGASYLVQVRARSEAGYGPFGQEHHSQTQL

DESEGWREQ
```

The processed sequence is (SEQ ID NO:17):

```
LEETLLNTKLETADLKWVTFPQVDGQWEELSGLDEEQHSVRTYEVCE

VQRAPGQAHWLRTGWVPRRGAVHVYATLRFTMLECLSLPRAGRSCKE

TFTVFYYESDADTATALTPAWMENPYIKVDTVAAEHLTRKRPGAEAT

GKVNVKTLRLGPLSKAGFYLAFQDQGACMALLSLHLFYKKCAQLTVN

LTRFPETVPRELVVPVAGSCVVDAVPAPGPSPSLYCREDGQWAEQPV

TGCSCAPGFEAAEGNTKCRACAQGTFKPLSGEGSCQPCPANSHSNTI

GSAVCQCRVGYFRARTDPRGAPCTTPPSAPRSVVSRLNGSSLHLEWS

APLESGGREDLTYALRCRECRPGGSCAPCGGDLTFDPGPRDLVEPWV

VVRGLRPDFTYTFEVTALNGVSSLATGPVPFEPVNVTTDREVPPAVS

DIRVTRSSPSSLSLAWAVPRAPSGAWLDYEVKYHEKGAEGPSSVRFL

KTSENRAELRGLKRGASYLVQVRARSEAGYGPFGQEHHSQTQLDESE

GWREQ
```

Biochemical Assays

A. Binding Assay

10 μl of Ni-NTA-Agarose were incubated in microcentrifuge tubes with 50 μl of indicated amount of B4ECv3 diluted in binding buffer BB (20 mM Tris-HCl, 0.15 M NaCl, 0.1% bovine serum albumin pH 8) After incubation for 30 min on shaking platform, Ni-NTA beads were washed twice with 1.4 ml of BB, followed by application of 50 μl of B2-AP in the final concentration of 50 nM. Binding was performed for 30 min on shaking platform, and then tubes were centrifuged and washed one time with 1.4 ml of BB. Amount of precipitated AP was measured colorimetrically after application of PNPP.

B. Inhibition Assay

Inhibition in Solution.

Different amounts of B4ECv3 diluted in 50 μl of BB were pre-incubated with 50 μl of 5 nM B2EC-AP reagent (protein fusion of Ephrin B2 ectodomain with placental alkaline phosphatase). After incubation for 1 h, unbound B2EC-AP was precipitated with 5,000 HEK293 cells expressing membrane-associated full-length EphB4 for 20 min. Binding reaction was stopped by dilution with 1.2 ml of BB, followed by centrifugation for 10 min. Supernatants were discarded and alkaline phosphatase activities associated with collected cells were measured by adding para-nitrophenyl phosphate (PNPP) substrate.

Cell Based Inhibition.

B4ECv3 was serially diluted in 20 mM Tris-HCl, 0.15 M NaCl, 0.1% BSA, pH 8 and mixed with 5,000 HEK293 cells expressing membrane-associated full-length Ephrin B2. After incubation for 1 h, 50 μl of 5 nM B4EC-AP reagent (protein fusion of EphB4 ectodomain with placental alkaline phosphatase were added into each tube for 30 min to detect unoccupied Ephrin B2 binding sites. Binding reactions were stopped by dilution with 1.2 ml of BB and centrifugation. Colorimetric reaction of cell-precipitated AP was developed with PNPP substrate.

C. B4EC-FC Binding Assay

Protein A-Agarose Based Assay.

10 μl of Protein A-agarose were incubated in Eppendorf tubes with 50 μl of indicated amount of B4EC-FC diluted in binding buffer BB (20 mM Tris-HCl, 0.15 M NaCl, 0.1% BSA pH 8). After incubation for 30 min on shaking platform, Protein A Aagarose beads were washed twice with 1.4 ml of BB, followed by application of 50 μl of B2ECAP reagent at the final concentration of 50 nM. Binding was performed for 30 min on shaking platform, and then tubes were centrifuged and washed once with 1.4 ml of BB. Colorimetric reaction of precipitated AP was measured after application of PNPP (FIG. 6).

Nitrocellulose Based Assay.

B4EC-FC was serially diluted in 20 mM Tris-HCl, 0.15 M NaCl, 50 µg/ml BSA, pH 8. 2 µl of each fraction were applied onto nitrocellulose strip and spots were dried out for 3 min. Nitrocellulose strip was blocked with 5% non-fat milk for 30 min, followed by incubation with 5 nM B2EC-AP reagent. After 45 min incubation for binding, nitrocellulose was washed twice with 20 mM Tris-HCl, 0.15 M NaCl, 50 µg/ml BSA, pH 8 and color was developed by application of alkaline phosphatase substrate Sigma Fast (Sigma).

D. B4EC-FC Inhibition Assay

Inhibition in Solution.

See above, for B4ECv3. The results were shown in FIG. 7.

Cell Based Inhibition.

See above, for B4ECv3.

E. B2EC-FC Binding Assay

Protein-A-Agarose Based Assay.

See above, for B4EC-FC. The results were shown in FIG. 8.

Nitrocellulose Based Assay.

See above, for B4EC-FC.

6) Cell-Based Assays

A. Growth Inhibition Assay

Human umbilical cord vein endothelial cells (HUVEC) (1.5×103) are plated in a 96-well plate in 100 µl of EBM-2 (Clonetic # CC3162). After 24 hours (day 0), the test recombinant protein (100 µl) is added to each well at 2× the desired concentration (5-7 concentration levels) in EBM-2 medium. On day 0, one plate is stained with 0.5% crystal violet in 20% methanol for 10 minutes, rinsed with water, and air-dried. The remaining plates are incubated for 72 h at 37° C. After 72 h, plates are stained with 0.5% crystal violet in 20% methanol, rinsed with water and airdried. The stain is eluted with 1:1 solution of ethanol: 0.1 M sodium citrate (including day 0 plate), and absorbance is measured at 540 nm with an ELISA reader (Dynatech Laboratories). Day 0 absorbance is subtracted from the 72 h plates and data is plotted as percentage of control proliferation (vehicle treated cells). $IC_{50}$ (drug concentration causing 50% inhibition) is calculated from the plotted data.

B. Cord Formation Assay (Endothelial Cell Tube Formation Assay)

Matrigel (60 µl of 10 mg/ml; Collaborative Lab #35423) is placed in each well of an ice-cold 96-well plate. The plate is allowed to sit at room temperature for 15 minutes then incubated at 37° C. for 30 minutes to permit the matrigel to polymerize. In the mean time, HUVECs are prepared in EGM-2 (Clonetic #CC3162) at a concentration of $2×10^5$ cells/ml. The test compound is prepared at 2× the desired concentration (5 concentration levels) in the same medium. Cells (500 µl) and 2× drug (500 µl) is mixed and 200 µl of this suspension are placed in duplicate on the polymerized matrigel. After 24 h incubation, triplicate pictures are taken for each concentration using a Bioquant Image Analysis system. Drug effect (IC50) is assessed compared to untreated controls by measuring the length of cords formed and number of junctions.

C. Cell Migration Assay

Migration is assessed using the 48-well Boyden chamber and 8 µm pore size collagen-coated (10 µg/ml rat tail collagen; Collaborative Laboratories) polycarbonate filters (Osmonics, Inc.). The bottom chamber wells receive 27-29 µl of DMEM medium alone (baseline) or medium containing chemo-attractant (bFGF, VEGF or Swiss 3T3 cell conditioned medium). The top chambers receive 45 µl of HUVEC cell suspension ($1×10^6$ cells/ml) prepared in DMEM+1% BSA with or without test compound. After 5 h incubation at 37° C., the membrane is rinsed in PBS, fixed and stained in Diff-Quick solutions. The filter is placed on a glass slide with the migrated cells facing down and cells on top are removed using a Kimwipe. The testing is performed in 4-6 replicates and five fields are counted from each well. Negative unstimulated control values are subtracted from stimulated control and drug treated values and data is plotted as mean migrated cell±S.D. IC50 is calculated from the plotted data.

Example 2

Extracellular Domain Fragments of EphB4 Receptor Inhibit Angiogenesis and Tumor Growth A. Globular Domain of EphB4 is Required for EphrinB2 Binding and for the Activity of EphB4-Derived Soluble Proteins in Endothelial Tube Formation Assay.

To identify subdomain(s) of the ectopic part of EphB4 necessary and sufficient for the anti-angiogenic activity of the soluble recombinant derivatives of the receptor, four recombinant deletion variants of EphB4EC were produced and tested (FIG. 16). Extracellular part of EphB4, similarly to the other members of EphB and EphA receptor family, contains N-terminal ligand-binding globular domain followed by cysteine-rich domain and two fibronectin type III repeats (FNIII). In addition to the recombinant B4-GCF2 protein containing the complete ectopic part of EphB4, we constructed three deletion variants of EphB4EC containing globular domain and Cys-rich domain (B4-GC); globular, Cys-rich and the first FNIII domain (GCF1) as well as the ECD version with deleted globular domain (CF2). Our attempts to produce several versions of truncated EphB4EC protein containing the globular domain alone were not successful due to the lack of secretion of proteins expressed from all these constructs and absence of ligand binding by the intracellularly expressed recombinant proteins. In addition, a non-tagged version of B4-GCF2, called GCF2-F, containing complete extracellular domain of EphB4 with no additional fused amino acids was expressed, purified and used in some of the experiments described here.

Figure 17A:
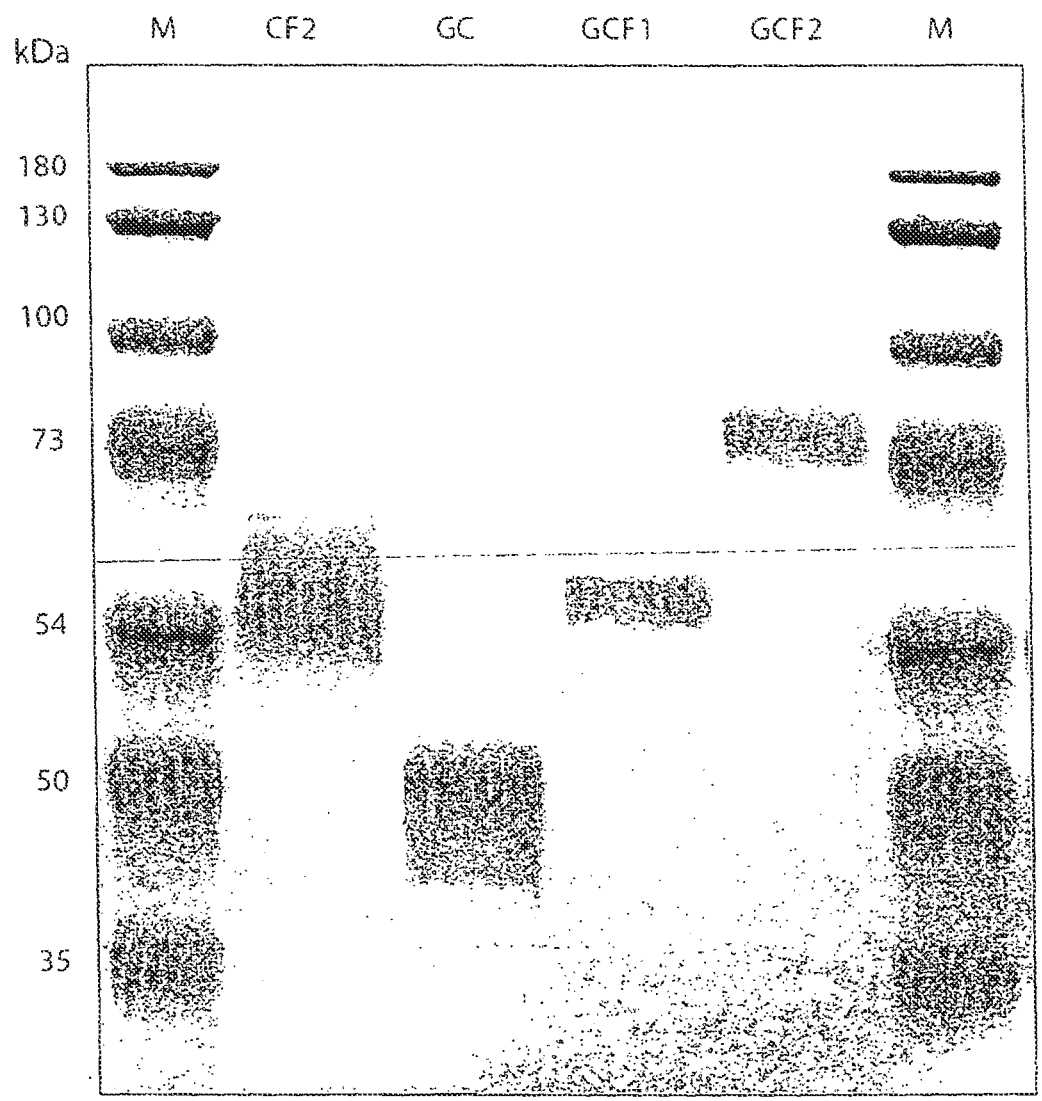
FIG. 17 shows purification and ligand binding properties of the EphB4EC proteins. A. SDS-PAAG gel electrophoresis of purified EphB4-derived recombinant soluble proteins (Coomassie-stained). B. Binding of Ephrin B2-AP fusion to EphB4-derived recombinant proteins immobilized on Ni-NTA-agarose beads. Results of three independent experiments are shown for each protein. Vertical axis—optical density at 420 nm.
Figure 17B:
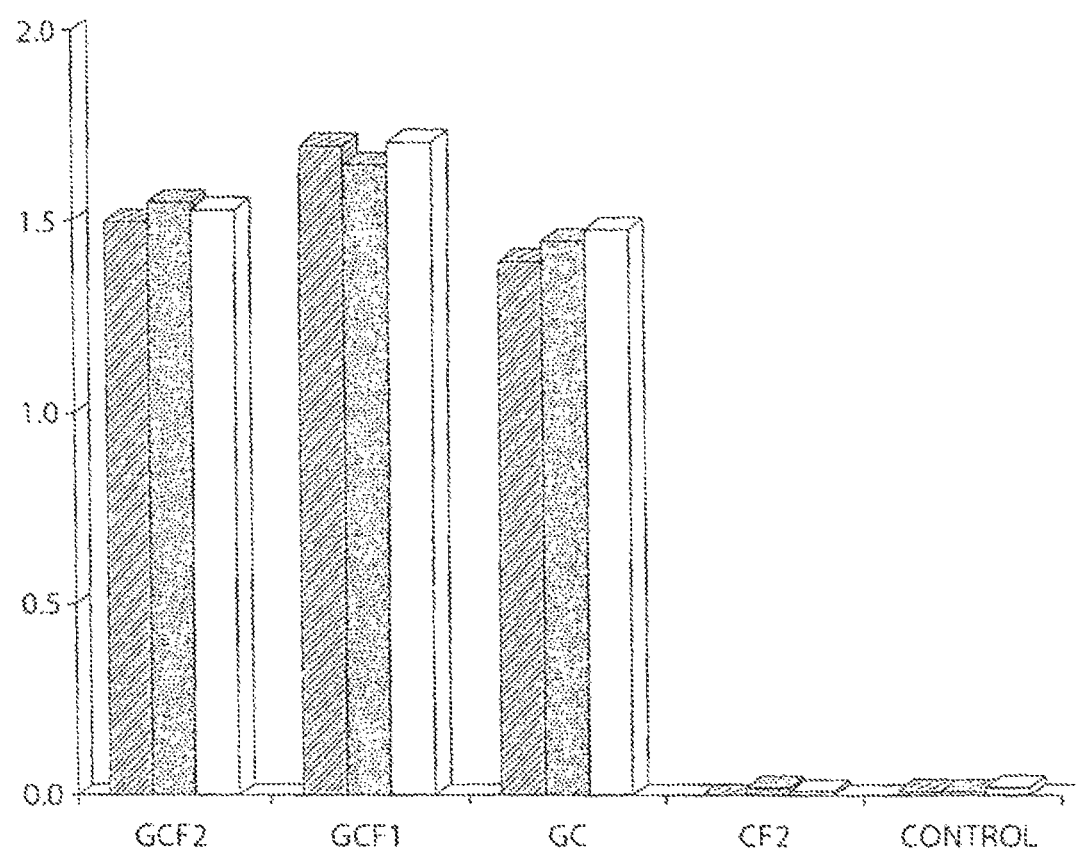

All four C-terminally 6×His tagged recombinant proteins were preparatively expressed in transiently transfected cultured mammalian cells and affinity purified to homogeneity from the conditioned growth media using chromatography on $Ni^{2+}$-chelate resin (FIG. 17). Apparently due to their glycosylation, the proteins migrate on SDS-PAAG somewhat higher than suggested by their predicted molecular weights of 34.7 kDa (GC), 41.5 (CF2), 45.6 kDa (GCF1) and 57.8 kDa (GCF2). Sequence of the extracellular domain of human EphB4 contains three predicted N-glycosylation sites (NXS/T) which are located in the Cys-rich domain, within the first fibronectin type III repeat and between the first and the second fibronectin repeats.

To confirm ability of the purified recombinant proteins to bind Ephrin B2, they were tested in an in vitro binding assay. As expected, GC, GCF1 and GCF2, but not CF2 are binding the cognate ligand Ephrin B2 as confirmed by interaction between Ephrin B2-alkaline phosphatase (Ephrin B2-AP) fusion protein with the B4 proteins immobilized on $Ni^{2+}$-resin or on nitrocellulose membrane (FIG. 17).

All four proteins were also tested for their ability to block ligand-dependent dimerization and activation of Eph B4 receptor kinase in PC3 cells. The PC3 human prostate cancer cell line is known to express elevated levels of human Eph B4. Stimulation of PC3 cells with Ephrin B2 IgG Fc fusion protein leads to a rapid induction of tyrosine phosphorylation of the receptor. However, preincubation of the ligand with GCF2, GCF1 or GC, but not CF2 proteins suppresses subsequent EphB4 autophosphorylation. Addition of the proteins alone to the PC3 cells or preincubation of the cells with the proteins followed by changing media and adding the ligand does not affect EphB4 phosphorylation status.

Further, we found that globular domain of EphB4 is required for the activity of EphB4-derived soluble proteins in endothelial tube formation assay.

B. Effects of Soluble EphB4 on HUV/AEC In Vitro.

Figure 18:
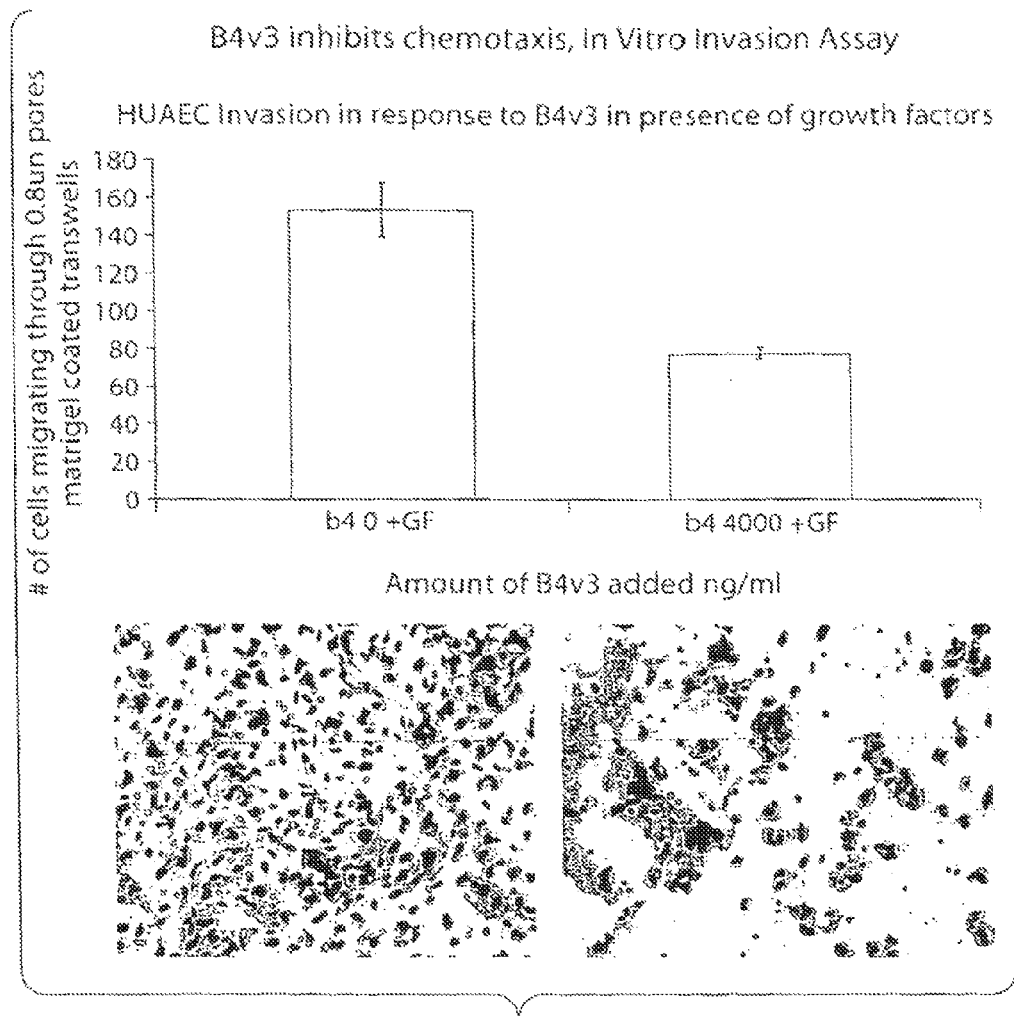
FIG. 18 shows that EphB4v3 inhibits chemotaxis.
Figure 19A:
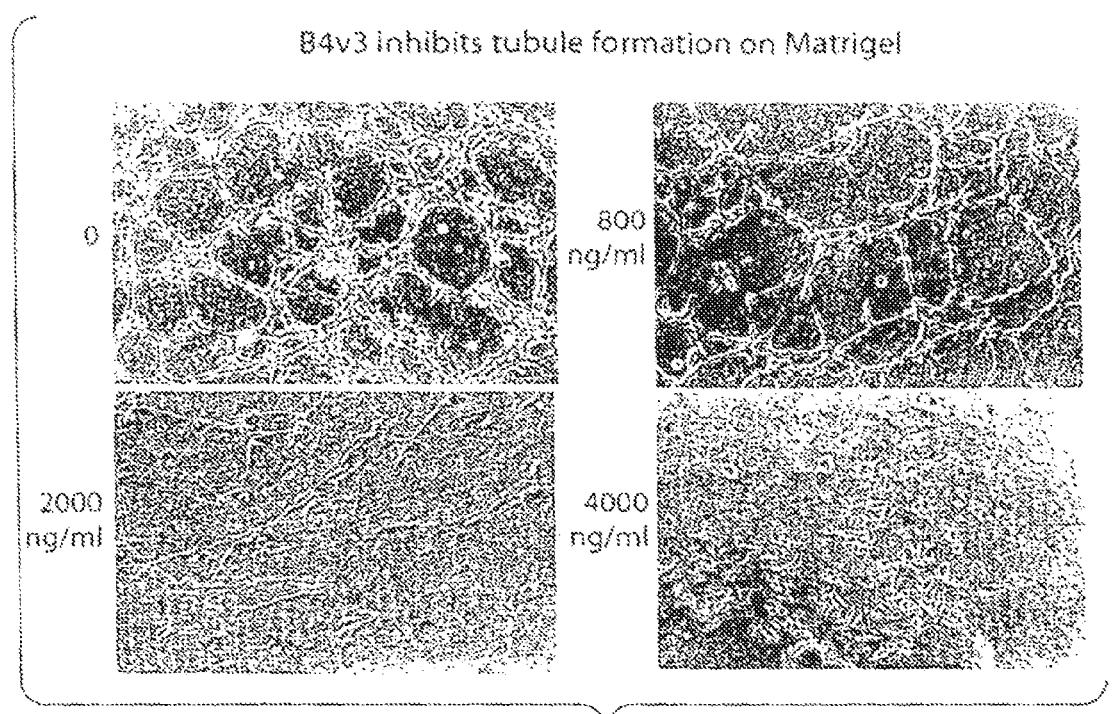
FIG. 19 shows that EphB4v3 inhibits tubule formation on Matrigel. A displays the strong inhibition of tubule formation by B4v3 in a representative experiment. B shows a quantitation of the reduction of tube-length obtained with B4v3 at increasing concentrations as well as a reduction in the number of junctions, in comparison to cells with no protein. Results are displayed as mean values±S.D. obtained from three independent experiments performed with duplicate wells.
Figure 19B:
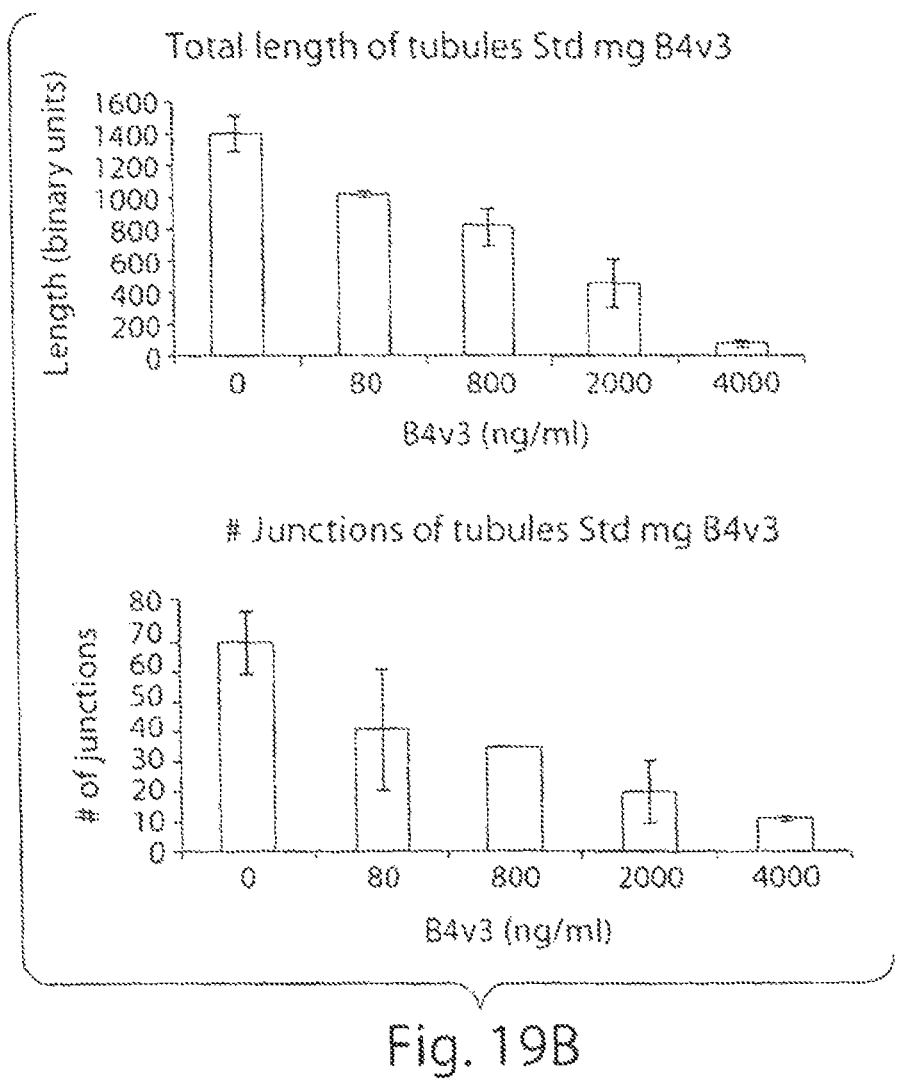
Figure 20:
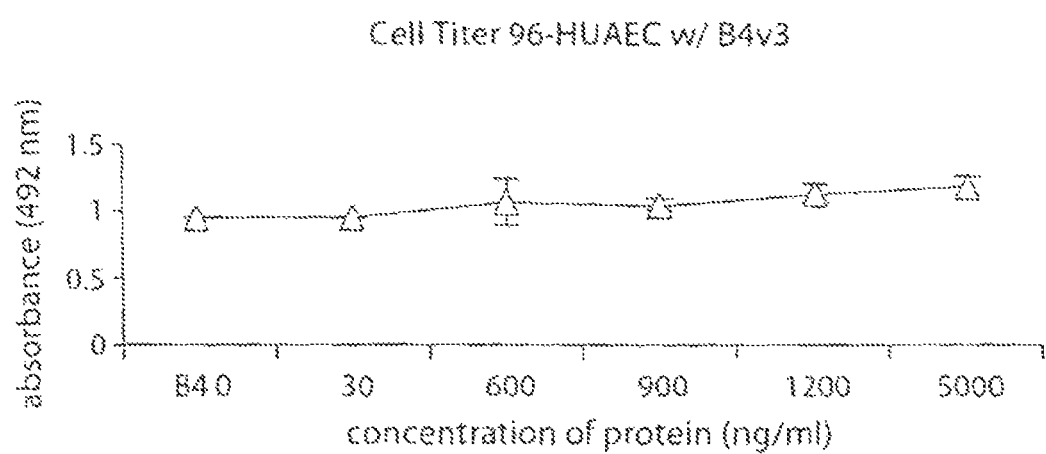
FIG. 20 shows that soluble EphB4 has no detectable cytotoxic effect as assessed by MTS assay.

Initial experiments were performed to determine whether soluble EphB4 affected the three main stages in the angiogenesis pathway. These were carried out by establishing the effects of soluble EphB4 on migration/invasion, proliferation and tubule formation by HUV/AEC in vitro. Exposure to soluble EphB4 significantly inhibited both bFGF and VEGF-induced migration in the Boyden chamber assay in a dose-dependent manner, achieving significance at nM (FIG. 18). Tubule formation by HUV/AECS on wells coated with Matrigel was significantly inhibited by soluble EphB4 in a dose-dependent manner in both the absence and presence of bFGF and VEGF (FIG. 19). We also assessed in vitro, whether nM of soluble EphB4 was cytotoxic for HUVECS. Soluble EphB4 was found to have no detectable cytotoxic effect at these doses, as assessed by MTS assay (FIG. 20).

C. Soluble EphB4 Receptor Inhibits Vascularization of Matrigel Plugs, In Vivo

To demonstrate that soluble EphB4 can directly inhibit angiogenesis in vivo, we performed a murine matrigel plug experiment. Matrigel supplemented with bFGF and VEGF with and without soluble EphB4 was injected s.c. into Balb/C nu/nu mice, forming semi-solid plugs, for six days. Plugs without growth factors had virtually no vascularization or vessel structures after 6 days (FIG. 21). In contrast, plugs supplemented with bFGF and VEGF had extensive vascularization and vessels throughout the plug. Plugs taken from mice treated with µg of soluble EphB4 had markedly reduced vascularization of plugs, comparable to plugs without growth factor (FIG. 21). Furthermore, histological examination of plugs showed decreased vessel staining (FIG. 21). Treatment at 0 µg/dose significantly inhibited the amount of infiltration in Matrigel plugs compared to control (FIG. 21).

Figure 22:
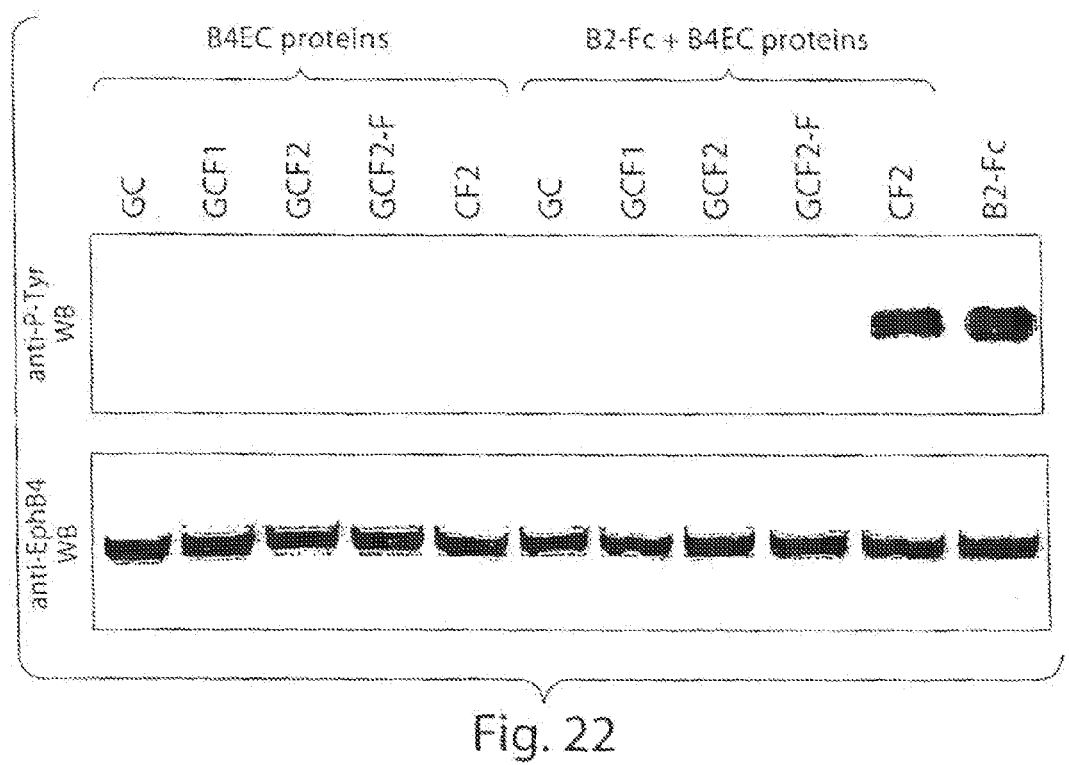
FIG. 22 shows tyrosine phosphorylation of EphB4 receptor in PC3 cells in response to stimulation with EphrinB2-Fc fusion in presence or absence of EphB4-derived recombinant soluble proteins.

We examined EphB4 receptor phosphorylation in HUVECs by performing Western blot analyses with lysates from soluble EphB4-treated cells and antibodies against phosphor-tyrosine. We found that soluble EphB4 treatment of serum-starved HUVECs stimulated a rapid and transient decrease in the level of phosphorylated EphB4, in the presence of EphrinB2Fc, EphB4 ligand dimer. Ephrin B2Fc without the soluble EphB4 protein induced phosphorylation of EphB4 receptor (FIG. 22).

D. Effects of Soluble EphB4 on Tumor Growth, In Vitro.

Figure 23A:
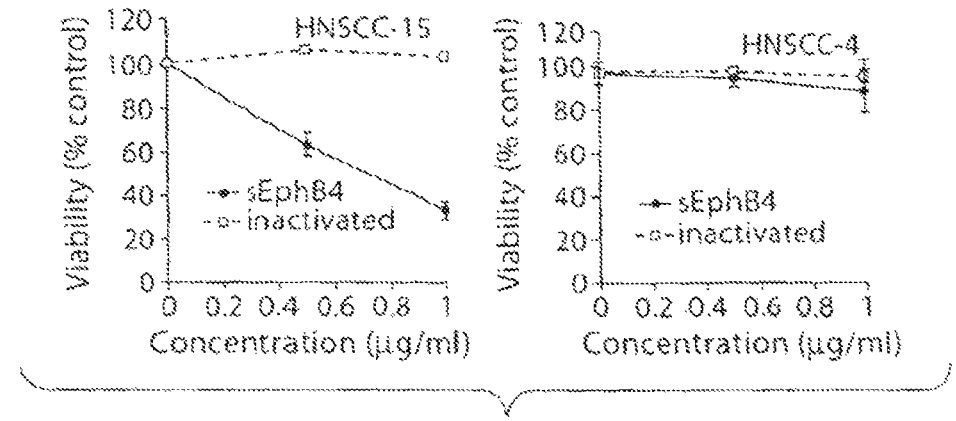
FIG. 23 shows effects of soluble EphB4ECD on viability and cell cycle. A) 3-day cell viability assay of two HNSCC cell lines. B) FACS analysis of cell cycle in HNSCC-15 cells treated as in A. Treatment of these cells resulted in accumulation in subG0/G1 and S/G2 phases as indicated by the arrows.
Figure 23B:
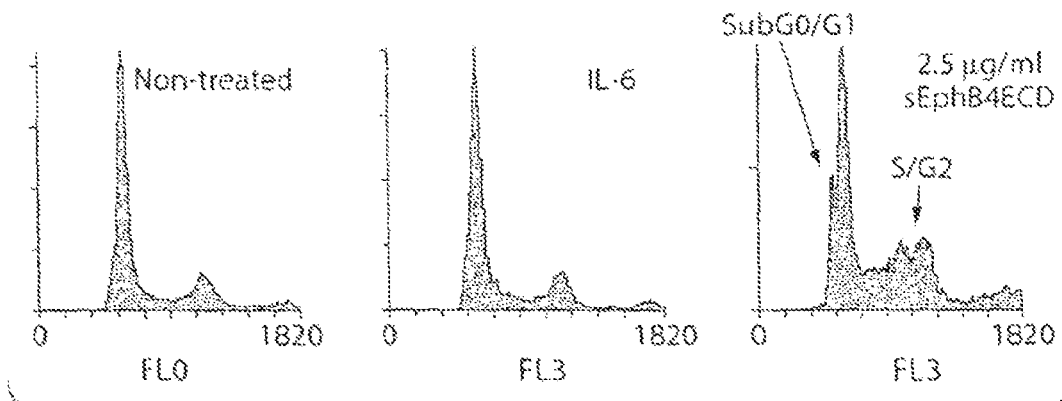

We found that soluble EphB4 inhibits the growth of SCC15 tumors grown in Balb/C Nu/Nu mice (FIG. 23).

E. Soluble EphB4 Inhibited Corneal Neovascularization

Figure 24:
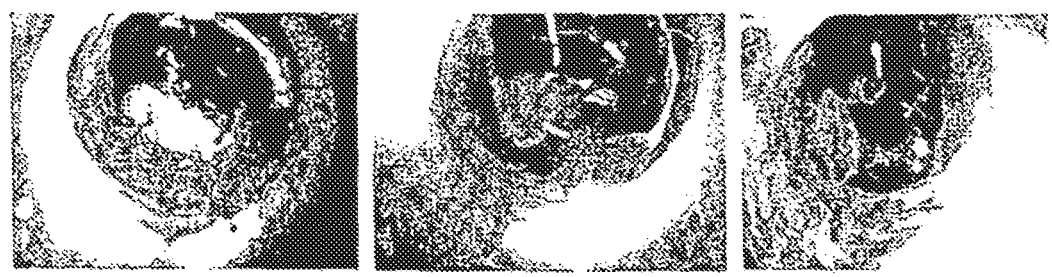
FIG. 24 shows that B4v3 inhibits endovascular response in a murine corneal hydron micropocket assay.

To further investigate the antiangiogenic activity of soluble EphB4 in vivo, we studied the inhibitory effect of administration of soluble EphB4 on neovascularization in the mouse cornea induced by bFGF. Hydron Pellets implanted into corneal micropocket could induce angiogenesis, in the presence of growth factors, in a typically avascular area. The angiogenesis response in mice cornea was moderate, the appearance of vascular buds was delayed and the new capillaries were sparse and grew slowly. Compared with the control group, on day 7 of implantation, the neovascularization induced by bFGF in mice cornea was markedly inhibited in soluble EphB4-treated group (FIG. 24).

F. Effects of Soluble EphB4 on Tumor Growth, In Vivo.

The same model was used to determine the effects of soluble EphB4 in vivo. SCC15 tumors implanted subcutaneously, pre-incubated with matrigel and with or w/o growth factors, as well as implanted sc alone, and mice treated sc or ip daily with 1-5 µg of soluble EphB4 were carried out.

Figure 25:
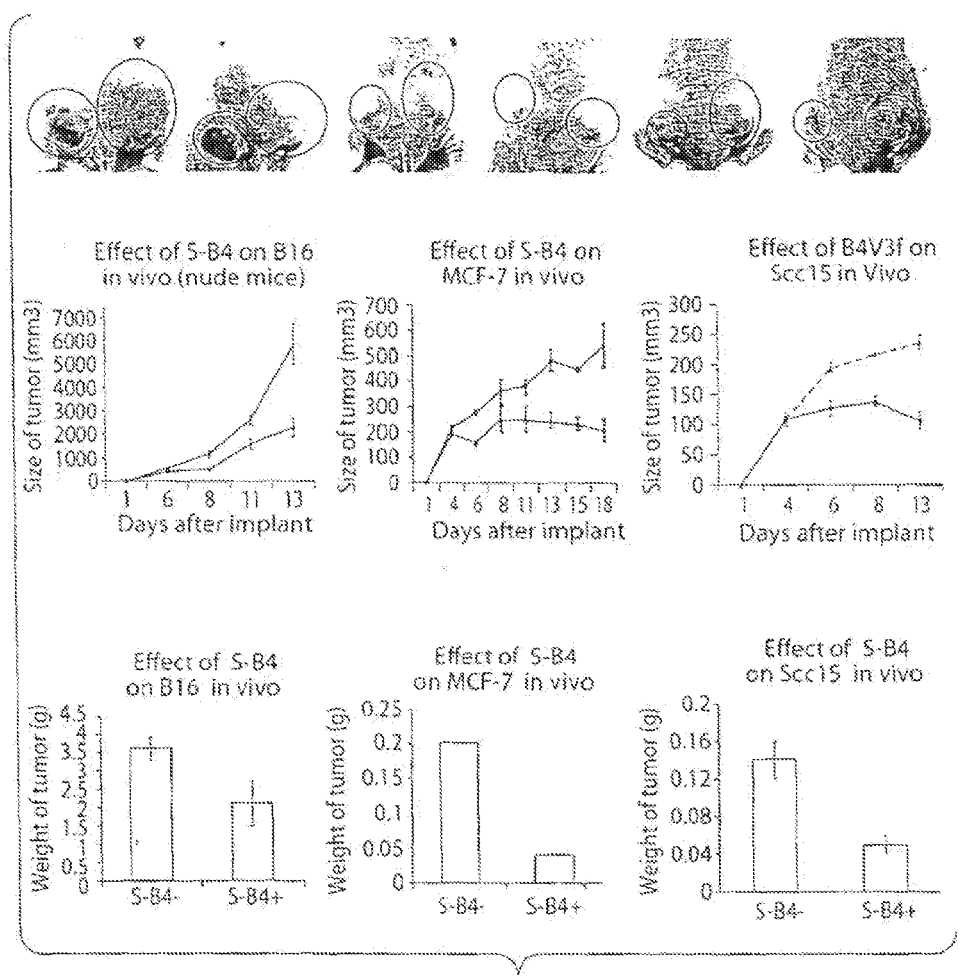
FIG. 25 shows that that SCC15, B16, and MCF-7 co-injected with sB4v3 in the presence of matrigel and growth factors, inhibits the in vivo tumor growth of these cells.

Tumors in the control group continued to grow steadily over the treatment period, reaching a final tumor volume of mm3. However, animals injected with soluble EphB4 exhibited a significantly ($p<0.0/$) reduced growth rate, reaching a final tumor volume of only mm3 (FIG. 25). Similar results were obtained in two further cohorts of such tumor-bearing mice. Soluble EphB4 administration appeared to be well tolerated in vivo, with no significant effect on body weight or the general well-being of the animals (as determined by the absence of lethargy, intermittent hunching, tremors or disturbed breathing patterns).

G. Effects of Soluble EphB4 on Tumor Histology.

Figure 26:
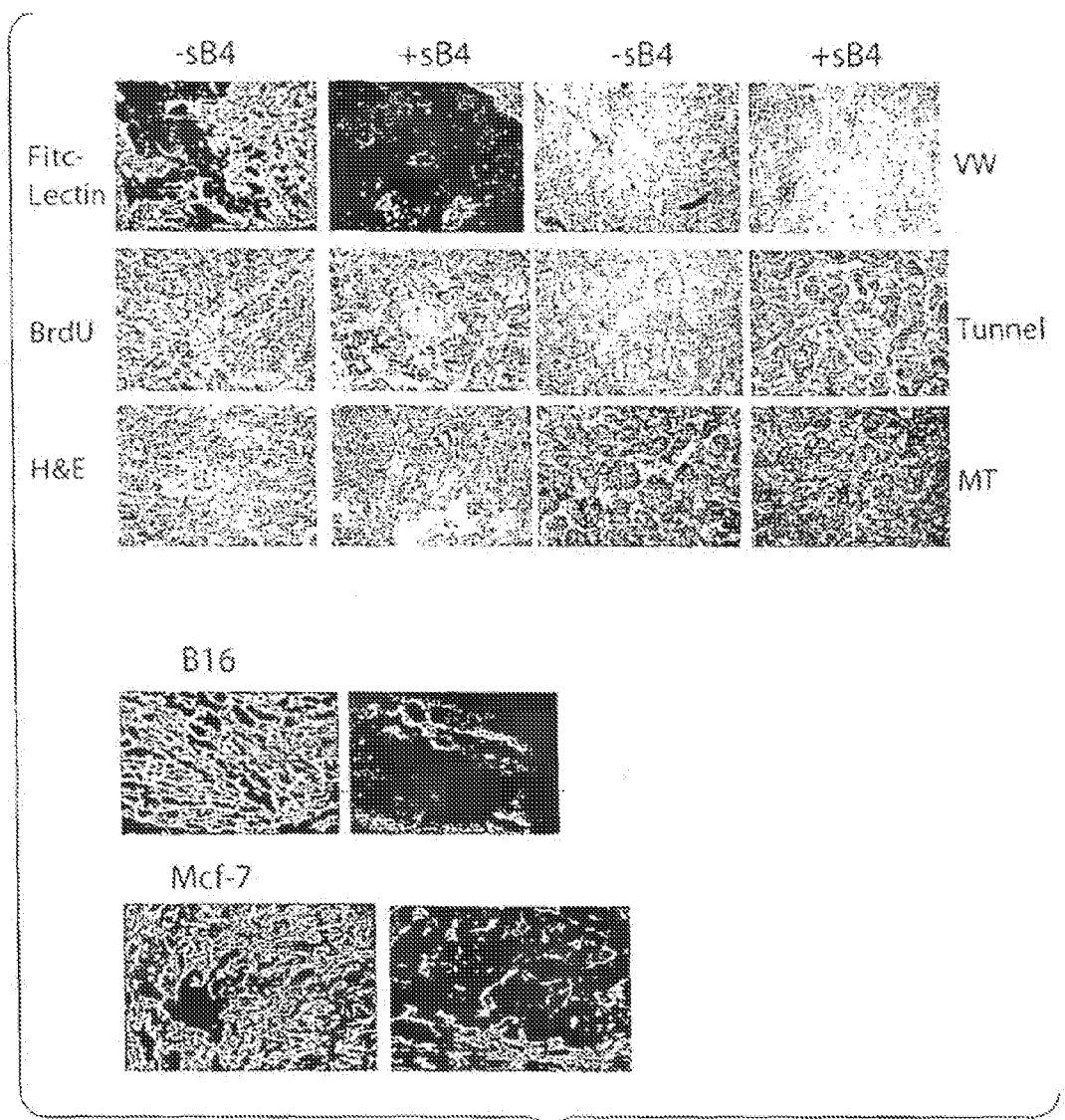
FIG. 26 shows that soluble EphB4 causes apoptosis, necrosis and decreased angiogenesis in three tumor types, B16 (melanoma), SCC15 (head and neck carcinoma), and MCF-7 (breast carcinoma). Tumors were injected premixed with Matrigel plus growth factors and soluble EphB4 subcutaneously. After 10 to 14 days, the mice were injected intravenously with FITC-lectin (green) to assess blood vessel perfusion. Tumors treated with control PBS displayed abundant tumor density and a robust angiogenic response. Tumors treated with sEphB4 displayed a decrease in tumor cell density and a marked inhibition of tumor angiogenesis in regions with viable tumor cells, as well as tumor necrosis and apoptosis.

Histological analysis revealed the presence of a central area of necrosis in all SCC15 tumors, which was usually surrounded by a viable rim of tumor cells um in width. The central necrotic areas were frequently large and confluent and showed loss of cellular detail. Necrosis, assessed as a percentage of tumor section area, was significantly ($p<0.02$) more extensive in the soluble EphB4-treated group (% necrosis in treated vs. control). To determine whether the reduced volume of soluble EphB4 treated tumors was due to an effect of this protein on the tumor vascular supply, endothelial cells in blood vessels were identified in tumor sections using immunostaining with an anti-platelet cell adhesion molecule (PECAM-1; CD31) antibody (FIG. 26) and the density of microvessels was assessed. Microvessel density was similar in the outer viable rim of tumor cells (the uniform layer of cells adjacent to the tumor periphery with well defined nuclei) in control and soluble EphB4-treated tumors. Microvessel density was significantly in the inner, less viable region of tumor cells abutting the necrotic central areas in soluble EphB4-treated than control tumors. Fibrin deposition, as identified by Masson's Trichrome staining, was increased in and around blood vessels in the inner viable rim and the central necrotic core of soluble EphB4 treated than control tumors. In the outer viable rim of soluble EphB4 treated tumors, although the vessel lumen remained patent and contained red blood cells, fibrin deposition was evident around many vessels. Soluble EphB4 was found to have no such effects on the endothelium in the normal tissues examined (lungs, liver and kidneys).

H. Materials and Methods

A detailed description of the materials and methods for this example may be found in U.S. Patent Publication No. 20050084873.

Cell-Based EphB4 Tyrosine Kinase Assay

The human prostate carcinoma cell line PC3 cells were maintained in RPMI medium with 10% dialyzed fetal calf serum and 1% penicillin/streptomycin/neomycin antibiotics mix. Cells were maintained at 37° C. in a humidified atmosphere of 5% $CO_2$/95% air. Typically, cells were grown in 60 mm dishes until confluency and were either treated with mouse Ephrin B2-Fc fusion at 1 µg/ml in RPMI for 10 min to activate EphB4 receptor or plain medium as a control. To study the effect of different derivatives of soluble EphB4 ECD proteins on EphB4 receptor activation, three sets of cells were used. In the first set, cells were treated with various proteins (5 proteins; GC, GCF1, GCF2, GCF2-F, CF2) at 5 µg/ml for 20 min. In the second set of cells, prior to application, proteins were premixed with ephrinB2-Fc at 1:5 (EphB4 protein:B2-Fc) molar ratio, incubated for 20 min and applied on cells for 10 min. In the third set of cells, cells were first treated with the proteins for 20 min at 5 µg/ml, media was replaced with fresh media containing 1 µg/ml of EphrinB2-Fc and incubated for another 10 min.

After the stimulation, cells were immediately harvested with protein extraction buffer containing 20 mM Tris-HCl, pH 7.4, 150 mM NaCl, 1% (v/v) Triton X100, 1 mM EDTA, 1 mM PMSF, 1 mM Sodium vanadate. Protein extracts were clarified by centrifugation at 14,000 rpm for 20 min at 4° C. Clarified protein samples were incubated overnight with protein A/G coupled agarose beads pre-coated with anti-EphB4 monoclonal antibodies. The IP complexes were washed twice with the same extraction buffer containing 0.1% Triton X100. The immunoprecipitated proteins were solubilized in 1×SDS-PAGE sample loading buffer and separated on 10% SDS-PAGE. For EphB4 receptor activation studies, electroblotted membrane was probed with anti-pTyr specific antibody 4G10 at 1:1000 dilution followed by Protein G-HRP conjugate at 1:5000 dilutions.

Endothelial Cell Tube Formation Assay

Matrigel (60 µl of 10 mg/ml; Collaborative Lab, Cat. No. 35423) was placed in each well of an ice-cold 96-well plate. The plate was allowed to sit at room temperature for 15 minutes then incubated at 37° C. for 30 minutes to permit Matrigel to polymerize. In the mean time, human umbilical vein endothelial cells were prepared in EGM-2 (Clonetic, Cat. No. CC3162) at a concentration of $2 \times 10^5$ cells/ml. The test protein was prepared at 2× the desired concentration (5 concentration levels) in the same medium. Cells (500 µl) and 2× protein (500 µl) were mixed and 200 µl of this suspension were placed in duplicate on the polymerized Matrigel. After 24 h incubation, triplicate pictures were taken for each concentration using a Bioquant Image Analysis system. Protein addition effect ($IC_{50}$) was assessed compared to untreated controls by measuring the length of cords formed and number of junctions.

Cell Migration Assay

Chemotaxis of HUVECs to VEGF was assessed using a modified Boyden chamber, transwell membrane filter inserts in 24 well plates, 6.5 mm diam, 8 µm pore size, 10 µm thick matrigel coated, polycarbonate membranes (BD Biosciences). The cell suspensions of HUVECs ($2 \times 10^5$ cells/ml) in 200 µl of EBM were seeded in the upper chamber and the soluble EphB4 protein were added simultaneously with stimulant (VEGF or bFGF) to the lower compartment of the chamber and their migration across a polycarbonate filter in response to 10-20 ng/ml of VEGF with or without 100 nM-1 µM test compound was investigated. After incubation for 4-24 h at 37° C., the upper surface of the filter was scraped with swab and filters were fixed and stained with Diff Quick. Ten random fields at 200× mag were counted and the results expressed as mean # per field. Negative unstimulated control values were subtracted from stimulated control and protein treated sample values and the data was plotted as mean migrated cell±S.D. $IC_{50}$ was calculated from the plotted data.

Growth Inhibition Assay

HUVEC ($1.5 \times 10^3$ cells) were plated in a 96-well plate in 100 µl of EBM-2 (Clonetic, Cat. No. CC3162). After 24 hours (day 0), the test recombinant protein (100 µl) is added to each well at 2× the desired concentration (5-7 concentration levels) in EBM-2 medium. On day 0, one plate was stained with 0.5% crystal violet in 20% methanol for 10 minutes, rinsed with water, and air-dried. The remaining plates were incubated for 72 h at 37° C. After 72 h, plates were stained with 0.5% crystal violet in 20% methanol, rinsed with water and air-dried. The stain was eluted with 1:1 solution of ethanol: 0.1M sodium citrate (including day 0 plate), and absorbance measured at 540 nm with an ELISA reader (Dynatech Laboratories). Day 0 absorbance was subtracted from the 72 h plates and data is plotted as percentage of control proliferation (vehicle treated cells). $IC_{50}$ value was calculated from the plotted data.

Murine Matrigel Plug Angiogenesis Assay

In vivo angiogenesis was assayed in mice as growth of blood vessels from subcutaneous tissue into a Matrigel plug containing the test sample. Matrigel rapidly forms a solid gel at body temperature, trapping the factors to allow slow release and prolonged exposure to surrounding tissues. Matrigel (8.13 mg/ml, 0.5 ml) in liquid form at 4° C. was mixed with Endothelial Cell Growth Supplement (ECGS), test proteins plus ECGS or Matrigel plus vehicle alone (PBS containing 0.25% BSA). Matrigel (0.5 ml) was injected into the abdominal subcutaneous tissue of female nu/nu mice (6 wks old) along the peritoneal mid line. There were 3 mice in each group. The animals were cared for in accordance with institutional and NIH guidelines. At day 6, mice were sacrificed and plugs were recovered and processed for histology. Typically the overlying skin was removed, and gels were cut out by retaining the peritoneal lining for support, fixed in 10% buffered formalin in PBS and embedded in paraffin. Sections of 3 µm were cut and stained with H&E or Masson's trichrome stain and examined under light microscope Mouse Corneal Micropocket Assay Mouse corneal micropocket assay was performed according to that detailed by Kenyon et al., 1996. Briefly, hydron pellets (polyhydroxyethylmethacrylate [polyHEMA], Interferon Sciences, New Brunswick, N.J., U.S.A.) containing either 90 ng of bFGF (R&D) or 180 ng of VEGF (R&D Systems, Minneapolis, Minn., U.S.A.) and 40 µg of sucrose aluminium sulfate (Sigma) were prepared. Using an operating microscope, a stromal linear keratotomy was made with a surgical blade (Bard-Parker no. 15) parallel to the insertion of the lateral rectus muscle in an anesthetized animal. An intrastromal micropocket was dissected using a modified von Graefe knife (2¨30 mm). A single pellet was implanted and advanced toward the temporal corneal limbus (within 0±7±1±0 mm for bFGF pellets and 0±5 mm for VEGF pellets). The difference in pellet location for each growth factor was determined to be necessary given the relatively weaker angiogenic stimulation of VEGF in this model. Antibiotic ointment (erythromycin.) was then applied to the operated eye to prevent infection and to decrease surface irregularities. The subsequent vascular response was measured extending from the limbal vasculature toward the pellet and the contiguous circumferential zone of neovascularization Data and clinical photos presented here were obtained on day 6 after pellet implantation, which was found to be the day of maximal angiogenic response.

In Vitro Invasion Assay

"Matrigel" matrix-coated 9-mm cell culture inserts (pore size, 8 µm; Becton Dickinson, Franklin Lakes, N.J.) were set in a 24-well plate. The HUVEC cells were seeded at a density of $5 \times 10^3$ cells per well into the upper layer of the culture insert and cultured with serum-free EBM in the presence of EphB4 ECD for 24 h. The control group was cultured in the same media without EphB4. Then 0.5 ml of the human SCC15 cell line, conditioned medium was filled into the lower layer of the culture insert as a chemo-attractant. The cells were incubated for 24 h, then the remaining cells in the upper layer were swabbed with cotton and penetrating cells in the lower layer were fixed with 5% glutaraldehyde and stained with Diff Quick. The total number of cells passing through the Matrigel matrix and each 8 µm pore of the culture insert was counted using optical microscopy and designated as an invasion index (cell number/area).

SCC15 Tumor Growth in Mice

Subcutaneously inject logarithmically growing SCC15, head and neck squamous cell carcinoma cell line, at $5 \times 10^6$ cell density; with or without EphB4 ECD in the presence or absence of human bFGF, into athymic Balb/c nude mice, along with Matrigel (BD Bioscience) synthetic basement membrane (1:1 v/v), and examine tumors within 2 weeks. Tumor volumes in the EphB4 ECD group, in the presence and absence of growth factor after implantation were three-fold smaller than those in the vehicle groups. There was no difference in body weight between the groups. Immunohistochemical examination of cross-sections of resected tumors and TUNEL-positive apoptosis or necrosis, CD34 immunostaining, and BrdU proliferation rate will be performed, after deparaffinized, rehydrated, and quenched for endogenous peroxidase activity, and after 10 min permeabilization with proteinase K. Quantitative assessment of vascular densities will also be performed. Local intratumoral delivery or IV delivery of EphB4 ECD will also be performed twice a week.

30 athymic nude mice, BALB/c (nu/nu), were each injected with $1 \times 10^6$ B16 melanoma cells with 0.1 ml PBS mixed with 0.1 ml matrigel or $1.5 \times 10^6$ SCC15 cells resuspended in 200 µl of DMEM serum-free medium and injected subcutaneously on day 0 on the right shoulder region of mice. Proteins were injected intravenously or subcutaneously, around the tumor beginning on day 1 at a loading dose of 4 µg/mg, with weekly injections of 2 ug/mg. (10 µg/g, 50 µg/kg/day), and at 2 weeks post-inoculation. Mice are sacrificed on Day 14. Control mice received PBS 50 µl each day.

Tumor Formation in Nude Mice

All animals were treated under protocols approved by the institutional animal care committees. Cancer cells ($5 \times 10^6$) were subcutaneously inoculated into the dorsal skin of nude mice. When the tumor had grown to a size of about 100 mm³ (usually it took 1□2 days), sEphB4 was either intraperitoneally or subcutaneously injected once/day, and tumorigenesis was monitored for 2 weeks. Tumor volume was calculated according to the formula $a^2 \times b$, where a and b are the smallest and largest diameters, respectively. A Student's t test was used to compare tumor volumes, with $P<0.05$ being considered significant.

Quantification of Microvessel Density

Tumors were fixed in 4% formaldehyde, embedded in paraffin, sectioned by 5 µm, and stained with hematoxylin□eosin. Vessel density was semi-quantitated using a computer-based image analyzer (five fields per section from three mice in each group).

Example 3

EphB4 is Upregulated and Imparts Growth Advantage in Prostate Cancer

A. Expression of EphB4 in Prostate Cancer Cell Lines

Figure 27A:
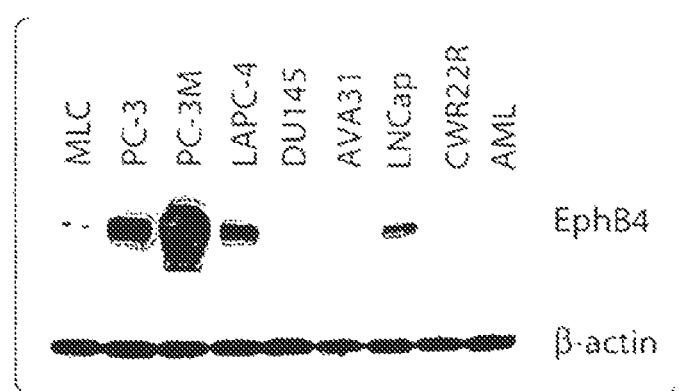
FIG. 27 shows expression of EphB4 in prostate cell lines. A) Western blot of total cell lysates of various prostate cancer cell lines, normal prostate gland derived cell line (MLC) and acute myeloblastic lymphoma cells (AML) probed with EphB4 monoclonal antibody. B) Phosphorylation of EphB4 in PC-3 cells determined by Western blot.
Figure 27B:
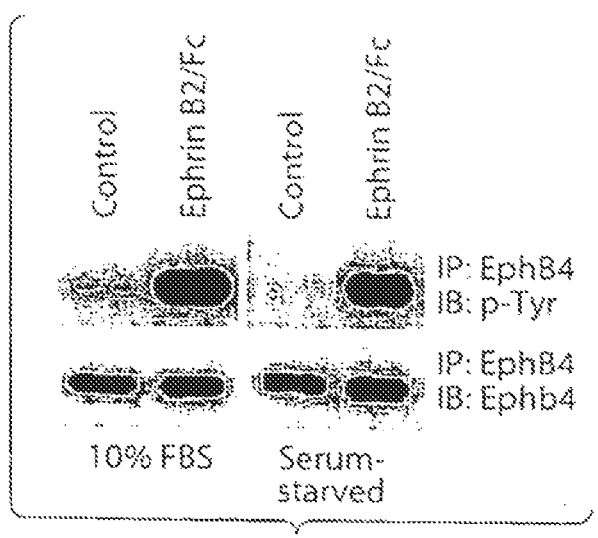

We first examined the expression of EphB4 protein in a variety of prostate cancer cell lines by Western blot. We found that prostate cancer cell lines show marked variation in the abundance of the 120 kD EphB4. The levels were relatively high in PC3 and even higher in PC3M, a metastatic clone of PC3, while normal prostate gland derived cell lines (MLC) showed low or no expression of EphB4 (FIG. 27A). We next checked the activation status of EphB4 in PC3 cells by phosphorylation study. We found that even under normal culture conditions, EphB4 is phosphorylated though it can be further induced by its ligand, ephrin B2 (FIG. 27B).

B. Expression of EphB4 in Clinical Prostate Cancer Samples

Figure 28:
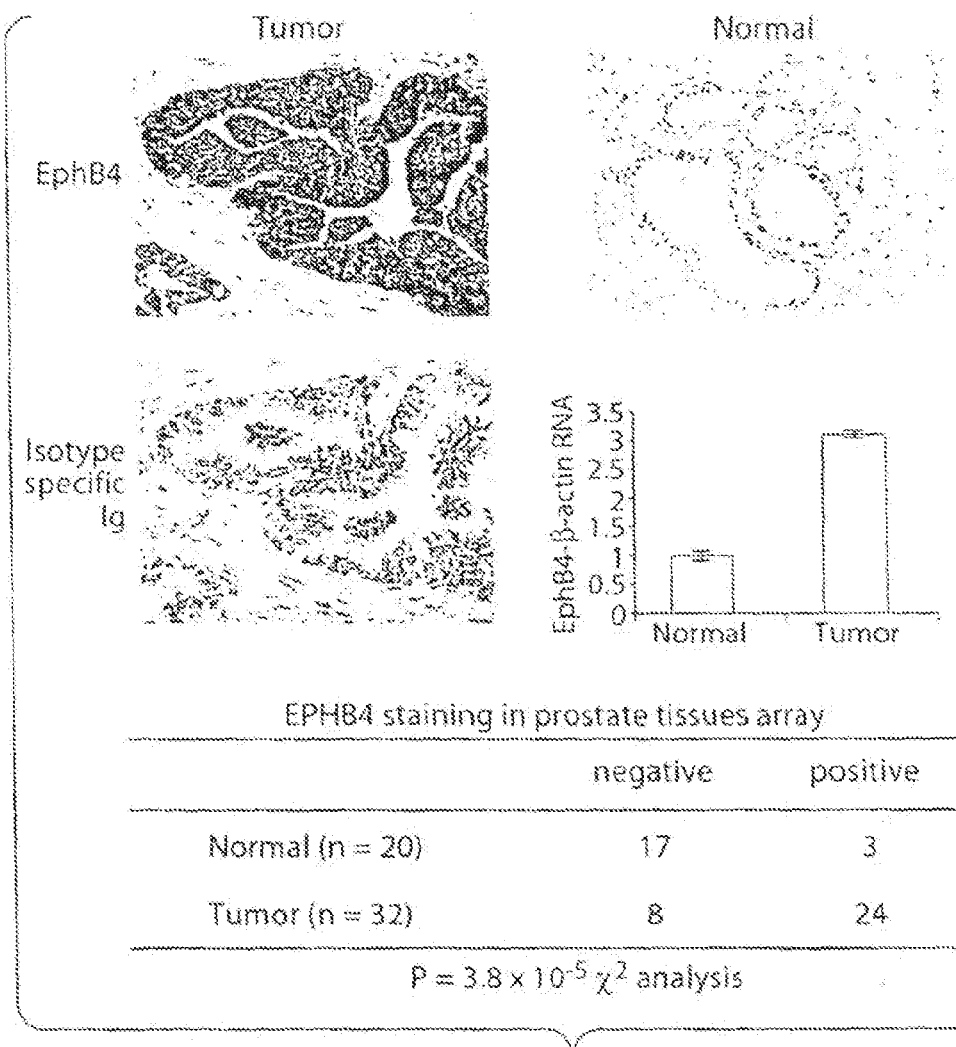
FIG. 28 shows expression of EphB4 in prostate cancer tissue. Representative prostate cancer frozen section stained with EphB4 monoclonal antibody (top left) or isotype specific control (bottom left). Adjacent BPH tissue stained with EphB4 monoclonal antibody (top right). Positive signal is brown color in the tumor cells. Stroma and the normal epithelia are negative. Note membrane localization of stain in the tumor tissue, consistent with transmembrane localization of EphB4. Representative QRT-PCR of RNA extracted from cancer specimens and adjacent BPH tissues (lower right).

To determine whether EphB4 is expressed in clinical prostate samples, tumor tissues and adjacent normal tissue from prostate cancer surgical specimens were examined. The histological distribution of EphB4 in the prostate specimens was determined by immunohistochemistry. Clearly, EphB4 expression is confined to the neoplastic epithelium (FIG. 28, top left), and is absent in stromal and normal prostate epithelium (FIG. 28, top right). In prostate tissue array, 24 of the 32 prostate cancers examined were positive. We found EphB4 mRNA is expressed both in the normal and tumor tissues of clinical samples by quantitative RT-PCR. However, tumor EphB4 mRNA levels were at least 3 times higher than in the normal in this case (FIG. 28, lower right).

C. P53 and PTEN Inhibited the Expression of EphB4 in PC3 Cells

Figure 29A:
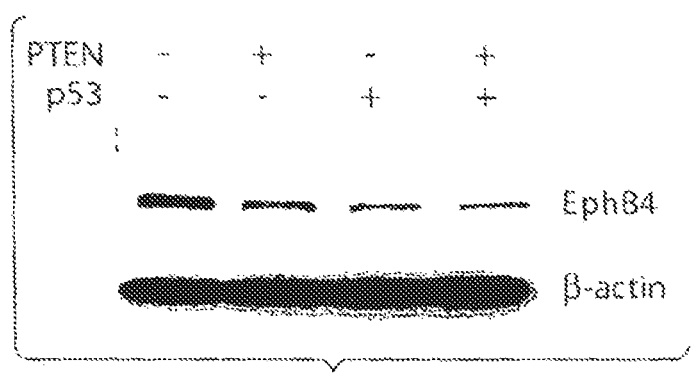
FIG. 29 shows downregulation of EphB4 in prostate cancer cells by tumor suppressors and RXR expression. A) PC3 cells were co-transfected with truncated CD4 and p53 or PTEN or vector only. 24 h later CD4-sorted cells were collected, lysed and analyzed sequentially by Western blot for the expression of EphB4 and β-actin, as a normalizer protein. B) Western blot as in (A) of various stable cell lines. LNCaP-FGF is a stable transfection clone of FGF-8, while CWR22R-RXR stably expresses the RXR receptor. BPH-1 was established from benign hypertrophic prostatic epithelium.

PC3 cells are known to lack PTEN expression (Davis, et al., 1994, Science. 266:816-819) and wild-type p53 function (Gale, et al., 1997, Cell Tissue Res. 290:227-241). We investigated whether the relatively high expression of EphB4 is related to p53 and/or PTEN by re-introducing wild-type p53 and/or PTEN into PC3 cells. To compensate for the transfection efficiency and the dilution effect, transfected cells were sorted for the cotransfected truncated CD4 marker. We found that the expression of EphB4 in PC3 cells was reduced by the re-introduction of either wild-type p53 or PTEN. The co-transfection of p53 and PTEN did not further inhibit the expression of EphB4 (FIG. 29A).

D. Retinoid X Receptor (RXR α) Regulates the Expression of EphB4

Figure 29B:
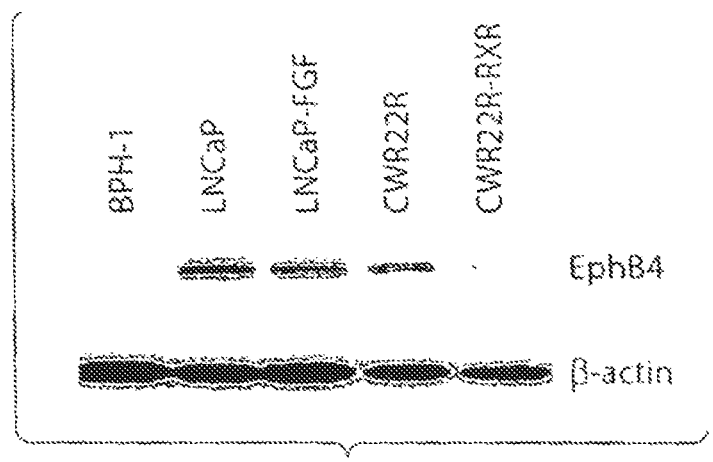

We previously found that RXRα was down-regulated in prostate cancer cell lines (Zhong, et al., 2003, Cancer Biol Ther. 2:179-184) and here we found EphB4 expression has the reverse expression pattern when we looked at "normal" prostate (MLC), prostate cancer (PC3), and metastatic prostate cancer (PC3M) (FIG. 27A), we considered whether RXRα regulates the expression of EphB4. To confirm the relationship, the expression of EphB4 was compared between CWR22R and CWR22R-RXRα, which constitutively expresses RXRα. We found a modest decrease in EphB4 expression in the RXRα overexpressing cell line, while FGF8 has no effect on EphB4 expression. Consistent with initial results, EphB4 was not found in "normal" benign prostate hypertrophic cell line BPH-1 (FIG. 29B).

Figure 30A:
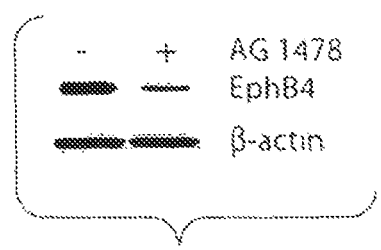
FIG. 30 shows regulation of EphB4 in prostate cancer cells by EGFR and IGFR-1. A) Western blot of PC3 cells treated with or without EGFR specific inhibitor AG1478 (1 nM) for 36 hours. Decreased EphB4 signal is observed after AG 1478 treatment. The membrane was stripped and reprobed with β-actin, which was unaffected. B) Western Blot of triplicate samples of PC3 cells treated with or without IGFR-1 specific neutralizing antibody MAB391 (2 µg/ml; overnight). The membrane was sequentially probed with EphB4, IGFR-1 and β-actin antibodies. IGFR-1 signal shows the expected repression of signal with MAB391 treatment.
Figure 30B:
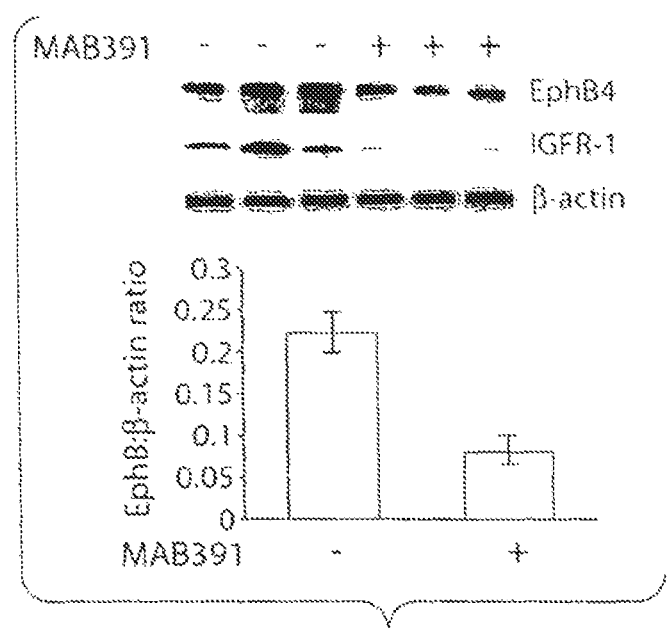

E. Growth Factor Signaling Pathway of EGFR and IGF-1R Regulates EphB4 Expression EGFR and IGF-1R have both been shown to have autocrine and paracrine action on PC3 cell growth. Because we found that EphB4 expression is higher in the more aggressive cell lines, we postulated that EphB4 expression might correlate with these pro-survival growth factors. We tested the relationship by independently blocking EGFR and IGF-1R signaling. EphB4 was down-regulated after blocking the EGFR signaling using EGFR kinase inhibitor AG 1478 (FIG. 30A) or upon blockade of the IGF-1R signaling pathway using IGF-1R neutralizing antibody (FIG. 30B).

F. EphB4 siRNA and Antisense ODNs Inhibit PC3 Cell Viability

Figure 31A:
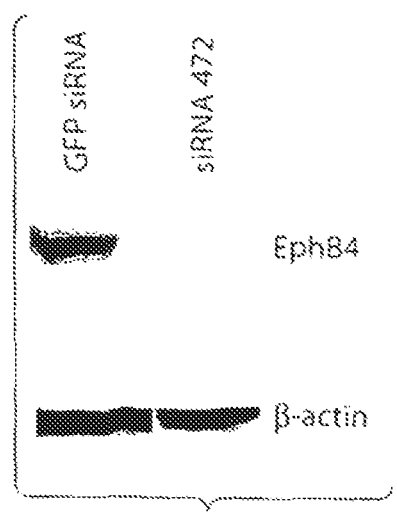
FIG. 31 shows effect of specific EphB4 AS-ODNs and siRNA on expression and prostate cell functions. A) 293 cells stably expressing full-length construct of EphB4 was used to evaluate the ability of siRNA 472 to inhibit EphB4 expression. Cells were transfected with 50 nM RNAi using Lipofectamine 2000. Western blot of cell lysates 40 h post transfection with control siRNA (green fluorescence protein; GFP siRNA) or EphB4 siRNA 472, probed with EphB4 monoclonal antibody, stripped and reprobed with β-actin monoclonal antibody. B) Effect of EphB4 AS-10 on expression in 293 transiently expressing full-length EphB4. Cells were exposed to AS-10 or sense ODN for 6 hours and analyzed by Western blot as in (A). C) 48 h viability assay of PC3 cells treated with siRNA as described in the Methods section. Shown is mean±s.e.m. of triplicate samples. D) 5-day viability assay of PC3 cells treated with ODNs as described in the Methods. Shown is mean±s.e.m. of triplicate samples. E) Scrape assay of migration of PC3 cells in the presence of 50 nM siRNAs transfected as in (A). Shown are photomicrographs of representative 20× fields taken immediately after the scrape was made in the monolayer (0 h) and after 20 h continued culture. A large number of cells have filled in the scrape after 20 h with control siRNA, but not with EphB4 siRNA 472. F) Shown is a similar assay for cells treated with AS-10 or sense ODN (both 10 µM). G) Matrigel invasion assay of PC3 cells transfected with siRNA or control siRNA as described in the methods. Cells migrating to the underside of the Matrigel coated insert in response to 5 mg/ml fibronectin in the lower chamber were fixed and stained with Giemsa. Shown are representative photomicrographs of control siRNA and siRNA 472 treated cells. Cell numbers were counted in 5 individual high-powered fields and the average±s.e.m. is shown in the graph (bottom right).
Figure 31B:
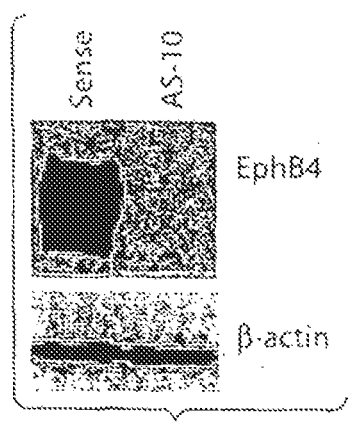
Figure 31C:
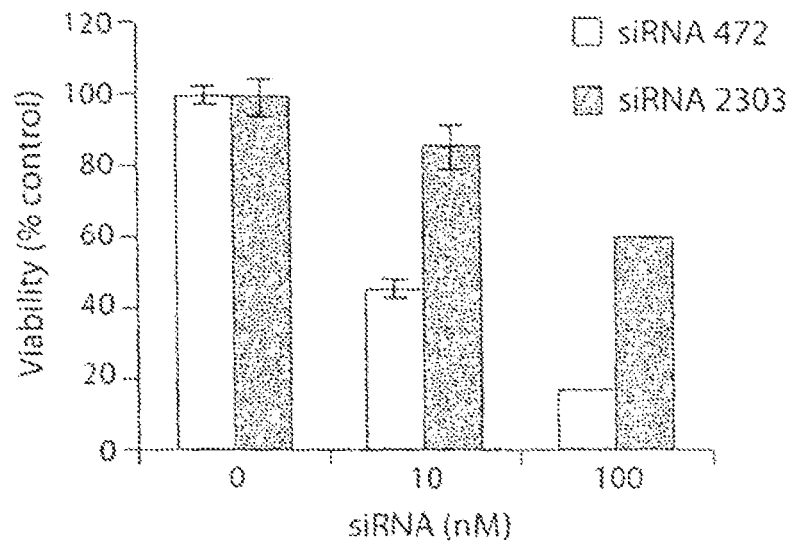
Figure 31D:
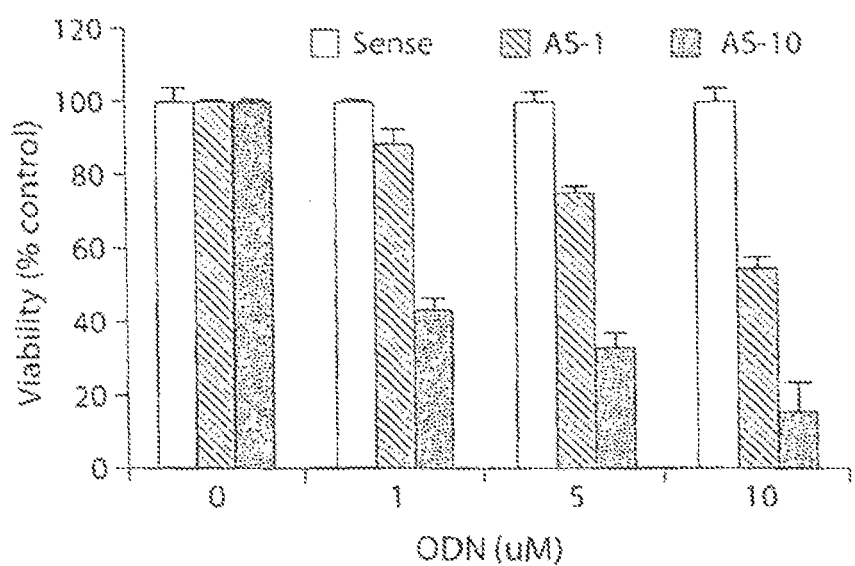

To define the significance of this EphB4 overexpression in our prostate cancer model, we concentrated our study on PC3 cells, which have a relatively high expression of EphB4. The two approaches to decreasing EphB4 expression were siRNA and AS-ODNs. A number of different phosphorothioate-modified AS-ODNs complementary to different segments of the EphB4 coding region were tested for specificity and efficacy of EphB4 inhibition. Using 293 cells transiently transfected with full-length EphB4 expression vector AS-10 was found to be the most effective (FIG. 31B). A Similar approach was applied to the selection of specific siRNA. EphB4 siRNA 472 effectively knocks down EphB4 protein expression (FIG. 31A). Both siRNA 472 and antisense AS-10 ODN reduced the viability of PC3 cells in a dose dependent manner (FIGS. 31C, D). Unrelated siRNA or sense oligonucleotide had no effect on viability.

G. EphB4 siRNA and Antisense ODNs Inhibit the Mobility of PC3 Cells

Figure 31E:
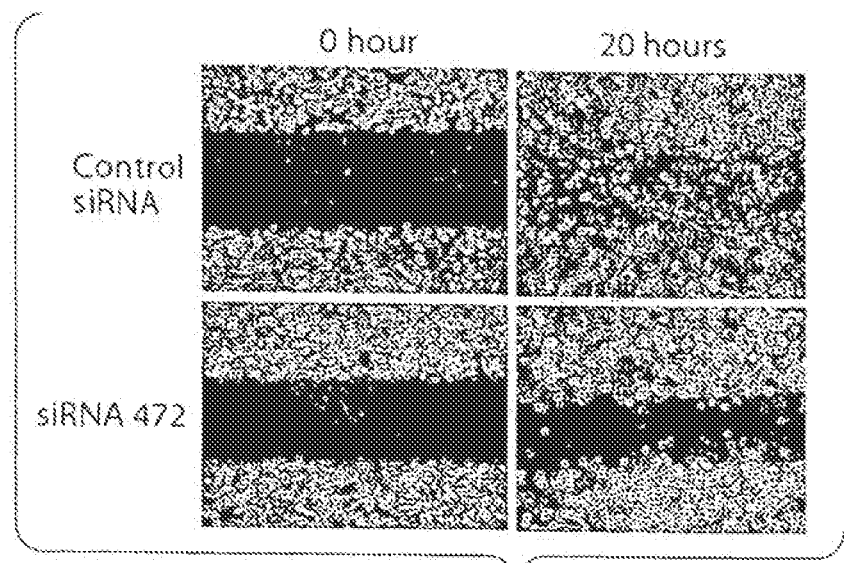
Figure 31F:
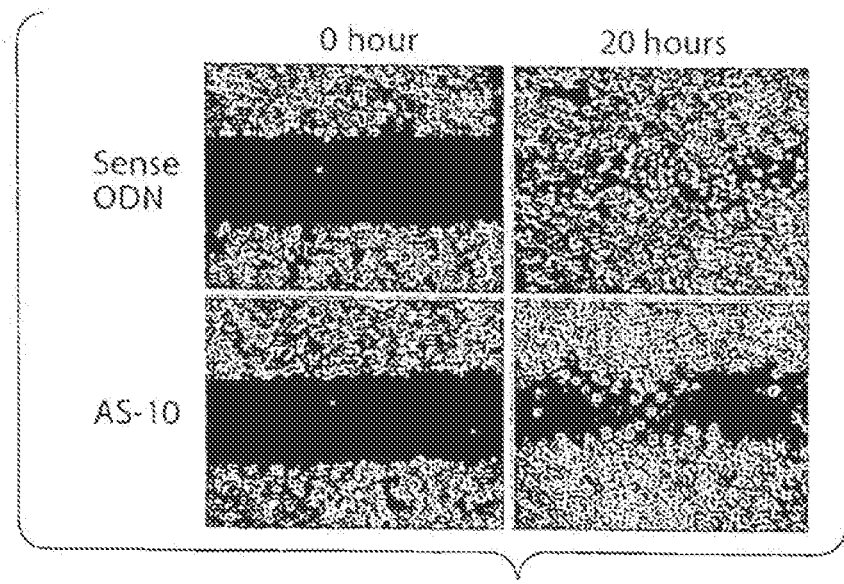
Figure 31G:
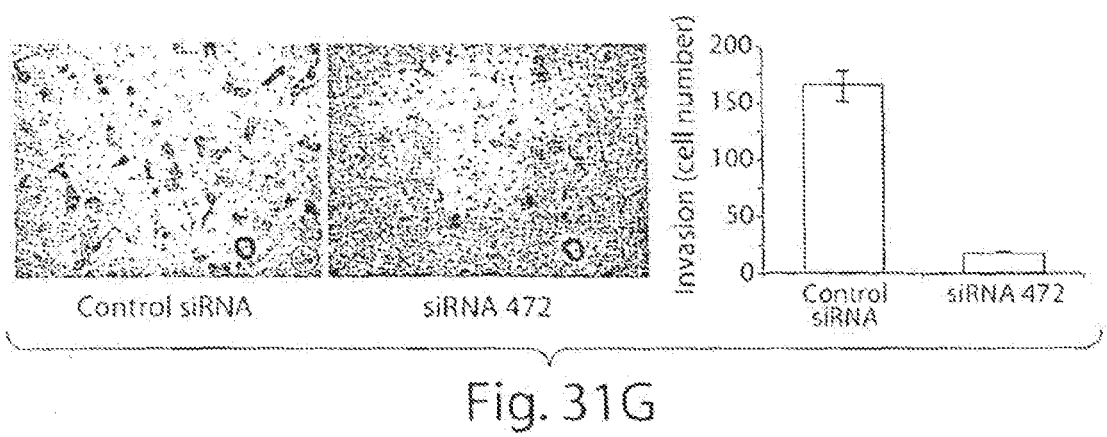

PC3 cells can grow aggressively locally and can form lymph node metastases when injected orthotopically into mice. In an effort to study the role of EphB4 on migration of PC3 cells in vitro, we performed a wound-healing assay. When a wound was introduced into a monolayer of PC3 cells, over the course of the next 20 hours cells progressively migrated into the cleared area. However, when cells were transfected with siRNA 472 and the wound was introduced, this migration was significantly inhibited (FIG. 31E). Pre-treatment of PC3 cells with 10 µM EphB4 AS-10 for 12 hours generated the same effect (FIG. 31F). In addition, knock-down of EphB4 expression in PC3 cells with siRNA 472 severely reduced the ability of these cells to invade Matrigel as assessed by a double-chamber invasion assay (FIG. 31G), compared to the control siRNA.

H. EphB4 siRNA Induces Cell Cycle Arrest and Apoptosis in PC3 Cells

Figure 32A:
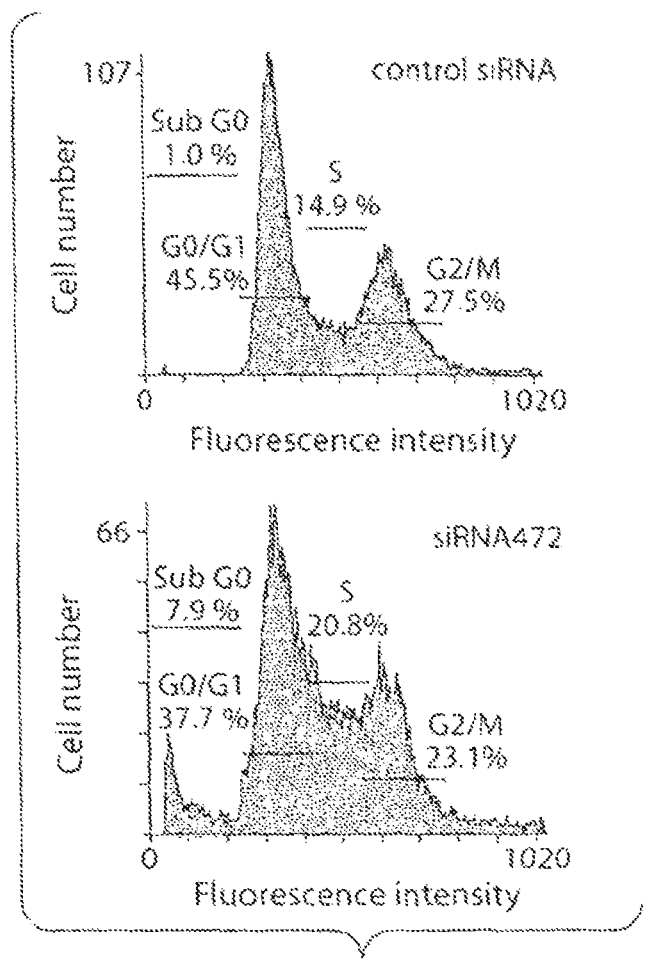
FIG. 32 shows effect of EphB4 siRNA 472 on cell cycle and apoptosis. A) PC3 cells transfected with siRNAs as indicated were analyzed 24 h post transfection for cell cycle status by flow cytometry as described in the Methods. Shown are the plots of cell number vs. propidium iodide fluorescence intensity. 7.9% of the cell population is apoptotic (in the Sub G0 peak) when treated with siRNA 472 compared to 1% with control siRNA. B) Apoptosis of PC3 cells detected by Cell Death Detection ELISA$^{plus}$ kit as described in the Methods. Absorbance at 405 nm increases in proportion to the amount of histone and DNA-POD in the nuclei-free cell fraction. Shown is the mean±s.e.m. of triplicate samples at the indicated concentrations of siRNA 472 and GFP siRNA (control).
Figure 32B:
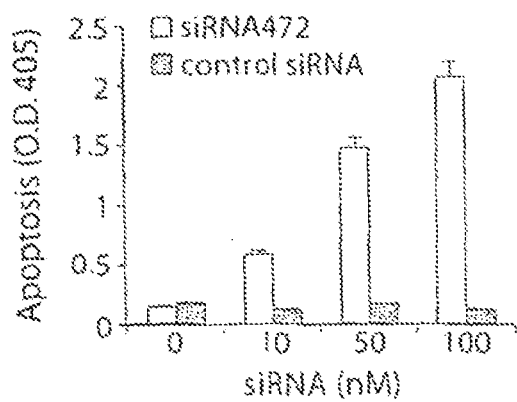

Since knock-down of EphB4 resulted in decreased cell viability (FIG. 31C) we sought to determine whether this was due to effects on the cell cycle. In comparison to control siRNA transfected cells, siRNA 472 resulted in an accumulation of cells in the sub G0 and S phase fractions compared to cells treated with control siRNA. The sub G0 fraction increased from 1% to 7.9%, and the S phase fraction from 14.9% to 20.8% in siRNA 472 treated cells compared to control siRNA treated cells (FIG. 32A). Cell cycle arrest at sub G0 and G2 is indicative of apoptosis. Apoptosis as a result of EphB4 knock-down was confirmed by ELISA assay. A dose-dependent increase in apoptosis was observed when PC3 cells were transfected with siRNA 472, but not with control siRNA (FIG. 32B). At 100 nM there was 15 times more apoptosis in siRNA 472 transfected than control siRNA transfected PC3 cells.

I. Materials and Methods

A detailed description of the materials and methods for this example may be found in U.S. Patent Publication No. 20050084873.

Example 4

Expression of EPHB4 in Mesothelioma: a Candidate Target for Therapy

Malignant mesothelioma (MM) is a rare neoplasm that most often arises from the pleural and peritoneal cavity serous surface. The pleural cavity is by far the most frequent site affected (>90%), followed by the peritoneum (6-10%) (Carbone et al., 2002, Semin Oncol. 29:2-17). There is a strong association with asbestos exposure, about 80% of malignant mesothelioma cases occur in individuals who have ingested or inhaled asbestos. This tumor is particularly resistant to the current therapies and, up to now, the prognosis of these patients is dramatically poor (Lee et al., 2000, Curr Opin Pulm Med. 6:267-74).

Several clinical problems regarding the diagnosis and treatment of malignant mesothelioma remain unsolved. Making a diagnosis of mesothelioma from pleural or abdominal fluid is notoriously difficult and often requires a thoracoscopic or laproscopic or open biopsy and Immunohistochemical staining for certain markers such as meosthelin expressed preferentially in this tumor. Until now, no intervention has proven to be curative, despite aggressive chemotherapeutic regimens and prolonged radiotherapy. The median survival in most cases is only 12-18 months after diagnosis.

In order to identify new diagnostic markers and targets to be used for novel diagnostic and therapeutic approaches, we assessed the expression of EPHB4 and its ligand EphrinB2 in mesothelioma cell lines and clinical samples.

A. EPHB4 and EphrinB2 is Expressed in Mesothelioma Cell Lines

Figure 33A:
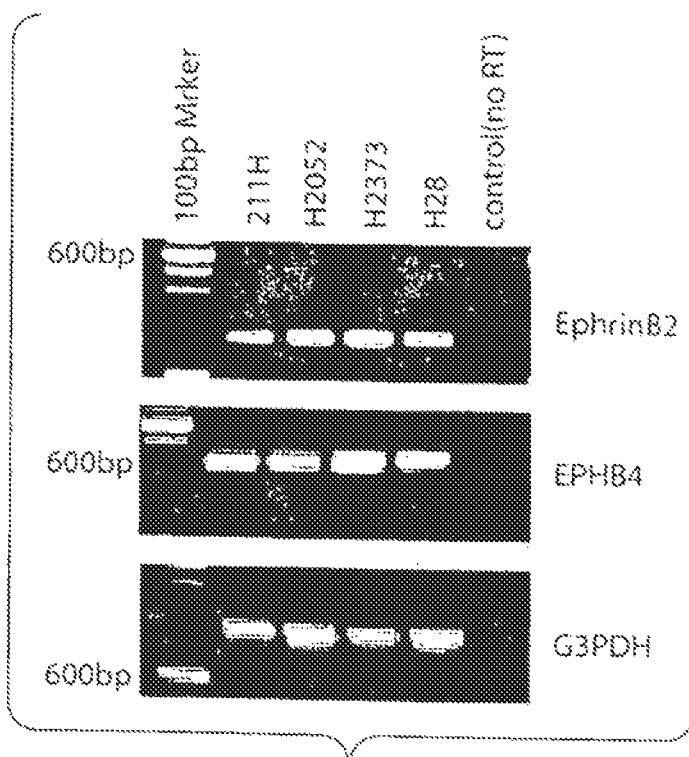
FIG. 33 shows that EphB4 and EphrinB2 are expressed in mesothelioma cell lines as shown by RT-PCR (A) and Western Blot (B).
Figure 33B:
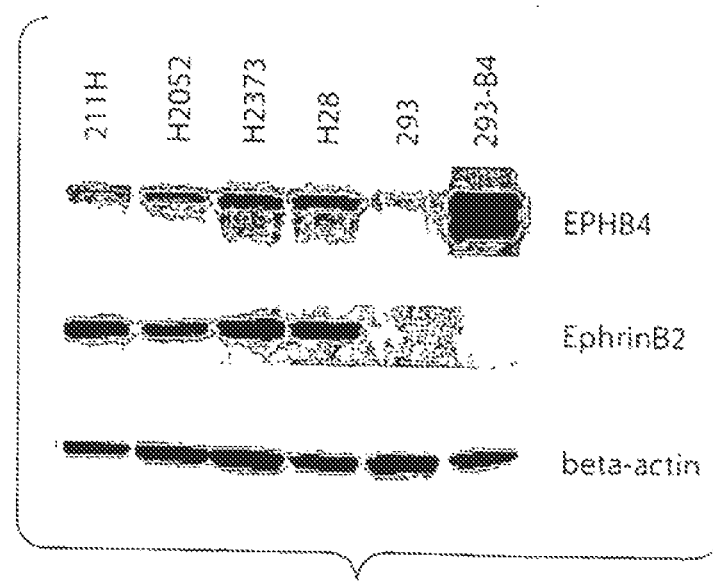

The expression of Ephrin B2 and EphB4 in malignant mesothelioma cell lines was determined at the RNA and protein level by a variety of methods. RT-PCR showed that all of the four cell lines express EphrinB2 and EPHB4 (FIG. 33A). Protein expression was determined by Western blot in these cell lines. Specific bands for EphB4 were seen at 120 kD. In addition, Ephrin B2 was detected in all cell lines tested as a 37 kD band on Western blot (FIG. 33B). No specific band for Ephrin B2 was observed in 293 human embryonic kidney cells, which were included as a negative control.

Figure 34:
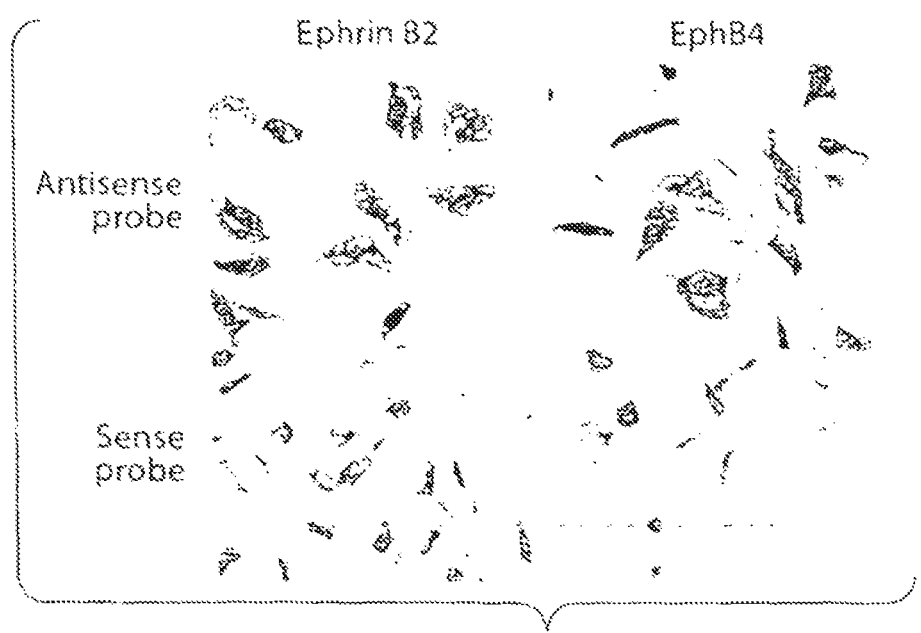
FIG. 34 shows expression of ephrin B2 and EphB4 by in situ hybridization in mesothelioma cells. NCI H28 mesothelioma cell lines cultured in chamber slides hybridized with antisense probe to ephrin B2 or EphB4 (top row). Control for each hybridization was sense (bottom row). Positive reaction is dark blue cytoplasmic stain.
Figure 35:
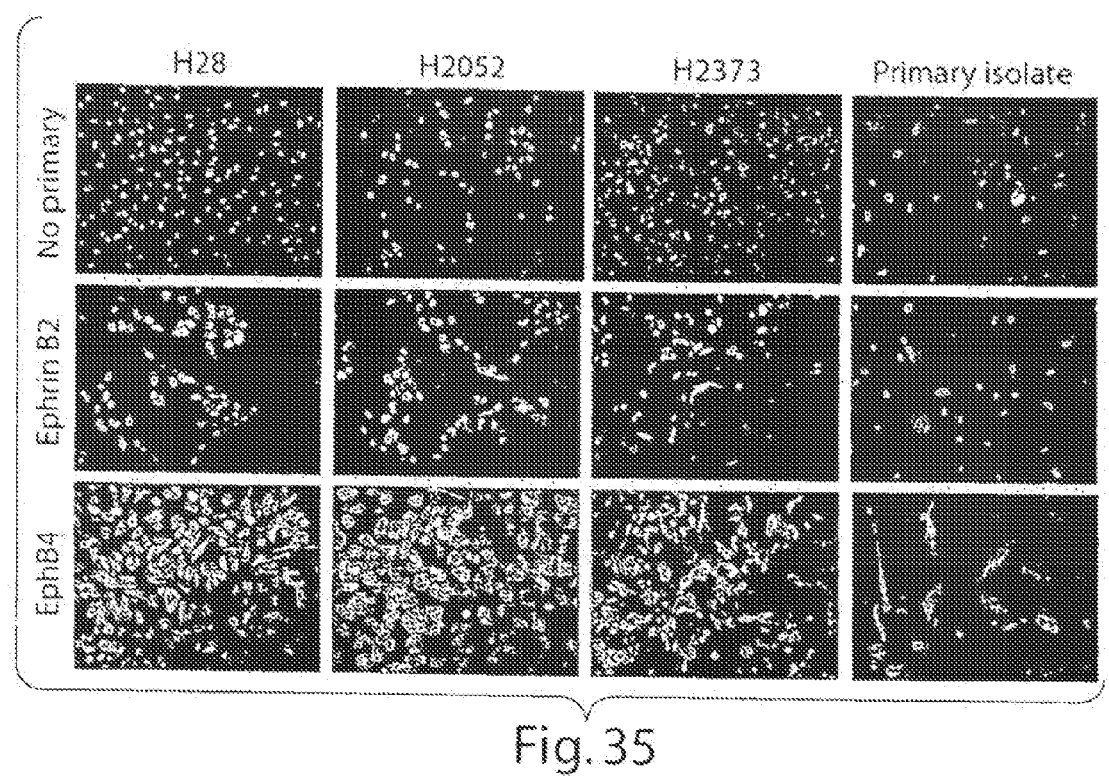
FIG. 35 shows cellular expression of EphB4 and ephrin B2 in mesothelioma cultures. Immunofluorescence staining of primary cell isolate derived from pleural effusion of a patient with malignant mesothelioma and cell lines NCI H28, NCI H2373, and NCI H2052 for ephrin B2 and EphB4. Green color is positive signal for FITC labeled secondary antibody. Specificity of immunofluorescence staining was demonstrated by lack of signal with no primary antibody (first row). Cell nuclei were counterstained with DAPI (blue color) to reveal location of all cells. Shown are merged images of DAPI and FITC fluorescence. Original magnification 200×.

To confirm the presence of EphB4 transcription in mesothelioma cells, in situ hybridization was carried out on NCI H28 cell lines cultured on chamber slides. Specific signal for EphB4 was detected using antisense probe Ephrin B2 transcripts were also detected in the same cell line. Sense probes for both EphB4 and Ephrin B2 served as negative controls and did not hybridize to the cells (FIG. 34). Expression of EphB4 and Ephrin B2 proteins was confirmed in the cell lines by immunofluorescence analysis (FIG. 35). Three cell lines showed strong expression of EphB4, whereas expression of Ephrin B2 was present in H28 and H2052, and weakly detectable in H2373.

B. Evidence of Expression of EPHB4 and EphrinB2 in Clinical Samples

Tumor cells cultured from the pleural effusion of a patient diagnosed with pleural malignant mesothelioma were isolated and showed positive staining for both EphB4 and Ephrin B2 at passage 1 (FIG. 35, bottom row). These results confirm co-expression of EphB4 and Ephrin B2 in mesothelioma cell lines. To determine whether these results seen in tumor cell lines were a real reflection of expression in the disease state, tumor biopsy samples were subjected to immunohistochemical staining for EphB4 and Ephrin B2.

Figure 36:
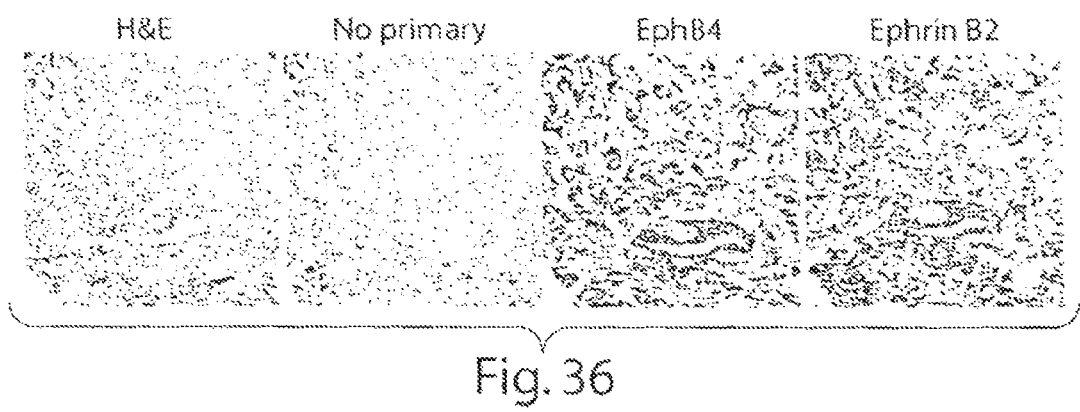
FIG. 36 shows expression of ephrin B2 and EphB4 in mesothelioma tumor. Immunohistochemistry of malignant mesothelioma biopsy. H&E stained section reveals tumor architecture; bottom left panel is background control with no primary antibody. EphB4 and ephrin B2 specific staining is brown color. Original magnification 200×.

Antibodies to both proteins revealed positive stain in the tumor cells. Representative data is shown in FIG. 36.

C. EPHB4 is Involved in the Cell Growth and Migration of Mesothelioma

Figure 37A:
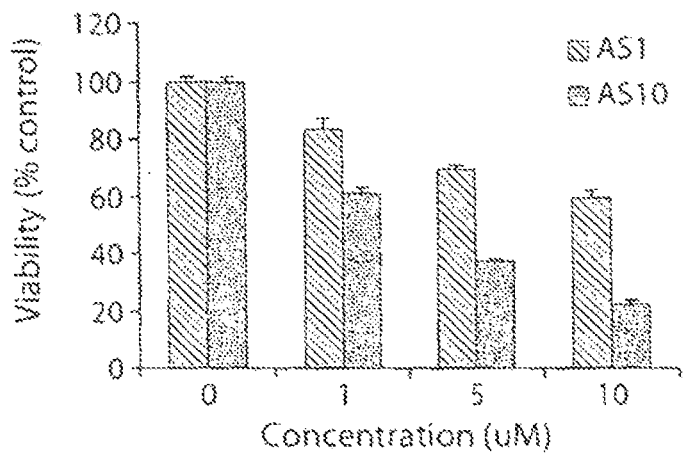
FIG. 37 shows effects of EPHB4 antisense probes (A) and EPHB4 siRNAs (B) on the growth of H28 cells.
Figure 37B:
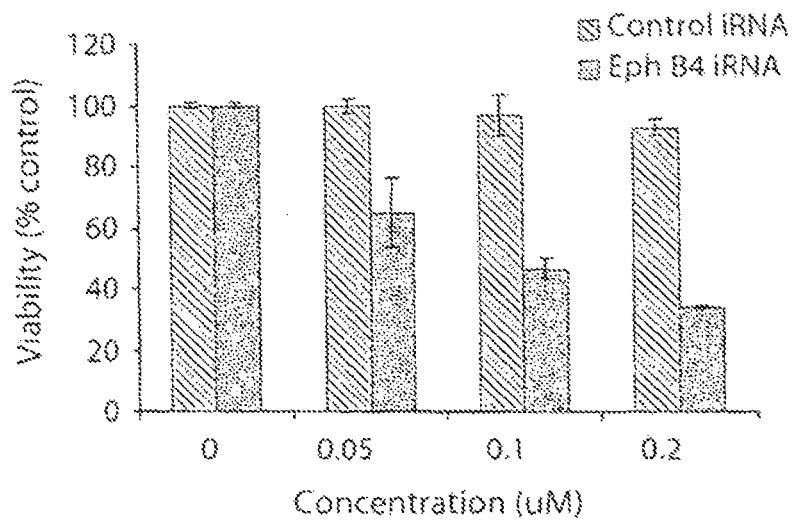

The role of EphB4 in cell proliferation was tested using EPHB4 specific antisepses oligonucleotides and siRNA. The treatment of cultured H28 with EPHB4 antisense reduced cell viability. One of the most active inhibitor of EphB4 expression is EPHB4AS-10 (FIG. 37A). Transfection of EPHB4 siRNA 472 generated the same effect (FIG. 37B).

Figure 38A:
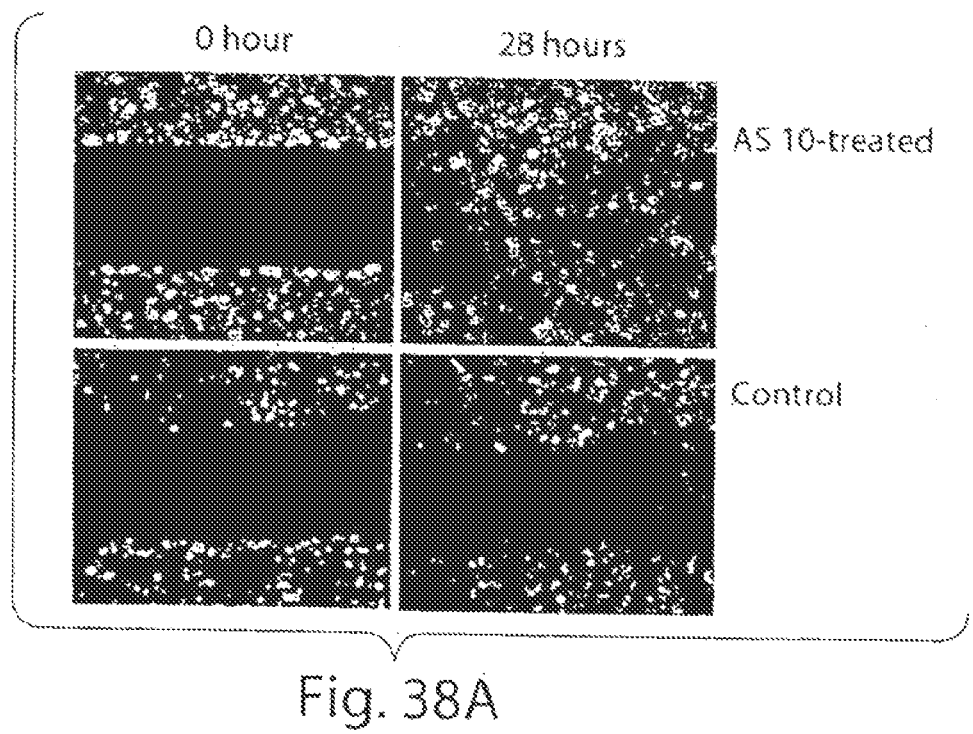
FIG. 38 shows effects of EPHB4 antisense probes (A) and EPHB4 siRNAs (B) on cell migration.
Figure 38B:
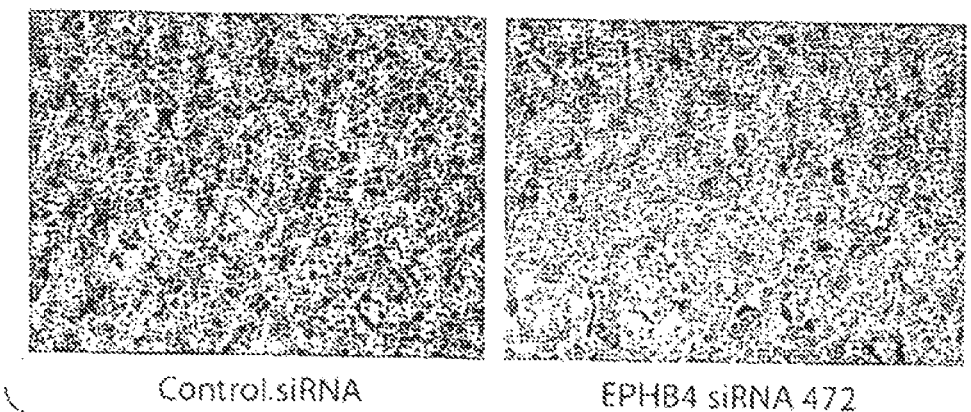

MM is a locally advancing disease with frequent extension and growth into adjacent vital structures such as the chest wall, heart, and esophagus. In an effort to study this process in vitro, we perform wound healing assay using previously described techniques (3:36). When a wound was introduced into sub confluent H28 cells, over the course of the next 28 hours cells would progressively migrate into the area of the wound. However, when cells were pretreated with EPHB4AS-10 for 24 hours, and the wound was introduced, this migration was virtually completely prevented (FIG. 38A). The migration study with Boyden Chamber assay with EPHB4 siRNA showed that cell migration was greatly inhibited with the inhibition of EPHB4 expression (FIG. 38B).

D. Materials and Methods

A detailed description of the materials and methods for this example may be found in U.S. Patent Publication No. 20050084873.

Example 5

EphB4 is Expressed in Squamous Cell Carcinoma of the Head and Neck: Regulation by Epidermal Growth Factor Signaling Pathway and Growth Advantage Squamous cell carcinoma of the head and neck (HNSCC) is the sixth most frequent cancer worldwide, with estimated 900,000 cases diagnosed each year. It comprises almost 50% of all malignancies in some developing nations. In the United States, 50,000 new cases and 8,000 deaths are reported each year. Tobacco carcinogens are believed to be the primary etiologic agents of the disease, with alcohol consumption, age, gender, and ethnic background as contributing factors.

The differences between normal epithelium of the upper aerodigestive tract and cancer cells arising from that tissue are the result of mutations in specific genes and alteration of their expression. These genes control DNA repair, proliferation, immortalization, apoptosis, invasion, and angiogenesis. For head and neck cancer, alterations of three signaling pathways occur with sufficient frequency and produce such dramatic phenotypic changes as to be considered the critical transforming events of the disease. These changes include mutation of the p53 tumor suppressor, overexpression of epidermal growth factor receptor (EGFR), and inactivation of the cyclin dependent kinase inhibitor p16. Other changes such as Rb mutation, ras activation, cyclin D amplification, and myc overexpression are less frequent in HNSCC.

Although high expression of EphB4 has been reported in hematologic malignancies, breast carcinoma, endometrial carcinoma, and colon carcinoma, there is limited data on the protein levels of EphB4, and complete lack of data on the biological significance of this protein in tumor biology such as HNSCC.

A. HNSCC Tumors Express EphB4

Figure 39A:
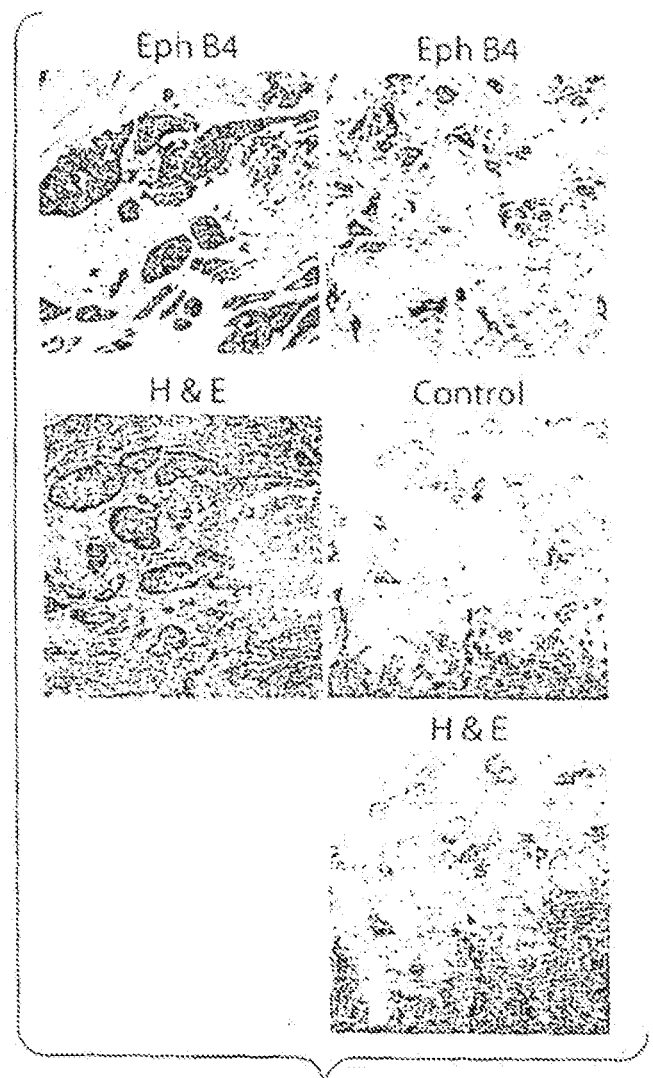
FIG. 39 shows that EphB4 is expressed in HNSCC primary tissues and metastases. A) Top: Immunohistochemistry of a representative archival section stained with EphB4 monoclonal antibody as described in the methods and visualized with DAB (brown color) localized to tumor cells. Bottom: Hematoxylin and Eosin (H&E) stain of an adjacent section. Dense purple staining indicates the presence of tumor cells. The right hand column are frozen sections of lymph node metastasis stained with EphB4 polyclonal antibody (top right) and visualized with DAB. Control (middle) was incubation with goat serum and H&E (bottom) reveals the location of the metastatic foci surrounded by stroma which does not stain. B) In situ hybridization of serial frozen sections of a HNSCC case probed with EphB4 (left column) and ephrin B2 (right column) DIG labeled antisense or sense probes generated by run-off transcription. Hybridization signal (dark blue) was detected using alkaline-phosphatase-conjugated anti-DIG antibodies and sections were counterstained with Nuclear Fast Red. A serial section stained with H&E is shown (bottom left) to illustrate tumor architecture. C) Western blot of protein extract of patient samples consisting of tumor (T), uninvolved normal tissue (N) and lymph node biopsies (LN). Samples were fractionated by polyacrylamide gel electrophoresis in 4-20% Tris-glycine gels and subsequently electroblotted onto nylon membranes. Membranes were sequentially probed with EphB4 monoclonal antibody and β-actin MoAb. Chemiluminescent signal was detected on autoradiography film. Shown is the EphB4 specific band which migrated at 120 kD and β-actin which migrated at 40 kD. The β-actin signal was used to control for loading and transfer of each sample.

We studied the expression of EphB4 in human tumor tissues by immunohistochemistry, in situ hybridization, and Western blot. Twenty prospectively collected tumor tissues following IRB approval have been evaluated with specific EphB4 monoclonal antibody that does not react with other members of the EphB and EphA family. EphB4 expression is observed in all cases, with varying intensity of staining. FIG. 39A (top left) illustrates a representative case, showing that EphB4 is expressed in the tumor regions only, as revealed by the H&E tumor architecture (FIG. 39A bottom left). Note the absence of staining for EphB4 in the stroma. Secondly, a metastatic tumor site in the lymph node shows positive staining while the remainder of the lymph node is negative (FIG. 39A, top right).

Figure 39B:
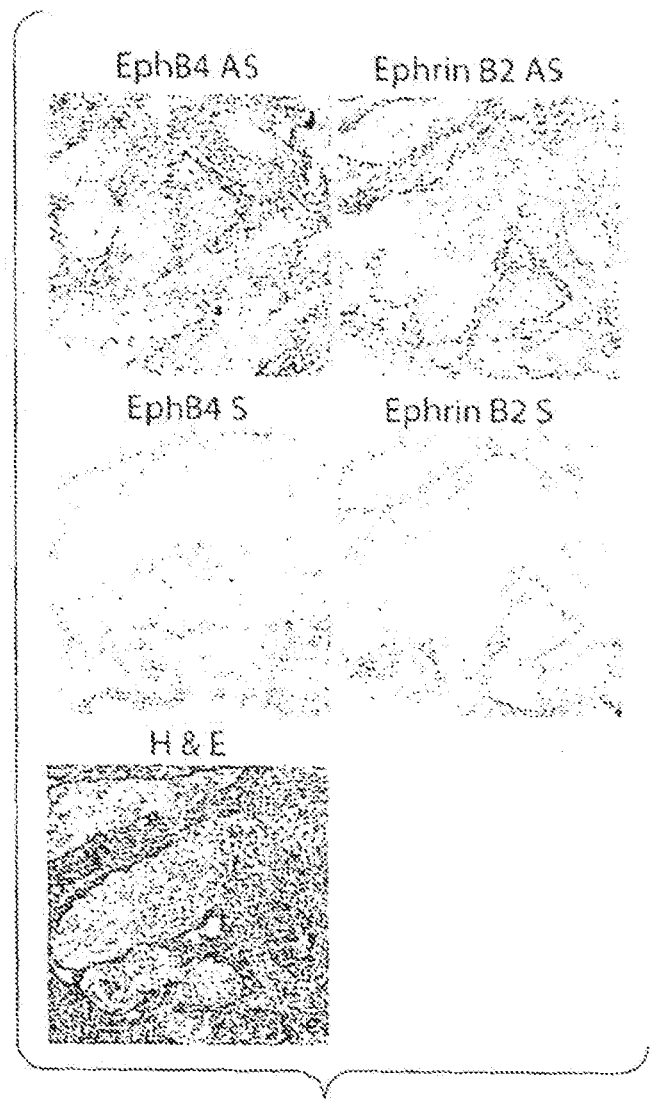

In situ hybridization was carried out to determine the presence and location of EphB4 transcripts in the tumor tissue. Strong signal for EphB4 specific antisense probe was detected indicating the presence of transcripts (FIG. 39 B, top left). Comparison with the H&E stain (FIG. 39B, bottom left) to illustrate tumor architecture reveals that the signal was localized to the tumor cells, and was absent from the stromal areas. Ephrin B2 transcripts were also detected in tumor sample, and as with EphB4, the signal was localized to the tumor cells (FIG. 39B, top right). Neither EphB4 nor ephrin B2 sense probes hybridized to the sections, proving specificity of the signals.

B. High Expression of EphB4 in Primary and Metastatic Sites of HNSCC

Figure 39C:
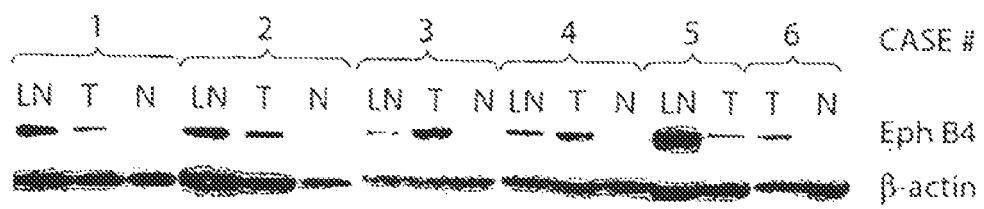

Western blots of tissue from primary tumor, lymph node metastases and uninvolved tissue were carried out to determine the relative levels of EphB4 expression in these sites. Tumor and normal adjacent tissues were collected on 20 cases, while lymph nodes positive for tumor were harvested in 9 of these 20 cases. Representative cases are shown in FIG. 39C. EphB4 expression is observed in each of the tumor samples. Similarly, all tumor positive lymph nodes show EphB4 expression that was equal to or greater than the primary tumor. No or minimal expression is observed in the normal adjacent tissue.

C. EphB4 Expression and Regulation by EGFR Activity in HNSCC Cell Lines

Figure 40A:
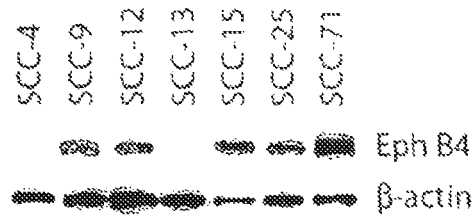
FIG. 40 shows that EphB4 is expressed in HNSCC cell lines and is regulated by EGF: A) Survey of EphB4 expression in SCC cell lines. Western blot of total cell lysates sequentially probed with EphB4 monoclonal antibody, stripped and reprobed with β-actin monoclonal antibody as described for FIG. 39C. B) Effect of the specific EGFR inhibitor AG1478 on EphB4 expression: Western blot of crude cell lysates of SCC15 treated with 0-1000 nM AG 1478 for 24 h in media supplemented with 10% FCS (left) or with 1 mM AG 1478 for 4, 8, 12 or 24 h (right). Shown are membranes sequentially probed for EphB4 and β-actin. C) Effect of inhibition of EGFR signaling on EphB4 expression in SCC cell lines: Cells maintained in growth media containing 10% FCS were treated for 24 hr with 1 µM AG 1478, after which crude cell lysates were analyzed by Western blots of cell lysates sequentially probed with for EGFR, EphB4, ephrin B2 and β-actin antibodies. Specific signal for EGFR was detected at 170 kD and ephrin B2 at 37 kD in addition to EphB4 and β-actin as described in FIG. 1C. β-actin serves as loading and transfer control.
Figure 40B:
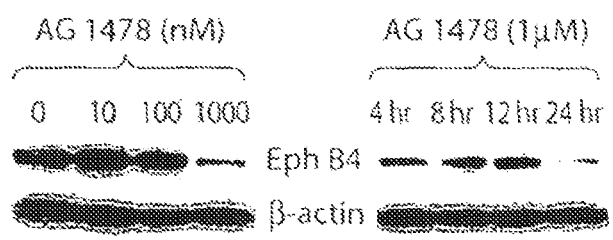
Figure 40C:
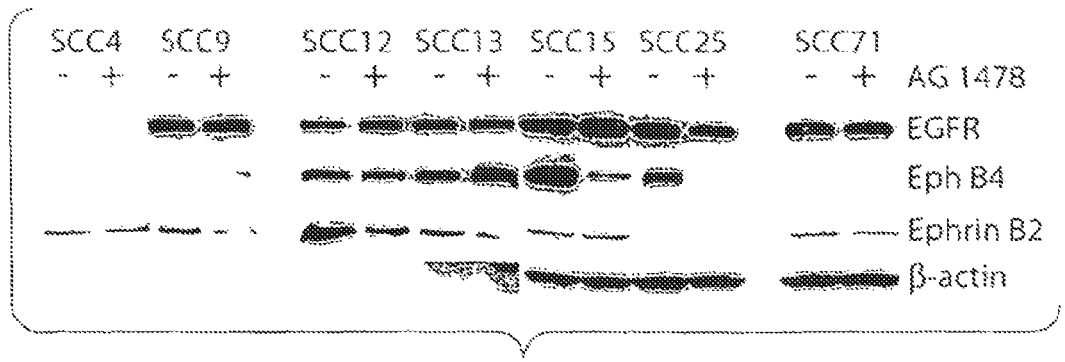

Having demonstrated the expression of EphB4 limited to tumor cells, we next sought to determine whether there was an in vitro model of EphB4 expression in HNSCC. Six HN SCC cell lines were surveyed for EphB4 protein expression by Western Blot (FIG. 40A). A majority of these showed strong EphB4 expression and thus established the basis for subsequent studies. Since EGFR is strongly implicated in HNSCC we asked whether EphB4 expression is associated with the activation of EGFR. Pilot experiments in SCC-15, which is an EGFR positive cell line, established an optimal time of 24 h and concentration of 1 mM of the specific EGFR kinase inhibitor AG 1478 (FIG. 40B) to inhibit expression of EphB4. When all the cell lines were studied, we noted robust EGFR expression in all but SCC-4, where it is detectable but not strong (FIG. 40C, top row). In response to EGFR inhibitor AG1478 marked loss in the total amount of EphB4 was observed in certain cell lines (SCC-15, and SCC-25) while no effect was observed in others (SCC-9, -12, -13 and -71). Thus SCC-15 and -25 serve as models for EphB4 being regulated by EGFR activity, while SCC-9, -12, -13 and -71 are models for regulation of EphB4 in HNSCC independent of EGFR activity, where there may be input from other factors such as p53, PTEN, IL-6 etc. We also noted expression of the ligand of EphB4, namely ephrin B2, in all of the cell lines tested. As with EphB4 in some lines ephrin B2 expression appears regulated by EGFR activity, while it is independent in other cell lines.

Figure 41A:
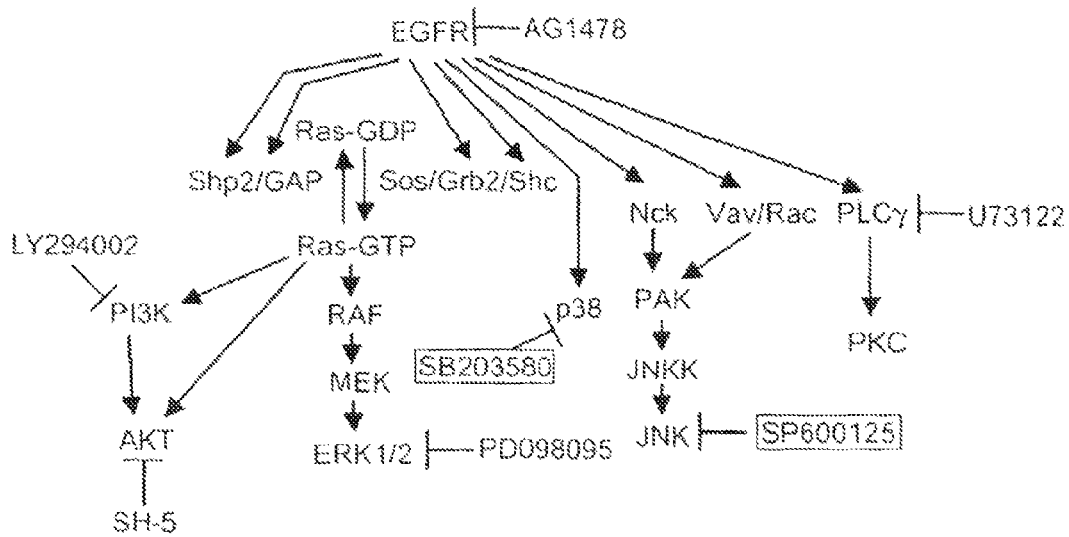
FIG. 41 shows mechanism of regulation of EphB4 by EGF: A) Schematic of the EGFR signaling pathways, showing in red the sites of action and names of specific kinase inhibitors used. B) SCC15 cells were serum-starved for 24 h prior to an additional 24 incubation as indicated with or without EGF (10 ng/ml), 3 µM U73122, or 5 µM SH-5, 5 µM SP600125, 25 nM LY294002, - - µM PD098095 or 5 µM SB203580. N/A indicates cultures that received equal volume of diluent (DMSO) only. Cell lysates were subjected to Western Blot with EphB4 monoclonal antibody. β-actin signal serves as control of protein loading and transfer.
Figure 41B:
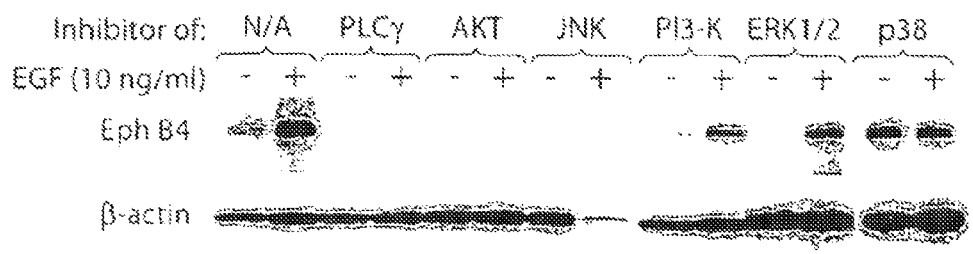

Clearly, inhibition of constitutive EGFR signaling repressed EphB4 levels in SCC15 cells. We next studied whether EGF could induce EphB4. We found that EphB4 levels were induced in SCC15 cells that had been serum starved for 24 h prior to 24 h treatment with 10 ng/ml EGF as shown in FIG. 41B (lanes 1 and 2). The downstream signaling pathways known for EGFR activation shown in FIG. 41A, (for review see Yarden & Slikowski 2001) were then investigated for their input into EGF mediated induction of EphB4. Blocking PLCg, AKT and JNK phosphorylation with the specific kinase inhibitors U73122, SH-5 and SP600125 respectively reduced basal levels and blocked EGF stimulated induction of EphB4 (FIG. 41B, lanes 3-8). In contrast, inhibition of ERK½ with PD098095 and PI3-K with LY294002 or Wortmannin had no discernible effect on EGF induction of EphB4 levels. However, basal levels of EphB4 were reduced when ERK½ phosphorylation was inhibited. Interestingly, inhibition of p38 MAPK activation with SB203580 increased basal, but not EGF induced EphB4 levels. Similar results were seen in the SCC25 cell line (data not shown).

Figure 42A:
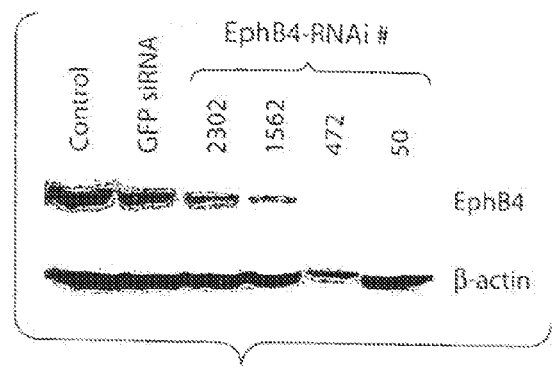
FIG. 42 shows that specific EphB4 siRNAs inhibit EphB4 expression, cell viability and cause cell cycle arrest. A) 293 cells stably expressing full length EphB4 were transfected with 50 nM RNAi using Lipofectamine™2000. 40 h post-transfection cells were harvested, lysed and processed for Western blot. Membranes were probed with EphB4 monoclonal antibody, stripped and reprobed with β-actin monoclonal antibody as control for protein loading and transfer. Negative reagent control was RNAi to scrambled green fluorescence protein (GFP) sequence and control is transfection with Lipofectamine™2000 alone. B) MTT cell viability assays of SCC cell lines treated with siRNAs for 48 h as described in the Methods section. Shown is mean+s.e.m. of triplicate samples. C) SCC15 cells transfected with siRNAs as indicated were analyzed 24 h post transfection for cell cycle status by flow cytometry as described in the Methods. Shown are the plots of cell number vs. propidium iodide fluorescence intensity. Top and middle row show plots for cells 16 h after siRNA transfection, bottom row shows plots for cells 36 h post transfection. Specific siRNA and concentration are indicated for each plot. Lipo=Lipofectamine™200 mock transfection.
Figure 42B:
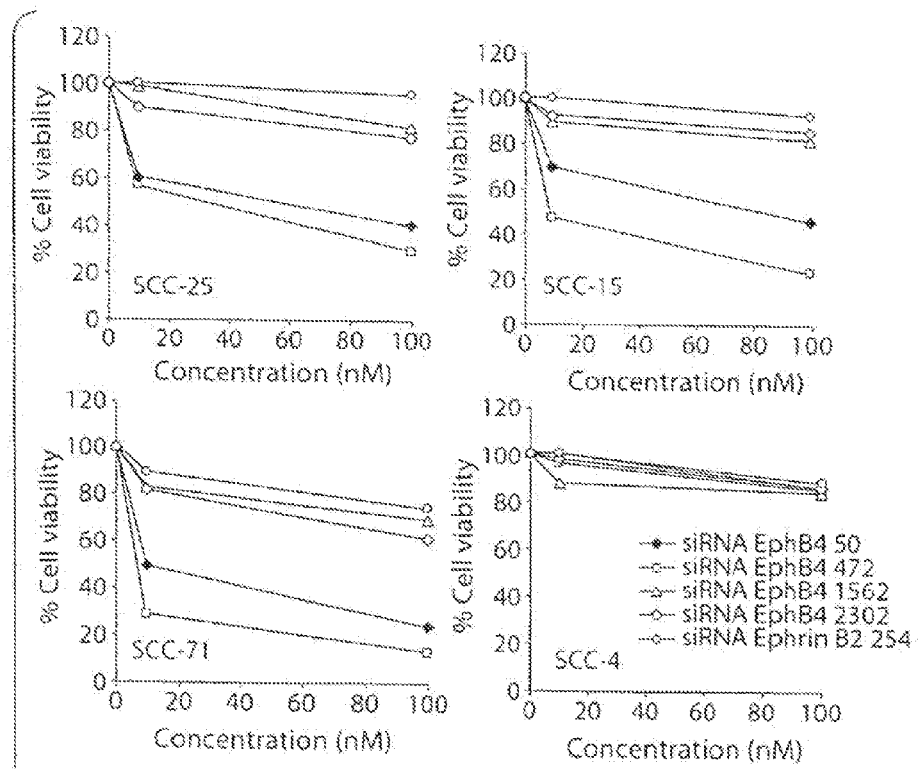
Figure 42C:
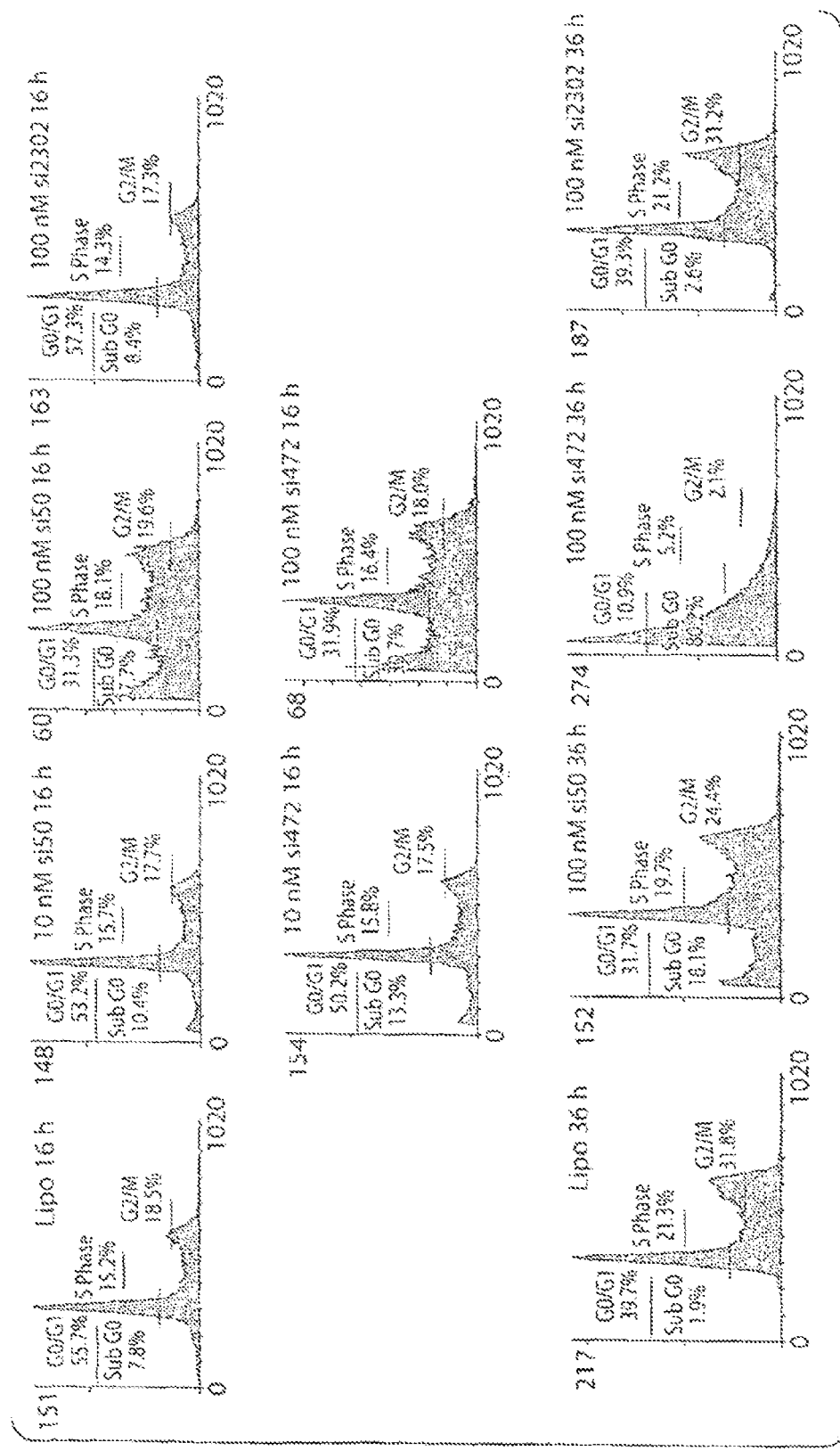

D. Inhibition of EphB4 in High Expressing Cell Lines Results in Reduced Viability and Causes Cell-Cycle Arrest We next turned to the role of EphB4 expression in HNSCC by investigating the effect of ablating expression using siRNA or AS-ODN methods. Several siRNAs to EphB4 sequence were developed (Table 1) which knocked-down EphB4 expression to varying degrees as seen in FIG. 42A. Viability was reduced in SCC-15, -25 and -71 cell lines transfected with siRNAs 50 and 472, which were most effective in blocking EphB4 expression (FIG. 42B). Little effect on viability was seen with EphB4 siRNA 1562 and 2302 or ephrin B2 siRNA 254. Note that in SCC-4, which does not express EphB4 (see FIG. 40A) there was no reduction in cell viability. The decreased cell viability seen with siRNA 50 and 472 treatment was attributable to accumulation of cells in sub G0, indicative of apoptosis. This effect was both time and dose-dependant (FIG. 42C and Table 2). In contrast, siRNA2302 that was not effective in reducing EphB4 levels and had only minor effects on viability did not produce any changes in the cell cycle when compared with the mock Lipofectamine™2000 transfection.

A detailed description of the siRNA constructs for this example may be found in U.S. Patent Publication No. 20050084873.

TABLE

Effect of different EphB4 siRNA on Cell Cycle

| Treatment | Sub G0 | G1 | S | G2 |
|---|---|---|---|---|
| 36 hr | | | | |
| Lipo alone | 1.9 | 39.7 | 21.3 | 31.8 |
| 100 nM 2302 | 2.0 | 39.3 | 21.2 | 31.2 |
| 100 nM 50 | 18.1 | 31.7 | 19.7 | 24.4 |
| 100 nM 472 | 80.2 | 10.9 | 5.2 | 2.1 |
| 16 hr | | | | |
| Lipo alone | 7.8 | 55.7 | 15.2 | 18.5 |
| 100 nM 2302 | 8.4 | 57.3 | 14.3 | 17.3 |
| 10 nM 50 | 10.4 | 53.2 | 15.7 | 17.7 |
| 100 nM 50 | 27.7 | 31.3 | 18.1 | 19.6 |
| 10 nM 472 | 13.3 | 50.2 | 15.8 | 17.5 |
| 100 nM 472 | 30.7 | 31.9 | 16.4 | 18.0 |

Figure 43A:
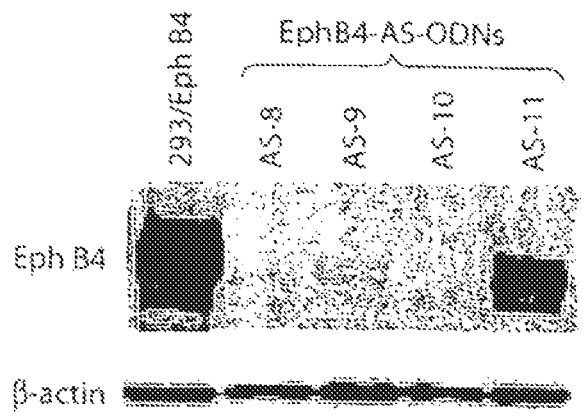
FIG. 43 shows in vitro effects of specific EphB4 AS-ODNs on SCC cells. A) 293 cells transiently transfected with EphB4 full-length expression plasmid were treated 6 h post transfection with antisense ODNs as indicated. Cell lysates were collected 24 h after AS-ODN treatment and subjected to Western Blot. B) SCC25 cells were seeded on 48 well plates at equal densities and treated with EphB4 AS-ODNs at 1, 5, and 10 µM on days 2 and 4. Cell viability was measured by MTT assay on day 5. Shown is the mean+s.e.m. of triplicate samples. Note that AS-ODNs that were active in inhibiting EphB4 protein levels were also effective inhibitors of SCC15 cell viability. C) Cell cycle analysis of SCC15 cells treated for 36 h with AS-10 (bottom) compared to cells that were not treated (top). D) Confluent cultures of SCC15 cells scraped with a plastic Pasteur pipette to produce 3 mm wide breaks in the monolayer. The ability of the cells to migrate and close the wound in the presence of inhibiting EphB4 AS-ODN (AS-10) and non-inhibiting AS-ODN (AS-1) was assessed after 48 h. Scrambled ODN is included as a negative control ODN. Culture labeled no treatment was not exposed to ODN. At initiation of the experiment, all cultures showed scrapes of equal width and similar to that seen in 1 µM EphB4 AS-10 after 48 h. The red brackets indicate the width of the original scrape. E) Migration of SCC15 cells in response to 20 mg/ml EGF in two-chamber assay as described in the Methods. Shown are representative photomicrographs of non-treated (NT), AS-6 and AS-10 treated cells and 10 ng/ml Taxol as positive control of migration inhibition. F) Cell numbers were counted in 5 individual high-powered fields and the average+s.e.m. is shown in the graph.
Figure 43B:
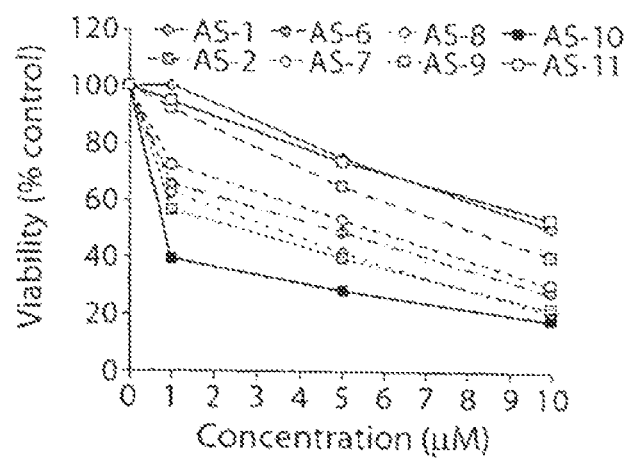
Figure 43C:
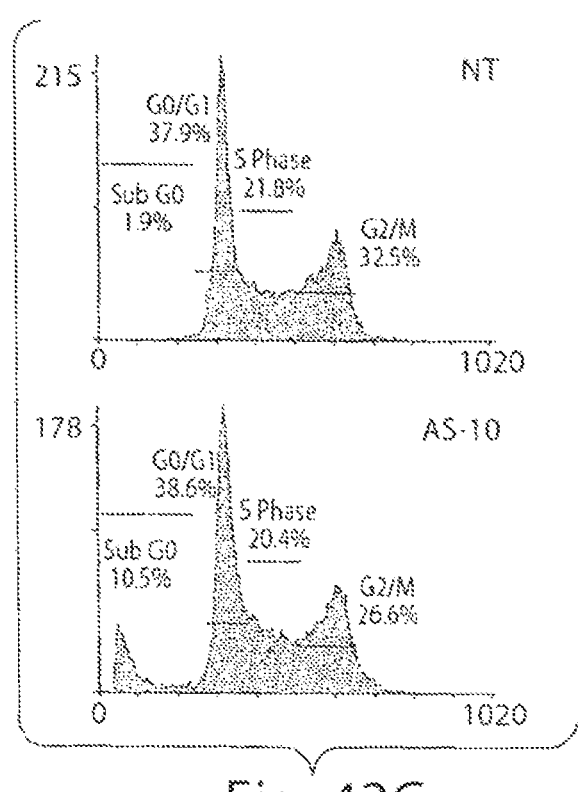

In addition, over 50 phosphorothioate AS-ODNs complementary to the human EphB4 coding sequences were synthesized and tested for their ability to inhibit EphB4 expression in 293 cells transiently transfected with full length EphB4 expression plasmid. FIG. 43A shows a representative sample of the effect of some of these AS-ODNs on EphB4 expression. Note that expression is totally abrogated with AS-10, while AS-11 has only a minor effect. The effect on cell viability in SCC15 cells was most marked with AS-ODNs that are most effective in inhibiting EphB4 expression as shown in FIG. 43B. The $IC_{50}$ for AS-10 was approximately 1 µM, while even 10 µM AS-11 was not sufficient to attain 50% reduction of viability. When the effect that AS-10 had on the cell cycle was investigated, it was found that the sub G0 fraction increased from 1.9% to 10.5% compared to non-treated cells, indicative of apoptosis (FIG. 43C).

E. EphB4 Regulates Cell Migration

Figure 43D:
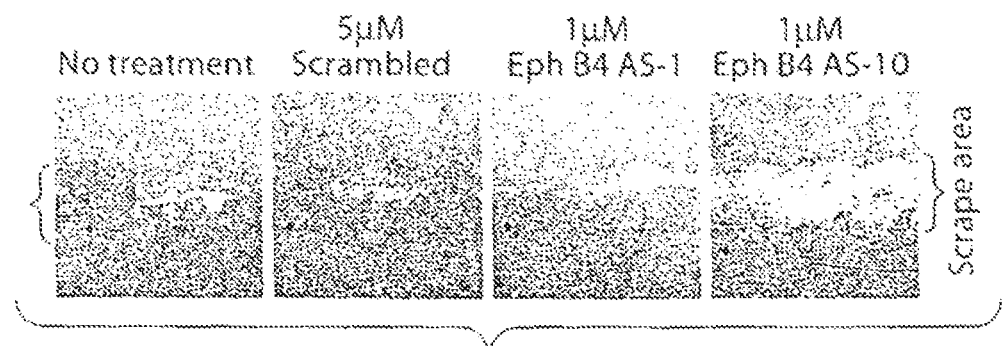
Figure 43E:
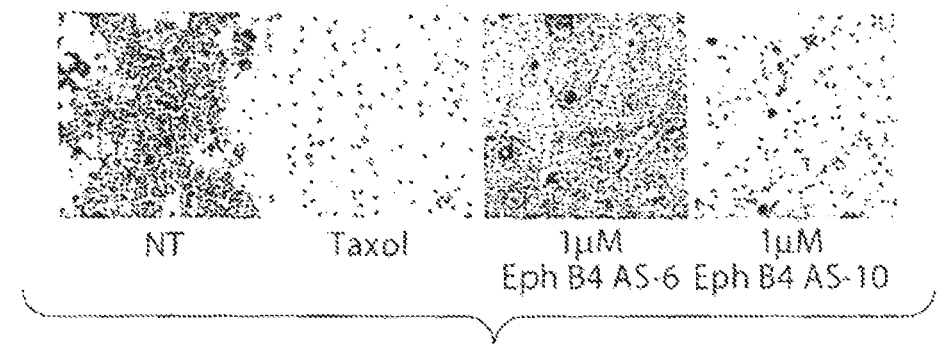
Figure 43F:
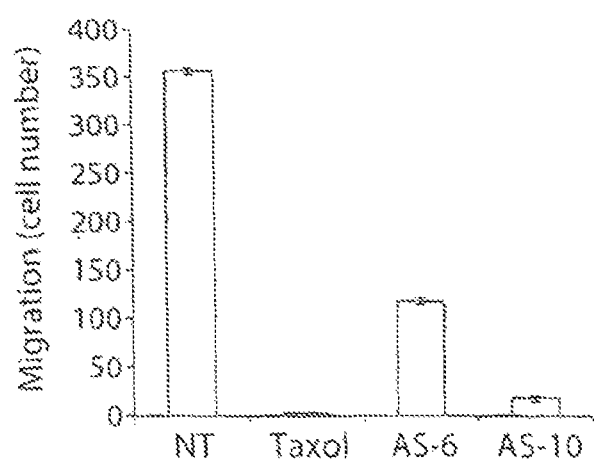

We next wished to determine if EphB4 participates in the migration of HNSCC. Involvement in migration may have implications for growth and metastasis. Migration was assessed using the wound-healing/scrape assay. Confluent SCC15 and SCC25 cultures were wounded by a single scrape with a sterile plastic Pasteur pipette, which left a 3 mm band with clearly defined borders. Migration of cells into the cleared area in the presence of test compounds was evaluated and quantitated after 24, 48 and 72 hr. Cell migration was markedly diminished in response to AS-10 that block EphB4 expression while the inactive compounds, AS-1 and scrambled ODN had little to no effect as shown in FIG. 43D. Inhibition of migration with AS-10 was also shown using the Boyden double chamber assay (FIG. 43E).

F. EphB4 AS-10 In Vivo Anti-Tumor Activity

Figure 44:
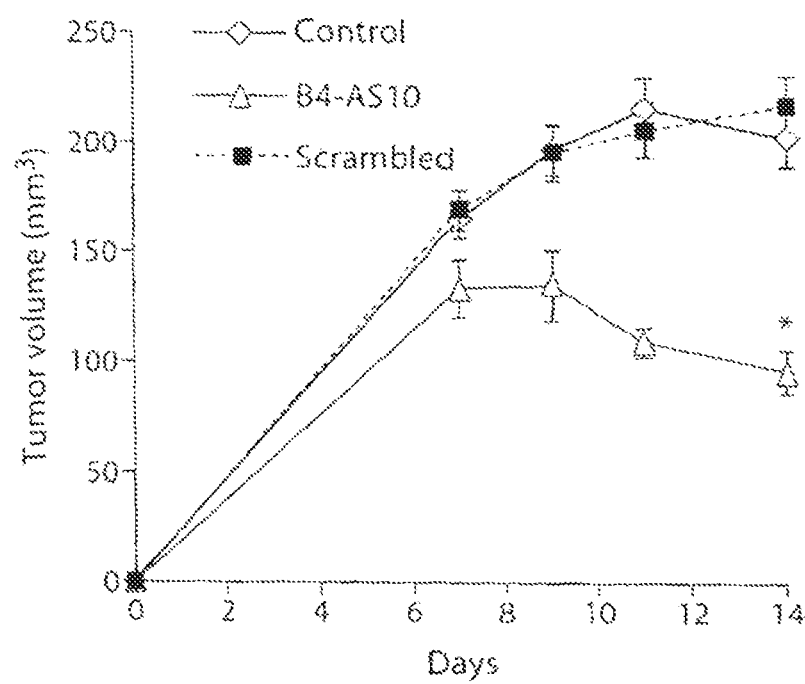
FIG. 44 shows that EphB4 AS-ODN inhibits tumor growth in vivo. Growth curves for SCC15 subcutaneous tumor xenografts in Balb/C nude mice treated with EphB4 AS-10 or scrambled ODN at 20 mg/kg/day starting the day following implantation of 5×106 cells. Control mice received and equal volume of diluent (PBS). Shown are the mean+s.e.m. of 6 mice/group. * P=0.0001 by Student's t-test compared to scrambled ODN treated group.

The effect of EphB4 AS-10, which reduces cell viability and motility, was determined in SCC15 tumor xenografts in Balb/C nude mice. Daily treatment of mice with 20 mg/kg AS-10, sense ODN or equal volume of PBS by I.P. injection was started the day following tumor cell implantation. Growth of tumors in mice receiving AS-10 was significantly retarded compared to mice receiving either sense ODN or PBS diluent alone (FIG. 44). Non-specific effects attributable to ODN were not observed, as there was no difference between the sense ODN treated and PBS treated groups.

G. Materials and Methods

A detailed description of the materials and methods for this example may be found in U.S. Patent Publication No. 20050084873.

Example 6

Ephrin B2 Expression in Kaposi's Sarcoma is Induced by Human Herpesvirus Type 8: Phenotype Switch from Venous to Arterial Endothelium Kaposi's Sarcoma (KS) manifests as a multifocal angio-proliferative disease, most commonly of the skin and mucus membranes, with subsequent spread to visceral organs (1) Hallmarks of the disease are angiogenesis, edema, infiltration of lymphomononuclear cells and growth of spindle-shaped tumor cells. Pathologically, established lesions exhibit an extensive vascular network of slit-like spaces. The KS vascular network is distinct from normal vessels in the lack of basement membranes and the abnormal spindle shaped endothelial cell (tumor cell) lining these vessels. Defective vasculature results in an accumulation of the blood components including albumin, red and mononuclear cells in the lesions (1). The KS tumor is endothelial in origin; the tumor cells express many endothelial markers, including lectin binding sites for *Ulex europeaus* agglutinin-1 (UEA-1), CD34, EN-4, PAL-E (2) and the endothelial cell specific tyrosine kinase receptors, VEGFR-1 (Flt-1), VEGFR-2 (Flk-1/KDR), VEGFR-3 (Flt-4), Tie-1 and Tie-2 (3, RM & PSG unpublished data). KS cells co-express lymphatic endothelial cell related proteins including LYVE and podoplanin (4).

The herpesvirus HHV-8 is considered the etiologic agent for the disease. In 1994 sequences of this new herpes virus were identified in KS tumor tissue (5), and subsequent molecular-epidemiology studies have shown that nearly all KS tumors contain viral genome. Sero-epidemiology studies show that HIV infected patients with KS have the highest prevalence of HHV-8 and secondly that those with HIV infection but no KS have increased risk of development of KS over the ensuing years if they are also seropositive for HHV-8 (6). Direct evidence for the role of HHV-8 in KS is the transformation of bone marrow endothelial cells after infection with HHV-8 (7). A number of HHV-8 encoded genes could contribute to cellular transformation (reviewed in 8). However, the most evidence has accumulated for the G-protein coupled receptor (vGPCR) in this role (9).

We investigated whether KS tumor cells are derived from arterial or venous endothelium. In addition, we investigated whether HHV-8 has an effect on expression of arterial or venous markers in a model of KS. KS tumor cells were found to express the ephrin B2 arterial marker. Further, ephrin B2 expression was induced by HHV-8 vGPCR in KS and endothelial cell lines. Ephrin B2 is a potential target for treatment of KS because inhibition of ephrin B2 expression or signaling was detrimental to KS cell viability and function.

A. KS Tumors Express Ephrin B2, but not EphB4

Figure 45A:
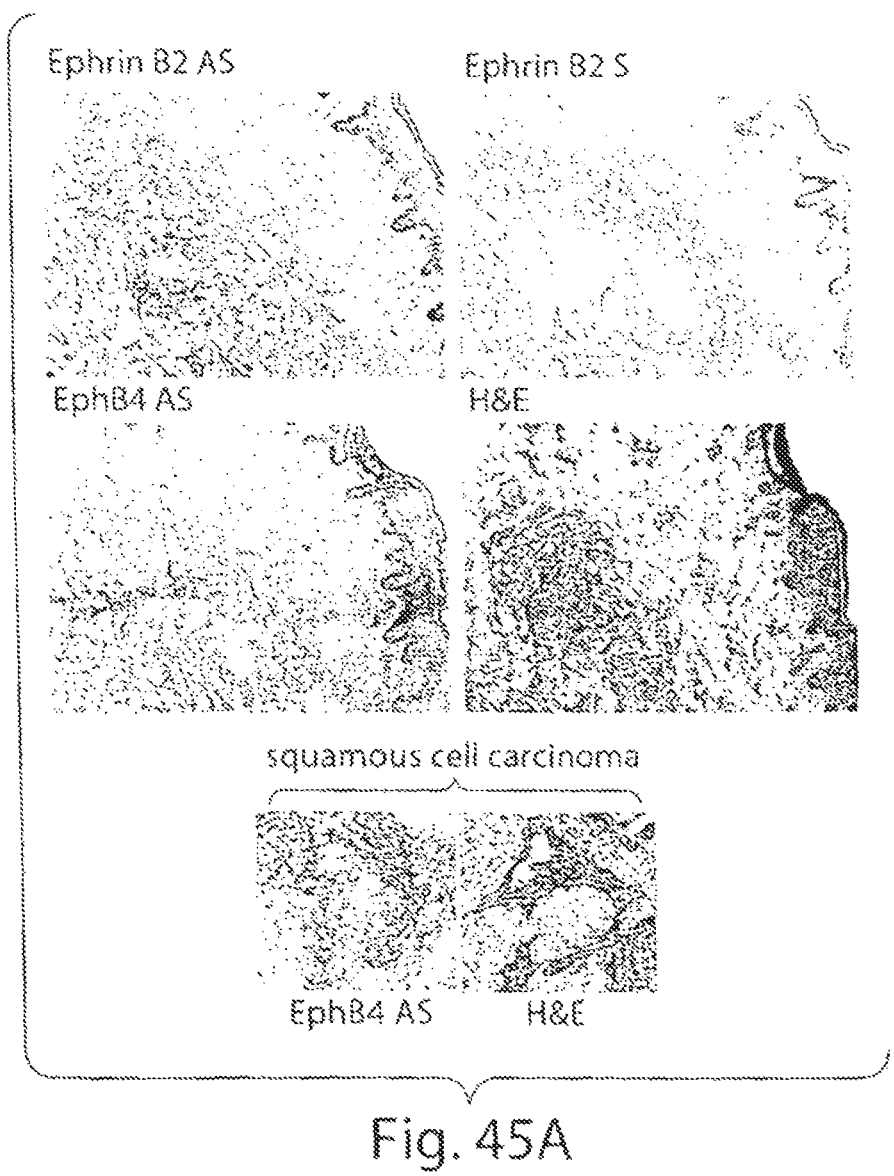
FIG. 45 shows that Ephrin B2, but not EphB4 is expressed in KS biopsy tissue. (A) In situ hybridization with antisense probes for ephrin B2 and EphB4 with corresponding H&E stained section to show tumor architecture. Dark blue color in the ISH indicates positive reaction for ephrin B2. No signal for EphB4 was detected in the Kaposi's sarcoma biopsy. For contrast, ISH signal for EphB4 is strong in squamous cell carcinoma tumor cells. Ephrin B2 was also detected in KS using EphB4-AP fusion protein (bottom left). (B) Detection of ephrin B2 with EphB4/Fc fusion protein. Adjacent sections were stained with H&E (left) to show tumor architecture, black rectangle indicates the area shown in the EphB4/Fc treated section (middle) detected with FITC-labeled anti-human Fc antibody as described in the methods section. As a control an adjacent section was treated with human Fc fragment (right). Specific signal arising from EphB4/Fc binding to the section is seen only in areas of tumor cells. (C) Co-expression of ephrin B2 and the HHV8 latency protein LANA1. Double-label confocal immunofluorescence microscopy with antibodies to ephrin B2 (red) LANA1 (green), or EphB4 (red) of frozen KS biopsy material directly demonstrates co-expression of LANA1 and ephrin B2 in KS biopsy. Coexpression is seen as yellow color. Double label confocal image of biopsy with antibodies to PECAM-1 (green) in cells with nuclear propidium iodide stain (red), demonstrating the vascular nature of the tumor.
Figure 45B:
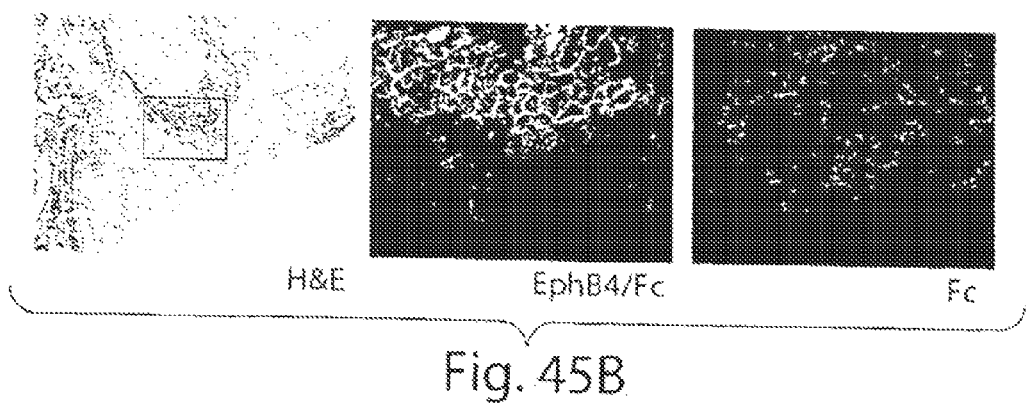
Figure 45C:
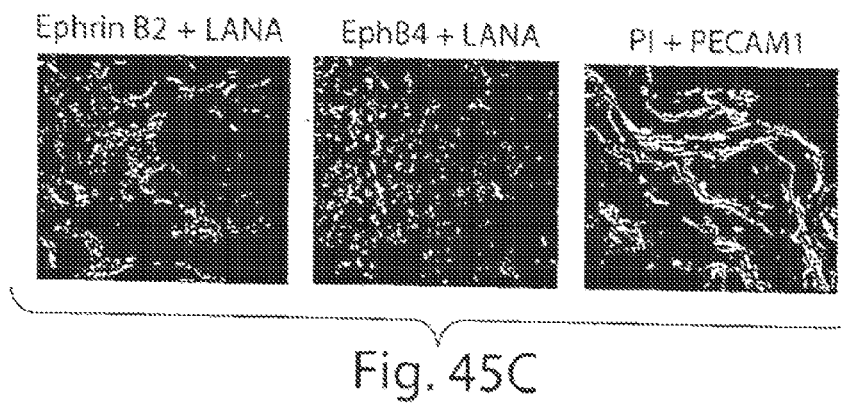

The highly vascular nature of KS lesions and the probable endothelial cell origin of the tumor cells prompted investigation of expression of EphB4 and ephrin B2 which are markers for venous and arterial endothelial cells, respectively. Ephrin B2, but not EphB4 transcripts were detected in tumor cells of KS biopsies by in situ hybridization (FIG. 45A). Comparison of the positive signal with ephrin B2 antisense probe and tumor cells as shown by H&E staining shows that ephrin B2 expression is limited to the areas of the biopsy that contain tumor cells. The lack of signal in KS with EphB4 antisense probe is not due to a defect in the probe, as it detected transcripts in squamous cell carcinoma, which we have shown expresses this protein (18). Additional evidence for the expression of ephrin B2 in KS tumor tissue is afforded by the localization of EphB4/Fc signal to tumor cells, detected by FITC conjugated anti human Fc antibody. Because ephrin B2 is the only ligand for EphB4 this reagent is specific for the expression of ephrin B2 (FIG. 45B, left). An adjacent section treated only with the secondary reagent shows no specific signal. Two-color confocal microscopy demonstrated the presence of the HHV-8 latency protein, LANA1 in the ephrin B2 positive cells (FIG. 45C, left), indicating that it is the tumor cells, not tumor vessels, which are expressing this arterial marker. Staining of tumor biopsy with PECAM-1 antibody revealed the highly vascular nature of this tumor (FIG. 45C, right). A pilot study of the prevalence of this pattern of ephrin B2 and EphB4 expression on KS biopsies was conducted by RT-PCR analysis. All six samples were positive for ephrin B2, while only 2 were weakly positive for EphB4 (data not shown).

Figure 46A:
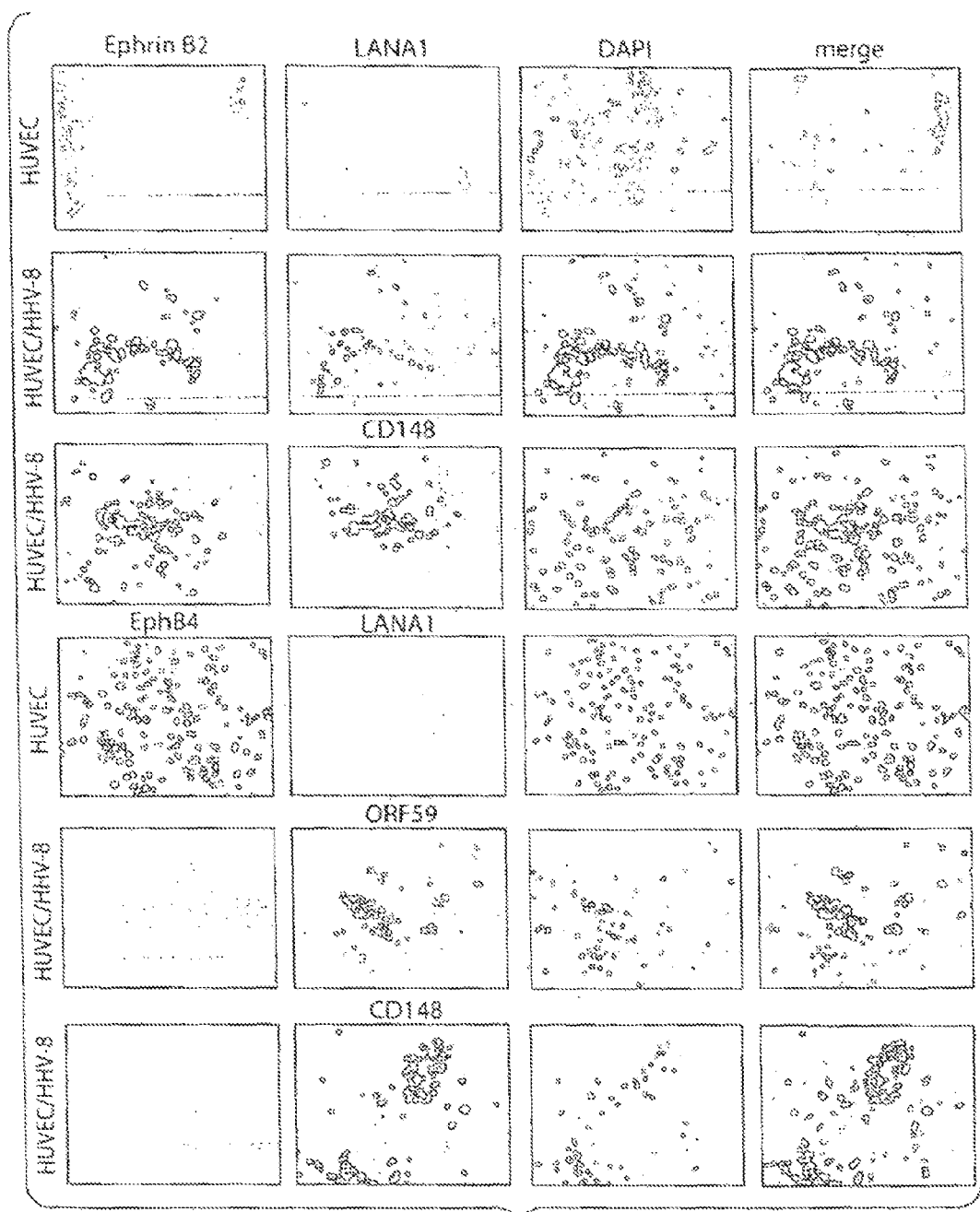
FIG. 46 shows that HHV-8 induces arterial marker expression in venous endothelial cells. (A) Immunofluorescence of cultures of HUVEC and HUVEC/BC-1 for artery/vein markers and viral proteins. Cultures were grown on chamber slides and processed for immunofluorescence detection of ephrin B2 (a, e, i), EphB4 (m, q, u), CD148 (j, v), and the HHV-8 proteins LANA1 (b, f, m) or ORF59 (r) as described in the Materials and Methods. Yellow color in the merged images of the same field demonstrate co-expression of ephrin B2 and LANA or ephrin B2 and CD148. The positions of viable cells were revealed by nuclear staining with DAPI (blue) in the third column (c, g, k, o, s, w). Photomicrographs are of representative fields. (B) RT-PCR of HUVEC and two HHV-8 infected cultures (HUVEC/BC-1 and HUVEC/BC-3) for ephrin B2 and EphB4. Ephrin B2 product (200 bp) is seen in HUVEC/BC-1, HUVEC/BC-3 and EphB4 product (400 bp) is seen in HUVEC. Shown also is β-actin RT-PCR as a control for amount and integrity of input RNA.
Figure 46B:
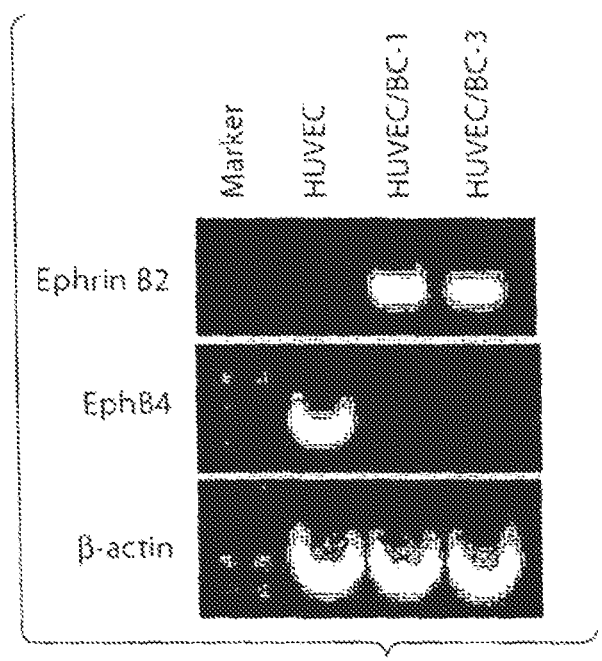

B. Infection of Venous Endothelial Cells with HHV-8 Causes a Phenotype Switch to Arterial Markers We next asked whether HHV-8, the presumed etiologic agent for KS, could itself induce expression of ephrin B2 and repress EphB4 expression in endothelial cells. Co-culture of HUVEC and BC-1 lymphoma cells, which are productively infected with HHV-8, results in effective infection of the endothelial cells (16). The attached monolayers of endothelial cells remaining after extensive washing were examined for ephrin B2 and EphB4 by RT-PCR and immunofluorescence. HUVEC express EphB4 venous marker strongly at the RNA level, but not ephrin B2 (FIG. 46B). In contrast, HHV-8 infected cultures (HUVEC/BC-1 and HUVEC/BC-3) express ephrin B2, while EphB4 transcripts are almost absent.

Immunofluorescence analysis of cultures of HUVEC and HUVEC/HHV-8 for artery/vein markers and viral proteins was undertaken to determine whether changes in protein expression mirrored that seen in the RNA. In addition, cellular localization of the proteins could be determined. Consistent with the RT-PCR data HUVEC are ephrin B2 negative and EphB4 positive (FIG. 46A(a & m)). As expected they do not express any HHV-8 latency associated nuclear antigen (LANA1) (FIG. 46A(b, n)). Co-culture of BC-1 cells, which are productively infected with HHV-8, resulted in infection of HUVEC as shown by presence of viral proteins LANA1 and ORF59 (FIG. 46A(f, r)). HHV-8 infected HUVEC now express ephrin B2 but not EphB4 (FIG. 46A(e, q, u), respectively). Expression of ephrin B2 and LANA1 co-cluster as shown by yellow signal in the merged image (FIG. 46A(h)). HHV-8 infected HUVEC positive for ephrin B2 and negative for Eph B4 also express the arterial marker CD148 (19) (FIG. 46A (j, v)). Expression of ephrin B2 and CD148 co-cluster as shown by yellow signal in the merged image (FIG. 46A(l)). Uninfected HUVEC expressing Eph B4 were negative for CD148 (not shown).

C. HHV-8 vGPCR Induces Ephrin B2 Expression

Figure 47A:
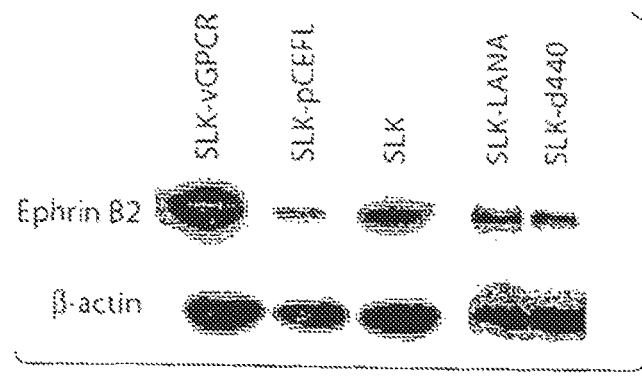
FIG. 47 shows that HHV-8 induces arterial marker expression in Kaposi's sarcoma cells. (A) Western blot for ephrin B2 on various cell lysates. SLK-vGPCR is a stable clone of SLK expressing the HHV-8 vGPCR, and SLK-pCEFL is control stable clone transfected with empty expression vector. SLK cells transfected with LANA or LANAΔ440 are SLK-LANA and SLK-Δ440 respectively. Quantity of protein loading and transfer was determined by reprobing the membranes with β-actin monoclonal antibody. (B) Transient transfection of KS-SLK cells with expression vector pvGPCR-CEFL resulted in the expression of ephrin B2 as shown by immunofluorescence staining with FITC (green), whereas the control vector pCEFL had no effect. KS-SLK cells (0.8×105/well) were transfected with 0.8 µg DNA using Lipofectamine 2000. 24 hr later cells were fixed and stained with ephrin B2 polyclonal antibody and FITC conjugated secondary antibody as described in the methods. (C) Transient transfection of HUVEC with vGPCR induces transcription from ephrin B2 luciferase constructs. 8×103 HUVEC in 24 well plates were transfected using Superfect with 0.8 µg/well ephrin B2 promoter constructs containing sequences from −2941 to −11 with respect to the translation start site, or two 5′-deletions as indicated, together with 80 ng/well pCEFL or pvGPCR-CEFL. Luciferase was determined 48 h post transfection and induction ratios are shown to the right of the graph. pGL3Basic is promoterless luciferase control vector. Luciferase was normalized to protein since GPCR induced expression of the cotransfected β-galactosidase. Graphed is mean+SEM of 6 replicates. Shown is one of three similar experiments.
Figure 47B:
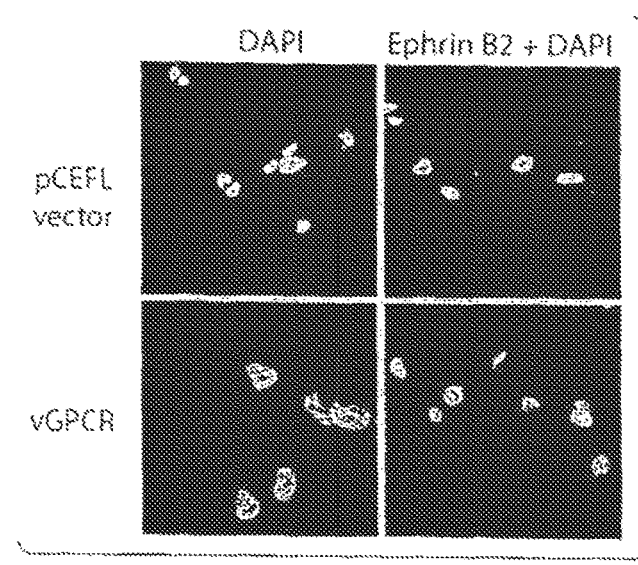
Figure 47C:
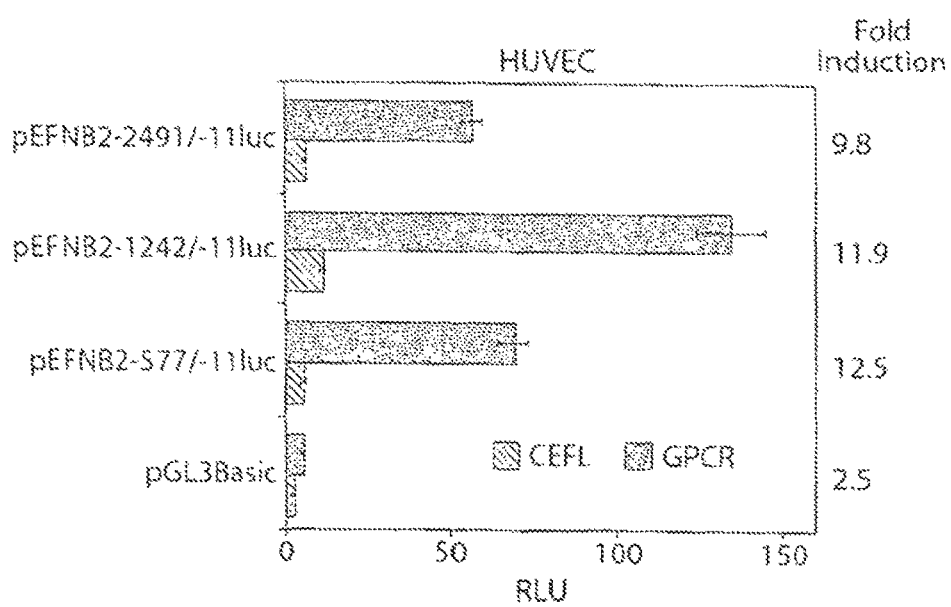

To test whether individual viral proteins could induce the expression of ephrin B2 seen with the whole virus KS-SLK cells were stably transfected with HHV-8 LANA, or LANAΔ440 or vGPCR. Western Blot of stable clones revealed a five-fold induction of ephrin B2 in KS-SLK transfected with vGPCR compared to SLK-LANA or SLK-LANAΔ440 (FIG. 47A). SLK transfected with vector alone (pCEFL) was used as a control. SLK-vGPCR and SLK-pCEFL cells were also examined for ephrin B2 and Eph B4 expression by immunofluorescence in transiently transfected KS-SLK cells. FIG. 47B shows higher expression of ephrin B2 in the SLK-vGPCR cells compared to SLK-pCEFL. No changes in Eph B4 were observed in SLK-vGPCR compared to SLK-pCEFL. This clearly demonstrates that SLK-vGPCR cells expressed high levels of ephrin B2 compared to SLK-pCEFL cells. This suggests that vGPCR of HHV-8 is directly involved in the induction of Ephrin B2 and the arterial phenotype switch in KS. Since we had shown that HHV-8 induced expression of ephrin B2 in HUVEC, we next asked if this could be mediated by a transcriptional effect. Ephrin B2 5'-flanking DNA-luciferase reporter plasmids were constructed as described in the Materials and Methods and transiently transfected into HUVECs. Ephrin B2 5'-flanking DNA sequences -2491/-11 have minimal activity in HUVEC cells (FIG. 47C). This is consistent with ephrin B2 being an arterial, not venous marker. However, we have noted that HUVEC in culture do express some ephrin B2 at the RNA level. Cotransfection of HHV-8 vGPCR induces ephrin B2 transcription approximately 10-fold compared to the control expression vector pCEFL. Roughly equal induction was seen with ephrin B2 sequences -2491/-11, -1242/-11, or -577/-11, which indicates that elements between -577 and -11 are sufficient to mediate the response to vGPCR, although maximal activity is seen with the -1242/-11 luciferase construct.

D. Expression of Ephrin B2 is Regulated by VEGF and VEGF-C

Figure 48A:
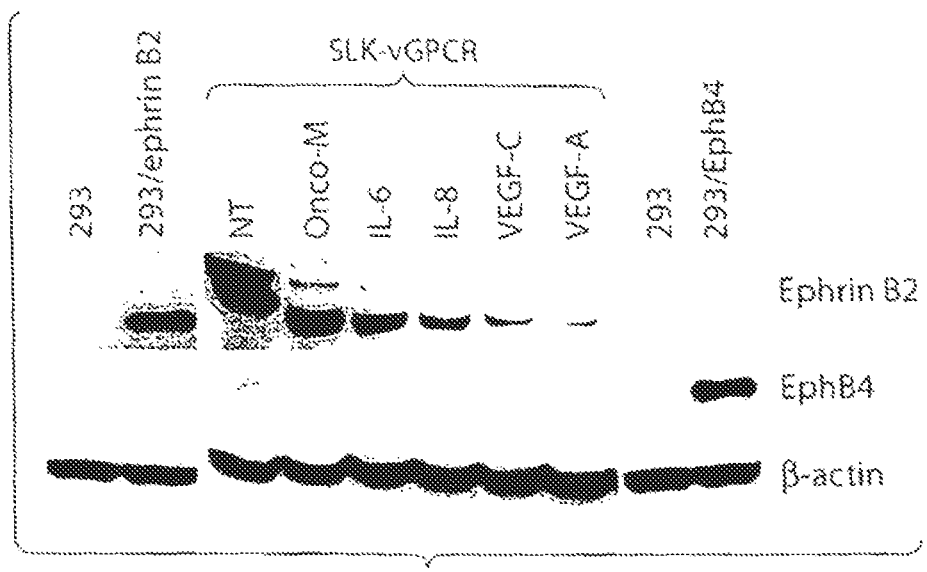
FIG. 48 shows that VEGF and VEGF-C regulate ephrin B2 expression. A) Inhibition of ephrin B2 by neutralizing antibodies. Cells were cultured in full growth medium and exposed to antibody (100 ng/ml) for 36 hr before collection and lysis for Western blot. B) For induction of ephrin B2 expression cells were cultured in EBM growth medium containing 5% serum lacking growth factors. Individual growth factors were added as indicated and the cells harvested after 36 h. Quantity of protein loading and transfer was determined by reprobing the membranes β-actin monoclonal antibody.
Figure 48B:
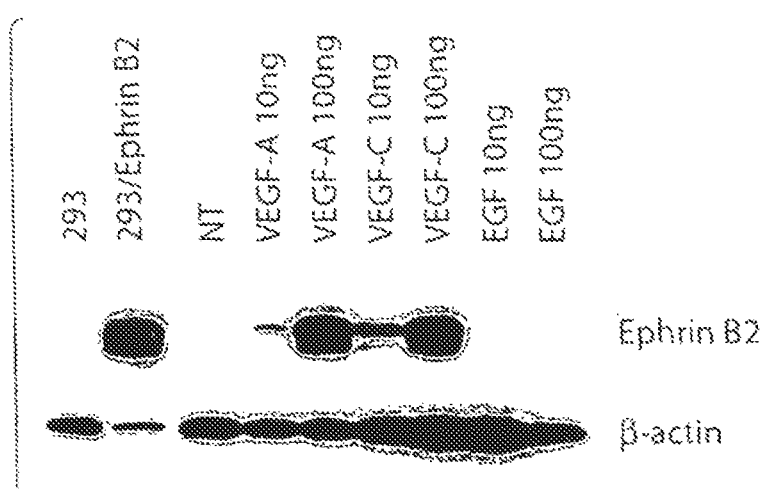

We next asked whether known KS growth factors could be involved in the vGPCR-mediated induction of ephrin B2 expression. SLK-vGPCR cells were treated with neutralizing antibodies to oncostatin-M, IL-6, IL-8, VEGF or VEGF-C for 36 hr. FIG. 48A shows that neutralization of VEGF completely blocked expression of ephrin B2 in SLK-vGPCR cells. A lesser, but significant decrease in ephrin B2 was seen neutralization of VEGF-C and IL-8. No appreciable effect was seen with neutralization of oncostatin-M or IL-6. To verify that VEGF and VEGF-C are integral to the induction of ephrin B2 expression we treated HUVEC with VEGF, VEGF-C or EGF. HUVECs were grown in EBM-2 media containing 5% FBS with two different concentration of individual growth factor (10 ng, 100 ng/ml) for 48 h. Only VEGF-A or VEGF-C induced ephrin B2 expression in a dose dependent manner (FIG. 48B). In contrast, EGF had no effect on expression of ephrin B2.

E. Ephrin B2 siRNA Inhibits the Expression of Ephrin B2 in KS

Figure 49A:
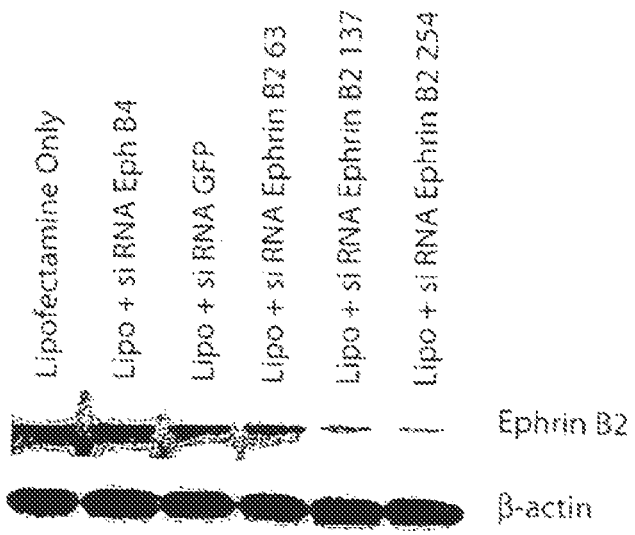
FIG. 49 shows that Ephrin B2 knock-down with specific siRNA inhibits viability in KS cells and HUVEC grown in the presence of VEGF but not IGF, EGF or bFGF. A) KS-SLK cells were transfected with various siRNA to ephrin B2 and controls. After 48 hr the cells were harvested and crude cell lysates fractionated on 4-20% SDS-PAGE. Western blot was performed with monoclonal antibody to ephrin B2 generated in-house. The membrane was stripped and reprobed with β-actin monoclonal antibody (Sigma) to illustrate equivalent loading and transfer. B) 3 day cell viability assay of KS-SLK cultures in the presence of ephrin B2 and EphB4 siRNAs. $1\times10^5$ cells/well in 24-well plates were treated with 0, 10 and 100 ng/ml siRNAs as indicated on the graph. Viability of cultures was determined by MTT assay as described in the methods section. Shown are the mean+standard deviation of duplicate samples. C) HUVE cells were seeded on eight wells chamber slides coated with fibronectin. The HUVE cells were grown overnight in EGM-2 media, which contains all growth supplements. On the following day, the media was replaced with media containing VEGF (10 ng/ml) or EGF, FGF and IGF as indicated. After 2 hrs of incubation at 37° C., the cells were transfected using Lipofectamine 2000 (Invitrogen) in Opti-MEM medium containing 10 nM of siRNA to ephrin B2, Eph B4 or green fluorescence protein (GFP) as control. The cells were incubated for 2 hr and then the fresh media containing growth factors or VEGF alone was added to their respective wells. After 48 hrs, the cells were stained with crystal violet and the pictures were taken immediately by digital camera at 10× magnification.

Three ephrin B2 siRNA were synthesized as described in the methods section. KS-SLK cells were transfected with siRNA and 48 h later ephrin B2 expression was determined by Western Blot. Ephrin B2 siRNAs 137 or 254 inhibited about 70% of ephrin B2 expression compared to control siRNA such as siRNA Eph B4 50 or siRNA GFP. Ephrin B2 63 siRNA was less effective than the above two siRNA Ephrin B2 (FIG. 49A).

Figure 49B:
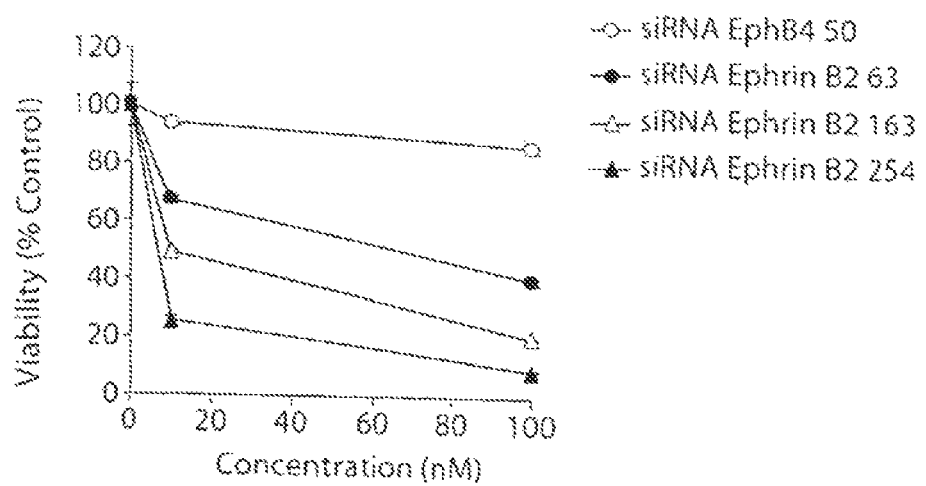
Figure 49C:
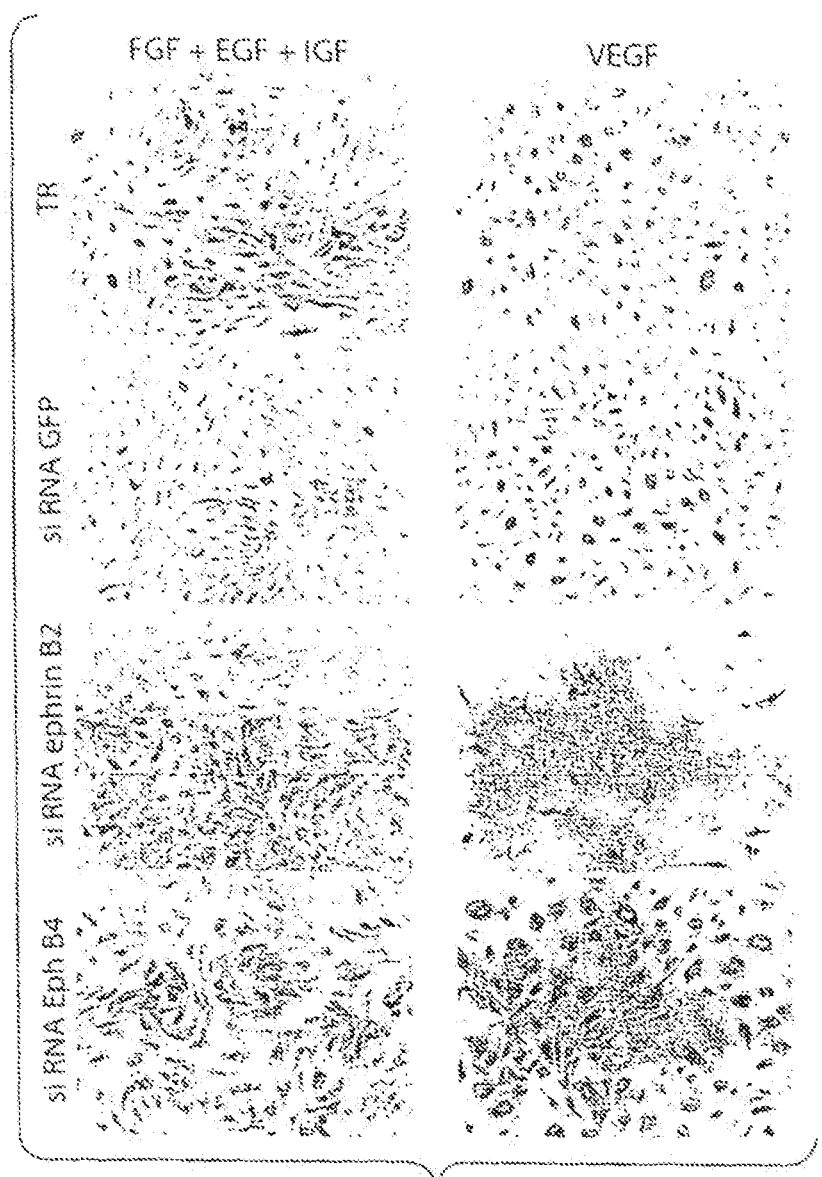
Figure 50:
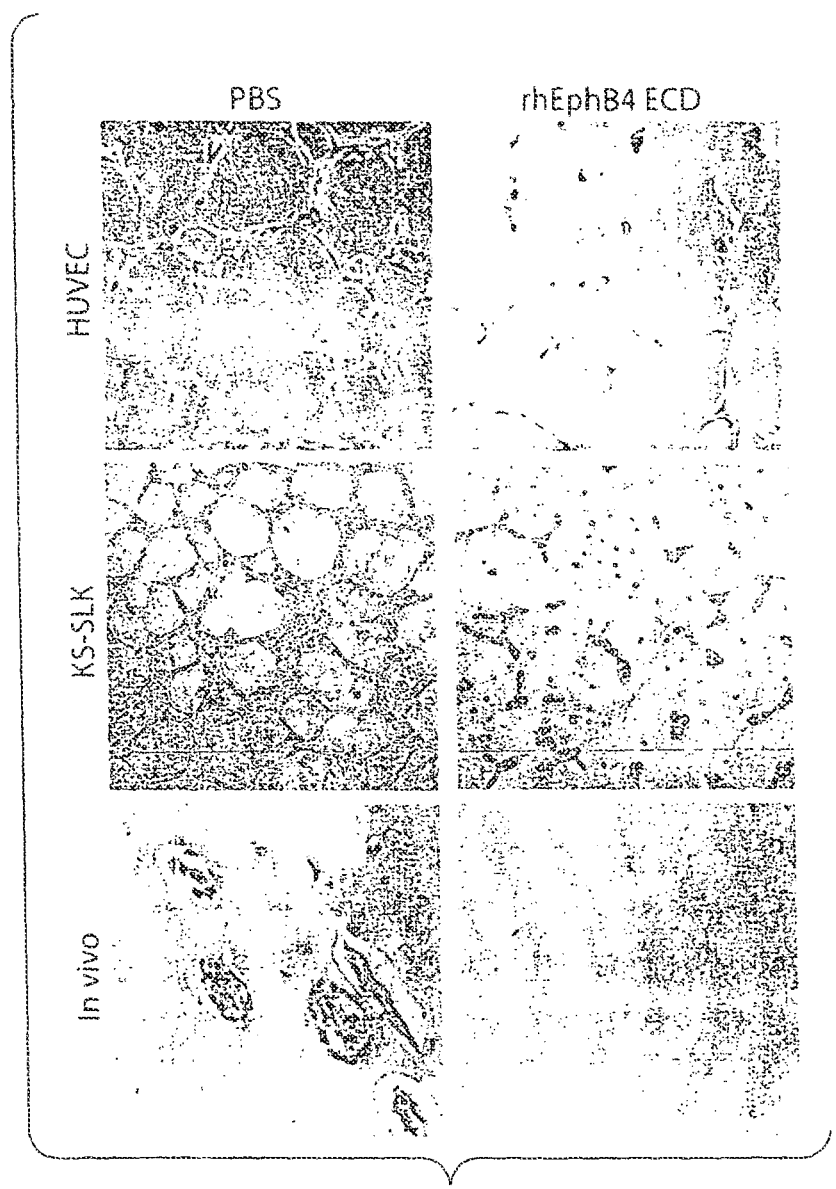
FIG. 50 shows that soluble EphB4 inhibits KS and EC cord formation and in vivo angiogenesis. Cord formation assay of HUVEC in Matrigel™ (upper row). Cells in exponential growth phase were treated overnight with the indicated concentrations of EphB4 extracellular domain (ECD) prior to plating on Matrigel™. Cells were trypsinized and plated ($1\times10^5$ cells/well) in a 24-well plate containing 0.5 ml Matrigel™. Shown are representative 20× phase contrast fields of cord formation after 8 hr plating on Matrigel™ in the continued presence of the test compounds as shown. Original magnification 200×. KS-SLK cells treated in a similar manner (middle row) in a cord formation assay on Matrigel™. Bottom row shows in vivo Matrigel™ assay: Matrigel™ plugs containing growth factors and EphB4 ECD or PBS were implanted subcutaneously in the mid-ventral region of mice. After 7 days the plugs were removed, sectioned and stained with H&E to visualize cells migrating into the matrix. Intact vessels with large lumens are observed in the control, whereas EphB4 ECD almost completely inhibited migration of cells into the Matrigel.

F. Ephrin B2 is Necessary for Full KS and EC Viability, Cord Formation and In Vivo Angiogenesis Activities The most effective ephrin B2 siRNA (254) was then used to determine whether inhibiting expression of ephrin B2 has any effect on the growth of KS-SLK or HUVEC cells. The viability of KS-SLK cells was decreased by the same siRNAs that inhibited ephrin B2 protein levels (FIG. 49B). KS-SLK express high levels of ephrin B2 and this result shows maintenance of ephrin B2 expression is integral to cell viability in this setting. HUVECs do not express ephrin B2, except when stimulated by VEGF as shown in FIG. 48B. Ephrin B2 siRNA 264 dramatically reduced growth of HUVECs cultured with VEGF as the sole growth factor. In contrast, no significant effect was seen when HUVECs were cultured with IGF, EGF and bFGF. As a control, EphB4 siRNA 50 had no detrimental effect on HUVECs in either culture condition (FIG. 49C). In addition to inhibition of viability of KS and primary endothelial cells, EphB4-ECD inhibits cord formation in HUVEC and KS-SLK and in vivo angiogenesis in the Matrigel™ plug assay (FIG. 50).

G. Methods and Materials

A detailed description of the materials and methods for this example may be found in U.S. Patent Publication No. 20050084873.

Example 7

Expression of EphB4 in Bladder Cancer: a Candidate Target for Therapy

FIG. 51 shows expression of EPHB4 in bladder cancer cell lines (A), and regulation of EPHB4 expression by EGFR signaling pathway (B).

Figure 52:
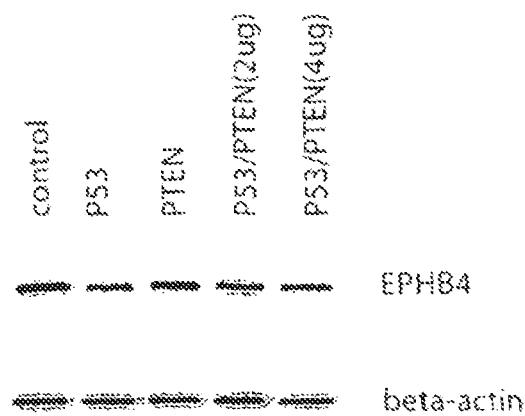
FIG. 52 shows that transfection of p53 inhibit the expression of EPHB4 in 5637 cell.

FIG. 52 shows that transfection of p53 inhibit the expression of EPHB4 in 5637 cell.

Figure 53:
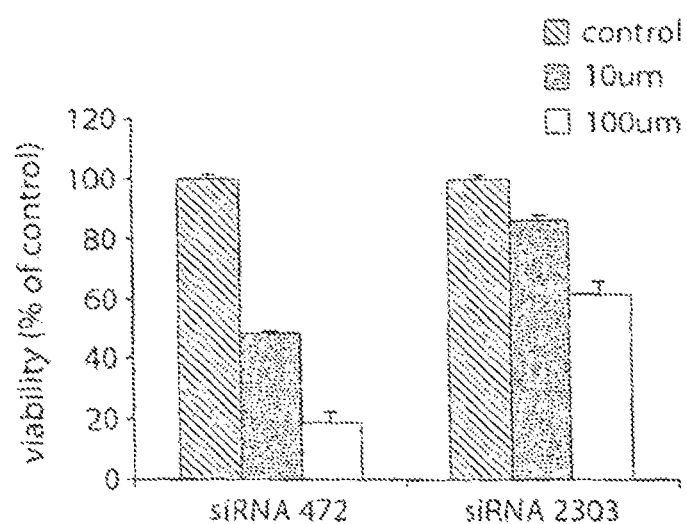
FIG. 53 shows growth inhibition of bladder cancer cell line (5637) upon treatment with EPHB4 siRNA 472.

FIG. 53 shows growth inhibition of bladder cancer cell line (5637) upon treatment with EPHB4 siRNA 472.

Figure 54:
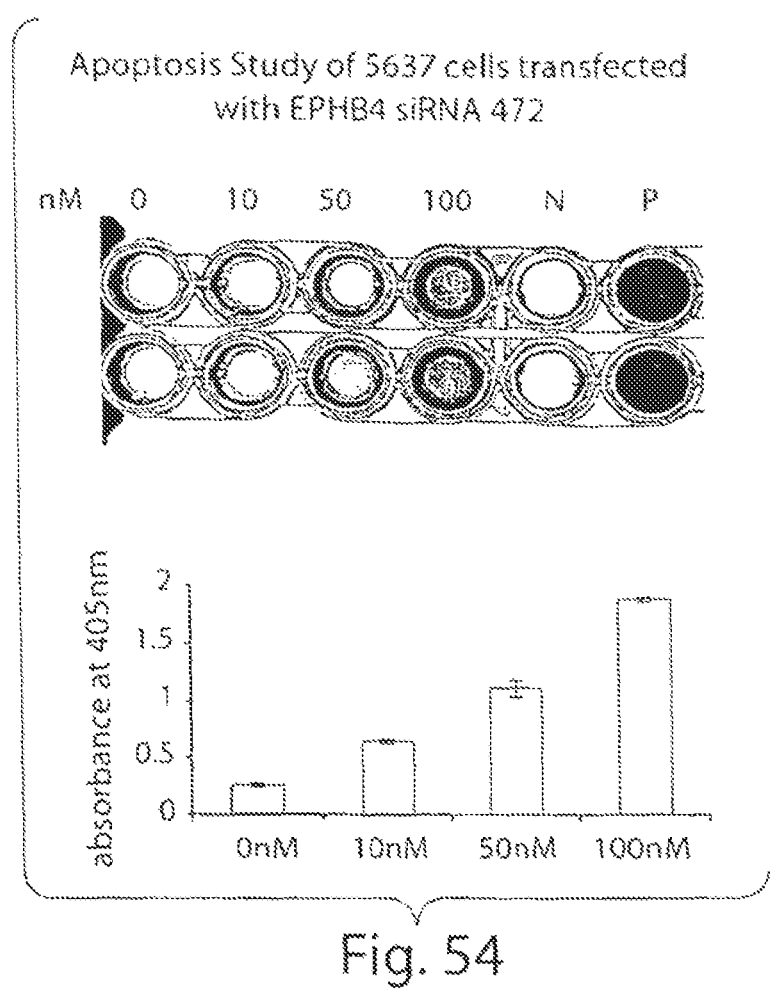
FIG. 54 shows results on apoptosis study of 5637 cells transfected with EPHB4 siRNA 472.

FIG. 54 shows results on apoptosis study of 5637 cells transfected with EPHB4 siRNA 472.

Figure 55:
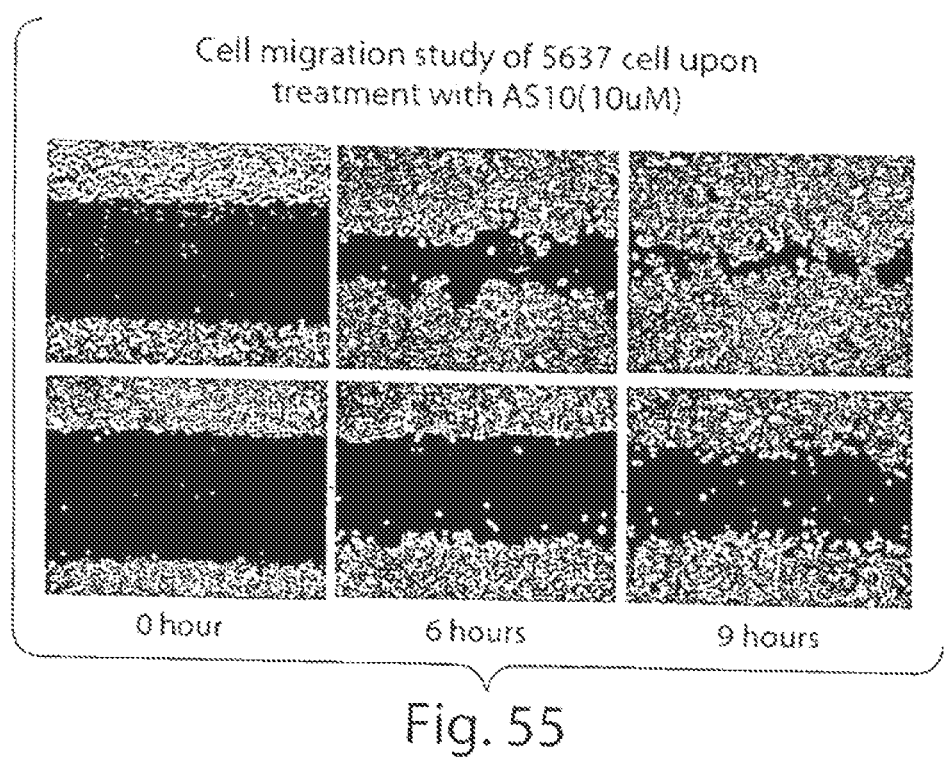
FIG. 55 shows effects of EPHB4 antisense probes on cell migration. 5637 cells were treated with EPHB4AS10 (10 µM) (bottom panels). Upper panels show control cells.

FIG. 55 shows effects of EPHB4 antisense probes on cell migration. 5637 cells were treated with EPHB4AS10 (10 μM).

Figure 56:
FIG. 56 shows effects of EPHB4 siRNA on cell invasion. 5637 cells were transfected with siRNA 472 or control siRNA.

FIG. 56 shows effects of EPHB4 siRNA on cell invasion. 5637 cells were transfected with siRNA 472 or control siRNA.

Example 8

Inhibition of EphB4 Gene Expression by EphB4 Antisense Probes and RNAi Probes

Cell lines expressing EphB4 were treated with the synthetic phosphorothioate modified oligonucleotides and harvested after 24 hr. Cell lysates were prepared and probed by western blot analysis for relative amounts of EphB4 compared to untreated control cells.

Studies on inhibition of cell proliferation were done in HNSCC cell lines characterized to express EphB4. Loss of cell viability was shown upon knock-down of EphB4 expression. Cells were treated in vitro and cultured in 48-well plates, seeded with 10 thousand cells per well. Test compounds were added and the cell viability was tested on day 3. The results on EphB4 antisense probes were summarized below in Table 6. The results on EphB4 RNAi probes were summarized below in Table 7.

A detailed description of the antisense and siRNA constructs for this example may be found in U.S. Patent Publication No. 20050084873.

Example 9

Inhibition of Ephrin B2 Gene Expression by Ephrin B2 Antisense Probes and RNAi Probes KS SLK, a cell line expressing endogenous high level of ephrin B2. Cell viability was tested using fixed dose of each oligonuceotide (5 uM). Gene expression downregulation was done using cell line 293 engineered to stably express full-length ephrin B2. KS SLK expressing EphrinB2 were also used to test the viability in response to RNAi probes tested at the fixed dose of 50 nM. Protein expression levels were measured using 293 cells stably expressing full-length EphrinB2, in cell lysates after 24 hr treatment with fixed 50 nM of RNAi probes.

The results on Ephrin B2 antisense probes were summarized below in Table 8. The results on Ephrin B2 RNAi probes were summarized below in Table 9.

A detailed description of the antisense and siRNA constructs for this example may be found in U.S. Patent Publication No. 20050084873.

Example 10

EphB4 Antibodies Inhibit Tumor Growth

Figure 57:
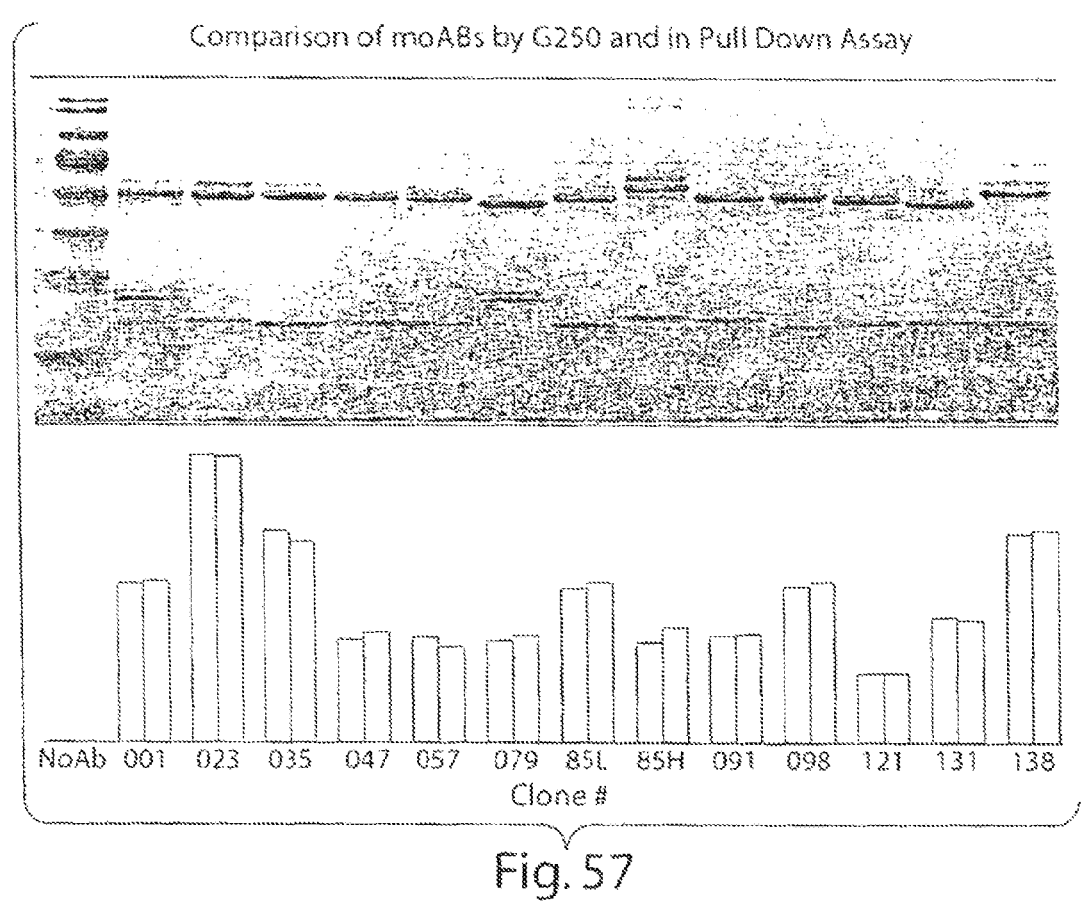
FIG. 57 shows comparison of EphB4 monoclonal antibodies by G250 and in pull-down assay.

FIG. 57 shows results on comparison of EphB4 monoclonal antibodies by G250 and in Pull-down assay.

Figure 58:
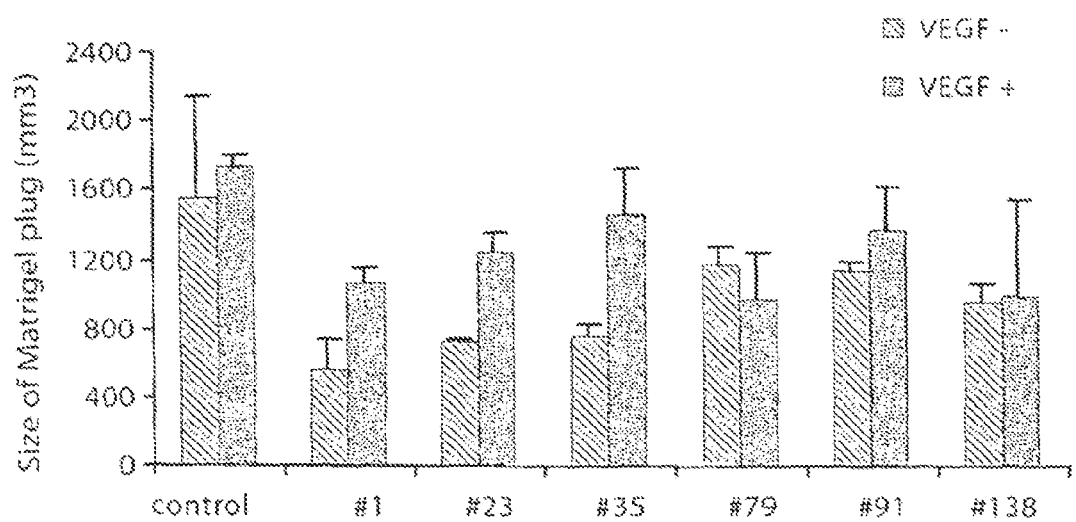
FIG. 58 shows that EphB4 antibodies inhibit the growth of SCC15 xenograft tumors.

FIG. 58 shows that EphB4 antibodies, in the presence of matrigel and growth factors, inhibit the in vivo tumor growth of SCC15 cells.

BalbC nude mice were injected subcutaneously with $2.5 \times 10^6$ viable tumor cells SCC15 is a head and neck squamous cell carcinoma line. Tumors were initiated in nu/nu mice by injecting 2.5–5×10⁶ cells premixed with matrigel and Growth factors, and Ab's subcutaneously to initiate tumor xenografts. Mice were opened 14 days after injections. SCC15 is a head and neck squamous cell carcinoma line, B16 is a melanoma cell line, and MCF-7 is a breast carcinoma line. The responses of tumors to these treatments were compared to control treated mice, which receive PBS injections. Animals were observed daily for tumor growth and subcutaneous tumors were measured using a caliper every 2 days. Antibodies #1 and #23 showed significant regression of SCC15 tumor size compared to control, especially with no additional growth factor added.

Figure 59:
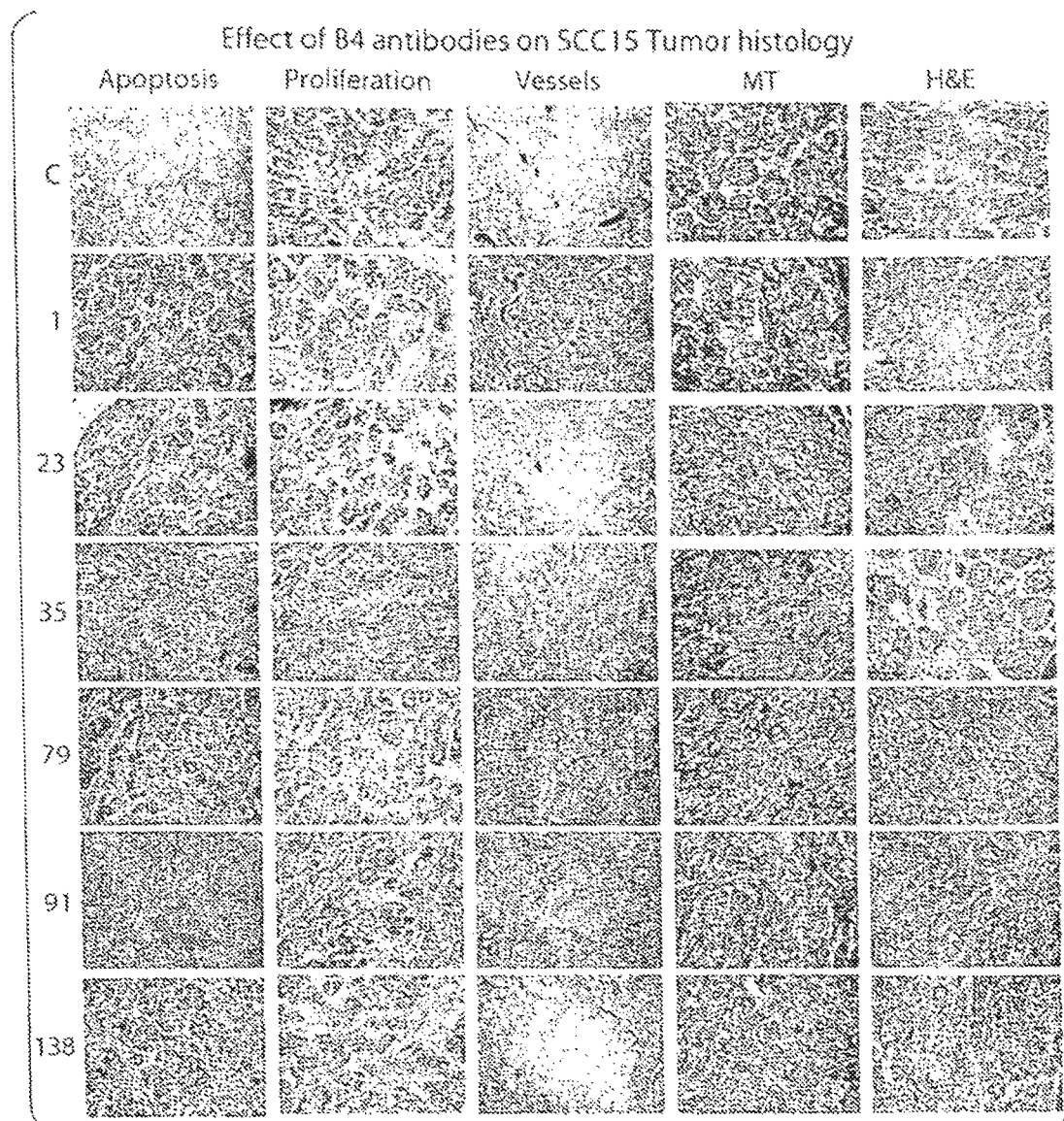
FIG. 59 shows that EphB4 antibodies cause apoptosis, necrosis and decreased angiogenesis in SCC15, head and neck carcinoma tumor type.

FIG. 59 shows that EphB4 antibodies cause apoptosis, necrosis and decreased angiogenesis in SCC15, head and neck carcinoma tumor type.

Angiogenesis was assessed by CD-31 immunohistochemistry. Tumor tissue sections from treated and untreated mice were stained for CD31. Apoptosis was assessed by immunohistochemical TUNNEL, and proliferation by BrdU assay. Following surgical removal, tumors were immediately sliced into 2 mm serial sections and embedded in paraffin using standard procedures. Paraffin embedded tissue were sectioned at 5 μm, the wax removed and the tissue rehydrated. The rehydrated tissues were microwave irradiated in antigen retreival solution. Slides were rinsed in PBS, and TUNNEL reaction mixture (Terminal deoxynucleotidyl transferase and flourescein labeled nucleotide solution), and BrdU were added in a humidity chamber completely shielded from light. The TUNNEL and BrdU reaction mixture were then removed, slides were rinsed and anti-flourescein antibody conjugated with horseradish peroxidase was added. After incubation and rinsing, 3, 3'diaminobenzidine was added. Masson's Trichrome and Hematoxylin and Eosin were also used to stain the slides to visualize morphology. Masson's Trichrome allows to visualize necrosis and fibrosis. The tumor gets blood support from tumor/skin, muscle boundary. As tumor grows, inner regions get depleted of nutrients. This leads to necrosis (cell death), preferably at the tumor center. After cells die, (tumor) tissue gets replaced with fibroblastic tissue. Slides were visualized under 20-fold magnification with digital images acquired. A different morphology was obtained on SCC tumors with each antibody administered. Ab #1 showed an increase in necrosis and fibrosis but not apoptosis. Ab #23 showed an increase in apoptosis, necrosis and fibrosis and a decrease in vessel infiltration. Ab #35 showed an increase in necrosis and fibrosis, and a small increase in apoptosis and a decrease in vessel infiltration. Ab #79 showed a large increase in apoptosis, and necrossis and fibrosis. Ab #91 showed no change in apoptosis but an increase in proliferation. And Ab #138 showed an increase in apoptosis, necrosis, fibrosis and a decrease in proliferation and vessel infiltration. Tumors treated with control PBS displayed abundant tumor density and a robust angiogenic response. Tumors treated with EphB4 antibodies displayed a decrease in tumor cell density and a marked inhibition of tumor angiogenesis in regions with viable tumor cells, as well as tumor necrosis and apoptosis.

FIG. 60 shows that systemic administration of antibodies on xenografts leads to tumor regression in SCC15 tumor xenografts.

Alternate day treatment with EphB4 monoclonal antibody or an equal volume of PBS as control were initiated on day 4, after the tumors have established, and continued for 14 days. Systemic administration was administered either IP or SC with no significant difference. All the experiments were carried out in a double-blind manner to eliminate investigator bias. Mice were sacrificed at the conclusion of the two week treatment period. Tumors were harvested immediately postmortem and fixed and processed for immunohistochemistry. EphB4 antibodies 40 mg per kg body weight were administered. Treatment with EphB4 antibody significantly inhibited human SCC tumor growth compared with control-treated mice (p<0.05). Treatment with EphB4 antibody significantly inhibited tumor weight compared with control-treated mice (p<0.05).

Example 11

HSA-EphB4 Ectodomain Fusion and PEG-Modified EphB4 Ectodomain

A. Generation of HSA-EphB4 Ectodomain Fusion

Human serum albumin fragment in XbaI-NotI form was PCR-amplified out for creating a fusion with GCF2, and TA-cloned into pEF6. In the next step, the resulting vector was cut with Xba I (partial digestion) and the HSA fragment (1.8 kb) was cloned into Xba I site of pEF6-GCF2-Xba to create fusion expression vector. The resulting vector had a point mutation C to T leading to Thr to Ile substitution in position 4 of the mature protein. It was called pEF6-GCF2-HSAmut. In the next cloning step, the mutation was removed by substituting wild type KpnI fragment from pEF6-GCF2-IF (containing piece of the vector and N-terminal part of GCF2) for the mutated one, this final vector was called pEF6-GCF2. The DNA sequence of pEF6-GCF2 was confirmed.

The predicted amino acid of the HSA-EphB4 precursor protein was as follows (SEQ ID NO:18):

MELRVLLCWASLAAALEETLLNTKLETADLKWVTFPQVDGQWEELSGL

DEEQHSVRTYEVCDVQRAPGQAHWLRTGWVPRRGAVHVYATLRFTMLE

CLSLPRAGRSCKETFTVFYYESDADTATALTPAWMENPYIKVDTVAAE

HLTRKRPGAEATGKVNVKTLRLGPLSKAGFYLAFQDQGACMALLSLHL

FYKKCAQLTVNLTRFPETVPRELVVPVAGSCVVDAVPAPGPSPSLYCR

EDGQWAEQPVTGCSCAPGFEAAEGNTKCRACAQGTFKPLSGEGSCQPC

PANSHSNTIGSAVCQCRVGYFRARTDPRGAPCTTPPSAPRSVVSRLNG

SSLHLEWSAPLESGGREDLTYALRCRECRPGGSCAPCGGDLTFDPGPR

DLVEPWVVVRGLRPDFTYTFEVTALNGVSSLATGPVPFEPVNVTTDRE

VPPAVSDIRVTRSSPSSLSLAWAVPRAPSGAVLDYEVKYHEKGAEGPS

SVRFLKTSENRAELRGLKRGASYLVQVRARSEAGYGPFGQEHHSQTQL

DESEGWREQSRDAHKSEVAHRFKDLGEENFKALVLIAFAQYLQQCPFE

DHVKLVNEVTEFAKTCVADESAENCDKSLHTLFGDKLCTVATLRETYG

EMADCCAKQEPERNECFLQHKDDNPNLPRLVRPEVDVMCTAFHDNEET

FLKKYLYEIARRHPYFYAPELLFFAKRYKAAFTECCQAADKAACLLPK

LDELRDEGKASSAKQRLKCASLQKFGERAFKAWAVARLSQRFPKAEFA

EVSKLVTDLTKVHTECCHGDLLECADDRADLAKYICENQDSISSKLKE

CCEKPLLEKSHCIAEVENDEMPADLPSLAADFVESKDVCKNYAEAKDV

FLGMFLYEYARRHPDYSVVLLLRLAKTYETTLEKCCAAADPHECYAKV

FDEFKPLVEEPQNLIKQNCELFKQLGEYKFQNALLVRYTKKVPQVSTP

TLVEVSRNLGKVGSKCCKHPEAKRMPCAEDYLSVVLNQLCVLHEKTPV

SDRVTKCCTESLVNRRPCFSALEVDETYVPKEFNAETFTFHADICTLS

EKERQIKKQTALVELVKHKPKATKEQLKAVMDDFAAFVEKCCKADDKE

TCFAEEGKKLVAASQAALGL

The predicted amino acid sequence of the mature form of the HSA-EphB4 protein was as follows (SEQ ID NO:19):

LEETLLNTKLETADLKWVTFPQVDGQWEELSGLDEEQHSVRTYEVCDV

QRAPGQAHWLRTGWVPRRGAVHVYATLRFTMLECLSLPRAGRSCKETF

TVFYYESDADTATALTPAWMENPYIKVDTVAAEHLTRKRPGAEATGKV

NVKTLRLGPLSKAGFYLAFQDQGACMALLSLHLFYKKCAQLTVNLTRF

PETVPRELVVPVAGSCVVDAVPAPGPSPSLYCREDGQWAEQPVTGCSC

APGFEAAEGNTKCRACAQGTFKPLSGEGSCQPCPANSHSNTIGSAVCQ

CRVGYFRARTDPRGAPCTTPPSAPRSVVSRLNGSSLHLEWSAPLESGG

REDLTYALRCRECRPGGSCAPCGGDLTFDPGPRDLVEPWVVVRGLRPD

FTYTFEVTALNGVSSLATGPVPFEPVNVTTDREVPPAVSDIRVTRSSP

SSLSLAWAVPRAPSGAVLDYEVKYHEKGAEGPSSVRFLKTSENRAELR

GLKRGASYLVQVRARSEAGYGPFGQEHHSQTQLDESEGWREQSRDAHK

SEVAHRFKDLGEENFKALVLIAFAQYLQQCPFEDHVKLVNEVTEFAKT

CVADESAENCDKSLHTLFGDKLCTVATLRETYGEMADCCAKQEPERNE

CFLQHKDDNPNLPRLVRPEVDVMCTAFHDNEETFLKKYLYEIARRHPY

FYAPELLFFAKRYKAAFTECCQAADKAACLLPKLDELRDEGKASSAKQ

RLKCASLQKFGERAFKAWAVARLSQRFPKAEFAEVSKLVTDLTKVHTE

CCHGDLLECADDRADLAKYICENQDSISSKLKECCEKPLLEKSHCIAE

VENDEMPADLPSLAADFVESKDVCKNYAEAKDVFLGMFLYEYARRHPD

YSVVLLLRLAKTYETTLEKCCAAADPHECYAKVFDEFKPLVEEPQNLI

KQNCELFKQLGEYKFQNALLVRYTKKVPQVSTPTLVEVSRNLGKVGSK

CCKHPEAKRMPCAEDYLSVVLNQLCVLHEKTPVSDRVTKCCTESLVNR

RPCFSALEVDETYVPKEFNAETFTFHADICTLSEKERQIKKQTALVEL

VKHKPKATKEQLKAVMDDFAAFVEKCCKADDKETCFAEEGKKLVAASQ

AALGL

The nucleic acid sequence of the pEF6-GCF2 plasmid was as follows (SEQ ID NO:20):

```
aatattattgaagcatttatcagggttattgtctcatgagcggatacatatttgaatgtatttagaaaaataaacaaatagggggttccgcgca
catttccccgaaaagtgccacctgacgtcgacggatcgggagatctcccgatcccctatggtcgactctcagtacaatctgctctgatgc
cgcatagttaagccagtatctgctccctgcttgtgtgttggaggtcgctgagtagtgcgcgagcaaaatttaagctacaacaaggcaag
gcttgaccgacaattgcatgaagaatctgcttagggttaggcgttttgcgctgcttcgcgatgtacgggccagatatacgcgttgacattg
attattgactaggcttttgcaaaaagctttgcaaagatggataaagttttaaacagagaggaatctttgcagctaatggaccttctaggtctt
gaaaggagtgcctcgtgaggctccggtgcccgtcagtgggcagagcgcacatcgcccacagtccccgagaagttgggggggaggg
gtcggcaattgaaccggtgcctagagaaggtggcgcggggtaaactgggaaagtgatgtcgtgtactggctccgccttttccccgagg
gtgggggagaaccgtatataagtgcagtagtcgccgtgaacgttcttttttcgcaacgggtttgccgccagaacacaggtaagtgccgt
gtgtggttcccgcgggcctggcctctttacgggttatggcccttgcgtgccttgaattacttccacctggctgcagtacgtgattcttgatc
ccgagcttcgggttggaagtgggtgggagagttcgaggccttgcgcttaaggagcccttcgcctcgtgcttgagUgaggcctggcc
tgggcgctggggccgccgcgtgcgaatctggtggcaccttcgcgcctgtctcgctgctttcgataagtctctagccatttaaaattttga
tgacctgctgcgacgctttttttctggcaagatagtcttgtaaatgcgggccaagatctgcacactggtatttcggttttttggggccgcggg
cggcgacggggcccgtgcgtcccagcgcacatgttcggcgaggcggggcctgcgagcgcggccaccgagaatcggacgggggt
agtctcaagctggccggcctgctctggtgcctggcctcgcgccgccgtgtatcgccccgccctgggcggcaaggctggcccggtcg
gcaccagttgcgtgagcggaaagatggccgcttcccggccctgctgcaggagctcaaaatggaggacgcggcgctcgggagag
cgggcgggtgagtcacccacacaaaggaaaagggcctttccgtcctcagccgtcgcttcatgtgactccacggagtaccgggcgcc
gtccaggcacctcgattagttctcgagcttttggagtacgtcgtctttaggttggggggagggggttttatgcgatggagtttccccacact
gagtgggtggagactgaagttaggccagcttggcacttgatgtaattctccttggaatttgcccttttttgagtttgatcttggttcattctca
agcctcagacagtggttcaaagttttttcttccatttcaggtgtcgtgaggaattagcttggtactaatacgactcactatagggagaccc
aagctggctaggtaagcttggtaccgagctcggatccactagtccagtgtggtggaattgcccttCAAGCTTGCCGCCAC
CATGGAGCTCCGGGTGCTGCTCTGCTGGGCTTCGTTGGCCGCAGCTTTGGAAGAG
ACCCTGCTGAACACAAAATTGGAAACTGCTGATCTGAAGTGGGTGACATTCCCTC
AGGTGGACGGGCAGTGGGAGGAACTGAGCGGCCTGGATGAGGAACAGCACAGC
```

```
GTGCGCACCTACGAAGTGTGTGACGTGCAGCGTGCCCCGGGCCAGGCCCACTGG

CTTCGCACAGGTTGGGTCCCACGGCGGGGCGCCGTCCACGTGTACGCCACGCTGC

GCTTCACCATGCTCGAGTGCCTGTCCCTGCCTCGGGCTGGGCGCTCCTGCAAGGA

GACCTTCACCGTCTTCTACTATGAGAGCGATGCGGACACGGCCACGGCCCTCACG

CCAGCCTGGATGGAGAACCCCTACATCAAGGTGGACACGGTGGCCGCGGAGCAT

CTCACCCGGAAGCGCCCTGGGGCCGAGGCCACCGGGAAGGTGAATGTCAAGACG

CTGCGCCTGGGACCGCTCAGCAAGGCTGGCTTCTACCTGGCCTTCCAGGACCAGG

GTGCCTGCATGGCCCTGCTATCCCTGCACCTCTTCTACAAAAAGTGCGCCCAGCT

GACTGTGAACCTGACTCGATTCCCGGAGACTGTGCCTCGGGAGCTGGTGTGCCC

GTGGCCGGTAGCTGCGTGGTGGATGCCGTCCCCGCCCCTGGCCCCAGCCCCAGCC

TCTACTGCCGTGAGGATGGCCAGTGGGCCGAACAGCCGGTCACGGGCTGCAGCT

GTGCTCCGGGCnTCGAGGCAGCTGAGGGGAACACCAAGTGCCGAGCCTGTGCCC

AGGGCACCTTCAAGCCCCTGTCAGGAGAAGGGTCCTGCCAGCCATGCCCAGCCA

ATAGCCACTCTAACACCATTGGATCAGCCGTCTGCCAGTGCCGCGTCGGGTACTT

CCGGGCACGCACAGACCCCCGGGGTGCACCCTGCACCACCCCTCCTTCGGCTCCG

CGGAGCGTGGTTTCCCGCCTGAACGGCTCCTCCCTGCACCTGGAATGGAGTGCCC

CCCTGGAGTCTGGTGGCCGAGAGGACCTCACCTACGCCCTCCGCTGCCGGGAGTG

TCGACCCGGAGGCTCCTGTGCGCCCTGCGGGGAGACCTGACTTTTGACCCCGGC

CCCCGGGACCTGGTGGAGCCCTGGGTGGTGGTTCGAGGGCTACGTCCTGACTTCA

CCTATACCTTTGAGGTCACTGCATTGAACGGGGTATCCTCCTTAGCCACGGGGCC

CGTCCCATTTGAGCCTGTCAATGTCACCACTGACCGAGAGGTACCTCCTGCAGTG

TCTGACATCCGGGTGACGCGGTCCTCACCCAGCAGCTTGAGCCTGGCCTGGGCTG

TTCCCCGGGCACCCAGTGGGGCTGTGCTGGACTACGAGGTCAAATACCATGAGA

AGGGCGCCGAGGGTCCCAGCAGCGTGCGGTTCCTGAAGACGTCAGAAAACCGGG

CAGAGCTGCGGGGGCTGAAGCGGGGAGCCAGCTACCTGGTGCAGGTACGGGCGC

GCTCTGAGGCCGGCTACGGGCCCTTCGGCCAGGAACATCACAGCCAGACCCAAC

TGGATGAGAGCGAGGGCTGGCGGGAGCAGtctagaGATGCACACAAGAGTGAGGTT

GCTCATCGGTTTAAAGATTTGGGAGAAGAAAATTTCAAAGCCTTGGTGTTGATTG

CCTTTGCTCAGTATCTTCAGCAGTGTCCATTTGAAGATCATGTAAAATTAGTGAA

TGAAGTAACTGAATTTGCAAAAACATGTGTAGCTGATGAGTCAGCTGAAAATTGT

GACAAATCACTTCATACCCTTTTTGGAGACAAATTATGCACAGTTGCAACTCTTC

GTGAAACCTATGGTGAAATGGCTGACTGCTGTGCAAAACAAGAACCTGAGAGAA

ATGAATGCTTCTTGCAACACAAAGATGACAACCCAAACCTCCCCCGATTGGTGAG

ACCAGAGGTTGATGTGATGTGCACTGCTTTTCATGACAATGAAGAGACATTTTTG

AAAAAATACITATATGAAATTGCCAGAAGACATCCTTACTTTTATGCCCCGGAAC

TCCTTTTCTTTGCTAAAAGGTATAAAGCTGCTTTTACAGAATGTTGCCAAGCTGCT

GATAAAGCTGCCTGCCTGTTGCCAAAGCTCGATGAACTTCGGGATGAAGGGAAG

GCTTCGTCTGCCAAACAGAGACTCAAATGTGCCATCTCCAAAAATTTGGAGAA

AGAGCTTTCAAAGCATGGGCAGTGGCTCGCCTGAGCCAGAGATTTCCCAAAGCT

GAGTTTGCAGAAGTTTCCAAGTTAGTGACAGATCTTACCAAAGTCCACACGGAAT
```

```
GCTGCCATGGAGATCTGCTTGAATGTGCTGATGACAGGGCGGACCTTGCCAAGTA

TATCTGTGAAAATCAGGATTCGATCTCCAGTAAACTGAAGGAATGCTGTGAAAA

ACCTCTGTTGGAAAAATCCCACTGCATTGCCGAAGTGGAAAATGATGAGATGCCT

GCTGACTTGCCTTCATTAGCTGCTGATTTTGTTGAAAGTAAGGATGTTTGCAAAA

ACTATGCTGAGGCAAAGGATGTCTTCCTGGGCATGTTTTTGTATGAATATGCAAG

AAGGCATCCTGATTACTCTGTCGTGCTGCTGCTGAGACtTGCCAAGACATATGAA

ACCACTCTAGAGAAGTGCTGTGCCGCTGCAGATCCTCATGAATGCTATGCCAAAG

TGTTCGATGAATTTAAACCTCTTGTGGAAGAGCCTCAGAATITAATCAAACAAAA

CTGTGAGCTTTTTAAGCAGCTTGGAGAGTACAAATTCCAGAATGCGCTATTAGTT

CGTTACACCAAGAAAGTACCCCAAGTGTCAACTCCAACTCTTGTAGAGGTCTCAA

GAAACCTAGGAAAAGTGGGCAGCAAATGTTGTAAACATCCTGAAGCAAAAAGA

ATGCCCTGTGCAGAAGACTATCTATCCGTGGTCCTGAACCAGTTATGTGTGTTGC

ATGAGAAAACGCCAGTAAGTGACAGAGTCACAAAATGCTGCACAGAGTCCTTGG

TGAACAGGCGACCATGCTTTTCAGCTCTGGAAGTCGATGAAACATACGTTCCCAA

AGAGTTTAATGCTGAAACATTCACCTTCCATGCAGATATATGCACACTTTCTGAG

AAGGAGAGACAAATCAAGAAACAAACTGCACTTGTTGAGCTTGTGAAACACAAG

CCCAAGGCAACAAAAGAGCAACTrGAAAGCTGTTATGGATGATTTCCGAGCTTTT

GTAGAGAAGTGCTGCAAGGCTGACGATAAGGAGACCTGCTTTGCCGAGGAGGGT

AAAAAACTTGTTGCTGCAAGTCAAGCTGCCTTAGGCTTATAAtagcggccgcttaagggcaat tctgcagatatccagcacagtggcggccgctcgagtctagagggcccgcggttcgaaggtaagcctatccctaaccctctcctcggtc tcgattctacgcgtaccggtcatcatcaccatcaccattgagtttaaacccgctgatcagcctcgactgtgccttctagttgccagccatct gttgtttgcccctcccccgtgccttccttgaccctggaaggtgccactcccactgtcctttcctaataaaatgaggaaattgcatcgcattg tctgagtaggtgtcattctattctggggggtggggtggggcaggacagcaagggggaggattgggaagacaatagcaggcatgctg gggatgcggtgggctctatggcttctgaggcggaaagaaccagctggggctctagggggtatccccacgcgccctgtagcggcgca ttaagcgcggcgggtgtggtggttacgcgcagcgtgaccgctacacttgccagcgccctagcgcccgctcctttcgctttcttcccttcc tttctcgccacgttcgccggctttccccgtcaagctctaaatcggggcatccctttagggttccgatttagtgctttacggcacctcgaccc caaaaaacttgattagggtgatggttcacgtagtgggccatcgccctgatagacggtttttcgccctttgacgttggagtccacgttcttta atagtggactcttgttccaaactggaacaacactcaaccctatctcggtctattcttttgatttataagggattttggggatttcggcctattg gttaaaaaatgagctgatttaacaaaaatttaacgcgaattaattctgtggaatgtgtgtcagttagggtgtggaaagtccccaggctccc caggcaggcagaagtatgcaaagcatgcatctcaattagtcagcaaccaggtgtggaaagtccccaggctccccagcaggcagaag tatgcaaagcatgcatctcaattagtcagcaaccatagtcccgcccctaactccgcccatcccgcccctaactccgcccagttccgccc attctccgccccatggctgactaatttttttatttatgcagaggccgaggccgcctctgcctctgagctattccagaagtagtgaggagg ctttttggaggcctaggcttttgcaaaaagctcccgggagcttgtatatccattttcggatctgatcagcacgtgttgacaattaatcatcg gcatagtatatcggcatagtataatacgacaaggtgaggaactaaaccatggccaagcctttgtctcaagaagaatccaccctcattga aagagcaacggctacaatcaacagcatccccatctctgaagactacagcgtcgccagcgcagctctctctagcgacggccgcatcttc actggtgtcaatgtatatcattttactgggggaccttgtgcagaactcgtggtgcttgggcactgctgctgctgcggcagctggcaacctg acttgtatcgtcgcgatcggaaatgagaacaggggcatcttgagcccctgcggacggtgtcgacaggtgcttctcgatctgcatcctgg gatcaaagcgatagtgaaggacagtgatgacagccgacggcagttgggattcgtgaattgctgccctctggttatgtgtgggagggc taagcacttcgtggccgaggagcaggactgacacgtgctacgagatttcgattccaccgccgccttctatgaaaggttgggcttcgga atcgttttccgggacgccggctggatgatcctccagcgcggggatctcatgctggagttcttcgcccaccccaacttgtttattgcagctt ataatggttacaaataaagcaatagcatcacaaatttcacaaataaagcatttttttcactgcattctagttgtggtttgtccaaactcatcaat
```

-continued

```
gtatcttatcatgtctgtataccgtcgacctctagctagagcttggcgtaatcatggtcatagctgtttcctgtgtgaaattgttatccgctca caattccacacaacatacgagccggaagcataaagtgtaaagcctggggtgcctaatgagtgagctaactcacattaattgcgttgcgc tcactgcccgctttccagtcgggaaacctgtcgttgccagctgcattaatgaatcggccaacgcgcggggagaggcggtttgcgtattg ggcgctcttccgcttcctcgctcactgactcgctgcgctcggtcgttcggctgcggcgagcggtatcagctcactcaaaggcggtaata cggttatccacagaatcaggggataacgcaggaaagaacatgtgagcaaaaggccagcaaaaggccaggaaccgtaaaaaggcc gcgttctggcgtttttccataggctccgcccccctgacgagcatcacaaaaatcgacgctcaagtcagaggtggcgaaacccgaca ggactataaagataccaggcgtttccccctggaagctccxtcgtgcgctctcctgttccgaccctgccgcttaccggatacctgtccgcc tttctcccttcgggaagcgtggcgctttctcaatgctcacgctgtaggtatctcagttcggtgtaggtcgttcgctccaagctgggctgtgt gcacgaaccccccgttcagcccgaccgctgcgccttatccggtaactatcgtcttgagtccaacccggtaagacacgacttatcgcca ctggcagcagccactggtaacaggattagcagagcgaggtatgtaggcggtgctacagagttcttgaagtggtggcctaactacggct acactagaaggacagtatttggtatctgcgctctgctgaagccagttaccttcggaaaaagagttggtagctcttgatccggcaaacaaa ccaccgctggtagcggtggtttttttgtttgcaagcagcagattacgcgcagaaaaaaaggatctcaagaagatcctttgatcttttctacg gggtctgacgctcagtggaacgaaaactcacgttaagggattttggtcatgagattatcaaaaaggatcttcacctagatccttttaaatta aaaatgaagttttaaatcaatctaaagtatatatgagtaaacttggtctgacagttaccaatgcttaatcagtgaggcacctatctcagcgat ctgtctatttcgttcatccatagttgcctgactccccgtcgtgtagataactacgatacgggagggcttaccatctggccccagtgctgca atgataccgcgagacccacgctcaccggctccagatttatcagcaataaaccagccagccggaagggccgagcgcagaagtggtc ctgcaactttatccgcctccatccagtctattaattgttgccgggaagctagagtaagtagttcgccagttaatagtttgcgcaacgttgttg ccattgctacaggcatcgtggtgtcacgctcgtcgtttggtatggcttcattcagctccggttcccaacgatcaaggcgagttacatgatc ccccatgttgtgcaaaaaagcggttagctccttcggtcctccgatcgttgtcagaagtaagttggccgcagtgttatcactcatggttatg gcagcactgcataanctcttactgtcatgccatccgtaagatgcttttctgtgactggtgagtactcaaccaagtcattctgagaatagtgt atgcggcgaccgagttcgtcttgcccggcgtcaatacgggataataccgcgccacatagcagaactttaaaagtgctcatcattggaaa acgttcttcggggcgaaaactctcaaggatcttaccgctgttgagatccagttgatgtaacccactcgtgcacccaactgatcttcagc atcttttactttcaccagcgtttctgggtgagcaaaaacaggaaggcaaaatgccgcaaaaaagggaataagggcgacacggaaatgt tgaatactcatactcttccttttc
```

B. Cell Culture and Transfections:

The human embryonic kidney cell line, 293T cells, was maintained in DMEM with 10% dialyzed fetal calf serum and 1% penicillin/streptomycin/neomycin antibiotics. Cells were maintained at 37° C. in a humidified atmosphere of 5% $CO_2$/95% air.

Transfections of plasmids encoding EphB4 ectodomain, fragments thereof, and EphB4-HSA fusions were performed using Lipofectamine 2000 reagent (Invitrogen) according to suggested protocol. One day before transfections, 293T cells were seeded at a high density to reach 80% confluence at the time of transfection. Plasmid DNA and Lipofectamine reagent at 1:3 ratio were diluted in Opti-MEM I reduced serum medium (Invitrogen) for 5 min and mixed together to form DNA-Lipofectamine complex. For each 10 cm culture dish, 10 μg of plasmid DNA was used. After 20 min, the above complex was added directly to cells in culture medium. After 16 hours of transfection, medium was aspirated, washed once with serum free DMEM and replaced with serum free DMEM. Secreted proteins were harvested after 48 hours by collecting conditional medium. Conditional medium was clarified by centrifugation at 10,000 g for 20 min and filtered through 0.2μ filter and used for purification.

C. Chromatographic Separation of EphB4 Ectodomain and EphB4 Ectodomain-HSA Fusion Protein The EphB4 ectodomain fused to HSA was purified as follows: 700 ml of media was harvested from transiently transfected 293 cells grown in serum free media and concentrated up to final volume of 120 ml. Membrane: (Omega, 76 mm), 50 kDa C/O. After concentration, pH of the sample was adjusted by adding 6 ml of 1M NaAc, pH 5.5. Then sample was dialyzed against starting buffer (SB): 20 mM NaAc, 20 mM NaCl, pH 5.5 for O/N. 5 ml of SP-Sepharose was equilibrated with SB and sample was loaded. Washing: 100 ml of SB. Elution by NaCl: 12 ml/fraction and increment of 20 mM. Most of the EphrinB2 binding activity eluted in the 100 mM and 120 mM fractions.

Fractions, active in EphrinB2 binding assay (See SP chromatography, fractions #100-120 mM) were used in second step of purification on Q-column. Pulled fractions were dialyzed against starting buffer#2 (SB2): 20 mM Tris-HCl, 20 mM NaCl, pH 8 for O/N and loaded onto 2 ml of Q-Sepharose. After washing with 20 ml of SB2, absorbed protein was eluted by NaCl: 3 ml/fraction with a concentration increment of 25 mM. Obtained fractions were analyzed by PAGE and in Ephrin-B2 binding assay. The 200 mM and 225 mM fractions were found to contain the most protein and the most B2 binding activity.

Soluble EphB4 ectodomain protein was purified as follows: 300 ml of conditional medium (see: Cell culture and transfections) were concentrated up to final volume of 100 ml, using ultrafiltration membrane with 30 kDa C/O. After concentration, pH of the sample was adjusted by adding 5 ml of 1 M Na-Acetate, pH 5.5. Then sample was dialyzed against starting buffer (StB): 20 mM Na-Acetate, 20 mM NaCl, pH 5.5 for O/N. 5 ml of SP-Sepharose was equilibrated with StB and sample was loaded. After washing the column with 20 ml of StB, absorbed proteins were eluted by linear gradient of concentration of NaCl (20-250 mM and total elution volume of 20 column's volumes). Purity of the proteins was analyzed by PAGE.

D. Biotinylation of sB4 and sB4-HSA Fusion Protein.

Both soluble EphB4 ectodomain protein (sB4) and EphB4 ectodomain fused to HSA (HSA-sB4) were biotin labeled through carbohydrate chains using sodium meta-periodate as an oxidant and EZ-Link Biotin Hydrazide (PIERCE, Cat. #21339) according to manufacture's protocol. The in vitro stability of the biotinylated sB4 protein was tested by incubating $2.0 \times 10^{-9}$ with 40 μL of mouse serum at 37° C. for 0, 0.5, 1, 2 and 3 days. Two μL of magnetic beads and B2-AP was added for an extra hour at room temperature. After washing twice with buffer, pnPP was added for 1 hour. Biotinylated sB4 protein was found to very stable over three days, with less than 10% of the B2 binding activity being lost over that time.

E. Ephrin-B2 Binding Properties of B4-HSA

Figure 67:
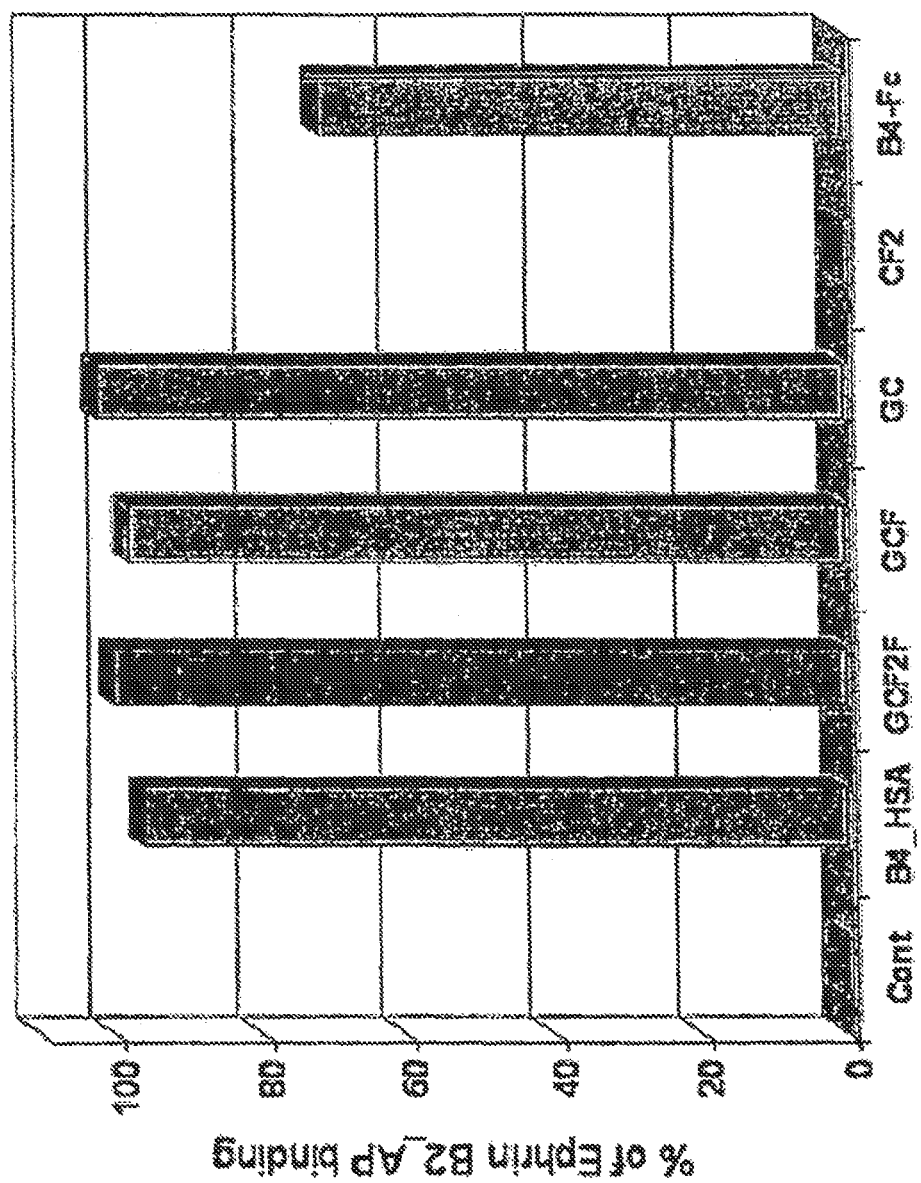
FIG. 67 shows a comparison of the EphrinB2 binding properties of the HSA-EphB4 fusion protein and other EphB4 polypeptides.

To test whether the B4-HSA fusion property retained the ability of the EphB4 extracellular domain to bind to EphrinB2, the ability of the purified B4-HSA fusion was compared to that of GCF2F, GCF2, GC, CF and B4-Fc fusion, which comprises the extracellular domain of B4 fused to hIgG1 Fc as described in Example 1. Biotinylated or His-tag protein samples were inoculated with the corresponding affinity magnetic beads and B2-AP for an hour at room temperature, before addition of PnPP. Results of binding assays are shown on FIG. 67. B4-HSA was found to retain most of its binding activity towards EphrinB2. Surprisingly, the B4-HSA protein was superior to the B4-Fc fusion in binding to EphrinB2.

An EphB4 ectodomain fusion to the C-terminus of HSA was also generated, and found to retain the ability to bind to EphrinB2 and was found to have enhanced stability in vivo over the EphB4 ectodomain.

F. Stability of B4-HSA Vs. sb4 in Mice

Figure 68:
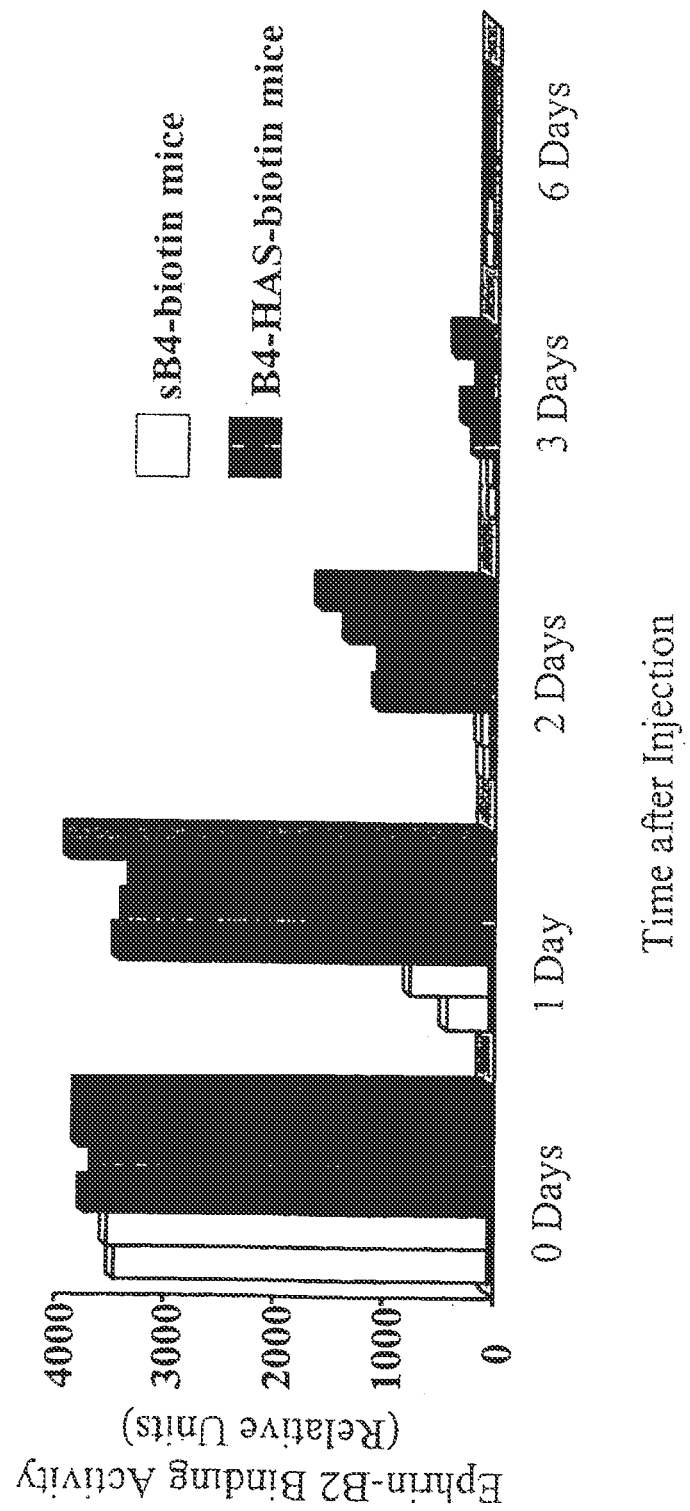
FIG. 68 shows a comparison between the in vivo stability of an EphB4-HSA fusion protein and an EphB4 polypeptide in mice.

The stability of the purified biotinylated sB4 and sB4-HSA were assayed in vivo. Each of the proteins were intravenously injected into the tail of mice in the amount of 0.5 nmoles per mouse. Blood from the eye of each mouse was taken in time frames of 15 min (0 days), 1, 2, 3 and 6 days. 10 ml of obtained serum was used in binding assay with Ephrin-B2-Alkaline Phosphatase fusion protein and Streptavidin-coated magnetic beads as a solid phase. The stability of the two proteins is shown on FIG. 68. sB4-HSA was found to have superior stability relative to sB4. For example, one day after injection, the levels of sB4-HSA in the blood of the mice were 5-fold greater than those of sB4.

G. PEGylation of Biotinylated sB4

Prior to PEGylation, biotinylated sB4 protein generated as described above was concentrated up to final concentration of 2 mg/ml using a 30 kDa MWCO ultra membrane. Sample was dialyzed O/N against coupling buffer: 30 mM phosphate, 75 mM NaCl, pH 8.00. Coupling to PEG was performed at 4° C. for 18 hours in 10 fold molar excess of reactive PEG unless otherwise indicated. The reactive PEG used was PEG-succinimidyl propionate, having a molecular weight of about 20 kda. Coupling to PEG may be similarly performed using branches PEGs, such as of 10 kDa, 20 kDa or 40 kDa. Other linear PEG molecules of 10 or 40 kDa may also be used.

Figure 69:
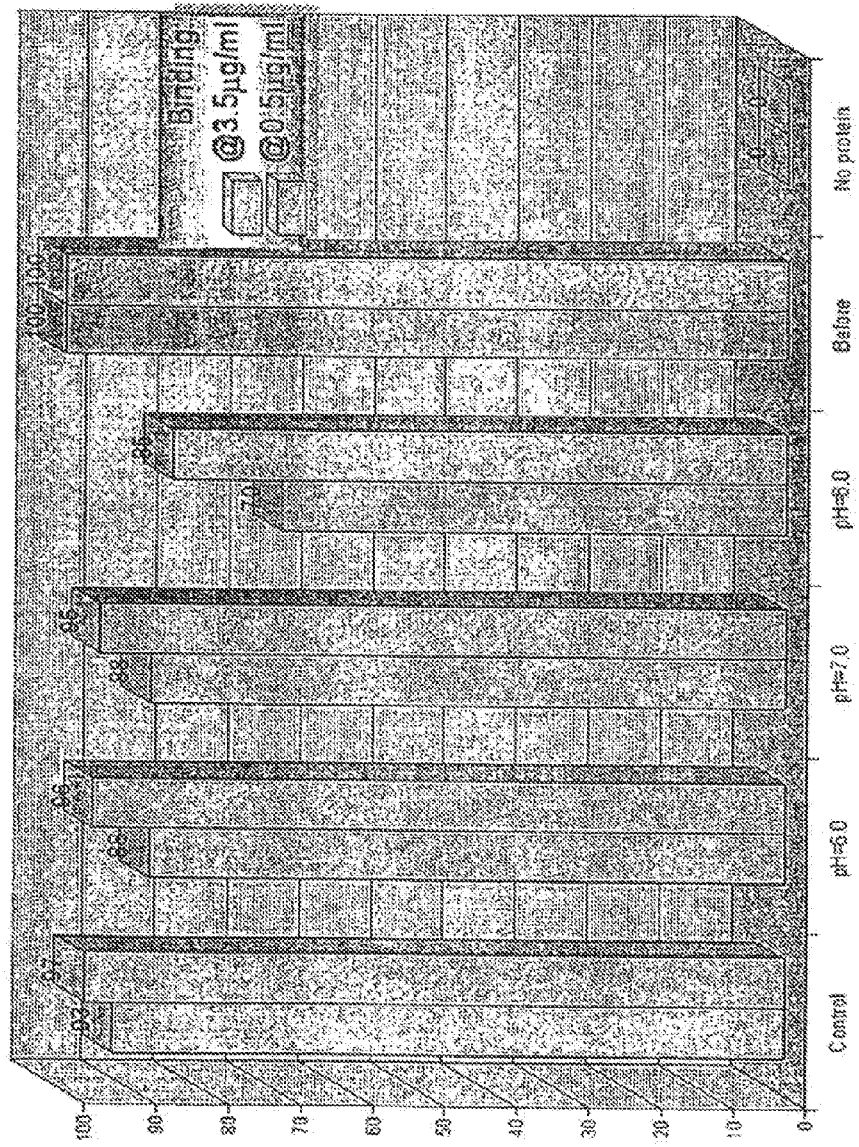
FIG. 69 shows the EphrinB2 binding activity of soluble EphB4 polypeptides pegylated under specific pH conditions.

After PEGylation, the protein sample containing EphB4 ectodomain was dialyzed against StB O/N. Three ml of SP-Sepharose was equilibrated with StB and sample was loaded. Washing and elution of absorbed proteins was performed as above (see: Purification of soluble EphB4 ectodomain and its fusion to HSA) with just one modification: total elution volume was 40 volumes of column. FIG. 69 shows chromatographic separation of PEG derivatives of EphB4 protein on SP-Sepharose columns. Purity of the PEG-modified EphB4 protein was analyzed by SDS-PAGE.

Double modified (PEGylated Biotinylated) sB4 was used on ion-exchange chromatography to separate non-PEGylated, mono-PEGylated and poly-PEGylated proteins from each other. Pegylated sample was dialyzed O/N against 20 mM Na-acetate, 20 mM NaCl, pH 5.5 and loaded onto 2 ml of SP-Sepharose. After washing with 10 ml of buffer, absorbed proteins were separated by gradual elution of NaCl: 3 ml/fraction and increment of 25 mM NaCl. Obtained fractions were analyzed by PAGE and in Ephrin-B2 binding assay.

H. Effect of PEGylation Conditions on sB4 Binding to EphrinB2

The effects of pegylating biotinylated sB4 under different pH conditions was determined. sB4 was pegylated at pH 6, 7 or 8, and the pegylated products were tested for binding to EphrinB2 as shown in FIG. 69. Ephrin2B binding activity was retained when PEGylation was performed at pH 6 and pH 7, but was partially lost at pH 8.

Figure 70:
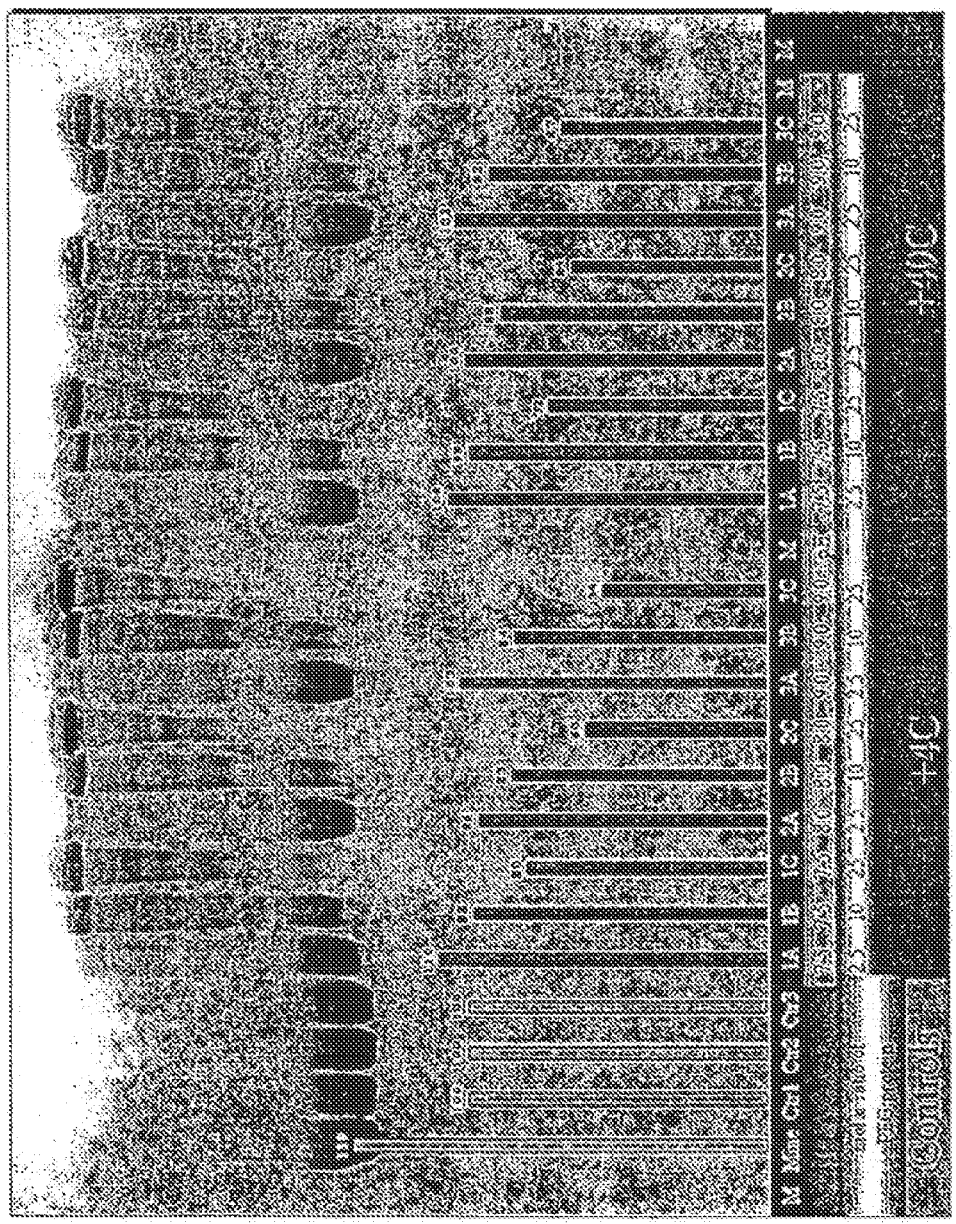
FIG. 70 shows the chromatographic separation of PEG derivatives of EphB4 protein on SP-Sepharose columns. Purity of the PEG-modified EphB4 protein was analyzed by PAGE. The EphrinB2 binding of the pegylation reaction products is also shown.

Additional combinations of parameters were tested, including temperature, pH and molar ratio of pegylation agent to sB4 protein, and the ability of the products of the pegylation reaction to bind to Ephrin-B2. The results of the optimization experiment are shown in FIG. 70. These results confirm the gradual decrease in B2 binding activity at basic pH.

I. Purification of Pegylated sB4 Species

Figure 71:
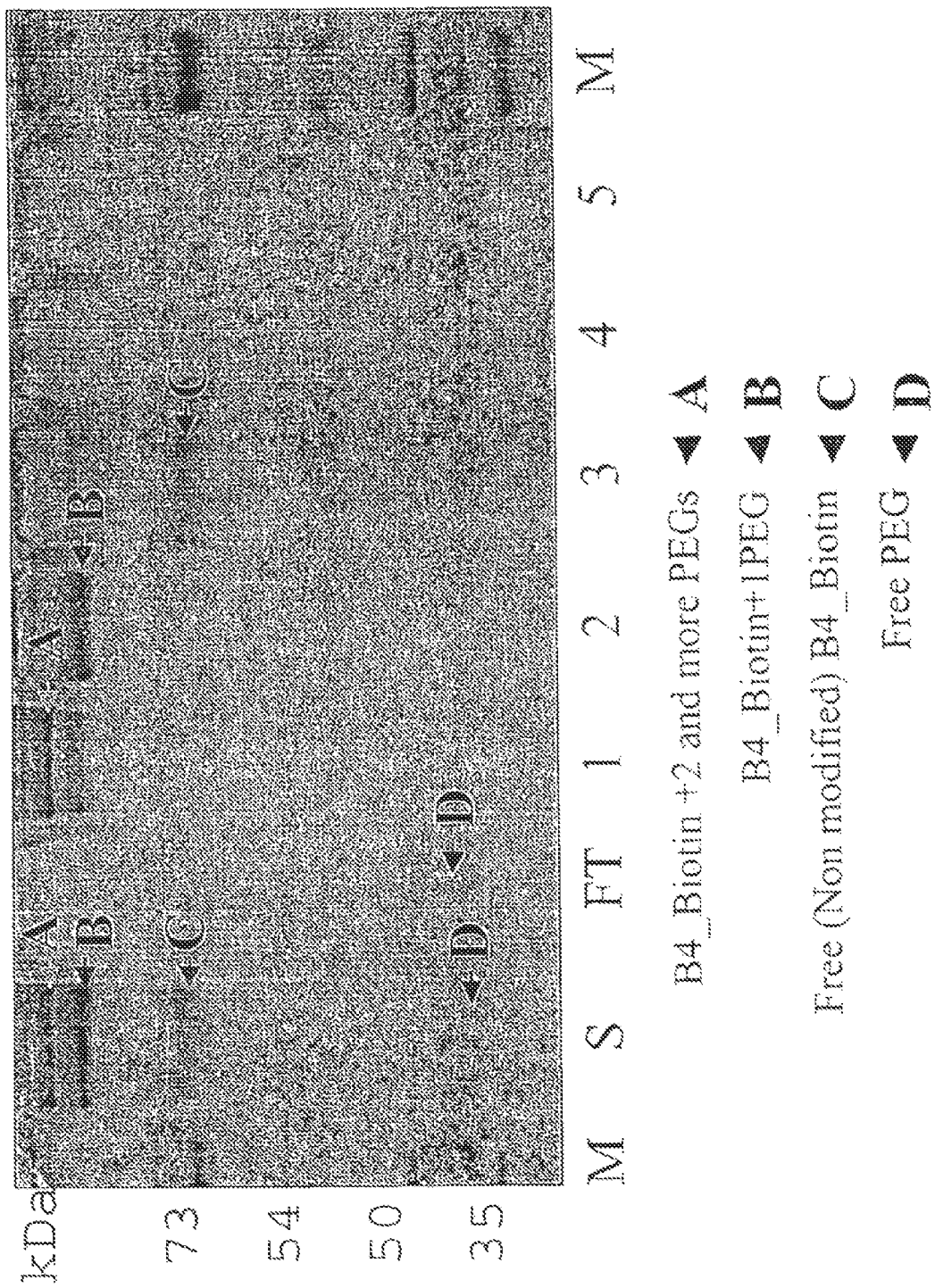
FIG. 71 shows the purity, as determined by SDS-PAGE, of chromatography-separated unpegylated, monopegylated and poly-pegylated EphB4 fractions.

Biotinylated sB4 protein was concentrated up to final concentration of 2 mg/ml using a 30 kDa MWCO ultra membrane. Sample was dialyzed O/N against coupling buffer: 30 mM phosphate, 75 mM NaCl, pH 8.00. Coupling to PEG was performed at 4° C. for 18 hours in 10 fold molar excess of reactive PEG. Double modified (PEGylated Biotinylated) sB4 was used on ion-exchange chromatography to separate non-PEGylated, mono-PEGylated and poly-PEGylated proteins from each other. Sample was dialyzed for O/N against 20 mM Na-Acetate, 20 mM NaCl, pH 5.5 and loaded onto 2 ml of SP-Sepharose. After washing with 10 ml of buffer, absorbed proteins were separated by gradual elution of NaCl: 3 ml/fraction and increment of 25 mM NaCl. Obtained fractions were analyzed by PAGE as shown in FIG. 71. Fractions 1, 2 and 3 were found to correspond to polypegylated, monopegylated and unpegylated biotinylated sB4.

J. In Vitro Properties of PEGylated EphB4 Derivatives

Figure 72:
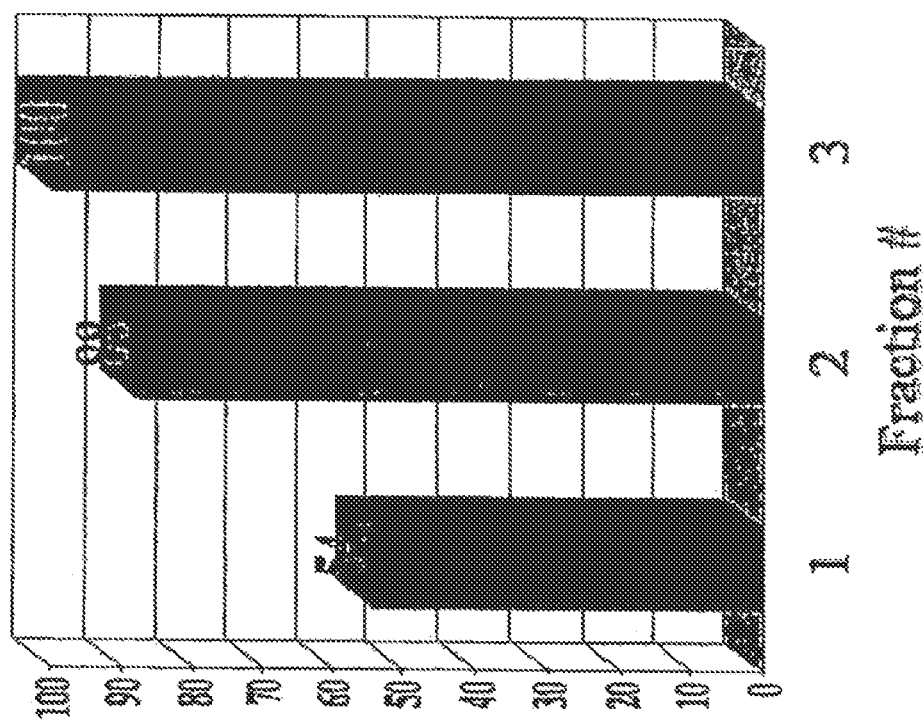
FIG. 72 shows the EphrinB2-binding activity of the chromatography fractions from the EphB4 pegylation reaction.

Fractions 1, 2 and 3 of biotinylated and PEGylated sB4 from the SP column purification, corresponding to polypegylated, monopegylated and unpegylated biotinylated sB4, were tested for their ability to bind EphrinB2 using the standard assay. Results of this experiment are shown on FIG. 72. The order of binding activity was found to be Unpegylated>monopegylated>polypegylated.

Figure 73:
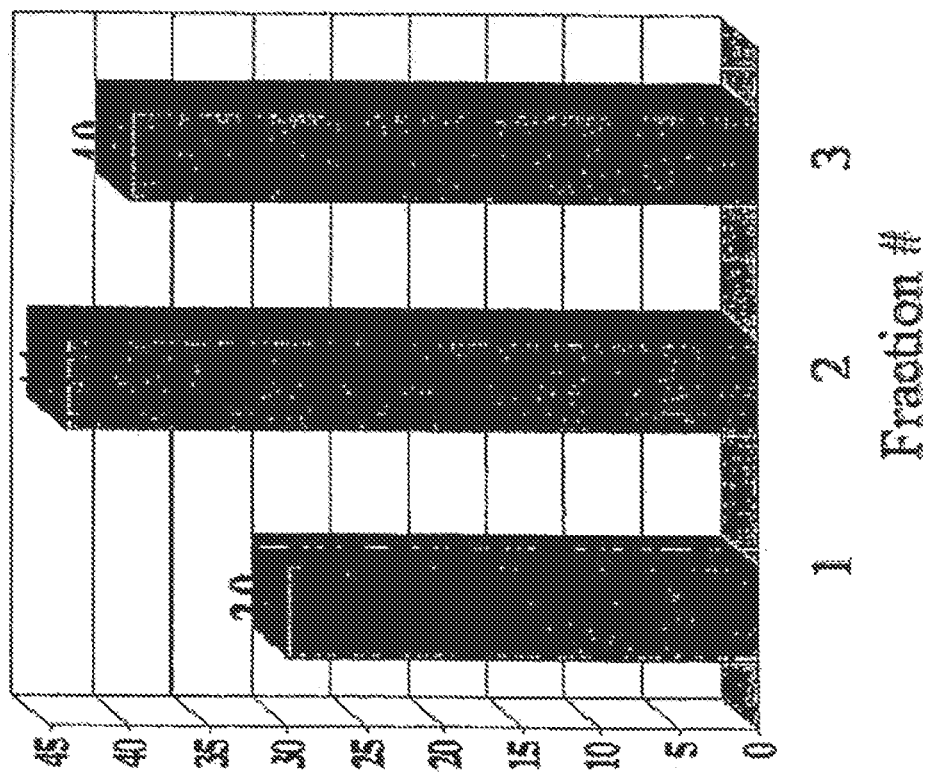
FIG. 73 shows the retention of EphrinB2-binding activity of the chromatography fractions from the EphB4 pegylation reaction after incubation in mouse serum at 37° C. for three days.

The fractions were also tested for their stability in vitro. The fractions were tested for retention of EphrinB2 binding activity after incubation in mouse serum at 37° C. for three days. The results of this experiment are shown in FIG. 73. The order of in vitro stability was found to be monopegylated>unpegylated>polypegylated.

Figure 74:
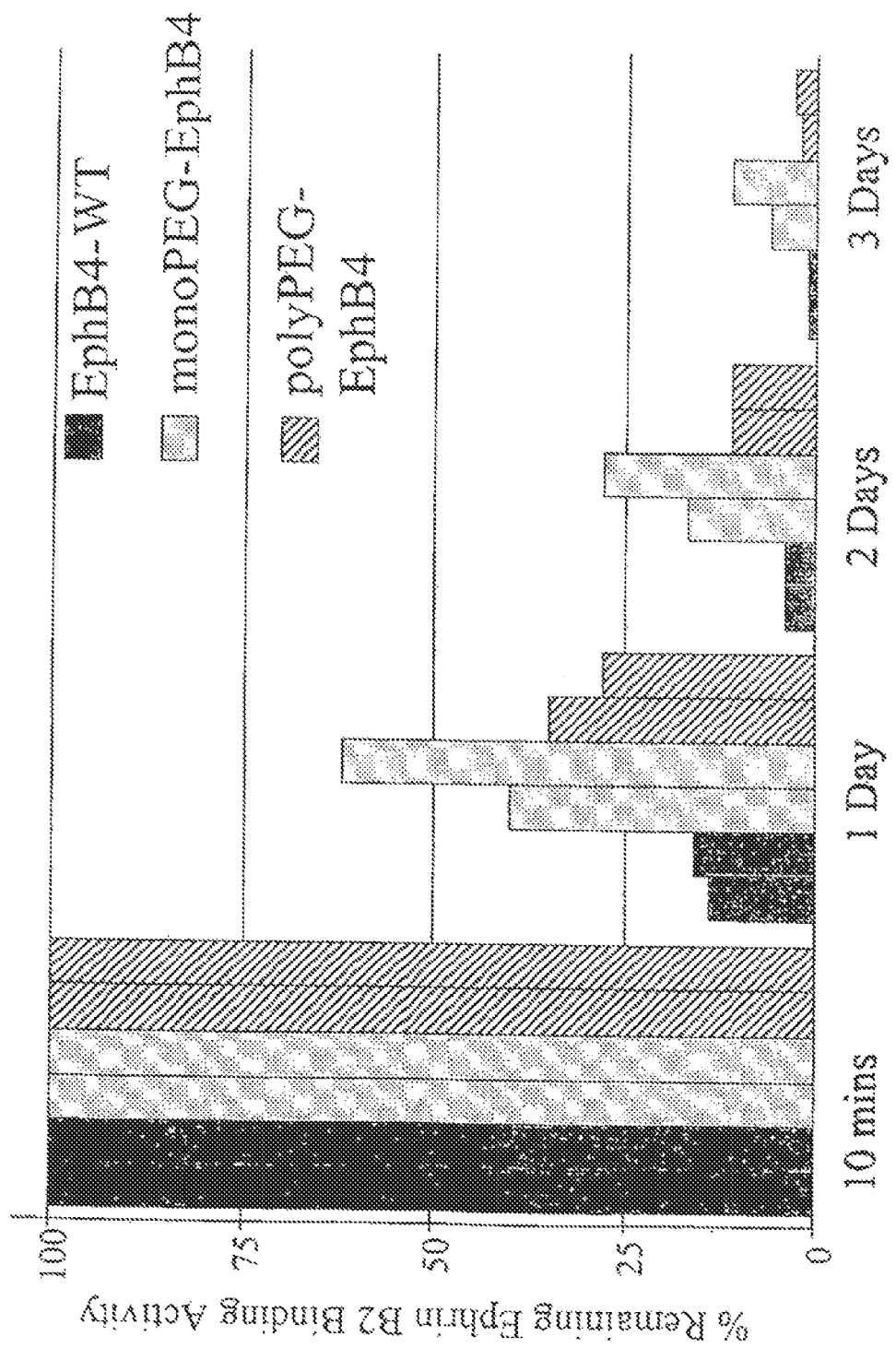
FIG. 74 shows the in vivo stability of unpegylated, monopegylated and polypegylated EphB4 in mice over time.

K. In Vivo Stability Analysis of PEGylated Derivatives of EphB4 Ectodomain in Mice Fractions 1, 2 and 3 of biotinylated and PEGylated sB4 from the SP column purification, corresponding to polypegylated, monopegylated and unpegylated biotinylated sB4, were introduced by intravenous injection into mice in the amount of 0.5 nMoles/mouse. Blood from each mouse was taken in time frame of 10 min, 1, 2 and 3 days. 10 ml of obtained serum was used in binding assay with Ephrin-B2-Alkaline Phosphatase fusion protein and Streptavidin-coated magnetic beads as a solid phase. Signals, obtained at 10 min were taken as 100%. The two mice for each protein were of a different strain. Results are shown in FIG. 74. Pegylation was found to increase the stability of EphB4 in vivo relative to unpegylated EphB4.

INCORPORATION BY REFERENCE

All publications and patents mentioned herein are hereby incorporated by reference in their entirety as if each individual publication or patent was specifically and individually indicated to be incorporated by reference.

While specific embodiments of the subject invention have been discussed, the above specification is illustrative and not restrictive. Many variations of the invention will become apparent to those skilled in the art upon review of this specification and the claims below. The full scope of the invention should be determined by reference to the claims, along with their full scope of equivalents, and the specification, along with such variations.

SEQUENCE LISTING

```
<160> NUMBER OF SEQ ID NOS: 22

<210> SEQ ID NO 1
<211> LENGTH: 570
<212> TYPE: PRT
<213> ORGANISM: Unknown
<220> FEATURE:
<223> OTHER INFORMATION: Recombinant B4ECv3 protein

<400> SEQUENCE: 1

Met Glu Leu Arg Val Leu Leu Cys Trp Ala Ser Leu Ala Ala Ala Leu
 1               5                  10                  15

Glu Glu Thr Leu Leu Asn Thr Lys Leu Glu Thr Ala Asp Leu Lys Trp
            20                  25                  30

Val Thr Phe Pro Gln Val Asp Gly Gln Trp Glu Glu Leu Ser Gly Leu
        35                  40                  45

Asp Glu Glu Gln His Ser Val Arg Thr Tyr Glu Val Cys Glu Val Gln
    50                  55                  60

Arg Ala Pro Gly Gln Ala His Trp Leu Arg Thr Gly Trp Val Pro Arg
65                  70                  75                  80

Arg Gly Ala Val His Val Tyr Ala Thr Leu Arg Phe Thr Met Leu Glu
                85                  90                  95

Cys Leu Ser Leu Pro Arg Ala Gly Arg Ser Cys Lys Glu Thr Phe Thr
            100                 105                 110

Val Phe Tyr Tyr Glu Ser Asp Ala Asp Thr Ala Thr Ala Leu Thr Pro
        115                 120                 125

Ala Trp Met Glu Asn Pro Tyr Ile Lys Val Asp Thr Val Ala Ala Glu
    130                 135                 140

His Leu Thr Arg Lys Arg Pro Gly Ala Glu Ala Thr Gly Lys Val Asn
145                 150                 155                 160

Val Lys Thr Leu Arg Leu Gly Pro Leu Ser Lys Ala Gly Phe Tyr Leu
                165                 170                 175

Ala Phe Gln Asp Gln Gly Ala Cys Met Ala Leu Leu Ser Leu His Leu
            180                 185                 190

Phe Tyr Lys Lys Cys Ala Gln Leu Thr Val Asn Leu Thr Arg Phe Pro
        195                 200                 205

Glu Thr Val Pro Arg Glu Leu Val Val Pro Val Ala Gly Ser Cys Val
    210                 215                 220

Val Asp Ala Val Pro Ala Pro Gly Pro Ser Pro Ser Leu Tyr Cys Arg
225                 230                 235                 240
```

```
Glu Asp Gly Gln Trp Ala Glu Gln Pro Val Thr Gly Cys Ser Cys Ala
                245                 250                 255

Pro Gly Phe Glu Ala Ala Glu Gly Asn Thr Lys Cys Arg Ala Cys Ala
            260                 265                 270

Gln Gly Thr Phe Lys Pro Leu Ser Gly Glu Gly Ser Cys Gln Pro Cys
        275                 280                 285

Pro Ala Asn Ser His Ser Asn Thr Ile Gly Ser Ala Val Cys Gln Cys
    290                 295                 300

Arg Val Gly Tyr Phe Arg Ala Arg Thr Asp Pro Arg Gly Ala Pro Cys
305                 310                 315                 320

Thr Thr Pro Pro Ser Ala Pro Arg Ser Val Val Ser Arg Leu Asn Gly
                325                 330                 335

Ser Ser Leu His Leu Glu Trp Ser Ala Pro Leu Glu Ser Gly Gly Arg
            340                 345                 350

Glu Asp Leu Thr Tyr Ala Leu Arg Cys Arg Glu Cys Arg Pro Gly Gly
        355                 360                 365

Ser Cys Ala Pro Cys Gly Gly Asp Leu Thr Phe Asp Pro Gly Pro Arg
    370                 375                 380

Asp Leu Val Glu Pro Trp Val Val Arg Gly Leu Arg Pro Asp Phe
385                 390                 395                 400

Thr Tyr Thr Phe Glu Val Thr Ala Leu Asn Gly Val Ser Ser Leu Ala
                405                 410                 415

Thr Gly Pro Val Pro Phe Glu Pro Val Asn Val Thr Thr Asp Arg Glu
            420                 425                 430

Val Pro Pro Ala Val Ser Asp Ile Arg Val Thr Arg Ser Ser Pro Ser
        435                 440                 445

Ser Leu Ser Leu Ala Trp Ala Val Pro Arg Ala Pro Ser Gly Ala Trp
    450                 455                 460

Leu Asp Tyr Glu Val Lys Tyr His Glu Lys Gly Ala Glu Gly Pro Ser
465                 470                 475                 480

Ser Val Arg Phe Leu Lys Thr Ser Glu Asn Arg Ala Glu Leu Arg Gly
                485                 490                 495

Leu Lys Arg Gly Ala Ser Tyr Leu Val Gln Val Arg Ala Arg Ser Glu
            500                 505                 510

Ala Gly Tyr Gly Pro Phe Gly Gln Glu His His Ser Gln Thr Gln Leu
        515                 520                 525

Asp Glu Ser Glu Gly Trp Arg Glu Gln Gly Ser Lys Arg Ala Ile Leu
    530                 535                 540

Gln Ile Glu Gly Lys Pro Ile Pro Asn Pro Leu Leu Gly Leu Asp Ser
545                 550                 555                 560

Thr Arg Thr Gly His His His His His
                565                 570

<210> SEQ ID NO 2
<211> LENGTH: 555
<212> TYPE: PRT
<213> ORGANISM: Unknown
<220> FEATURE:
<223> OTHER INFORMATION: Recombinant B4ECv3NT protein

<400> SEQUENCE: 2

Met Glu Leu Arg Val Leu Leu Cys Trp Ala Ser Leu Ala Ala Ala Leu
1               5                   10                  15

Glu Glu Thr Leu Leu Asn Thr Lys Leu Glu Thr Ala Asp Leu Lys Trp
            20                  25                  30
```

```
Val Thr Phe Pro Gln Val Asp Gly Gln Trp Glu Glu Leu Ser Gly Leu
         35                  40                  45

Asp Glu Glu Gln His Ser Val Arg Thr Tyr Glu Val Cys Glu Val Gln
 50                  55                  60

Arg Ala Pro Gly Gln Ala His Trp Leu Arg Thr Gly Trp Val Pro Arg
 65                  70                  75                  80

Arg Gly Ala Val His Val Tyr Ala Thr Leu Arg Phe Thr Met Leu Glu
                 85                  90                  95

Cys Leu Ser Leu Pro Arg Ala Gly Arg Ser Cys Lys Glu Thr Phe Thr
            100                 105                 110

Val Phe Tyr Tyr Glu Ser Asp Ala Asp Thr Ala Thr Ala Leu Thr Pro
            115                 120                 125

Ala Trp Met Glu Asn Pro Tyr Ile Lys Val Asp Thr Val Ala Ala Glu
130                 135                 140

His Leu Thr Arg Lys Arg Pro Gly Ala Glu Ala Thr Gly Lys Val Asn
145                 150                 155                 160

Val Lys Thr Leu Arg Leu Gly Pro Leu Ser Lys Ala Gly Phe Tyr Leu
                165                 170                 175

Ala Phe Gln Asp Gln Gly Ala Cys Met Ala Leu Leu Ser Leu His Leu
            180                 185                 190

Phe Tyr Lys Lys Cys Ala Gln Leu Thr Val Asn Leu Thr Arg Phe Pro
            195                 200                 205

Glu Thr Val Pro Arg Glu Leu Val Val Pro Val Ala Gly Ser Cys Val
            210                 215                 220

Val Asp Ala Val Pro Ala Pro Gly Pro Ser Pro Ser Leu Tyr Cys Arg
225                 230                 235                 240

Glu Asp Gly Gln Trp Ala Glu Gln Pro Val Thr Gly Cys Ser Cys Ala
                245                 250                 255

Pro Gly Phe Glu Ala Ala Glu Gly Asn Thr Lys Cys Arg Ala Cys Ala
            260                 265                 270

Gln Gly Thr Phe Lys Pro Leu Ser Gly Glu Gly Ser Cys Gln Pro Cys
            275                 280                 285

Pro Ala Asn Ser His Ser Asn Thr Ile Gly Ser Ala Val Cys Gln Cys
290                 295                 300

Arg Val Gly Tyr Phe Arg Ala Arg Thr Asp Pro Arg Gly Ala Pro Cys
305                 310                 315                 320

Thr Thr Pro Pro Ser Ala Pro Arg Ser Val Val Ser Arg Leu Asn Gly
                325                 330                 335

Ser Ser Leu His Leu Glu Trp Ser Ala Pro Leu Glu Ser Gly Gly Arg
            340                 345                 350

Glu Asp Leu Thr Tyr Ala Leu Arg Cys Arg Glu Cys Arg Pro Gly Gly
            355                 360                 365

Ser Cys Ala Pro Cys Gly Gly Asp Leu Thr Phe Asp Pro Gly Pro Arg
370                 375                 380

Asp Leu Val Glu Pro Trp Val Val Arg Gly Leu Arg Pro Asp Phe
385                 390                 395                 400

Thr Tyr Thr Phe Glu Val Thr Ala Leu Asn Gly Val Ser Ser Leu Ala
                405                 410                 415

Thr Gly Pro Val Pro Phe Glu Pro Val Asn Val Thr Thr Asp Arg Glu
            420                 425                 430

Val Pro Pro Ala Val Ser Asp Ile Arg Val Thr Arg Ser Ser Pro Ser
435                 440                 445

Ser Leu Ser Leu Ala Trp Ala Val Pro Arg Ala Pro Ser Gly Ala Trp
```

```
            450                 455                 460
Leu Asp Tyr Glu Val Lys Tyr His Glu Lys Gly Ala Glu Gly Pro Ser
465                 470                 475                 480

Ser Val Arg Phe Leu Lys Thr Ser Glu Asn Arg Ala Glu Leu Arg Gly
                485                 490                 495

Leu Lys Arg Gly Ala Ser Tyr Leu Val Gln Val Arg Ala Arg Ser Glu
            500                 505                 510

Ala Gly Tyr Gly Pro Phe Gly Gln Glu His His Ser Gln Thr Gln Leu
        515                 520                 525

Asp Glu Ser Glu Gly Trp Arg Glu Gln Gly Ser Lys Arg Ala Ile Leu
530                 535                 540

Gln Ile Ser Ser Thr Val Ala Ala Ala Arg Val
545                 550                 555

<210> SEQ ID NO 3
<211> LENGTH: 233
<212> TYPE: PRT
<213> ORGANISM: Unknown
<220> FEATURE:
<223> OTHER INFORMATION: Recombinant B2EC protein

<400> SEQUENCE: 3

Met Ala Val Arg Arg Asp Ser Val Trp Lys Tyr Cys Trp Gly Val Leu
1               5                   10                  15

Met Val Leu Cys Arg Thr Ala Ile Ser Lys Ser Ile Val Leu Glu Pro
                20                  25                  30

Ile Tyr Trp Asn Ser Ser Asn Ser Lys Phe Leu Pro Gly Gln Gly Leu
            35                  40                  45

Val Leu Tyr Pro Gln Ile Gly Asp Lys Leu Asp Ile Ile Cys Pro Lys
50                  55                  60

Val Asp Ser Lys Thr Val Gly Gln Tyr Glu Tyr Tyr Lys Val Tyr Met
65                  70                  75                  80

Val Asp Lys Asp Gln Ala Asp Arg Cys Thr Ile Lys Lys Glu Asn Thr
                85                  90                  95

Pro Leu Leu Asn Cys Ala Lys Pro Asp Gln Asp Ile Lys Phe Thr Ile
            100                 105                 110

Lys Phe Gln Glu Phe Ser Pro Asn Leu Trp Gly Leu Glu Phe Gln Lys
        115                 120                 125

Asn Lys Asp Tyr Tyr Ile Ile Ser Thr Ser Asn Gly Ser Leu Glu Gly
130                 135                 140

Leu Asp Asn Gln Glu Gly Gly Val Cys Gln Thr Arg Ala Met Lys Ile
145                 150                 155                 160

Leu Met Lys Val Gly Gln Asp Ala Ser Ser Ala Gly Ser Thr Arg Asn
                165                 170                 175

Lys Asp Pro Thr Arg Arg Pro Glu Leu Glu Ala Gly Thr Asn Gly Arg
            180                 185                 190

Ser Ser Thr Thr Ser Pro Phe Val Lys Pro Asn Pro Gly Ser Ser Thr
        195                 200                 205

Asp Gly Asn Ser Ala Gly His Ser Gly Asn Asn Ile Leu Gly Ser Glu
210                 215                 220

Val Gly Ser His His His His His His
225                 230

<210> SEQ ID NO 4
<211> LENGTH: 771
<212> TYPE: PRT
```

<213> ORGANISM: Unknown
<220> FEATURE:
<223> OTHER INFORMATION: Recombinant B4ECv3-FC protein

<400> SEQUENCE: 4

```

```
            385                 390                 395                 400
        Thr Tyr Thr Phe Glu Val Thr Ala Leu Asn Gly Val Ser Ser Leu Ala
                        405                 410                 415
        Thr Gly Pro Val Pro Phe Glu Pro Val Asn Val Thr Thr Asp Arg Glu
                    420                 425                 430
        Val Pro Pro Ala Val Ser Asp Ile Arg Val Thr Arg Ser Ser Pro Ser
                435                 440                 445
        Ser Leu Ser Leu Ala Trp Ala Val Pro Arg Ala Pro Ser Gly Ala Trp
            450                 455                 460
        Leu Asp Tyr Glu Val Lys Tyr His Glu Lys Gly Ala Glu Gly Pro Ser
        465                 470                 475                 480
        Ser Val Arg Phe Leu Lys Thr Ser Glu Asn Arg Ala Glu Leu Arg Gly
                        485                 490                 495
        Leu Lys Arg Gly Ala Ser Tyr Leu Val Gln Val Arg Ala Arg Ser Glu
                    500                 505                 510
        Ala Gly Tyr Gly Pro Phe Gly Gln Glu His His Ser Gln Thr Gln Leu
                515                 520                 525
        Asp Glu Ser Glu Gly Trp Arg Glu Gln Asp Pro Glu Pro Lys Ser Cys
            530                 535                 540
        Asp Lys Thr His Thr Cys Pro Pro Cys Pro Ala Pro Glu Leu Leu Gly
        545                 550                 555                 560
        Gly Pro Ser Val Phe Leu Phe Pro Pro Lys Pro Lys Asp Thr Leu Met
                        565                 570                 575
        Ile Ser Arg Thr Pro Glu Val Thr Cys Val Val Val Asp Val Ser His
                    580                 585                 590
        Glu Asp Pro Glu Val Lys Phe Asn Trp Tyr Val Asp Gly Val Glu Val
                595                 600                 605
        His Asn Ala Lys Thr Lys Pro Arg Glu Glu Gln Tyr Asn Ser Thr Tyr
            610                 615                 620
        Arg Val Val Ser Val Leu Thr Val Leu His Gln Asp Trp Leu Asn Gly
        625                 630                 635                 640
        Lys Glu Tyr Lys Cys Lys Val Ser Asn Lys Ala Leu Pro Ala Pro Ile
                        645                 650                 655
        Glu Lys Thr Ile Ser Lys Ala Lys Gly Gln Pro Arg Glu Pro Gln Val
                    660                 665                 670
        Tyr Thr Leu Pro Pro Ser Arg Asp Glu Leu Thr Lys Asn Gln Val Ser
                675                 680                 685
        Leu Thr Cys Leu Val Lys Gly Phe Tyr Pro Ser Asp Ile Ala Val Glu
            690                 695                 700
        Trp Glu Ser Asn Gly Gln Pro Glu Asn Asn Tyr Lys Thr Thr Pro Pro
        705                 710                 715                 720
        Val Leu Asp Ser Asp Gly Ser Phe Phe Leu Tyr Ser Lys Leu Thr Val
                        725                 730                 735
        Asp Lys Ser Arg Trp Gln Gln Gly Asn Val Phe Ser Cys Ser Val Met
                    740                 745                 750
        His Glu Ala Leu His Asn His Tyr Thr Gln Lys Ser Leu Ser Leu Ser
                755                 760                 765
        Pro Gly Lys
            770

<210> SEQ ID NO 5
<211> LENGTH: 459
<212> TYPE: PRT
<213> ORGANISM: Unknown
```

<220> FEATURE:
<223> OTHER INFORMATION: Recombinant B2EC-FC protein

<400> SEQUENCE: 5

```
Met Ala Val Arg Arg Asp Ser Val Trp Lys Tyr Cys Trp Gly Val Leu
 1               5                  10                  15

Met Val Leu Cys Arg Thr Ala Ile Ser Lys Ser Ile Val Leu Glu Pro
            20                  25                  30

Ile Tyr Trp Asn Ser Ser Asn Ser Lys Phe Leu Pro Gly Gln Gly Leu
            35                  40                  45

Val Leu Tyr Pro Gln Ile Gly Asp Lys Leu Asp Ile Ile Cys Pro Lys
 50                  55                  60

Val Asp Ser Lys Thr Val Gly Gln Tyr Glu Tyr Tyr Lys Val Tyr Met
 65                  70                  75                  80

Val Asp Lys Asp Gln Ala Asp Arg Cys Thr Ile Lys Lys Glu Asn Thr
                85                  90                  95

Pro Leu Leu Asn Cys Ala Lys Pro Asp Gln Asp Ile Lys Phe Thr Ile
                100                 105                 110

Lys Phe Gln Glu Phe Ser Pro Asn Leu Trp Gly Leu Glu Phe Gln Lys
            115                 120                 125

Asn Lys Asp Tyr Tyr Ile Ile Ser Thr Ser Asn Gly Ser Leu Glu Gly
            130                 135                 140

Leu Asp Asn Gln Glu Gly Gly Val Cys Gln Thr Arg Ala Met Lys Ile
145                 150                 155                 160

Leu Met Lys Val Gly Gln Asp Ala Ser Ser Ala Gly Ser Thr Arg Asn
                165                 170                 175

Lys Asp Pro Thr Arg Arg Pro Glu Leu Glu Ala Gly Thr Asn Gly Arg
            180                 185                 190

Ser Ser Thr Thr Ser Pro Phe Val Lys Pro Asn Pro Gly Ser Ser Thr
            195                 200                 205

Asp Gly Asn Ser Ala Gly His Ser Gly Asn Asn Ile Leu Gly Ser Glu
 210                 215                 220

Val Asp Pro Glu Pro Lys Ser Cys Asp Lys Thr His Thr Cys Pro Pro
225                 230                 235                 240

Cys Pro Ala Pro Glu Leu Leu Gly Gly Pro Ser Val Phe Leu Phe Pro
                245                 250                 255

Pro Lys Pro Lys Asp Thr Leu Met Ile Ser Arg Thr Pro Glu Val Thr
            260                 265                 270

Cys Val Val Val Asp Val Ser His Glu Asp Pro Glu Val Lys Phe Asn
            275                 280                 285

Trp Tyr Val Asp Gly Val Glu Val His Asn Ala Lys Thr Lys Pro Arg
 290                 295                 300

Glu Glu Gln Tyr Asn Ser Thr Tyr Arg Val Val Ser Val Leu Thr Val
305                 310                 315                 320

Leu His Gln Asp Trp Leu Asn Gly Lys Glu Tyr Lys Cys Lys Val Ser
                325                 330                 335

Asn Lys Ala Leu Pro Ala Pro Ile Glu Lys Thr Ile Ser Lys Ala Lys
            340                 345                 350

Gly Gln Pro Arg Glu Pro Gln Val Tyr Thr Leu Pro Pro Ser Arg Asp
            355                 360                 365

Glu Leu Thr Lys Asn Gln Val Ser Leu Thr Cys Leu Val Lys Gly Phe
 370                 375                 380

Tyr Pro Ser Asp Ile Ala Val Glu Trp Glu Ser Asn Gly Gln Pro Glu
385                 390                 395                 400
```

```
Asn Asn Tyr Lys Thr Thr Pro Pro Val Leu Asp Ser Asp Gly Ser Phe
            405                 410                 415
Phe Leu Tyr Ser Lys Leu Thr Val Asp Lys Ser Arg Trp Gln Gln Gly
        420                 425                 430
Asn Val Phe Ser Cys Ser Val Met His Glu Ala Leu His Asn His Tyr
            435                 440                 445
Thr Gln Lys Ser Leu Ser Leu Ser Pro Gly Lys
    450                 455
```

<210> SEQ ID NO 6
<211> LENGTH: 26000
<212> TYPE: DNA
<213> ORGANISM: Homo sapiens

<400> SEQUENCE: 6

```
ggggtttcat catgttggcc aggctggtct tgaactcctg acctcaaatg atccgcctgc     60
ctctgcctcc caaaatgctg ggactacagg cgtgagccac cgcgcccgcc acacccacct    120
tttctttacc gttgtttcct cgattttttct ctactcccta gcgcagctta gtgcgcgcct    180
cctctggaca ttttttcaggg cttggttgcg cgcacagtag gtccccaaca ctgaatgttt    240
atggggtgac tgtgtgaacg ttcgctgcaa ggctatccaa actgggattg ctccttgagg    300
cccccctgggc ggccgtcaat tctccaaagc ttctactccc ttttccttcc ttttcccccca   360
aaacgcagtc cctgcgccca ctagagggtg gtgggcgcat ccaagagcgg catctagagt    420
ccgcagcaag gtcagagcgg gctttgtgtg cgcggtgaac atttacgtgc acgcctgggc    480
ggccctccgt gttgctgctg ggtgtgtgtt ttctctgctc cctggtgcca gccgggttcg    540
ggcctgtccc gggggtccct gggccccagc ccgacatgc tcggtcctgg acagcgcgca     600
ccgccacggc gcacatctgg gcggtcccgg ggttcctcac ccgccgcccc tccccttct     660
ccaaactttc tctcaacttc ccgacctgct ccactcggtg cccctctccg cttccctcat    720
gaattattca gtagcgtgag ctccaatcag gcgcccggg gctcactcgc ggagcccccg     780
cgttgggaga gctgccccccg cccccgcgc gccctccct ccgggcccg gcgccgcccg      840
gcccagttcc agcgcagctc agcccctgcc cggcccggcc cgcccggctc cgcgccgcag    900
tctccctccc tcccgctccg tcccgctcg ggctcccacc atccccgccc gcgaggagag     960
cactcggccc ggcggcgcga gcagagccac tccaggagg gggggagacc cgcgagcggcc   1020
ggctcagccc ccgccacccg ggcgggacc ccgaggcccc ggagggaccc caactccagc    1080
cacgtcttgc tgcgcgcccg cccggcgcgg ccactgccag cacgctccgg gcccgccgcc    1140
cgcgcgcgcg gcacagacgc ggggccacac ttggcgccgc cgcccggtgc cccgcacgct    1200
cgcatgggcc cgcgctgagg gccccgacga ggagtcccgc gcggagtatc ggcgtccacc    1260
cgcccaggga gagtcagacc tgggggggcg agggcccccc aaactcagtt cggatcctac    1320
ccgagtgagg cggcgccatg gagctccggg tgctgctctg ctgggcttcg ttggccgcag    1380
ctttggaagg tgagtttcct tgcgggggggg ggcgcacccc gtcactcctg ggacctcccc    1440
cccaacatct gggcctcgga gtggagggc cggcctctga ctaccctac ccgggcactg     1500
cagtcccaaa cacttcggac cgatagtgct ggaacgggag ggggcgggg aagaggcgcc    1560
cgacgggtag tggagttttc tttttgtttgg gaaagagatg gagtctggct acgacccggg   1620
acattcccct gcccgggctc ccgaactct cactgctgat tacatacgcc cctggctgcc    1680
tttcctttcc tccctacccc actattcaaa actatctgca aagtttctgt cccagtccca    1740
```

```
cctcccgccg tacatgaggg aaggtttctg gagaagcaac agcagacaag gcacaacttt    1800
tcgtgctagg ccctaaaacg acccccagcg ccaattcctt agcgatcaca ccttgatcct    1860
ccagttccac actcctgcaa caggatggcc tcctttgcat tcacacagca aaccccccaaa  1920 ccgctctccc gcccactgct cctgccctg gtatagggtg gctccttggt ttctacaggc    1980
tgcaccccat ccctttaaat gcggtctaga ccccggcccc aggtgagtcc cgggcttccc   2040
ttgagaccta ggagcgggta gaaactgacc tacacagccc ccaggtagaa actgacctac   2100
acagccccca catcgcccta actaacccag tctatctccc acctcctggt ctctccaagc   2160
atttctttgg ccatggatcg ctgtccctcc tggtcccta aagggggagc caagagccct    2220
agaaactctc ctgtgtccct aatgtccttt cagtgagctg ccaacacccc cctttctctg   2280
tctggtatga agtggttat ggggcggtag ctatgaggg actcccaaag gaaggattc      2340 agcggcgtta gaaaaaccct ctccccctgg ctgggcagga ctgccctggg ctggggatca   2400
aaggctaggt gtggggttgg gagtgagggg aggcttgccc agctcagaga acggagaagg   2460
gggaacaaaa accatgaacg agggggaagag gaaggcaaa ggggtggaaa aaccacgagg    2520
acgaggtgtg gtgagaagga aagacgcaaa gaggaaatgg tgattgtgac acctattacc   2580
tgagtgtttc caagcaccag gcctgtgctg agcgccttac aaatattaat ttcacccatc   2640
cagcaacgct aagggtggtg ctattattgc ccccatttt cagatgagga ggctggggct    2700
tagttaaggt taagtagttt atccaaggcc ctgtgccgcg aggaacagcg agaagtggag    2760
gccgaaagcg aaggagagat agtgactgtc agaaagagaa acggaggtgg acagagagtg   2820
gaggagagat aggtgagaga catgcgaact gacagatcaa agcgtggctg cagctgagct   2880
gggacgcaga aagggagcct gcgcttgctc tgggctgcgg acagcccgag gcagagacag   2940
tgtgtaaatt ggagacagga aaacactatc ccggctggaa caatggaggg tggagacggc   3000
agcctctatc cacccccttc ccagaaccg gcatcctgt ccccagtgag cagggctgtc     3060
tcttgccacc catggggacc ttgcgcctct cacctcaggc tggctggctt cccatctgac   3120
ccctagctgg aggacatcat ttggtcccca ggaagaggct gcctcaccca cctctttct    3180 cttctctcct gcagctccca tggggtggga gccaggtgtt ctggctcccc tctccaccct   3240
tcccagcgcc caatgccccc cacattgccg gcccccgagg ggattcctgt accctccctc   3300
ctccactctc cactgccagg ggctgtgcag ttttccctaa tccccccct tcctccagtg    3360 cctgtcccct ccccgatga tccgagccaa gccaggtgtg ttcacccctc ccattcatac    3420 cgcccccag aatctcctcc cctctgcctt cccataacca aatccagatg tgaggcctcg    3480
gcgggagcct gggaacccta gcatcccgac ctccagtgct tcctgatcag ggcactcgtg   3540
gggagggagg tactgggatg ggggccaggg ctatgcccca ggcacggagc gctcccttca   3600
aggagggaag gacgggtgt ttggtctgaa agcagagagg ggtcttggac agggaatgaa    3660
attgtggggt agagaggctg attctgggac ttaggggagg aaacgtggag gctgagacaa   3720
gaggttcccc tcccacacca gcagcctctg ctcgtggggg tcaggaccag ggcgcagctc   3780
tcattttaac cctttctgag ctgccgcccc ttctccccgt acattttgat ctccctccct   3840
cctccaggga ggcctagatc tggggtatcc caagggagcc ccatgcctac cagatgttgg   3900 gggtgggtt ggcacttagc agaagaggcc agaaatcagg cgggtgcaga gggcagggct    3960
tgctcccctc ttggcccccc aactcctcta gctcagagct aagaggatcc acctgcctcg   4020
gttcccaggg atctggtctt cctgacctcc ctccccacc ccaggcactg actctgtctc    4080
tctgtctgtc tcagagaccc tgctgaacac aaaattggaa actgctgatc tgaagtgggt   4140
```

```
gacattccct caggtggacg ggcaggtgag agctgcaccc aggagctgga gctctggagg    4200
gaaactgagg gaggagaggg cgcctgtgcc gcctgctttc tgtgtgccac tcctctcccc    4260
tgtcccccca gatgacagca gcccagcag tgtcgtctga gcccttctca gaggcgccct     4320
cctcgcagta ccagcagccc cccttctca gtccctctca ctttatagga ttacccccat    4380
gcagccctct ccctggcggc tccccagccc ccttgctgac ctccttctct gcacagtggg    4440
aggaactgag cggcctggat gaggaacagc acagcgtgcg cacctacgaa gtgtgtgacg    4500
tgcagcgtgc cccgggccag gcccactggc ttcgcacagg ttgggtccca cggcggggcg    4560
ccgtccacgt gtacgccacg ctgcgcttca ccatgctcga gtgcctgtcc ctgcctcggg    4620
ctgggcgctc ctgcaaggag accttcaccg tcttctacta tgagagcgat gcggacacgg    4680
ccacggccct cacgccagcc tggatggaga acccctacat caaggtacct gggtgccccc    4740
agggctcagc cacagccaag gtgggattcc agccagcagg cccgtggcct ggagggcagc    4800
cgatgtagtt gcgaggcctc tggcccgcgc gctgggggct ggaagcagga ggcttaggtc    4860
tggggaggga aggggtgat cttctgggcg gaggagcaga atatacgggg gctgcctggc     4920 ccggcccca gggaggccca agggtcaggc ttctcctcca gtcacctcaa ccaccctacc     4980
ccactgtgct ccagccacac tgagtttctc ccattccctg actgcacctg ctggtttcc    5040 agctcaagac tttgcagcgg tgatgtctcc acctgggggc ctctctgcct ctcacacccc    5100
tacttgtctt cggagttcca gctcccgaga tcttgcctgt gccaccttgg ctgactctct    5160
cctccctaca atcctgcata cctctgtcca cctgcctgtc tcggcactca ttttacttta    5220 tttattttc ttttatatct atatttttaa agcggggtct tctacgttac ccaggctggt     5280
ctctaactcc tgggctcaag agatttctcc cacctcggcc tcctaaagtg ctgggattat    5340
aggcatgagg cactacgccc ggcctcatgg tactttataa cttccccagg attcattcat    5400
cgctgtctcc ttgactctga ggtcaaggcc tggcatggcg tcagtgtcag taaatgtttg    5460
tagaacgagt gaataaaaag ggggagaggt gcaggccaga ggccgggcat atcgcaggag    5520 cttttgcaagg ctgaatggac agtgtggggg cctgcagaaa gtgtgccctg gggaaggtgg    5580
agggaagatt ctggaacggg aaccaaggag gtccgggagg gtgagctggg aagaacacaa    5640
cagtccgctg ggtcctcagg gagtggggac agcagcggtg tgcctccccc ccgccggcag    5700
gtggacacgg tggccgcgga gcatctcacc cggaagcgcc ctggggccga ggccaccggg    5760
aaggtgaatg tcaagacgct gcgtctggga ccgctcagca aggctggctt ctacctggcc    5820
ttccaggacc agggtgcctg catggccctg ctatccctgc acctcttcta caaaaagtgc    5880
gcccagctga ctgtgaacct gactcgattc ccggagactg tgcctcggga gctggttgtg    5940
cccgtggccg gtagctgcgt ggtggatgcc gtccccgccc ctggcccag ccccagcctc     6000 tactgccgtg aggatggcca gtgggccgaa cagccggtca cgggctgcag ctgtgctccg    6060
gggttcgagg cagctgaggg gaacaccaag tgccgaggtg agagctggag cttcccctgc    6120
gactgctgct catccggggg agagtcctga actccactca ggacccactt cttaagtttc    6180
cattttgtat agttagatgt tgaaatggag gcttgctctg tcacccaggc tggagtgcag    6240
tggcacaatc tctgctcaac tgcaacctt gcctcccggg tccctgttca agcagttctc     6300
ctgcctcagc ctcgtgagta gctgggacta caggcacacg ccaccacgcc cggctaattt    6360
ttgtatttta gtagagacgg ggtttcgcca tgttggccag gctggtctcg aactcctgac    6420
ctgaagtgat ttgcccgcct cggcctccca aagtgctggg attacaggcg tgcgtcacca    6480
```

```
cacccagctg gaaaaaaaaa agactttatt ttcacctgaa attcattaat ttccacttga    6540
aattccacct gcagttgtag caggacctga cacttgggcc ccatggaaat cacaggtatt    6600
gcctgacaca gtggttcatg cccatagtgc cagcactttg agatgccaag gtgggaggat    6660
cacttgagcc caggagttcg agatcagcct gggtgacaga gcaagacccc gtctctaaaa    6720
aaaattcttt ttttttttc aagacagagt cttgctctgt cgcccaggct ggagtgcagt    6780
ggtgcgatct cggctcactg caagctccgc ctcccaagtt aacaccattc tcctgcctca    6840
gcctcccgag tagctgggac tacaggcccc gccaccacgc ccggctaatt tcttgtattt    6900
ttagtagaga tggagtttca ccgtgttagc caggatggtc tcgatctcct gacctcatga    6960
tctgcccgcc ttggcctccc aaagtgctgg gattacaggt gtgagccacc acacccggat    7020
tacaaaaact ttttagataa ttatctgggc gacctgcctg accaacatgg agaaaccctg    7080
tctctactaa aaatacaaaa ttagccggac atggtggcgc atgcctgtaa tcccagctac    7140
ttgggaggct gaggcaggag aatcatttga acccaggaag cagaggttgc ggtaagccga    7200
gatcatgcca ctgcactccg gtctgggagt gcactccaac aagaaggagt ttcgctcttt    7260
ttgcccaggc tggagtgcag tggtgggatc tcagctcacc gcaacctcca cctcccgggt    7320
tcaggcgatt ctcctgcctc agcctcccaa ggagtagctg ggattatagg tatgcatcgt    7380
cacacccggc tacttttgta tttttagtag aggcaggttt ccaccatgtt ggccaggctg    7440
gtcttgaact caagtgatct gccctctttg gcctccttct caggaaaaaa aaaaaatcac    7500
aggtatttac aggccattcc aagtgccaaa agattgtttt tgctcatggt gacttcagta    7560
tcacagatgt taggagactt gctgctatat gttaagaaag aagcacaaat gttgctgtag    7620
cccaaacttt tttcctcatg tttcattgca tttcagctta attggttccc ctggtattcc    7680
tatgtatttt gtggagtgct tttaaaatca taagttggag tagaggtctt tctgtgggct    7740
tcaccagact gccgagatca gggtcgaaac aggtgaggac cccttctctg gagagagtct    7800
cctttctcct ctaagaggaa aggttttgag atcttttgtc cattttccca ccttagcact    7860
tcatcagcct taaaagaagc tggaattttt ttttttttt ttggagatgg gatctcgata    7920
tgttgcccag gctggtcttg aaccccttgg ctcaagcgat cctccagcct cagcctccca    7980
aagtgctggg attcgaggca tgagccaccg agcccaccgt gcagatggat gttttttgtgc    8040 atgcttttga tgaatgcttt ctctctctca gcctgtgccc agggcacctt caagcccctg    8100
tcaggagaag ggtcctgcca gccatgccca gccaatagcc actctaacac cattggatca    8160
gccgtctgcc agtgccgcgt cgggtacttc cgggcacgca cagacccccg gggtgcaccc    8220
tgcaccagta agtgaccagc acccaggtgc agttcactgg ggaggggtca cagacctctg    8280
aggtggaccc tcacatggcc cccatcctcc ctgggcttct tcccttttgtc cctggcatgc    8340 ttgtccctag cccggaggaa catgtggagc ccactgtctc caaggcaaga gtccagcatg    8400
gctgctggtg cctccattgc cctctcccca ccaccgcaga gcaggtcggc ctctgcctga    8460
ctccctggtc tcctgcagcc cctccttcgg ctccgcggag cgtggttccc cgcctgaacg    8520
gctcctccct gcacctggaa tggagtgccc cctggagtc tggtggccga gaggacctca    8580 cctacgcccct ccgctgccgg gagtgccgac ccggaggctc ctgtgcgccc tgcggggag    8640 acctgacttt tgaccccggc cccgggacc tggtggagcc ctgggtggtg gttcgagggc    8700
tacgtcctga cttcacctat accttttgagg tcactgcatt gaacgggta tcctccttag    8760 ccacggggcc cgtcccattt gagcctgtca atgtcaccac tgaccgagag ggtgagactt    8820
gggggctggg gcggctggtg gtctggcggg agagatgtca ctgagggcct gaaggggaga    8880
```

```
ggcaggggct gtgaagttgg gtaccccgga agtgtgaggg gctaaggctt tgggggcaag    8940
aggcagaaag agggcaatgg ctgggcgcag tggctcacgc ctgtaatccc agcactttca    9000
gaggctgaga caggcggatc acttgagccc tggagttcaa gaccagcctg ggtaacatag    9060
gaagatctct ctacaaaaaa taaaaatatt agccaggcga ggtggtgcat gcctgtggtc    9120
ccagctactc aagaggctga ggcaggagga ttgcttgagc ccaggagtcg gaggctgcag    9180
tgagctatga tcgcaccgct gcatgccagc ctgggtgaca gagcagtgtg agatcctctc    9240
tcaaaataaa tgaataagaa agagagggtg aggagctcgt aaagctgggc tggagagtta    9300
agtacaggaa ggcccccagt gggactgggg ccagagagaa tcagaaggaa ttctcgaaac    9360
agccaggggg aaattgagac aagtgtagcc agcagaggaa gtgttggaaa agataaggga    9420
catggccagg ctgatcacaa ggtcaggagt caagactag cctggccaac gtggtgaaac    9480
cccatgtcta ctaaaaataa aaaaattagc caggcatggt ggtgggcacc tgtaatccac    9540
ttgggaagca accagaagaa ttgcttgaac ccaggaggcg gaggttgcag taagctgaga    9600
ctgcgccact gcactccagc ctgggtgata gagcacgact ccgtctcgaa aaaaaaatt    9660 tttttttaagt taagggacag agctaccatg cacaagggtt ccctgtgtct ctgcctctca    9720
cagtacctcc tgcagtgtct gacatccggg tgacgcggtc ctcacccagc agcttgagcc    9780
tggcctgggc tgttccccgg gcacccagtg gggctgtgct ggactacgag gtcaaatacc    9840
atgagaaggt aaggccatcc cccagccctg gggtgggtgg gcaatgggtt gtgctctcct    9900
ggctgggaca cctgggttgc aggcacctgg caggcatttg aattccagct ctgccatgga    9960
ttccctgggc agccttgggt aagccccttg gcctgtctga gcctcagact cttcatctat   10020
aaaatagtta ctgtaatagt taccagcagc tggacacagt ggctgaggtt gggtgcggtg   10080
gctcacgcct gtaataccaa gcactttggg aggctgaggc gggcagaatg cttgagccta   10140
ggagtttgag accagcctgg gcaacatggt gaaacttcat ctctataaaa aacttaaaat   10200
gggccgggcg cggtagctta cgcctgtaat cccagcactt tgggaggccg aggtgggcgg   10260
atcacaaggt caggagtatc gagaccatcc tggctaacac ggtgaaaccc catctctact   10320
aaaaatacaa aaaattagcc aggcgcggtg gcaggcgcct gtagtcccag ctactcggga   10380
ggctgaggca ggagaatggc gtgaacccag gaggcggagc ttgcagtgag ccgagatagc   10440
gccactgcag tccggcctgg gcgaaagaac aagactctgt ctccaaaaaa aaaaaaaaa   10500 aaaaaaacg caaaaaatac ttaaaatgaa aaaaattaga ctgggcacag tggctcatgc   10560
ctgtaatccc ggcactttgg gaggccgagg tgggtagaac acctggggtg aagagttcga   10620
gaccagcctg gccaacaagg tgaaatcccc gtctctacta caaatagcaa atcagctga   10680 gtgtgttggc gggcccctgt aatcccagct actcaggagg ctgagacagg agaatcactg   10740
gaacccaagt gattctcgac ttgaggtcga ggctgcagtg agtcgtgttt gcaccattgc   10800
attccagcct gagaaagtga gaccttgtct taaaaaaaag gaatgatatt atgaatacag   10860
cacatggctt gcatgcgtaa gttctcccaa aggcctcacc agttgcaagg caggctagtg   10920
atgggagtgg agggcgaggg aaggaggcag gaagagcaac aggaacttgg gttcccgggt   10980
gacggccacc ccactacctc tcccggacag ggcgccgagg gtcccagcag cgtgcggttc   11040
ctgaagacgt cagaaaaccg ggcagagctg cggggggctga agcggggagc cagctacctg   11100
gtgcaggtac gggcgcgctc tgaggccggc tacgggccct tcggccagga acatcacagc   11160
cagacccaac tggatggtga gcctggggaa ggggtgagg gtgggggttg gaaagaccccc   11220
```

```
caaagttcct gggaagaccc caggtctcca aagtcccatc atctttttt ttttttttt   11280
tttttgagat ggagtcttgc tctgtccctc aggctggagt gcagtggcac catctccgct   11340
cactgcaacc tccgcctccc ggattcaagc cattctcctg cctcagcctc ccgagtagct   11400
gggattacag gcgcctgcca ccgcgcctgg ccgattttt gtattttag tagagacggg   11460
gcttcaccgc gttggccagg ctggtctcga actcctgacc ttgtgattcg cccgcctcgg   11520
cctcccgaag tgctgggatt acaggcatga gccactgcac ccggtcaaag tcctatcttc   11580
atgtccttct tcctgtggat cacatggcat gccctagaga ggagagaacg taagatgtcg   11640
aaaccaaaac caacagctga gttttgtgaa gtctggcctg cttcactctg tacccccagg   11700
ctggagcgca gttgctcgat caaagctcac tgcacagcca ggcacagtgg ctcaccctgt   11760
aaccccagca ctttgggagg ctgaagcagg aggatcactt gaggtcagga gttcgagacc   11820
agtctgacca gcatggtgaa accgcgtctc tactaaaaat atagaagtta gctgagcgtg   11880
gtggtgcaca cctgtaatcc cagctactcg ggaggctgag gcaggagaat cgcttgaacc   11940
tgggaggtgg aggttgcagt gagctgagat tgtgccagtg cactccagcc tgggcaacag   12000
agcaagactc tgtctcaaaa aaaaaaaagc tcaccgcagg cttgactttt agcaacaacc   12060
tgaccctga gctccccatt ccccatccaa caaaatggga atatcatgaa gcttcctgca   12120
gggctttgag gattggaggt aacaggttat ttttaatatg ctaggccagt ggctttcttt   12180
tttctttcac atttttttt ttgagacgga gtctcactct gttgcccagg ctggagtgcg   12240
gtggcgcgat ctcagctcac cgcaagctcc acctcctggt ctcgatctgc tgacctcctg   12300
atccacccgc ctcggcttcc cgaaatgctg ggactgctgg cgtgagccac cacgcccggc   12360
ctaactttt cttttttta agagacacgg tctttttat cacccaggct ggagtgcggt   12420
ggcaccatca tagctcattg cagcctacaa ctcccgagct caaccaatcc ttccaccttca   12480
gcctcccaag tagctggggc tataggcatg tgctaccgtg ctcaactaaa ttttttta   12540
tgttttgttg agacagtttc cctatgttgc ccaggctggt ctcaaattcc tgacctcgag   12600
caatcctccc gcatcggcct cccaaagtgc tgggattaca ggcatgagcc gccacaccca   12660
gcattggacc agtggctttc taaaccttgt aattttctgt aatagcttta ctgaaataca   12720
gttccctgc catacaattt gcctgttcaa agtgtacaat cgatgacttt tgatacattc   12780
acagaattgt gcagtcacca ccacaagtaa ttttgggaca ttttcagcac cctcaaaaga   12840
gaccctatag cccttagcca tcacccccca cccagatctt tctgttgcct tagtccctgg   12900
caagcactaa cccactttct gtcttgaaat cttccagtgt ggtcttttgt gactgttcac   12960
cgagcagaat gttttcaagg tttatgtatg ttgtagtata tatccgtggg ttttttggt   13020
tgtggtttgt ttttgttg ttttggaaac agggtctcgc tctgtcaccc aggctggagt   13080
gcagtggttc aattacagct cactgcagcc tcaacctccc aggctcaagt gatcctccca   13140
cctcagcctc caagcagct gggactgtag gcatgagcca ccatgcccag ctaattttt   13200
ttggtatttt ttgtaaagac agggtttcac catgtttccc aggctggtct cgaactcctg   13260
agctcaggca atccacccac ctcagcctcc caaagtgctg tgattacagg catgagccac   13320
tggacctggc ctgtttttg tttttgtttt gaacacacga ttttgctttg tcacccaggc   13380
tggaatgtaa tggtctgatc atagtgcatt gcagcctcaa actcctgggc tcaagcgatc   13440
ctcctacctc agcctcctga gtatctggga ccacacgtgc tcaccaccat gcttggctaa   13500
ttattattat ttttttgatag agacggggtc ttgctatgtt tcccaggctg gtcttgaaca   13560
cctggcctca cacaatcctc ccacctcagt atctcagagt gctgggatta caggcatgag   13620
```

```
ccactgctcc tggccaatat ttcatttctt tttatggaga cgtaataatc agttgtatgg    13680
aaatagctga ttttgttttt tattgtatct tttggtgaac atttcaattg tatcgacttt    13740
ttggataaaa acctgaaaat gtttcacctt tagaacgttt cattgaatgg agatttttt    13800 gtggactctg gtatttatac tagaaccaaa tcaaaaccac tctggcggct gggcatgcct    13860
aggctggttt gagactagcc tgtccaacct ggtgaaagcc catctctact aaaaatacac    13920
aaattagccg agcatggtgg tacacacctg taatcccagc tactcaggag ctgaggcag    13980 gagaatcgca gaacccggga ggcggagatt gcagtgagct gagattgcgc cactgcactc    14040
cagcctgggc gacagagtga gactgcgtct caaaaaaaca aacaaaaaat tactctggca    14100
gtaagaaaag atttcgaaac ttcctccctt gccctgaggt acttcagagg agcctgctgg    14160
cccctggggg agagtttgaa acccactgtt tgttccctga ccttgcctgc ttgtgtcctc    14220
tccctccacc tgtcccctgt actggggacc tgttctcagg agatcacagt tcattgctca    14280
aagccggggc tggggcctcc tacaggacca tcagtttctc ctgatcagca gccttccctt    14340
ccgcagagag cgagggctgg cgggagcagc tggccctgat tgcgggcacg gcagtcgtgg    14400
gtgtggtcct ggtcctggtg gtcattgtgg tcgcagttct ctgcctcagg taagggctct    14460
gacacccaga ggcccctgga agccctcagt tgatggccac ctgcctgggt gctacaggac    14520 aagccttct ggctgtcccc agcctctttt tacttgaaat cttctccaat ccctgctcct    14580
tcctttggtg tgtgtgcctc ataaagatgt gtgactcagt ttacctttg ttcctttccc    14640 atcggctaca ggaagcagag caatgggaga gaagcagaat attcggacaa acacggacag    14700
tatctcatcg gacatggtgg gttgccctaa tttgatggga ataggggctt ggggccgggt    14760
gtggtggctc ctatctataa tcccagcact ttgggaggca gaggtgggca gatcacttga    14820
ggtcaggagt tcgagaccag cctggccaac atgttgaaac tccatctcta taaaaaatac    14880
atcagtcagc caggcatggt ggtgggcacc tgtaatccca gctactcagg aggctgaggc    14940
agaagaatca ttttaacccg ggaggcggag attgcagtga gccaagatcg cgccactgcg    15000
ctccaggcct gggtgacaga gcgagactcc atctcaggaa aaaaaaaaa aaaaaaaaa    15060 accacggaga caggggtttg gggctaaaag ctatgagccg agcctccgag tccagtggga    15120
gttaattccc agctgacggg gccctgcctg atttctcagg tactaaggtc tacatcgacc    15180
ccttcactta tgaagaccct aatgaggctg tgagggaatt tgcaaagag atcgatgtct    15240 cctacgtcaa gattgaagag gtgattggtg caggtgagag ccgaaggctg cccgggcacc    15300
tgggaacgaa gcggggtgg gcagggccac actggagcgg gagagctgat gacctctgcg    15360
tccttgtttg aaggtgagtt tggcgaggtg tgccggggc ggctcaaggc cccagggaag    15420
aaggagagct gtgtggcaat caagaccctg aagggtggct acacggagcg gcagcggcgt    15480
gagtttctga gcgaggcctc catcatgggc cagttcgagc accccaatat catccgcctg    15540
gagggcgtgg tcaccaacag catgcccgtc atgattctca cagagttcat ggagaacggc    15600
gccctggact ccttcctgcg ggtgagcacc ctccctggct tctgcggcca cccggagttc    15660
ccacttacac ccagaggcca cttgggttaa gaagccagga cagacagtgg gtcccaggtc    15720
acctcctcca gccttttcct cttgggctaa gccctggtcc tctgcctttt cttttttta    15780 agacagagcc tcgctctgtc gcccaggctg gagtgcagtg gcgcgatctc ggctcattgc    15840
tgtctccacc tccagggttc aagcgattct cctgcctcag tctcccaagt agctggtact    15900
ataggcatgc accaccatgc tgactaattt ttgtattttt agtagacaca gggtttcacc    15960
```

```
atgtaggcca ggctggtatc aaactcctga cctcaagtga tctccccacc tcagcctccc   16020
aaagtgctgg tattacaggt gtgaggcacc acgcctggcc agccctctgc ctttaatttt   16080
ccctctggga aaggctgggc tcctgggacc ttcctttccc actgccccat acagctgaag   16140
gttgtcattc cttcttttt tttttaattt tgttttaatt gaattttttt ttttgagat   16200
ggagtttcac tcttgttgcc caggccggag tgcaatggca agatcttggc tcaccgcaac   16260
ctccgcctcc caggttcaag cgattctcct gccttagcct ccccagtagc tgggattata   16320
ggcatgtgcc accacgcttg actaattttg tattttagt agagacgggg gtttctctgt   16380
gttggtcagg ctggtctcga actcccgacc tcaggtgatc cgcctgcctc ggcctcccaa   16440
agtgctggga ttacagacgt gagccaccgc gcccggccaa tttttttttt ttttttttaa   16500
gacagagtct cactctgtcc tctaggctgg agtgcagtgg tgcattcata gctcactgta   16560
gccttgacct cctgggctca agtgatcctc ccgcctcagc ctcctgagta gctggaacta   16620
cactcatgta ccaccatgct cagcaaaattt ttaaaatttt ttgtagagac aggatctcga   16680
taggttgccc aggctggtct gaactcctgg cctcaagcga gctccctcc tcagcctccc   16740
acagcactgg gattgcaggc atgagccact gtgcctggcc tgtcattcct tcttttgaca   16800
aatatttact gagtgctttc tacgcaccgg tcatcctccc agtccccagg aataaagcta   16860
tacacacggc aaactggatt tctcctcttg gggagcagag ggtctaatgg ggcaggggga   16920
ctgaaaatta gcaagtaaat agacaggctt tttaaaaaag taaacaaatc atttcaaatg   16980
tgaaaaaaag caaacggggt ccttcatgca gatgtggcta gagaggaaag agaactgctt   17040
aatttatttg gtcactttac cagatttta tgactttttt ttttttttta actttattaa   17100
gcttttcttt tttcttgaga tggagtttcc atctgtcacc caggctggag tgcagtggtg   17160
cgttcttggc tcaccgcaac gtccacctcc tgggttcaag tgattctcct gcctcagcct   17220
cctgagtagc ttggaattgc atggcatgca ccaccatacc cagctgatgt ttgtattttt   17280
agtagagaca gggtttcatc atgttgccca ggctggtctt gaactcctgg gctcaagtga   17340
tccacccatc tcggcccctc aaagtgctgg gattacaggc atgagccacc atgcctggcc   17400
taggcatctt tttaaaaaaa tcaaaacatt tttctatgta gcaaaataac attgcattga   17460
acagagttat agcgattccc tagcgtcatt gaatacccag ttgattttca cgtttctcta   17520
gttgttctaa agatgtcctt cactgctgct ttattccaac caggatccag ttcaagaccg   17580
ggctttgtac ctggttatta tatatatttt atttatttat tttagaaaca aggtcttgcc   17640
ctttcgccca gttagagtg cagtggtgca atcatagctc actgcagcct ccaaactcct   17700
tggctcaggt gatcctcctg cctcagcctc ctgggtagct ggaactacag gtgcacacca   17760
ccacacctgg ctaattttta aattttttac ggagatgggg gtctcgctat gttgcccagg   17820
ctggtctcaa actcctggac tcaagcgatc ctccctcctt aacctctcaa agtgctggga   17880
ttacaggcgt gagccaccac gcctgctgat tattatattt tcgagcctct ctaaatcttg   17940
agcagttcct catgatgaca ctgacacact gaagggttag gtcccttgtc cgcctgaatg   18000
tcttgatttc tggatttatg aaattcttct tatgggatca tttagcttgt ctctctgtat   18060
ttcctgtaag agaagctcta tctgatgtgg ggttttttg gttttgtttg tttgtttttt   18120
gagatggagt cctgctgtcg cccaggctgg agtgcagtgg cacaatctcg gctcactgca   18180
acctccgcct cctgggttca agagattctt ctgcctcagc ctcctgagta gctgggacta   18240
caggcgagtg ccaccatgcc cagctaattt ttgtatttt agtagagaca gggtttcacc   18300
atattggcca ggatggtctc gaacttctga cctcgtgatc tgcccaccac ctcagcctcc   18360
```

```
cacagtgctg ggattacagg catgagccac tatgcccggc taattttttgt atttttagta   18420
gagacagggc ttcgccatgt tggccaggct gatctgaaac ccctggcctc aagccatcca   18480
ccctccttgg cctcccaaag tgctgggatt aaacgcgtga gccaccgtgc ctggtcgaag   18540
agacagaaag ggtcttaaag gttcagtgac acacacctgt aatcccagca ctttgggaag   18600
ctgaggctgg tggatcactc gaggccagga gttagagatc accctgggca acatggtgaa   18660
accccgtctc tacacaaaat acaaaaatgg cagagcatg atggtgcata tctgtagtcc   18720
cagctactcg ggaggctgag gcgggaggat cacttaagcc tgggagatcg aggctgtagt   18780
gagccatcat tgcactactg cattccagcc tgggcgatcc catctcttaa aaagagagag   18840
agatgggaag accagcacag gtgaaactgg tgaacagagg agagatggta gatgctgcat   18900
tgggcagtgt gacgggaacc cgctggaggg ctttggcagg agagtagttt aagaggatcc   18960
cagctgggca cagtggctca cacttgtgat cccagcactt ggggaggccg gggcaggtgg   19020
atcacttgag gtcaggagtt cgagaccagc ctggccaaca tggtgaaacc ctgtctgtac   19080
taaaaataca aaaaccagcc aggcatggtg gtgcacccct gtaatcccag ctactcagga   19140
gactaagaca ggagaatcgc ttgaactcag gaggcagagg ttgcagtgag ccaagatcac   19200
gccactttac tccagcctgg gcagtagagc gagactccat ctcaaaaaaa taaataaata   19260
aaagacctc tttgctgggt gctagggagc aagagcagga gctgggagag gcctgcagca   19320
gaagcctgtt gccagcatcc aggccgtggg gtgaagggaa gggtttggat ttgggacatg   19380
tcttggaagc atcaccagca gaacttgctg atggattgga agtggctggt gagggagaaa   19440
aggggggtcaa aggaaactct gaggtctata ccctgaccat ctggcaagtg gtggtgttgc   19500
cacaaactga gcggggagta gggcaggtgc aggtctggag gatggattca aaattcagtt   19560
tttggagtct atgtccctgg ttctgtaggg ctgcagatgg tctgccaaat cttagcggaa   19620
cccagaatac gggatttgtt tactgtctgt gacttgttgg tttccctggt gagagcaaac   19680
tctttaaagg tcaaggttgg gcttcagacc ttggtttttg caccgatcat tggtcatact   19740
gcagttcctc actcttctct tgcaaatcca tacacagcta gtccaagaga gctgaacagc   19800
tttgtggttg gatcagcacc aatgtatctc cacctgtaga cgggttgctc aggtgactca   19860
tgcctgtaat cccagcacct ggggaggcca aggtgggaag attgcttgag gccaggagtt   19920
ggagacaagc ctgggaaaca cagtgagacc ccatatctac caaaaaaacc cctttgtttt   19980
aattagccag gtgcagtggt gtgcacctat agtcccagct actaaggagg ctgaggcaga   20040
aggatcattt gagcccagga gtttaaggct gcggtgaacc atgatcgtgc cactgcactc   20100
caacctgggg gaaagaaaga gaccttgtct ctaaaaaaac taaaaaacag aaaagcattt   20160
gttgagtatt tcctgggtat aaagcagtgt accaggttaa atgaaggaa aagttgaaat   20220
aattttttcaa ctcataatcc gattgggaga gactgaatgc ttaccattga agcaggaacc   20280
attgtaagca atgtgttgtg atactgtagc aagagctgag aaaacttggg aaaagagaaa   20340
ggaggaaggc tcacctgagg gagttggggg gcttgcccta caggtgagtt gtgaggtggg   20400
tctggaagtg acagatgcag tttaggaagt ggacgggagg ctgggtacgg tgactcaaca   20460
tctgtaatcc cagtgctttg ggagacccag gcggaaggat cgcttcaggc caggagttaa   20520
agaccagcct gggcaacata gtgggaacct atctctacta aaaattaaaa aattatccag   20580
gcataatggc acatgcctat tgttccagct actcaggagg cttgcctgag cccaggaggt   20640
tgaggctgca gtgagctatg atggcaccac tgcactccag cctgggcgac agaacaagac   20700
```

```
cctgtctcta aaaaaaaaag atgtggatgg gaggggaac ggtgggtggg ctgtcctcac    20760
caagcccca ccctatctgc tctccagcta acgacggac agttcacagt catccagctc    20820
gtgggcatgc tgcggggcat cgcctcgggc atgcggtacc ttgccgagat gagctacgtc    20880
caccgagacc tggctgctcg caacatccta gtcaacagca acctcgtctg caaagtgtct    20940
gactttggcc tttcccgatt cctggaggag aactcttccg atcccaccta cacgagctcc    21000
ctggtaatgc tgggggtaat actgggtgtg agcttcttag gccaggtgg gcagggcagg    21060
ttggaaaggt gggaggctga gggtttggca gccctgctcc agggagagga tacaggagca    21120
ggctgtgggt gggggacag tcagctccag gaagccgact tccagatgtc taggaaaata    21180
acagttggat aacctgggca acatagcaag accccatctc tacaaaaaaa ttaaaagatt    21240
agccaggcgc agtggcatgc acctgtagtc ccagctactt gggaggttga ggcaggagga    21300
ttgcttaagc ccaggagttg gaggctgcag tgagctatga atgtgccact gtactgcaga    21360
ctgggcgaca gagcaagacc ctgtctcaaa agaacagtgg ccaggtgtgg tggctcacgc    21420
ctgtaaatcc agcactttgg gaggctgagg caggaggatc gcctgaggtc aggagttcga    21480
gaccagcctg gccaacatgg gaaaaccctg tcgctactaa aaatacaaaa ttagctgagg    21540
gtggtggtac acgcctgtaa tccgagctac tcaggaggct gaggtaggag aaccagttga    21600
acccgggagg cggagtttca gtgagccaag atcgcaccac tgcactccaa cctgggcaaa    21660
cagagttgga gagtaggagg cttgggcct gagctagggg gaaaaagcag aggcaggtgg    21720
gggactgggg ggcagtgtgc tgggtctggt gagtccctca gtgagtcccc cagctcacct    21780
tttctccttt ttctgcaggg aggaaagatt cccatccgat ggactgcccc ggaggccatt    21840
gccttccgga agttcacttc cgccagtgat gcctggagtt acgggattgt gatgtgggag    21900
gtgatgtcat ttggggagag gccgtactgg gacatgagca atcaggacgt aagtgtcccg    21960
tggtcctacc aagctttcct cgagtgttct ctcacctggg atttggggtg aagggtgggt    22020
tcccagagag tcatcactgc tgggttcttg agaccatgga gatgacaaaa aggagaattg    22080
atctttgtat caaagagttg agatacaggg ccaggcctag tggctcaagc ctgtaatccc    22140
agcactttgg gaggccaagg tgggcagatc acctaaggtt aggagttcaa gaccagcctg    22200
gccaacatgg tgaaaccccg tctctaaaaa aatacaaaaa attagcccag catgatgggc    22260
gggtgcctgt aatcccagct actcaggagg ctgagacagg ataatcgctt gaacccagga    22320
acagaggttg cagtgagctg agatcacgcc attgctttcc agcctgggca actgagcgag    22380
actctgtctt aataaataaa taaaagagtt gggtacagca tatttgggtc gcagaaggat    22440
gcagagatgg agggcagggt tgagaggtaa catgtctgta tcatagccca agagctgctg    22500
gggccttcag ccacagagag cttcaactcc ggctaggagg attcctggat ctgttatttt    22560
ttgggggggct gtggctccta tcctaccatc ttccaagtca ccatttcctg ggcctgttag    22620
catctttgct tttcctggac agcctcaccc agagcttctt cccctctttc caggtgatca    22680
atgccattga acaggactac cggctgcccc cgccccaga ctgtcccacc tccctccacc    22740
agctcatgct ggactgttgg cagaaagacc ggaatgcccg gccccgcttc ccccaggtgg    22800
tcagcgccct ggacaagatg atccggaacc ccgccagcct caaaatcgtg gcccgggaga    22860
atggcgggtg aggactgcag agaatgggcc ctccttcccg ctctctgccc ccactccttg    22920
cccagaagtg tccgttcatt ggtgttgggt gggagggcct ctgtccgcct ctgcaaggct    22980
gggttccacc tcctccccccg gacctgggcc tggtactcag cattcctccc catccttgcc    23040
ccctagggcc tcacaccctc tcctggacca gcggcagcct cactactcag cttttggctc    23100
```

```
tgtgggcgag tggcttcggg ccatcaaaat gggaagatac gaagaaagtt tcgcagccgc   23160
tggctttggc tccttcgagc tggtcagcca gatctctgct gagtaagcag tggcaggagc   23220
tggagtgggg ctgggagagc ggggcagctg gagtcaggcc cacggggtct ccagggcgtt   23280
ttggggtcag cttcgggtgc caatgctgtc ttcttgcact gcgctcatgc catgcctaga   23340
agggccccag aggagcagtc acagccccat ggagctgagg acccaaggac tctttggggc   23400
cagcctgccc gcctcacctc ctcctgccat cacagccctg ggccatcgcg cttccgcctc   23460
tcacttctag ctatctttgt gcatctatct gcattccagg cccggctctc acggtaacaa   23520
tgtgtcaact cgggttctct ttttccaacc ataaaaggag aagattgggc taggttttgg   23580
agatcctctt cagcttttat gtgaaatggt tttatgattc cttgcctccc aaaggctgcg   23640
tatccccact tggcctttgt ctgctactcc ccctttctgc cttcccgttc ctctcccaag   23700
atctcctctc accccaggtt gaataacaga aatagaagga atagaaatct gaaggccggg   23760
catggtggct catgcctgta atgccagcac tttgggaggc cgaggtgggc agatcacttg   23820
aggttaggag ttcgagacca ttgtggacaa cttggtgaaa ccttatgtct actaaaaata   23880
caaaaattag ctgggcatgg tggtgcgtgc ctgtaatacc agctactgag gaggctgagg   23940
caggagaatc gcttgaaccc gggaggtgga ggttgcagtg agccgagatc gcaccactgc   24000
actccagcct ggatgacaga gtgaaattcc atctcaaaaa aaaaaaaaaa aaaaaaaag    24060 aaatgtgaag gccaggtggt ggctcacgcc tgtaatctca gcactttggg aggctcaggt   24120
ggaccgattg cttgagccca ggagtttgag agcagcctgg ccaaaatagc aaaaccccat   24180
ctctacaaaa caaaaacaaa aaattagct gggcatggtg gtgcgtgcct gtggtcccag    24240
ctactcagga ggctagagcc agagggtctc aggccagtct gcccctgccc cacggggcct   24300
gggcacatcc ctccctaatt cttcccagcc tctctctgac ccaggggggcc tcctctccct  24360 tttttcccct tatctcagcc tccagccatc agcaacctcc tcttcctctc cacccagctc   24420
ttcctctccc acttcggcct tttctttctc acactccatt tccctctacg gcaatctgtg   24480
cagcctcttc ccccagtctc attttgcggg cttttctctc ttttcttttcc ttccctggca  24540 cccaagccaa aggccctgcc tctggcctcc agccctaccc ccttctgcgg ttgcacagaa   24600
ggatggctgc ccagctctta aaaaaactgc ccgggaactg ttgacatctg ttctccctcc   24660
cccgctggct tttctgattg gcttacaatc ctgaggctag gaccgtctca ggagccaaga   24720
gaggagagcg gccacaggga acctagggtc tcaccaagct ctcctttcct tctgcaggga   24780
cctgctccga atcggagtca ctctggcggg acaccagaag aaaatcttgg ccagtgtcca   24840
gcacatgaag tcccaggcca agccgggaac cccgggtggg acaggaggac cggccccgca   24900
gtactgacct gcaggaactc cccacccag ggacaccgcc tccccatttt ccggggcaga    24960
gtggggactc acagaggccc ccagccctgt gccccgctgg attgcacttt gagcccgtgg   25020
ggtgaggagt tggcaatttg gagagacagg atttgggggt tctgccataa taggagggga   25080
aaatcacccc ccagccacct cggggaactc cagaccaagg gtgagggcgc ctttccctca   25140
ggactgggtg tgaccagagg aaaaggaagt gcccaacatc tcccagcctc cccaggtgcc   25200
cccctcacct tgatgggtgc gttcccgcag accaaagaga gtgtgactcc cttgccagct   25260
ccagagtggg ggggctgtcc caggggggcaa gaagggggtgt cagggcccag tgacaaaatc  25320
attgggtttt gtagtcccaa cttgctgctg tcaccaccaa actcaatcat ttttttccct   25380
tgtaaatgcc cctcccccag ctgctgcctt catattgaag gttttttgagt tttgttttttg  25440
```

```
gtcttaattt ttctccccgt tcccttttg tttcttcgtt ttgttttct accgtccttg    25500 tcataacttt gtgttggagg gaacctgttt cactatggcc tcctttgccc aagttgaaac    25560
aggggcccat catcatgtct gtttccagaa cagtgccttg gtcatcccac atccccggac    25620
cccgcctggg acccccaagc tgtgtcctat gaaggggtgt ggggtgaggt agtgaaaagg    25680
gcggtagttg gtggtggaac ccagaaacgg acgccggtgc ttggaggggt tcttaaatta    25740
tatttaaaaa agtaacttt tgtataaata aagaaaatg ggacgtgtcc cagctccagg    25800
ggtgatgggg gtgatggact agatttctaa ggagagtggg gctgggtagg gagggctttg    25860
tggctgaccg agaggtgtca gaggtctgga ggctgcaggg ctgtaggggc tggaacttgg    25920
ttatcagccc cagggtatgt ttgaggtggt ggggtgggg ccgagcgaga tgaatcattc    25980
gcagctgctt ctaacgtctc                                              26000

<210> SEQ ID NO 7
<211> LENGTH: 4235
<212> TYPE: DNA
<213> ORGANISM: Homo sapiens

<400> SEQUENCE: 7
ctcggcccgg cggcgcgagc agagccactc cagggagggg gggagaccgc gagcggccgg      60
ctcagccccc gccacccggg gcgggacccc gaggccccgg agggacccca actccagcca     120
cgtcttgctg cgccgccgcc cggcgcggcc actgccagca cgctccgggc ccgccgcccg     180
cgcgcgcggc acagacgcgg ggccacactt ggcgccgccg cccggtgccc cgcacgctcg     240
catgggcccg cgctgagggc cccgacgagg agtcccgcgc ggagtatcgg cgtccacccg     300
cccagggaga gtcagacctg ggggggcgag ggccccccaa actcagttcg gatcctaccc     360
gagtgaggcg cgccatggga gctccgggtg ctgctctgct gggcttcgtt ggccgcagct     420
ttggaagaga ccctgctgaa cacaaaattg gaaactgctg atctgaagtg ggtgacattc     480
cctcaggtgg acgggcagtg ggaggaactg agcggcctgg atgaggaaca gcacagcgtg     540
cgcacctacg aagtgtgtga cgtgcagcgt gccccgggcc aggccactg gcttcgcaca     600 ggttgggtcc cacggcgggg cgccgtccac gtgtacgcca cgctgcgctt caccatgctc     660
gagtgcctgt ccctgcctcg ggctgggcgc tcctgcaagg agaccttcac cgtcttctac     720
tatgagagcg atgcggacac ggccacggcc ctcacgccag cctggatgga gaaccccta     780 atcaaggtgg acacggtggc cgcggagcat ctcacccgga agcgccctgg ggccgaggcc     840
accgggaagg tgaatgtcaa gacgctgcgt ctgggaccgc tcagcaaggc tggcttctac    900
ctggccttcc aggaccaggg tgcctgcatg gccctgctat ccctgcacct cttctacaaa    960
aagtgcgccc agctgactgt gaacctgact cgattcccgg agactgtgcc tcgggagctg    1020
gttgtgcccg tggccggtag ctgcgtggtg gatgccgtcc ccgcccctgg ccccagcccc    1080
agcctctact gccgtgagga tggccagtgg gccgaacagc cggtcacggg ctgcagctgt    1140
gctccggggt tcgaggcagc tgaggggaac accaagtgcc gagcctgtgc ccaggcacc    1200 ttcaagcccc tgtcaggaga agggtcctgc cagccatgcc cagccaatag ccactctaac    1260
accattggat cagccgtctg ccagtgccgc gtcgggtact ccgggcacg cacagacccc    1320 cggggtgcac cctgcaccac cctccttcg gctccgcgga gcgtggtttc ccgcctgaac    1380
ggctcctccc tgcacctgga atggagtgcc cctggagt ctggtggccg agaggacctc    1440
acctacgccc tccgctgccg ggagtgccga cccgaaggct cctgtgcgcc ctgcgggga    1500 gacctgactt ttgaccccgg ccccgggac ctggtggagc cctgggtggt ggttcgaggg    1560
```

```
ctacgtcctg acttcaccta tacctttgag gtcactgcat tgaacggggt atcctcctta    1620
gccacggggc ccgtcccatt tgagcctgtc aatgtcacca ctgaccgaga ggtacctcct    1680
gcagtgtctg acatccgggt gacgcggtcc tcacccagca gcttgagcct ggcctgggct    1740
gttccccggg cacccagtgg ggctgtgctg gactacgagg tcaaatacca tgagaagggc    1800
gccgagggtc ccagcagcgt gcggttcctg aagacgtcag aaaaccgggc agagctgcgg    1860
gggctgaagc ggggagccag ctacctggtg caggtacggg cgcgctctga ggccggctac    1920
gggcccttcg gccaggaaca tcacagccag acccaactgg atgagagcga gggctggcgg    1980
gagcagctgg ccctgattgc gggcacggca gtcgtgggtg tggtcctggt cctggtggtc    2040
attgtggtcg cagttctctg cctcaggaag cagagcaatg ggagagaagc agaatattcg    2100
gacaaacacg gacagtatct catcggacat ggtactaagg tctacatcga ccccttcact    2160
tatgaagacc ctaatgaggc tgtgagggaa tttgcaaaag agatcgatgt ctcctacgtc    2220
aagattgaag aggtgattgg tgcaggtgag tttggcgagg tgtgccgggg gcggctcaag    2280
gccccaggga agaaggagag ctgtgtggca atcaagaccc tgaagggtgg ctacacggag    2340
cggcagcggc gtgagtttct gagcgaggcc tccatcatgg gccagttcga gcaccccaat    2400
atcatccgcc tggagggcgt ggtcaccaac agcatgcccg tcatgattct cacagagttc    2460
atggagaacg gcgccctgga ctccttcctg cggctaaacg acggacagtt cacagtcatc    2520
cagctcgtgg gcatgctgcg gggcatcgcc tcgggcatgc ggtaccttgc cgagatgagc    2580
tacgtccacc gagacctggc tgctcgcaac atcctagtca acagcaacct cgtctgcaaa    2640
gtgtctgact ttggcctttc ccgattcctg gaggagaact cttccgatcc cacctacacg    2700
agctccctgg gaggaaagat tcccatccga tggactgccc cggaggccat tgccttccgg    2760
aagttcactt ccgccagtga tgcctggagt tacgggattg tgatgtggga ggtgatgtca    2820
tttgggagag ggccgtactg ggacatgagc aatcaggacg tgatcaatgc cattgaacag    2880
gactaccggc tgcccccgcc cccagactgt cccacctccc tccaccagct catgctggac    2940
tgttggcaga agaccggaaa tgcccggccc cgcttccccc aggtggtcag cgccctggac    3000
aagatgatcc ggaaccccgc cagcctcaaa atcgtgccc gggagaatgg cggggcctca    3060
caccctctcc tggaccagcg gcagcctcac tactcagctt ttggctctgt gggcgagtgg    3120
cttcgggcca tcaaaatggg aagatacgaa gaaagtttcg cagccgctgg ctttggctcc    3180
ttcgagctgg tcagccagat ctctgctgag gacctgctcc gaatcggagt cactctggcg    3240
ggacaccaga agaaaatctt ggccagtgtc cagcacatga gtcccaggc caagccggga    3300 accccgggtg ggacaggagg accggccccg cagtactgac ctgcaggaac tccccacccc    3360
agggacaccg cctcccccatt ttccgggca gagtggggac tcacagaggc ccccagccct    3420
gtgccccgct ggattgcact ttgagcccgt ggggtgagga gttggcaatt tggagagaca    3480
ggatttgggg gttctgccat aataggaggg gaaaatcacc cccagccac ctcggggaac    3540 tccagaccaa gggtgagggc gcctttccct caggactggg tgtgaccaga ggaaaaggaa    3600
gtgcccaaca tctcccagcc tccccaggtg ccccctcac cttgatgggt gcgttcccgc    3660
agaccaaaga gagtgtgact cccttgccag ctccagagtg gggggctgt cccaggggc    3720 aagaaggggt gtcagggccc agtgacaaaa tcattggggt ttgtagtccc aacttgctgc    3780
tgtcaccacc aaactcaatc atttttttcc cttgtaaatg cccctcccc agctgctgcc    3840 ttcatattga aggttttttga gttttgtttt tggtcttaat ttttctcccc gttcccttt    3900
```

| | |
|---|---|
| tgtttcttcg ttttgttttt ctaccgtcct tgtcataact ttgtgttgga gggaacctgt | 3960 |
| ttcactatgg cctcctttgc ccaagttgaa acaggggccc atcatcatgt ctgtttccag | 4020 |
| aacagtgcct tggtcatccc acatccccgg accccgcctg ggaccccaa gctgtgtcct | 4080 |
| atgaagggt gtggggtgag gtagtgaaaa gggcggtagt tggtggtgga acccagaaac | 4140 |
| ggacgccggt gcttggaggg gttcttaaat tatatttaaa aaagtaactt tttgtataaa | 4200 |
| taaaagaaaa tgggacgtgt cccagctcca ggggt | 4235 |

<210> SEQ ID NO 8
<211> LENGTH: 43948
<212> TYPE: DNA
<213> ORGANISM: Homo sapiens

<400> SEQUENCE: 8

| | |
|---|---|
| gcgcctcgga gctgcctgcg ggcgcacgcc gtcttcccg ccagtctgcc ccggaggatt | 60 |
| gggggtccca gcctgcgtcc cgtcagtccc ttcttggccc ggagtgcgcg gagctgggag | 120 |
| tggcttcgcc atggctgtga aagggactc cgtgtggaag tactgctggg gtgttttgat | 180 |
| ggttttatgc agaactgcga tttccaaatc gatagtttta gagcctatct attggaattc | 240 |
| ctcgaactcc aagtaagtgg cgtccgcgat ccccctatgt ccccgcccg gggtccgccg | 300 |
| cgccgtccgg gcgggaggag gggtcagtcc gcggggcctc ggagcctgtt tctggaacct | 360 |
| cggttccccg tccccaccc caaccccg ccccatttca ctaggtggag actcctcgct | 420 |
| cggctttcca acccgagccc cgctggaacg gacggtctct ccgccttcc tcccccgaac | 480 |
| gctcccaggc gctaaaagct actatcggct cgggtgtcaa gtccgggaag gtgtccgatg | 540 |
| gcgatacctg accctctcct gttttcgagg acgaaggaca tggccacaat ctaggctggc | 600 |
| cggcacgcgg ggactggtgg gctctggaga gaggcggaga tgctgcattc gcggggagcg | 660 |
| cgggcggcgt ggtccggggc ccgcgggcgg gcgaccgggg tggcaggacg ctggcagcga | 720 |
| agcgcgttct ggagagggga gcctggagtc gctacgctgc ccgcagagcc ctggagccgg | 780 |
| ggcgccttgg caccgcgccg ccagcccgag ggtgcgcggg gagctcgcct gcttcgcagg | 840 |
| agaactcggg cgtcgagccc tttcctccgc gccggggaga cgggccttag gcttctccct | 900 |
| gagggcccgc cgcacctcgg cctcccgctt cgttcataag ccggtagccc cggagtatgc | 960 |
| ggtctcgatg gccgacctga ttgtaatgca cttcctataa aagcttaggg ccctgcccag | 1020 |
| tcgacactgc tcctgaagcc ttctccctcg ggaccctggt aggaatggga tccttaggat | 1080 |
| cagatttgct cttaccggac tctacagccg ggagcgagcc aggccttgtg gagagtaact | 1140 |
| ttcagtttgg gccaccagag tgcattcaga atttagaaaa tcccatccat ccctaaatct | 1200 |
| gtgtggtcat aactcgtagt catctgggta ttcagtactg tgtatcccct tatttcgaat | 1260 |
| cacagccaaa acatatttta cagaatcttg gaattgtagt ctcgggaaac ttggagaaga | 1320 |
| agtatgcaga cattagctgg tttctggaga aaacgtttga gatcagaagc aaaatcaatg | 1380 |
| gcctaattga agttgagcaa gttgggcctg gttttaggag aaaagaaatg ggggattgat | 1440 |
| ttagaaatca cgtcttaaag gagtgtgtcc attctcttaa aagtgtcaaa tttcaaattc | 1500 |
| actaacatgt taaccaagaa tcccttcatg aaaagggcga aaacgtcggt tacaaatcgg | 1560 |
| tttaaacaaa tgtttgtatg atgctagaag gcactttcaa caccgctcat acggagaagt | 1620 |
| tacttagctc tgcctccttc catgtagtct gctcttgcat ggattatatt tttaatgtaa | 1680 |
| attgttgtat ttgctgatga agtactgccg gcggcatctt tgcatcgatg ccggctcggg | 1740 |
| aggcgccagg tggtgccgga aggagccggg ctaggacctc gcgcagcagc gggtcccgga | 1800 |

```
gtccgggaga ggcgggcggg cgggcgaggc ggtcgcgggg agcccgcggc gccgctgccc    1860
gcccggtgcc tccagaggtc actcttccat gcggaatcgc gcagcgccag gcctcgcccc    1920
tcccccaggc cgcctgctcc agccactctg cactttcact gaccggttct ctttgaggct    1980
gttttttttt ttcttatgag gatttaatat ttctgtttaa atctagttga aagcaattcc    2040
gttagcctct tcagcgttta gttcggtgtg tgtatcttta tctttgcgct atattaacta    2100
ttagtttgtg tgtatccggt aggagaatta gaaataccta gttgggagaa aaagaaaagt    2160
agaacaatag ttatttcaac ctaaggttta gacgttaata acttcttttt gtaatgtgtc    2220
gagatggggg gtcctggggg gaggtgacag gtactcacca ctcccccccc ccattctgat    2280
gatgaagatg agtctgtctt tccagctatg tccagacctg cgagggccct gcgtttctgg    2340
aagcctgccg tttgcgcggt tgaggttgct gctgctgtct tgtcctccac agcagcattt    2400
cttttaaaat tctcctgata acggcctgcc tggatgactg gataatgtgt gcctggaaaa    2460
ggtctccctt gcagctgaat gctagctcca gagatcagaa agatttcttc ctgtaggagc    2520
cataggaaag agtcctctct aagtttttga gaatgcatac aaccccctga tgacaggggg    2580
tcgctttcct tggggaagtt ttatatttat ttccagagga aagttgaat cggtaaaatat    2640 gatgtggcag gaaggtaatc aaatgcattg aagtttcaca tcagttccta tgaactgtgg    2700
aacaattcat ttgtaatgaa gccgccatca gtaattagat ttgtttcatt cagaggtcag    2760
cttttttagc aggtggtcga cacagggagc atgcagcagc tgtttggata cagggtccag    2820
aaaacccttt gtaaattcag cgtctccgta actactttaa tcacattgtc ggctctcccg    2880
tccctgactg tatgtaataa tggaaagatg tcctgcgtgc tgaaacagta gctgccctgt    2940
taggttattc acattgcttt gatacgttct ggtagagttg ggtccgttgt agccattttg    3000
gttgtttaaa gttttggttt ttttttttgtt ttttttttaa ttcagcagag aacagtaatg    3060
cctagcttcc gtttttaact taacacttca gtagaacatt ttcttccaag agggagattt    3120
tggcctaagt aaagtagtgg gctctttttt aaaaaaaaat taattttact ttaatgtgag    3180
caaatctgta ttggtatggt gttctgcaat gcattacact gactttgaaa atttcgagta    3240
ctaatgcctt atgtctgggg ttaccattcc ctgtgcatca catactagtt agttaacata    3300
gcattttgct tttcccatgt aattttttcc ctatataata ctggattcct gatactaatt    3360
gacttgatac aaaagaatgg ctggatgata tccagataac gtataataca tgggcttcac    3420
cacaatcagg ctctgaataa atacagacct gtcagagatt gataaaataa actacaatgg    3480
atagtgctgt ttaaacagtc cattcaataa catatataag ccagcctgcc ttccattgtg    3540
tctgaaattc ttatttttgt aggtaaacaa atgcacattc agcactgatt gaatagcccc    3600
ttgaactatg ctccacagtt tgcgtttggg ttaatcttgt cggttttaat atagagagaa    3660
aaaagctcaa agcaccaggg gtggaattgt tagtgctttc acatccacat tcctcacatt    3720
ttgtcaggat gataaactgt aggtaatgga ctgtcgttgt tctgcaggac aactgagcca    3780
ggcagagcac aaagactaag ctaaagcgat acctcacaac atgcttggta gccttctttt    3840
cagatgagaa tttatttgag aatcatgtgt ctagggactg cacatcttaa cctcaacagt    3900
tacagcttca agccccagaa acaggagctg gaggttaaga tgatttgcta agcacctggt    3960
tctaaatctt ttacaaagca taagctgttg acgctggttc tgccgacgca aagacatgca    4020
gatgactcca acatttccag aggcttctga cttaagctaa agtgtgtgga caggtgaatt    4080
cgccatgggc ctggagacca gcttgctaaa aactatgtgt ttgaatggtt cctccagaca    4140
```

```
gagtcagctg aagaacaatt ggtggattta tattaaaacc tcttgtctgt aaacttactg    4200
aggtgcatcc ttcggttggt ggatcagtga gataattgcc ttcagatgga cattgcaact    4260
ggagcaacta atccttgct gtctttcctt cctctgaaat cttccaggta gctcccgaga    4320
gcttcagtat gacaccaaac ttcgggcgac gttttagagt gcgttcacct aatgggaaac    4380
tattcgagat cccagcgtga ctgcagtaat gcgtcatagg aatgggagtg cagggggaaa    4440
aggaaataca gattgtagac cctaataaaa aaattttag gaaagatatt tctttaacgt    4500
tttatgagaa cttcattctt aaaatactta attgcaaatt agacaaatag aagtgctctt    4560
ctaaggaagg tgattaaact ggtcctccta tcagcctaat ctctgcctgc ctttgctgct    4620
gacataaaga acctgttttt caggtcactt aatatacatc tacatagatt tgcttatgag    4680 ctcaccccttt gtgtagcgga gtagagcctt aaagaggagt gctcaactgt ttaaaatatt    4740
ttgattaaaa tatgcagaac ccatagaact ataagcttct agtcaggaat tagctctttc    4800
agggaacagc tcccccctcc tttttaaggg gggaattaga aggaggctgg gggaggaata    4860
taagaacagc aaagaaggaa ggatagcaaa tgggacatgt tccgaacagc ttggaaaaac    4920
tcctgtggct tcattgtctc tataaagcca aagaatacaa agacataagc aattcagccc    4980
ttctcccatg atgaagatg taaaccgttg acatgcctcc cctgtttaac ttgtttaatt    5040
ctcattttaa attcagcacg atactagccg tgtgaactct gaagatttct ttagtaatcc    5100
attttgtagt tccgaatcaa aaacaaagtg aaagggtctg acacaatttg cttttatttt    5160
taggcaaatc aaccctggtc atagttaata aggggattac aactcagact aggtctttac    5220
agatgtgatg taaatcaagg gcagagtata aagaaactga tcccttttga ttgaagtata    5280 gtaaaaggc atagagaaac tagcagcagt aatctgattg tatggcaata aaaccaccat    5340
tttctgtctt tcagataaaa ataatgtggt aaatccatgc agttcataag atgtaaaggc    5400
agataaaggg tgaagccatg gcaacatata gattagcttg atgttagaaa tgacacgtct    5460
ctgaaaaggg cgcgggacga aggcccttgc ctccaggctg ttgggcatta tgtgagaacc    5520
acacagactt ggaaactggg attaggaagt atgaaagctc tacttgtggt ctgggatggc    5580
tgaggcagta aagaaaagct gctcagttct tgctcattgg tggtggataa tatggcaaag    5640
gtagatttca ttgactgcct ttttttataga ttgagattgg ggctgattaa aacttcagat    5700
cactgcagtt gttagggcct gggagatttt cctttttaac tcctggccta acagcagcag    5760
ccgttctgta ggattaactg cacttcgcgg tcgttgcctt aatctatttg ggcttcaggc    5820
agggacatgc tgggaaggaa cagagaccag aggggatagg tagggctggg gttatctgaa    5880
aagaaaacag agacctttgg atttcagcca tcttttcaga cccagctccc tctcccgctg    5940
catgggagaa gcaaaggtaa acaggacaca ttgtccctct ccctcagcca cagagctctt    6000
ctgtgagttt tgtctttccc accctggaaa aaaagataaa atacaatttt taaaagggga    6060
gggaggaatt tagtttttaat tcaaatgagt agtaatccaa tatgccaaaa gcagtgggct    6120
ctacctagat gtaattttac tcgtaaatgt gagtcttaaa ctttgagttg aatggggcag    6180
gctgttagag gtggtgtaaa ttacaggatt ataaaatgt tagtgctgcc cagccttaaa    6240
gtcaaaaaca gaaaaatctc tgtgctgttg agtcttcccg ccctctctcc tgaacaacct    6300
tgtaagtaag ctagactttt gttttgcct tccatacttt ccatttcagc cattaaacaa    6360
aataagccat tgaaaccacg attgggttcc atgcagagtg acatccgcaa tcgggtcaag    6420
ccagaaggaa atacttgctc gattgccccc tatttggcat tacaggaaag tctccacact    6480
ttggaagagt ctgaactctc aagacattga aaatgccaaa ggctgcaaac accctgtgtc    6540
```

```
tttcttgatg gagtgcatct tggtgtgttt tacaaagggg aattcagtgc tgttttttg     6600
ttgttgttgt tgttttttt ttttaaagag cagcataggg cccttctaga ctcttggatt     6660
ctgtgtctga caaaatggt cattaaatga gcaatattat aatttagacc catttcactg     6720
attttgttcc aaattctcaa ctgacttgag catctgtttg gggctgtaga tacattgccc     6780
ttgttgactg ttttctcgt ttctatggga attactgtag ccattactat gtagctttca     6840
tagactcaaa acatttttaa agtattgcat ataggctggc catatccagt gcctgttact     6900
ttaccttctt tttctaactt aatgcagcag tctgtattaa cagatccatt tcatttgtct     6960
agcttcatca gagagaggct acccctgat ttacaggctg ctcacatcca agcaccttgc      7020
attctacact tgacagtgat tgctaatggc ccattcaact aaagtatttg cttgttaaca     7080
gggaacagaa catgataaat gtccagcaag cttgctgcct ccttcagctt tcaaacgca     7140
gactggtgca tatttatggc aggcaaatga caaagaaaa agctgaattg ccctggcctc      7200
cagcttcta tcagaaacag ggttaaagtg attaaagcaa tcattcaaga aagcctgcc      7260
gtttgtttac taaccttcat ccaacattta gctttgtagt ctacctgtga aagatattt      7320
cagaagtatt agagataagg aaggaggatc tagcaaacca gtgaaaagag taggtgacca     7380
gttataaaat gctttccatg cacattgaat gccaggcgaa cctatttctg ttattccagc     7440
agacaatcag cagtggctct agattattaa catattttcc tttcatgtat aaattcaaat     7500
atgtaattct agtccaaagc attctgtggc tggtaagcac atacttgctg atttcaaata     7560
agaaaacata gcaagggaaa gctccattaa acaagttgtt tctgcccta gtaattctct      7620
aaacaagata ggaagaaaaa gtggacagta gtggagtatt aatagtgtgc tcttttcatt     7680
ctctaaagca cgagtaagta agcgttcaaa ctactctgtg gtgggcatac atttagagcg     7740
ctgtgaatga accactgctg ttctgccata cttaatttat ttatattatt attttattt     7800
tattgttgtt tttatgtatt attataatta tttatttata ttactaattt atttctcaa     7860
tttaaatcct gttgcatcca attttaatta cagttttgt atctgccttc ccatacttgc     7920
tacccacgtc cccattgcca ctgcggcctt atccatgttt tctgtgtaca ccactctcgt     7980
atcacccccag aataattatg agtgctaccc agacttttga aaccactaga gtcaacatgt    8040
ttgtctttga ggaaagccaa tgatgcttta gcatttttgg caggggtgga tgtgtgttta    8100
agtgggtgg gtgcagctcc ttattgtctg cctattctac tgttgttccc aatccacatt     8160
ccctgcgggg cacctaacct gtgtgcatag caaagaattt ccgaccttca gagccagaag    8220
tgtttctcaa ttgatctctt ccagcctagg gttatagctg atgaattata atccttgctc    8280
tttccacacc tttacctggg cttaccatgg ccctaaaaca tttgcccaga atcagaattg    8340
tctcatgagt gagtggggca aggcaaatcc tgttccagac cagctgagaa tgtacctagc    8400
tgcagaagaa gttagaaagt gtcatctttt acttatctac cagaactata ttcgaggtac    8460
attttagatt taaaaaaaaa gcaagttctc gtaggccttg aatcccccc ttgctatggg     8520
aaaatggatc attattataa tggactgtcc agtaaagttc atgatttctc ctagacatgt    8580
tctctctctt tatgacctag atcaagagtg atctctttaa gtcttttctt cataatccca    8640
cagcactttg tacttagatg tacttagaaa gaaccatata cacggtacgt catgattgat    8700
atgcaagcct tcaccactct acctgtccta aaagtcaggg acacaccttc ttcatttcat    8760
cagtccctac ttctatccag cattggcatc cagtaagtat tagtggaatg gacagacaac    8820
ccgaatttgt gctgatggca gtttaccctg ttttaactgt catccttctg ctactagaca    8880
```

```
tggatgagac ctgagacgat gggactgctc agaggtccct ggctcttgaa ctttagggca   8940
ccagaatccc ctgcagggct tgagaaaaca ggggtttctg ggccccaccc ccagagttcc   9000
tgattcctga ggtctggggt ggggcttgaa gatggacatg tttaacaagc tcccaggtga   9060
cgctggcaac tgctgcctca gggccatgct gagaaccctc gccctacaca aacctttctg   9120
ggaaaacaac tcaacattaa agctgtttgg ggatctctga agaaatctgt agtccttgcc   9180
ttgttggggg agcatcaggg atctaaccat tgatggtgga gtatttgttg ttaattcagc   9240
aagcaactat taagtgttag gcctgttact cggctctaac aatacaaggc agagtgacct   9300
gtaccctcga gatttaaagt ctaagtcctg tagagagaag cccaggtggg agcaagcaca   9360
tttagagtta ggtgcttggt gcaaggtggg gacacagaag aagggaatgg catttgcctc   9420
tggaggggtc cggaaacagc ctagggagga ggagcttgag tcttgaaata ctgtgggcat   9480
ctctaagcaa agtcacagta gacagctgaa ataagaaaa tagtaagcaa gccaaagaaa    9540
cagtatttca gccaagggca gcgtgtgtct atcacgtcca cctgtgaaca cgtcccagga   9600
ttctctgcat ccggccattg ctcaagacag atccctcaca ggaacagcta agccactgat   9660
ttcagctacc tgttcacgtg agaattatca gtacctactg cttttcaaaa tgagtatgat   9720
catggatagg tgaggcaatt cagtttcgca gagacagtag ggcaagtgcc actgtagttt   9780
agttaagggc acatgcttta gagtttggct atgtgagtcc aatcccagtt tagccattta   9840
ttagctgggt agctttagga gcagtagcct tagtgtctct cagttgtccc atctctataa   9900
tagggacaat aacataatag tgctgaataa aagagtaaca aaattttggt caacatttaa   9960
tgtatttaaa gagctaagct ccgtgattgg cacaatgaac caatcaatca acaccagtt   10020
gttattaata aaagtcagtt gaatatgtac tgtgtgcctg gccgtggttc aatttgcctt  10080
tgcatacaag gaaaaaatta aaatactctg ttaataaaga ctatagcata atactttcac  10140
cttaaacttc ttgatgttaa tttatttttgt ttacctgcca aacttctact cattccttat  10200
gactttctgc tacatgaaac acccttgta attcttttgt cctattaaat taagttctct   10260
ctcctctgct ttcctgcttt tggtgctttc taataacact tttaaccctg gactttctca  10320
ttcagctgtg caactgtgga ctgagaggag gctctttgaa ttcattttgt atattctagt  10380
agagagtact gtgagcagtt gggttgttga atgaatacat taattcaacc tggagggatg  10440
ggcagtattg cattttttac attgatatta catgatattt agaaaactgc ttaactggtg  10500
gacgttgttt tattaacagc attttgtgta tagcactcac tatgtgccag ctgctattct  10560
aactgcctga caaatactcc tgaaaccttc atggtaacca tatgagggaa gcactttaa   10620
tatatccata ataccaacgg ggagactgtg gccaaattgg ttaattaact tagccaaagt  10680
catattgaac taataagtgg atttaaaccc agctagtctg gggccagggt ccctctttta  10740
atcttctgcc tcctgcttat gctgttgcat ggagtagtct ttatcatata actaaattaa  10800
gcatgcattt gcttaaagca gtgcatacat gatggatcaa aaagtttgtg gtataattgg  10860
tttaattctg tcattatcca ttttgattta tagtcacttt cttatgatgg tcgtgtagtt  10920
ttaaatggaa cctttgaatc tttgatataa taaggttatg tcaaatcttg ggtataataa  10980
ggttataccc aatggaaaca gaataatgat cagcccattt aaaggatgac tggagagtta  11040
ttacaataca taatagtcat gcatatattg agtagtattc ctttggtaac attttccttt  11100
taaaaattgt aacatttgat tgttccttgt tgggagaaaa ggaggtcaga ttttttgaggg  11160
gagatccatt tggtgagatg ctgagtgtgt gtcaagctaa ggagatagta tgacatcttt  11220
tttagagtct agtcacaatt aaatgccatt ttatttttgga ttttgggatc cgtgccagct  11280
```

```
tccagcttgt cagagctgag aagactcaaa tcaagtccag gcttatttct acagcaaact    11340
gggattctgg cttcttgccg gtggattcat tcagtacagc ccatctggct tttgatgttc    11400
tgcaagtttg gagccatttg ttgaaggaag ccaggcggtg aatattggtg gtcctggggt    11460
tctcttgact ccaagtggtg ccccttggtt tgcattttca ccatgcttag catctgctta    11520
cctggagacc atgcagccgc cggccagagg tctccaacaa ccaaatcttc atgcctttta    11580
gaactcagag tccccagcac atcctccttc ctcctccttg tccaattact ttcatgcagt    11640
tctcagtagc tgcttgtttg aatcacttat agtatttaac ttctagggtg ttttttgggtt   11700 ttggtcaagg taattccagg ctgaatgtgg tgactaagca ggaaataaat gggtcgtcct    11760
caaagttaca gtggagcgct gtttctattt tcctaaggta cacagttgtg ggggcgatcc    11820
gtatggaagt caggaaccca gtctgatttt gcttcctttt gatggtagca gtacagacct    11880
ggctgttttg tagcctgctt tgttttttctt cctttttcttc cctaacttca cgggctgtgg   11940
caaagccctg agacgtgcag gaaaatgtct cctgtcatac gcccacagca gacctagccc    12000
tgaccctcct ctgaagccca ggaaggaggt atctgtgaag cagcctgctt gtaaagcaat    12060
tgcacacagc cttgtaaact gtgttactgg gctgattata cttgattggc aaggtgaatc    12120
tcttatagca aaagagaact tggagagttt tatctcatct tatgccttat taatttgttc    12180
attctttaat tacacagcca cctattgagc accctattta tgcaaggtac ctggtcgggg    12240
gtcagaggga gggtcccatg gtaaacgaga cagactcaat cctggaggag caggaatggc    12300
agcccctcgc tgggctgttg gccccaccaa aagggaaagg tttcattta ataatacatg     12360 ggtgaatcat ttttgtcaat aggcaaaatt ctttgtagtt aaaaaaaaat atgatggtag    12420
gaaggaaagg gatgggcaga gggttaaaac aaaagatatg ctctccctaa ctctagattg    12480
tagtattgtt atgcttgtca ctgtagctga attccatttc tttgagtttt ttcaatgcca    12540
aggcattccc tgtatgactt acgtgagcct ttcatctccg cgattttttcc cattcaggta   12600 aatgagcaaa tggatttgaa cactcatatc taaaacaaga gagaaccagc tggaaatgcc    12660
ctttgaattt cttctctat gtaaaccatt tttcttttctg gtgcctcacc tataaataac    12720
aggagttcca ccttccttta tagactcttg ctgaaagcat ggtttggaac aagaccgtac    12780
aggtgcacac aaaattacagt tgggaaagaa gcctgcagtg catcttgtct ctgaaggtta    12840
tgaaatcctc cttttagtaa tggagctggc gtgatcaagc cagcaggatg aaatttggca    12900
tttgtgagat cacccccctt ctcacttgcc cactgtacat agcatcccag ccttactctt    12960
caaatctcca cattttttct tatctagcta caaaattcat aggctgattt ttttggggtg    13020
cgtgtgtggt tttttttttg ttttttttggt aaataaagac ctgcattttt attttgatat   13080
aggtggttga gttttgtctt taatttcatg acagagattt aactagtctc aacttttgaa    13140
aagacaacaa tgatatttgg ggatcacaca cttaaagtta gatttctaga tgattaatac    13200
caaagtagat gattttttag cctcagccat ttataggtat gcccttctgt gaattttta    13260 tgacagtgaa aatcatggca cagataaaaa ttaaataaat acttctgtta ttttcctgaa    13320
gaaaaaaaaa aaaagcttaa actatgagaa tactgtcttt gagcacttta aaataaaatt    13380
gacttcagcc agcaggattt tgagcattac atcacaaata aaaacaaga ttaacatcaa     13440 aaggagtcag ttttcattca attgtgcagc actgtgggct gtgaaattta atattatttt    13500
gactcatatg ctaattgtag actgacagag gaaaatggat tgtgtttaaa taaaggata    13560 cacagcatca cacgcagctg tatcaaatac aagttgaggt ctttgggcca ggaactgggg    13620
```

```
gccctctagc tctgttattg cagattcaag tttgacaaat aaaactttcc tttagactgt    13680
agtttaatta ctttttttca aaggtatgcg tgatgaagag gcacaaatac acctcacctt    13740
gaagagttgc taaactggtt tgtgtgccga tcagttcacc gtgtgtttga atttctgtgc    13800
ttctcatctt tcctttcttt gaaaagattt tgcttgtcat tggtgtgaat tgtacccccc    13860
accccacccc atctagtctt tgctctcaga tttataacac tttaatggtt ccaaattgta    13920
tagcctgctc ttagacccct tttcttttcc ttgaataaat caggttcatg ttgcagacga    13980
tatttgtttt aggaaagtgt gaaagaaggg gcacctgtga aaacacgcaa ttgttccaac    14040
acacatatac atccaaatta aagcagaaaa tgtcaaagcc tccaatcact accttatttc    14100
ttggaggttt aaagccgctg agaagatagt ggtgccctcg ctggaagttt taaggtaatt    14160
actttttact ctaagcagta gtatctggta acctaattcc gtataaacct gacaccctat    14220
cgctacaccc cagtatttct ctgatttcag aataagtctg cgtagaaact tgttctgatg    14280
ttaaagtgca aaaggggggca gtaaagtgct atccacaaaa aaggaaaaac attttccaag    14340
tatttcttat tactgcctgt gtctttcgta ggccctgcct ttatttattc attttataac    14400
aaaactctta tgtttggggc attcagagaa taccttatta agctgttgca gcaatctagc    14460
attaaatgga agacatgcaa gactgaagat cctgcctgtt tatgaagtgt gccatcaaat    14520
tcacatgctc atgatgcaga gtccttcttt gggagtattc gtattcccaa gtgcacagag    14580
cacttcggaa aggagccttg gtcttttggtg ttaatgctct cctagctccg tatagatgtg    14640
gcaggcccaa agtacatggt ggggtgaagg gtcaagggtt tgggcttatc cagagcagcg    14700
tgcatccttt gtcaggaggt gactggaaac accagccaat tacagcagaa ctgcagactg    14760
ctcatctgca ttcggaattg cagatgaacc agtttgtact cgacttctct tcttcactgt    14820
aggctttgac atttaattaa aaattaaagc cttttatgga aaaagtacat gttttccaaa    14880
atggggtaaa ttcgaagtat acttgataca gaacactggc ttgggaataa acctgtgata    14940
ttacatgact tttggtttgc aactgctagg ctgagcctct tgtaaagct gggatttaga    15000 atctttgaaa tgtttgtaca gttcaatgat taagcataaa ttgtatatat tccctttttt    15060
tcacttattt gagtaaacaa gtttgttact acagcttctg tggactcaga gatttatgta    15120
ttaaataggc cacaacttca actaggataa ttttatttat ctgcttgtta gggaattgca    15180
tcaaagtttt aagtctgtag gcattaaata ttttaaatgc ttattttaa agtcaattat    15240 gaaagatagc acaaagtttt tctgaaacta cattaaaaaa ataatgtttt aatcttatca    15300
caaaagcatt gactatttat tgcaaagaaa acacagaaag ctaaaaatca ttctaagtcc    15360
accattcagt agcccaaagt ggtctcaggt aaaggcggtg tgtgtgacca tttgtttatg    15420
gttgtctccg tgcagtcagc aaaataaaca gaacaacatg ccatatatta ttgatgtgta    15480
tattttcaac tgaaattagc catctgctta caatgatcat atacactaat ggtataattt    15540
tgaaatgaaa agaaaaataa aataattctt tgtggagagt aatgcgaatt gacttatgaa    15600
tctcgccctg cttggcagtt tgctctagag gtagaagagc tttatgtgtg ggcctcctcc    15660
ccccccacac atttattctg ctcacacttg caccagcatc catgtcagga ctcaccttgt    15720
cctgttacat gagtaacatg gccctgattc tcaagtgcat gataactgcc ataattacac    15780
ataaatatta aatatttaaa tagatcttta cgtgtgtaat attaggtaga agtggctctg    15840
gatcgaatct gatgcttttt aaatagaagc tttcccacaa catttccaag cactgtcatc    15900
gtgtctgtct cgatttgggg tttacctggc ctagttatct gtctgggtgt agaaactggt    15960
agttcctgtt tgtatctttt ttgttctgat ctctttattc tgtgtcagct aaatattctt    16020
```

```
gcagtcagtt actaacatat taactcatcc ttgtttggaa actttggcat atccttccat   16080
ggtttccttc cgtggacctg tcgcgtctct caggagagcc accaggtata ttgtcacaca   16140
tttcgcatgt attttcagag actacagcag catcaagtgg cccccagcg atttgggttt    16200
tcttctcggt taatctacac tctttggcca accgtgagaa aacttgtaag aaggcatcag   16260
atgtttgtgc taaggtgcgt gtagtatggt cagaggaaga aagaagcagg gaaaatggag   16320
tggccgtggg tgggagggga agcagggagt gcaatttcgg gttcactaca cagctctcca   16380
taaacttctc cactgctggc ttcccacgga tcctcctatt acactgggca aagtgcagaa   16440
atagatcagg cgaccactgc ctccgtccat ttcccaggca ccctgtgaga cccgataatg   16500
caatacaggt cagcagaaaa gtccagactt gacatcccaa cgtgccatgg tctggtctgt   16560
gaatgaaaat cacatgaggt gacctctgaa ctctaagtgg ctggtttatg ttttcagtgt   16620
attaggcccg tgttttaaac aagcatgtgc tcgtagtgta ggttaaaact ttctgttgtc   16680
ttcattaatt atgctgtgtt ctagtctatt aatattaaag aatattgtgt tgcataatga   16740
ctaattttt tattttttgg agacggagtc ttgctctgtc acccaggctg gagtgcagta    16800
gtgcgatctc ggctcactgc aacctccgcc tctcggattc aagcaattct ctgtctcagc   16860
ctccgagtaa ctaggactac aggcgcccgc caccatgccc agctaagtgt tgtatttta    16920
atagagacgg ggttttacca tcttggccag gctggtcttg aactcctgac ctcgtgatcc   16980
acccgcctca gcctcccaaa gtgctgggat tataggcgtg agccaccacg cctggcaaca   17040
taaggactat tttttaaagt ttttacaatt atgactgtga agttgaaatg tctaaattat   17100
tagagatcca gtttagatta ctaaatattt atgtctaatt gagatgatta gacttagcca   17160
aagtatccat gtagaagtat tagagtctag attggtgaaa aacttgaaaa agcttggctt   17220
aagttcaata ggtaatccaa gagtaaaaac agattccaat atcagatctt ttcaccatag   17280
tcatgttaag tttggaagcc ctacttgagt gttttccagtt ttttccacat tatattgtgt   17340
ctatatttga ttcaaaggca gggcatctat tgtcttgctt aggactgatt cactgggaaa   17400
agccactgga gttgcctatt tccactcagt atgcctcact cttagagtag cttcccatgg   17460
ttcccaggca ggccctccag tgagaatgca ccaagccaca cgccatggcc tgggaagcag   17520
tcctgaacct ggagattgtc ttgatggaaa ggaagaggca gccttcccct cccaggaaga   17580
tagtagagag cctgctctga cttcgctcag ggatggaact ggtctggctc agttctctct   17640
cctgtgtggg acatgaatca ctcttggtgg tctttgcttt ttatttgggc ttaaaatcag   17700
cagactttat taaatgacac ctctctctaa ccactctctg tctgggcgaa gtttaacaag   17760
aacagcctcc ccccatgtgg tatgggttgt aactgtggcg gtttccctct gctgtttttg   17820
gttacaagat gaacattatc tgaacacaca gaaagaaatc tgtatttggc atccataatg   17880
gaaagtcagt ttagtaattt aaacttagcc agttatcatc atcataattc tttttaacac   17940
tttcaaagtc agcataggag aagtgtattg ttgaatatta caaatatttt agggcataga   18000
tagatgtgct gtgtagtttg atttgttaat gtgtctaagc aatcaaagca acagaattca   18060
aatataaacc ccatcacttc caaaatagga actctgttta ctgacttgat tataacatat   18120
ggaactcaat tgttttccat taaaaaatga tactattagg aaaactcaccc cattttctttt 18180
tcatatatat tctgctattt gcataattgt ctggagtcca tatgtaatat taaatgtaaa   18240
acacaaatgc catgtagctg gtctgttttct tcctcacctt ttggttcctg gcctcctggg  18300
gaagggttgc acatctgagc cgtggtctca gatgactgcc tcggaagaag cctcttccct   18360
```

```
tcaggcacca ctgatgtgtg cttggtgtgg agctagactt tccctggctc tccatgtgac   18420
gctcacatgt gcgtgtcttg atttccctta acttcatggc ttatctatga acagcttgat   18480
ttgggggaaa aaaatgtgtt tcccaatgct ggagttataa ttgaatgtgc tgcagtcaaa   18540
actgaaatgt gtgcagagaa aggggctttt tcctgtcatg ctcattgggc accagtgtgt   18600
cttcacctgt tttgtgtgtt aggtccatgc gtcatgctga aatgaagaac atgggatgta   18660
tggggctttg gacagtgctg agccaaaagc aagtgctcaa aagcagctgt gtttgtatta   18720
ttagtggttc tggaggtggc tgattgcctt gcattttaag tagagaggga ttgtagaaga   18780
ctgccaatac ttagaacttt ttccagagag aagggtcag aaactgcatc tgcagggctc    18840
cttgctctcc agaaatgcca gtgtgcctgg gagggcatct tcagaaatcc agtctctcct   18900
cctcagtgtg tcctgtaccg actcagtggt tctgtcttca gaattcctat catgtctgtg   18960
atctgcaaat agtggtattt aatttgactt caatttgtat aaatgttagc ttctatttgt   19020
tcattcctat ttttgttca attaatacat tatttattga gcatctactc tgtgtcagcc    19080
ccttgggtgt ttaatactga attagtcaca tgtgggactt gcctgccctc agggagctag   19140
actataaatt cctaatgatc agtggtctcc acttttctgt cactcataat gtctggcaca   19200
acataggtta cttgagttgt tacactcaca gtactgttgt ttgctgccat ggtgctttag   19260
gaagtgtgag agttcccggg aggcagagtc aataatgcag actacacgta gtgaaaacat   19320
ggccaggaga gctgtagttc aggctctcag ctcaactgca ctctgtccac tgagaagcca   19380
taatttcttc acttaaagtg actgtgcgct atggctgttt atatatacgc ttaaaaagta   19440
aaagctgcta aaccactcaa ggattggggc cttttgtatt gatttaatta aaggaacaat   19500
cattgtttta atgagctcta gaaacaatta cttttgaaga gccgaggatc aaattcttgc   19560
ctcacgtttt gccacagtgt gttctgaaag gtgaattaat gcttttggaa tcatcaggaa   19620
tagtgagctt tgtcacgatt tacttttttac aagcgtatct aatatgcata ttgaaatgtg   19680
agcctcccca ccacacttcc gctttgataa gcatccccg gattgccgtc actgaccatt    19740
atagattttt aacaaagttg gacagtacac actgaatgaa aactttacat caaggaaggc   19800
ctggcgtgtt tgtaaaatga attaaaaggc tcattaaatg atttatatga cttacgcctt   19860
ctgaaaatat ggcctcaaac acagagatcc ccaaagccac accgacccct gcgtcccatg   19920
ttctcgacct caccgcatca gcaccagcaa gacctgtcgc tgagacggtg agtgatgaga   19980
gtcaagagga gtgacttgca tggcctggga ggaaacctcc tgtgaatctt tagttaagca   20040
ggaaaaaaaa aatcctcatg aaggaaacag gatcttggga gcattttgaa tgaagaagga   20100
gcttagtgag ccaaacttga gacatagggt gtaatgtggg agagtttaa gatttgcaga    20160 gatgtacagc ttgggagggg gtgtaatgca ttttcttaaa agagctgaat gaatggttga   20220
ggaaatgggt acatctggtt tggttaagga tcctaatctc tgaagcctgg gatgccccca   20280
gggcttgtaa tttaggaata cttcccctaa tagtagctaa cccttatata gtgctgtctg   20340
tgcaggctac aaaaggagca gattaaggat agaaaaggtt tggagtgtat gagaaaccct   20400
aggcaggaat tgactcctgg tgtttgtaaa ccttaaagat gtcctaaaaa ggtcaaggaa   20460
taagacagga gaaaaggaa atgtcaggaa gatgatcaat ttaatgttta tggaatttag    20520
tttgtactta ctgcccggca tcttgcctga ggttttaac ctcagcagca catcagaatt    20580
actgtgtgtg tgttggaggg gctgggggag ataagaaat tagcctcatc ccaaacattc    20640
tgattcagtc tgttacttga gaaactgaat tgtgttttgt ccataaagaa gatgaaattg   20700
tctacagaga acacattgcc attcacaagg ttgaggggat accacagaga ggctcccact   20760
```

```
gtgatttgca tttgtcaaaa gttctagaga attcttcaac agtacacaca tggttgtttt   20820
aaatatatca ttgttataaa aattcgtttt gagttctgtt tcacagaaag ttttttttgaa  20880 tgaatgaatg tcatatatcc ttgctaaagg agctcagtta aaaaaaaagg gaccatcctt   20940
ctcttttggg ggttgtacag taacacattc ccaagaaaga ggtaacagcc acatacattt   21000
ttcttcccaa taaagagtgt gggttttaa tatgaatcca tagtatgatt tctgttatgt    21060
tttgtgctgc ttcataacca cactcatgca cttttcagaa aattaatacc attcattagc   21120
ataaatcata aactattccc ttggtatggg tttgaaattg ggggtgccct atcatccttg   21180
ctttatctct tagtgaatta tgaccctgta gtcatcatgg ctggtgggcg tctctggtta   21240
aagaaagggt tggattggaa ggattcagag gcgattcttt gttcttaggc tttaatattt   21300
taatgagcct gcaggcttgg ctgcttacga acgagctgag atttctaagt gtgttgttag   21360
tgttagcact tgtagaagga tgttcattag gaagttcttg tttcagtttt tcagagaaac   21420
tccccattaa gaaagatcat tcaggaacat ggctaccaag aaagaggaaa gggaggaggg   21480
aggctttcag ctataagcat taaggggata ttgtatcagt agtcttagtt ctaaagattt   21540
gcttctgaga attaattgga gcaaatacat ctcaagggaa gaaaaaaaaa gatttatagg   21600
gcagggacag tagttgtcct tgcaagtaga ggacacttca ttttgcagct gaatcaatac   21660
cacaactaat tatttctggt tatctttac gcatttgtaa gacattgctt ttgttcagtg    21720
taataaaaaa cccattgttt gatcagtgac tgactaatta tgataagtaa tttgaaacat   21780
tcttgatgaa acttgtctgt taattaacat caacagcaca gggaaactaa caggacaaca   21840
aagtattagt ggatccactg ttccctccaa ttgacgagct ttctctgtgg catgcccaat   21900
aaactaaagc tgccaatggt taaaaaataa caaacatgtg ggagatctga ctcaccacgg   21960
aggaagagtt atggtaaagt tacacaaagg agtactgaaa tattacaagc gaggggtgg    22020 taaagaaatg tcagcaggta gcctgatcct acagcttaga gtaaggaaag tggtttcttt   22080
ctgtctttcc ttttctttt aaagcttaat tccaaaatac attcatccca tattgatctg    22140
aagtaagaga cttttgataa attaaagtgt gaatctgaaa atgtgtagtt tgggattatg   22200
ggcattgcct ggctatcttg taactgtcat taatactgtt aattttate aactcaatgg    22260 cttttttttc ttatgctttt agatttctac ctggacaagg actggtacta tacccacaga   22320
taggagacaa attggatatt attgccca aagtggactc taaaactgtt ggccagtatg     22380
aatattataa agtttatatg gttgataaag accaagcaga cagatgcact attaagaagg   22440 aaaataccc tctcctcaac tgtgccaaac cagaccaaga tatcaaattc accatcaagt    22500
ttcaagaatt cagccctaac ctctggggtc tagaatttca gaagaacaaa gattattaca   22560
ttatatgtaa gtataatttt attcatttat tttatagaaa ttaagataag ctatataggt   22620
ttgtatcaat ttttttgtttc cttaaaatta ttgtgacaaa taatttgatg aaaatctatg   22680
tggaaaaatt gtccccccccc cctttttttt tttcaaagaa aacttcattg aatttgggac   22740
cctgtgctac cagtattcat taagtataca tacccaaaga gaaaaaaaaa cactagaatt   22800
cttaatagta ttgaaataaa tgtattatat gaatatattc agcatctcta ctgacaaaac   22860
catttttaag gaccattggt ggattttgat aggtaaatct tgtgcattgc cttttctctt   22920
cacccatcca tccattcatt cactcattca tttcgtattt attctgtgcc agagactgtg   22980
cttaagggct agggattcag cagtgaaagg tggtaaaata gcatgttttc ctcaagaagt   23040
taacagtcta gagaagatgg agctcataaa ttcgaaagat ggggatgaca ggtcacatta   23100
```

```
aaaccagatt cagaagaaaa agacgaaact tggtttgctt agtacattac tcttttttgc    23160
atacatatat ataatttgac acgctgtttc aagaagagat ggtacgtatc ccttgggtca    23220
tatctgaggc tgacttgtga ggatgtgaag tcagctgatg agcacatttg gagcccacgc    23280
ctactatgtg cagatctctc gtcagcgtca ttcccagggc cccaggtggt gttaaagtct    23340
aggtgactca gacagctgtt cgcgtcattc aagcaatgaa gtcttttttc ttaatttctt    23400
tggtttaaaa ttatactcat aattaattgg gttgaatttt ccagtggctt ggttaccata    23460
gacttcagtt tattagggaa ctgctatctg ccactggttt attatttgcc ccaaggtgga    23520
ctctaaaact ttaggtagga gactcttggt gatcaaactg aaactcttgc atctcaacct    23580
atgagccgca ctttattgtt atttttatttt tttagagaca gggtctagct tgttgccga    23640 ggctggcgtg cagtggcatg atcacagctc actgtagcct tgaactccag ggctcaagtg    23700
atcctcccac ctcagcctcc aagtagctcg gactacaggc atgtgccact gcacccagct    23760
caagagctac acttcaaagc acagaatgaa aacctatttt taaagccaac ttgatacata    23820
gagtagctta ccaagaatta gtaacaacaa caacaagaaa aaaagagag aatgtggtag     23880 agtatatact tagtaaggag taattattat aaaataaaag cattctgaaa tgaaacaggt    23940
agatggggtg gccaagtatg cagcatagta gggaaatctt tgaaaatgta aaatagttac    24000
caggtaaaat aaatggaaac tttaagcttt tggaagccta acaatgtatt tatattagta    24060
aagactttat tttttattt tatttttattt tattttgag acggagtctc tctcttttcgt     24120 caggctggag tgcagtggcg tgatctcggc tcactgcaac ctccacctcc tgggttcaag    24180
tgattctcct gcctcagcct cccaagtagc tgggactaca ggtgtgcgct aattttttgta   24240 tttttagtca agacggggtt tcaccatgtt ggccaggatc atctggatct cttgaccttg    24300
tgatccttcc gccttggcct cccaaagtac tgggattcca ggcgtgagcc accgcgcctg    24360
gccttagtaa agacttttaa agtaagactt tttcagtgaa agctactgtt aggcatgaca    24420
tttacaggca actgaaactg atcagatgca tttattaaga aggttaatgc ccctaggtgg    24480
ggtgggagaa agaaggtcgt ggtacgggaa gaggggacac actagagatg agatgcccta    24540
gggcagtgaa cgcatgtccc taatgcgtgg atgcagccca cgtccaccga taatgccgac    24600
acacccagag tctctcttct tactttagct tatgacttca cgaagaatgc tttgcaaatt    24660
ctaagttcgc actgggcgca agtggaattt tagtaaacat taagagttta acctttagtg    24720
tgaaataata tgcaagatat gcaaataatt gtttaccaac atctctttgc ttaatgtggt    24780
gagcatttaa taattgcttt ttattaatac atgagagatt tgtatttaga agcagtttaa    24840
tttataatta taatattaat ctacacaata acgacatcta ttattttctt tttttggaaa    24900
ctcttcatac cacactaaca ggttcattgc agttactgaa ctactctggc catcagagct    24960
ctccttagag ttacgattta ccatgcaaaa gcatatggta gcctgggata aatgaatctt    25020
tcttaataca gaattgaggg tctcaagttt gaaactacga gaggctattt gaatgttgct    25080
ttgggggact gtcataaggg ctgggtggag gactcagggc taagaagttt gccaggaagt    25140
ccagttgaga ctttcagcag agttgaaaga cttccacgat ggcgtaggca gaggaaggcg    25200
tttcagatac ttgggaaaat atagaagcca atttctcacc caccctacag caaagctcat    25260
tgatctacaa gtttccctag aaaggaaatg ggaaatgcag agaacaaatg ttaaaatagt    25320
tttagaaatt aatattgact ttgtattgct tctgcataag ttccaagaca ccaaaacaat    25380
gaatggattt taaaaagtca ctactttgca tatcagacaa atgcacacac acacacacac    25440
acacacacac acacacacac acacacagtc aagctctgta ctggcttttt tgagaaggaa    25500
```

```
agtgtttgaa gttagtaatt tttatatcag tacatttata aatagtgcta ggtagcatga   25560
cggaaagtat taaaatttac atgtatattt ttaacacttc aaatcgttgg ttcactttga   25620
gacagtaaat aatattagca tttgagttca gctttaataa attctacatg ggtttaaccc   25680
caaatctgag tgtctagttg gtaagcgcct tcagaacgag cagtgttata ataaatatgt   25740
tattgtgtgc tggtttcttt ccatggagag gaaaaagaga cctgatgctt tggaggagtg   25800
cttgactttt ccccagtgag gagtagtcca gagggactga cttgcattgg ggagtaccct   25860
acatgaacag catttcagaa gaattaaacc aggaacctag agtcctactt gctagtcctg   25920
cttcctaagc ttaatgagaa agtcaatttt atttctttga actttaattt atttccctaa   25980
aaaacgcttt tagtattgtc attgttctgg ctaatgatgg cggtctcctc cagtttcaag   26040
ccaccttagg gctgggcata caaatgcaat ataggatcac ttgttagtgt ggtttcaaat   26100
ggacatgatc ctctgtaaat tctttaaaaa catttaattt gatttgtggt gttacctgct   26160
ttaaaatata gtcatcacac ttgtgagttt cagacgtgaa tatgaatttt taatttgaac   26220
tgtattttta aacacactaa gtattaacta agtccccttag ggagatatgt ggcaaactga   26280
tatgcatcct cattcattct tctcatagat ggttatttgt tttttaactt gtggcaaaat   26340
tatatatgaa tggtcaccga cttaaaatag ttccacttaa attttcaac tttctgatgg   26400
gtttattgga gtattaaatg tattttcaat ttaatgatat tttcagctta ccttgtgctt   26460
atcaagtatc aagacatagc cccacctaag tcatggagca tctgtatatg ggttttttatt   26520
cttgtttaga attgacttttt tcaagtgacc tatttcagta attagccctg ggcctgattt   26580
gcataatgag atctcctaat cttcaagtaa tgcaaagatg gagatattat ggccatgtgg   26640
tctgaagaga cctttctttt attatgttca gatctttaat tgccttaaaa atagagtagc   26700
taatttacct aacctctagt tattttatta ttgtctttaa agtttttttt aatgttcatg   26760
aaataactgt tctgaaattg cctatttttca agggaagctg tgtcttagac ttactaaatg   26820
ctccagttga tactgggaaa gccttcttgt gttcgtagcc tttatccgta gagttttctt   26880
tgcagcattt tctgtgcctg gtttagtttc ttttcagagg cgacacccag agctgaatga   26940
gtcagcaggt ttggtgtgtc gacccttgc aacagctgtc cttacgaagg ttctgtgggc   27000
tggttattct accttcgcat aaaaccttgc aaaataaccc acaaagaggt tttcgtcaca   27060
ctaccaaaat catgtgagtc agagatggat gaaaaatgaa tgccattgtg ttcatacttt   27120
tccagtgaac agtagctaca gcagagctgt tagacaaaga aaaccgtatt aatgaagcgc   27180
ctcccaattt agcttcatat ggcttttgca ttattttgct gcaaatccat agctaagaca   27240
catcttgtgg catagtccgt aagtcatctt tccgaaggac tgtttgatta aaggttgttc   27300
tgtgagatcc accctgtgtt gttcatggca tcctcttgga ggcctccctc actctccatg   27360
ccttggcaaa gtcttcctta aggaacactg aacaagtctg gagaagctgc catttcttag   27420
ggccctcatt ggttcagttg tctatagctt tttattttttt attttttttt taataaagag   27480
tatgtaaaat tggaaagctt cacaaacagc tttgctattt tttagacatg tactccactt   27540
ctaagcaaaa tcacaaaata aagtaaaatg cttccacaaa tataatgaaa caatattctt   27600
aaagaatcaa agcagaagaa cttcagagtc tgttgcttat gttaagcata tatttgtttt   27660
cttctctgct tttgatttac ttatttctgg ggtgtaggtt tggcaagtag tactgaaacg   27720
tactgaatgc actgttcttt agcaagatag ttacaggagc tttcaaatgt cctcttaaca   27780
tatagatttc ttttagaata tagaataatg tgtgggctgt ataaagcgat tatgtgcttt   27840
```

```
atttgatgaa ttatttatgt acgataaatg tagcaaaagc cacatttcca tcattaaatg    27900
taatcccatt tggtgataca gcaacatcag cctgtcattt gggtcctctg attgagggt     27960 gaggatttct gtttgatacc ttgtgcataa tggctgcgtt caagcattta aactcatttt    28020
tatttctaac ctacagctgt catctttgta ataggatatt catcagaatc ttgccagaga    28080
ctgtgcattt gggatcttgg gggatacagc accaccacca ccctcccct gtccaagaga     28140 aacagatcaa catcttaggt tgagagtctg gggtctggaa gacccgagtt cctgagtgcc    28200
ctttgacaag taacttaacc cctgtctgcc tcagtctctt catctgtaaa gtgggataa     28260 tgacagcacc tgcttcacag ggttgatggg aatccagatg tggtgggata tagaaaatgc    28320
ttattacttc cacctttgac accaaataca tataactaag agttaacttt ggagcagggg    28380
aggaagtgtg aggctccagg ctggaggcag acctgtgttc ggctgcaagc tggagaggat    28440
ggaccccaaa agcttggctg atttgaagtc catccataaa atggaactcc agagagttta    28500
cacgtttcag taatgctgca taacttaatt ataagatctt ctctcttgt cttctttcag     28560 tgttataaaa gctcttttgt ccttgagctt cctttaccaa gaaacatgca tttatgtatc    28620
tttttgttca tggaattgcc caagcttgtt agcagatcct ttgtaagacc caaagagac     28680 agacagggga ggagtcttca gatacatata atcattttc ccaatttcca tgttaccagc     28740
cttgccagga cttttctca gttccctgtt acacaatgaa aatagtgtct ctttattgat     28800
aattttagta gcatcctaat gtggtataaa tcgtcttcca gagaagaaaa tgtgtcaggg    28860
ttgcgttatc actgaggcta gctgggaaag tagatcagcc cattagtctg ataattcgaa    28920
gcgttgtttc tgttatttct gaacatcatg tgaactcctt ttctgggtgt attaaaggtt    28980
ttcccagtgt gtgtcagtga gactcctgat tgaatttaat atgaataaag ataaattctt    29040
tacatttaag gattaaagtc tcagcttctg cttaacttga gattgcactg agaaactcct    29100
ggctctcggg tatagcggag tcacgacctg gggatgtctg tcccatatgg ctctgtgtgt    29160
aagaagaaaa agctgctgtg gacggagact ctgttcacat taaatgacat cacctaagcc    29220
atcatgacag caagaattat ttaggaattg ctcagaataa aactgccttc attatttcat    29280
aaaatgtatc ttggtatctt tagcaccta tttatggctt tttaaaggtt cactgggatt     29340
tataaataat tggacaatgc tagagaccta gtacaagaat gaaagaggac aggcttcttt    29400
cttaataacc tttaaacatt catcaggaag ataaaacttt aaagcaaaat aaaacacatg    29460
aaaatagcca agatgcacag accagacaag caaatactac tttaacttat ttgtatagtt    29520
cttaagagtc acatttgttc ctgaagtttc aaaatctcgg gctgagtgtt tgatcactta    29580
gggaagtgtt gtggccttca catactcttg tctcactttg aagtctagaa acacaggtct    29640
tagagcaatt tttatcactg tgagaaagct gaaacttagt gtgagtagct tagtacaatt    29700
cagttggcca tcaaatgtca gaaacaaaac tcagtccagg gccgctggac ccttaggccg    29760
gcgttgttag tttacaacag tgcctcctgg gtccaaacat ctaagtgcac atgtagcaat    29820
agtaaagata gtatgtatgc atacataaca catatgtaga gacagcagag tatacgtaca    29880
cacatgttgc atacatagca acagcagaga agctcatgaa ctataaagga tggactgtat    29940
gcttgtatca gacattttgg tactgacgct ttgtcatata ttgtgtaaca tataaccagc    30000
ttgcaatcat ctgcccccaa agttgaacta agaaaatcct acagggtact aggaaaggaa    30060
ggccattggg aaaaggtggt tatagtggca atttgttagc tcttatgaat tttcttttc     30120 tttttagaca tactcttaat tccattttt caataaatct atactatttt gtgttttat      30180 gttagcaagt actttaagcc cctcaataga aagttgctac atcatatagt gattaaaaat    30240
```

```
aaaaatctct caaacataca agtagaggtg gtatgagact tcaaattccc ttagccaagt    30300
acaagtgcag cagttttgtt ggctggctgg ctgcatagaa ggactgatgg attggcagac    30360
cctcaagctg gagtgtaatt gatctcatta cagaggagcc aggctgggtg acagttgtgc    30420
tttgcaagtg gttttttgca ttggtgaagt agcccatttt gttgttcctg atgttaaaca    30480
ggggatgaag gtattctttt attggcacaa acgcgggaaa ttgctctgga ttcttagagg    30540
atagaacatg tcccctggac ggaataaggt tcatgtgtag ggcaaattta gatagggggca    30600 ccttattggg gttactactg gtctctagat ggtcaaagca aacaacatgt ccatctaagc    30660
tgtgatgtcc atctaagctg tgtgtgtcca tgagagtgac gcattttctc ctctgcagtg    30720
ttgttatatt ctaaactgtc agcagacatt aattcggtcg ctggtgaagt cccaccgcct    30780
agagatgaac tctgcctccg atggatgttt tccacttcag tgccactcgt ctcgcaatta    30840
ctgggtcatt aatatcattg catgcaatta gtgacagtag aaagagctag agggttgtgg    30900
gatgtgcacc ctccccacca tgaacttttt actctgaccc tttcccagct agaccttttc    30960
gtatcttggc aaggatattt taatgattga gactgtcaga atcttcagag caggcactgg    31020
attatgtgct ggaaataatt cactcaaaca cctgcttctc catggttcag aatattttca    31080
ttagatatta tcactatccc ttccctggga agtttcattt ttaaaaatct gatgcttaag    31140
tacagctaat atagacaata gggaattatg ttttatcttt agaactctta cattattctt    31200
ttctttaaaa atgtgagctg agtcattgct attgcagtgg tcatctggcc gcctattttt    31260
aaaacacaat tcctctatct tagtagattt tggcccatat taagcatatc aagaatgact    31320 ttttttttt caagacatgg ggtttttattg ggggcttata tacaaggaaa gagagagtcc    31380
agtggcagtg ggctggacaa gatatccaca tggccctgtg gcagtgagct gggcaggaaa    31440
actgcaactg cttgcaaaca gcatgtagtt catctatagc attttcactt aacaccaccc    31500
agctaatgac ttccacctgg caaccttcat ttaatccaga acttaggacc tcgagtccct    31560
gtacggccca tgttccacag gatgggccga gggctcagct gttcctcata gacaaggaat    31620
gactctccac attggccact cccggattcc ctagctcagg acacatattc aggtgtgtct    31680
aaggctggct cttctatgtg aagttactta ttctttacc attgactctc atgttccac     31740 tatattaagt ttttctgaat tactgtggca ataagaaacg gtcccttaaa ttatactaga    31800
agaaaagctt tttttttgtt ttgttttta ttttgaaatt atgttaaatt ttttttctta    31860
actgagagat tccacctgca taaatcgtca taacttttaa cagtaagatc ttagacttag    31920
aaagtgatgt ttttcctcaa cagaatttat taaaaatcaa gacaccaagc tgttccaaac    31980
aatagtttga ggggaaataa aataaacaac tccataaata atcttatgtt gttaaacatg    32040
tctctagcaa aacaaacaaa caaaaaagtc ggggggtggg ggaggtgcag tttattgcca    32100
gtactgtctg gtcttctca gaaaagcgtc agtgtacatc actgagcctg acggtatgt     32160 tttcttgatc tataccccct atgtgtacat gtgcttgcac gcacacacat gtagacacgc    32220
acacatgtgc acctgccatc actttctgct cttccgtctt ttcactcttg agtgtctgta    32280
gccagtagct ttccaggtct gtatagtcaa agatacctat ggccctgaat gtcttcactg    32340
attgctattt gacattcata cggttttaa tggttaaaag gctttatgcg aaagctgtga    32400
tagaatttct cctgttctag atgtggtgtt tattgcttta ttttgtgact tttctctcag    32460
tagattgacc ttctcccctca gtgtccaagc ctcgcatagc atgatggcac ctgtaaactc    32520
agttctgtat cctggtatcc tttctcttcc caagtagaag caattaagta atatatgtca    32580
```

```
tcaaaacctt ttaagtgcac atacaaacaa aatcaactta ccaaactgct tcaaagttgt    32640
tccatgttta acactcttct ttctgagctc tgggtagaat gtcctattat tgttcatcat    32700
gaatatttga aattaaagaa ataaaactgt accattttct ttaagagcat ccatttgtac    32760
ttgataacat cttcagtcat atttcaatgc tggcaaagag gagggagtt ctaaactgtg     32820 actcaatttt agaatctact ttttccaaat tattctgttt agtgcagaaa actaattaat    32880
agtgttgcat agaaaagtca ctgaagctaa gccagttatt acttcttaat gcatgattta    32940
ctgctttaag ttttcaaaac acaaccatag caatgtggta ttaattcaag tgattcttcc    33000
tatcatattg aacgatattt tcacgggtga aaaactcaca catcctacat cactgatagt    33060
ttatacagtg ttttagctgt ggctccctgc atgcaaaata agagttaatc aaatgtcagt    33120
gagaaccatc tcatcaagta gagggcttgt tttgtttaaa ttaactttgc taagtataaa    33180
tttcttcttg aaaataaatt ctgggccggg cgcggtggct cacgcctgta atcctagcac    33240
tttgggaggc cgaggcgggc ggatcacgag gtcaggagat cgagaccaaa ctggctaaca    33300
ctgtgaaacc ccgtctctac taaaaataca aaaaatgagc cgggtgtggt ggcgggctcc    33360
tgtagtccca gctactcggg aggctgaggc aggagaatgg cgtgaacctg ggaggcagag    33420
cttgtggtga gccaagatca caccactgca ctccagcctg ggtgacagag cgagactccg    33480
tctcaaaaaa aaaaaaaagg aaaataaatt cttctgtatt tttctttctt caagtgaggc    33540
catttagggg aaagtatacc ataaaacttg ctctaagata aggcaaattt ggtattatag    33600
gatgaagtgc tatgtgattt gaagtaatgc tgaatttttt aaatatatta aactaaacaa    33660
gaataatgag gccctcggaa agtcatgatt atatttctca tttttctcat tttaaagcca    33720
cagtgaaaaa cacataaaag gaagaagtta gaaaaaaaaa tgaatgaaat tcttttttc     33780 cttttggcaa attaaataga tgtttctgtt tcagaagatt ttattaatta actttaaaga    33840
aacagtcatt tattttggc attcagtgaa cactatcatt tccatgttta gaacttttct     33900
tctaagttag catcttaaaa gataactgtg aaactcaagg cattcaacta cattaatttg    33960
agtttcagaa attgaattct tgtttctaga gtacatagtt tgaattgatg tcagggtgtt    34020
aaatagataa atcttagctt cctaggttgt atattcacac taattatttt tttatcagcc    34080
ttcttatttt tcaacttacc ttattctttt tgttttttg acactcagat tgatagccc      34140 tgtggtagaa gaaacagta atacagtttg gtttgttgtt gtgtttgtgt ttatttaaa      34200 gtcacggctt tgcttccat gttgttactg gattatgctt tttttaattc ttcagtttgc     34260
caagataaca gtcttccgat cttcagaagt ctgtatcaag cttaaggaaa ctgatgtgta    34320
ggaagactcg cctaagaagt ccaaattagc aaggctagca tgtgaggaca tgctggaaaa    34380
gaatagttcc catagatatt gacagagaat gttcataaaa tgctacttgt tttgtggtta    34440
catgagagta acttgtgtcc agtgcagctg tatgtaaggg caacgttttt attctgacga    34500
ctctgtggtt ttcatgaccc tggatgctta tcatgtctct ctgttggact tcttcaacgg    34560
agttgataca aatacttgct tccaagtgtc catctgccct ctcctccatc ctggcccat     34620 acaaatacgc tacatttta aataatttga aatacctca atagtattta tatttcctgg     34680
tgcttcattc tttccataag aactgtgata ccattattct gtaggattt tttgtgcttc     34740 cccgtttcac atctctgtgc cagtgagacc catatatcgg tgcaaatcca gaagtttgat    34800
tgtccatctg attagcacac tgttagcaat gtggtggact aaacacagcc aagatgtggg    34860
gctggagctt agcctcctgg gagcagacg gtgaacatca gatgaagaca tgtgaaaatg     34920
gagtactact tcctcttcct ggggatgggc taaaaagcac agccagaaat attcttgccc    34980
```

```
ttccagtctg ctttacagtt actcactggt tctcttttt ttcctactca gataaccagt    35040
atactcttcc cagtgactaa gaactgcaga taagtatagg tgcaaataga tggcaaaccg    35100
cagatggcag ctgtgtggtt tcagatgtgc tgcagaactt ttagacgatg tgaacgcaag    35160
gaactttttt gctgagcagt aatctctacc cactggaaat taggccctgg ggggaacaat    35220
gtagtgactt ctatatactt actacatgca gttagacccc tgaagcaaaa gcttttaaaa    35280
acaggctgta aaatgcccat gtatctttat taagcctatt ttccaactgg atagagaaat    35340
tttctggtaa ttttaaatt tgtaaagtct attttttcc tgagccaagg gaaaaaaat      35400
atctgggccc taaaagctta gttataacaa tgttattttt tctatctctg aatgattaaa    35460
tgtgatttca tttatgtagc aatactatga ttgtggctgc attagatcac gctgatagaa    35520
agatacaaag aaaaactaag tataatgaac taacaattta ttttcactct ttctctaagt    35580
taaaaattcc cagtacattc aaatgaacaa tgaaataat tgcagaattg tctcctgaaa     35640
tggaaataga ttttttttcc caagcattag caatttcttg ttattttca aaatcagcca    35700
ctaagccttt cagagcttct tggtgactat tgcaggagaa atcagaatat taatcttgtg    35760
gttttatttc agagttcgct gccaggaagg aggtataatt gggataggag acttttttt    35820
tttagctgtg tcactgttca aggagggggg tttggaacct cagcataaga attacactct    35880
gtgatgagga tgtagcaggg gagaagaaag gtgattttca ctatgggaag ctatacttac    35940
atcaagtata aaatagactg aagtcatttt gaattacgtt atacttgtaa agtttacctc    36000
ctggagtttc agttagtacc agtgtactaa ctgggttaaa acagttcatg gcaccttaga    36060
tcatttctaa ctcatggcaa aaatctttcc tggtggaacg tgtaactgta ttttaaatgc    36120
cccttaataa gcaaccaagt atttgggatg ttatttgat attagtagtg aatttttcag    36180
tatcttccag tacccttttgc aagtcacagg ttgacttaaa aggaaaagaa gcaaaatgct   36240
gaatatagca gaaaaactgt ctgcattcag actgttcagc ccacttttgc tccccacgtg    36300
gcaagcacac tcccccaaac aagcaatagc ctgtggcttc agaggaacct acaaaggcag    36360
catctgtaga ttttttcctt ctcaactcta agacttgaat gtttccctct tcccacaca    36420
cttttttttt aaaccaagaa ataaaaaagt tttcactctt aaaggtgcaa agcagtttca    36480
ttcttatgca acacagcctt cctcctactg tcttatagtc tgtggatgtt aaattataga    36540
ttccaattga atttaatac tctagagatt ttacattgt ggttgtcaag accccgtttt      36600
ggtaaaccta gggagctccg cacaaaagca ttgatattca gaaaaggcac tgacctacaa    36660
attaaaagaa aaaaaaatca aataatgtgc acctcttgtg cttccagttt gacaaagcag    36720
aagtcatcag cagtttctcc ctctgcagac gcagttctca attctattta caagtaactg    36780
ctctactgtg cctgtttttc tcttgctgat actcatttaa ttgtttttct tttggatctg    36840
aatctttgac tgtcttttcc ccctcaagat taaaataaat acatctgtat tcctcccctt    36900
tctttctgtg cactgccctt cagatctcat tttgtcattt ttcagcttag tgttgaaact    36960
tttagcaaca aaaagtcagt tacttacttt gagtaagtaa ctcaaagtaa gttaactttg    37020
agtttgagtg cacttttgcg tgtaggttca tttatgtgct tgtgaattta aaaacattgg    37080
gattccacct gaatgaagta aaccaaacat tttaaactat cagccagata gagacatcag    37140
cctttcactt ctttctatat gcagacatat cctaattttt tagaaaaatc aaataggaaa    37200
attctcaaca attaattgaa gattatagct ctgctctgaa atggtccaga ataggatct    37260
gctcatagaa actcatagtt tgaagcctct gggaggaaag gatactttaa aatttagtca    37320
```

```
catatttgga ggagggaaaa gggaaagagc agaatgaaga actgaaaaaa atcacacacc   37380
ggggcctgtc gtgaggtggg ggactggggg agggatagca ttaggagata tacctaatgt   37440
aaatgacgag ttaacaggcg cagcccacca acatggcaca cgtatacata tgtaacaaac   37500
ctgcacgttg tgcacatgta ccctagaact taaagtataa taaaaaaaaa ttttaatagc   37560
cccattaaat aattaaaaag attttttta gattcacaga agtgtacaaa attttaggt    37620 ttttttttt ttaagctgtc tgctgaatag tttcttaatg gtctacaatg tttgtatcta   37680
caaacagata ctgtctgctt cttactaccc ttccaagaca agtattatta tggcaattat   37740
tgcccagttt cccgggaaaa atttatccac agttacagaa gaatgagatg caattgtgag   37800
actgtaaagt ttaagcaagc actcagagaa gcacagtgat atgtatgcac agaagaggca   37860
gtctttgttt tgaggaaaac agtgaaagta aagttaattc aagaccacaa agacaagtaa   37920
ataagtgcct tatttttgta gttaatataa tttcagtgga atgcatattt ctaccataaa   37980
tgcatataga acttgtttgc tgacctactg ttttggaaaac aaacaatccc attagaagaa   38040
tgtctttggg atttattttt accagaaaat caatccttt ttcagtccct tgcaaagtac   38100
agtgttacaa gccaagactt tgataatcag gtagaaaatg gatttaaatt gcagaaatgt   38160
atatgaaaca ctttgttcc ttgccccttg aactttaggg gaatgaaaat gtctagcact   38220
ctccaccttc tttctctcc tggaacttga actgtaattc aaagcctgtt tctcattaaa   38280
gtacctggca gcctatctct ttacagcttg agttacaaag ctattcagag acctcgctgg   38340
tctaaagaga cagaacaagg atgtgtttaa atagagcata ggctgttgaa aaaaaaatg    38400 ctgaaaatgg taaaatgatt ctgtccttcc ttccactcct cactgctgag gtggagaggg   38460
aattcagttg gtgaacacca gcaagtggct ggtaaaagtc cccactttct ctccagggct   38520
gccacaggac ccagaatgag tggtgggcat gtgtgtgaac cctctattca gccagagttt   38580
tcccgcaaca ggtagtttgg ttgaagaggt tgactaaggt tgacattggc agtaataaca   38640
cgtatgttct tctgatttac aaaacgatgg aggaaaaagg ggagattttg aagacctgat   38700
ttctggtata cttcttaagc atgcataagg ctgaaaaaag aagacaaggg ttgtgggagg   38760
ctcctggtct agtgtttaca gaacttggat gcttgacaaa cagagcgtca agctaattgt   38820
tcttgaagca ggaaatctgc agtggaggaa gcaggtgtgg ggggatgatt accacgtttg   38880
gaaatggctg cattaactat tttgctcttc tgagtttggc cccaaaagag tccatagact   38940
ttttgaagga tgccatccct tttatttata gactaacatt aaatcagtca tttgtgaagg   39000
aaggagaaag tgcctaaata aatttggagt cagatagcat acgtgcggca gtgtttccga   39060
tatccatttc tctttatttc ttttttcttt tcttttggc tttcagcatc cccatacttt   39120
cagaaaactt gtgactaaga gtgaattctt attttcaaa ttgttttcag acatttcatg    39180
ttcatgtaaa cttggcttat tgatttcctg attttctttt attttttgt tttgtccatt    39240 ttattttaa tcagctacat caaatgggtc tttggagggc ctggataacc aggagggagg   39300
ggtgtgccag acaagagcca tgaagatcct catgaaagtt ggacaaggta aagaccatct   39360
gctgcttcat gacgccactg tgacctggtg tagcccccag ctagtatggt gctaatgttg   39420
ccgatgccca ccttcattcg ctcttctttt agttttcaa agcaaaccct tctgcacttt   39480
gagccactga cagatttcct caagtcaatg tactaagctt ttattggaga tctaagagtt   39540
aagatcagca aggtagaatg tctattgcca tagatagata gatagataga tagataatag   39600
atagatagat agatagatag atatttcttt ttaaaaagca aaacactttg gttcaaaatc   39660
aaaatatcca gaatgaaaac taaaagcttg tgcagttttg ctcatttctg aatcttgact   39720
```

```
acagaagagt tttgttcatt gtgacttttc caatatagat aacctattgt gcagaaagaa   39780
ataattattc ttctaattaa aaattggtat agtagtcaat caacttgctc agttaaattg   39840
aaatgtcatc tgcaatgctt tgcctgccaa atgcaagaat ccctatagtt tccacagatg   39900
gcctcacgtt ctaaacctct gaataacta  gtataaccat tttgttttaa aagaaaaatt   39960
atattcttgt atttcacagt actttgcata aagactctta tgttcattgc tattcatgcc   40020
tgttgaaata tatatgcagc tcctaaagct agatattgtc agatgtctgt gccgtaatta   40080
atcatttgtt tttcatatag atgcaagttc tgctggatca accaggaata aagatccaac   40140
aagacgtcca gaactagaag ctggtacaaa tggaagaagt tcgacaacaa gtcccttgt    40200
aaaaccaaat ccaggtataa cagcatgatc tgtgtgtatg gaggtctgtg ggtaccacat   40260
tcttagtagt atcttaaaag gtagggcaga gtctaaagac ttctaaccag ttaggattag   40320
ctggaagtta cagtgatcag gaatctttgc tgtcagtgag tcattattaa ttacactcaa   40380
taagaacaaa ataactcatt ccaatgaaag tcatatattc aaaggagtag agttcatgag   40440
ctgtaagtgc cagttattag aactactctg tcaggccaaa ggtttcattg gctgacattt   40500
tatcaagctg gttgtcaact ccagcttaaa gctgatgtta atgtatatgt aattaatgtg   40560
ctaatccctc atctaattat atctaagcca cagagggttt aattgatcct cttctaaatt   40620
ttaaatggta acattttaa  atattgcata atagtatttt ttcaggtggt tatcgttatt   40680
ttgtttcaca ttttccatgt aaaagaaaat attaaacagg tccctgacaa aagtgtagaa   40740
taccagataa aattgtccgt cgttgacctt cgttttctta acagtcttgg aacaaatagt   40800
tctgtatttg ttaccatgct aatgaaggtt ttatagagta gctgttgagc agacatcagc   40860
agttttgtat taggattgtt gtgtgcttgc ttggtcgttg tgcaaattta tcgtctgcag   40920
caatattcca tcccttttcca agagtcaagg agggaagttg ttatttctaa ctttcaatga   40980
caagatgtgt caaattcttg tgacaaactg ataaatggat aatataatga tgccaggcag   41040
tttttttagtg cttaacattt gggctggcag tctgttcggt gtgagagttt ctgctgcctt   41100
ccaaatatat tttaagtgta aatcaaataa tacagacgag ttacgagctg aacatttttcc  41160
caggccccct cactccttcc gcgttcccga gctgttctgt tctgccagga ggcagggctc   41220
ttctttagaa ggcaggccct ttgaaggttt gcatgaaact cccttctca  aggaggcgg    41280
aagagcaata ccacataaac gctcaccgct gacctggaga attggccact tcccttttc    41340
ttccctgccg ctgccccagg ctggctgaca cgggttagaa gatgaagcaa gatcaagggc   41400
tggctgtcac cgacagtctg tgctcttgct ggataatgat acaaaggaaa ccctgtggct   41460
tgggagggta gggaagtccc tcctagagat acctctcatt cctttttgcg ttgagctctt   41520
agacgaggta ttggcgaggc aaagtccagc ttctagttag taataagcct ggcttatttt   41580
tcacattttt aagggtcata aaagcagtcc gtctgcactg ggacagcagt aactatctct   41640
gaccttttct gtctccgcgt ctgcaggttc tagcacagac ggcaacagcg ccggacattc   41700
ggggaacaac atcctcggtt ccgaagtggc cttatttgca gggattgctt caggatgcat   41760
catcttcatc gtcatcatca tcacgctggt ggtcctcttg ctgaagtacc ggaggagaca   41820
caggaagcac tcgccgcagc acacgaccac gctgtcgctc agcacactgg ccacacccaa   41880
gcgcagcggc aacaacaacg gctcagagcc cagtgacatt atcatcccgc taaggactgc   41940
ggacagcgtc ttctgccctc actacgagaa ggtcagcggc gactacgggc acccggtgta   42000
catcgtccag gagatgcccc cgcagagccc ggcgaacatt tactacaagg tctgagaggg   42060
```

```
accctggtgg tacctgtgct ttcccagagg acacctaatg tcccgatgcc tcccttgagg    42120
gtttgagagc ccgcgtgctg gagaattgac tgaagcacag caccggggga gagggacact    42180
cctcctcgga agagcccgtc gcgctggaca gcttacctag tcttgtagca ttcggccttg    42240
gtgaacacac acgctccctg gaagctggaa gactgtgcag aagacgccca ttcggactgc    42300
tgtgccgcgt cccacgtctc ctcctcgaag ccatgtgctg cggtcactca ggcctctgca    42360
gaagccaagg gaagacagtg gtttgtggac gagagggctg tgagcatcct ggcaggtgcc    42420
ccaggatgcc acgcctggaa gggccggctt ctgcctgggg tgcatttccc ccgcagtgca    42480
taccggactt gtcacacgga cctcgggcta gttaaggtgt gcaaagatct ctagagttta    42540
gtccttactg tctcactcgt tctgttaccc agggctctgc agcacctcac ctgagacctc    42600
cactccacat ctgcatcact catggaacac tcatgtctgg agtcccctcc tccagccgct    42660
ggcaacaaca gcttcagtcc atgggtaatc cgttcataga aattgtgttt gctaacaagg    42720
tgccctttag ccagatgcta ggctgtctgc gaagaaggct aggagttcat agaagggagt    42780
ggggctgggg aaagggctgg ctgcaattgc agctcactgc tgctgcctct gaaacagaaa    42840
gttggaaagg aaaaagaaa  aaagcaatta ggtagcacag cactttggtt ttgctgagat    42900
cgaagaggcc agtaggagac acgacagcac acacagtgga ttccagtgca tggggaggca    42960
ctcgctgtta tcaaatagcg atgtgcagga agaaaagccc ctcttcattc cggggaacaa    43020
agacgggtat tgttgggaaa ggaacaggct tggagggaag ggagaaagta ggccgctgat    43080
gatatattcg ggcaggactg ttgtggtact ggcaataaga tacacagctc cgagctgtag    43140
gagagtcggt ctgctttgga tgattttta  agcagactca gctgctatac ttatcacatt    43200
ttattaaaca cagggaaagc atttaggaga atagcagaga gccaaatctg acctaaaagt    43260
tgaaaagcca aaggtcaaac aggctgtaat tccatcatca tcgttgttat taagaatcc    43320 ttatctataa aaggtaggtc agatccccct cccccaggt  tcctccttcc cctcccgatt    43380
gagccttacg acactttggt ttatgcggtg ctgtccgggt gccagggctg cagggtcggt    43440
actgatggag gctgcagcgc ccggtgctct gtgtcaaggt gaagcacata cggcagacct    43500
cttagagtcc ttaagacgga agtaaattat gatgtccagg gggagaagga agataggacg    43560
tatttataat aggtatatag aacacaaggg ataaaaatg  aaagattttt actaatatat    43620
attttaaggt tgcacacagt acacaccaga agatgtgaaa ttcatttgtg gcaattaagt    43680
ggtcccaatg ctcagcgctt aaaaaaacaa attggacagc tacttctggg aaaaacaaca    43740
tcattccaaa aagaacaata atgagagcaa atgcaaaaat aaccaagtcc tccgaaggca    43800
tctcacggaa ccgtagacta ggaagtacga gccccacaga gcaggaagcc gatgtgactg    43860
catcatatat ttaacaatga caagatgttc cggcgtttat ttctgcgttg ggttttccct    43920
tgccttatgg gctgaagtgt tctctaga                                      43948
```

<210> SEQ ID NO 9
<211> LENGTH: 4335
<212> TYPE: DNA
<213> ORGANISM: Homo sapiens

<400> SEQUENCE: 9

```
gcgcggagct gggagtggct tcgccatggc tgtgagaagg gactccgtgt ggaagtactg     60
ctggggtgtt ttgatggttt tatgcagaac tgcgatttcc aaatcgatag ttttagagcc    120
tatctattgg aattcctcga actccaaatt tctacctgga caaggactgg tactataccc    180
acagatagga gacaaattgg atattatttg ccccaaagtg gactctaaaa ctgttggcca    240
```

```
gtatgaatat tataaagttt atatggttga taaagaccaa gcagacagat gcactattaa    300
gaaggaaaat acccctctcc tcaactgtgc caaaccagac caagatatca aattcaccat    360
caagtttcaa gaattcagcc ctaacctctg ggtctagaa tttcagaaga acaaagatta    420
ttacattata tctacatcaa atgggtcttt ggagggcctg gataaccagg agggaggggt    480
gtgccagaca agagccatga agatcctcat gaaagttgga caagatgcaa gttctgctgg    540
atcaaccagg aataaagatc caacaagacg tccagaacta gaagctggta caaatggaag    600
aagttcgaca acaagtccct ttgtaaaacc aaatccaggt tctagcacag acggcaacag    660
cgccggacat tcggggaaca acatcctcgg ttccgaagtg gccttatttg cagggattgc    720
ttcaggatgc atcatcttca tcgtcatcat catcacgctg gtggtcctct tgctgaagta    780
ccggaggaga cacaggaagc actcgccgca gcacacgacc acgctgtcgc tcagcacact    840
ggccacaccc aagcgcagcg gcaacaacaa cggctcagag cccagtgaca ttatcatccc    900
gctaaggact gcggacagcg tcttctgccc tcactacgag aaggtcagcg gggactacgg    960
gcacccggtg tacatcgtcc aggagatgcc cccgcagagc ccggcgaaca tttactacaa   1020
ggtctgagag ggaccctggt ggtacctgtg ctttcccaga ggacacctaa tgtcccgatg   1080
cctcccttga gggtttgaga gcccgcgtgc tggagaattg actgaagcac agcaccgggg   1140
gagagggaca ctcctcctcg gaagagcccg tcgcgctgga cagcttacct agtcttgtag   1200
cattcggcct tggtgaacac acacgctccc tggaagctgg aagactgtgc agaagacgcc   1260
cattcggact gctgtgccgc gtcccacgtc tcctcctcga agccatgtgc tgcggtcact   1320
caggcctctg cagaagccaa gggaagacag tggtttgtgg acgagagggc tgtgagcatc   1380
ctggcaggtg ccccaggatg ccacgcctgg aagggccggc ttctgcctgg ggtgcatttc   1440
ccccgcagtg cataccggac ttgtcacacg gacctcgggc tagttaaggt gtgcaaagat   1500
ctctagagtt tagtccttac tgtctcactc gttctgttac ccagggctct gcagcacctc   1560
acctgagacc tccactccac atctgcatca ctcatggaac actcatgtct ggagtcccct   1620
cctccagccg ctggcaacaa cagcttcagt ccatgggtaa tccgttcata gaaattgtgt   1680
ttgctaacaa ggtgcccttt agccagatgc taggctgtct gcgaagaagg ctaggagttc   1740
atagaaggga gtggggctgg ggaaagggct ggctgcaatt gcagctcact gctgctgcct   1800
ctgaaacaga aagttggaaa ggaaaaaaga aaaagcaat taggtagcac agcactttgg   1860
ttttgctgag atcgaagagg ccagtaggag acacgacagc acacacagtg gattccagtg   1920
catggggagg cactcgctgt tatcaaatag cgatgtgcag gaagaaaagc ccctcttcat   1980
tccggggaac aaagacgggt attgttggga aaggaacagg cttggaggga agggagaaag   2040
taggccgctg atgatatatt cgggcaggac tgttgtggta ctggcaataa gatacacagc   2100
tccgagctgt aggagagtcg gtctgctttg gatgatttt taagcagact cagctgctat   2160
acttatcaca tttttattaaa cacagggaaa gcatttagga gaatagcaga gagccaaatc   2220
tgacctaaaa gttgaaaagc caaaggtcaa acaggctgta attccatcat catcgttgtt   2280
attaaagaat ccttatctat aaaaggtagg tcagatcccc ctccccccag gttcctcctt   2340
cccctcccga ttgagcctta cgacactttg gtttatgcgg tgctgtccgg gtgccagggc   2400
tgcagggtcg gtactgatgg aggctgcagc gcccggtgct ctgtgtcaag gtgaagcaca   2460
tacggcagac ctcttagagt ccttaagacg gaagtaaatt atgatgtcca gggggagaag   2520
gaagatagga cgtatttata ataggtatat agaacacaag ggatataaaa tgaaagattt   2580
```

```
ttactaatat atattttaag gttgcacaca gtacacacca gaagatgtga aattcatttg    2640
tggcaattaa gtggtcccaa tgctcagcgc ttaaaaaaac aaattggaca gctacttctg    2700
ggaaaaacaa catcattcca aaaagaacaa taatgagagc aaatgcaaaa ataaccaagt    2760
cctccgaagg catctcacgg aaccgtagac taggaagtac gagccccaca gagcaggaag    2820
ccgatgtgac tgcatcatat atttaacaat gacaagatgt tccggcgttt atttctgcgt    2880
tgggttttcc cttgccttat gggctgaagt gttctctaga atccagcagg tcacactggg    2940
ggcttcaggt gacgatttag ctgtggctcc ctcctcctgt cctcccccgc accccctccc    3000
ttctgggaaa caagaagagt aaacaggaaa cctactttt atgtgctatg caaaatagac     3060
atctttaaca tagtcctgtt actatggtaa cactttgctt tctgaattgg aagggaaaaa    3120
aaatgtagcg acagcatttt aaggttctca gacctccagt gagtacctgc aaaaatgagt    3180
tgtcacagaa attatgatcc tctatttcct gaacctggaa atgatgttgg tccaaagtgc    3240
gtgtgtgtat gtgtgagtgg gtgcgtggta tacatgtgta catatatgta taatatatat    3300
ctacaatata tattatatat atctatatca tatttctgtg gagggttgcc atggtaacca    3360
gccacagtac atatgtaatt ctttccatca ccccaacctc tcctttctgt gcattcatgc    3420
aagagtttct tgtaagccat cagaagttac ttttaggatg ggggagaggg gcgagaaggg    3480
gaaaaatggg aaatagtctg attttaatga aatcaaatgt atgtatcatc agttggctac    3540
gttttggttc tatgctaaac tgtgaaaaat cagatgaatt gataaagag ttccctgcaa     3600
ccaattgaaa agtgttctgt gcgtctgttt tgtgtctggt gcagaatatg acaatctacc    3660
aactgtccct ttgtttgaag ttggtttagc tttggaaagt tactgtaaat gccttgcttg    3720
tatgatcgtc cctggtcacc cgactttgga atttgcacca tcatgtttca gtgaagatgc    3780
tgtaaatagg ttcagattt actgtctatg gatttgggt gttacagtag ccttattcac       3840
ctttttaata aaatacaca tgaaacaag aagaaatgg cttttcttac ccagattgtg         3900
tacatagagc aatgttggtt ttttataaag tctaagcaag atgttttgta taaaatctga    3960
attttgcaat gtatttagct acagcttgtt taacggcagt gtcattcccc tttgcactgt    4020
aatgaggaaa aaatggtata aaaggttgcc aaattgctgc atatttgtgc cgtaattatg    4080
taccatgaat atttatttaa aatttcgttg tccaatttgt aagtaacaca gtattatgcc    4140
tgagttataa atatttttt ctttctttgt tttattttaa tagcctgtca taggttttaa      4200
atctgcttta gtttcacatt gcagttagcc ccagaaaatg aaatccgtga agtcacattc    4260
cacatctgtt tcaaactgaa tttgttctta aaaaaataaa atatttttt cctatggaaa      4320
aaaaaaaaaa aaaaa                                                     4335
```

<210> SEQ ID NO 10
<211> LENGTH: 987
<212> TYPE: PRT
<213> ORGANISM: Homo sapiens

<400> SEQUENCE: 10

```
Met Glu Leu Arg Val Leu Leu Cys Trp Ala Ser Leu Ala Ala Ala Leu
  1               5                  10                  15

Glu Glu Thr Leu Leu Asn Thr Lys Leu Glu Thr Ala Asp Leu Lys Trp
             20                  25                  30

Val Thr Phe Pro Gln Val Asp Gly Gln Trp Glu Glu Leu Ser Gly Leu
         35                  40                  45

Asp Glu Glu Gln His Ser Val Arg Thr Tyr Glu Val Cys Asp Val Gln
     50                  55                  60
```

-continued

```
Arg Ala Pro Gly Gln Ala His Trp Leu Arg Thr Gly Trp Val Pro Arg
 65                  70                  75                  80

Arg Gly Ala Val His Val Tyr Ala Thr Leu Arg Phe Thr Met Leu Glu
                 85                  90                  95

Cys Leu Ser Leu Pro Arg Ala Gly Arg Ser Cys Lys Glu Thr Phe Thr
            100                 105                 110

Val Phe Tyr Tyr Glu Ser Asp Ala Asp Thr Ala Thr Ala Leu Thr Pro
        115                 120                 125

Ala Trp Met Glu Asn Pro Tyr Ile Lys Val Asp Thr Val Ala Ala Glu
    130                 135                 140

His Leu Thr Arg Lys Arg Pro Gly Ala Glu Ala Thr Gly Lys Val Asn
145                 150                 155                 160

Val Lys Thr Leu Arg Leu Gly Pro Leu Ser Lys Ala Gly Phe Tyr Leu
                165                 170                 175

Ala Phe Gln Asp Gln Gly Ala Cys Met Ala Leu Leu Ser Leu His Leu
            180                 185                 190

Phe Tyr Lys Lys Cys Ala Gln Leu Thr Val Asn Leu Thr Arg Phe Pro
        195                 200                 205

Glu Thr Val Pro Arg Glu Leu Val Val Pro Val Ala Gly Ser Cys Val
    210                 215                 220

Val Asp Ala Val Pro Ala Pro Gly Pro Ser Pro Ser Leu Tyr Cys Arg
225                 230                 235                 240

Glu Asp Gly Gln Trp Ala Glu Gln Pro Val Thr Gly Cys Ser Cys Ala
                245                 250                 255

Pro Gly Phe Glu Ala Ala Glu Gly Asn Thr Lys Cys Arg Ala Cys Ala
            260                 265                 270

Gln Gly Thr Phe Lys Pro Leu Ser Gly Glu Gly Ser Cys Gln Pro Cys
        275                 280                 285

Pro Ala Asn Ser His Ser Asn Thr Ile Gly Ser Ala Val Cys Gln Cys
    290                 295                 300

Arg Val Gly Tyr Phe Arg Ala Arg Thr Asp Pro Arg Gly Ala Pro Cys
305                 310                 315                 320

Thr Thr Pro Pro Ser Ala Pro Arg Ser Val Val Ser Arg Leu Asn Gly
                325                 330                 335

Ser Ser Leu His Leu Glu Trp Ser Ala Pro Leu Glu Ser Gly Gly Arg
            340                 345                 350

Glu Asp Leu Thr Tyr Ala Leu Arg Cys Arg Glu Cys Arg Pro Gly Gly
        355                 360                 365

Ser Cys Ala Pro Cys Gly Gly Asp Leu Thr Phe Asp Pro Gly Pro Arg
    370                 375                 380

Asp Leu Val Glu Pro Trp Val Val Arg Gly Leu Arg Pro Asp Phe
385                 390                 395                 400

Thr Tyr Thr Phe Glu Val Thr Ala Leu Asn Gly Val Ser Ser Leu Ala
                405                 410                 415

Thr Gly Pro Val Pro Phe Glu Pro Val Asn Val Thr Thr Asp Arg Glu
            420                 425                 430

Val Pro Pro Ala Val Ser Asp Ile Arg Val Thr Arg Ser Ser Pro Ser
        435                 440                 445

Ser Leu Ser Leu Ala Trp Ala Val Pro Arg Ala Pro Ser Gly Ala Val
    450                 455                 460

Leu Asp Tyr Glu Val Lys Tyr His Glu Lys Gly Ala Glu Gly Pro Ser
465                 470                 475                 480
```

```
Ser Val Arg Phe Leu Lys Thr Ser Glu Asn Arg Ala Glu Leu Arg Gly
                485                 490                 495

Leu Lys Arg Gly Ala Ser Tyr Leu Val Gln Val Arg Ala Arg Ser Glu
            500                 505                 510

Ala Gly Tyr Gly Pro Phe Gly Gln Glu His His Ser Gln Thr Gln Leu
        515                 520                 525

Asp Glu Ser Glu Gly Trp Arg Glu Gln Leu Ala Leu Ile Ala Gly Thr
    530                 535                 540

Ala Val Val Gly Val Val Leu Val Leu Val Val Ile Val Val Ala Val
545                 550                 555                 560

Leu Cys Leu Arg Lys Gln Ser Asn Gly Arg Glu Ala Glu Tyr Ser Asp
                565                 570                 575

Lys His Gly Gln Tyr Leu Ile Gly His Gly Thr Lys Val Tyr Ile Asp
            580                 585                 590

Pro Phe Thr Tyr Glu Asp Pro Asn Glu Ala Val Arg Glu Phe Ala Lys
        595                 600                 605

Glu Ile Asp Val Ser Tyr Val Lys Ile Glu Glu Val Ile Gly Ala Gly
    610                 615                 620

Glu Phe Gly Glu Val Cys Arg Gly Arg Leu Lys Ala Pro Gly Lys Lys
625                 630                 635                 640

Glu Ser Cys Val Ala Ile Lys Thr Leu Lys Gly Gly Tyr Thr Glu Arg
                645                 650                 655

Gln Arg Arg Glu Phe Leu Ser Glu Ala Ser Ile Met Gly Gln Phe Glu
            660                 665                 670

His Pro Asn Ile Ile Arg Leu Glu Gly Val Val Thr Asn Ser Met Pro
        675                 680                 685

Val Met Ile Leu Thr Glu Phe Met Glu Asn Gly Ala Leu Asp Ser Phe
    690                 695                 700

Leu Arg Leu Asn Asp Gly Gln Phe Thr Val Ile Gln Leu Val Gly Met
705                 710                 715                 720

Leu Arg Gly Ile Ala Ser Gly Met Arg Tyr Leu Ala Glu Met Ser Tyr
                725                 730                 735

Val His Arg Asp Leu Ala Ala Arg Asn Ile Leu Val Asn Ser Asn Leu
            740                 745                 750

Val Cys Lys Val Ser Asp Phe Gly Leu Ser Arg Phe Leu Glu Glu Asn
        755                 760                 765

Ser Ser Asp Pro Thr Tyr Thr Ser Ser Leu Gly Gly Lys Ile Pro Ile
    770                 775                 780

Arg Trp Thr Ala Pro Glu Ala Ile Ala Phe Arg Lys Phe Thr Ser Ala
785                 790                 795                 800

Ser Asp Ala Trp Ser Tyr Gly Ile Val Met Trp Glu Val Met Ser Phe
                805                 810                 815

Gly Glu Arg Pro Tyr Trp Asp Met Ser Asn Gln Asp Val Ile Asn Ala
            820                 825                 830

Ile Glu Gln Asp Tyr Arg Leu Pro Pro Pro Asp Cys Pro Thr Ser
        835                 840                 845

Leu His Gln Leu Met Leu Asp Cys Trp Gln Lys Asp Arg Asn Ala Arg
850                 855                 860

Pro Arg Phe Pro Gln Val Ser Ala Leu Asp Lys Met Ile Arg Asn
865                 870                 875                 880

Pro Ala Ser Leu Lys Ile Val Ala Arg Glu Asn Gly Gly Ala Ser His
                885                 890                 895

Pro Leu Leu Asp Gln Arg Gln Pro His Tyr Ser Ala Phe Gly Ser Val
```

```
              900                 905                 910
Gly Glu Trp Leu Arg Ala Ile Lys Met Gly Arg Tyr Glu Glu Ser Phe
            915                 920                 925

Ala Ala Ala Gly Phe Gly Ser Phe Glu Leu Val Ser Gln Ile Ser Ala
930                 935                 940

Glu Asp Leu Leu Arg Ile Gly Val Thr Leu Ala Gly His Gln Lys Lys
945                 950                 955                 960

Ile Leu Ala Ser Val Gln His Met Lys Ser Gln Ala Lys Pro Gly Thr
                965                 970                 975

Pro Gly Gly Thr Gly Gly Pro Ala Pro Gln Tyr
            980                 985

<210> SEQ ID NO 11
<211> LENGTH: 333
<212> TYPE: PRT
<213> ORGANISM: Homo sapiens

<400> SEQUENCE: 11

Met Ala Val Arg Arg Asp Ser Val Trp Lys Tyr Cys Trp Gly Val Leu
1               5                   10                  15

Met Val Leu Cys Arg Thr Ala Ile Ser Lys Ser Ile Val Leu Glu Pro
            20                  25                  30

Ile Tyr Trp Asn Ser Ser Asn Ser Lys Phe Leu Pro Gly Gln Gly Leu
        35                  40                  45

Val Leu Tyr Pro Gln Ile Gly Asp Lys Leu Asp Ile Ile Cys Pro Lys
    50                  55                  60

Val Asp Ser Lys Thr Val Gly Gln Tyr Glu Tyr Tyr Lys Val Tyr Met
65                  70                  75                  80

Val Asp Lys Asp Gln Ala Asp Arg Cys Thr Ile Lys Lys Glu Asn Thr
                85                  90                  95

Pro Leu Leu Asn Cys Ala Lys Pro Asp Gln Asp Ile Lys Phe Thr Ile
            100                 105                 110

Lys Phe Gln Glu Phe Ser Pro Asn Leu Trp Gly Leu Glu Phe Gln Lys
        115                 120                 125

Asn Lys Asp Tyr Tyr Ile Ile Ser Thr Ser Asn Gly Ser Leu Glu Gly
    130                 135                 140

Leu Asp Asn Gln Glu Gly Gly Val Cys Gln Thr Arg Ala Met Lys Ile
145                 150                 155                 160

Leu Met Lys Val Gly Gln Asp Ala Ser Ser Ala Gly Ser Thr Arg Asn
                165                 170                 175

Lys Asp Pro Thr Arg Arg Pro Glu Leu Glu Ala Gly Thr Asn Gly Arg
            180                 185                 190

Ser Ser Thr Thr Ser Pro Phe Val Lys Pro Asn Pro Gly Ser Ser Thr
        195                 200                 205

Asp Gly Asn Ser Ala Gly His Ser Gly Asn Asn Ile Leu Gly Ser Glu
    210                 215                 220

Val Ala Leu Phe Ala Gly Ile Ala Ser Gly Cys Ile Ile Phe Ile Val
225                 230                 235                 240

Ile Ile Ile Thr Leu Val Val Leu Leu Leu Lys Tyr Arg Arg Arg His
                245                 250                 255

Arg Lys His Ser Pro Gln His Thr Thr Thr Leu Ser Leu Ser Thr Leu
            260                 265                 270

Ala Thr Pro Lys Arg Ser Gly Asn Asn Asn Gly Ser Glu Pro Ser Asp
        275                 280                 285
```

```
Ile Ile Ile Pro Leu Arg Thr Ala Asp Ser Val Phe Cys Pro His Tyr
290                 295                 300

Glu Lys Val Ser Gly Asp Tyr Gly His Pro Val Tyr Ile Val Gln Glu
305                 310                 315                 320

Met Pro Pro Gln Ser Pro Ala Asn Ile Tyr Tyr Lys Val
                325                 330

<210> SEQ ID NO 12
<211> LENGTH: 332
<212> TYPE: PRT
<213> ORGANISM: Unknown
<220> FEATURE:
<223> OTHER INFORMATION: Recombinant B4EC-GC

<400> SEQUENCE: 12

Met Glu Leu Arg Val Leu Leu Cys Trp Ala Ser Leu Ala Ala Ala Leu
1               5                   10                  15

Glu Glu Thr Leu Leu Asn Thr Lys Leu Glu Thr Ala Asp Leu Lys Trp
            20                  25                  30

Val Thr Phe Pro Gln Val Asp Gly Gln Trp Glu Glu Leu Ser Gly Leu
        35                  40                  45

Asp Glu Glu Gln His Ser Val Arg Thr Tyr Glu Val Cys Glu Val Gln
50                  55                  60

Arg Ala Pro Gly Gln Ala His Trp Leu Arg Thr Gly Trp Val Pro Arg
65                  70                  75                  80

Arg Gly Ala Val His Val Tyr Ala Thr Leu Arg Phe Thr Met Leu Glu
                85                  90                  95

Cys Leu Ser Leu Pro Arg Ala Gly Arg Ser Cys Lys Glu Thr Phe Thr
            100                 105                 110

Val Phe Tyr Tyr Glu Ser Asp Ala Asp Thr Ala Thr Ala Leu Thr Pro
        115                 120                 125

Ala Trp Met Glu Asn Pro Tyr Ile Lys Val Asp Thr Val Ala Ala Glu
130                 135                 140

His Leu Thr Arg Lys Arg Pro Gly Ala Glu Ala Thr Gly Lys Val Asn
145                 150                 155                 160

Val Lys Thr Leu Arg Leu Gly Pro Leu Ser Lys Ala Gly Phe Tyr Leu
                165                 170                 175

Ala Phe Gln Asp Gln Gly Ala Cys Met Ala Leu Leu Ser Leu His Leu
            180                 185                 190

Phe Tyr Lys Lys Cys Ala Gln Leu Thr Val Asn Leu Thr Arg Phe Pro
        195                 200                 205

Glu Thr Val Pro Arg Glu Leu Val Val Pro Val Ala Gly Ser Cys Val
    210                 215                 220

Val Asp Ala Val Pro Ala Pro Gly Pro Ser Pro Ser Leu Tyr Cys Arg
225                 230                 235                 240

Glu Asp Gly Gln Trp Ala Glu Gln Pro Val Thr Gly Cys Ser Cys Ala
                245                 250                 255

Pro Gly Phe Glu Ala Ala Glu Gly Asn Thr Lys Cys Arg Ala Cys Ala
            260                 265                 270

Gln Gly Thr Phe Lys Pro Leu Ser Gly Glu Gly Ser Cys Gln Pro Cys
        275                 280                 285

Pro Ala Asn Ser His Ser Asn Thr Ile Gly Ser Ala Val Cys Gln Cys
    290                 295                 300

Arg Val Gly Tyr Phe Arg Ala Arg Thr Asp Pro Arg Gly Ala Pro Cys
305                 310                 315                 320
```

```
Thr Thr Pro Pro Ser Ala His His His His His
            325                 330
```

<210> SEQ ID NO 13
<211> LENGTH: 431
<212> TYPE: PRT
<213> ORGANISM: Unknown
<220> FEATURE:
<223> OTHER INFORMATION: Recombinant GCF

<400> SEQUENCE: 13

```
Met Glu Leu Arg Val Leu Leu Cys Trp Ala Ser Leu Ala Ala Ala Leu
 1               5                  10                  15

Glu Glu Thr Leu Leu Asn Thr Lys Leu Glu Thr Ala Asp Leu Lys Trp
            20                  25                  30

Val Thr Phe Pro Gln Val Asp Gly Gln Trp Glu Glu Leu Ser Gly Leu
        35                  40                  45

Asp Glu Glu Gln His Ser Val Arg Thr Tyr Glu Val Cys Glu Val Gln
 50                  55                  60

Arg Ala Pro Gly Gln Ala His Trp Leu Arg Thr Gly Trp Val Pro Arg
 65                  70                  75                  80

Arg Gly Ala Val His Val Tyr Ala Thr Leu Arg Phe Thr Met Leu Glu
                85                  90                  95

Cys Leu Ser Leu Pro Arg Ala Gly Arg Ser Cys Lys Glu Thr Phe Thr
            100                 105                 110

Val Phe Tyr Tyr Glu Ser Asp Ala Asp Thr Ala Thr Ala Leu Thr Pro
        115                 120                 125

Ala Trp Met Glu Asn Pro Tyr Ile Lys Val Asp Thr Val Ala Ala Glu
130                 135                 140

His Leu Thr Arg Lys Arg Pro Gly Ala Glu Ala Thr Gly Lys Val Asn
145                 150                 155                 160

Val Lys Thr Leu Arg Leu Gly Pro Leu Ser Lys Ala Gly Phe Tyr Leu
                165                 170                 175

Ala Phe Gln Asp Gln Gly Ala Cys Met Ala Leu Leu Ser Leu His Leu
            180                 185                 190

Phe Tyr Lys Lys Cys Ala Gln Leu Thr Val Asn Leu Thr Arg Phe Pro
        195                 200                 205

Glu Thr Val Pro Arg Glu Leu Val Val Pro Val Ala Gly Ser Cys Val
    210                 215                 220

Val Asp Ala Val Pro Ala Pro Gly Pro Ser Pro Ser Leu Tyr Cys Arg
225                 230                 235                 240

Glu Asp Gly Gln Trp Ala Glu Gln Pro Val Thr Gly Cys Ser Cys Ala
                245                 250                 255

Pro Gly Phe Ala Glu Gly Asn Thr Lys Cys Arg Ala Cys Ala Gln Gly
            260                 265                 270

Thr Phe Lys Pro Leu Ser Gly Glu Gly Ser Cys Gln Pro Cys Pro Ala
        275                 280                 285

Asn Ser His Ser Asn Thr Ile Gly Ser Ala Val Cys Gln Cys Arg Val
    290                 295                 300

Gly Tyr Phe Arg Ala Arg Thr Asp Pro Arg Gly Ala Pro Cys Thr Thr
305                 310                 315                 320

Pro Pro Ser Ala Pro Arg Ser Val Val Ser Arg Leu Asn Gly Ser Ser
                325                 330                 335

Leu His Leu Glu Trp Ser Ala Pro Leu Glu Ser Gly Gly Arg Glu Asp
            340                 345                 350
```

```
Leu Thr Tyr Ala Leu Arg Cys Arg Glu Cys Arg Pro Gly Gly Ser Cys
            355                 360                 365

Ala Pro Cys Gly Gly Asp Leu Thr Phe Asp Pro Gly Pro Arg Asp Leu
        370                 375                 380

Val Glu Pro Trp Val Val Arg Gly Leu Arg Pro Asp Phe Thr Tyr
385                 390                 395                 400

Thr Phe Glu Val Thr Ala Leu Asn Gly Val Ser Ser Leu Ala Thr Gly
                405                 410                 415

Pro Val Pro Phe Glu Pro Val Asn Val His His His His His His
        420                 425                 430
```

<210> SEQ ID NO 14
<211> LENGTH: 570
<212> TYPE: PRT
<213> ORGANISM: Unknown
<220> FEATURE:
<223> OTHER INFORMATION: Recombinant FL-hB4EC

<400> SEQUENCE: 14

```
Met Glu Leu Arg Val Leu Leu Cys Trp Ala Ser Leu Ala Ala Ala Leu
1               5                   10                  15

Glu Glu Thr Leu Leu Asn Thr Lys Leu Glu Thr Ala Asp Leu Lys Trp
            20                  25                  30

Val Thr Phe Pro Gln Val Asp Gly Gln Trp Glu Glu Leu Ser Gly Leu
        35                  40                  45

Asp Glu Glu Gln His Ser Val Arg Thr Tyr Glu Val Cys Glu Val Gln
    50                  55                  60

Arg Ala Pro Gly Gln Ala His Trp Leu Arg Thr Gly Trp Val Pro Arg
65                  70                  75                  80

Arg Gly Ala Val His Val Tyr Ala Thr Leu Arg Phe Thr Met Leu Glu
                85                  90                  95

Cys Leu Ser Leu Pro Arg Ala Gly Arg Ser Cys Lys Glu Thr Phe Thr
            100                 105                 110

Val Phe Tyr Tyr Glu Ser Asp Ala Asp Thr Ala Thr Ala Leu Thr Pro
        115                 120                 125

Ala Trp Met Glu Asn Pro Tyr Ile Lys Val Asp Thr Val Ala Ala Glu
    130                 135                 140

His Leu Thr Arg Lys Arg Pro Gly Ala Glu Ala Thr Gly Lys Val Asn
145                 150                 155                 160

Val Lys Thr Leu Arg Leu Gly Pro Leu Ser Lys Ala Gly Phe Tyr Leu
                165                 170                 175

Ala Phe Gln Asp Gln Gly Ala Cys Met Ala Leu Leu Ser Leu His Leu
            180                 185                 190

Phe Tyr Lys Lys Cys Ala Gln Leu Thr Val Asn Leu Thr Arg Phe Pro
        195                 200                 205

Glu Thr Val Pro Arg Glu Leu Val Val Pro Val Ala Gly Ser Cys Val
    210                 215                 220

Val Asp Ala Val Pro Ala Pro Gly Pro Ser Pro Ser Leu Tyr Cys Arg
225                 230                 235                 240

Glu Asp Gly Gln Trp Ala Glu Gln Pro Val Thr Gly Cys Ser Cys Ala
                245                 250                 255

Pro Gly Phe Glu Ala Ala Glu Gly Asn Thr Lys Cys Arg Ala Cys Ala
            260                 265                 270

Gln Gly Thr Phe Lys Pro Leu Ser Gly Glu Gly Ser Cys Gln Pro Cys
        275                 280                 285
```

Pro Ala Asn Ser His Ser Asn Thr Ile Gly Ser Ala Val Cys Gln Cys
            290                 295                 300

Arg Val Gly Tyr Phe Arg Ala Arg Thr Asp Pro Arg Gly Ala Pro Cys
305                 310                 315                 320

Thr Thr Pro Pro Ser Ala Pro Arg Ser Val Val Ser Arg Leu Asn Gly
                325                 330                 335

Ser Ser Leu His Leu Glu Trp Ser Ala Pro Leu Glu Ser Gly Gly Arg
            340                 345                 350

Glu Asp Leu Thr Tyr Ala Leu Arg Cys Arg Glu Cys Arg Pro Gly Gly
            355                 360                 365

Ser Cys Ala Pro Cys Gly Gly Asp Leu Thr Phe Asp Pro Gly Pro Arg
            370                 375                 380

Asp Leu Val Glu Pro Trp Val Val Arg Gly Leu Arg Pro Asp Phe
385                 390                 395                 400

Thr Tyr Thr Phe Glu Val Thr Ala Leu Asn Gly Val Ser Ser Leu Ala
                405                 410                 415

Thr Gly Pro Val Pro Phe Glu Pro Val Asn Val Thr Thr Asp Arg Glu
            420                 425                 430

Val Pro Pro Ala Val Ser Asp Ile Arg Val Thr Arg Ser Ser Pro Ser
435                 440                 445

Ser Leu Ser Leu Ala Trp Ala Val Pro Arg Ala Pro Ser Gly Ala Trp
            450                 455                 460

Leu Asp Tyr Glu Val Lys Tyr His Glu Lys Gly Ala Glu Gly Pro Ser
465                 470                 475                 480

Ser Val Arg Phe Leu Lys Thr Ser Glu Asn Arg Ala Glu Leu Arg Gly
                485                 490                 495

Leu Lys Arg Gly Ala Ser Tyr Leu Val Gln Val Arg Ala Arg Ser Glu
            500                 505                 510

Ala Gly Tyr Gly Pro Phe Gly Gln Glu His His Ser Gln Thr Gln Leu
            515                 520                 525

Asp Glu Ser Glu Gly Trp Arg Glu Gln Gly Ser Lys Arg Ala Ile Leu
            530                 535                 540

Gln Ile Glu Gly Lys Pro Ile Pro Asn Pro Leu Leu Gly Leu Asp Ser
545                 550                 555                 560

Thr Arg Thr Gly His His His His His His
                565                 570

<210> SEQ ID NO 15
<211> LENGTH: 401
<212> TYPE: PRT
<213> ORGANISM: Unknown
<220> FEATURE:
<223> OTHER INFORMATION: Recombinant B4-CF2

<400> SEQUENCE: 15

Met Glu Leu Arg Val Leu Leu Cys Trp Ala Ser Leu Ala Ala Ala Leu
1               5                   10                  15

Glu Glu Thr Leu Leu Asn Thr Lys Leu Glu Thr Gln Leu Thr Val Asn
                20                  25                  30

Leu Thr Arg Phe Pro Glu Thr Val Pro Arg Glu Leu Val Val Pro Val
            35                  40                  45

Ala Gly Ser Cys Val Val Asp Ala Val Pro Ala Pro Gly Pro Ser Pro
        50                  55                  60

Ser Leu Tyr Cys Arg Glu Asp Gly Gln Trp Ala Glu Gln Pro Val Thr
65                  70                  75                  80

Gly Cys Ser Cys Ala Pro Gly Phe Glu Ala Glu Gly Asn Thr Lys
            85                  90                  95

Cys Arg Ala Cys Ala Gln Gly Thr Phe Lys Pro Leu Ser Gly Glu Gly
            100                 105                 110

Ser Cys Gln Pro Cys Pro Ala Asn Ser His Ser Asn Thr Ile Gly Ser
            115                 120                 125

Ala Val Cys Gln Cys Arg Val Gly Tyr Phe Arg Ala Arg Thr Asp Pro
            130                 135                 140

Arg Gly Ala Pro Cys Thr Thr Pro Pro Ser Ala Pro Arg Ser Val Val
145                 150                 155                 160

Ser Arg Leu Asn Gly Ser Ser Leu His Leu Glu Trp Ser Ala Pro Leu
            165                 170                 175

Glu Ser Gly Gly Arg Glu Asp Leu Thr Tyr Ala Leu Arg Cys Arg Glu
            180                 185                 190

Cys Arg Pro Gly Gly Ser Cys Ala Pro Cys Gly Gly Asp Leu Thr Phe
            195                 200                 205

Asp Pro Gly Pro Arg Asp Leu Val Glu Pro Trp Val Val Val Arg Gly
            210                 215                 220

Leu Arg Pro Asp Phe Thr Tyr Thr Phe Glu Val Thr Ala Leu Asn Gly
225                 230                 235                 240

Val Ser Ser Leu Ala Thr Gly Pro Val Pro Phe Glu Pro Val Asn Val
            245                 250                 255

Thr Thr Asp Arg Glu Val Pro Pro Ala Val Ser Asp Ile Arg Val Thr
            260                 265                 270

Arg Ser Ser Pro Ser Ser Leu Ser Leu Ala Trp Ala Val Pro Arg Ala
            275                 280                 285

Pro Ser Gly Ala Trp Leu Asp Tyr Glu Val Lys Tyr His Glu Lys Gly
            290                 295                 300

Ala Glu Gly Pro Ser Ser Val Arg Phe Leu Lys Thr Ser Glu Asn Arg
305                 310                 315                 320

Ala Glu Leu Arg Gly Leu Lys Arg Gly Ala Ser Tyr Leu Val Gln Val
            325                 330                 335

Arg Ala Arg Ser Glu Ala Gly Tyr Gly Pro Phe Gly Gln Glu His His
            340                 345                 350

Ser Gln Thr Gln Leu Asp Glu Ser Glu Gly Trp Arg Glu Gln Gly Gly
            355                 360                 365

Arg Ser Ser Leu Glu Gly Pro Arg Phe Glu Gly Lys Pro Ile Pro Asn
            370                 375                 380

Pro Leu Leu Gly Leu Asp Ser Thr Arg Thr Gly His His His His His
385                 390                 395                 400

His

<210> SEQ ID NO 16
<211> LENGTH: 537
<212> TYPE: PRT
<213> ORGANISM: Unknown
<220> FEATURE:
<223> OTHER INFORMATION: Recombinant B4-GCF2F

<400> SEQUENCE: 16

Met Glu Leu Arg Val Leu Leu Cys Trp Ala Ser Leu Ala Ala Ala Leu
1               5                   10                  15

Glu Glu Thr Leu Leu Asn Thr Lys Leu Glu Thr Ala Asp Leu Lys Trp
            20                  25                  30

Val Thr Phe Pro Gln Val Asp Gly Gln Trp Glu Glu Leu Ser Gly Leu

```
                35                  40                  45
Asp Glu Glu Gln His Ser Val Arg Thr Tyr Glu Val Cys Glu Val Gln
 50                  55                  60
Arg Ala Pro Gly Gln Ala His Trp Leu Arg Thr Gly Trp Val Pro Arg
 65                  70                  75                  80
Arg Gly Ala Val His Val Tyr Ala Thr Leu Arg Phe Thr Met Leu Glu
                     85                  90                  95
Cys Leu Ser Leu Pro Arg Ala Gly Arg Ser Cys Lys Glu Thr Phe Thr
                100                 105                 110
Val Phe Tyr Tyr Glu Ser Asp Ala Asp Thr Ala Thr Ala Leu Thr Pro
            115                 120                 125
Ala Trp Met Glu Asn Pro Tyr Ile Lys Val Asp Thr Val Ala Ala Glu
            130                 135                 140
His Leu Thr Arg Lys Arg Pro Gly Ala Glu Ala Thr Gly Lys Val Asn
145                 150                 155                 160
Val Lys Thr Leu Arg Leu Gly Pro Leu Ser Lys Ala Gly Phe Tyr Leu
                165                 170                 175
Ala Phe Gln Asp Gln Gly Ala Cys Met Ala Leu Leu Ser Leu His Leu
                180                 185                 190
Phe Tyr Lys Lys Cys Ala Gln Leu Thr Val Asn Leu Thr Arg Phe Pro
            195                 200                 205
Glu Thr Val Pro Arg Glu Leu Val Val Pro Val Ala Gly Ser Cys Val
210                 215                 220
Val Asp Ala Val Pro Ala Pro Gly Pro Ser Pro Ser Leu Tyr Cys Arg
225                 230                 235                 240
Glu Asp Gly Gln Trp Ala Glu Gln Pro Val Thr Gly Cys Ser Cys Ala
                245                 250                 255
Pro Gly Phe Glu Ala Ala Glu Gly Asn Thr Lys Cys Arg Ala Cys Ala
                260                 265                 270
Gln Gly Thr Phe Lys Pro Leu Ser Gly Glu Gly Ser Cys Gln Pro Cys
            275                 280                 285
Pro Ala Asn Ser His Ser Asn Thr Ile Gly Ser Ala Val Cys Gln Cys
290                 295                 300
Arg Val Gly Tyr Phe Arg Ala Arg Thr Asp Pro Arg Gly Ala Pro Cys
305                 310                 315                 320
Thr Thr Pro Pro Ser Ala Pro Arg Ser Val Val Ser Arg Leu Asn Gly
                325                 330                 335
Ser Ser Leu His Leu Glu Trp Ser Ala Pro Leu Glu Ser Gly Gly Arg
                340                 345                 350
Glu Asp Leu Thr Tyr Ala Leu Arg Cys Arg Glu Cys Arg Pro Gly Gly
            355                 360                 365
Ser Cys Ala Pro Cys Gly Gly Asp Leu Thr Phe Asp Pro Gly Pro Arg
            370                 375                 380
Asp Leu Val Glu Pro Trp Val Val Arg Gly Leu Arg Pro Asp Phe
385                 390                 395                 400
Thr Tyr Thr Phe Glu Val Thr Ala Leu Asn Gly Val Ser Ser Leu Ala
                405                 410                 415
Thr Gly Pro Val Pro Phe Glu Pro Val Asn Val Thr Thr Asp Arg Glu
                420                 425                 430
Val Pro Pro Ala Val Ser Asp Ile Arg Val Thr Arg Ser Ser Pro Ser
            435                 440                 445
Ser Leu Ser Leu Ala Trp Ala Val Pro Arg Ala Pro Ser Gly Ala Trp
450                 455                 460
```

```
Leu Asp Tyr Glu Val Lys Tyr His Glu Lys Gly Ala Glu Gly Pro Ser
465                 470                 475                 480

Ser Val Arg Phe Leu Lys Thr Ser Glu Asn Arg Ala Glu Leu Arg Gly
                485                 490                 495

Leu Lys Arg Gly Ala Ser Tyr Leu Val Gln Val Arg Ala Arg Ser Glu
            500                 505                 510

Ala Gly Tyr Gly Pro Phe Gly Gln Glu His His Ser Gln Thr Gln Leu
            515                 520                 525

Asp Glu Ser Glu Gly Trp Arg Glu Gln
530                 535

<210> SEQ ID NO 17
<211> LENGTH: 522
<212> TYPE: PRT
<213> ORGANISM: Unknown
<220> FEATURE:
<223> OTHER INFORMATION: Recombinant processed B4-GCF2F

<400> SEQUENCE: 17

Leu Glu Glu Thr Leu Leu Asn Thr Lys Leu Glu Thr Ala Asp Leu Lys
1               5                   10                  15

Trp Val Thr Phe Pro Gln Val Asp Gly Gln Trp Glu Glu Leu Ser Gly
                20                  25                  30

Leu Asp Glu Glu Gln His Ser Val Arg Thr Tyr Glu Val Cys Glu Val
            35                  40                  45

Gln Arg Ala Pro Gly Gln Ala His Trp Leu Arg Thr Gly Trp Val Pro
        50                  55                  60

Arg Arg Gly Ala Val His Val Tyr Ala Thr Leu Arg Phe Thr Met Leu
65                  70                  75                  80

Glu Cys Leu Ser Leu Pro Arg Ala Gly Arg Ser Cys Lys Glu Thr Phe
                85                  90                  95

Thr Val Phe Tyr Tyr Glu Ser Asp Ala Asp Thr Ala Thr Ala Leu Thr
                100                 105                 110

Pro Ala Trp Met Glu Asn Pro Tyr Ile Lys Val Asp Thr Val Ala Ala
            115                 120                 125

Glu His Leu Thr Arg Lys Arg Pro Gly Ala Glu Ala Thr Gly Lys Val
        130                 135                 140

Asn Val Lys Thr Leu Arg Leu Gly Pro Leu Ser Lys Ala Gly Phe Tyr
145                 150                 155                 160

Leu Ala Phe Gln Asp Gln Gly Ala Cys Met Ala Leu Leu Ser Leu His
                165                 170                 175

Leu Phe Tyr Lys Lys Cys Ala Gln Leu Thr Val Asn Leu Thr Arg Phe
                180                 185                 190

Pro Glu Thr Val Pro Arg Glu Leu Val Val Pro Val Ala Gly Ser Cys
            195                 200                 205

Val Val Asp Ala Val Pro Ala Pro Gly Pro Ser Pro Ser Leu Tyr Cys
        210                 215                 220

Arg Glu Asp Gly Gln Trp Ala Glu Gln Pro Val Thr Gly Cys Ser Cys
225                 230                 235                 240

Ala Pro Gly Phe Glu Ala Ala Glu Gly Asn Thr Lys Cys Arg Ala Cys
                245                 250                 255

Ala Gln Gly Thr Phe Lys Pro Leu Ser Gly Glu Gly Ser Cys Gln Pro
            260                 265                 270

Cys Pro Ala Asn Ser His Ser Asn Thr Ile Gly Ser Ala Val Cys Gln
        275                 280                 285
```

-continued

```
Cys Arg Val Gly Tyr Phe Arg Ala Arg Thr Asp Pro Arg Gly Ala Pro
        290                 295                 300
Cys Thr Thr Pro Pro Ser Ala Pro Arg Ser Val Val Ser Arg Leu Asn
305                 310                 315                 320
Gly Ser Ser Leu His Leu Glu Trp Ser Ala Pro Leu Glu Ser Gly Gly
                325                 330                 335
Arg Glu Asp Leu Thr Tyr Ala Leu Arg Cys Arg Glu Cys Arg Pro Gly
            340                 345                 350
Gly Ser Cys Ala Pro Cys Gly Gly Asp Leu Thr Phe Asp Pro Gly Pro
        355                 360                 365
Arg Asp Leu Val Glu Pro Trp Val Val Arg Gly Leu Arg Pro Asp
    370                 375                 380
Phe Thr Tyr Thr Phe Glu Val Thr Ala Leu Asn Gly Val Ser Ser Leu
385                 390                 395                 400
Ala Thr Gly Pro Val Pro Phe Glu Pro Val Asn Val Thr Thr Asp Arg
                405                 410                 415
Glu Val Pro Pro Ala Val Ser Asp Ile Arg Val Thr Arg Ser Ser Pro
            420                 425                 430
Ser Ser Leu Ser Leu Ala Trp Ala Val Pro Arg Ala Pro Ser Gly Ala
        435                 440                 445
Trp Leu Asp Tyr Glu Val Lys Tyr His Glu Lys Gly Ala Glu Gly Pro
    450                 455                 460
Ser Ser Val Arg Phe Leu Lys Thr Ser Glu Asn Arg Ala Glu Leu Arg
465                 470                 475                 480
Gly Leu Lys Arg Gly Ala Ser Tyr Leu Val Gln Val Arg Ala Arg Ser
                485                 490                 495
Glu Ala Gly Tyr Gly Pro Phe Gly Gln Glu His His Ser Gln Thr Gln
            500                 505                 510
Leu Asp Glu Ser Glu Gly Trp Arg Glu Gln
        515                 520

<210> SEQ ID NO 18
<211> LENGTH: 1124
<212> TYPE: PRT
<213> ORGANISM: Unknown
<220> FEATURE:
<223> OTHER INFORMATION: Recombinant HSA-EphB4 precursor protein

<400> SEQUENCE: 18

Met Glu Leu Arg Val Leu Leu Cys Trp Ala Ser Leu Ala Ala Ala Leu
1               5                   10                  15
Glu Glu Thr Leu Leu Asn Thr Lys Leu Glu Thr Ala Asp Leu Lys Trp
            20                  25                  30
Val Thr Phe Pro Gln Val Asp Gly Gln Trp Glu Glu Leu Ser Gly Leu
        35                  40                  45
Asp Glu Glu Gln His Ser Val Arg Thr Tyr Glu Val Cys Asp Val Gln
    50                  55                  60
Arg Ala Pro Gly Gln Ala His Trp Leu Arg Thr Gly Trp Val Pro Arg
65                  70                  75                  80
Arg Gly Ala Val His Val Tyr Ala Thr Leu Arg Phe Thr Met Leu Glu
                85                  90                  95
Cys Leu Ser Leu Pro Arg Ala Gly Arg Ser Cys Lys Glu Thr Phe Thr
            100                 105                 110
Val Phe Tyr Tyr Glu Ser Asp Ala Asp Thr Ala Thr Ala Leu Thr Pro
        115                 120                 125
```

```
Ala Trp Met Glu Asn Pro Tyr Ile Lys Val Asp Thr Val Ala Ala Glu
        130                 135                 140

His Leu Thr Arg Lys Arg Pro Gly Ala Glu Ala Thr Gly Lys Val Asn
145                 150                 155                 160

Val Lys Thr Leu Arg Leu Gly Pro Leu Ser Lys Ala Gly Phe Tyr Leu
                165                 170                 175

Ala Phe Gln Asp Gln Gly Ala Cys Met Ala Leu Leu Ser Leu His Leu
                180                 185                 190

Phe Tyr Lys Lys Cys Ala Gln Leu Thr Val Asn Leu Thr Arg Phe Pro
            195                 200                 205

Glu Thr Val Pro Arg Glu Leu Val Pro Val Ala Gly Ser Cys Val
210                 215                 220

Val Asp Ala Val Pro Ala Pro Gly Pro Ser Pro Ser Leu Tyr Cys Arg
225                 230                 235                 240

Glu Asp Gly Gln Trp Ala Glu Gln Pro Val Thr Gly Cys Ser Cys Ala
                245                 250                 255

Pro Gly Phe Glu Ala Ala Glu Gly Asn Thr Lys Cys Arg Ala Cys Ala
                260                 265                 270

Gln Gly Thr Phe Lys Pro Leu Ser Gly Glu Gly Ser Cys Gln Pro Cys
            275                 280                 285

Pro Ala Asn Ser His Ser Asn Thr Ile Gly Ser Ala Val Cys Gln Cys
290                 295                 300

Arg Val Gly Tyr Phe Arg Ala Arg Thr Asp Pro Arg Gly Ala Pro Cys
305                 310                 315                 320

Thr Thr Pro Pro Ser Ala Pro Arg Ser Val Val Ser Arg Leu Asn Gly
                325                 330                 335

Ser Ser Leu His Leu Glu Trp Ser Ala Pro Leu Glu Ser Gly Gly Arg
            340                 345                 350

Glu Asp Leu Thr Tyr Ala Leu Arg Cys Arg Glu Cys Arg Pro Gly Gly
            355                 360                 365

Ser Cys Ala Pro Cys Gly Gly Asp Leu Thr Phe Asp Pro Gly Pro Arg
370                 375                 380

Asp Leu Val Glu Pro Trp Val Val Arg Gly Leu Arg Pro Asp Phe
385                 390                 395                 400

Thr Tyr Thr Phe Glu Val Thr Ala Leu Asn Gly Val Ser Ser Leu Ala
                405                 410                 415

Thr Gly Pro Val Pro Phe Glu Pro Val Asn Val Thr Thr Asp Arg Glu
                420                 425                 430

Val Pro Pro Ala Val Ser Asp Ile Arg Val Thr Arg Ser Ser Pro Ser
            435                 440                 445

Ser Leu Ser Leu Ala Trp Ala Val Pro Arg Ala Pro Ser Gly Ala Val
450                 455                 460

Leu Asp Tyr Glu Val Lys Tyr His Glu Lys Gly Ala Glu Gly Pro Ser
465                 470                 475                 480

Ser Val Arg Phe Leu Lys Thr Ser Glu Asn Arg Ala Glu Leu Arg Gly
                485                 490                 495

Leu Lys Arg Gly Ala Ser Tyr Leu Val Gln Val Arg Ala Arg Ser Glu
            500                 505                 510

Ala Gly Tyr Gly Pro Phe Gly Gln Glu His His Ser Gln Thr Gln Leu
            515                 520                 525

Asp Glu Ser Glu Gly Trp Arg Glu Gln Ser Arg Asp Ala His Lys Ser
530                 535                 540
```

-continued

```
Glu Val Ala His Arg Phe Lys Asp Leu Gly Glu Asn Phe Lys Ala
545                 550                 555                 560

Leu Val Leu Ile Ala Phe Ala Gln Tyr Leu Gln Gln Cys Pro Phe Glu
                565                 570                 575

Asp His Val Lys Leu Val Asn Glu Val Thr Glu Phe Ala Lys Thr Cys
            580                 585                 590

Val Ala Asp Glu Ser Ala Glu Asn Cys Asp Lys Ser Leu His Thr Leu
        595                 600                 605

Phe Gly Asp Lys Leu Cys Thr Val Ala Thr Leu Arg Glu Thr Tyr Gly
610                 615                 620

Glu Met Ala Asp Cys Cys Ala Lys Gln Glu Pro Glu Arg Asn Glu Cys
625                 630                 635                 640

Phe Leu Gln His Lys Asp Asp Asn Pro Asn Leu Pro Arg Leu Val Arg
                645                 650                 655

Pro Glu Val Asp Val Met Cys Thr Ala Phe His Asp Asn Glu Glu Thr
            660                 665                 670

Phe Leu Lys Lys Tyr Leu Tyr Glu Ile Ala Arg Arg His Pro Tyr Phe
        675                 680                 685

Tyr Ala Pro Glu Leu Leu Phe Phe Ala Lys Arg Tyr Lys Ala Ala Phe
690                 695                 700

Thr Glu Cys Cys Gln Ala Ala Asp Lys Ala Ala Cys Leu Leu Pro Lys
705                 710                 715                 720

Leu Asp Glu Leu Arg Asp Glu Gly Lys Ala Ser Ser Ala Lys Gln Arg
                725                 730                 735

Leu Lys Cys Ala Ser Leu Gln Lys Phe Gly Glu Arg Ala Phe Lys Ala
            740                 745                 750

Trp Ala Val Ala Arg Leu Ser Gln Arg Phe Pro Lys Ala Glu Phe Ala
        755                 760                 765

Glu Val Ser Lys Leu Val Thr Asp Leu Thr Lys Val His Thr Glu Cys
770                 775                 780

Cys His Gly Asp Leu Leu Glu Cys Ala Asp Asp Arg Ala Asp Leu Ala
785                 790                 795                 800

Lys Tyr Ile Cys Glu Asn Gln Asp Ser Ile Ser Ser Lys Leu Lys Glu
                805                 810                 815

Cys Cys Glu Lys Pro Leu Leu Glu Lys Ser His Cys Ile Ala Glu Val
            820                 825                 830

Glu Asn Asp Glu Met Pro Ala Asp Leu Pro Ser Leu Ala Ala Asp Phe
        835                 840                 845

Val Glu Ser Lys Asp Val Cys Lys Asn Tyr Ala Glu Ala Lys Asp Val
850                 855                 860

Phe Leu Gly Met Phe Leu Tyr Glu Tyr Ala Arg Arg His Pro Asp Tyr
865                 870                 875                 880

Ser Val Val Leu Leu Leu Arg Leu Ala Lys Thr Tyr Glu Thr Thr Leu
                885                 890                 895

Glu Lys Cys Cys Ala Ala Ala Asp Pro His Glu Cys Tyr Ala Lys Val
            900                 905                 910

Phe Asp Glu Phe Lys Pro Leu Val Glu Glu Pro Gln Asn Leu Ile Lys
        915                 920                 925

Gln Asn Cys Glu Leu Phe Glu Gln Leu Gly Glu Tyr Lys Phe Gln Asn
930                 935                 940

Ala Leu Leu Val Arg Tyr Thr Lys Lys Val Pro Gln Val Ser Thr Pro
945                 950                 955                 960

Thr Leu Val Glu Val Ser Arg Asn Leu Gly Lys Val Gly Ser Lys Cys
```

```
                        965                 970                 975

Cys Lys His Pro Glu Ala Lys Arg Met Pro Cys Ala Glu Asp Tyr Leu
                    980                 985                 990

Ser Val Leu Asn Gln Leu Cys Val Leu His Glu Lys Thr Pro Val
                    995                1000                1005

Ser Asp Arg Val Thr Lys Cys Cys Thr Glu Ser Leu Val Asn Arg Arg
       1010                1015                1020

Pro Cys Phe Ser Ala Leu Glu Val Asp Glu Thr Tyr Val Pro Lys Glu
    1025                1030                1035                1040

Phe Asn Ala Glu Thr Phe Thr Phe His Ala Asp Ile Cys Thr Leu Ser
                   1045                1050                1055

Glu Lys Glu Arg Gln Ile Lys Lys Gln Thr Ala Leu Val Glu Leu Val
                   1060                1065                1070

Lys His Lys Pro Lys Ala Thr Lys Glu Gln Leu Lys Ala Val Met Asp
                   1075                1080                1085

Asp Phe Ala Ala Phe Val Glu Lys Cys Cys Lys Ala Asp Asp Lys Glu
    1090                1095                1100

Thr Cys Phe Ala Glu Glu Gly Lys Lys Leu Val Ala Ala Ser Gln Ala
    1105                1110                1115                1120

Ala Leu Gly Leu

<210> SEQ ID NO 19
<211> LENGTH: 1109
<212> TYPE: PRT
<213> ORGANISM: Unknown
<220> FEATURE:
<223> OTHER INFORMATION: Recombinant HSA-EphB4 mature protein

<400> SEQUENCE: 19

Leu Glu Glu Thr Leu Leu Asn Thr Lys Leu Glu Thr Ala Asp Leu Lys
     1               5                  10                  15

Trp Val Thr Phe Pro Gln Val Asp Gly Gln Trp Glu Glu Leu Ser Gly
                    20                  25                  30

Leu Asp Glu Glu Gln His Ser Val Arg Thr Tyr Glu Val Cys Asp Val
                    35                  40                  45

Gln Arg Ala Pro Gly Gln Ala His Trp Leu Arg Thr Gly Trp Val Pro
        50                  55                  60

Arg Arg Gly Ala Val His Val Tyr Ala Thr Leu Arg Phe Thr Met Leu
    65                  70                  75                  80

Glu Cys Leu Ser Leu Pro Arg Ala Gly Arg Ser Cys Lys Glu Thr Phe
                    85                  90                  95

Thr Val Phe Tyr Tyr Glu Ser Asp Ala Asp Thr Ala Thr Ala Leu Thr
                   100                 105                 110

Pro Ala Trp Met Glu Asn Pro Tyr Ile Lys Val Asp Thr Val Ala Ala
                   115                 120                 125

Glu His Leu Thr Arg Lys Arg Pro Gly Ala Glu Ala Thr Gly Lys Val
                   130                 135                 140

Asn Val Lys Thr Leu Arg Leu Gly Pro Leu Ser Lys Ala Gly Phe Tyr
    145                 150                 155                 160

Leu Ala Phe Gln Asp Gln Gly Ala Cys Met Ala Leu Leu Ser Leu His
                   165                 170                 175

Leu Phe Tyr Lys Lys Cys Ala Gln Leu Thr Val Asn Leu Thr Arg Phe
                   180                 185                 190

Pro Glu Thr Val Pro Arg Glu Leu Val Val Pro Val Ala Gly Ser Cys
                   195                 200                 205
```

```
Val Val Asp Ala Val Pro Ala Pro Gly Pro Ser Pro Ser Leu Tyr Cys
    210                 215                 220

Arg Glu Asp Gly Gln Trp Ala Glu Gln Pro Val Thr Gly Cys Ser Cys
225                 230                 235                 240

Ala Pro Gly Phe Glu Ala Ala Glu Gly Asn Thr Lys Cys Arg Ala Cys
                245                 250                 255

Ala Gln Gly Thr Phe Lys Pro Leu Ser Gly Glu Gly Ser Cys Gln Pro
            260                 265                 270

Cys Pro Ala Asn Ser His Ser Asn Thr Ile Gly Ser Ala Val Cys Gln
        275                 280                 285

Cys Arg Val Gly Tyr Phe Arg Ala Arg Thr Asp Pro Arg Gly Ala Pro
    290                 295                 300

Cys Thr Thr Pro Pro Ser Ala Pro Arg Ser Val Val Ser Arg Leu Asn
305                 310                 315                 320

Gly Ser Ser Leu His Leu Glu Trp Ser Ala Pro Leu Glu Ser Gly Gly
                325                 330                 335

Arg Glu Asp Leu Thr Tyr Ala Leu Arg Cys Arg Glu Cys Arg Pro Gly
            340                 345                 350

Gly Ser Cys Ala Pro Cys Gly Gly Asp Leu Thr Phe Asp Pro Gly Pro
        355                 360                 365

Arg Asp Leu Val Glu Pro Trp Val Val Arg Gly Leu Arg Pro Asp
    370                 375                 380

Phe Thr Tyr Thr Phe Glu Val Thr Ala Leu Asn Gly Val Ser Ser Leu
385                 390                 395                 400

Ala Thr Gly Pro Val Pro Phe Glu Pro Val Asn Val Thr Thr Asp Arg
                405                 410                 415

Glu Val Pro Pro Ala Val Ser Asp Ile Arg Val Thr Arg Ser Ser Pro
            420                 425                 430

Ser Ser Leu Ser Leu Ala Trp Ala Val Pro Arg Ala Pro Ser Gly Ala
        435                 440                 445

Val Leu Asp Tyr Glu Val Lys Tyr His Glu Lys Gly Ala Glu Gly Pro
    450                 455                 460

Ser Ser Val Arg Phe Leu Lys Thr Ser Glu Asn Arg Ala Glu Leu Arg
465                 470                 475                 480

Gly Leu Lys Arg Gly Ala Ser Tyr Leu Val Gln Val Arg Ala Arg Ser
                485                 490                 495

Glu Ala Gly Tyr Gly Pro Phe Gly Gln Glu His His Ser Gln Thr Gln
            500                 505                 510

Leu Asp Glu Ser Glu Gly Trp Arg Glu Gln Ser Arg Asp Ala His Lys
        515                 520                 525

Ser Glu Val Ala His Arg Phe Lys Asp Leu Gly Glu Glu Asn Phe Lys
    530                 535                 540

Ala Leu Val Leu Ile Ala Phe Ala Gln Tyr Leu Gln Gln Cys Pro Phe
545                 550                 555                 560

Glu Asp His Val Lys Leu Val Asn Glu Val Thr Glu Phe Ala Lys Thr
                565                 570                 575

Cys Val Ala Asp Glu Ser Ala Glu Asn Cys Asp Lys Ser Leu His Thr
            580                 585                 590

Leu Phe Gly Asp Lys Leu Cys Thr Val Ala Thr Leu Arg Glu Thr Tyr
        595                 600                 605

Gly Glu Met Ala Asp Cys Cys Ala Lys Gln Glu Pro Glu Arg Asn Glu
    610                 615                 620
```

```
Cys Phe Leu Gln His Lys Asp Asp Asn Pro Asn Leu Pro Arg Leu Val
625                 630                 635                 640

Arg Pro Glu Val Asp Val Met Cys Thr Ala Phe His Asp Asn Glu Glu
            645                 650                 655

Thr Phe Leu Lys Lys Tyr Leu Tyr Glu Ile Ala Arg Arg His Pro Tyr
        660                 665                 670

Phe Tyr Ala Pro Glu Leu Leu Phe Phe Ala Lys Arg Tyr Lys Ala Ala
    675                 680                 685

Phe Thr Glu Cys Cys Gln Ala Ala Asp Lys Ala Ala Cys Leu Leu Pro
690                 695                 700

Lys Leu Asp Glu Leu Arg Asp Glu Gly Lys Ala Ser Ser Ala Lys Gln
705                 710                 715                 720

Arg Leu Lys Cys Ala Ser Leu Gln Lys Phe Gly Glu Arg Ala Phe Lys
            725                 730                 735

Ala Trp Ala Val Ala Arg Leu Ser Gln Arg Phe Pro Lys Ala Glu Phe
        740                 745                 750

Ala Glu Val Ser Lys Leu Val Thr Asp Leu Thr Lys Val His Thr Glu
    755                 760                 765

Cys Cys His Gly Asp Leu Leu Glu Cys Ala Asp Asp Arg Ala Asp Leu
770                 775                 780

Ala Lys Tyr Ile Cys Glu Asn Gln Asp Ser Ile Ser Ser Lys Leu Lys
785                 790                 795                 800

Glu Cys Cys Glu Lys Pro Leu Leu Glu Lys Ser His Cys Ile Ala Glu
            805                 810                 815

Val Glu Asn Asp Glu Met Pro Ala Asp Leu Pro Ser Leu Ala Ala Asp
        820                 825                 830

Phe Val Glu Ser Lys Asp Val Cys Lys Asn Tyr Ala Glu Ala Lys Asp
    835                 840                 845

Val Phe Leu Gly Met Phe Leu Tyr Glu Tyr Ala Arg Arg His Pro Asp
850                 855                 860

Tyr Ser Val Val Leu Leu Leu Arg Leu Ala Lys Thr Tyr Glu Thr Thr
865                 870                 875                 880

Leu Glu Lys Cys Cys Ala Ala Ala Asp Pro His Glu Cys Tyr Ala Lys
            885                 890                 895

Val Phe Asp Glu Phe Lys Pro Leu Val Glu Glu Pro Gln Asn Leu Ile
        900                 905                 910

Lys Gln Asn Cys Glu Leu Phe Glu Gln Leu Gly Glu Tyr Lys Phe Gln
    915                 920                 925

Asn Ala Leu Leu Val Arg Tyr Thr Lys Lys Val Pro Gln Val Ser Thr
930                 935                 940

Pro Thr Leu Val Glu Val Ser Arg Asn Leu Gly Lys Val Gly Ser Lys
945                 950                 955                 960

Cys Cys Lys His Pro Glu Ala Lys Arg Met Pro Cys Ala Glu Asp Tyr
            965                 970                 975

Leu Ser Val Val Leu Asn Gln Leu Cys Val Leu His Glu Lys Thr Pro
        980                 985                 990

Val Ser Asp Arg Val Thr Lys Cys Cys Thr Glu Ser Leu Val Asn Arg
    995                 1000                1005

Arg Pro Cys Phe Ser Ala Leu Glu Val Asp Glu Thr Tyr Val Pro Lys
        1010                1015                1020

Glu Phe Asn Ala Glu Thr Phe Thr Phe His Ala Asp Ile Cys Thr Leu
1025                1030                1035                1040

Ser Glu Lys Glu Arg Gln Ile Lys Lys Gln Thr Ala Leu Val Glu Leu
```

```
                  1045                1050                1055
    Val Lys His Lys Pro Lys Ala Thr Lys Glu Gln Leu Lys Ala Val Met
                      1060                1065                1070

Asp Asp Phe Ala Ala Phe Val Glu Lys Cys Cys Lys Ala Asp Asp Lys
                  1075                1080                1085

Glu Thr Cys Phe Ala Glu Glu Gly Lys Lys Leu Val Ala Ala Ser Gln
                  1090                1095                1100

Ala Ala Leu Gly Leu
    1105

<210> SEQ ID NO 20
    <211> LENGTH: 9244
    <212> TYPE: DNA
    <213> ORGANISM: Artificial Sequence
    <220> FEATURE:
    <223> OTHER INFORMATION: PEF6-GCF2 plasmid sequence

<400> SEQUENCE: 20
```

| | | | | | |
|---|---|---|---|---|---|
| aatattattg | aagcatttat | cagggttatt | gtctcatgag | cggatacata | tttgaatgta | 60 |
| tttagaaaaa | taaacaaata | ggggttccgc | gcacatttcc | ccgaaaagtg | ccacctgacg | 120 |
| tcgacggatc | gggagatctc | ccgatcccct | atggtcgact | ctcagtacaa | tctgctctga | 180 |
| tgccgcatag | ttaagccagt | atctgctccc | tgcttgtgtg | ttggaggtcg | ctgagtagtg | 240 |
| cgcgagcaaa | atttaagcta | caacaaggca | aggcttgacc | gacaattgca | tgaagaatct | 300 |
| gcttagggtt | aggcgttttg | cgctgcttcg | cgatgtacgg | gccagatata | cgcgttgaca | 360 |
| ttgattattg | actagctttt | gcaaaaagc | tttgcaaaga | tggataaagt | tttaaacaga | 420 |
| gaggaatctt | tgcagctaat | ggaccttcta | ggtcttgaaa | ggagtgcctc | gtgaggctcc | 480 |
| ggtgcccgtc | agtgggcaga | gcgcacatcg | cccacagtcc | ccgagaagtt | ggggggaggg | 540 |
| gtcggcaatt | gaaccggtgc | ctagagaagg | tggcgcgggg | taaactggga | aagtgatgtc | 600 |
| gtgtactggc | tccgcctttt | tcccgagggt | ggggagaac | cgtatataag | tgcagtagtc | 660 |
| gccgtgaacg | ttcttttttcg | caacgggttt | gccgccagaa | cacaggtaag | tgccgtgtgt | 720 |
| ggttcccgcg | ggcctggcct | ctttacgggt | tatgggccctt | gcgtgccttg | aattacttcc | 780 |
| acctggctgc | agtacgtgat | tcttgatccc | gagcttcggg | ttggaagtgg | gtgggagagt | 840 |
| tcgaggcctt | gcgcttaagg | agccccttcg | cctcgtgctt | gagttgaggc | ctggcctggg | 900 |
| cgctggggcc | gccgcgtgcg | aatctggtgg | caccttcgcg | cctgtctcgc | tgctttcgat | 960 |
| aagtctctag | ccatttaaaa | ttttgatga | cctgctgcga | cgcttttttt | ctggcaagat | 1020 |
| agtcttgtaa | atgcgggcca | agatctgcac | actggtattt | cggttttttgg | ggccgcgggc | 1080 |
| ggcgacgggg | cccgtgcgtc | ccagcgcaca | tgttcggcga | ggcggggcct | gcgagcgcgg | 1140 |
| ccaccgagaa | tcggacgggg | gtagtctcaa | gctggccggc | ctgctctggt | gcctggcctc | 1200 |
| gcgccgccgt | gtatcgcccc | gccctgggcg | gcaaggctgg | cccggtcggc | accagttgcg | 1260 |
| tgagcggaaa | gatggccgct | tcccggccct | gctgcaggga | gctcaaaatg | gaggacgcgg | 1320 |
| cgctcgggag | agcgggcggg | tgagtcaccc | acacaaagga | aaagggcctt | tccgtcctca | 1380 |
| gccgtcgctt | catgtgactc | cacggagtac | cgggcgccgt | ccaggcacct | cgattagttc | 1440 |
| tcgagctttt | ggagtacgtc | gtctttaggt | tggggggagg | ggttttatgc | gatggagttt | 1500 |
| ccccacactg | agtgggtgga | gactgaagtt | aggccagctt | ggcacttgat | gtaattctcc | 1560 |
| ttggaatttg | ccctttttga | gtttggatct | tggttcattc | tcaagcctca | gacagtggtt | 1620 |
| caaagttttt | ttcttccatt | tcaggtgtcg | tgaggaatta | gcttggtact | aatacgactc | 1680 |

```
actatateggga gacccaagct ggctaggtaa gcttggtacc gagctcggat ccactagtcc   1740
agtgtggtgg aattgcccct caagcttgcc gccaccatgg agctccgggt gctgctctgc   1800
tgggcttcgt tggccgcagc tttggaagag accctgctga acacaaaatt ggaaactgct   1860
gatctgaagt gggtgacatt ccctcaggtg acgggcagt gggaggaact gagcggcctg   1920
gatgaggaac agcacagcgt gcgcacctac gaagtgtgtg acgtgcagcg tgccccgggc   1980
caggcccact ggcttcgcac aggttgggtc cacggcggg gcgccgtcca cgtgtacgcc   2040
acgctgcgct tcaccatgct cgagtgcctg tccctgcctc gggctgggcg ctcctgcaag   2100
gagaccttca ccgtcttcta ctatgagagc gatgcggaca cggccacggc cctcacgcca   2160
gcctggatgg agaacccta catcaaggtg acacggtgg ccgcggagca tctcacccgg   2220
aagcgccctg gggccgaggc caccgggaag gtgaatgtca agacgctgcg cctgggaccg   2280
ctcagcaagg ctggcttcta cctggccttc caggaccagg gtgcctgcat ggccctgcta   2340
tccctgcacc tcttctacaa aaagtgcgcc cagctgactg tgaacctgac tcgattcccg   2400
gagactgtgc ctcgggagct ggttgtgccc gtggccggta gctgcgtggt ggatgccgtc   2460
cccgcccctg gccccagccc cagcctctac tgccgtgagg atggccagtg ggccgaacag   2520
ccggtcacgg gctgcagctg tgctccgggg ttcgaggcag ctgaggggaa caccaagtgc   2580
cgagcctgtg cccagggcac cttcaagccc ctgtcaggag aagggtcctg ccagccatgc   2640
ccagccaata gccactctaa caccattgga tcagccgtct gccagtgccg cgtcgggtac   2700
ttccgggcac gcacagaccc ccgggggtgca ccctgcacca cccctccttc ggctccgcgg   2760
agcgtggttt cccgcctgaa cggctcctcc ctgcacctgg aatggagtgc cccctggag   2820
tctggtggcc gagaggacct cacctacgcc ctccgctgcc gggagtgtcg acccggaggc   2880
tcctgtgcgc cctgcggggg agacctgact tttgaccccg gccccggga cctggtggag   2940
ccctgggtgg tggttcgagg gctacgtcct gacttcacct ataccttga ggtcactgca   3000
ttgaacgggg tatcctcctt agccacgggg cccgtcccat ttgagcctgt caatgtcacc   3060
actgaccgag aggtacctcc tgcagtgtct gacatccggg tgacgcggtc ctcacccagc   3120
agcttgagcc tggcctgggc tgttcccgg gcacccagtg gggctgtgct ggactacgag   3180
gtcaaatacc atgagaaggg cgccgagggt cccagcagcg tgcggttcct gaagacgtca   3240
gaaaaccggg cagagctgcg ggggctgaag cggggagcca gctacctggt gcaggtacgg   3300
gcgcgctctg aggccggcta cgggcccttc ggccaggaac atcacagcca gacccaactg   3360
gatgagagcg agggctggcg ggagcagtct agagatgcac acaagagtga ggttgctcat   3420
cggtttaaag atttgggaga agaaaatttc aaagccttgg tgttgattgc ctttgctcag   3480
tatcttcagc agtgtccatt tgaagatcat gtaaaattag tgaatgaagt aactgaattt   3540
gcaaaaacat gtgtagctga tgagtcagct gaaaattgtg acaaatcact tcataccctt   3600
tttgagacaa aattatgcac agttgcaact cttcgtgaaa cctatggtga aatggctgac   3660
tgctgtgcaa aacaagaacc tgagagaaat gaatgcttct gcaacacaa agatgacaac   3720
ccaaacctcc cccgattggt gagaccagag gttgatgtga tgtgcactgc ttttcatgac   3780
aatgaagaga cattttgaa aaaatactta tatgaaattg ccagaagaca tccttactt   3840
tatgccccgg aactcctttt ctttgctaaa aggtataaag ctgcttttac agaatgttgc   3900
caagctgcta taaagctgc ctgcctgttg ccaaagctcg atgaacttcg ggatgaaggg   3960
aaggcttcgt ctgccaaaca gagactcaaa tgtgccagtc tccaaaaatt tggagaagag   4020
```

```
gctttcaaag catgggcagt ggctcgcctg agccagagat ttcccaaagc tgagtttgca    4080
gaagtttcca agttagtgac agatcttacc aaagtccaca cggaatgctg ccatggagat    4140
ctgcttgaat gtgctgatga cagggcggac cttgccaagt atatctgtga aaatcaggat    4200
tcgatctcca gtaaactgaa ggaatgctgt gaaaaacctc tgttggaaaa atcccactgc    4260
attgccgaag tggaaaatga tgagatgcct gctgacttgc cttcattagc tgctgatttt    4320
gttgaaagta aggatgtttg caaaaactat gctgaggcaa aggatgtctt cctgggcatg    4380
tttttgtatg aatatgcaag aaggcatcct gattactctg tcgtgctgct gctgagactt    4440
gccaagacat atgaaaccac tctagagaag tgctgtgccg ctgcagatcc tcatgaatgc    4500
tatgccaaag tgttcgatga atttaaacct cttgtggaag agcctcagaa tttaatcaaa    4560
caaaactgtg agcttttaa gcagcttgga gagtacaaat tccagaatgc gctattagtt    4620
cgttacacca agaaagtacc ccaagtgtca actccaactc ttgtagaggt ctcaagaaac    4680
ctaggaaaag tgggcagcaa atgttgtaaa catcctgaag caaaaagaat gccctgtgca    4740
gaagactatc tatccgtggt cctgaaccag ttatgtgtgt tgcatgagaa aacgccagta    4800
agtgacagag tcacaaaatg ctgcacagag tccttggtga acaggcgacc atgcttttca    4860
gctctggaag tcgatgaaac atacgttccc aaagagttta tgctgaaaac attccacttc    4920
catgcagata tatgcacact ttctgagaag gagagacaaa tcaagaaaca aactgcactt    4980
gttgagcttg tgaaacacaa gcccaaggca acaaaagagc aactgaaagc tgttatggat    5040
gatttcgcag cttttgtaga gaagtgctgc aaggctgacg ataaggagac ctgctttgcc    5100
gaggagggta aaaaacttgt tgctgcaagt caagctgcct taggcttata atagcggccg    5160
cttaagggca attctgcaga tatccagcac agtggcggcc gctcgagtct agagggcccg    5220
cggttcgaag gtaagcctat ccctaaccct ctcctcggtc tcgattctac gcgtaccggt    5280
catcatcacc atcaccattg agtttaaacc cgctgatcag cctcgactgt gccttctagt    5340
tgccagccat ctgttgtttg cccctccccc gtgccttcct tgaccctgga aggtgccact    5400
cccactgtcc tttcctaata aaatgaggaa attgcatcgc attgtctgag taggtgtcat    5460
tctattctgg ggggtggggt ggggcaggac agcaagggg aggattggga agacaatagc    5520
aggcatgctg gggatgcggt gggctctatg gcttctgagg cggaaagaac cagctggggc    5580 tctaggggt atccccacgc gccctgtagc ggcgcattaa gcgcggcggg tgtggtggtt    5640
acgcgcagcg tgaccgctac acttgccagc gccctagcgc ccgctccttt cgctttcttc    5700
ccttcctttc tcgccacgtt cgccggcttt ccccgtcaag ctctaaatcg ggcatccct    5760 ttagggttcc gatttagtgc tttacggcac ctcgacccca aaaaacttga ttagggtgat    5820
ggttcacgta gtgggccatc gccctgatag acggtttttc gccctttgac gttggagtcc    5880
acgttcttta atagtggact cttgttccaa actggaacaa cactcaaccc tatctcggtc    5940
tattcttttg atttataagg gattttgggg atttcggcct attggttaaa aaatgagctg    6000
atttaacaaa aatttaacgc gaattaattc tgtggaatgt gtgtcagtta gggtgtggaa    6060
agtccccagg ctccccaggc aggcagaagt atgcaaagca tgcatctcaa ttagtcagca    6120
accaggtgtg gaaagtcccc aggctcccca gcaggcagaa gtatgcaaag catgcatctc    6180
aattagtcag caaccatagt cccgccccta actccgccca tcccgcccct aactccgccc    6240
agttccgccc attctccgcc ccatggctga ctaattttt ttatttatgc agaggccgag    6300
gccgcctctg cctctgagct attccagaag tagtgaggag ctttttttgg aggcctaggc    6360
ttttgcaaaa agctcccggg agcttgtata tccattttcg gatctgatca gcacgtgttg    6420
```

```
acaattaatc atcggcatag tatatcggca tagtataata cgacaaggtg aggaactaaa    6480
ccatggccaa gcctttgtct caagaagaat ccaccctcat tgaaagagca acggctacaa    6540
tcaacagcat ccccatctct gaagactaca gcgtcgccag cgcagctctc tctagcgacg    6600
gccgcatctt cactggtgtc aatgtatatc attttactgg gggaccttgt gcagaactcg    6660
tggtgctggg cactgctgct gctgcggcag ctggcaacct gacttgtatc gtcgcgatcg    6720
gaaatgagaa caggggcatc ttgagcccct gcggacggtg tcgacaggtg cttctcgatc    6780
tgcatcctgg gatcaaagcg atagtgaagg acagtgatgg acagccgacg gcagttggga    6840
ttcgtgaatt gctgccctct ggttatgtgt gggagggcta agcacttcgt ggccgaggag    6900
caggactgac acgtgctacg agatttcgat tccaccgccg ccttctatga aggttgggc    6960 ttcggaatcg ttttccggga cgccggctgg atgatcctcc agcgcgggga tctcatgctg    7020
gagttcttcg cccaccccaa cttgtttatt gcagcttata atggttacaa ataaagcaat    7080
agcatcacaa atttcacaaa taaagcattt ttttcactgc attctagttg tggtttgtcc    7140
aaactcatca atgtatctta tcatgtctgt ataccgtcga cctctagcta gagcttggcg    7200
taatcatggt catagctgtt tcctgtgtga aattgttatc cgctcacaat tccacacaac    7260
atacgagccg gaagcataaa gtgtaaagcc tggggtgcct aatgagtgag ctaactcaca    7320
ttaattgcgt tgcgctcact gcccgctttc cagtcgggaa acctgtcgtg ccagctgcat    7380
taatgaatcg gccaacgcgc ggggagaggc ggtttgcgta ttgggcgctc ttccgcttcc    7440
tcgctcactg actcgctgcg ctcggtcgtt cggctgcggc gagcggtatc agctcactca    7500
aaggcggtaa tacggttatc cacagaatca ggggataacg caggaaagaa catgtgagca    7560
aaaggccagc aaaaggccag gaaccgtaaa aaggccgcgt tgctggcgtt tttccatagg    7620
ctccgccccc ctgacgagca tcacaaaaat cgacgctcaa gtcagaggtg gcgaaacccg    7680
acaggactat aaagatacca ggcgtttccc cctggaagct ccctcgtgcg ctctcctgtt    7740
ccgaccctgc cgcttaccgg atacctgtcc gcctttctcc cttcgggaag cgtggcgctt    7800
tctcaatgct cacgctgtag gtatctcagt tcggtgtagg tcgttcgctc caagctgggc    7860
tgtgtgcacg aaccccccgt tcagcccgac cgctgcgcct tatccggtaa ctatcgtctt    7920
gagtccaacc cggtaagaca cgacttatcg ccactggcag cagccactgg taacaggatt    7980
agcagagcga ggtatgtagg cggtgctaca gagttcttga agtggtggcc taactacggc    8040
tacactagaa ggacagtatt tggtatctgc gctctgctga agccagttac cttcggaaaa    8100
agagttggta gctcttgatc cggcaaacaa accaccgctg gtagcggtgg tttttttgtt    8160
tgcaagcagc agattacgcg cagaaaaaaa ggatctcaag aagatccttt gatcttttct    8220
acggggtctg acgctcagtg gaacgaaaac tcacgttaag ggattttggt catgagatta    8280
tcaaaaagga tcttcaccta gatccttta aattaaaaat gaagttttaa atcaatctaa    8340
agtatatatg agtaaacttg gtctgacagt taccaatgct taatcagtga ggcacctatc    8400
tcagcgatct gtctatttcg ttcatccata gttgcctgac tccccgtcgt gtagataact    8460
acgatacggg agggcttacc atctggcccc agtgctgcaa tgataccgcg agacccacgc    8520
tcaccggctc cagatttatc agcaataaac cagccagccg aagggccga gcgcagaagt    8580 ggtcctgcaa ctttatccgc ctccatccag tctattaatt gttgccggga agctagagta    8640
agtagttcgc cagttaatag tttgcgcaac gttgttgcca ttgctacagg catcgtggtg    8700
tcacgctcgt cgtttggtat ggcttcattc agctccggtt cccaacgatc aaggcgagtt    8760
```

```
acatgatccc ccatgttgtg caaaaaagcg gttagctcct tcggtcctcc gatcgttgtc    8820
agaagtaagt tggccgcagt gttatcactc atggttatgg cagcactgca taattctctt    8880
actgtcatgc catccgtaag atgcttttct gtgactggtg agtactcaac caagtcattc    8940
tgagaatagt gtatgcggcg accgagttgc tcttgcccgg cgtcaatacg ggataatacc    9000
gcgccacata gcagaacttt aaaagtgctc atcattggaa aacgttcttc ggggcgaaaa    9060
ctctcaagga tcttaccgct gttgagatcc agttcgatgt aacccactcg tgcacccaac    9120
tgatcttcag catcttttac tttcaccagc gtttctgggt gagcaaaaac aggaaggcaa    9180
aatgccgcaa aaagggaat aagggcgaca cggaaatgtt gaatactcat actcttcctt    9240
tttc                                                                  9244
```

<210> SEQ ID NO 21
<211> LENGTH: 11
<212> TYPE: PRT
<213> ORGANISM: Unknown
<220> FEATURE:
<223> OTHER INFORMATION: linker peptide sequence

<400> SEQUENCE: 21

Gly Gly Gly Gly Ser Gly Gly Gly Gly Ser
1               5                   10

<210> SEQ ID NO 22
<211> LENGTH: 17
<212> TYPE: PRT
<213> ORGANISM: Unknown
<220> FEATURE:
<223> OTHER INFORMATION: linker peptide sequence

<400> SEQUENCE: 22

Ser Ser Ser Ser Gly Ser Ser Ser Ser Gly Ser Ser Ser Ser Gly Ser
1               5                   10                  15
Pro

We claim:

1. An isolated fusion polypeptide consisting of a sequence selected from the group consisting of: residues 16-197, 16-321, 16-326, 16-427, 16-429, and 16-526 of SEQ ID NO: 10; and (b) an albumin protein or fragment thereof, wherein the fusion polypeptide is a monomer, binds specifically to an Ephrin B2 polypeptide, and inhibits signaling that results from interaction between EphB4 and Ephrin B2.

2. The isolated fusion polypeptide of claim 1, wherein the fusion polypeptide has one or more activities selected from:
   (a) inhibition of Ephrin B2 activity;
   (b) inhibition of Ephrin B2 kinase activity;
   (c) inhibition of the interaction between EphB4 and Ephrin B2;
   (d) inhibition of EphB4 kinase activity;
   (e) inhibition of clustering of Ephrin B2; and
   (f) inhibition of clustering of EphB4.

3. The isolated fusion polypeptide of claim 1, wherein the fusion polypeptide has enhanced in vivo stability relative to said extracellular domain of an EphB4 protein.

4. The isolated fusion polypeptide of claim 1, wherein the albumin protein or fragment thereof is mature human serum albumin (HSA).

5. The isolated fusion polypeptide of claim 1, wherein the EphB4 extracellular domain consists of residues 16-326 of SEQ ID NO: 10.

6. The isolated fusion polypeptide of claim 1, wherein the fusion polypeptide sequence consists of residues 16-326 of SEQ ID NO: 10 fused to residues 525-1109 of SEQ ID NO: 19.

7. A pharmaceutical composition comprising an isolated fusion polypeptide of claim 1 and a pharmaceutically acceptable carrier.

* * * * *